US012731340B2

(12) United States Patent
Shelton, IV et al.

(10) Patent No.: US 12,731,340 B2
(45) Date of Patent: Sep. 8, 2026

(54) METHOD FOR INTRAOPERATIVE DISPLAY FOR SURGICAL SYSTEMS

(71) Applicant: Cilag GmbH International, Zug (CH)

(72) Inventors: Frederick E. Shelton, IV, Hillsboro, OH (US); Shane R. Adams, Lebanon, OH (US); Matthew D. Cowperthwait, Cincinnati, OH (US); Kevin M. Fiebig, Cincinnati, OH (US); Jason L. Harris, Lebanon, OH (US); Matjaz Jogan, Philadelphia, PA (US); Zhifan F. Huang, Mason, OH (US); Shaun B. Schaeffer, Cincinnati, OH (US); Tyler N. Brehm, Cincinnati, OH (US); John E. Brady, Cincinnati, OH (US); Demetrius N. Harris, Austin, TX (US); Ellen E. Burkart, Liberty Township, OH (US); Madison K. Vanosdoll, Cincinnati, OH (US); Christopher Q. Seow, Cincinnati, OH (US); Cory G. Kimball, Hamilton, OH (US); Monica L. Z. Rivard, Cincinnati, OH (US); Leonardo N. Rossoni, Rahway, NJ (US); Risto Kojcev, Santa Clara, CA (US); Felix J. Bork, Schnürpflingen (DE)

(73) Assignee: Cilag GmbH International, Zug (CH)

(*) Notice: Subject to any disclaimer, the term of this patent is extended or adjusted under 35 U.S.C. 154(b) by 466 days.

(21) Appl. No.: 17/688,589

(22) Filed: Mar. 7, 2022

(65) Prior Publication Data

US 2022/0331047 A1 Oct. 20, 2022

Related U.S. Application Data

(60) Provisional application No. 63/284,326, filed on Nov. 30, 2021, provisional application No. 63/174,674, filed on Apr. 14, 2021.

(51) Int. Cl.
*G06T 11/00* (2006.01)
*A61B 34/00* (2016.01)
(Continued)

(52) U.S. Cl.
CPC ............ *G06T 19/006* (2013.01); *A61B 34/20* (2016.02); *A61B 34/25* (2016.02); *A61B 34/30* (2016.02);
(Continued)

(58) Field of Classification Search
CPC .......... G06T 11/00; A61B 34/20; A61B 34/25
See application file for complete search history.

(56) References Cited

U.S. PATENT DOCUMENTS 4,171,700 A 10/1979 Farin
4,849,752 A 7/1989 Bryant
(Continued)

FOREIGN PATENT DOCUMENTS

CA 3003058 A1 5/2017
CN 112603496 A 4/2021
(Continued)

OTHER PUBLICATIONS

"ATM-MPLS Network Interworking Version 2.0, af-aic-0178.001" ATM Standard, The ATM Forum Technical Committee, published Aug. 2003.
(Continued)

*Primary Examiner* — Matthew Salvucci
(74) *Attorney, Agent, or Firm* — Condo Roccia Koptiw LLP

(57) ABSTRACT

A method for presenting surgical data onto a livestream of a surgical field on a display during a surgical procedure is disclosed. The method includes detecting, by a control module, surgical data, assigning, by the control module, display priority values to the surgical data, determining, by
(Continued)

the control module, a display arrangement of the surgical data on the display based on the display priority values, and presenting onto the livestream visual representations of the surgical data in accordance with the display arrangement.

22 Claims, 166 Drawing Sheets

(51) Int. Cl.

| | |
|---|---|
| ***A61B 34/20*** | (2016.01) |
| ***A61B 34/30*** | (2016.01) |
| ***A61B 34/32*** | (2016.01) |
| ***A61B 90/00*** | (2016.01) |
| ***G06F 3/14*** | (2006.01) |
| ***G06F 3/147*** | (2006.01) |
| ***G06T 7/00*** | (2017.01) |
| ***G06T 7/20*** | (2017.01) |
| ***G06T 11/60*** | (2006.01) |
| ***G06T 19/00*** | (2011.01) |
| ***G06V 20/20*** | (2022.01) |
| ***G08B 21/18*** | (2006.01) |
| ***G16H 20/40*** | (2018.01) |
| ***G16H 40/67*** | (2018.01) |
| ***H04L 9/40*** | (2022.01) |
| ***H04L 67/12*** | (2022.01) |
| ***H04W 24/10*** | (2009.01) |
| ***H04W 76/14*** | (2018.01) |
| *A61B 34/10* | (2016.01) |

(52) U.S. Cl.

CPC .............. *A61B 34/32* (2016.02); *A61B 34/76* (2016.02); *A61B 90/36* (2016.02); *A61B 90/361* (2016.02); *A61B 90/37* (2016.02); *A61B 90/39* (2016.02); *G06F 3/14* (2013.01); *G06F 3/1454* (2013.01); *G06F 3/147* (2013.01); *G06T 7/0012* (2013.01); *G06T 7/20* (2013.01); *G06T 11/00* (2013.01); *G06T 11/60* (2013.01); *G06V 20/20* (2022.01); *G08B 21/182* (2013.01); *G16H 20/40* (2018.01); *G16H 40/67* (2018.01); *H04L 63/105* (2013.01); *H04L 67/12* (2013.01); *H04W 24/10* (2013.01); *H04W 76/14* (2018.02); *A61B 2034/102* (2016.02); *A61B 2034/2055* (2016.02); *A61B 2034/2072* (2016.02); *A61B 2034/252* (2016.02); *A61B 2034/254* (2016.02); *A61B 2090/365* (2016.02); *A61B 2090/368* (2016.02); *A61B 2090/371* (2016.02); *A61B 2090/372* (2016.02); *A61B 2090/373* (2016.02); *A61B 2090/3937* (2016.02); *A61B 2090/3975* (2016.02); *G06T 2207/10028* (2013.01); *G06T 2207/30024* (2013.01); *G06T 2210/41* (2013.01)

(56) References Cited

U.S. PATENT DOCUMENTS

| | | | |
|---|---|---|---|
| D303,787 | S | 10/1989 | Messenger et al. |
| D327,061 | S | 6/1992 | Soren et al. |
| 5,189,277 | A | 2/1993 | Boisvert et al. |
| 5,204,669 | A | 4/1993 | Dorfe et al. |
| 5,318,563 | A | 6/1994 | Malis et al. |
| 5,325,270 | A | 6/1994 | Wenger et al. |
| 5,425,375 | A | 6/1995 | Chin et al. |
| D379,346 | S | 5/1997 | Mieki |
| 5,690,504 | A | 11/1997 | Scanlan et al. |
| 5,693,042 | A | 12/1997 | Boiarski et al. |
| 5,724,468 | A | 3/1998 | Leone et al. |
| 6,049,467 | A | 4/2000 | Tamarkin et al. |
| 6,055,458 | A | 4/2000 | Cochran et al. |
| D431,811 | S | 10/2000 | Nishio et al. |
| 6,179,136 | B1 | 1/2001 | Kluge et al. |
| 6,269,411 | B1 | 7/2001 | Reasoner |
| 6,288,606 | B1 | 9/2001 | Ekman et al. |
| 6,416,471 | B1 | 7/2002 | Kumar et al. |
| 6,501,485 | B1 | 12/2002 | Dash et al. |
| 6,546,270 | B1 | 4/2003 | Goldin et al. |
| 6,584,358 | B2 | 6/2003 | Carter et al. |
| 6,611,793 | B1 | 8/2003 | Burnside et al. |
| 6,731,514 | B2 | 5/2004 | Evans |
| 6,760,218 | B2 | 7/2004 | Fan |
| 6,839,238 | B2 | 1/2005 | Derr et al. |
| 6,843,657 | B2 | 1/2005 | Driscoll et al. |
| 6,913,471 | B2 | 7/2005 | Smith |
| 7,009,511 | B2 | 3/2006 | Mazar et al. |
| 7,044,949 | B2 | 5/2006 | Orszulak et al. |
| 7,074,205 | B1 | 7/2006 | Duffy et al. |
| 7,134,994 | B2 | 11/2006 | Alpert et al. |
| 7,171,784 | B2 | 2/2007 | Eenigenburg |
| 7,217,269 | B2 | 5/2007 | El-Galley et al. |
| 7,252,664 | B2 | 8/2007 | Nasab et al. |
| 7,331,699 | B2 | 2/2008 | Gawalkiewicz et al. |
| 7,344,532 | B2 | 3/2008 | Goble et al. |
| 7,353,068 | B2 | 4/2008 | Tanaka et al. |
| 7,408,439 | B2 | 8/2008 | Wang et al. |
| D579,876 | S | 11/2008 | Novotney et al. |
| D583,328 | S | 12/2008 | Chiang |
| 7,496,418 | B2 | 2/2009 | Kim et al. |
| D589,447 | S | 3/2009 | Sasada et al. |
| 7,500,747 | B2 | 3/2009 | Howell et al. |
| 7,518,502 | B2 | 4/2009 | Austin et al. |
| 7,563,259 | B2 | 7/2009 | Takahashi |
| 7,601,149 | B2 | 10/2009 | DiCarlo et al. |
| 7,637,907 | B2 | 12/2009 | Blaha |
| 7,656,671 | B2 | 2/2010 | Liu et al. |
| 7,757,028 | B2 | 7/2010 | Druke et al. |
| D631,252 | S | 1/2011 | Leslie |
| 7,932,826 | B2 | 4/2011 | Fritchie et al. |
| 7,945,065 | B2 | 5/2011 | Menzl et al. |
| 7,945,342 | B2 | 5/2011 | Tsai et al. |
| 7,982,776 | B2 | 7/2011 | Dunki-Jacobs et al. |
| 7,995,045 | B2 | 8/2011 | Dunki-Jacobs |
| 8,019,094 | B2 | 9/2011 | Hsieh et al. |
| 8,086,008 | B2 | 12/2011 | Coste-maniere et al. |
| D655,678 | S | 3/2012 | Kobayashi et al. |
| D657,368 | S | 4/2012 | Magee et al. |
| 8,239,066 | B2 | 8/2012 | Jennings et al. |
| D667,838 | S | 9/2012 | Magee et al. |
| D675,164 | S | 1/2013 | Kobayashi et al. |
| D676,392 | S | 2/2013 | Gassauer |
| D678,196 | S | 3/2013 | Miyauchi et al. |
| D678,304 | S | 3/2013 | Yakoub et al. |
| 8,423,182 | B2 | 4/2013 | Robinson et al. |
| D687,146 | S | 7/2013 | Juzkiw et al. |
| 8,504,136 | B1 | 8/2013 | Sun et al. |
| 8,540,709 | B2 | 9/2013 | Allen |
| 8,567,393 | B2 | 10/2013 | Hickle et al. |
| D704,839 | S | 5/2014 | Juzkiw et al. |
| 8,795,001 | B1 | 8/2014 | Lam et al. |
| 8,819,581 | B2 | 8/2014 | Nakamura et al. |
| D716,333 | S | 10/2014 | Chotin et al. |
| 8,917,513 | B1 | 12/2014 | Hazzard |
| 8,920,186 | B2 | 12/2014 | Shishikura |
| 8,923,012 | B2 | 12/2014 | Kaufman et al. |
| 8,968,296 | B2 | 3/2015 | McPherson |
| 8,986,288 | B2 | 3/2015 | Konishi |
| 9,017,326 | B2 | 4/2015 | Dinardo et al. |
| D729,267 | S | 5/2015 | Yoo et al. |
| 9,055,870 | B2 | 6/2015 | Meador et al. |
| 9,065,394 | B2 | 6/2015 | Lim et al. |
| 9,129,054 | B2 | 9/2015 | Nawana et al. |
| 9,160,853 | B1 | 10/2015 | Daddi et al. |
| 9,168,054 | B2 | 10/2015 | Turner et al. |
| 9,168,085 | B2 | 10/2015 | Juzkiw et al. |
| 9,168,091 | B2 | 10/2015 | Janssen et al. |
| 9,198,711 | B2 | 12/2015 | Joseph |
| 9,220,570 | B2 | 12/2015 | Kim et al. |

(56) References Cited

U.S. PATENT DOCUMENTS

| | | | |
|---|---|---|---|
| 9,226,766 | B2 | 1/2016 | Aldridge et al. |
| 9,226,791 | B2 | 1/2016 | McCarthy et al. |
| 9,237,921 | B2 | 1/2016 | Messerly et al. |
| 9,265,429 | B2 | 2/2016 | St. Pierre et al. |
| 9,277,961 | B2 | 3/2016 | Panescu et al. |
| 9,277,969 | B2 | 3/2016 | Brannan et al. |
| 9,281,615 | B1 | 3/2016 | Plaza et al. |
| 9,320,646 | B2 | 4/2016 | Todd et al. |
| 9,345,481 | B2 | 5/2016 | Hall et al. |
| 9,345,900 | B2 | 5/2016 | Wu et al. |
| 9,351,653 | B1 | 5/2016 | Harrison |
| 9,427,255 | B2 | 8/2016 | Griffith et al. |
| 9,463,646 | B2 | 10/2016 | Payne et al. |
| 9,474,565 | B2 | 10/2016 | Shikhman et al. |
| D772,252 | S | 11/2016 | Myers et al. |
| 9,486,271 | B2 | 11/2016 | Dunning |
| 9,491,895 | B2 | 11/2016 | Steeves et al. |
| 9,503,681 | B1 | 11/2016 | Popescu et al. |
| 9,532,827 | B2 | 1/2017 | Morgan et al. |
| 9,600,031 | B2 | 3/2017 | Kaneko et al. |
| 9,603,277 | B2 | 3/2017 | Morgan et al. |
| D783,675 | S | 4/2017 | Yagisawa et al. |
| D784,270 | S | 4/2017 | Bhattacharya |
| 9,666,974 | B2 | 5/2017 | Bopp |
| 9,713,503 | B2 | 7/2017 | Goldschmidt |
| 9,715,271 | B2 | 7/2017 | Kaestner |
| 9,750,563 | B2 | 9/2017 | Shikhman et al. |
| 9,770,103 | B2 | 9/2017 | Cochran et al. |
| 9,773,093 | B2 | 9/2017 | Bernini et al. |
| 9,782,214 | B2 | 10/2017 | Houser et al. |
| 9,788,907 | B1 | 10/2017 | Alvi et al. |
| 9,804,977 | B2 | 10/2017 | Ghosh et al. |
| 9,867,670 | B2 | 1/2018 | Brannan et al. |
| 9,892,564 | B1 | 2/2018 | Cvetko et al. |
| 9,907,196 | B2 | 2/2018 | Susini et al. |
| 9,935,794 | B1 | 4/2018 | Cao et al. |
| 9,971,395 | B2 | 5/2018 | Chenault et al. |
| 9,974,595 | B2 | 5/2018 | Anderson et al. |
| 9,987,068 | B2 | 6/2018 | Anderson et al. |
| 9,987,072 | B2 | 6/2018 | McPherson |
| 10,028,402 | B1 | 7/2018 | Walker |
| 10,039,589 | B2 | 8/2018 | Virshek et al. |
| D832,211 | S | 10/2018 | Ladd et al. |
| 10,098,527 | B2 | 10/2018 | Weisenburgh, II et al. |
| 10,105,470 | B2 | 10/2018 | Reasoner et al. |
| 10,109,835 | B2 | 10/2018 | Yang |
| D834,541 | S | 11/2018 | You et al. |
| 10,117,702 | B2 | 11/2018 | Danziger et al. |
| 10,128,612 | B1 | 11/2018 | Casto |
| 10,136,954 | B2 | 11/2018 | Johnson et al. |
| 10,137,245 | B2 | 11/2018 | Melker et al. |
| 10,147,148 | B2 | 12/2018 | Wu et al. |
| 10,166,019 | B2 | 1/2019 | Nawana et al. |
| 10,166,061 | B2 | 1/2019 | Berry et al. |
| 10,170,205 | B2 | 1/2019 | Curd et al. |
| 10,201,365 | B2 | 2/2019 | Boudreaux et al. |
| 10,262,453 | B2 | 4/2019 | Mountney et al. |
| 10,339,496 | B2 | 7/2019 | Matson et al. |
| 10,357,184 | B2 | 7/2019 | Crawford et al. |
| 10,386,990 | B2 | 8/2019 | Shikhman et al. |
| 10,441,345 | B2 | 10/2019 | Aldridge et al. |
| 10,449,004 | B2 | 10/2019 | Ferro et al. |
| 10,475,244 | B2 | 11/2019 | Cvetko et al. |
| 10,493,287 | B2 | 12/2019 | Yoder et al. |
| 10,499,847 | B2 | 12/2019 | Latimer et al. |
| 10,499,996 | B2 | 12/2019 | de Almeida Barreto |
| 10,523,122 | B2 | 12/2019 | Han et al. |
| 10,531,579 | B2 | 1/2020 | Hsiao et al. |
| D876,466 | S | 2/2020 | Kobayashi et al. |
| 10,561,753 | B2 | 2/2020 | Thompson et al. |
| 10,602,007 | B2 | 3/2020 | Takano |
| 10,610,310 | B2 | 4/2020 | Todd et al. |
| 10,624,667 | B2 | 4/2020 | Faller et al. |
| 10,624,691 | B2 | 4/2020 | Wiener et al. |
| 10,675,100 | B2 | 6/2020 | Frushour |
| 10,687,884 | B2 | 6/2020 | Wiener et al. |
| 10,729,502 | B1 | 8/2020 | Wolf et al. |
| 10,743,872 | B2 | 8/2020 | Leimbach et al. |
| 10,758,309 | B1 | 9/2020 | Chow et al. |
| 10,758,310 | B2 | 9/2020 | Shelton, IV et al. |
| 10,772,673 | B2 | 9/2020 | Allen, IV et al. |
| 10,878,966 | B2 | 12/2020 | Wolf et al. |
| 10,881,399 | B2 | 1/2021 | Shelton, IV et al. |
| 10,898,256 | B2 | 1/2021 | Yates et al. |
| 10,925,598 | B2 | 2/2021 | Scheib et al. |
| 10,932,705 | B2 | 3/2021 | Muhsin et al. |
| 10,932,772 | B2 | 3/2021 | Shelton, IV et al. |
| 10,950,982 | B2 | 3/2021 | Regnier et al. |
| 10,987,176 | B2 | 4/2021 | Poltaretskyi et al. |
| 10,989,724 | B1 | 4/2021 | Holmes et al. |
| 11,000,270 | B2 | 5/2021 | Scheib et al. |
| 11,006,100 | B1 | 5/2021 | Douglas |
| D924,139 | S | 7/2021 | Jayme |
| 11,056,244 | B2 | 7/2021 | Shelton, IV et al. |
| 11,058,497 | B2 | 7/2021 | Altmann et al. |
| 11,065,079 | B2 | 7/2021 | Wolf et al. |
| 11,071,595 | B2 | 7/2021 | Johnson et al. |
| D928,725 | S | 8/2021 | Oberkircher et al. |
| D928,726 | S | 8/2021 | Asher et al. |
| 11,083,489 | B2 | 8/2021 | Fujii et al. |
| 11,114,199 | B2 | 9/2021 | Moctezuma De La Barrera |
| 11,116,587 | B2 | 9/2021 | Wolf et al. |
| D939,545 | S | 12/2021 | Oberkircher et al. |
| 11,218,822 | B2 | 1/2022 | Morgan et al. |
| 11,259,793 | B2 | 3/2022 | Scheib et al. |
| 11,259,875 | B2 | 3/2022 | Boutin et al. |
| 11,272,839 | B2 | 3/2022 | Al-Ali et al. |
| 11,284,963 | B2 | 3/2022 | Shelton, IV et al. |
| 11,296,540 | B2 | 4/2022 | Kirleis et al. |
| 11,298,128 | B2 | 4/2022 | Messerly et al. |
| 11,304,763 | B2 | 4/2022 | Shelton, IV et al. |
| 11,314,846 | B1 | 4/2022 | Colin et al. |
| 11,341,726 | B2 | 5/2022 | Tsuda et al. |
| 11,350,978 | B2 | 6/2022 | Henderson et al. |
| 11,369,366 | B2 | 6/2022 | Scheib et al. |
| 11,382,699 | B2 | 7/2022 | Wassall et al. |
| 11,382,700 | B2 | 7/2022 | Calloway et al. |
| 11,419,604 | B2 | 8/2022 | Scheib et al. |
| 11,424,027 | B2 | 8/2022 | Shelton, IV |
| 11,432,877 | B2 | 9/2022 | Nash et al. |
| 11,464,581 | B2 | 10/2022 | Calloway |
| 11,471,206 | B2 | 10/2022 | Henderson et al. |
| 11,478,820 | B2 | 10/2022 | Bales, Jr. et al. |
| 11,504,192 | B2 | 11/2022 | Shelton, IV et al. |
| 11,510,720 | B2 | 11/2022 | Morgan et al. |
| 11,510,750 | B2 | 11/2022 | Dulin et al. |
| 11,823,374 | B2 | 11/2023 | Schneider et al. |
| 11,836,863 | B2 | 12/2023 | Flexman et al. |
| 12,349,861 | B2 | 7/2025 | Charles et al. |
| 2001/0029315 | A1 | 10/2001 | Sakurai et al. |
| 2003/0078631 | A1 | 4/2003 | Nelson et al. |
| 2003/0199794 | A1 | 10/2003 | Sakurai et al. |
| 2003/0199864 | A1 | 10/2003 | Eick |
| 2004/0030328 | A1 | 2/2004 | Eggers et al. |
| 2004/0059323 | A1 | 3/2004 | Sturm et al. |
| 2004/0111045 | A1 | 6/2004 | Sullivan et al. |
| 2004/0164983 | A1 | 8/2004 | Khozai |
| 2005/0010209 | A1 | 1/2005 | Lee et al. |
| 2005/0013459 | A1 | 1/2005 | Maekawa |
| 2005/0113823 | A1 | 5/2005 | Reschke et al. |
| 2005/0165390 | A1 | 7/2005 | Mauti et al. |
| 2005/0229110 | A1 | 10/2005 | Gegner et al. |
| 2005/0251233 | A1 | 11/2005 | Kanzius |
| 2006/0082542 | A1 | 4/2006 | Morita et al. |
| 2006/0085049 | A1 | 4/2006 | Cory et al. |
| 2006/0136622 | A1 | 6/2006 | Rouvelin et al. |
| 2006/0149418 | A1 | 7/2006 | Anvari |
| 2006/0256516 | A1 | 11/2006 | Cho |
| 2007/0076363 | A1 | 4/2007 | Liang et al. |
| 2007/0211930 | A1 | 9/2007 | Dolwick et al. |
| 2007/0282321 | A1 | 12/2007 | Shah et al. |
| 2008/0072896 | A1 | 3/2008 | Setzer et al. |
| 2008/0129465 | A1 | 6/2008 | Rao |
| 2008/0249377 | A1 | 10/2008 | Molducci et al. |

(56) References Cited

U.S. PATENT DOCUMENTS

2008/0316304 A1 12/2008 Claus et al.
2009/0036884 A1 2/2009 Gregg et al.
2009/0131929 A1 5/2009 Shimizu
2009/0192524 A1 7/2009 Itkowitz et al.
2009/0216091 A1 8/2009 Arndt
2009/0234352 A1 9/2009 Behnke et al.
2010/0036405 A1 2/2010 Giordano et al.
2010/0042010 A1 2/2010 Dekker et al.
2010/0053213 A1 3/2010 Ishida et al.
2010/0069939 A1 3/2010 Konishi
2010/0076453 A1 3/2010 Morris et al.
2010/0092006 A1 4/2010 Rosen
2010/0120266 A1 5/2010 Rimborg
2010/0198200 A1 8/2010 Horvath
2010/0312239 A1 12/2010 Sclig
2011/0105895 A1 5/2011 Kornblau et al.
2011/0118748 A1 5/2011 Itkowitz
2011/0125149 A1 5/2011 El-Galley et al.
2011/0130689 A1 6/2011 Cohen et al.
2011/0190588 A1 8/2011 Mckay
2011/0245630 A1 10/2011 St. Pierre et al.
2011/0273465 A1 11/2011 Konishi et al.
2011/0298814 A1 12/2011 Mathew et al.
2011/0306840 A1 12/2011 Allen et al.
2012/0029304 A1 2/2012 Medina et al.
2012/0082036 A1 4/2012 Abedi et al.
2012/0116380 A1 5/2012 Madan et al.
2012/0132661 A1 5/2012 Gu et al.
2013/0031201 A1 1/2013 Kagan et al.
2013/0038707 A1 2/2013 Cunningham et al.
2013/0176220 A1 7/2013 Merschon et al.
2013/0197357 A1 8/2013 Green et al.
2013/0197503 A1 8/2013 Orszulak
2013/0267975 A1 10/2013 Timm et al.
2013/0268283 A1 10/2013 Vann et al.
2013/0303851 A1 11/2013 Griffith et al.
2013/0321159 A1 12/2013 Schofield et al.
2014/0009894 A1 1/2014 Yu
2014/0052150 A1 2/2014 Taylor et al.
2014/0058714 A1 2/2014 Boyer
2014/0087573 A1 3/2014 Kroeckel
2014/0155721 A1 6/2014 Hauck et al.
2014/0179997 A1 6/2014 Von Grunberg et al.
2014/0194683 A1 7/2014 Nakaguchi
2014/0221740 A1 8/2014 Kawula et al.
2014/0226572 A1 8/2014 Thota et al.
2014/0262598 A1 9/2014 Miki et al.
2014/0263552 A1 9/2014 Hall et al.
2014/0343358 A1 11/2014 Hameed et al.
2015/0019259 A1* 1/2015 Qureshi ................. G16H 40/20
705/3
2015/0057575 A1 2/2015 Tsusaka et al.
2015/0070388 A1 3/2015 Sheaffer et al.
2015/0190189 A1 7/2015 Yates et al.
2015/0265369 A1 9/2015 Garbey et al.
2015/0272575 A1 10/2015 Leimbach et al.
2015/0289929 A1 10/2015 Toth et al.
2016/0045247 A1 2/2016 Heim et al.
2016/0058286 A1 3/2016 Joshua et al.
2016/0066184 A1 3/2016 Bhargav-Spantzel et al.
2016/0074096 A1 3/2016 Lieu
2016/0120591 A1 5/2016 Smith et al.
2016/0174897 A1 6/2016 Sherman
2016/0225192 A1 8/2016 Jones et al.
2016/0287312 A1 10/2016 Tegg et al.
2016/0287337 A1 10/2016 Aram et al.
2017/0000553 A1 1/2017 Wiener et al.
2017/0090507 A1 3/2017 Wiener et al.
2017/0189096 A1 7/2017 Danziger et al.
2017/0202595 A1 7/2017 Shelton, IV
2017/0209225 A1 7/2017 Wu
2017/0251305 A1 8/2017 Fathollahi
2017/0252091 A1 9/2017 Honda
2017/0258526 A1 9/2017 Lang
2017/0296036 A1 10/2017 Newman
2017/0296213 A1 10/2017 Swensgard et al.
2017/0319259 A1 11/2017 Dunning
2017/0333275 A1 11/2017 Itkowitz et al.
2017/0360466 A1 12/2017 Brown et al.
2017/0367766 A1 12/2017 Mahfouz
2018/0014872 A1 1/2018 Dickerson
2018/0032130 A1 2/2018 Meglan
2018/0042659 A1 2/2018 Rupp et al.
2018/0043037 A1 2/2018 Dalma-Weiszhausz et al.
2018/0049795 A1 2/2018 Swayze et al.
2018/0065248 A1 3/2018 Barral et al.
2018/0078216 A1 3/2018 Baker et al.
2018/0082480 A1 3/2018 White et al.
2018/0092699 A1 4/2018 Finley
2018/0099161 A1 4/2018 Honda
2018/0168741 A1 6/2018 Swayze et al.
2018/0173323 A1 6/2018 Harvey et al.
2018/0221005 A1 8/2018 Hamel et al.
2018/0228528 A1 8/2018 Fraasch et al.
2018/0228555 A1 8/2018 Charron et al.
2018/0235441 A1 8/2018 Huang et al.
2018/0243573 A1 8/2018 Yoder et al.
2018/0262916 A1 9/2018 Polley et al.
2018/0263557 A1 9/2018 Kahlman
2018/0289338 A1 10/2018 Meador et al.
2018/0317826 A1 11/2018 Muhsin et al.
2018/0333207 A1 11/2018 Moctezuma De La Barrera
2018/0368930 A1 12/2018 Esterberg et al.
2019/0006047 A1 1/2019 Gorek et al.
2019/0035153 A1 1/2019 Dange
2019/0038362 A1 2/2019 Nash et al.
2019/0069957 A1 3/2019 Barral et al.
2019/0104919 A1 4/2019 Shelton, IV et al.
2019/0117326 A1 4/2019 Wada
2019/0125361 A1 5/2019 Shelton, IV et al.
2019/0125451 A1 5/2019 Srimohanarajah et al.
2019/0125454 A1 5/2019 Stokes et al.
2019/0125455 A1 5/2019 Shelton, IV et al.
2019/0125459 A1 5/2019 Shelton et al.
2019/0183576 A1 6/2019 Fahim et al.
2019/0183591 A1 6/2019 Johnson et al.
2019/0200844 A1 7/2019 Shelton, IV et al.
2019/0200906 A1 7/2019 Shelton, IV et al.
2019/0200981 A1 7/2019 Harris et al.
2019/0200987 A1 7/2019 Shelton, IV et al.
2019/0201046 A1 7/2019 Shelton, IV et al.
2019/0201102 A1 7/2019 Shelton, IV et al.
2019/0201114 A1 7/2019 Shelton, IV et al.
2019/0201116 A1 7/2019 Shelton, IV et al.
2019/0201117 A1 7/2019 Yates et al.
2019/0201127 A1 7/2019 Shelton, IV et al.
2019/0201136 A1 7/2019 Shelton, IV et al.
2019/0201137 A1 7/2019 Shelton, IV et al.
2019/0201140 A1 7/2019 Yates et al.
2019/0201158 A1 7/2019 Shelton, IV et al.
2019/0205001 A1 7/2019 Messerly et al.
2019/0206004 A1 7/2019 Shelton, IV et al.
2019/0206562 A1 7/2019 Shelton, IV et al.
2019/0206563 A1 7/2019 Shelton, IV et al.
2019/0206565 A1 7/2019 Shelton, IV
2019/0206569 A1 7/2019 Shelton et al.
2019/0224434 A1 7/2019 Silver et al.
2019/0236840 A1 8/2019 Zuckerman et al.
2019/0247141 A1 8/2019 Batchelor et al.
2019/0278262 A1 9/2019 Taylor et al.
2019/0279524 A1 9/2019 Stoyanov et al.
2019/0282307 A1 9/2019 Azizian et al.
2019/0290297 A1 9/2019 Haider et al.
2019/0348169 A1 11/2019 Gibby et al.
2019/0371012 A1 12/2019 Flexman et al.
2020/0004487 A1 1/2020 Hanajima et al.
2020/0015895 A1 1/2020 Frielinghaus et al.
2020/0015898 A1 1/2020 Scheib et al.
2020/0015899 A1 1/2020 Scheib et al.
2020/0015900 A1 1/2020 Scheib et al.
2020/0015902 A1 1/2020 Scheib et al.
2020/0015906 A1 1/2020 Scheib et al.
2020/0015907 A1 1/2020 Scheib
2020/0015914 A1 1/2020 Scheib et al.

(56) References Cited

U.S. PATENT DOCUMENTS

| | | | |
|---|---|---|---|
| 2020/0015924 | A1 | 1/2020 | Scheib et al. |
| 2020/0038120 | A1 | 2/2020 | Ziraknejad et al. |
| 2020/0078070 | A1 | 3/2020 | Henderson et al. |
| 2020/0078071 | A1 | 3/2020 | Asher |
| 2020/0078076 | A1 | 3/2020 | Henderson et al. |
| 2020/0078078 | A1 | 3/2020 | Henderson et al. |
| 2020/0078080 | A1 | 3/2020 | Henderson et al. |
| 2020/0078081 | A1 | 3/2020 | Jayme et al. |
| 2020/0078082 | A1 | 3/2020 | Henderson et al. |
| 2020/0078083 | A1 | 3/2020 | Sprinkle et al. |
| 2020/0078089 | A1 | 3/2020 | Henderson et al. |
| 2020/0078110 | A1 | 3/2020 | Henderson et al. |
| 2020/0078111 | A1 | 3/2020 | Oberkircher et al. |
| 2020/0078112 | A1 | 3/2020 | Henderson et al. |
| 2020/0078113 | A1 | 3/2020 | Sawhney et al. |
| 2020/0078114 | A1 | 3/2020 | Asher et al. |
| 2020/0078115 | A1 | 3/2020 | Asher et al. |
| 2020/0078116 | A1 | 3/2020 | Oberkircher et al. |
| 2020/0078117 | A1 | 3/2020 | Henderson et al. |
| 2020/0078118 | A1 | 3/2020 | Henderson et al. |
| 2020/0078119 | A1 | 3/2020 | Henderson et al. |
| 2020/0078120 | A1 | 3/2020 | Aldridge et al. |
| 2020/0081585 | A1 | 3/2020 | Petre et al. |
| 2020/0090808 | A1 | 3/2020 | Carroll et al. |
| 2020/0093357 | A1 | 3/2020 | Scott et al. |
| 2020/0100825 | A1 | 4/2020 | Henderson et al. |
| 2020/0100830 | A1 | 4/2020 | Henderson et al. |
| 2020/0106220 | A1 | 4/2020 | Henderson et al. |
| 2020/0159313 | A1 | 5/2020 | Gibby et al. |
| 2020/0237031 | A1 | 7/2020 | Daniels et al. |
| 2020/0237452 | A1 | 7/2020 | Wolf et al. |
| 2020/0246084 | A1 | 8/2020 | Azizian |
| 2020/0268469 | A1 | 8/2020 | Wolf et al. |
| 2020/0268472 | A1 | 8/2020 | Wolf et al. |
| 2020/0305924 | A1 | 10/2020 | Carroll |
| 2020/0305945 | A1 | 10/2020 | Morgan et al. |
| 2020/0315707 | A1 | 10/2020 | Venkataraman |
| 2020/0315734 | A1 | 10/2020 | El Amm |
| 2020/0322516 | A1 | 10/2020 | Doser et al. |
| 2020/0342228 | A1 | 10/2020 | Prevrhal et al. |
| 2020/0359892 | A1 | 11/2020 | Rollins et al. |
| 2020/0384287 | A1 | 12/2020 | Hetz |
| 2020/0405529 | A1 | 12/2020 | Taylor et al. |
| 2021/0000564 | A1 | 1/2021 | Amanatullah et al. |
| 2021/0015343 | A1 | 1/2021 | Uyama et al. |
| 2021/0093390 | A1 | 4/2021 | Poltaretskyi et al. |
| 2021/0121246 | A1 | 4/2021 | Gudalo |
| 2021/0128254 | A1 | 5/2021 | Geric et al. |
| 2021/0158779 | A1 | 5/2021 | Singh |
| 2021/0169578 | A1 | 6/2021 | Calloway et al. |
| 2021/0169581 | A1 | 6/2021 | Calloway et al. |
| 2021/0174956 | A1 | 6/2021 | Mcginley et al. |
| 2021/0192759 | A1 | 6/2021 | Lang |
| 2021/0193681 | A1 | 6/2021 | Baek |
| 2021/0196381 | A1 | 7/2021 | Eckert et al. |
| 2021/0196383 | A1 | 7/2021 | Shelton, IV et al. |
| 2021/0196425 | A1 | 7/2021 | Shelton et al. |
| 2021/0203889 | A1 | 7/2021 | Fung et al. |
| 2021/0205020 | A1 | 7/2021 | Shelton, IV et al. |
| 2021/0212717 | A1 | 7/2021 | Yates et al. |
| 2021/0236755 | A1 | 8/2021 | King et al. |
| 2021/0259789 | A1 | 8/2021 | Wright et al. |
| 2021/0264680 | A1 | 8/2021 | Cvetko et al. |
| 2021/0267664 | A1 | 9/2021 | Lennartz et al. |
| 2021/0306691 | A1 | 9/2021 | Thomas et al. |
| 2021/0307861 | A1 | 10/2021 | Hufford et al. |
| 2021/0313052 | A1 | 10/2021 | Makrinich et al. |
| 2021/0333864 | A1 | 10/2021 | Harvey et al. |
| 2021/0346092 | A1 | 11/2021 | Redmond et al. |
| 2021/0369394 | A1 | 12/2021 | Braido et al. |
| 2021/0385889 | A1 | 12/2021 | Patel |
| 2022/0032442 | A1 | 2/2022 | Sheffield et al. |
| 2022/0104896 | A1 | 4/2022 | Shelton, IV et al. |
| 2022/0104897 | A1 | 4/2022 | Shelton, IV et al. |
| 2022/0104911 | A1 | 4/2022 | Shelton, IV et al. |
| 2022/0104912 | A1 | 4/2022 | Shelton, IV et al. |
| 2022/0142573 | A1 | 5/2022 | Li et al. |
| 2022/0151704 | A1 | 5/2022 | Nikou |
| 2022/0155910 | A1 | 5/2022 | Jeong |
| 2022/0160428 | A1 | 5/2022 | Murray et al. |
| 2022/0188545 | A1 | 6/2022 | Nagar et al. |
| 2022/0237878 | A1 | 7/2022 | Tartz et al. |
| 2022/0257333 | A1 | 8/2022 | Haider |
| 2022/0261056 | A1 | 8/2022 | Motoi et al. |
| 2022/0283631 | A1 | 9/2022 | Peng |
| 2022/0287676 | A1 | 9/2022 | Steines et al. |
| 2022/0313338 | A1 | 10/2022 | Carroll et al. |
| 2022/0313341 | A1 | 10/2022 | Wiener et al. |
| 2022/0313342 | A1 | 10/2022 | Leuck et al. |
| 2022/0313357 | A1 | 10/2022 | Geresy et al. |
| 2022/0313369 | A1 | 10/2022 | Oberkircher et al. |
| 2022/0313370 | A1 | 10/2022 | Morgan et al. |
| 2022/0313371 | A1 | 10/2022 | Morgan et al. |
| 2022/0313372 | A1 | 10/2022 | Herman et al. |
| 2022/0313373 | A1 | 10/2022 | Morgan et al. |
| 2022/0317750 | A1 | 10/2022 | Jayme et al. |
| 2022/0317751 | A1 | 10/2022 | Samuel et al. |
| 2022/0318179 | A1 | 10/2022 | Morgan et al. |
| 2022/0319685 | A1 | 10/2022 | Vachon et al. |
| 2022/0319693 | A1 | 10/2022 | Oberkircher et al. |
| 2022/0321059 | A1 | 10/2022 | Samuel et al. |
| 2022/0322523 | A1 | 10/2022 | Jayme et al. |
| 2022/0331013 | A1 | 10/2022 | Shelton, IV et al. |
| 2022/0331047 | A1 | 10/2022 | Shelton, IV et al. |
| 2022/0331048 | A1 | 10/2022 | Shelton, IV et al. |
| 2022/0331049 | A1 | 10/2022 | Shelton, IV et al. |
| 2022/0331050 | A1 | 10/2022 | Shelton, IV et al. |
| 2022/0331051 | A1 | 10/2022 | Shelton, IV et al. |
| 2022/0331052 | A1 | 10/2022 | Shelton, IV et al. |
| 2022/0331053 | A1 | 10/2022 | Kimball et al. |
| 2022/0331054 | A1 | 10/2022 | Kimball et al. |
| 2022/0331056 | A1 | 10/2022 | Shelton, IV et al. |
| 2022/0334787 | A1 | 10/2022 | Jogan et al. |
| 2022/0335604 | A1 | 10/2022 | Vanosdoll et al. |
| 2022/0335660 | A1 | 10/2022 | Shelton, IV et al. |
| 2022/0335696 | A1 | 10/2022 | Shelton, IV et al. |
| 2022/0336078 | A1 | 10/2022 | Wise et al. |
| 2022/0336097 | A1 | 10/2022 | Shelton, IV et al. |
| 2022/0337891 | A1 | 10/2022 | Burnley et al. |
| 2022/0338049 | A1 | 10/2022 | Ross et al. |
| 2022/0387128 | A1 | 12/2022 | Bail et al. |
| 2023/0038130 | A1 | 2/2023 | Cvetko et al. |
| 2023/0061534 | A1 | 3/2023 | Stopek |
| 2023/0071306 | A1 | 3/2023 | Miller et al. |
| 2023/0072423 | A1 | 3/2023 | Osborn et al. |
| 2023/0121709 | A1 | 4/2023 | Xu et al. |
| 2023/0157757 | A1 | 5/2023 | Braido et al. |
| 2023/0157762 | A1 | 5/2023 | Braido et al. |
| 2024/0130795 | A1 | 4/2024 | Clayton et al. |
| 2024/0138931 | A1 | 5/2024 | Lefauconnier |
| 2024/0176441 | A1 | 5/2024 | Yang et al. |
| 2024/0325085 | A1 | 10/2024 | Ryan et al. |

FOREIGN PATENT DOCUMENTS

| | | | |
|---|---|---|---|
| EP | 0408160 | A1 | 1/1991 |
| EP | 0473987 | A1 | 3/1992 |
| EP | 0929263 | B1 | 7/1999 |
| EP | 1006892 | B1 | 6/2009 |
| EP | 2942023 | A2 | 11/2015 |
| EP | 3053279 | A1 | 8/2016 |
| EP | 3387982 | A1 | 10/2018 |
| JP | 2000-271145 | A | 10/2000 |
| JP | 2001029353 | A | 2/2001 |
| JP | 2006-149560 | A | 6/2006 |
| JP | 2007-007041 | A | 1/2007 |
| JP | 2007-029232 | A | 2/2007 |
| JP | 2021-045341 | A | 3/2021 |
| WO | WO-0112089 | A1 | 2/2001 |
| WO | WO-2008053485 | A1 | 5/2008 |
| WO | 2014/010177 | A1 | 1/2014 |
| WO | WO-2014031800 | A1 | 2/2014 |
| WO | WO-2014071184 | A1 | 5/2014 |
| WO | WO-2015047693 | A1 | 4/2015 |

(56) References Cited

FOREIGN PATENT DOCUMENTS

| | | | |
|---|---|---|---|
| WO | 2016/013636 | A1 | 1/2016 |
| WO | 2016154557 | A1 | 9/2016 |
| WO | WO-2017058617 | A2 | 4/2017 |
| WO | 2017/099153 | A1 | 6/2017 |
| WO | 2017/221367 | A1 | 12/2017 |
| WO | WO-2018116247 | A1 | 6/2018 |
| WO | WO-2019215354 | A1 | 11/2019 |
| WO | 2020112217 | A1 | 6/2020 |
| WO | 2020180917 | A1 | 9/2020 |
| WO | WO-2021044136 | A1 | 3/2021 |
| WO | 2021/146313 | A1 | 7/2021 |

OTHER PUBLICATIONS

IEEE Std 802.3-2012 (Revision of IEEE Std 802.3-2008, published Dec. 28, 2012.

Li et al., "Wearable Energy Harvesters Generating Electricity From Low-Frequency Human Limb Movement," Microsystems & Nanoengineering (2018), vol. 4(24), 13 pages.

Qian, et al., "A Review of Augmented Reality in Robotic-Assisted Surgery", IEEE Transactions on Medical Robotics and Bionics, IEEE, vol. 2, No. 1, pp. 1-16, Feb. 2020.

Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

Yu et al., "Skin-Integrated Wireless Haptic Interfaces for Virtual and Augmented Reality," Nature, vol. 575, pp. 473-479, Nov. 21, 2019.

Zhu et al. "Haptic-feedback smart glove as a creative human-machine interface (HMI) for virtual/augmented reality applications," Sci. Adv, vol. 6, No. 19, May 8, 2020.

Vávra et al., "Recent Development of Augmented Reality in Surgery: A Review", Journal of Healthcare Engineering, vol. 2017, Article ID 4574172, Aug. 21, 2017, pp. 1-9.

International Search Report and Written Opinion received for PCT Application No. PCT/IB2022/053360, Mailed on Jul. 4, 2022, 12 pages.

International Search Report and Written Opinion received for PCT Application No. PCT/IB2022/053362, Mailed on Jul. 1, 2022, 13 pages.

International Search Report and Written Opinion received for PCT Application No. PCT/IB2022/053363, Mailed on Jun. 30, 2022, 14 pages.

International Search Report and Written Opinion received for PCT Application No. PCT/IB2022/053364, Mailed on Jul. 8, 2022, 11 pages.

International Search Report and Written Opinion received for PCT Application No. PCT/IB2022/053365, Mailed on Jul. 4, 2022, 16 pages.

International Search Report and Written Opinion received for PCT Application No. PCT/IB2022/053369, Mailed on Jul. 13, 2022, 12 pages.

International Search Report and Written Opinion received for PCT Application No. PCT/IB2022/053370, Mailed on Jul. 15, 2022, 14 pages.

International Search Report and Written Opinion received for PCT Application No. PCT/IB2022/053371, Mailed on Jul. 5, 2022, 12 pages.

International Search Report and Written Opinion received for PCT Application No. PCT/IB2022/053375, Mailed on Oct. 4, 2022, 22 pages.

International Search Report and Written Opinion received for PCT Application No. PCT/IB2022/053377, Mailed on Jun. 22, 2022, 12 pages.

International Search Report and Written Opinion received for PCT Application No. PCT/IB2022/053378, Mailed on Jul. 7, 2022, 13 pages.

Invitation to Pay Additional Fees received for PCT Application No. PCT/IB2022/053375, Mailed on Jul. 15, 2022, 11 pages.

Kaushik et al., "Emerging Thermal Technology Enabled Augmented Reality", Advanced Functional Materials, vol. 31, No. 39, Feb. 17, 2021., pp. 1-27.

Zherdeva et al., "Virtual Scalpel Simulation In the VR and AR Environments", Proceedings Of SPIE, vol. 11310, Feb. 19, 2020, 7 pages.

* cited by examiner 11200b
11202b
11204b
11206b
11208b
11210b
SUPPORT ZONE 1
SUPPORT ZONE 2
SUPPORT ZONE 3
SUPPORT ZONE 4
SUPPLY ZONE 1
SURGICAL TABLE ZONE 1
SURGICAL TABLE ZONE 2

12100

Visual Indicators

| Status | LED |
|---|---|
| Pairing Mode | Red and Blue flashing alternately |
| Rx Mode Connecting | Blue LED flashing |
| Rx Mode Connected | Blue LED is solid |
| Tx Mode Connecting | Red LED flashing |
| Tx ModeConnected | Red LED is solid |
| Not Connected | Red or Blue flash every 0.5 seconds |
| Searching | 0.5 seconds |

| | | | | | | |
|---|---|---|---|---|---|---|
| 0 | 0 | 0 | 0 | 0 | C | ENDa 45 |
| 0 | 0 | 0 | 0 | 1 | S | ENDb 45 |
| 0 | 0 | 0 | 1 | 0 | L | ENDb 45 |
| 0 | 0 | 0 | 1 | 1 | C | ENDb 60 |
| 0 | 0 | 1 | 0 | 0 | S | ENDb 60 |
| 0 | 0 | 1 | 0 | 1 | L | ENDb 60 |
| 0 | 0 | 1 | 1 | 0 | C | ENDc 45 |
| 0 | 0 | 1 | 1 | 1 | S | ENDc 45 |
| 0 | 1 | 0 | 0 | 0 | L | ENDc 45 |
| 0 | 1 | 0 | 0 | 1 | C | ENDc 60 |
| 0 | 1 | 0 | 1 | 0 | S | ENDc 60 |
| 0 | 1 | 0 | 1 | 1 | L | ENDc 60 |
| 0 | 1 | 1 | 0 | 0 | C | ENDd 45 |
| 0 | 1 | 1 | 0 | 1 | S | ENDd 45 |
| 0 | 1 | 1 | 1 | 0 | L | ENDd 45 |
| 0 | 1 | 1 | 1 | 1 | C | ENDd 60 |
| 1 | 0 | 0 | 0 | 0 | S | ENDd 60 |
| 1 | 0 | 0 | 0 | 1 | L | ENDd 60 |
| 1 | 0 | 0 | 1 | 0 | | ENDe 35 |
| 1 | 0 | 0 | 1 | 1 | | ENDe XX |
| 1 | 0 | 1 | 0 | 0 | | ENDe XX |
| 1 | 0 | 1 | 0 | 1 | C | ENDf 45 |
| 1 | 0 | 1 | 1 | 0 | S | ENDf 45 |
| 1 | 0 | 1 | 1 | 1 | L | ENDf 45 |
| 1 | 1 | 0 | 0 | 0 | C | ENDf 60 |
| 1 | 1 | 0 | 0 | 1 | S | ENDf 60 |
| 1 | 1 | 0 | 1 | 0 | L | ENDf 60 |
| 1 | 1 | 0 | 1 | 1 | | extra |
| 1 | 1 | 1 | 0 | 0 | | extra |
| 1 | 1 | 1 | 0 | 1 | | extra |
| 1 | 1 | 1 | 1 | 0 | | extra |
| 1 | 1 | 1 | 1 | 1 | | extra |

15010 Imaging Device(s)

15012 Structured Light Sensor(s)

15014 LIDAR Sensors(s)

15016 Floor Sensor(s)

15018 Acoustic Sensor(s)

15020 Fiducial Marker(s)

15022 User/Device Sensor(s)

15024 GPS Sensor(s)

Tracking System 15006

Visualization System 15008

Hub 15002

Operating Room Mapping Module 15004

AR Device 66

15100

15102 15104 15106 15108 15110 15112 15114 15116

| Object Interaction | Time Stamp | Position (X,Y,Z) | Glove ID | Device ID | Device Portion | Action | Tracking Source |
|---|---|---|---|---|---|---|---|
| Glove to Glove connection (two surgeons) | 1621964600 | (0,0,0) (0,0,0) | 123 | 124 | N/A | Initiation | Wearable |
| | 1621964605 | (0,0,0) (0,0,0) | 125 | 126 | N/A | Initiation | Wearable |
| No surgeon is touching the trocar | 1621964666 | (10.1,200.3,50.9) (12.2, 89.1,70.4) | 0 | Trocar 1 | N/A | Standby | Camera |
| Single surgeon One surgeon | 1621965000 | (12.1,201.4,40.1) (10.2, 69.1,60.4) | 123 | Trocar 1 | N/A | In-use | Camera |
| | 1621965000 | (12.1,201.4,40.1) (10.2, 69.1,60.4) | 123 | Endocutter 1 | Handle | Clamping (12lbf) | Wearable |
| Multiple surgeon with single surgeon holding device | 1621965000 | (12.1,201.4,40.1) (10.2, 69.1,60.4) | 123 | Trocar 1 | N/A | In-use | Camera |
| | 1621965000 | (12.1,201.4,40.1) (10.2, 69.1,60.4) | 123 | Endocutter 1 | Handle | Device Unclamped | Wearable |
| Multiple surgeon Line 1 with | 1621965014 | (12.0,205.4,39.1) (11.2, 59.1,59.4) | 123,125 | Trocar 1 | N/A | In-use | Camera |
| | 1621965014 | (12.0,205.4,39.1) (11.2, 59.1,59.4) | 123,125 | Endocutter 1 | Handle,Handle | Hand-off Initiated | Camera |
| Multiple surgeon Line 2 middle of switch | 1621965016 | (12.0,205.4,39.1) (11.2, 59.1,59.4) | 125,123 | Trocar 1 | N/A | In-use | Camera |
| | 1621965016 | (12.0,205.4,39.1) (11.2, 59.1,59.4) | 125,123 | Endocutter 1 | Handle,Handle | Hand-off | Camera |
| Multiple surgeon Line 2 after of switch | 1621965017 | (11.0,204.4,38.1) (10.2, 57.1,58.4) | 125 | Trocar 1 | N/A | In-use | Camera |
| | 1621965017 | (11.0,204.4,38.1) (10.2, 57.1,58.4) | 125 | Endocutter 1 | Handle | Hand-off Complete | Combination |
| Example of multi part device | 1621965030 | (9.0,210.4,35.1) (16.2, 62.1,70.4) | 125,123 | Circular 1 | Handle,Shaft | Rotating Knob, AttachingAnvil | Wearable, Device (anvil detection sensor) |
| Example of unknown user | 1621965035 | (4.0,150.0,32.0) (18.1,180.0,40.0) | 0 | Endocutter 1 | Device | Blue Reload inserted | Camera |

Classified motion

M10 M9 M8 M7 M6 M5 M4 M3 M2 M1 NoM

Classified

Misclassified

Normalized EMG signals

Ch. 1 Ch. 2 Ch. 3 Ch. 4 Ch. 5

1.0 0.5 0

Time [s]

16640

16660

4060

| Category | Concept | Description |
|---|---|---|
| Pairing | ☆ User Selectable Pairing | The user would start a pairing mode on the capital equipment via a touchscreen. The capital equipment would then attempt to identify all valid devices of that type within a region, and the user would simply select the devices that they would like to connect to.<br>Would like to continue broadcasting even after time has elapsed |
| | | |
| Pairing | ☆ Connect on Powerup | Could enable bluetooth radio on powerup for the surgical device, if not connected to client within time, turn it off. The capital equipment is constantly scanning for new devices and connects to it. |
| Pairing | Connect on Powerup with Button Press | Could enable bluetooth radio on powerup for the surgical device, if not connected to client within time, turn it off. The capital equipment has a pairing button pressed, and once pressed scans / connects to the Surgical device. |
| Pairing | ☆ RFID Token | The user utilizes an RFID card, packaged with each device, as a method for scanning in the new device and pairing with the capital equipment. |

FIG. 185

METHOD FOR INTRAOPERATIVE DISPLAY FOR SURGICAL SYSTEMS

CROSS-REFERENCE TO RELATED APPLICATIONS

This application claims the benefit under 35 U.S.C. § 119(e) to U.S. Provisional Patent Application No. 63/174,674, titled HEADS UP DISPLAY, filed Apr. 14, 2021 and to U.S. Provisional Patent Application No. 63/284,326, titled INTRAOPERATIVE DISPLAY FOR SURGICAL SYSTEMS, filed Nov. 30, 2021, the disclosure of each of which is herein incorporated by reference in its entirety.

BACKGROUND

This disclosure relates to apparatuses, systems, and methods for providing an augmented reality interactive experience during a surgical procedure. During a surgical procedure it would be desirable to provide an augmented reality interactive experience of a real-world environment where objects that reside in the real world are enhanced by overlaying computer-generated perceptual information, sometimes across multiple sensory modalities, including visual, auditory, haptic, somatosensory, and olfactory. In the context of this disclosure, images of a surgical field and surgical instruments and other objects appearing in the surgical field are enhanced by overlaying computer-generated visual, auditory, haptic, somatosensory, olfactory, or other sensory information onto the real world images of the surgical field and instruments or other objects appearing in the surgical field. The images may be streamed in real time or may be still images.

Real world surgical instruments include a variety of surgical devices. Energy based surgical devices include, without limitation, radio-frequency (RF) based monopolar and bipolar electrosurgical instruments, ultrasonic surgical instruments, combination RF electrosurgical and ultrasonic instruments, combination RF electrosurgical and mechanical staplers, among others. Surgical stapler devices are surgical instruments used to cut and staple tissue in a variety of surgical procedures, including bariatric, thoracic, colorectal, gynecologic, urologic and general surgery.

SUMMARY

In various instances, this disclosure provides a method for presenting surgical data onto a livestream of a surgical field on a display during a surgical procedure is disclosed. The method includes detecting, by a control module, surgical data, assigning, by the control module, display priority values to the surgical data, determining, by the control module, a display arrangement of the surgical data on the display based on the display priority values, and presenting onto the livestream visual representations of the surgical data in accordance with the display arrangement.

In various instances, this disclosure provides a method for presenting surgical data onto a livestream of a surgical field on a display during a surgical procedure. The method includes detecting, by a control module, first surgical data, generating, by a control module, a first visual representation of the first surgical data for presenting the first surgical data on the display, detecting, by a control module, second surgical data, generating, by a control module, a second visual representation of the second surgical data for presenting the second surgical data on the display, detecting, by a control module, a display conflict between the first surgical data and the second surgical data, determining, by a control module, a resolution of the display conflict in favor of one of one of the first visual representation and the second visual representation based on at least one of the first surgical data and the second surgical data, and determining, by a control module, a display arrangement of the first visual representation and the second visual representation in accordance with the resolution.

a method for presenting surgical data onto a livestream of a surgical field on a display during a surgical procedure. The method includes detecting a failure of a system resource to meet competing needs of different components of a computer-implemented interactive surgical system, in response to detecting the failure, displaying resource-allocation controls of the system resource on the livestream, displaying recommended adjustments to the resource-allocation controls, and adjusting power consumption of one or more of the different components based on user input through the resource-allocation controls.

FIGURES

The various aspects described herein, both as to organization and methods of operation, together with further objects and advantages thereof, may best be understood by reference to the following description, taken in conjunction with the accompanying drawings as follows.

Figure 27C:
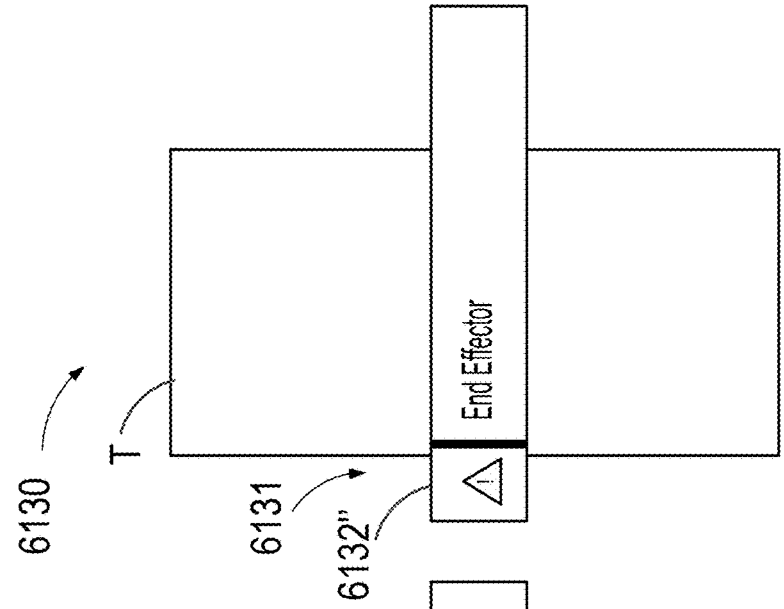
Figure 27B:
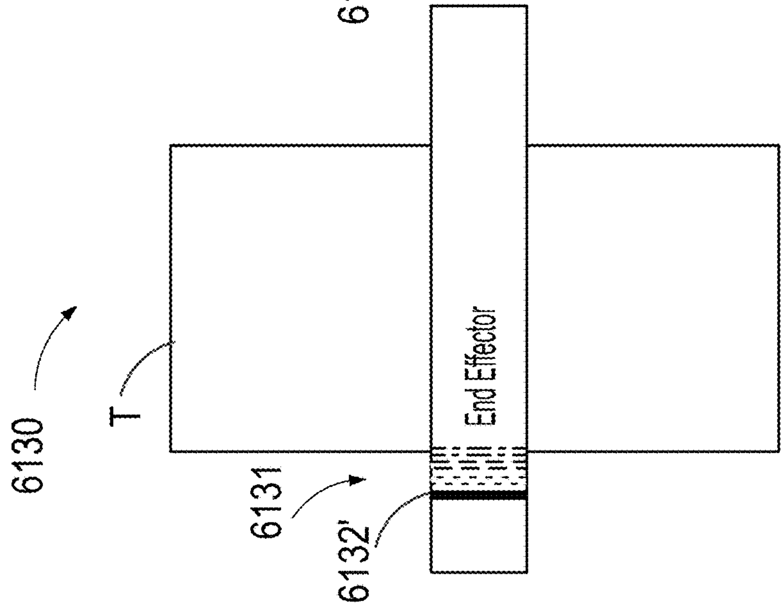
Figure 27A:
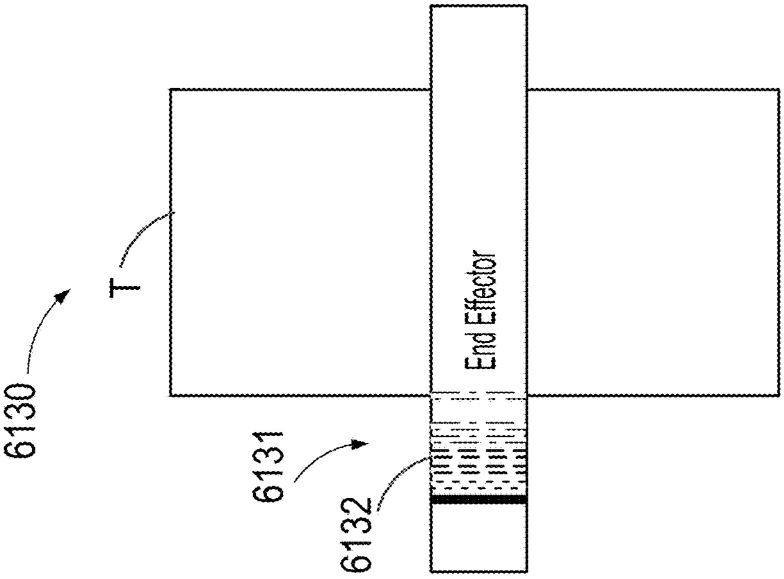

FIGS. 27A, 27B, and 27C illustrate a display arrangement, in accordance with methods of the present disclosure.

Figure 28:
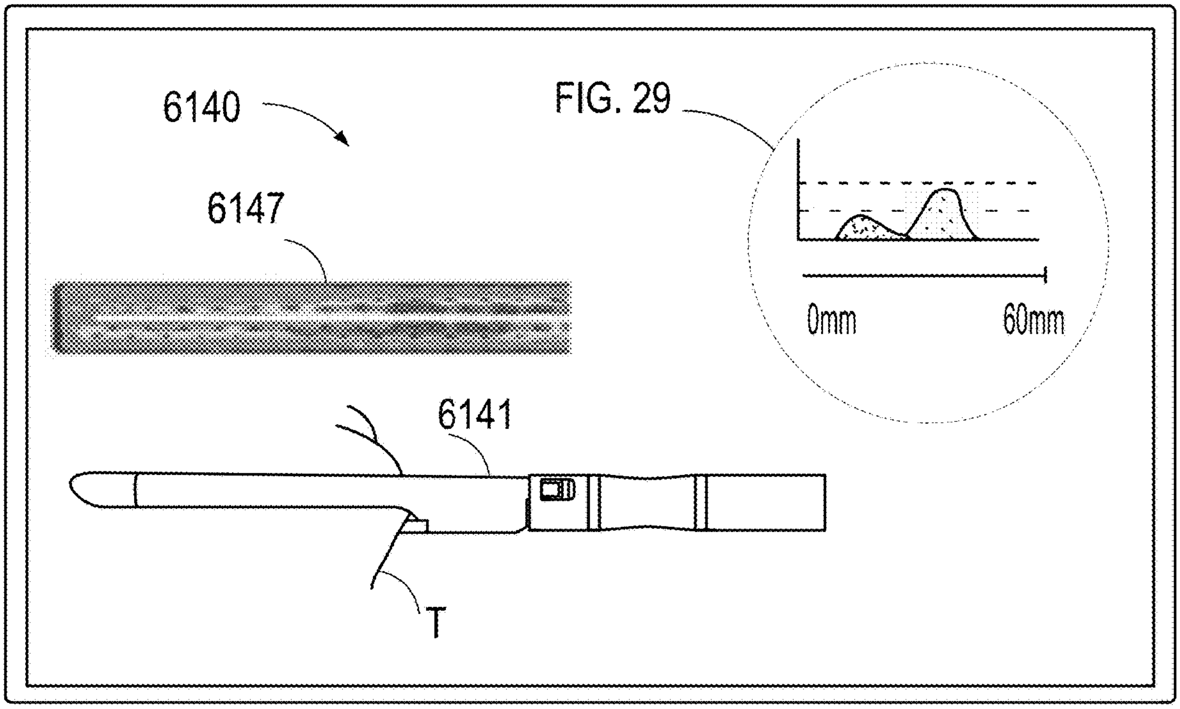

FIG. 28 illustrates a display arrangement, in accordance with methods of the present disclosure.

Figure 29:
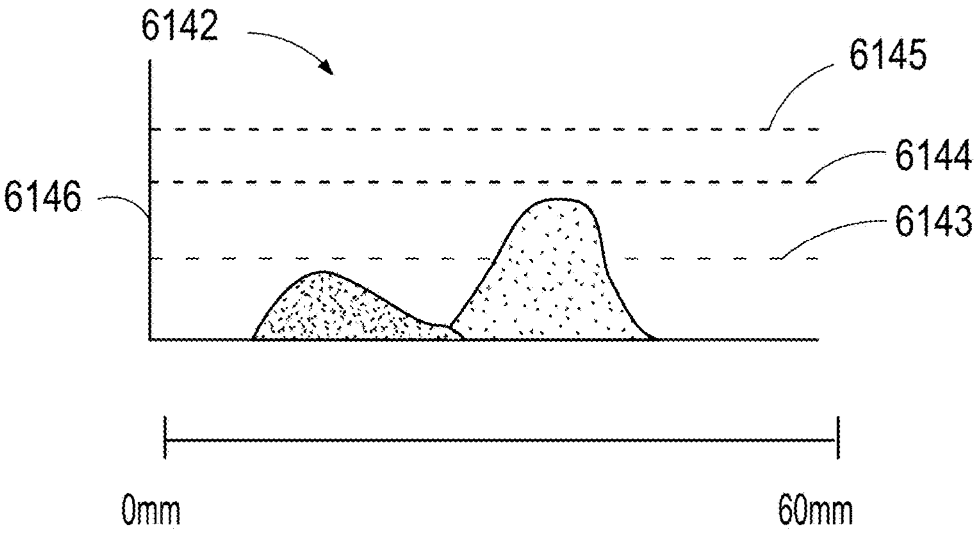

FIG. 29 illustrates a display arrangement, in accordance with methods of the present disclosure.

Figure 30:
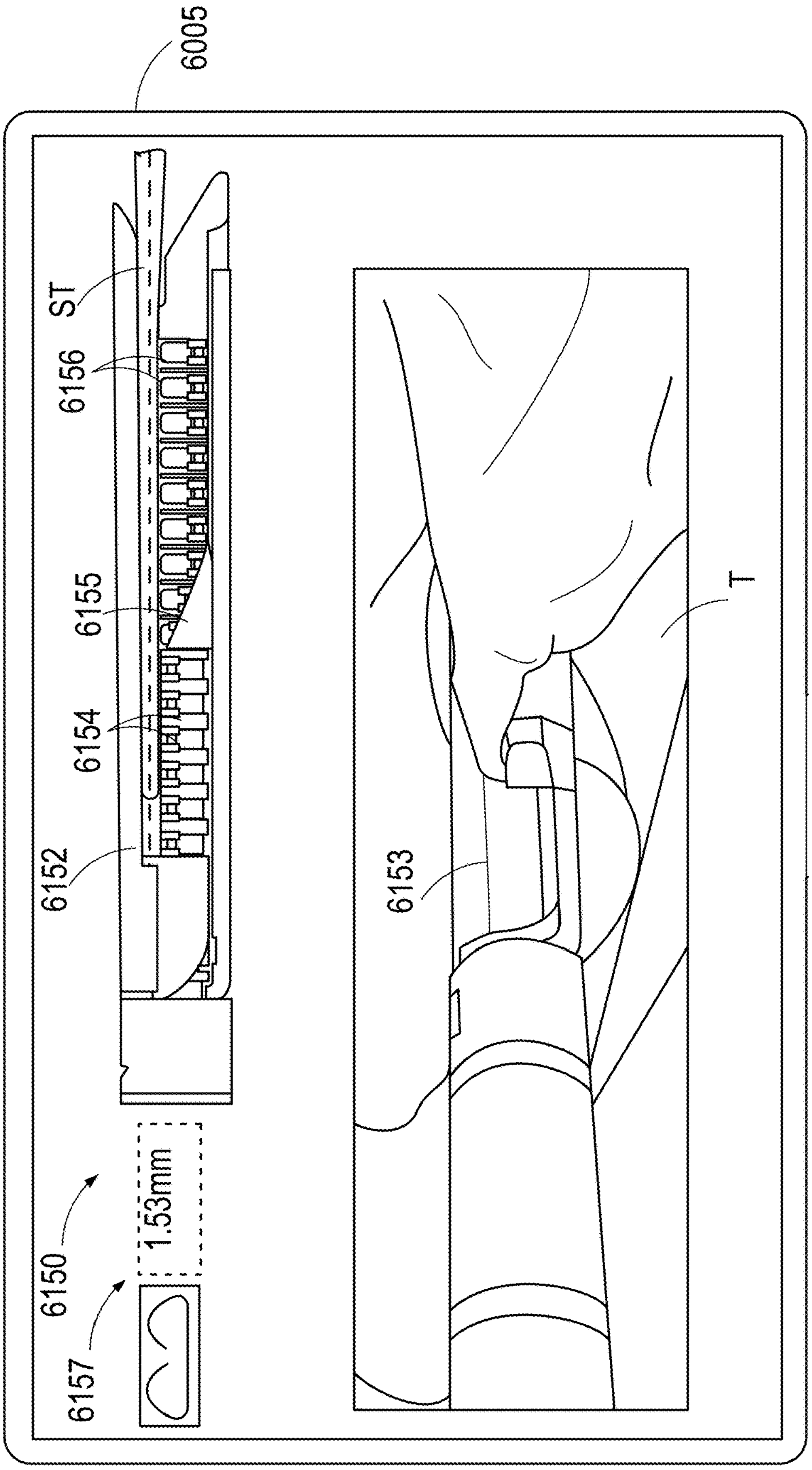

FIG. 30 illustrates a display arrangement, in accordance with methods of the present disclosure.

Figure 31:
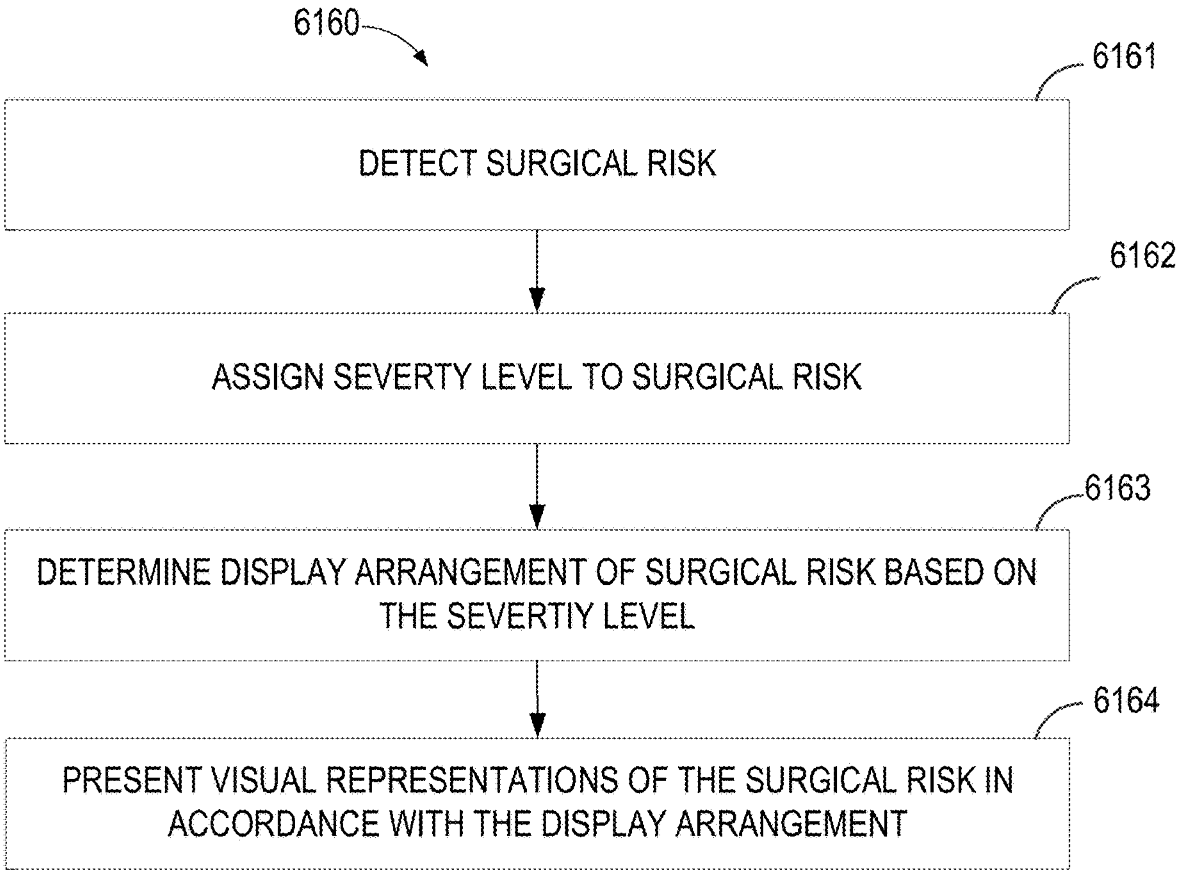

FIG. 31 is a logic diagram showing operations of a method for risk-based manipulation of a display arrangement during a surgical procedure, according to one aspect of this disclosure.

Figure 32:
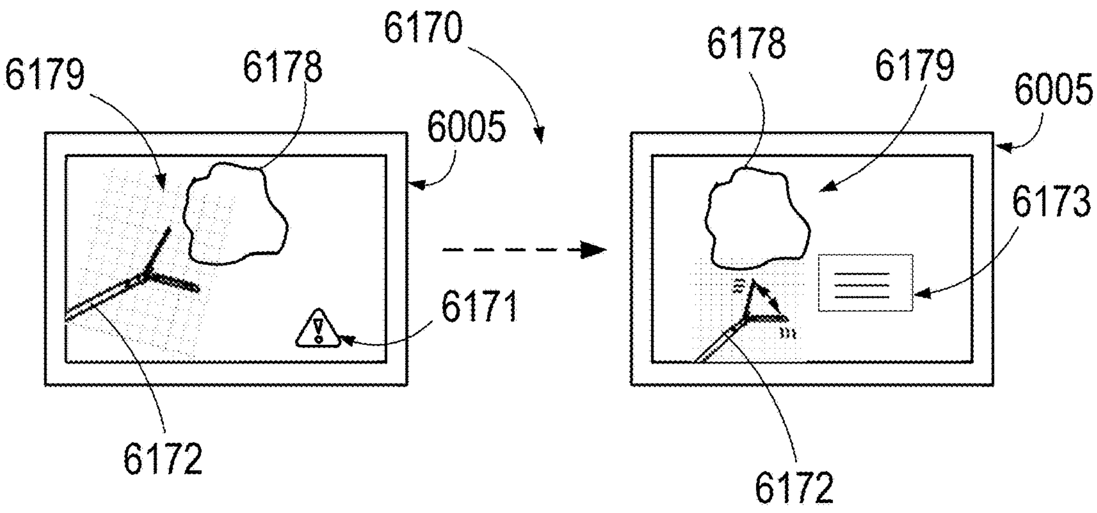

FIG. 32 illustrates a display arrangement, according to one aspect of this disclosure.

Figure 33:
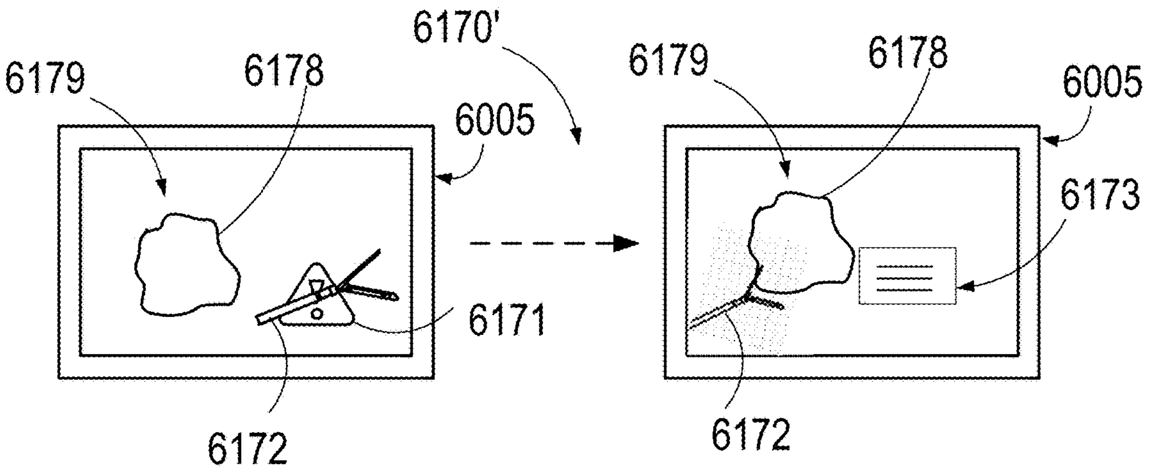

FIG. 33 illustrates a display arrangement, according to one aspect of this disclosure.

Figure 34:
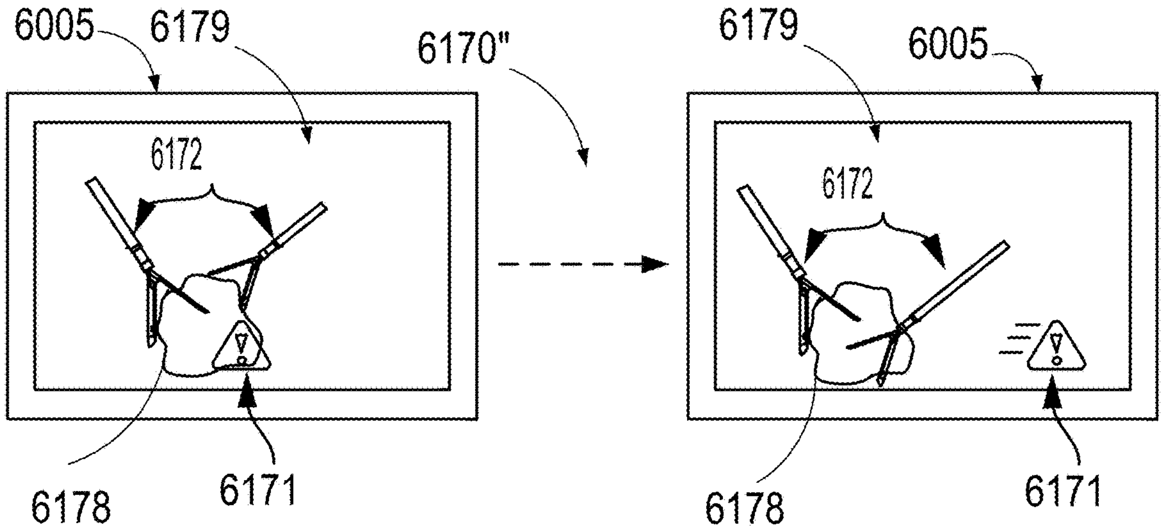

FIG. 34 illustrates a display arrangement, according to one aspect of this disclosure.

Figure 35:
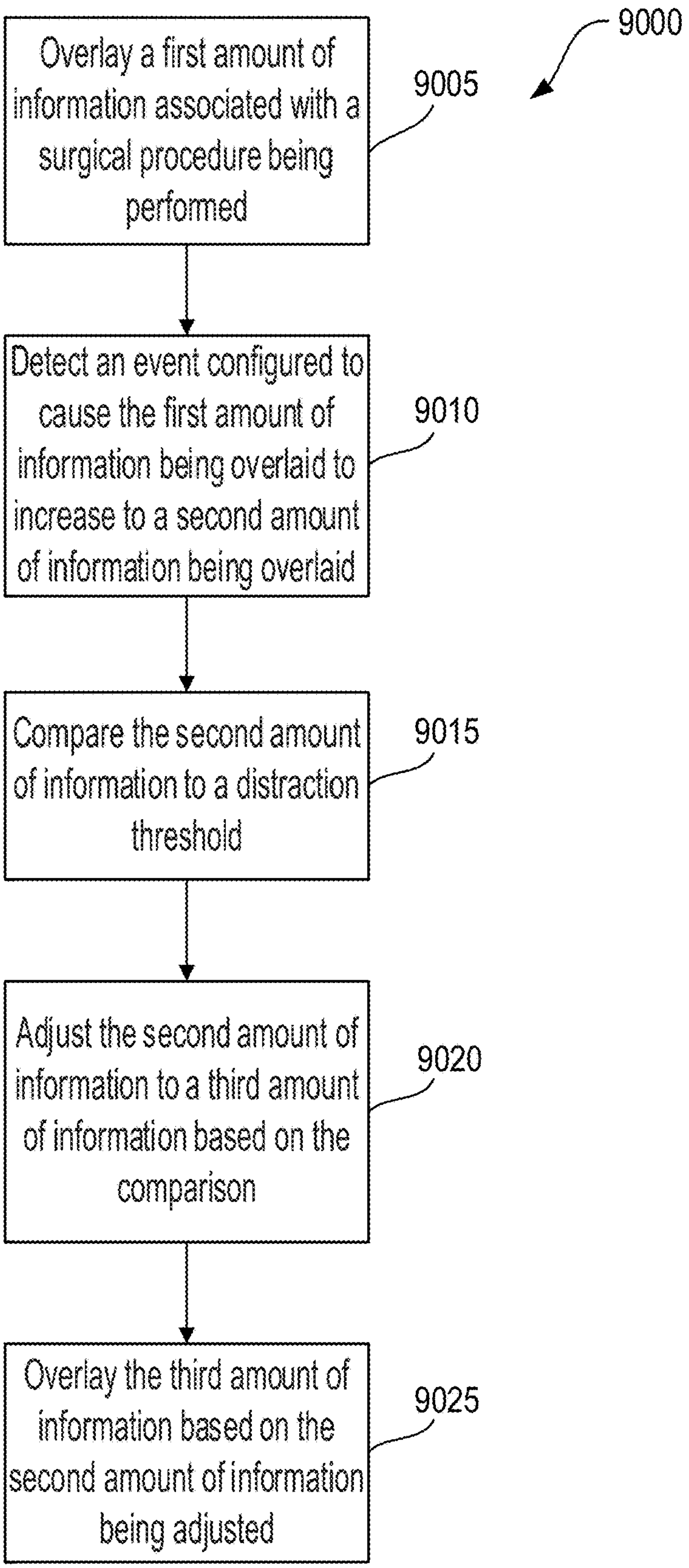

FIG. 35 illustrates a method for determining a display arrangement of surgical data competing for presentation onto a display that is showing a livestream of a surgical field, according to one aspect of this disclosure.

Figure 36:
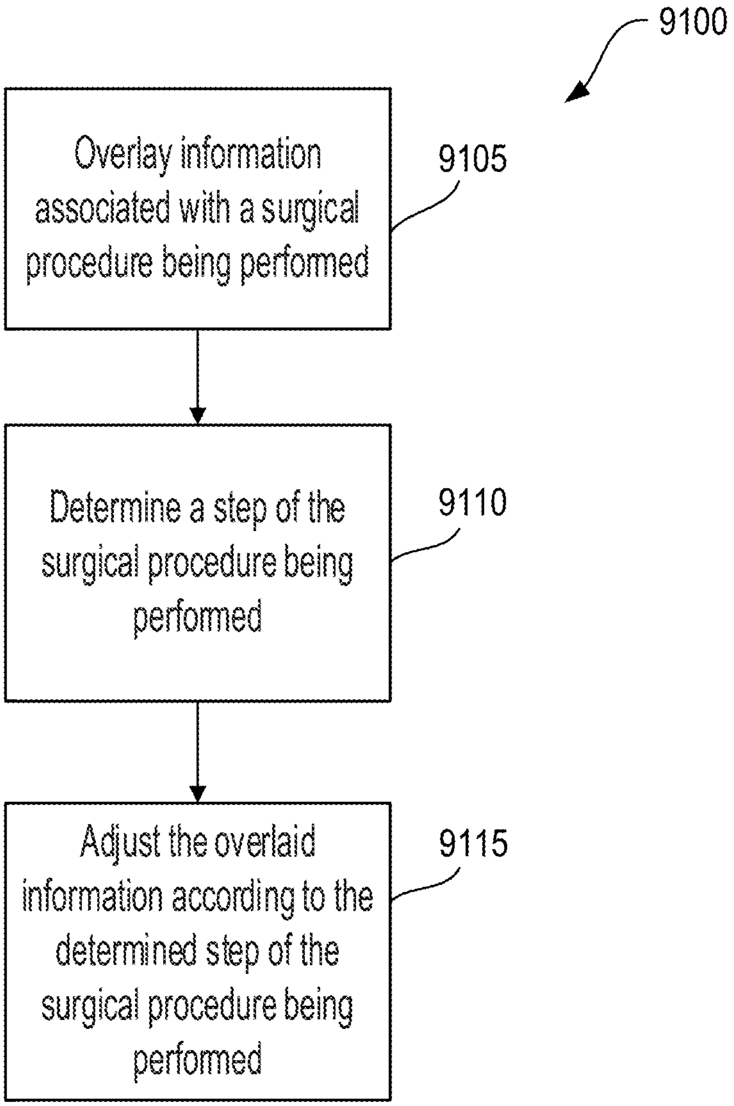

FIG. 36 illustrates a method for determining a display arrangement of surgical data competing for presentation onto a display that is showing a livestream of a surgical field, according to one aspect of this disclosure.

Figure 37:
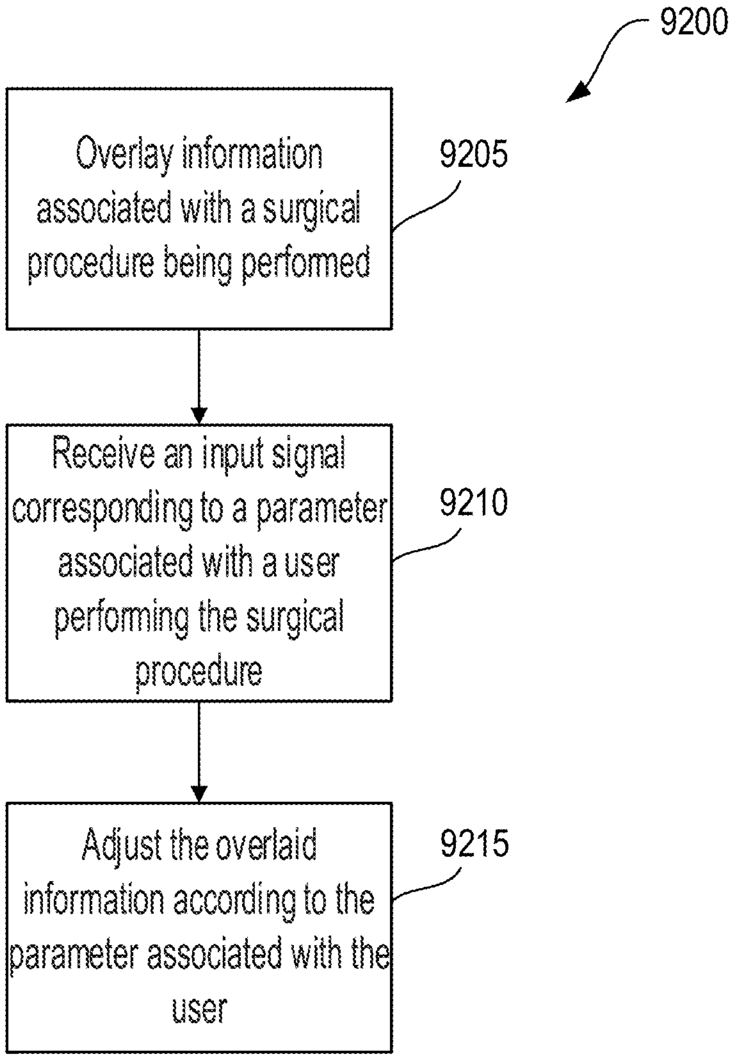

FIG. 37 illustrates a method for determining a display arrangement of surgical data competing for presentation onto a display that is showing a livestream of a surgical field, according to one aspect of this disclosure.

Figure 38:
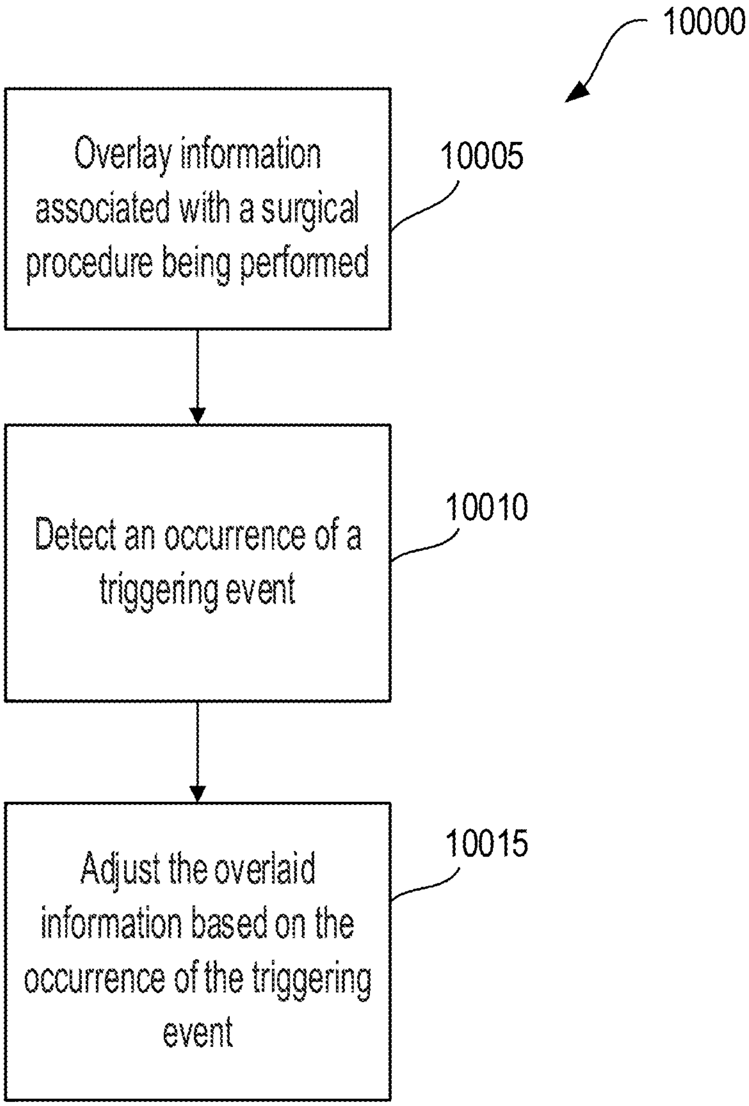

FIG. 38 illustrates a method for determining a display arrangement of surgical data competing for presentation onto a display that is showing a livestream of a surgical field, according to one aspect of this disclosure.

Figure 39:
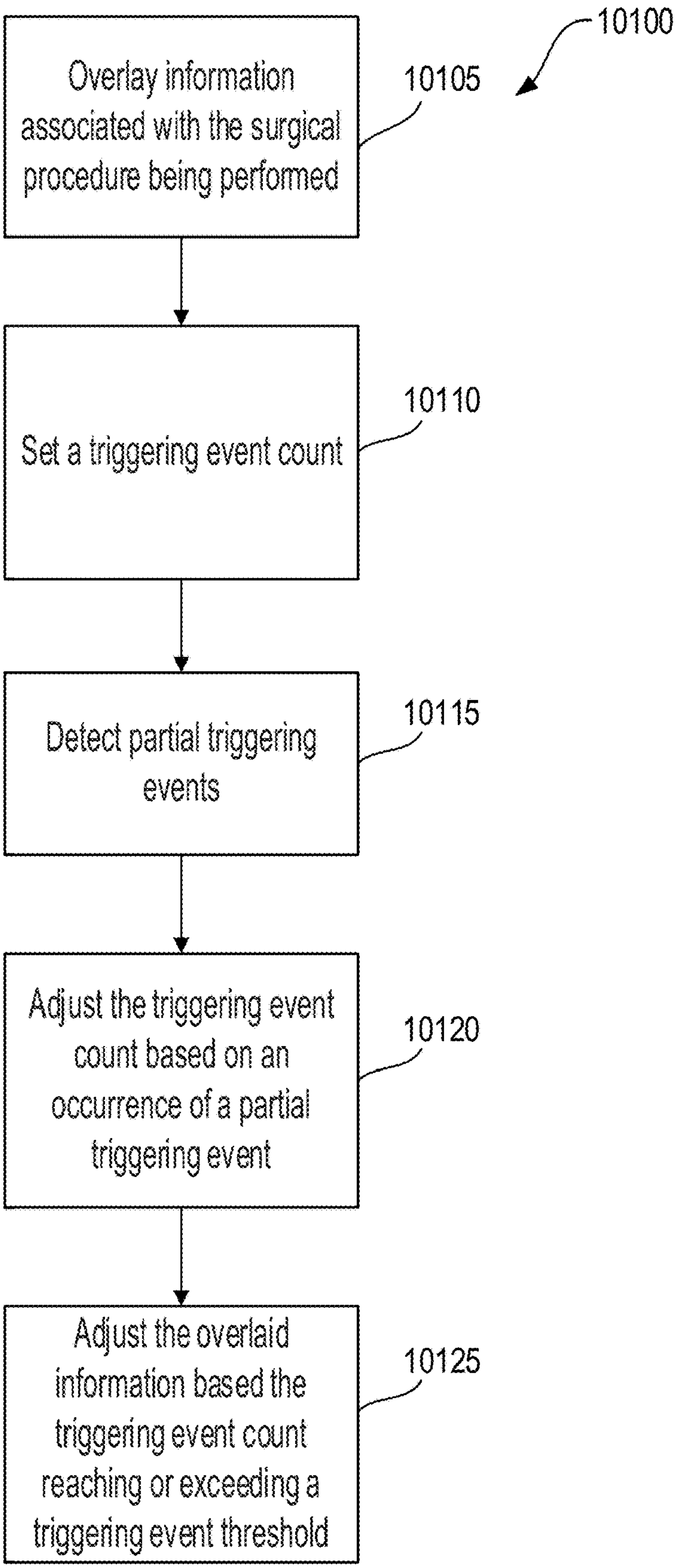

FIG. 39 illustrates a method for determining a display arrangement of surgical data competing for presentation onto a display that is showing a livestream of a surgical field, according to one aspect of this disclosure.

Figure 40:
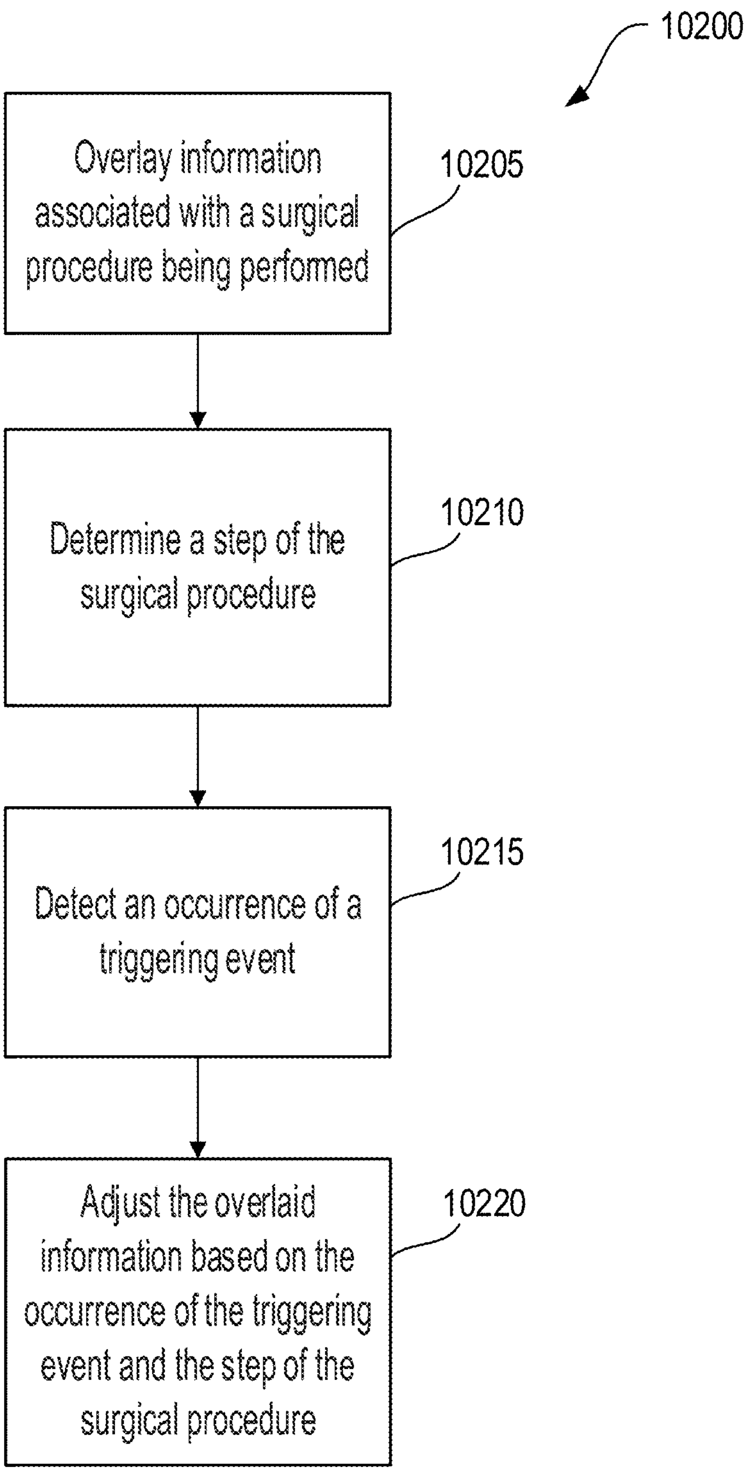

FIG. 40 illustrates a method for determining a display arrangement of surgical data competing for presentation onto a display that is showing a livestream of a surgical field, according to one aspect of this disclosure.

Figure 41A:
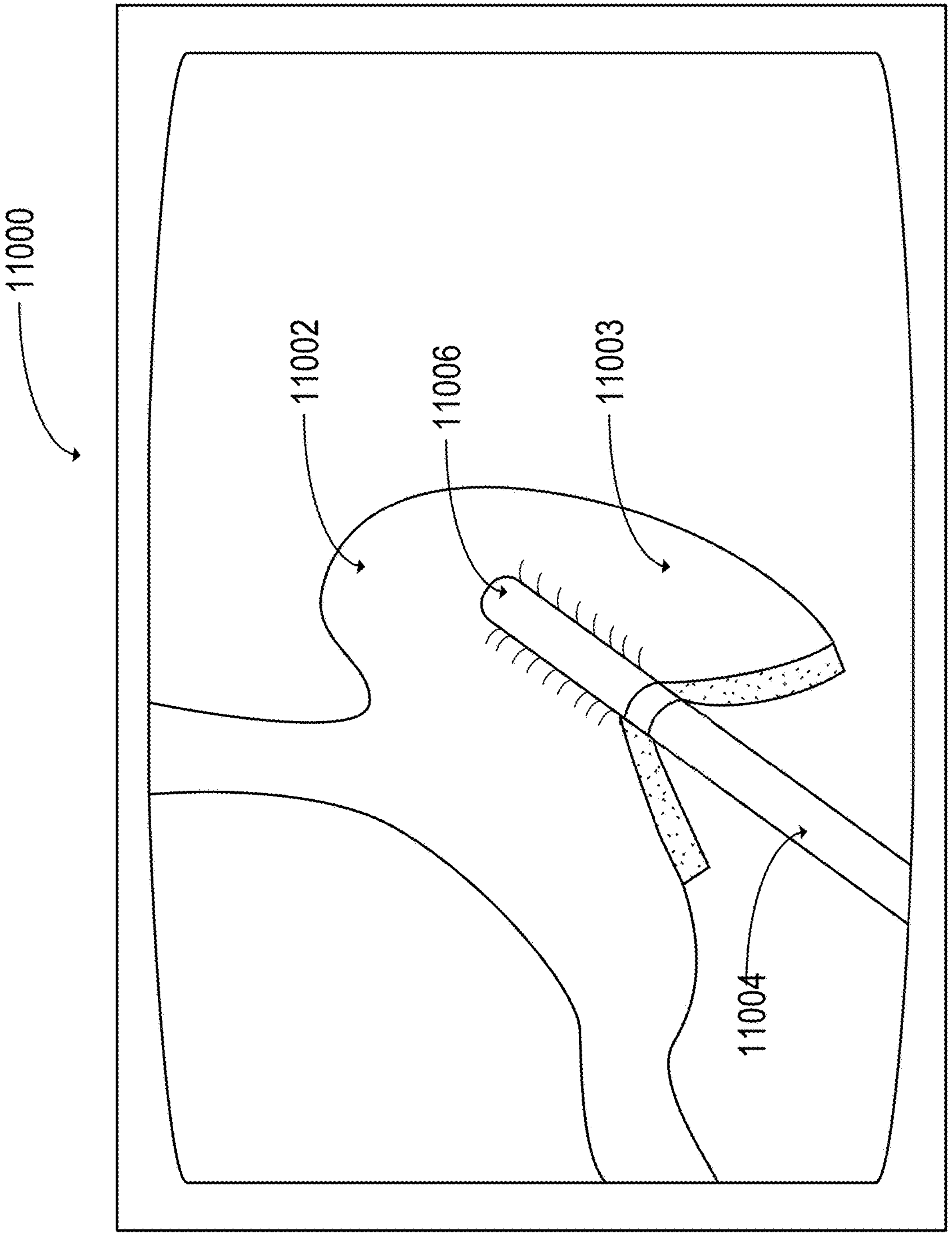

FIG. 41A illustrates a surgical display obtained from a surgical imaging device during a laparoscopic sleeve gastrectomy procedure, according to one aspect of this disclosure.

Figure 41B:
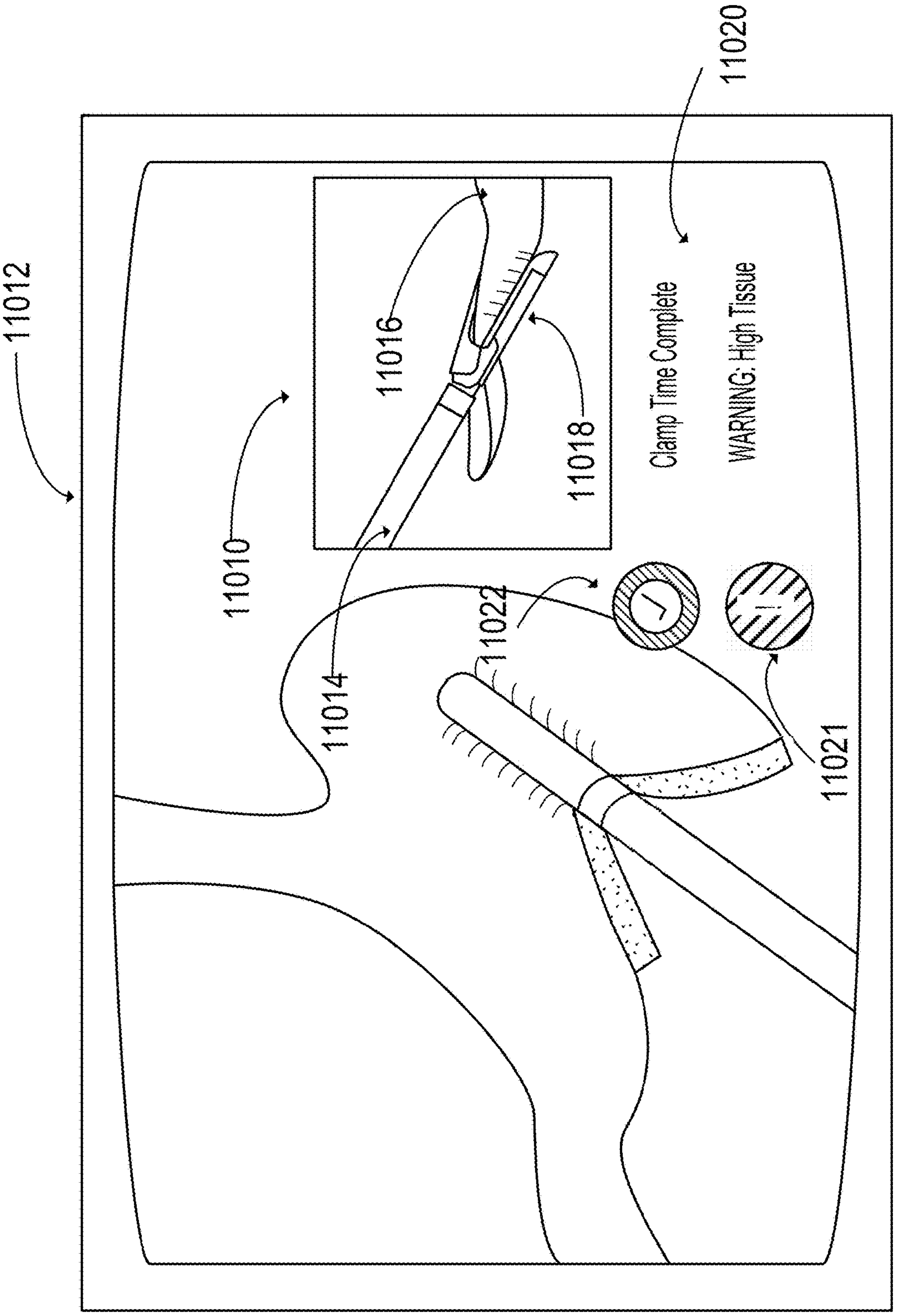

FIG. 41B illustrates an augmented reality image comprising the surgical display along with a virtual secondary view overlaid thereon, according to one aspect of this disclosure.

Figure 42A:
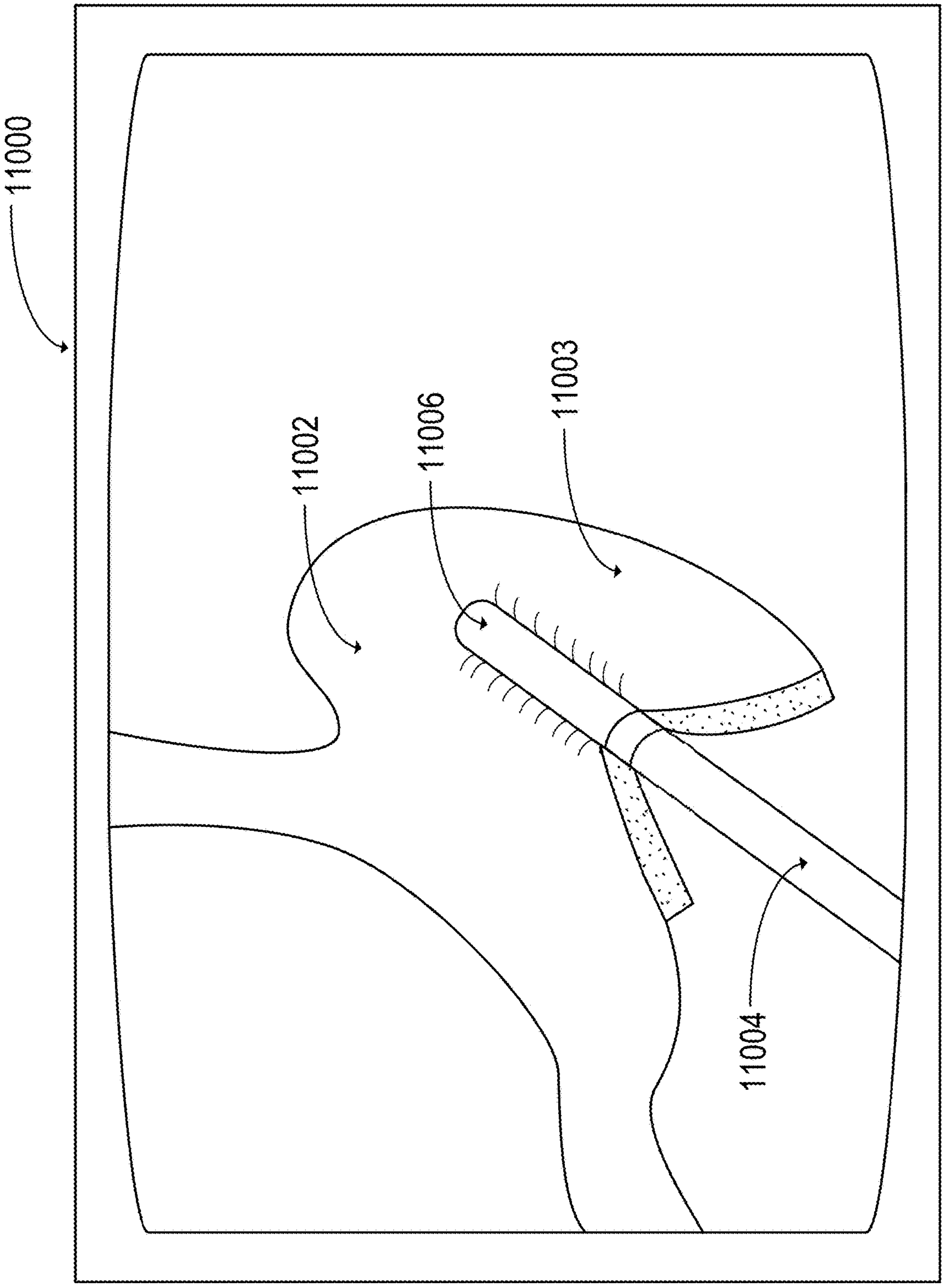

FIG. 42A illustrates a surgical display obtained from a surgical imaging device during a laparoscopic sleeve gastrectomy procedure in which a portion of the fundus of a patient's stomach is removed, according to one aspect of this disclosure.

Figure 42B:
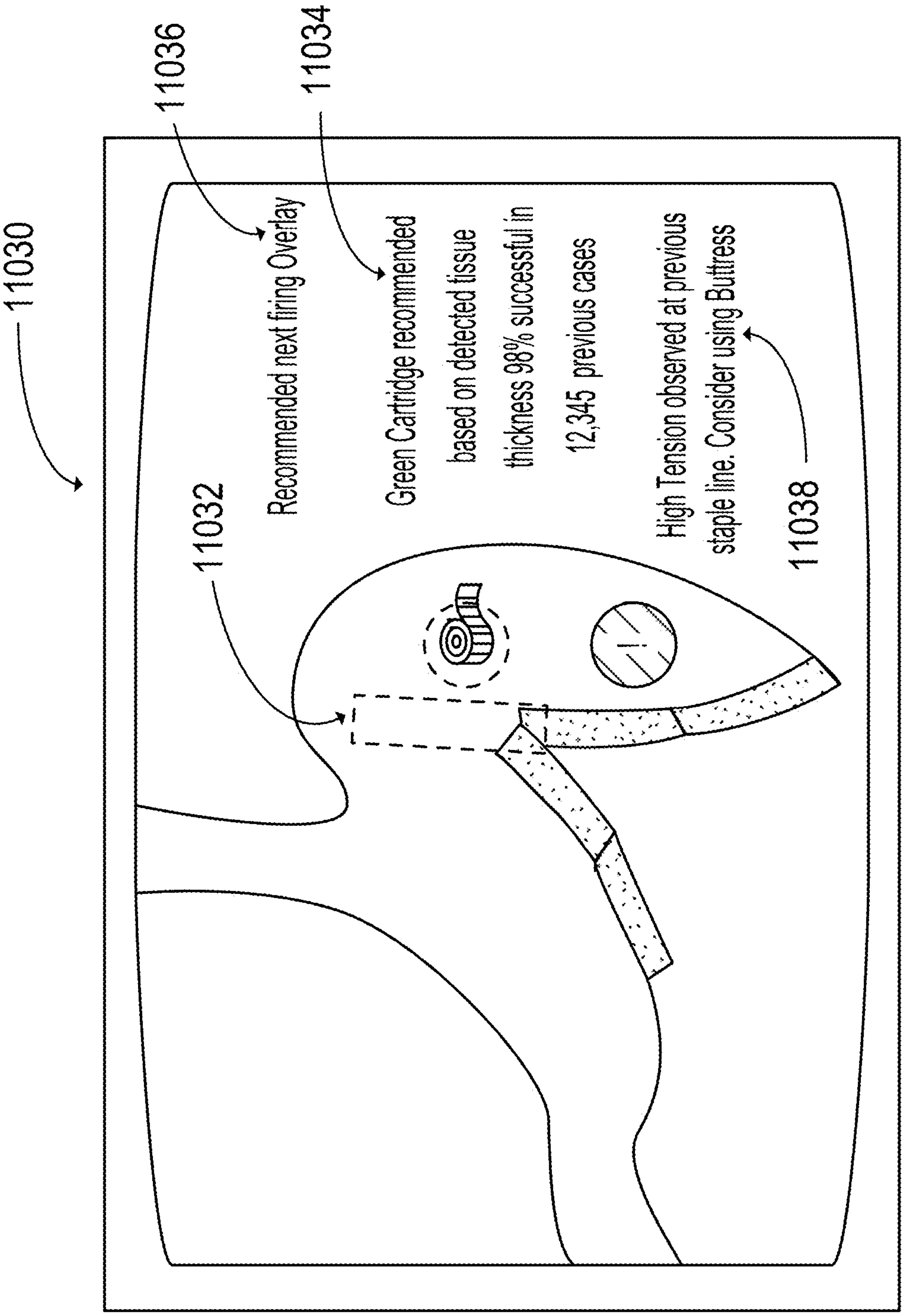

FIG. 42B illustrates an augmented reality image including the surgical display along with a predicted or recommended placement of the stapler, according to one aspect of this disclosure.

Figure 43:
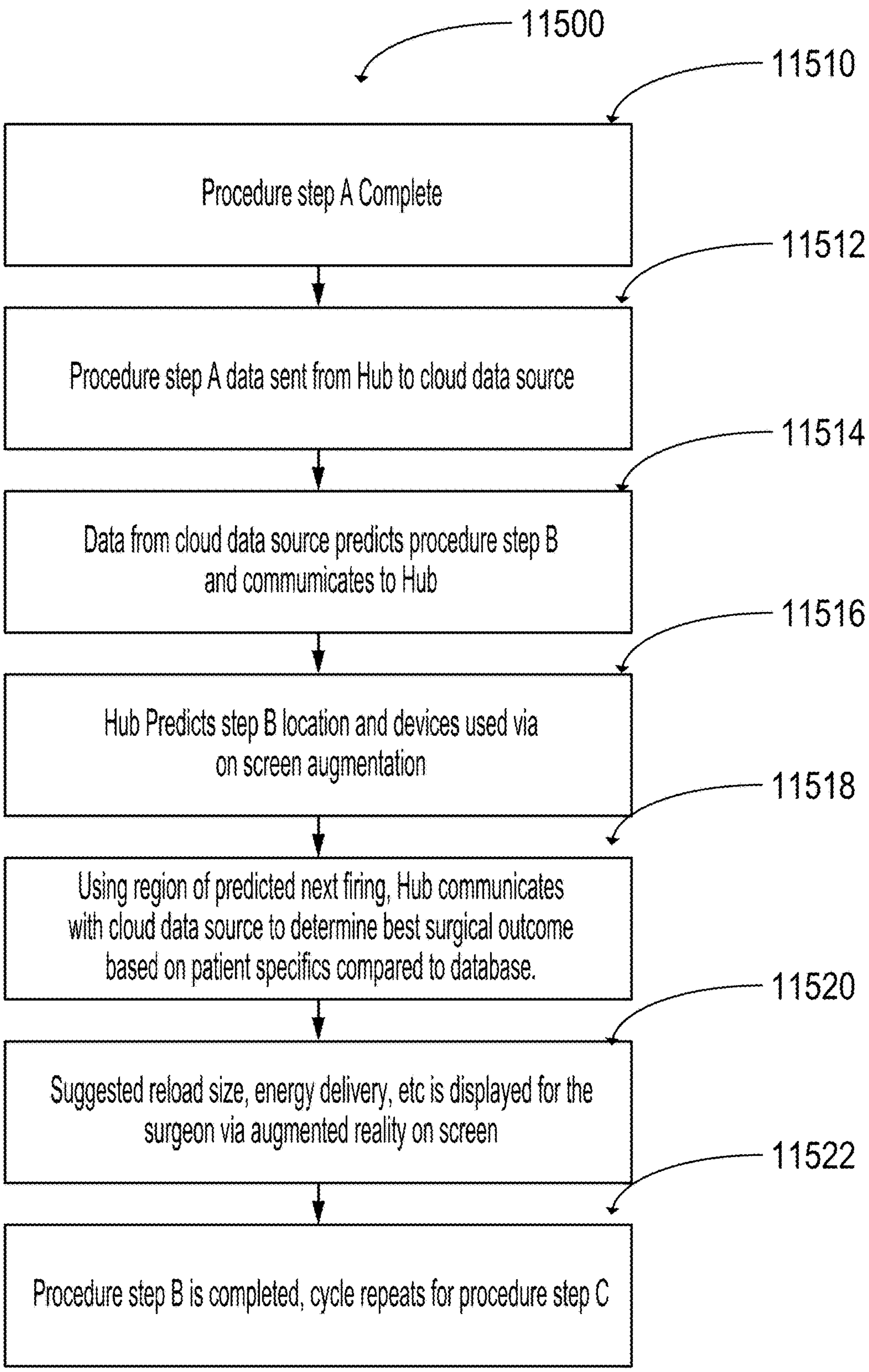

FIG. 43 illustrates a logic diagram depicting a method by which an interactive surgical system may receive surgical procedure information and suggest next procedural steps, according to one aspect of this disclosure.

Figure 44A:
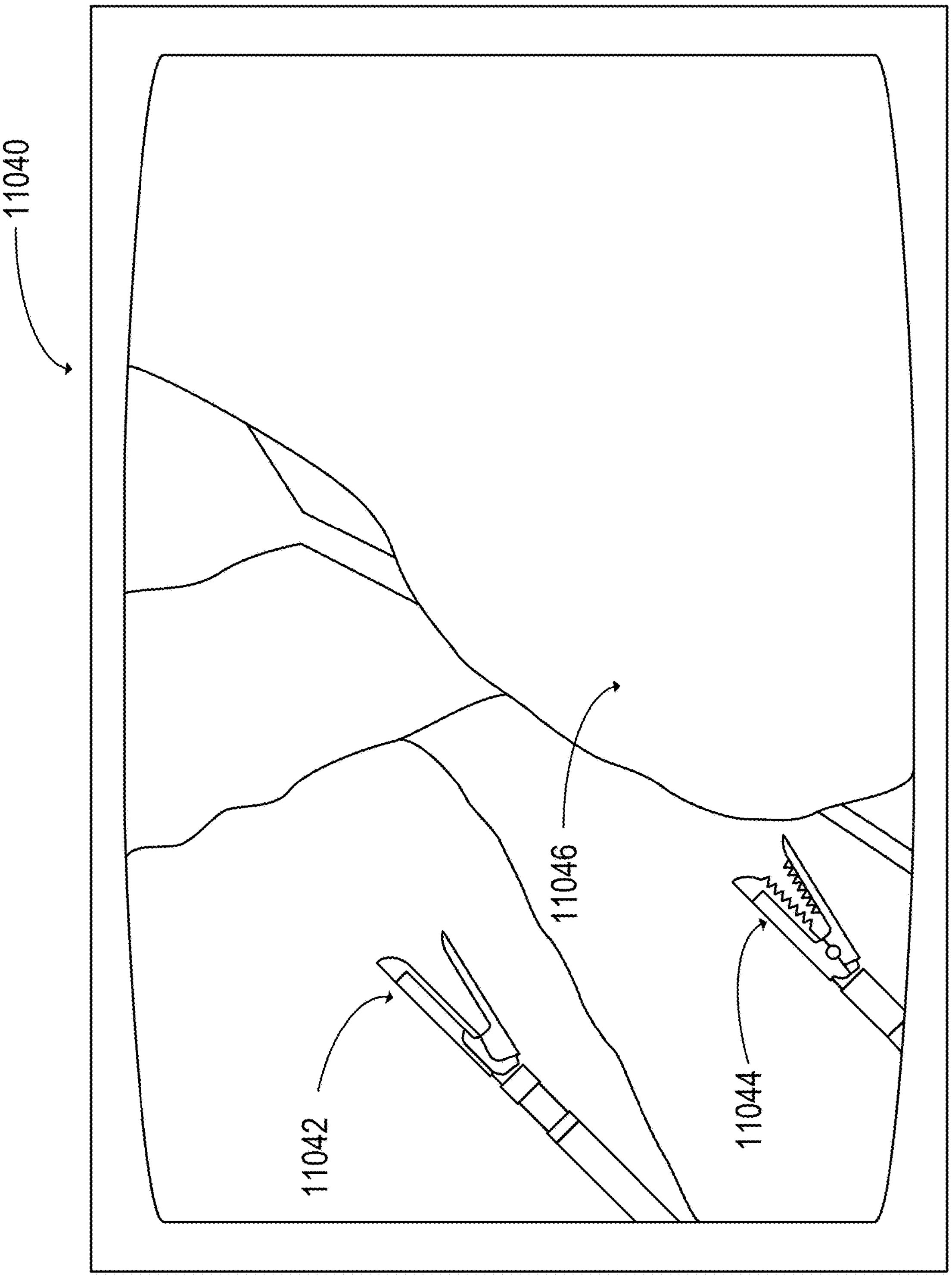

FIG. 44A illustrates a surgical display obtained from a surgical imaging device during a laparoscopic procedure, according to one aspect of this disclosure.

Figure 44B:
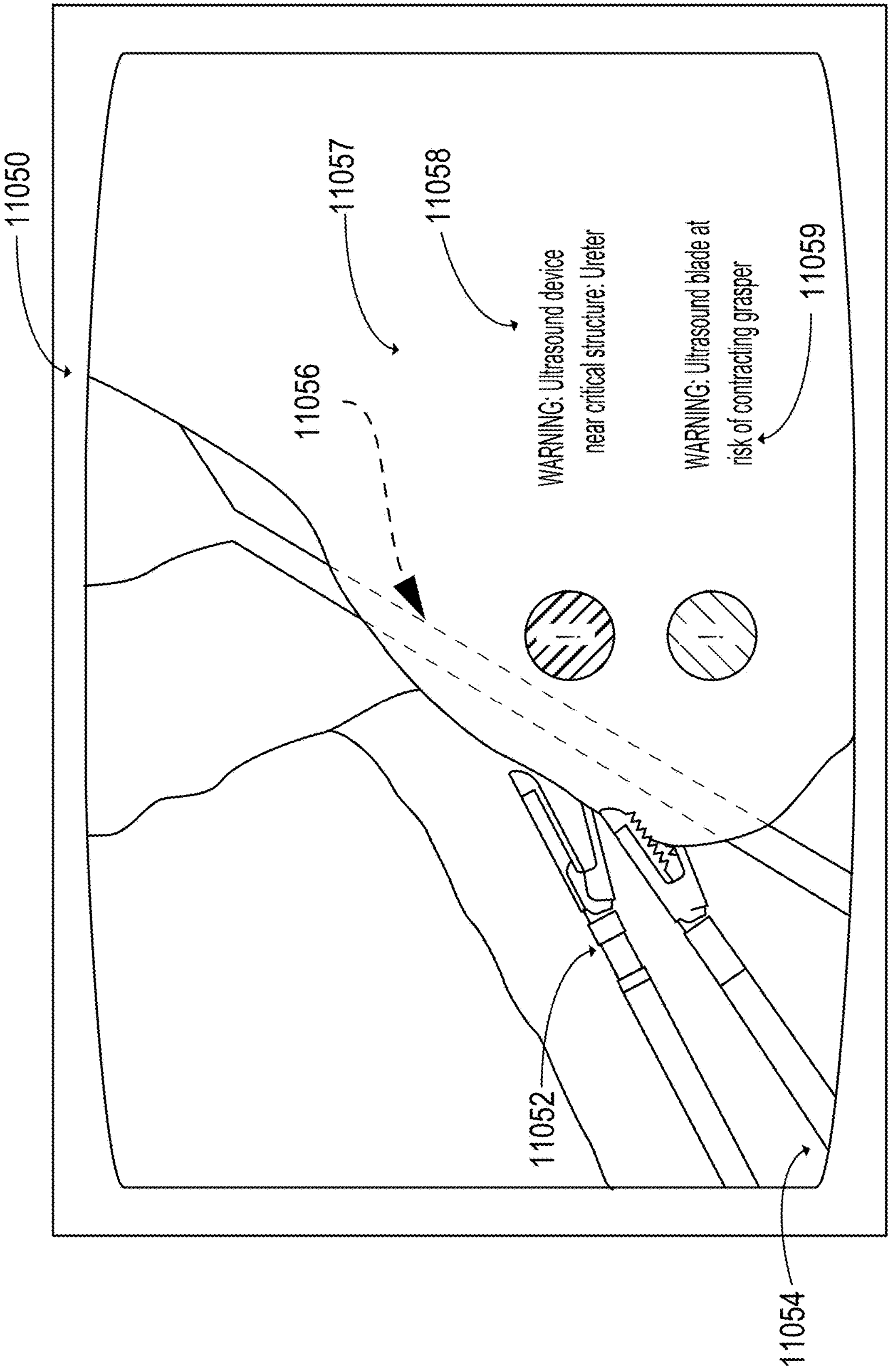

FIG. 44B illustrates an augmented reality image comprising the surgical display along with an augmented reality virtual object presenting an outline of the ureter underlying the tissue to be resected, according to one aspect of this disclosure.

Figure 45:
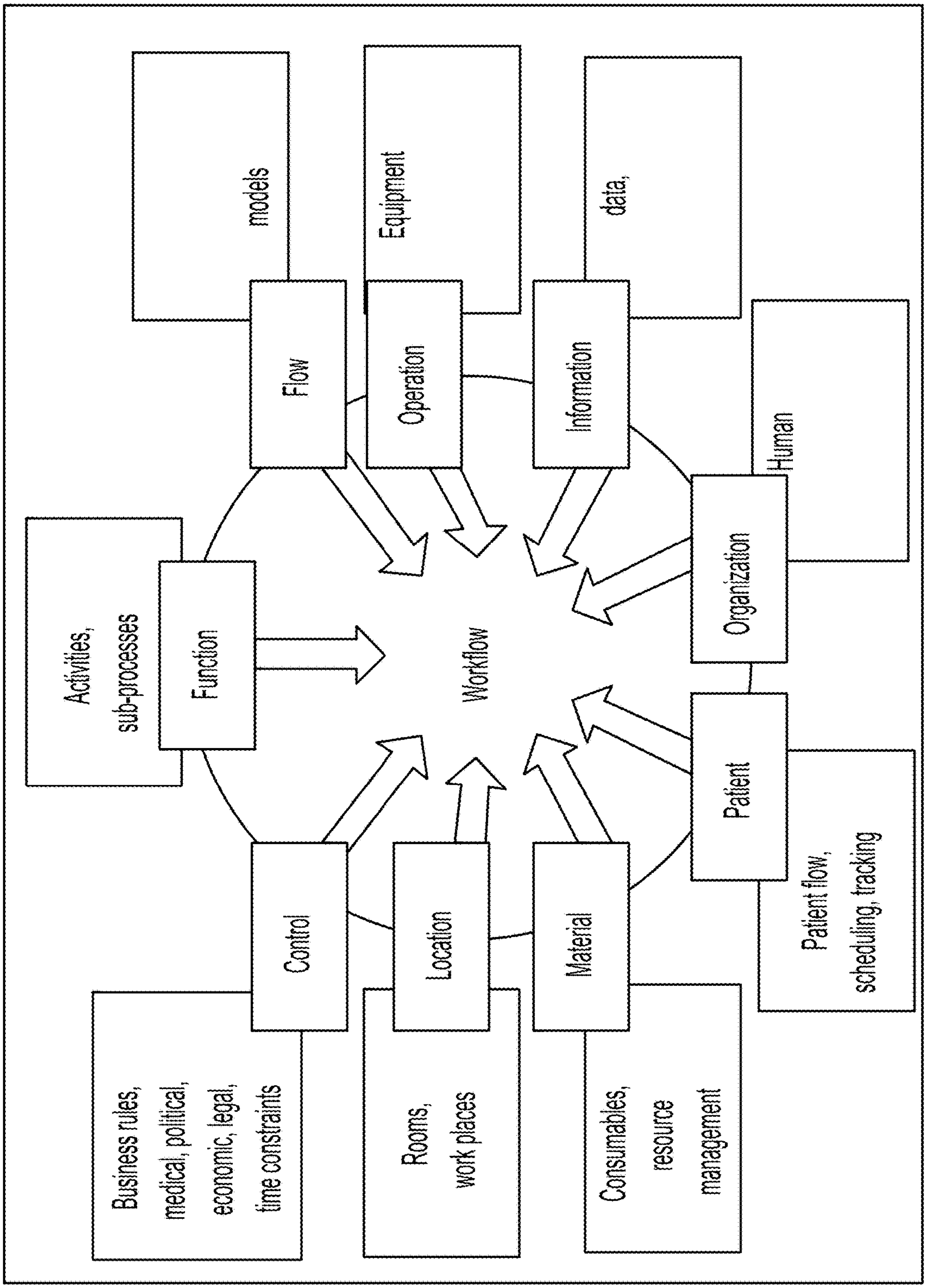

FIG. 45 illustrates the various aspects associated with a surgical procedure that may be tracked by the interactive surgical system, and which may be analyzed to develop optimization strategies, according to one aspect of this disclosure.

Figure 46:
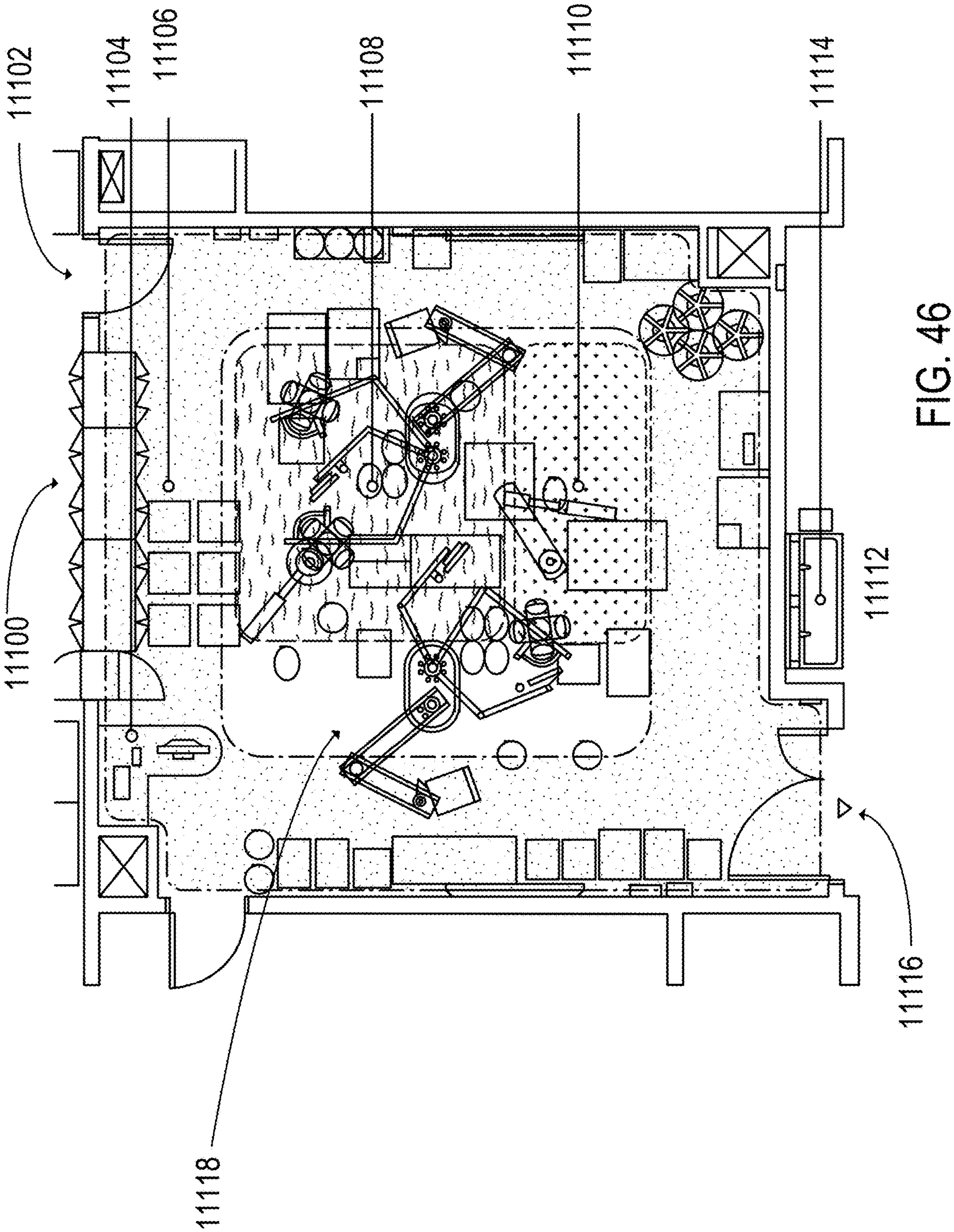

FIG. 46 illustrates aspects of an operating room which may be modeled for tracking purposes, according to one aspect of this disclosure.

Figure 47:
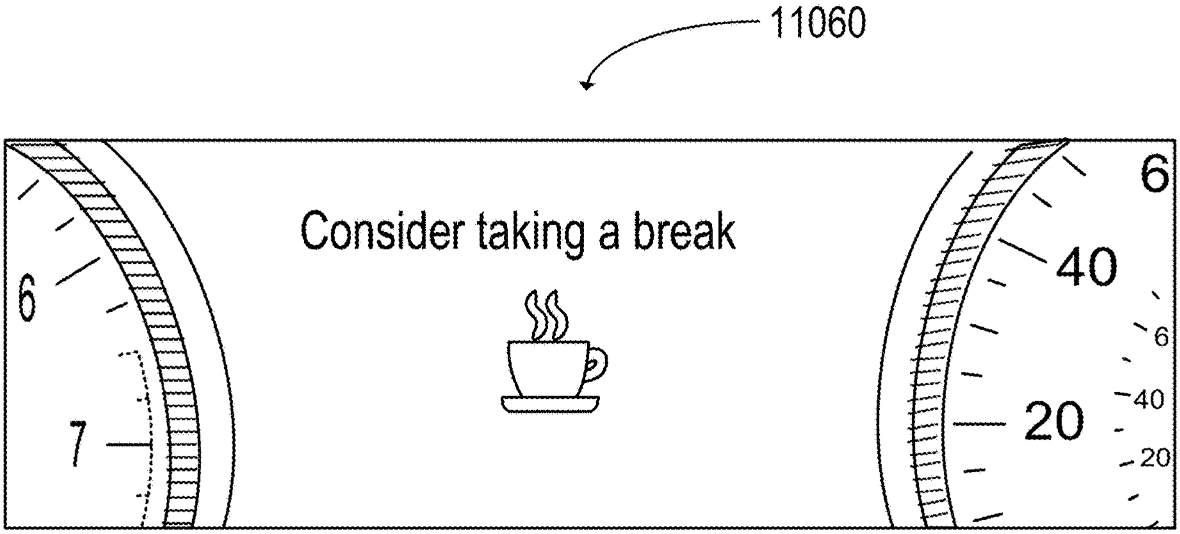

FIG. 47 illustrates an example of a virtual objection warning of surgical member fatigue, according to one aspect of this disclosure.

Figure 48B:
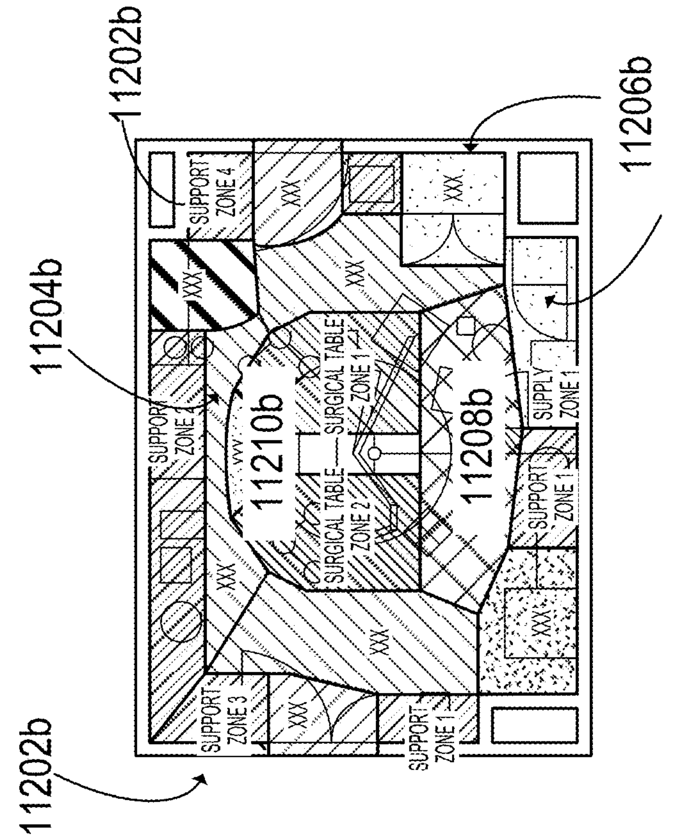
Figure 48A:
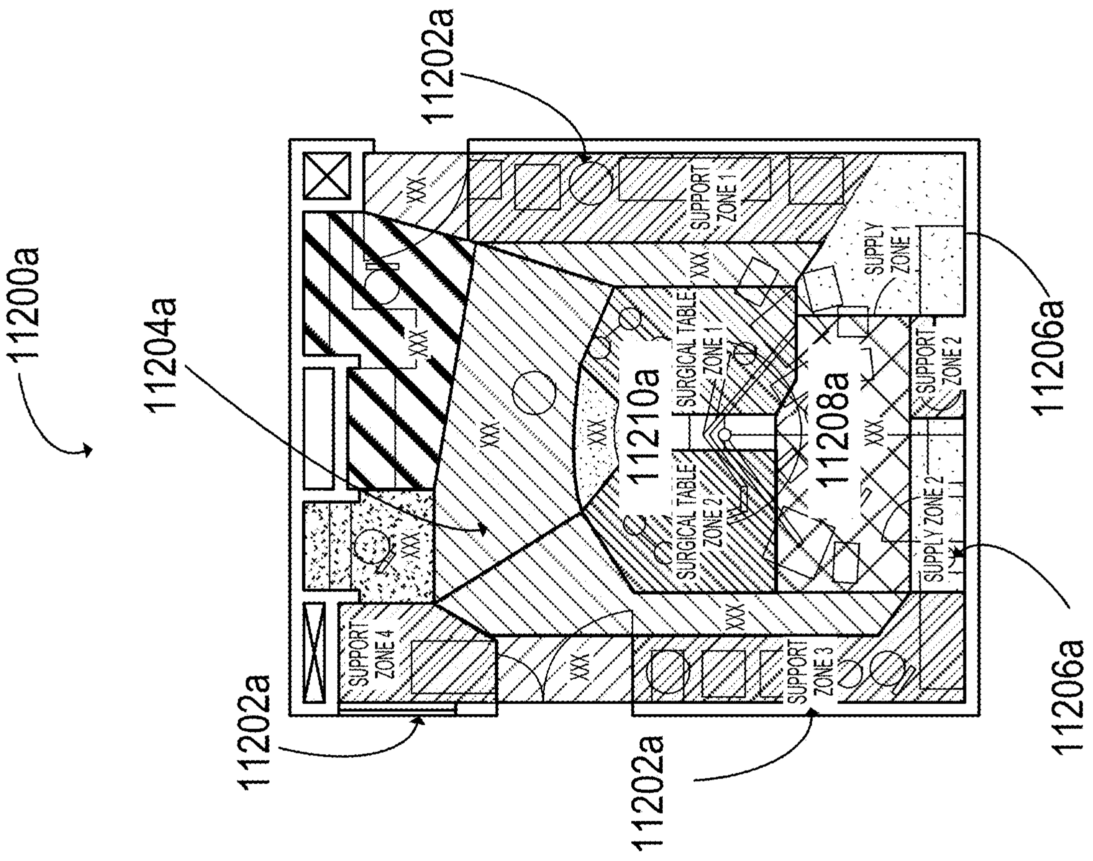
Figure 48C:
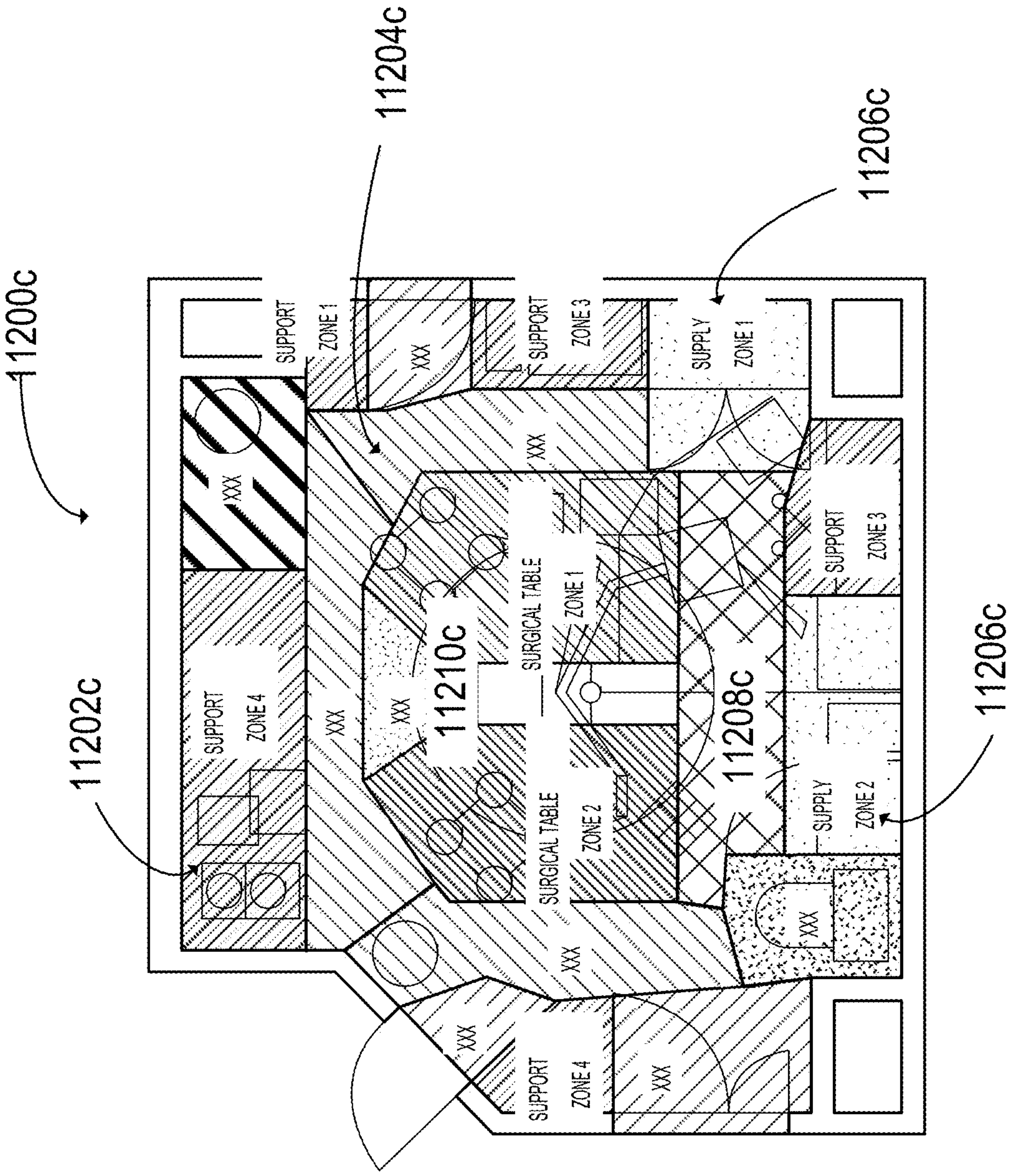

FIG. 48A, 48B, 48C illustrates some exemplary depictions of optimized operating rooms, according to one aspect of this disclosure.

Figure 49:
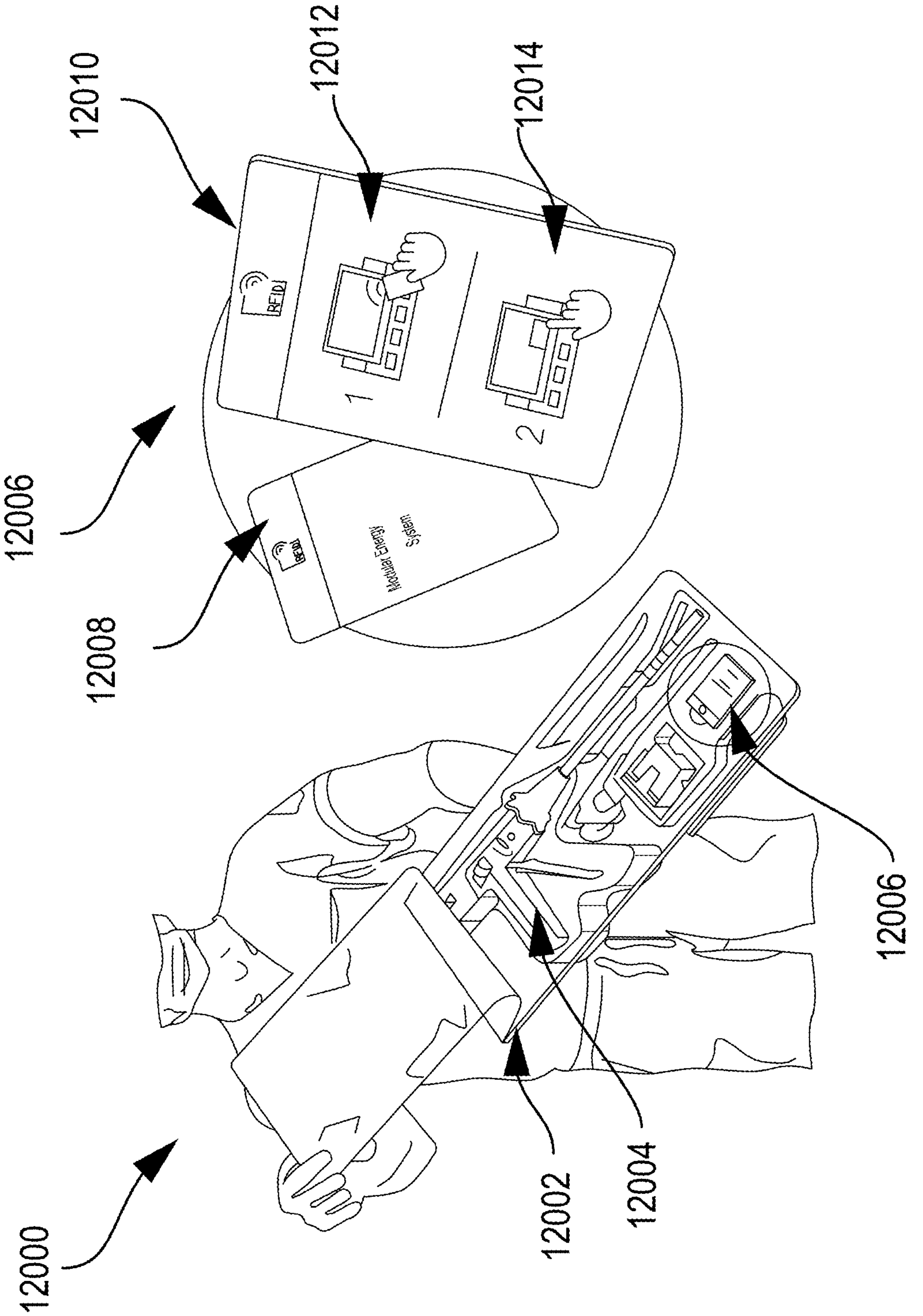

FIG. 49 is a perspective view of a packaging system for a wireless surgical instrument capable of RFID token-based pairing, according to one aspect of this disclosure.

Figure 50:
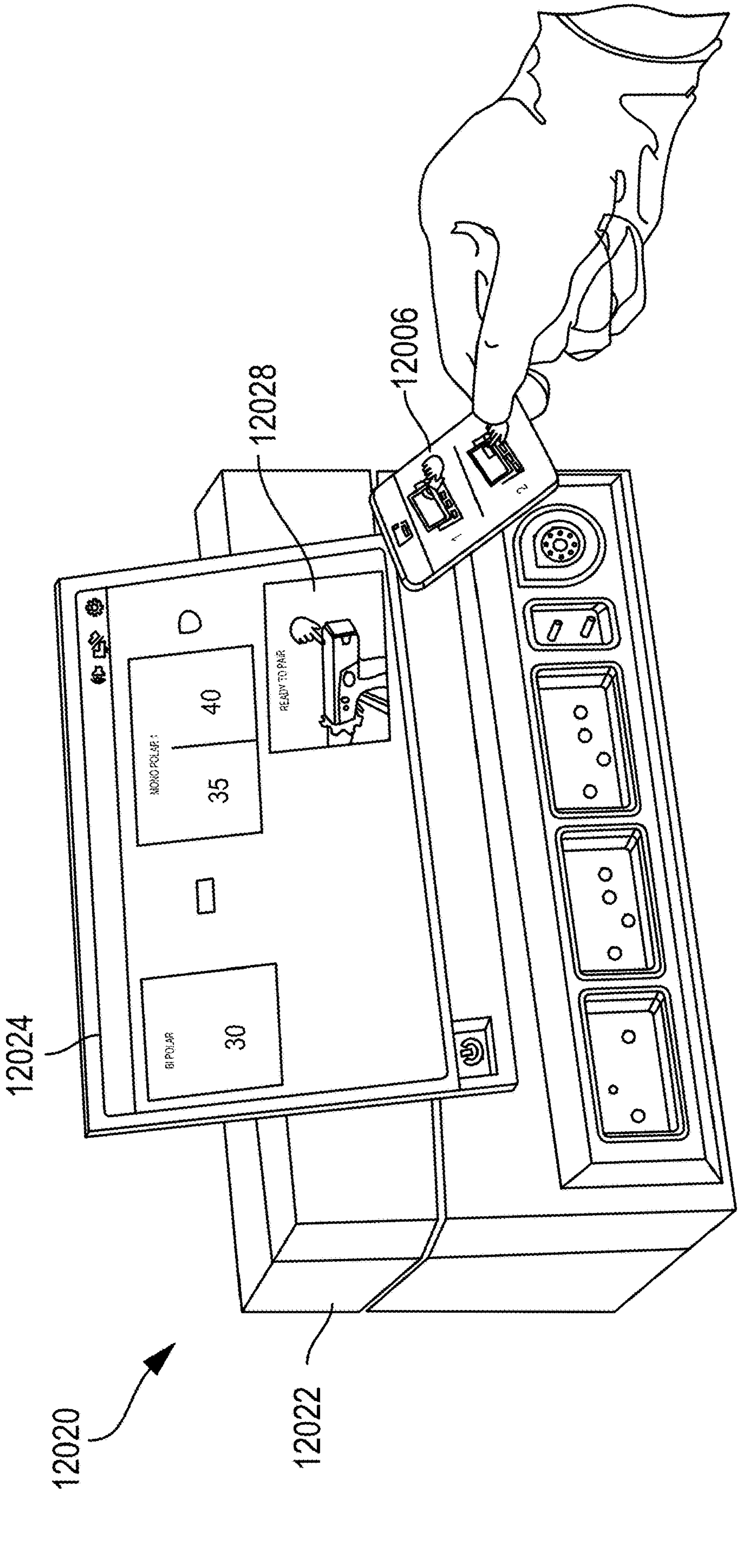

FIG. 50 is a perspective view of a user holding an RFID card proximal to a display screen of a modular energy system to initiate RFID token-based pairing, according to one aspect of this disclosure.

Figure 51:
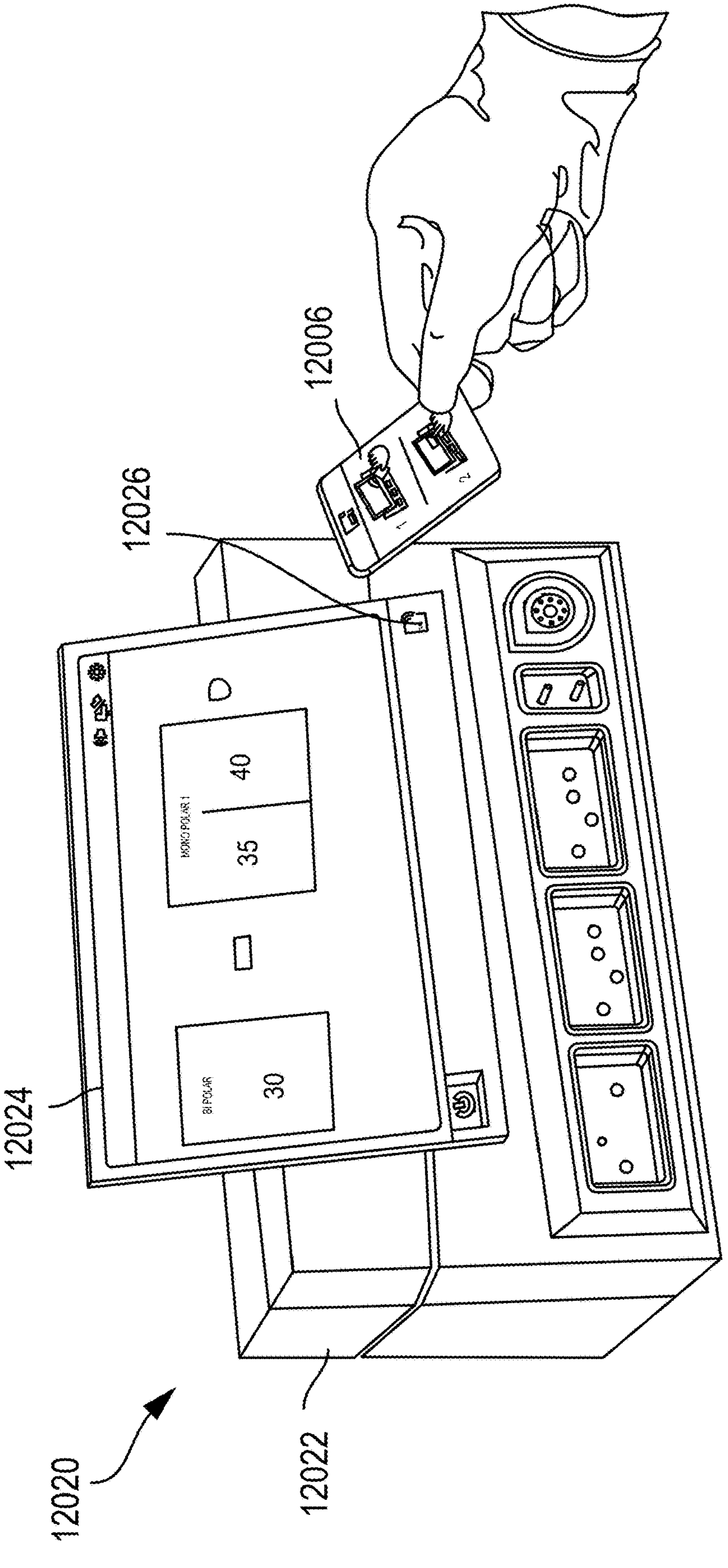

FIG. 51 is a perspective view of a display screen displaying illustrated instructions for wirelessly pairing a surgical instrument to a modular energy system, according to one aspect of this disclosure.

FIG. 52 is a list of visual indicia associated with different functions during a wireless communication pairing of two instruments, according to one aspect of this disclosure.

Figure 53:
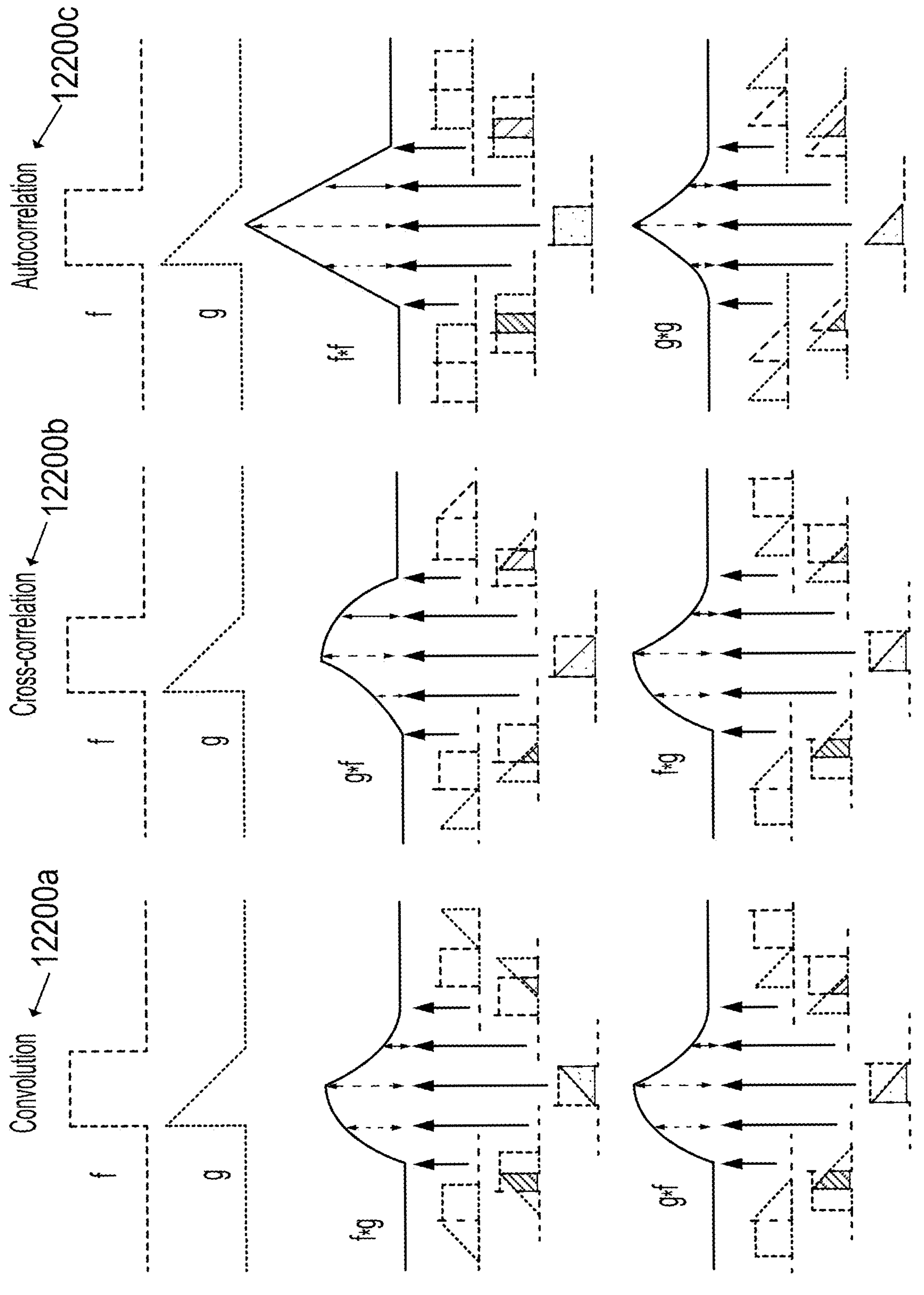

FIG. 53 depicts various mathematical combinations of functions derived from communication initiation syncwords, according to one aspect of this disclosure.

Figure 54:
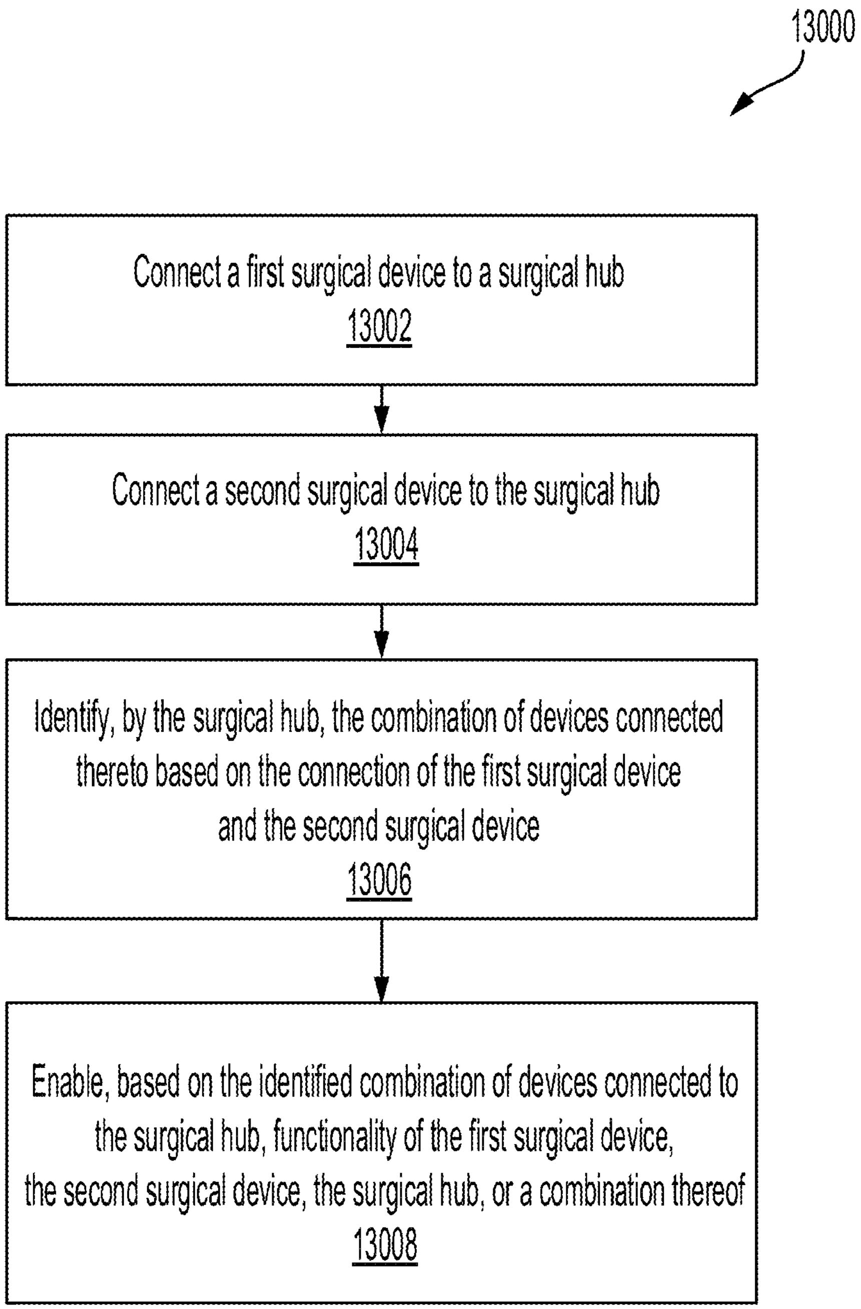

FIG. 54 illustrates a logic diagram of a method for enabling functionality based on combinations of connected surgical devices, according to one aspect of this disclosure.

Figure 55:
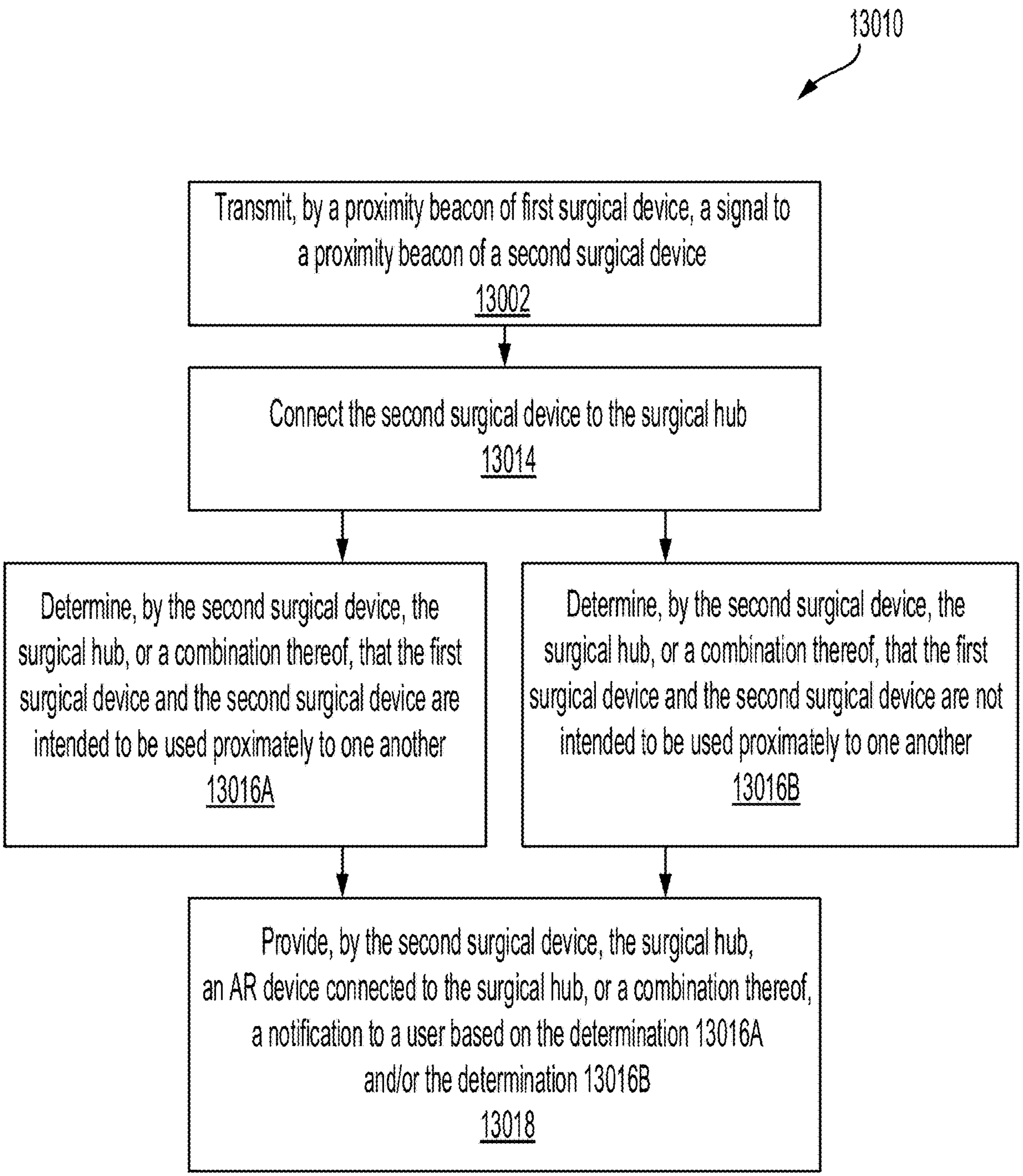

FIG. 55 illustrates a logic diagram of a method for determining if multiple surgical instruments are intended to be used in proximity to one another, according to one aspect of this disclosure.

Figure 56:
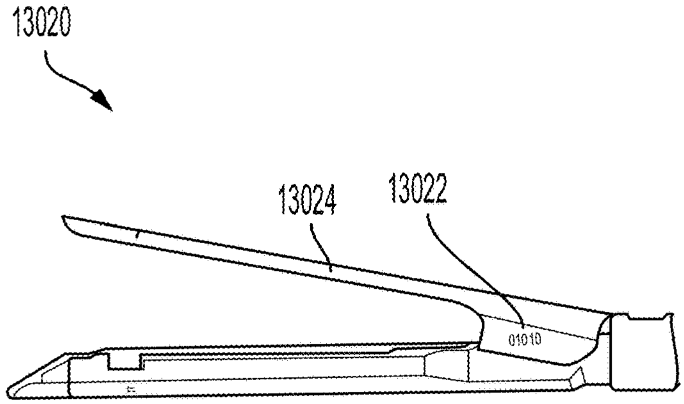

FIG. 56 illustrates a surgical instrument including an identification code as well as a corresponding identification code table, according to one aspect of this disclosure.

Figure 57A:
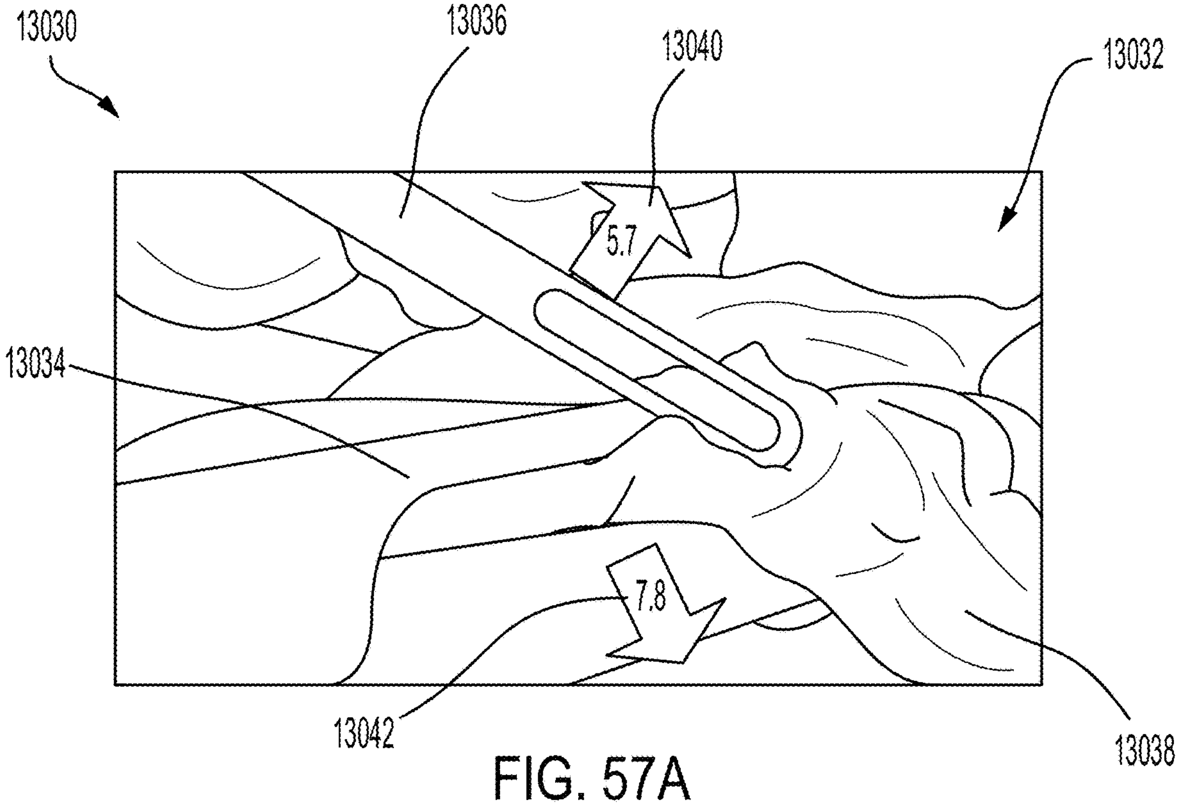
Figure 57B:
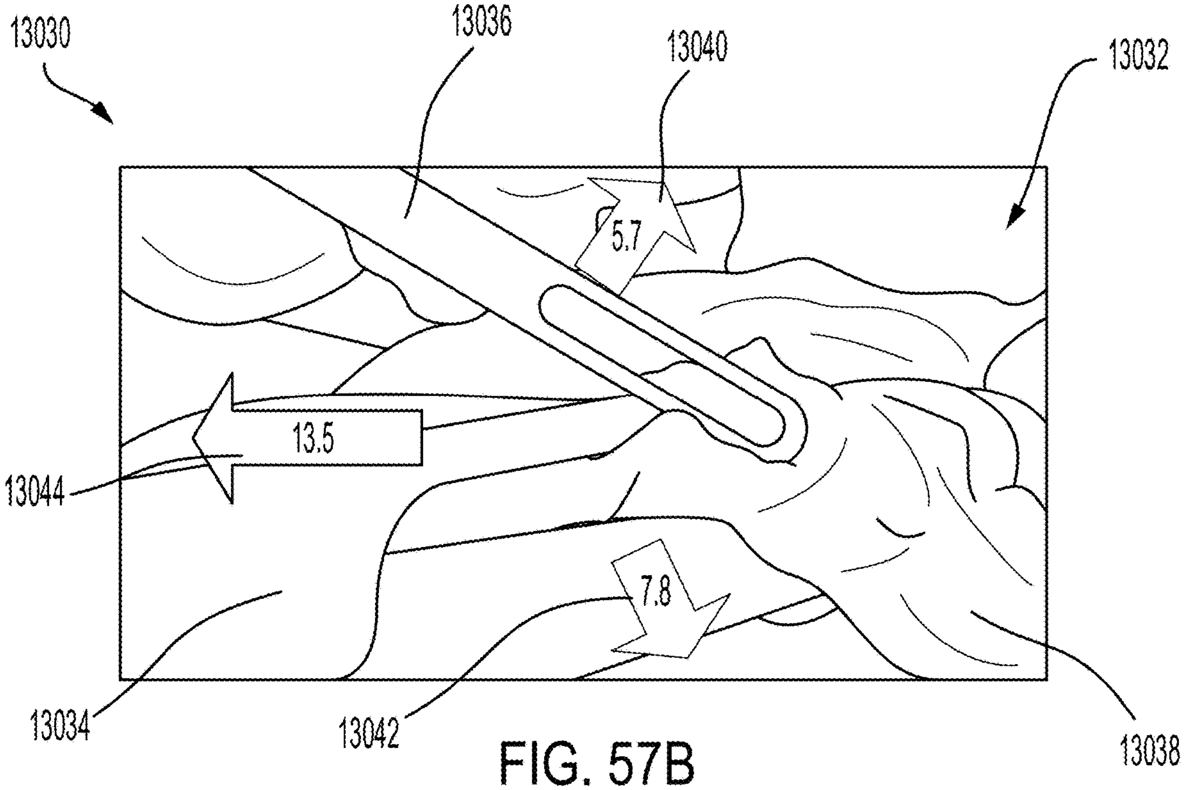

FIGS. 57A and 57B illustrate an exemplary intraoperative display displaying an endo-cutter and a surgical grasper interacting with tissue in a surgical field, according to one aspect of this disclosure.

FIGS. 58A, 58B, 58C, and 58D illustrate an exemplary intraoperative display displaying the performance of an anastomosis procedure using an anvil and a device deck, according to one aspect of this disclosure.

Figure 59:
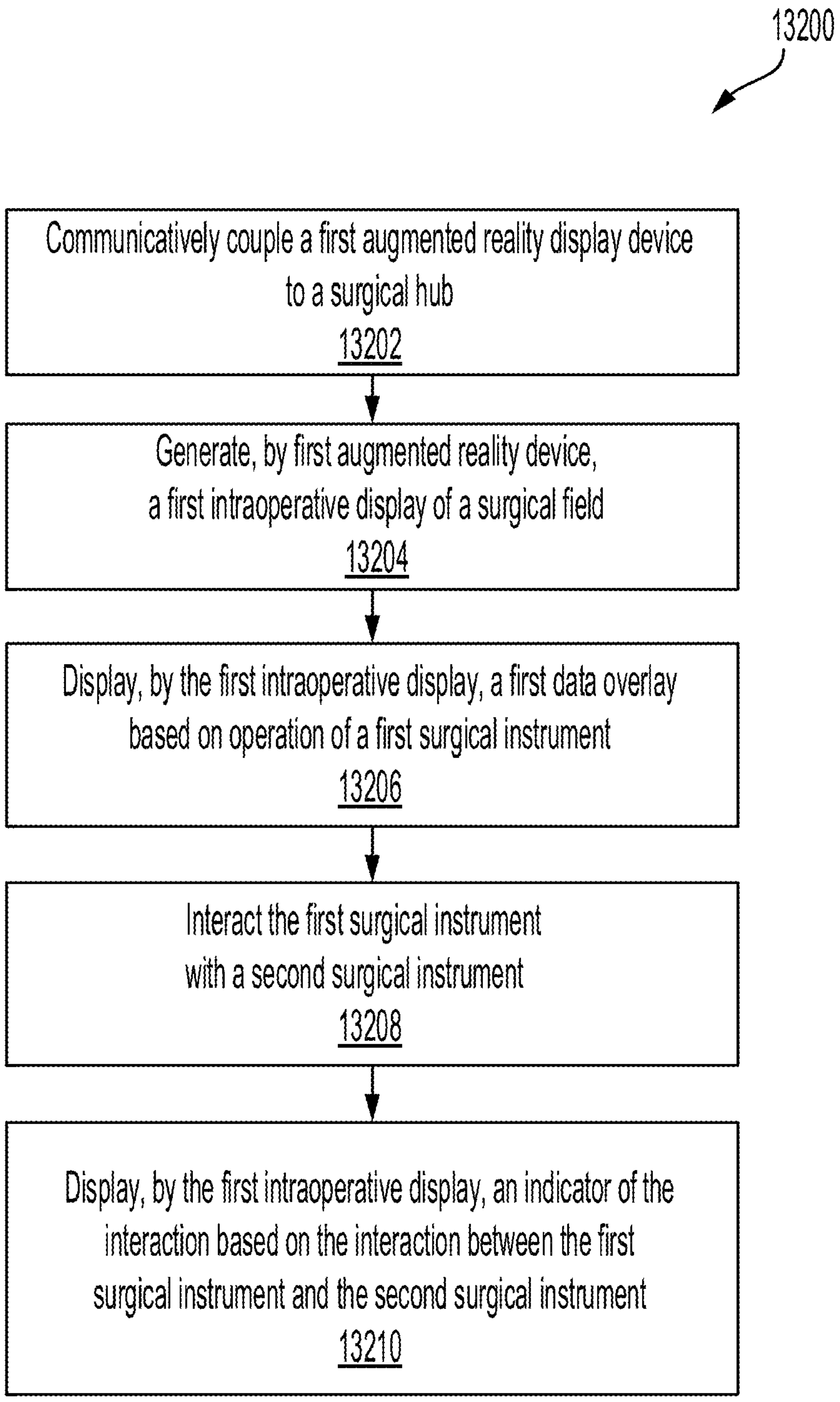

FIG. 59, illustrates a logic diagram of method for displaying a cooperative overlay of interacting instruments, according to one aspect of this disclosure.

Figure 60:
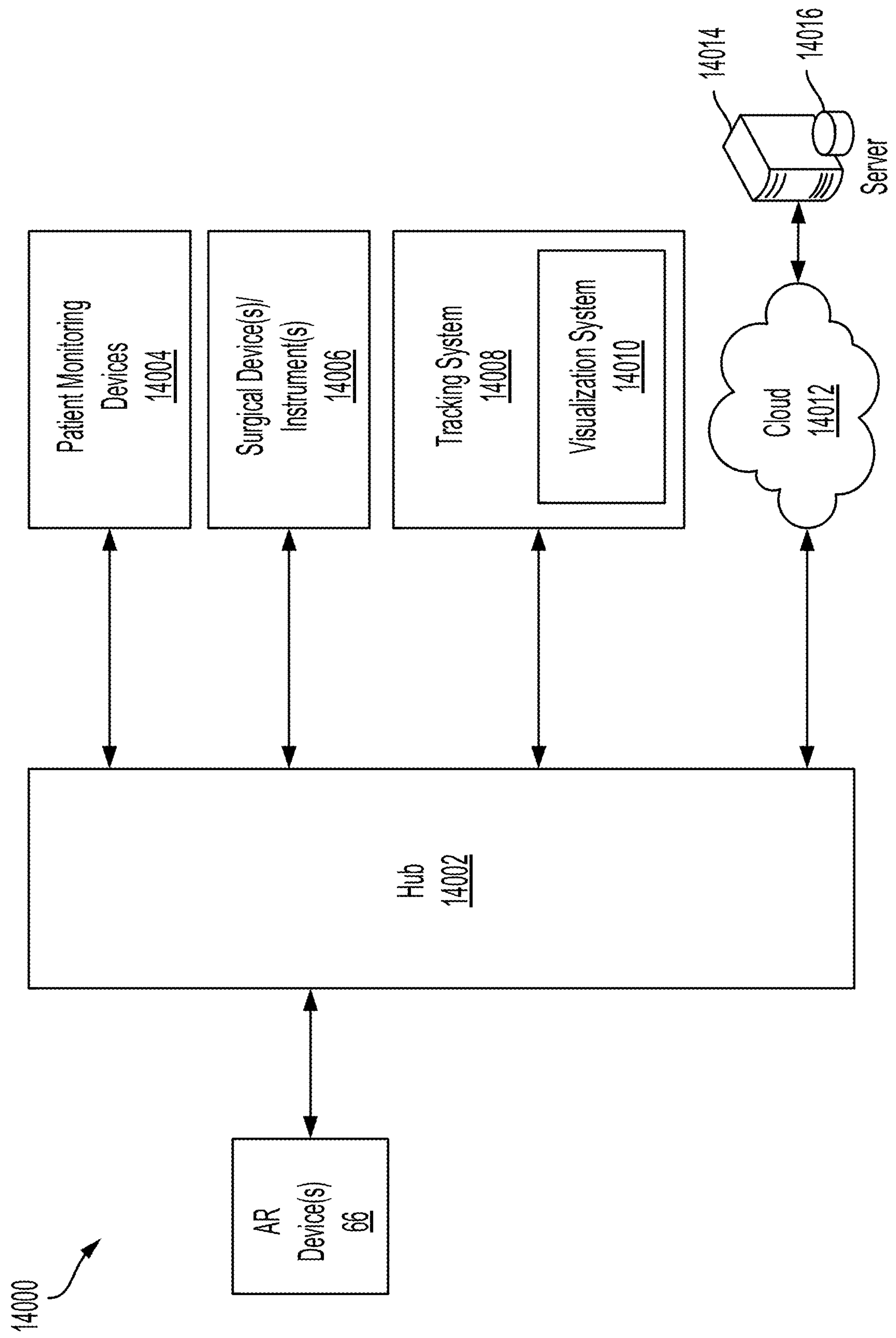

FIG. 60 illustrates a surgical system configured to display interactive overlays for multiple users based on a plurality of data streams, according to one aspect of this disclosure.

Figure 61:
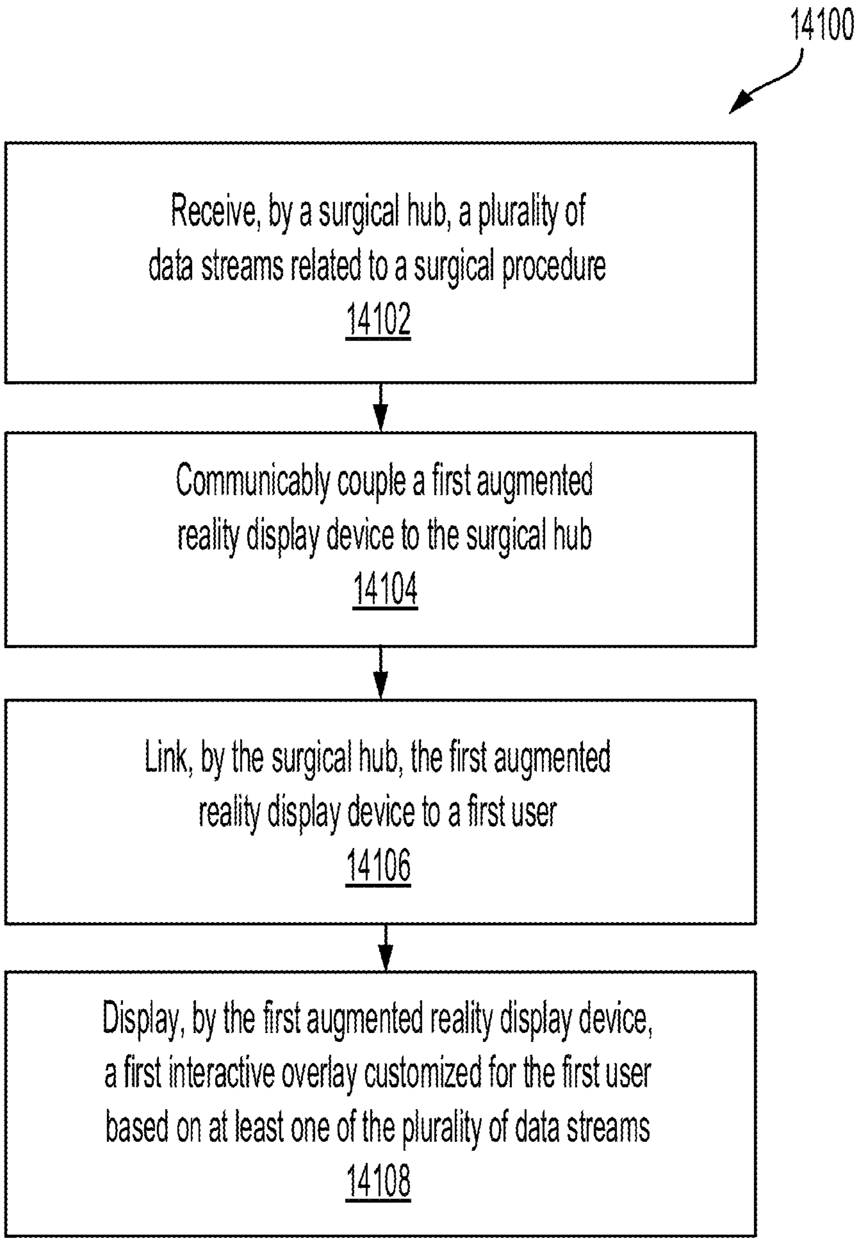

FIG. 61 illustrates a method of displaying interactive overlays for multiple users of a surgical system, according to one aspect of this disclosure.

Figure 62:
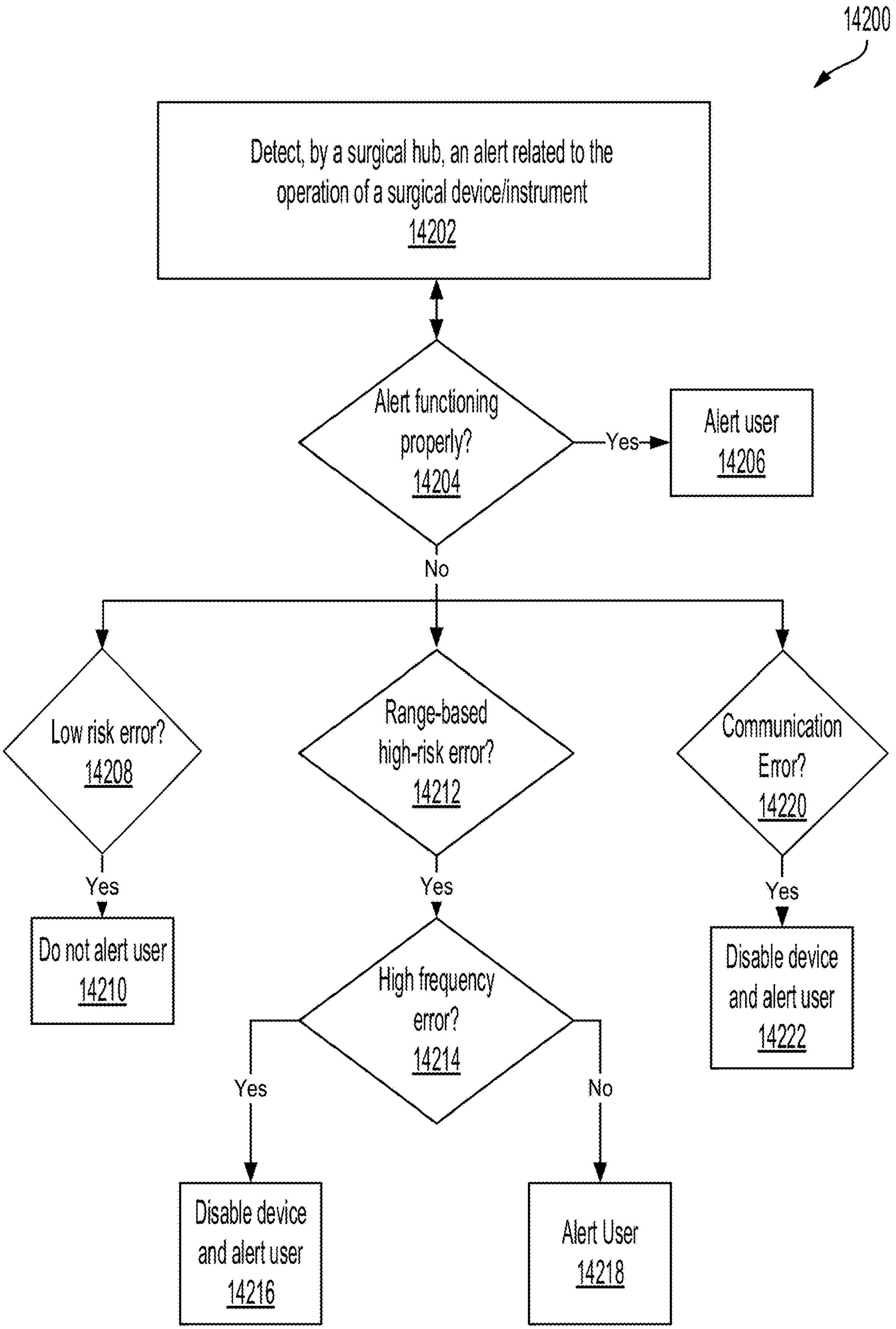

FIG. 62 illustrates a method for detecting a device-related error and determining actions to implement based on the detected error, according to one aspect of this disclosure.

FIGS. 63A, 63B, 63C, 63D, 63E, and 63F illustrate an exemplary implementation of the method of FIG. 62 during a thyroidectomy procedure, according to one aspect of this disclosure.

Figure 64:
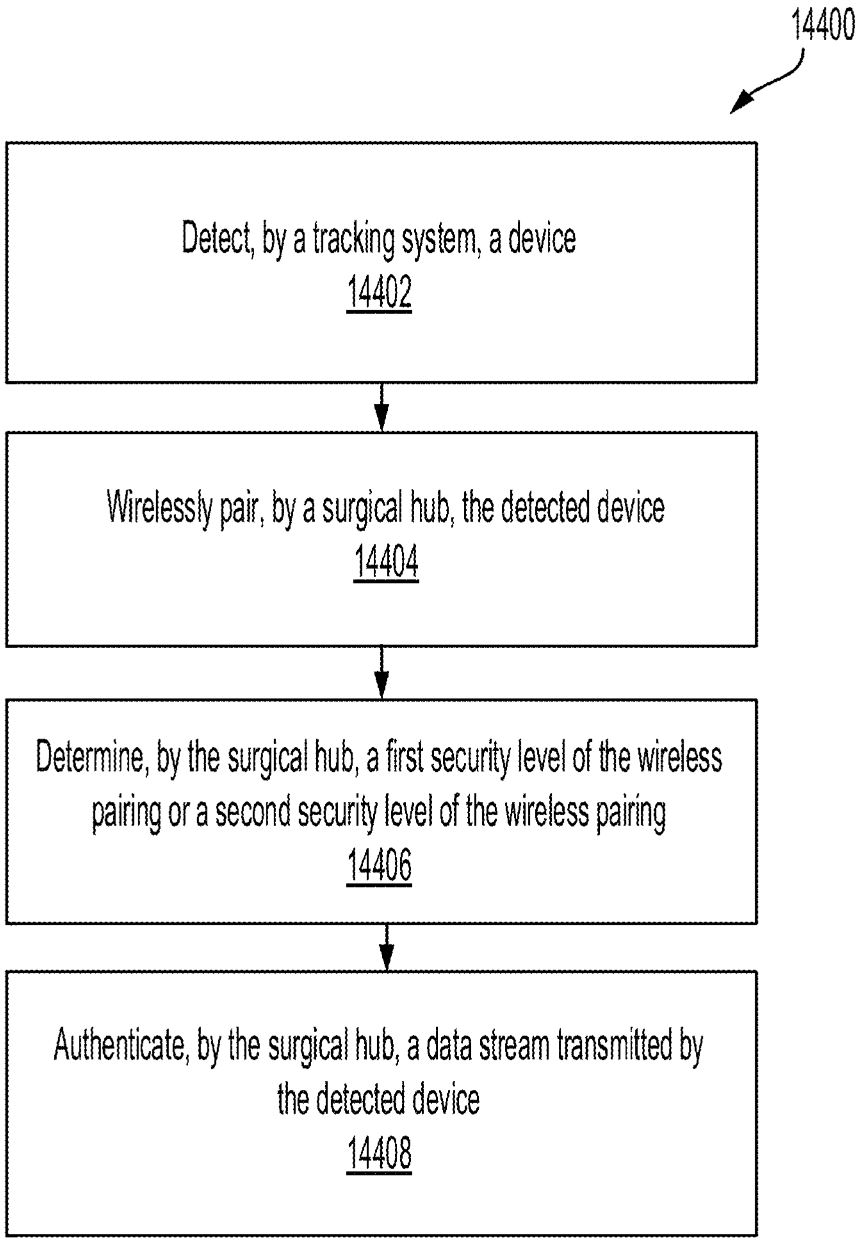

FIG. 64 illustrates a method for ensuring the secure wireless paring of smart devices to a surgical system, according to one aspect of this disclosure.

Figure 65:
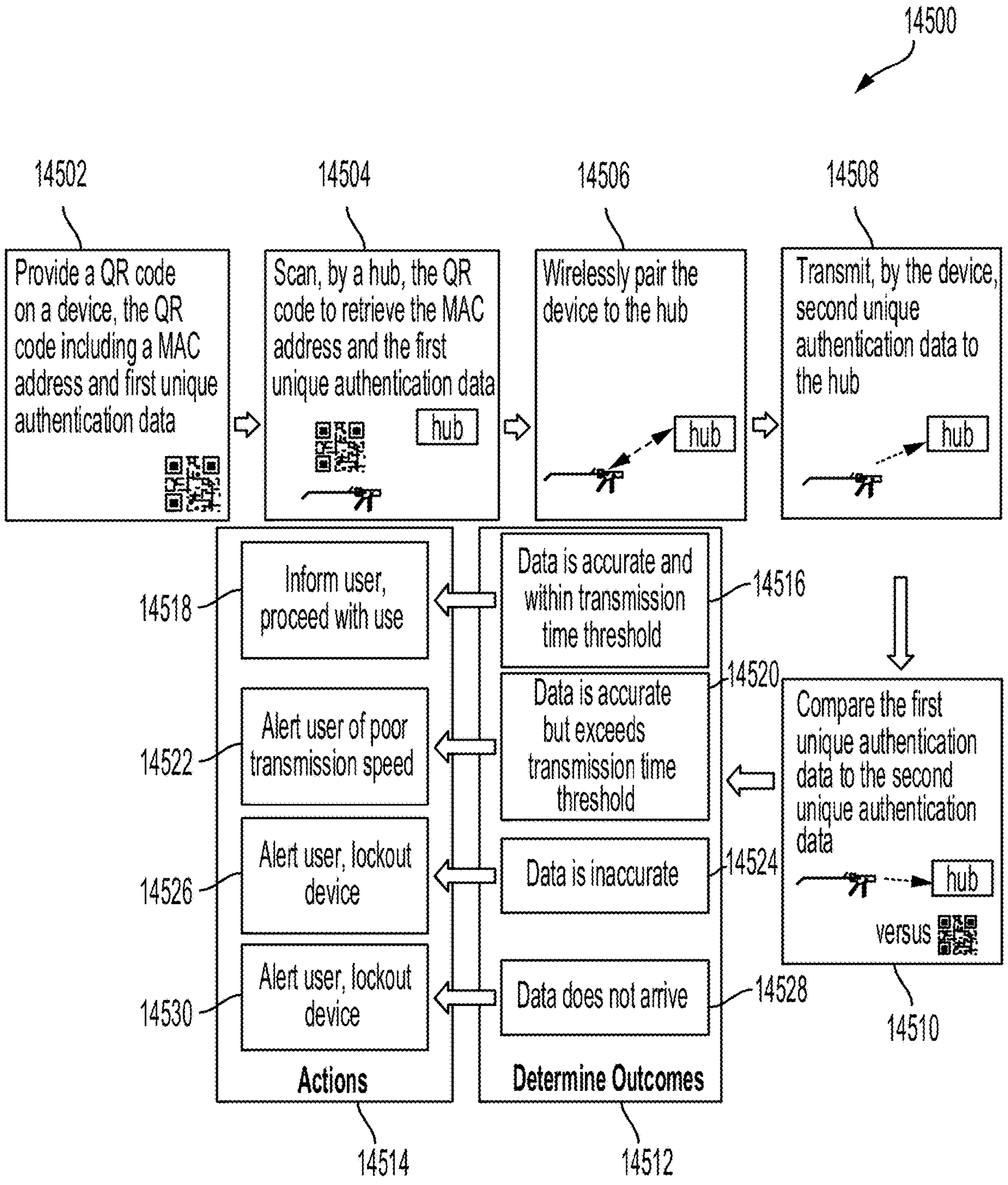

FIG. 65 illustrates a method for ensuring data authenticity and/or integrity after initial device pairing, according to one aspect of this disclosure.

Figure 66:
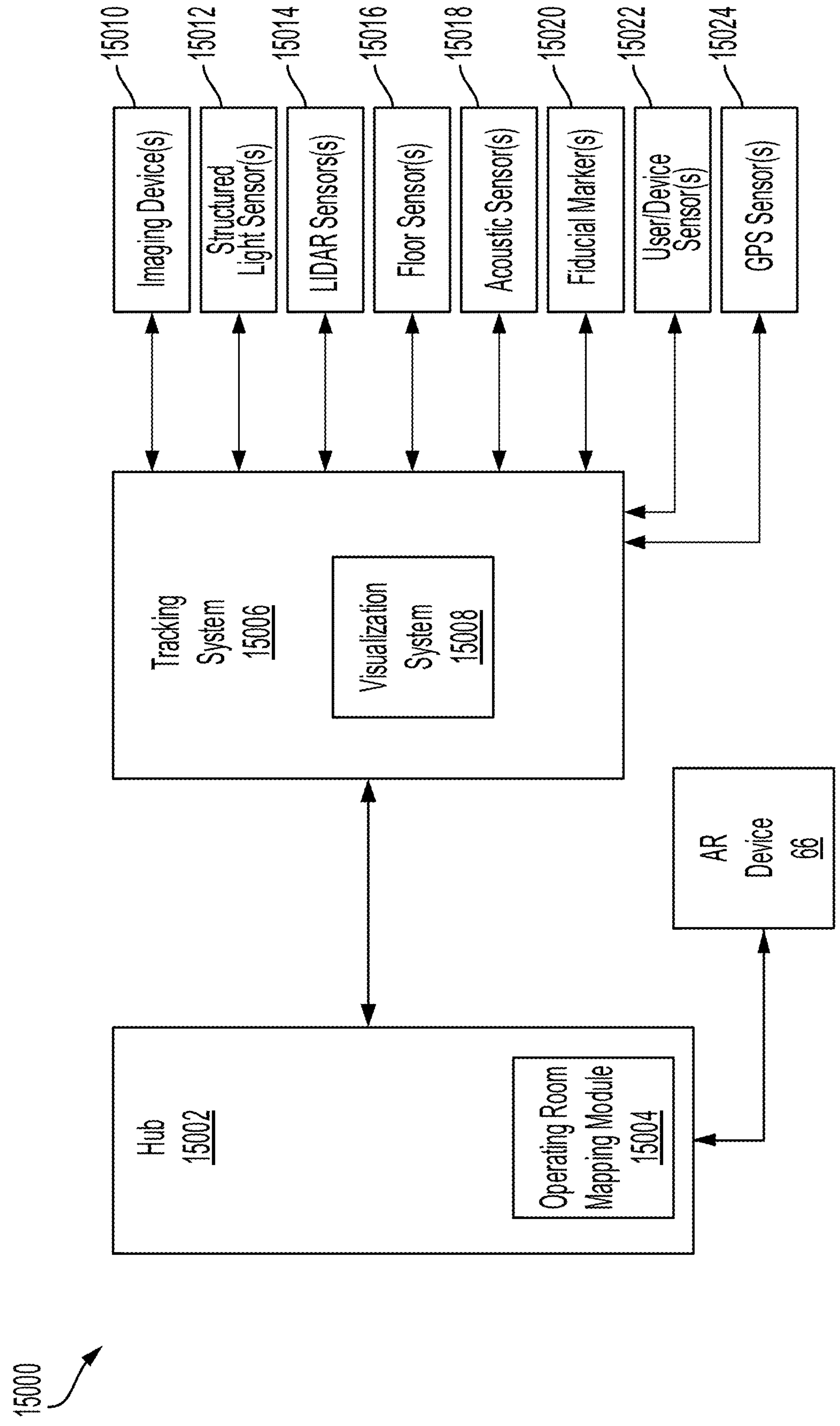

FIG. 66 illustrates a surgical system including a tracking system configured to track objects within an operating room, according to one aspect of this disclosure.

Figure 67:
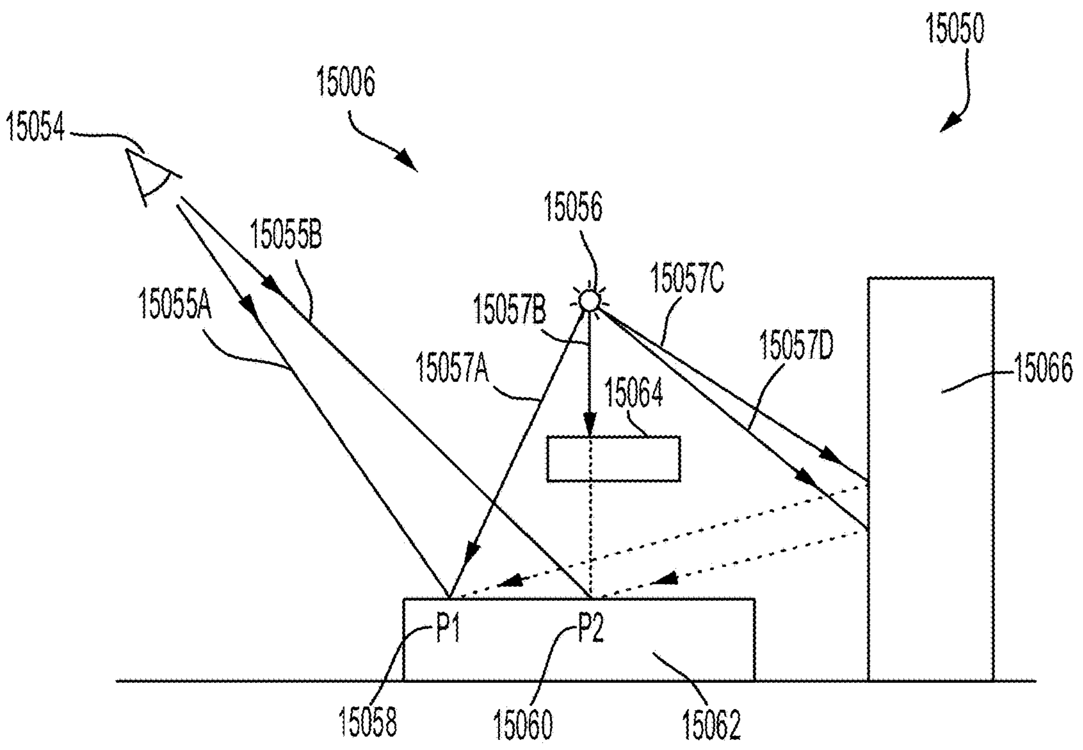

FIG. 67 illustrates a schematic side view of an exemplary implementation the tracking system of FIG. 66 in an operating room, according to one aspect of this disclosure.

Figure 68:
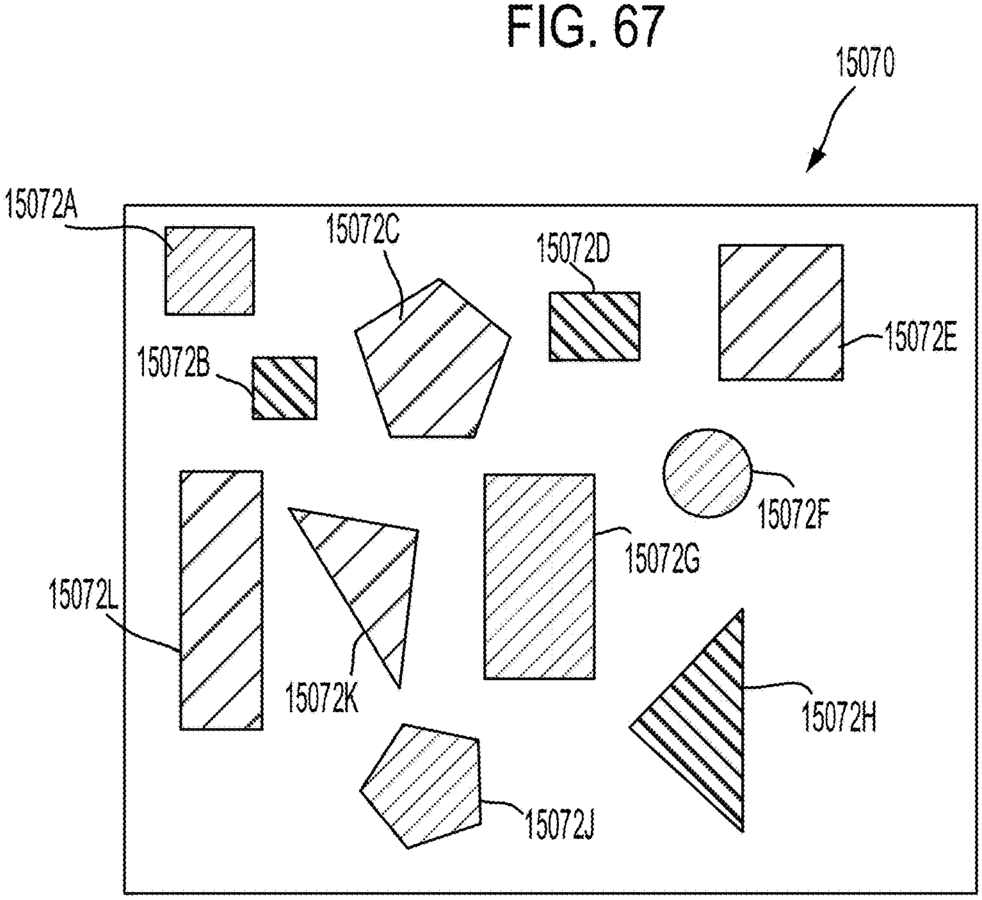

FIG. 68 illustrates a schematic plan view of an exemplary operating room map generated by an operating room mapping module, according to one aspect of this disclosure.

FIG. 69 is a table of exemplary tracked object interactions determined by a surgical hub based on data generated by a tracking system, according to one aspect of this disclosure.

Figure 70A:
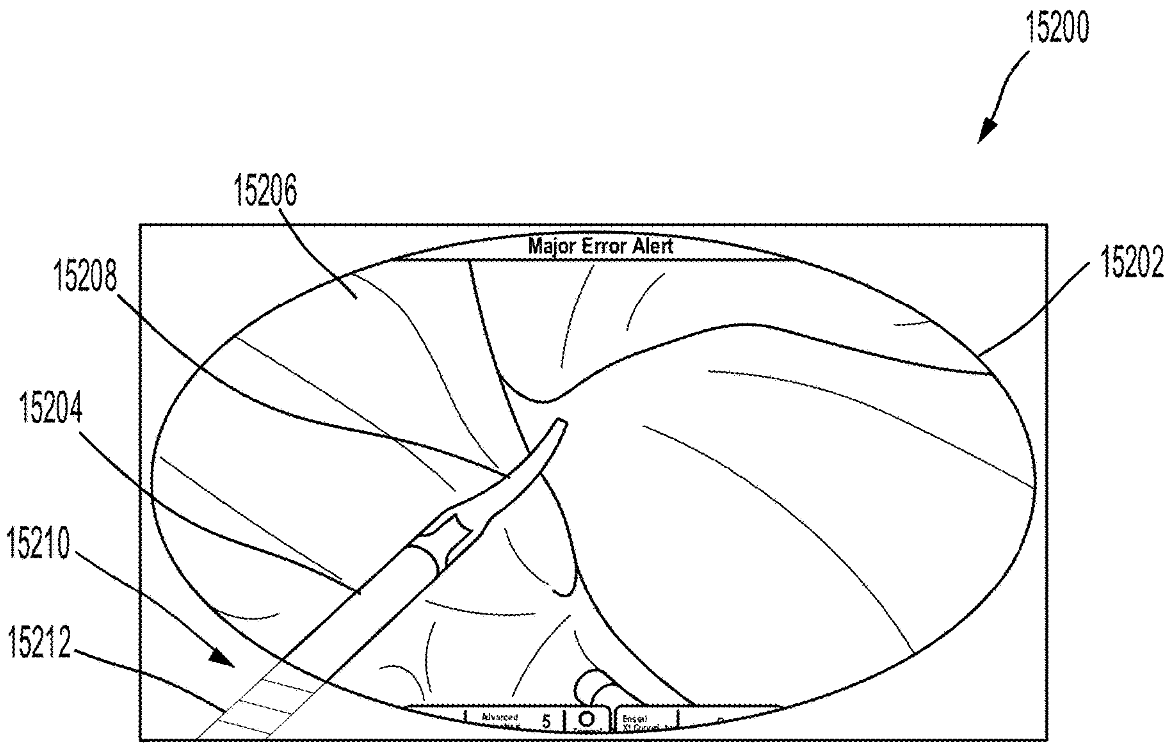
Figure 70B:
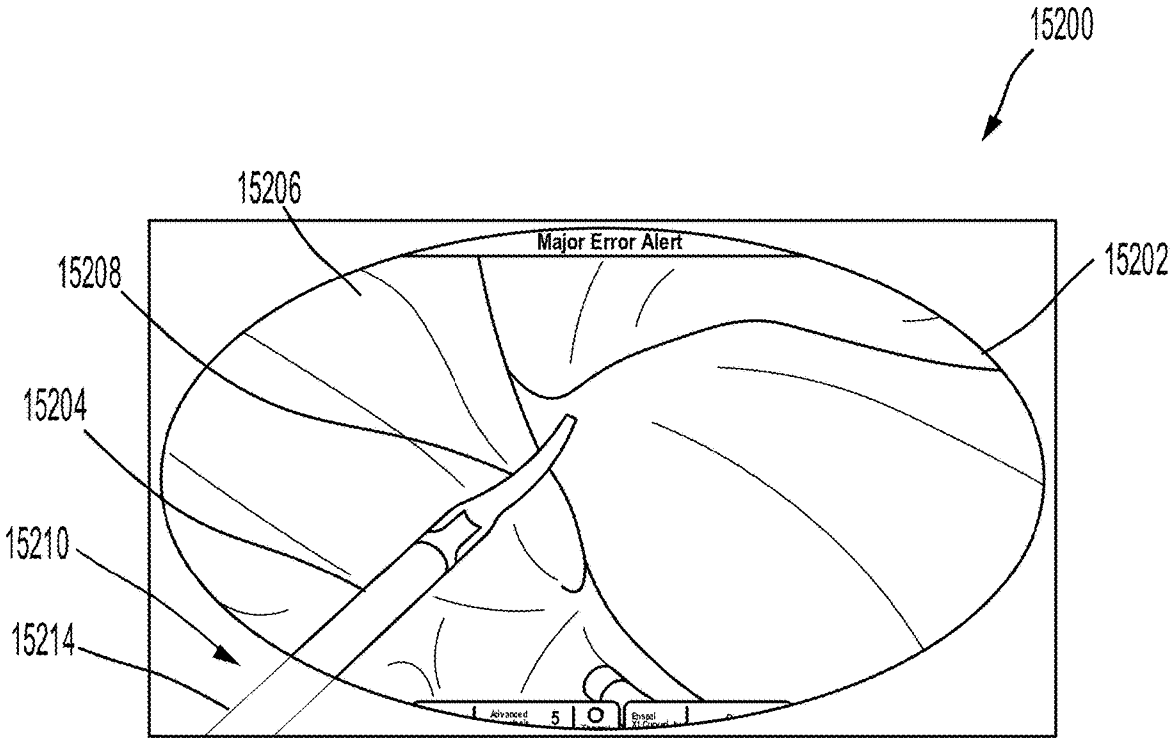

FIGS. 70A and 70B illustrate exemplary intraoperative displays including an image of a surgical instrument in a surgical field and a graphic representing a portion of the surgical instrument outside of the field of view, according to one aspect of this disclosure.

Figure 71A:
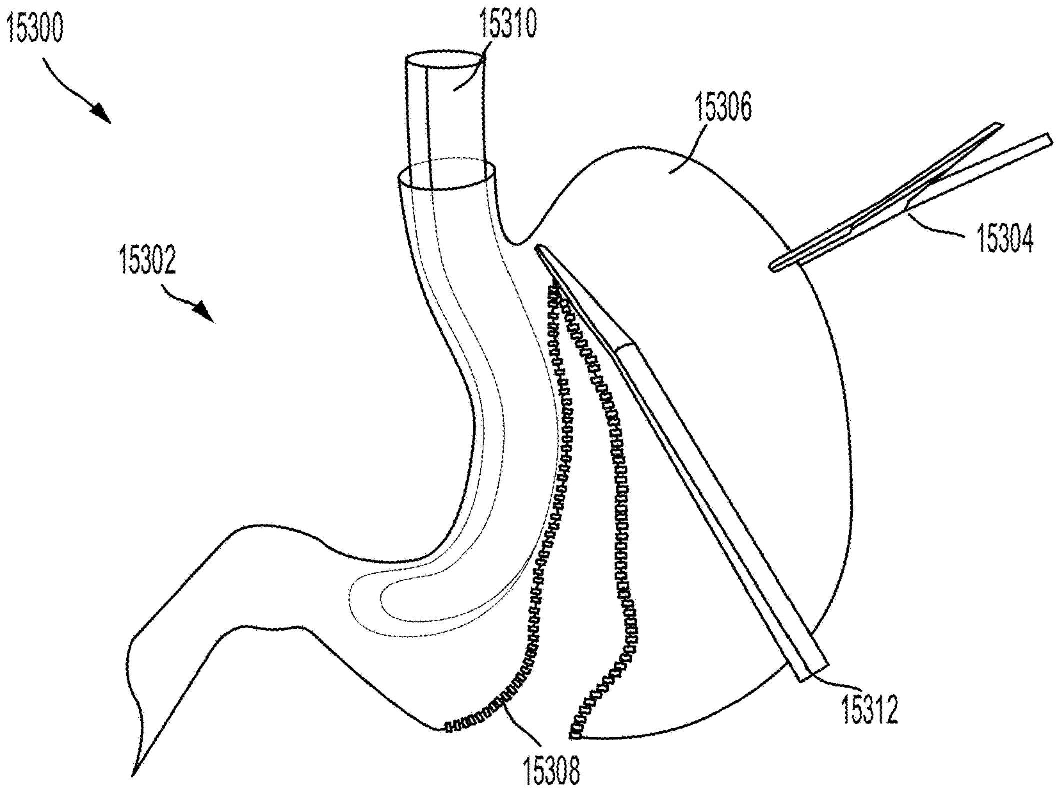
Figure 71B:
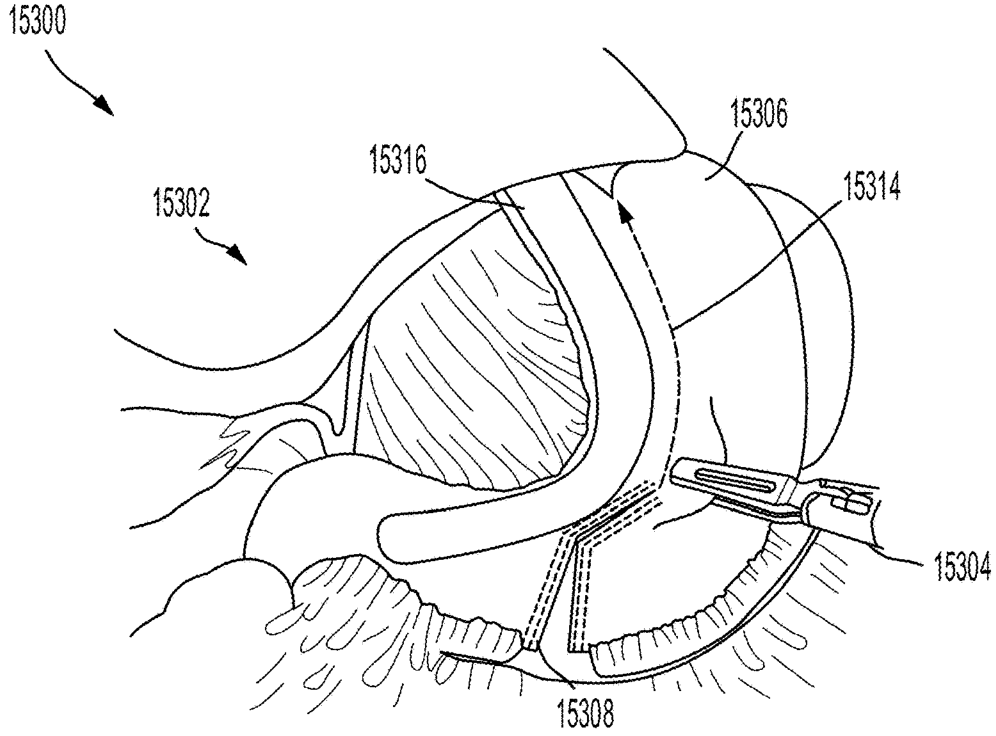

FIGS. 71A and 71B illustrate exemplary intraoperative displays including an image of stomach tissue as a surgeon makes a cut line in the stomach tissue using an endo-cutter, according to one aspect of this disclosure.

Figure 72:
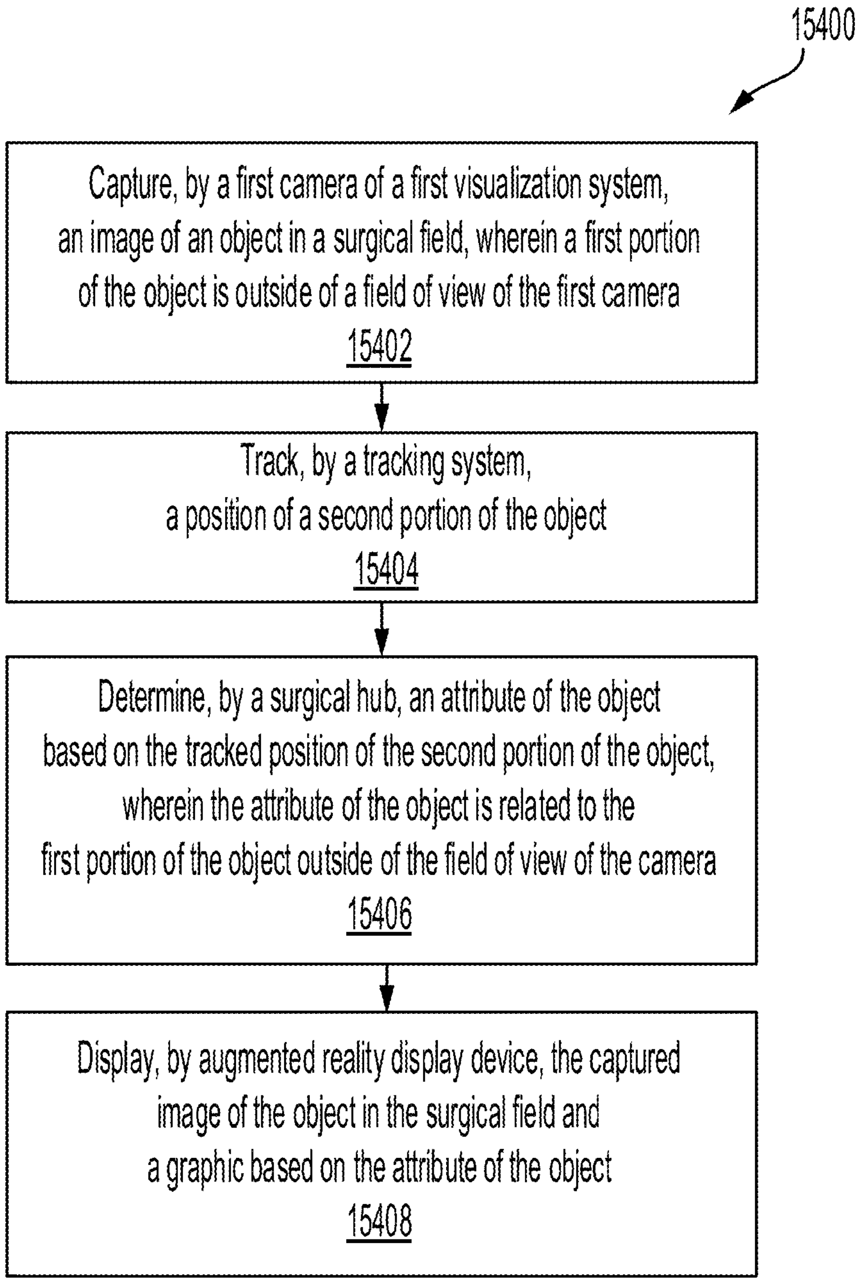

FIG. 72 illustrates a method for mixed reality visualization of a surgical system, according to one aspect of this disclosure.

Figure 73:
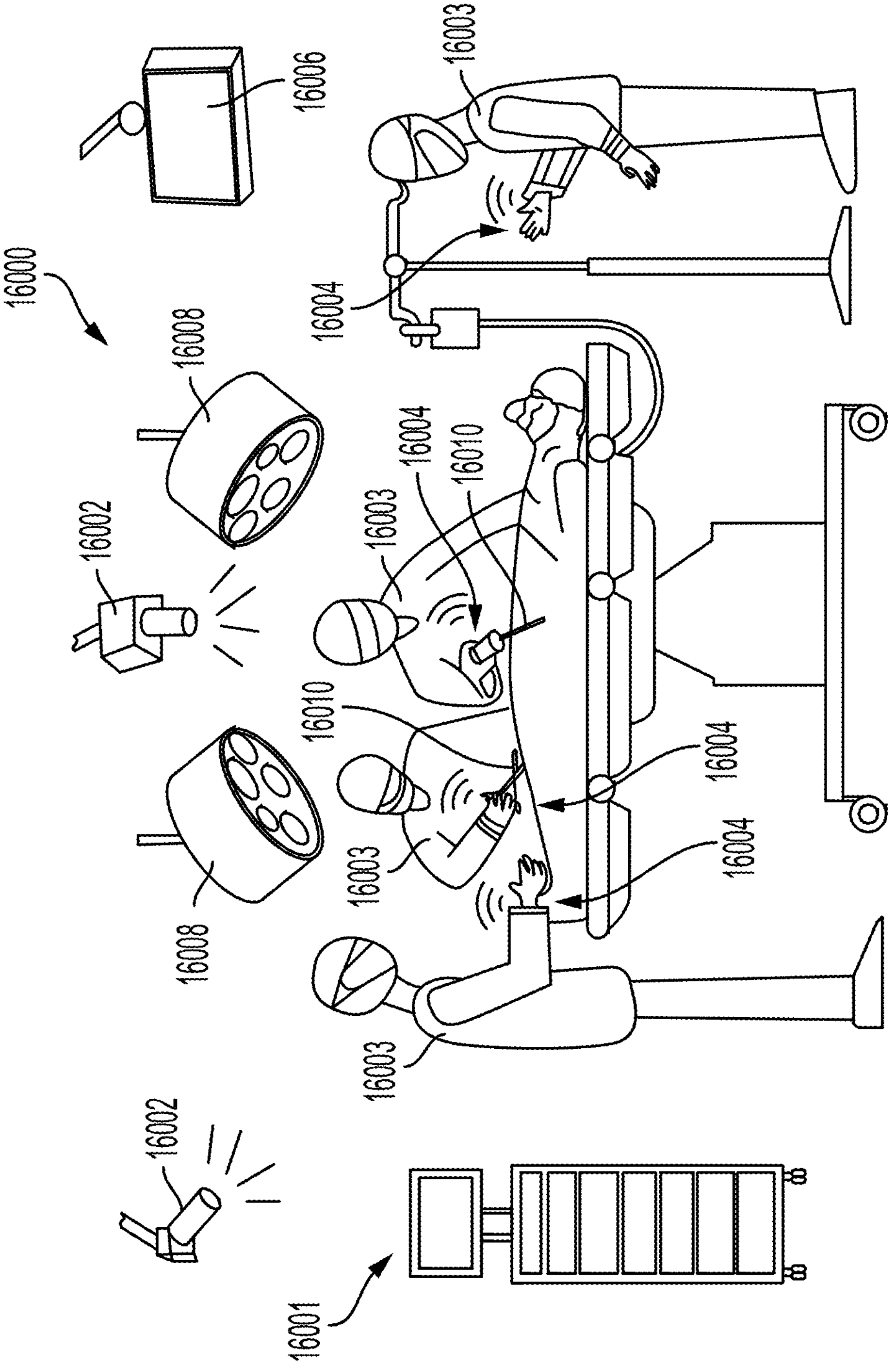

FIG. 73 is a diagram of an illustrative OR setup with a passive tracking camera system, according to one aspect of this disclosure.

Figure 74:
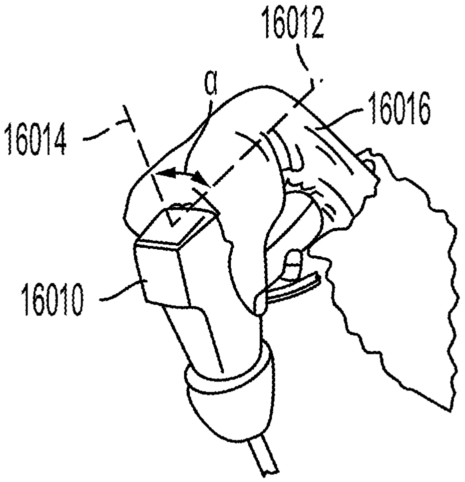

FIG. 74 shows a surgical hub configured to determine the position of a surgical instrument, based on the wrist angle of the surgical staff members, according to one aspect of this disclosure.

Figure 75:
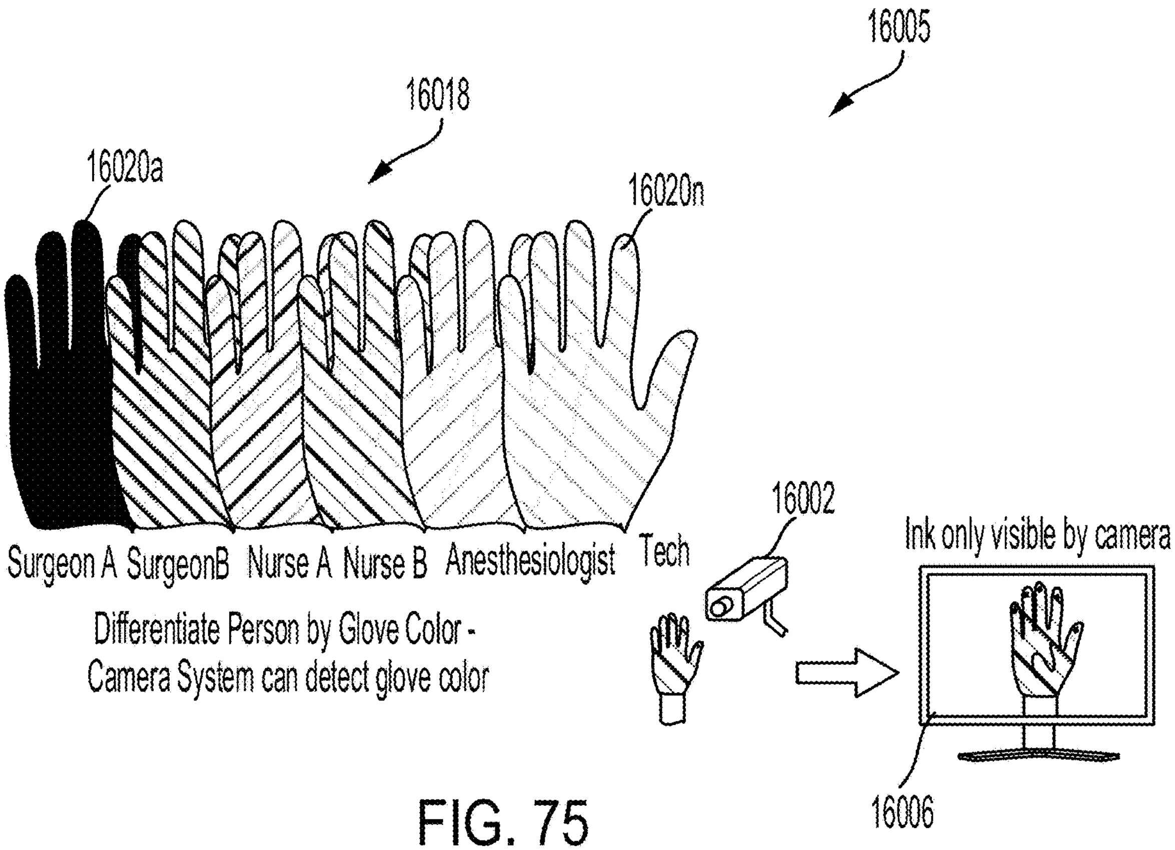

FIG. 75 shows a passive tracking system comprising one or more cameras configured to uniquely identify and differentiate surgical staff members, in an operating room, according to one aspect of this disclosure.

Figure 76:
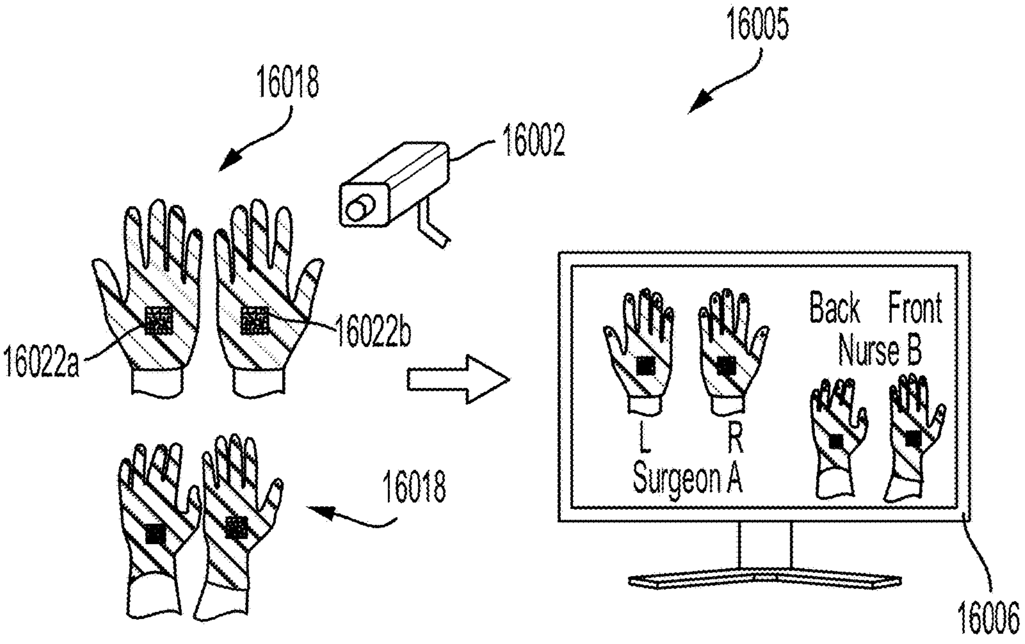

FIG. 76 shows an initialization sequence in a passive tracking system, according to one aspect of this disclosure.

Figure 77:
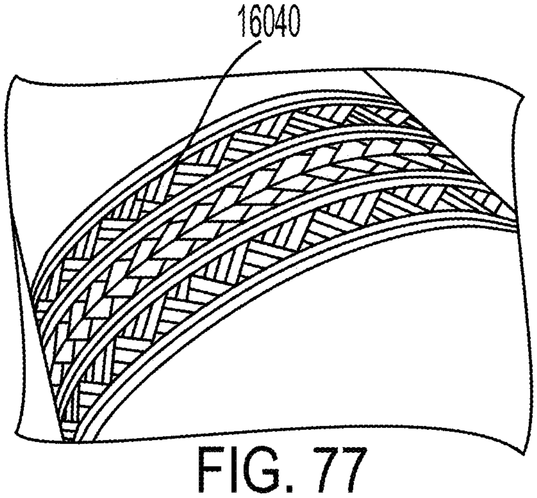

FIG. 77 shows a directional pattern than may be used to differentiate between a left and right appendage or aid the passive tracking cameras in detecting movement, according to one aspect of this disclosure.

Figure 78:
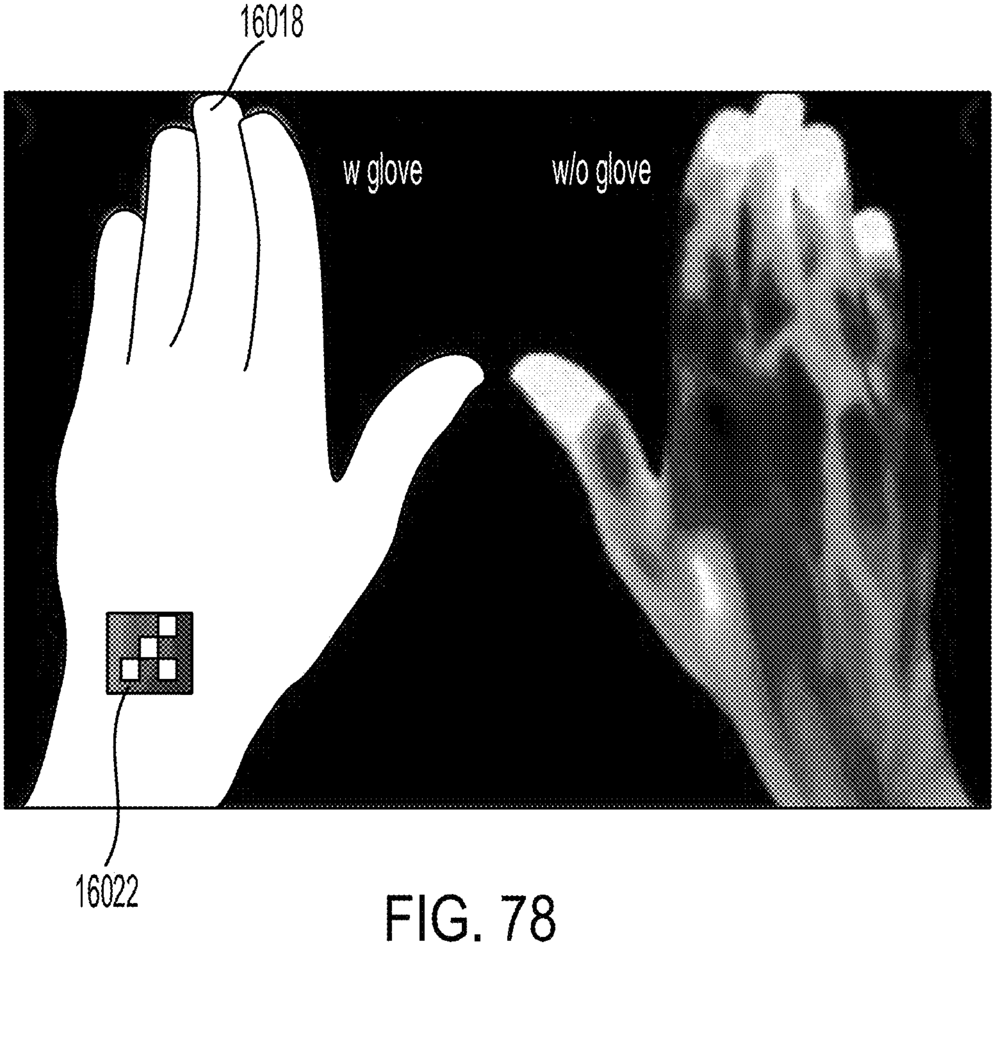

FIG. 78 shows an identifying code on the dorsal side of a surgical glove, detected by a thermal imaging or inferred (IR) camera, according to one aspect of this disclosure.

Figure 79:
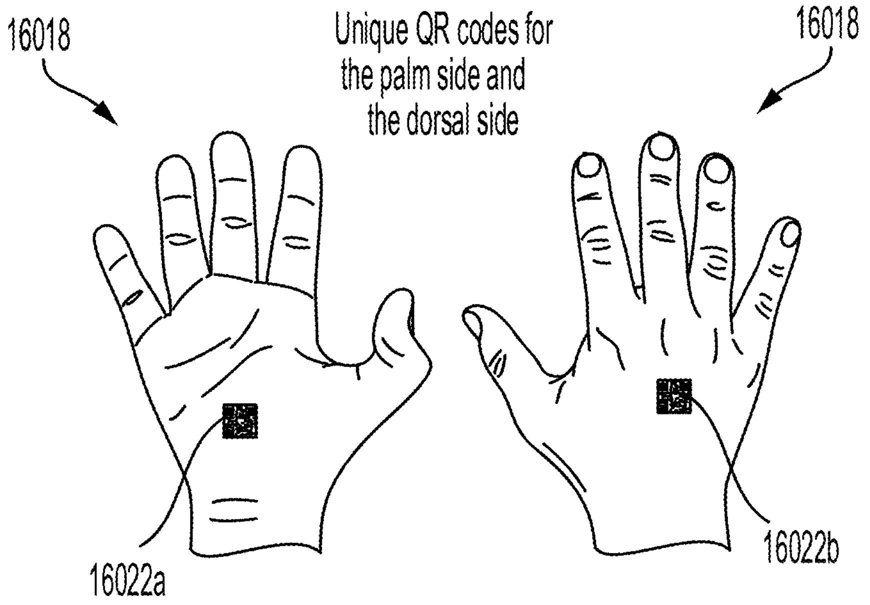

FIG. 79 shows an identifying code on both the dorsal side and palm side a surgical glove, according to one aspect of this disclosure.

Figure 80:
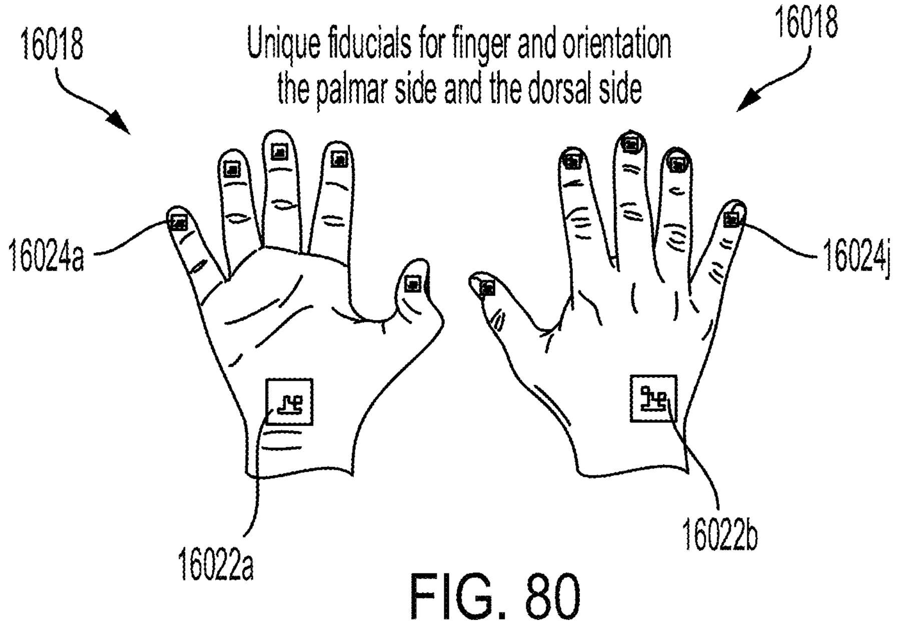

FIG. 80 shows identifying QR codes assigned to each finger of a surgical staff member, according to one aspect of this disclosure.

Figure 81:
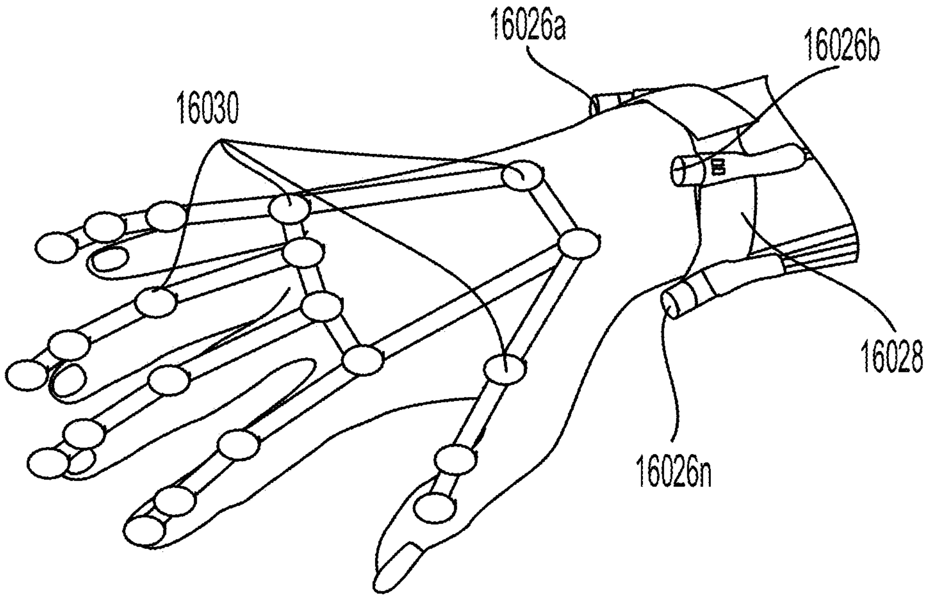

FIG. 81 shows a wrist-mounted camera configured to monitor and track the finger and wrist movement of a single staff member, according to one aspect of this disclosure.

Figure 82:
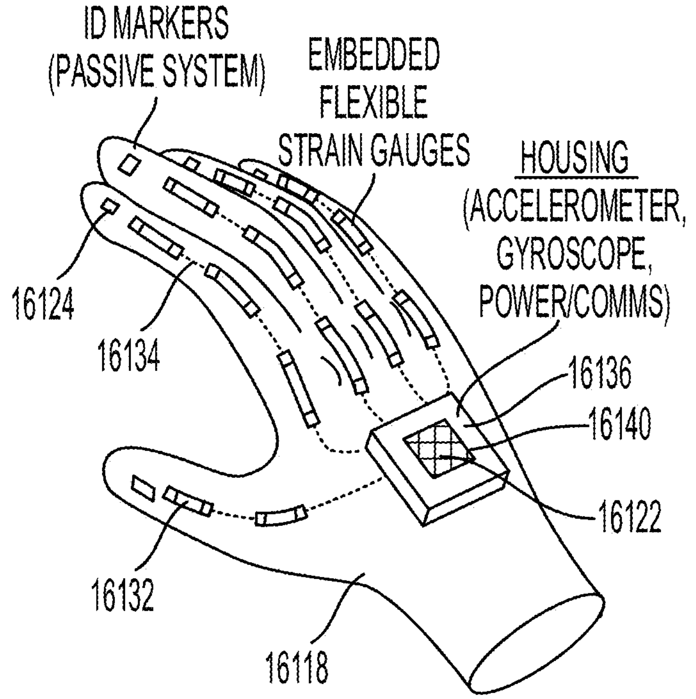

FIG. 82 shows an active surgical glove comprising fiducial markers on each of the fingers, a plurality of embedded strain gauges, and gyroscope coupled to a control circuit, according to one aspect of this disclosure.

Figure 83:
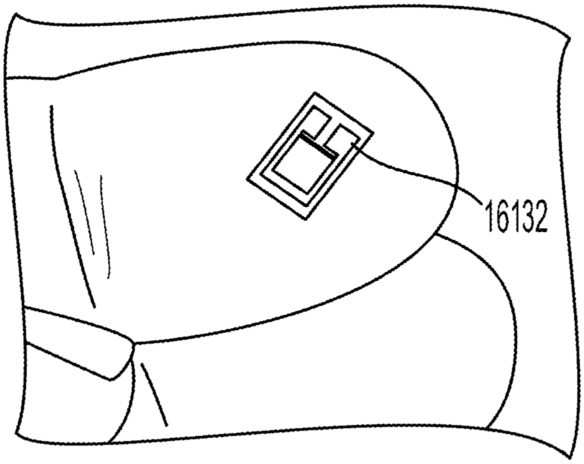

FIG. 83 show a single strain gauge sensor is relation to the tip of a finger, according to one aspect of this disclosure.

Figure 84:
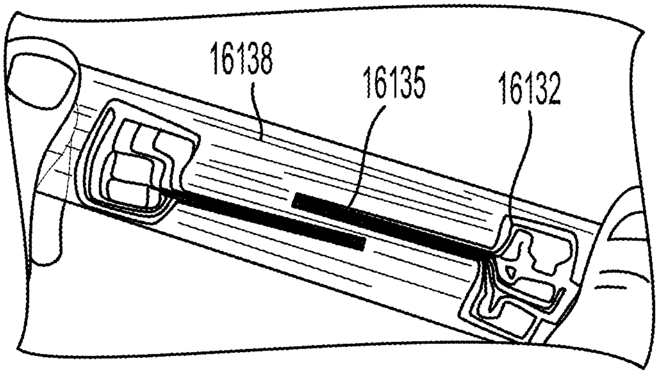

FIG. 84 shows a flexible circuit that is printed into a sterile material such as latex, nitrile, or other sterile materials used in surgical gloves, according to one aspect of this disclosure.

Figure 85:
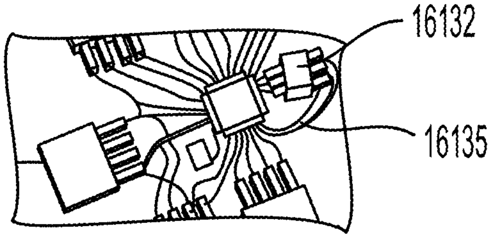

FIG. 85 shows a flexible circuits that may be used to connect the strain gauges to the control circuit, according to one aspect of this disclosure.

Figure 86:
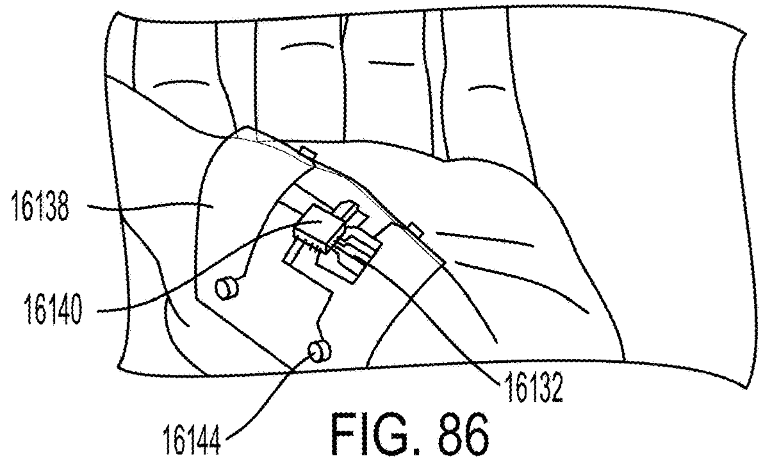

FIG. 86 shows active fiducial markers connected to a control circuit, printed directly on a sterile material, according to one aspect of this disclosure.

Figure 87:
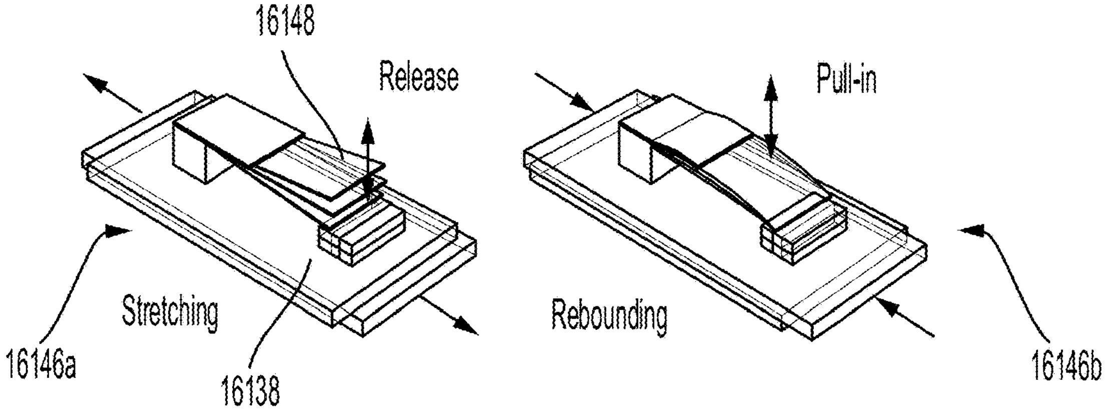

FIG. 87 shows a piezoelectric ceramics power cell that harvests energy from movement and can be used to power the control circuit, strain gauge, gyroscope, accelerometer, and/or active fiducial markers, according to one aspect of this disclosure.

Figure 88:
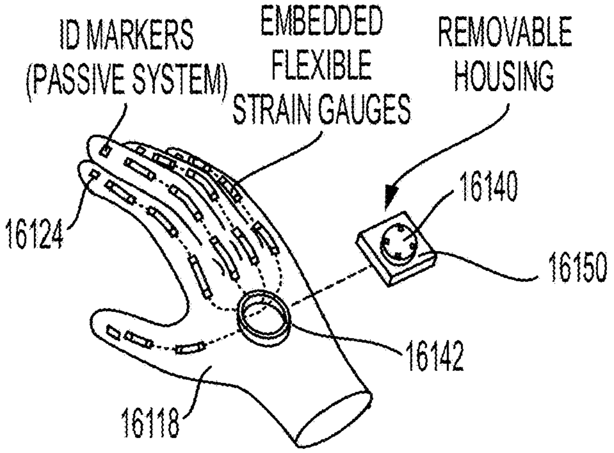

FIG. 88 shows an active sensor glove with a removable housing that comprises the control circuit housing and the gyroscope, according to one aspect of this disclosure.

Figure 89:
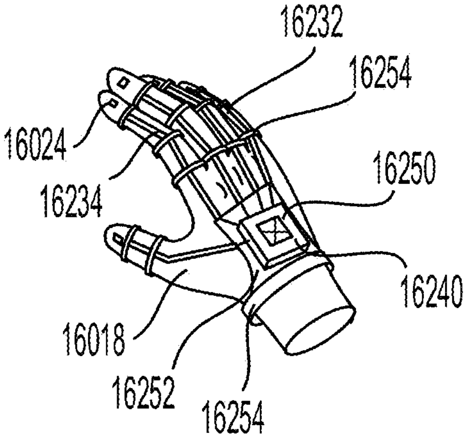

FIG. 89 shows a removable active sensor harness comprising a plurality of embedded strain gauge sensors communicably coupled to a control circuit with flexible wires, within a housing, according to one aspect of this disclosure.

Figure 90:
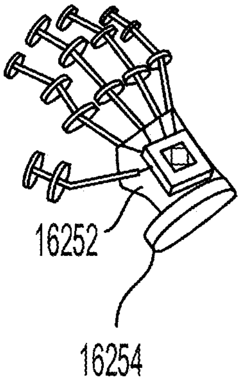

FIG. 90 shows an active sensor harness, removed from a hand, according to one aspect of this disclosure.

Figure 91:
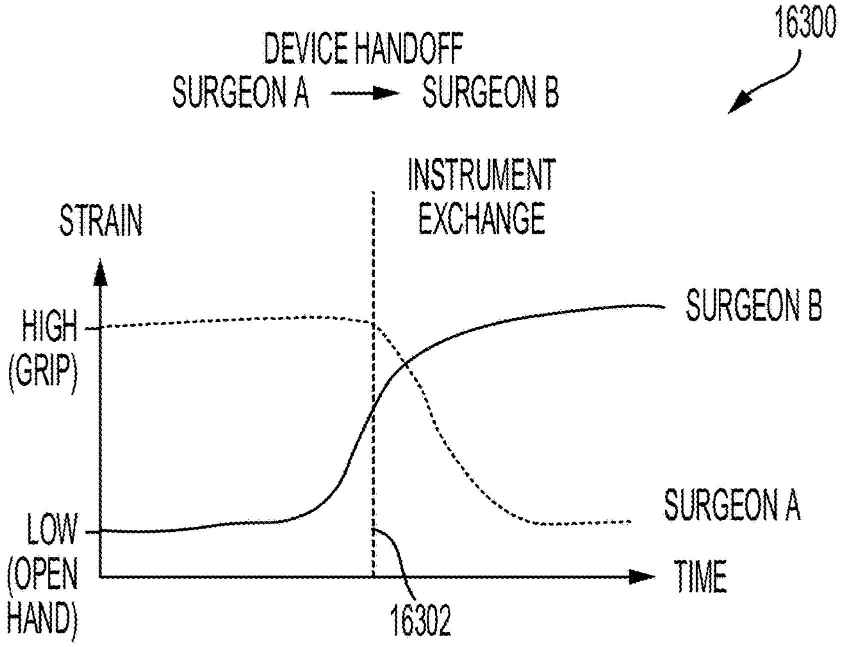

FIG. 91 shows a graphical representation of a surgical instrument hand-off between a first surgeon and a second surgeon, according to one aspect of this disclosure.

Figure 92:
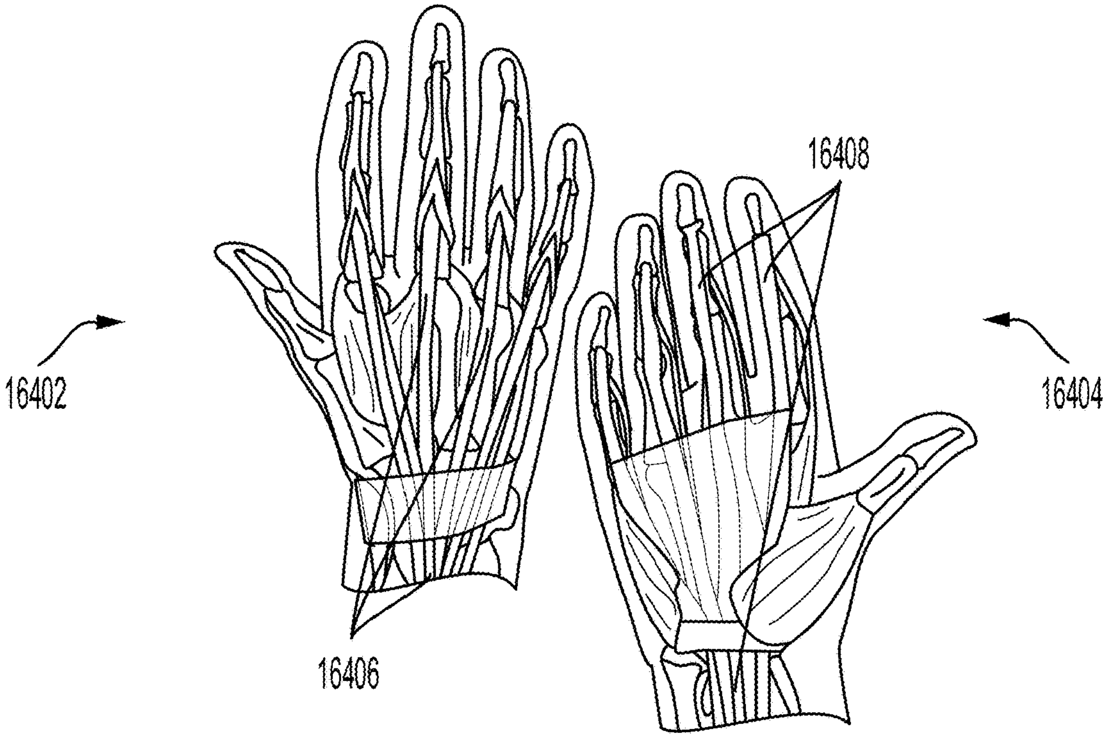

FIG. 92 shows a musculoskeletal view of human hands, according to one aspect of this disclosure.

Figure 93:
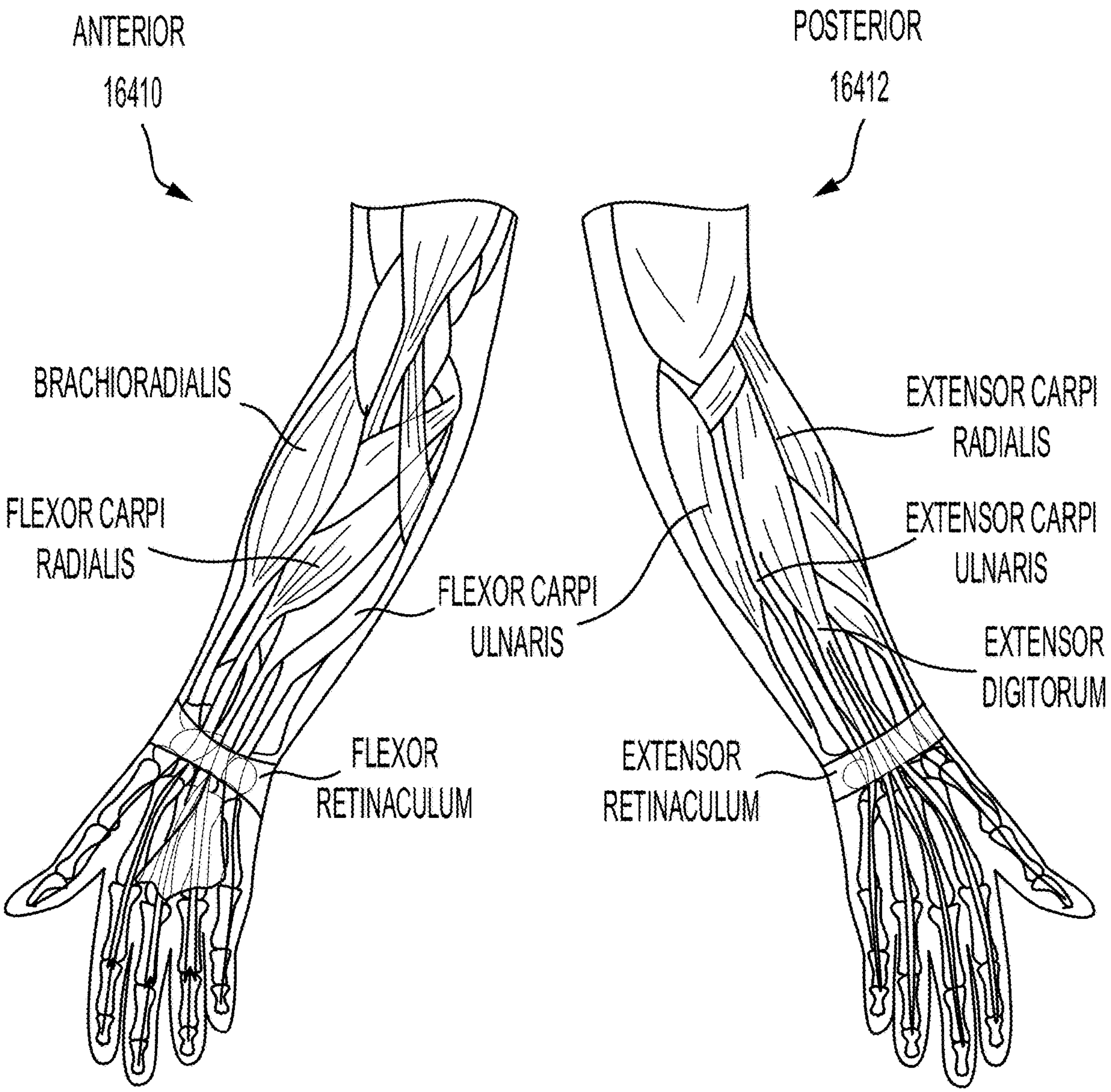

FIG. 93 shows the anterior and posterior side of a right arm, according to one aspect of this disclosure.

Figure 94:
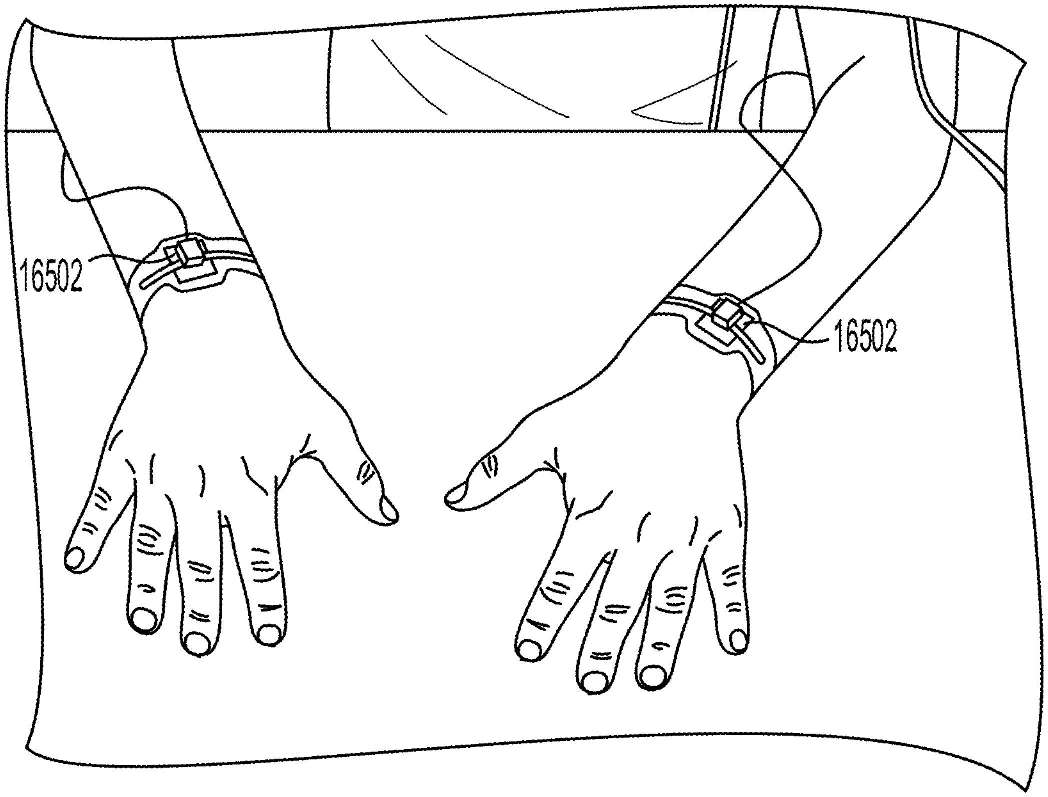

FIG. 94 shows a pair of wrist-mounted sensors communicably coupled to a surgical hub, according to one aspect of this disclosure.

Figure 95:
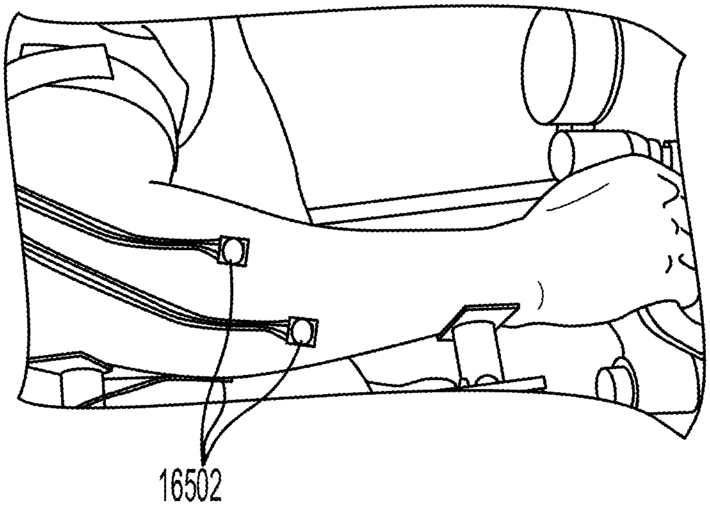

FIG. 95 shows a plurality of MMG sensors mounted directly to the muscles in the forearms, according to one aspect of this disclosure.

Figure 96:
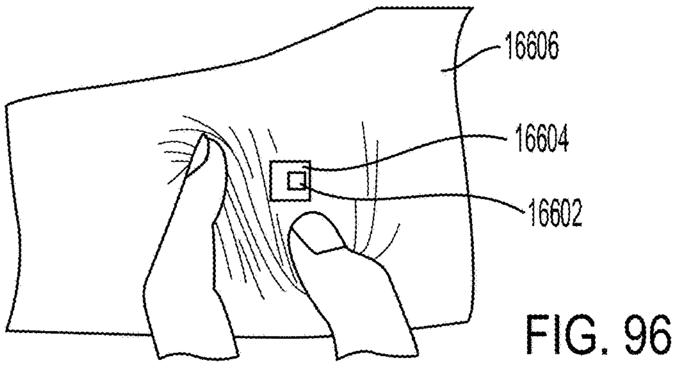

FIG. 96 shows a flexible wireless sensor coupled to a flexible adhesive medium that adheres directly to the skin, according to one aspect of this disclosure.

Figure 97:
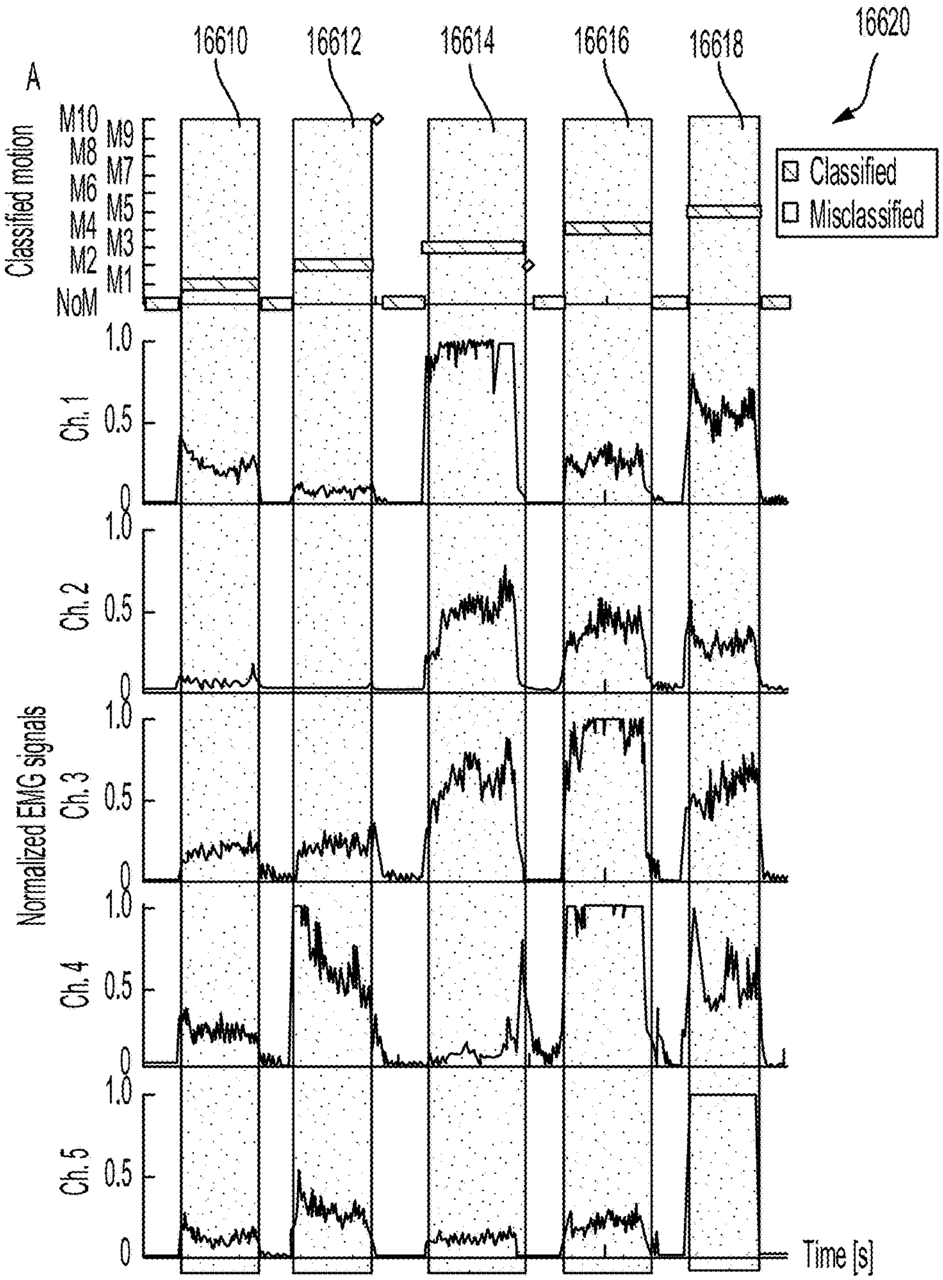

FIG. 97 shows a graphical plot of five EMG channels corresponding the movement of four fingers and a thumb in a hand, according to one aspect of this disclosure.

Figure 98:
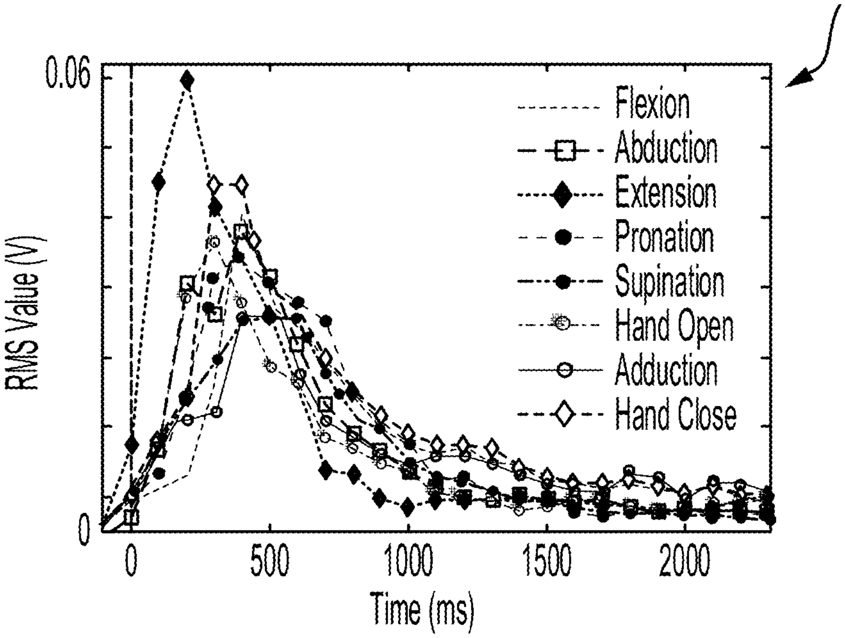

FIG. 98 shows a graphical plot of MMG signals corresponding to the movement and position of a hand, according to one aspect of this disclosure.

Figure 99:
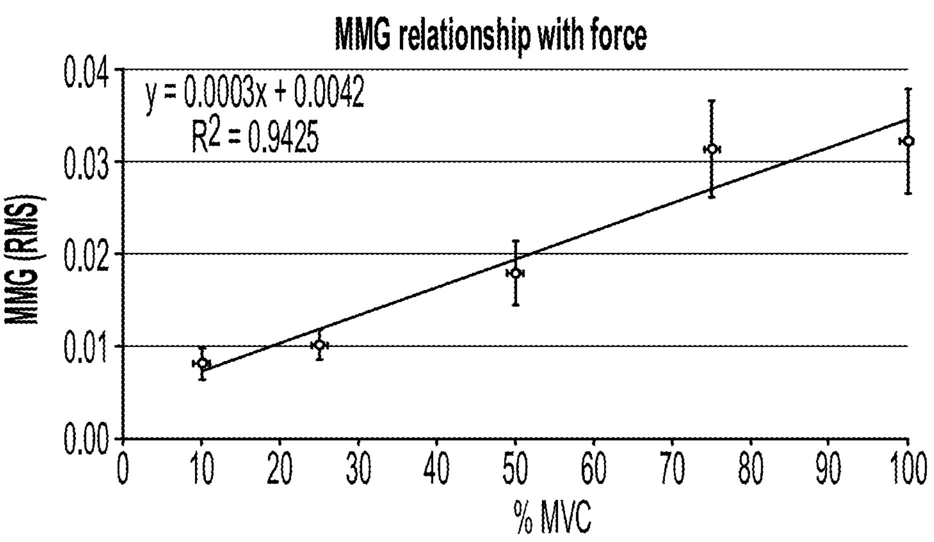

FIG. 99 shows a model that correlates amplitude values for the maximal muscle contraction, measured in Vrms, and the percentage of maximal voluntary contraction (% MCV), according to one aspect of this disclosure.

Figure 100:
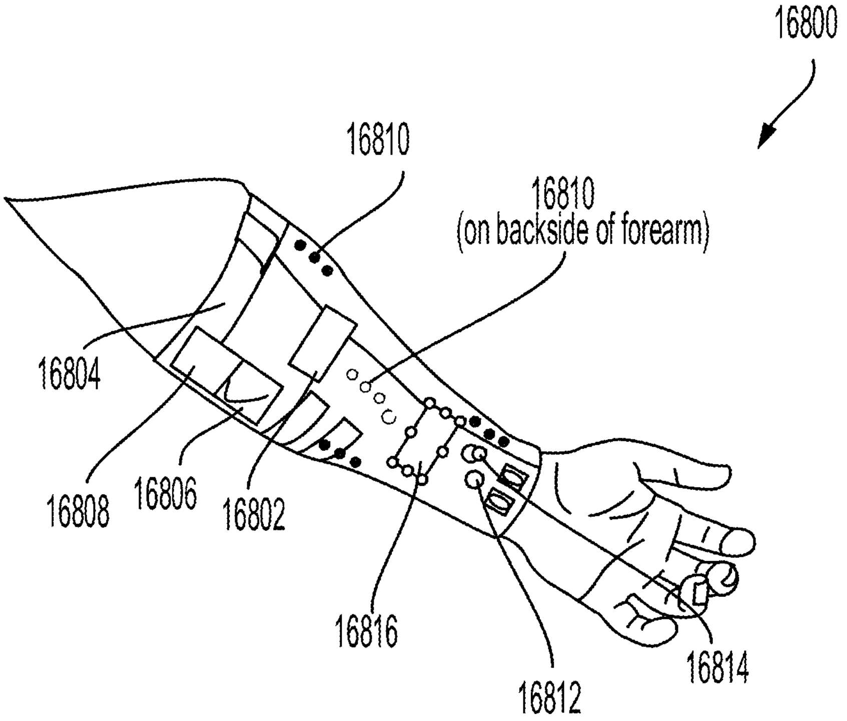

FIG. 100 shows an active sensor sleeve comprising a plurality of active sensors that measure MMG and/or EMG signals, according to one aspect of this disclosure.

Figure 101:
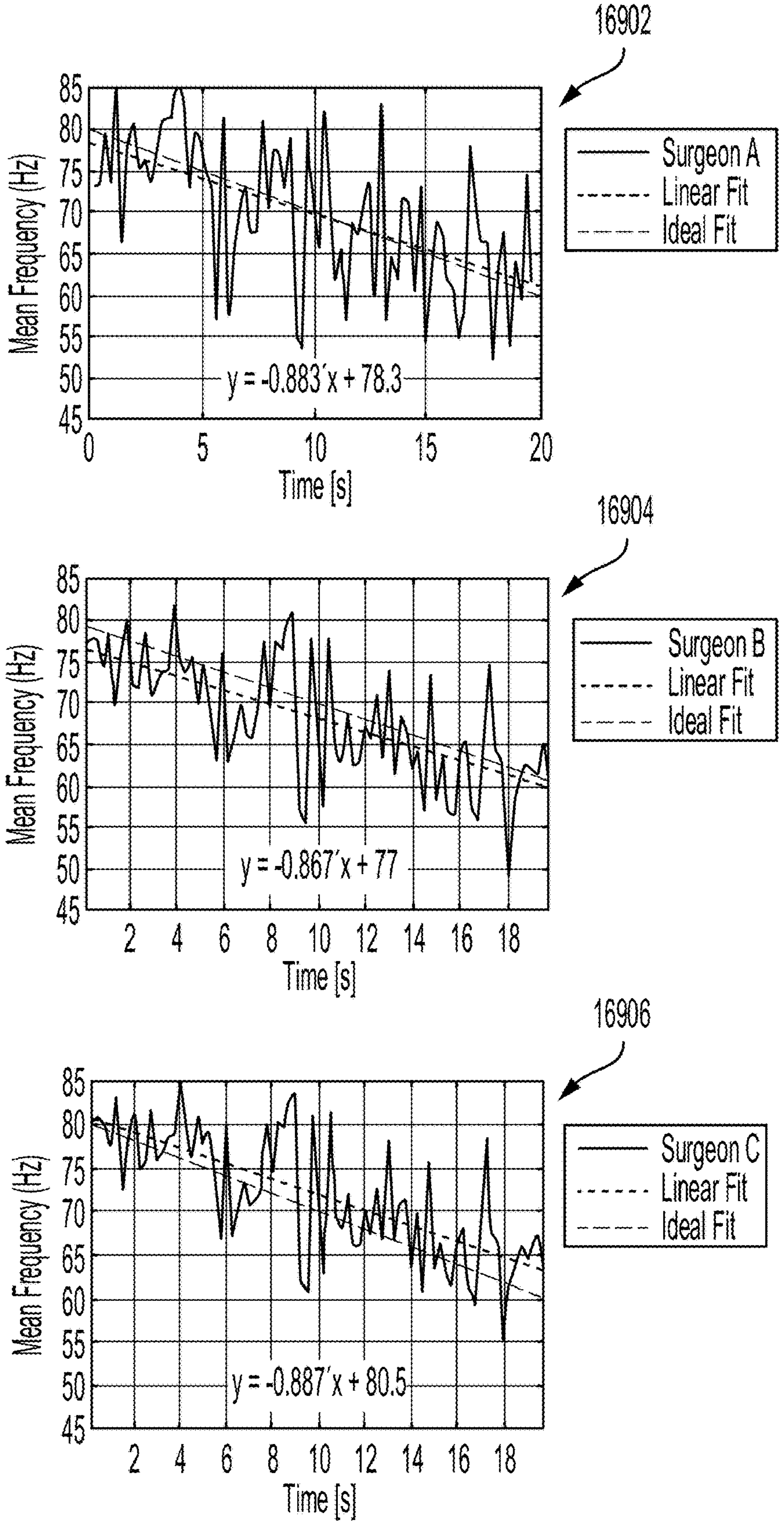

FIG. 101 shows three linear regression models that analyze EMG signals that evaluate muscle fatigue over time, according to one aspect of this disclosure.

Figure 102:
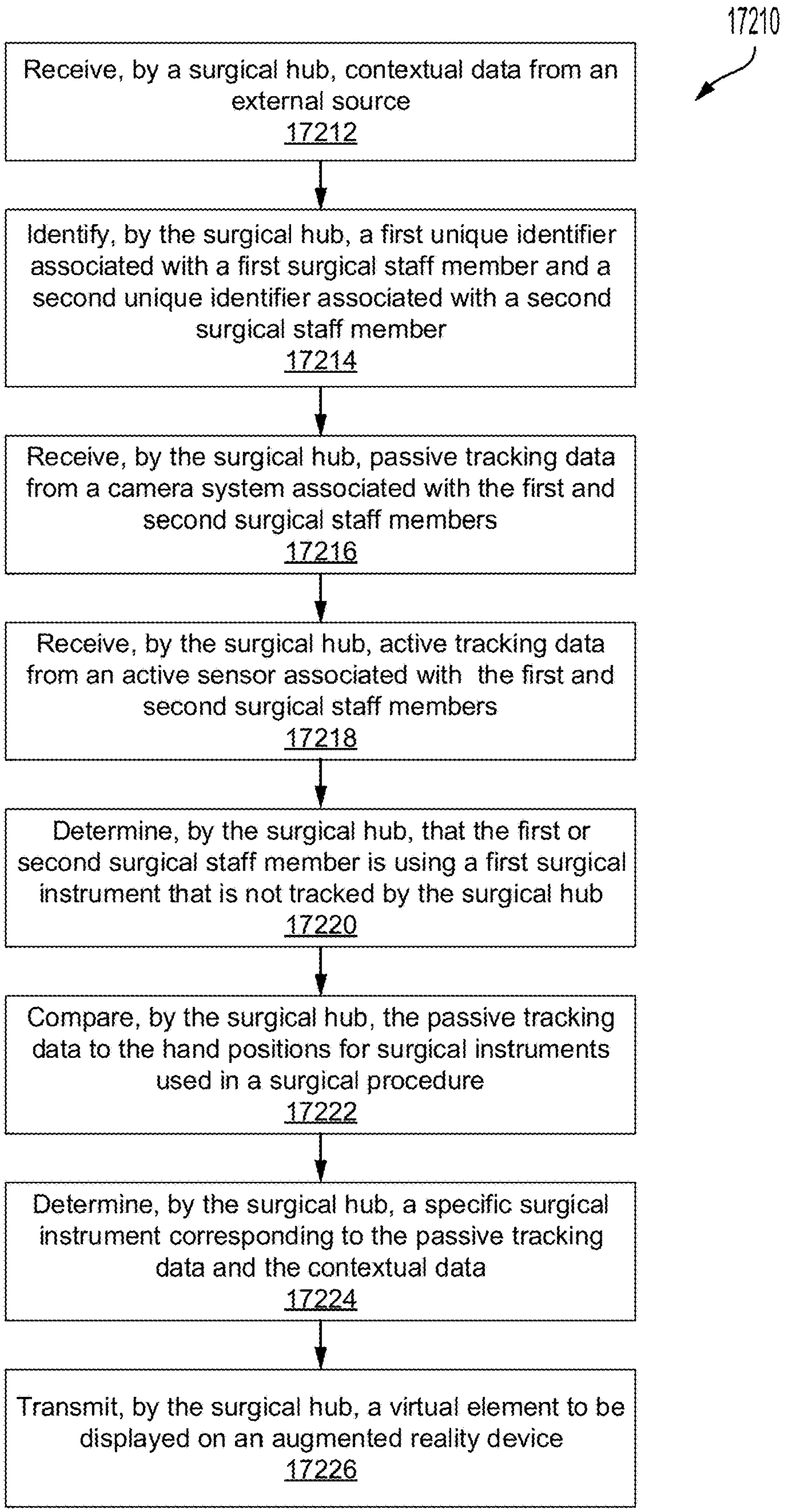

FIG. 102 is a logic diagram of a method for tracking movement of operating room staff members, according to one aspect of this disclosure.

Figure 103:
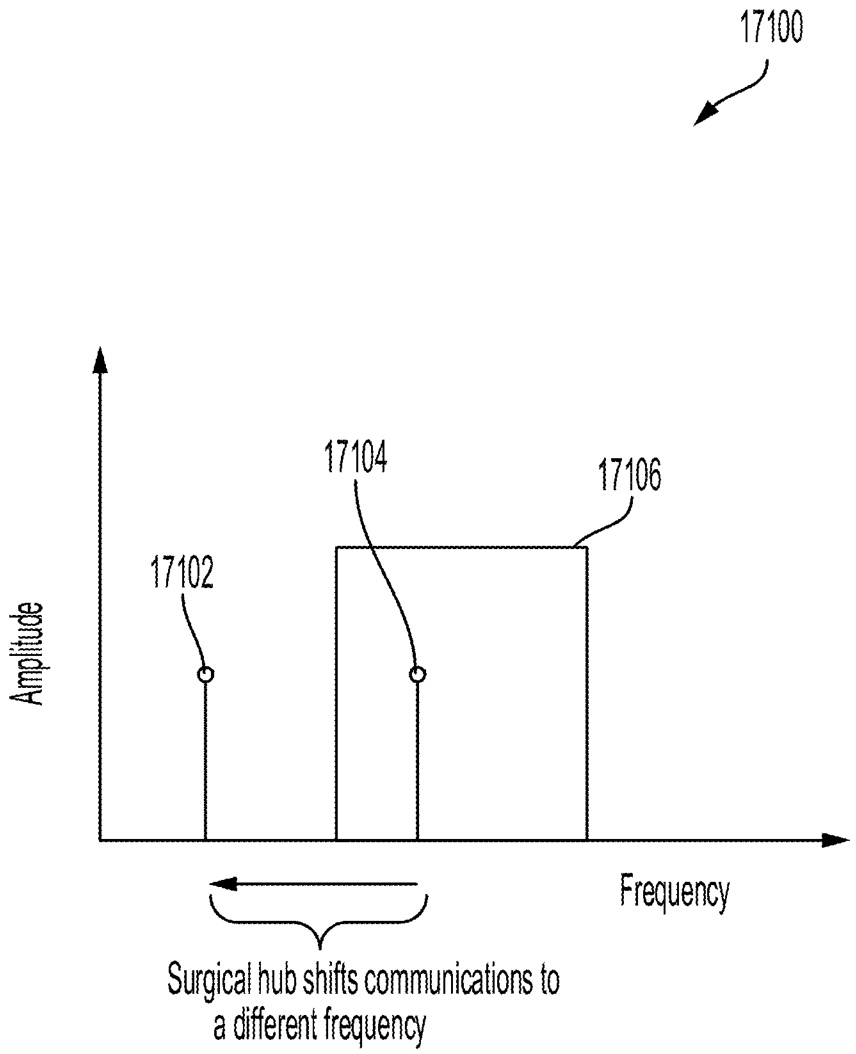

FIG. 103 shows a graphical representation of frequency shifting response by a surgical hub to anticipated signal interference, according to one aspect of this disclosure.

Figure 104:
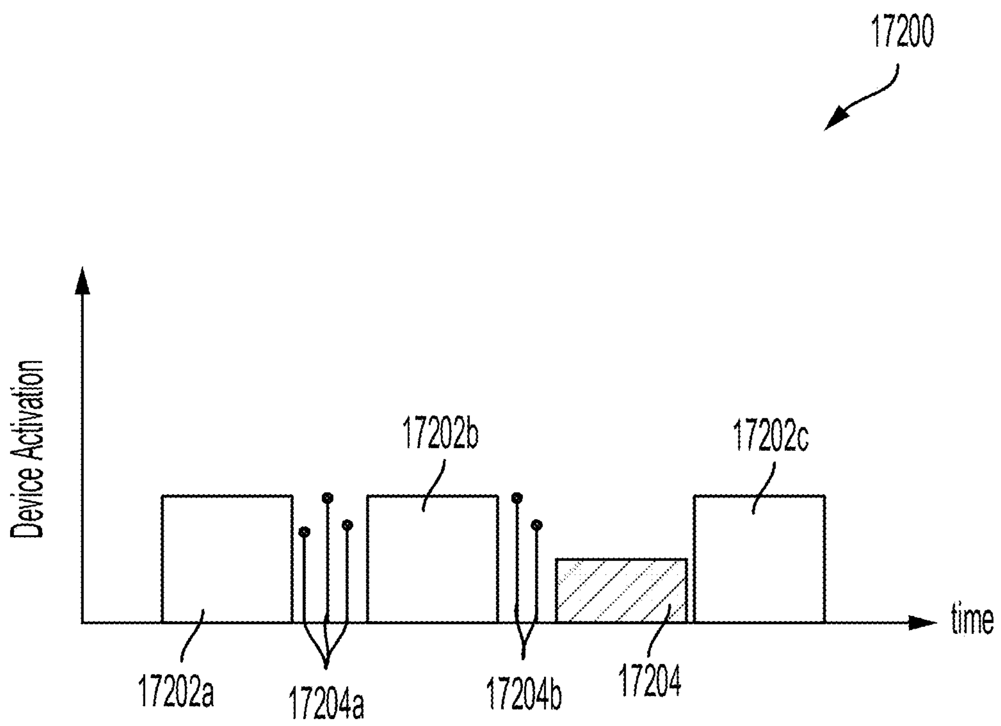

FIG. 104 shows a timeline of device activation and communication transmissions scheduled by a surgical hub, according to one aspect of this disclosure.

Figure 105:
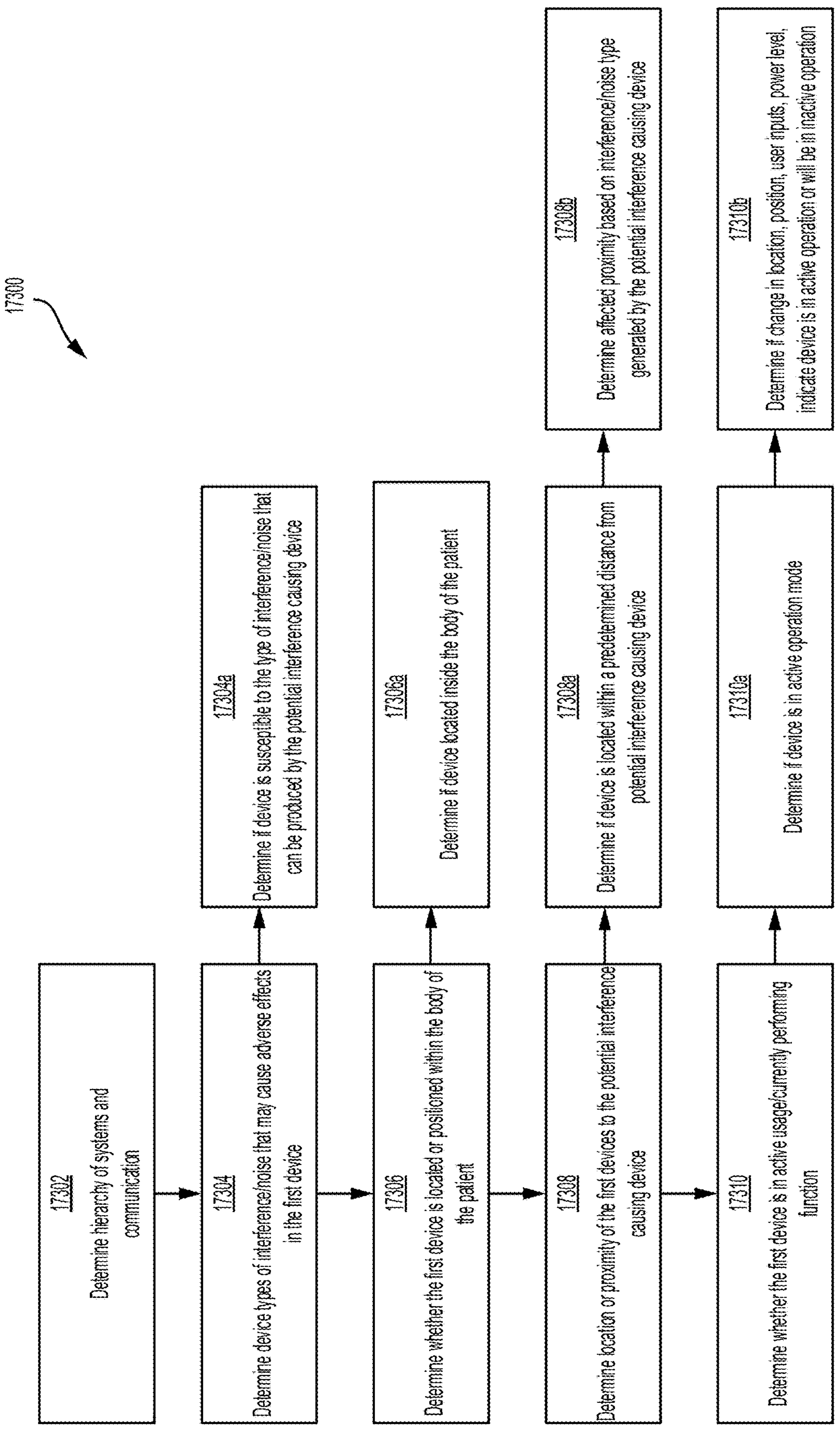

FIG. 105 shows a flow diagram to evaluate a plurality of factors and determine a hierarchy of communication and device activation, according to one aspect of this disclosure.

Figure 106:
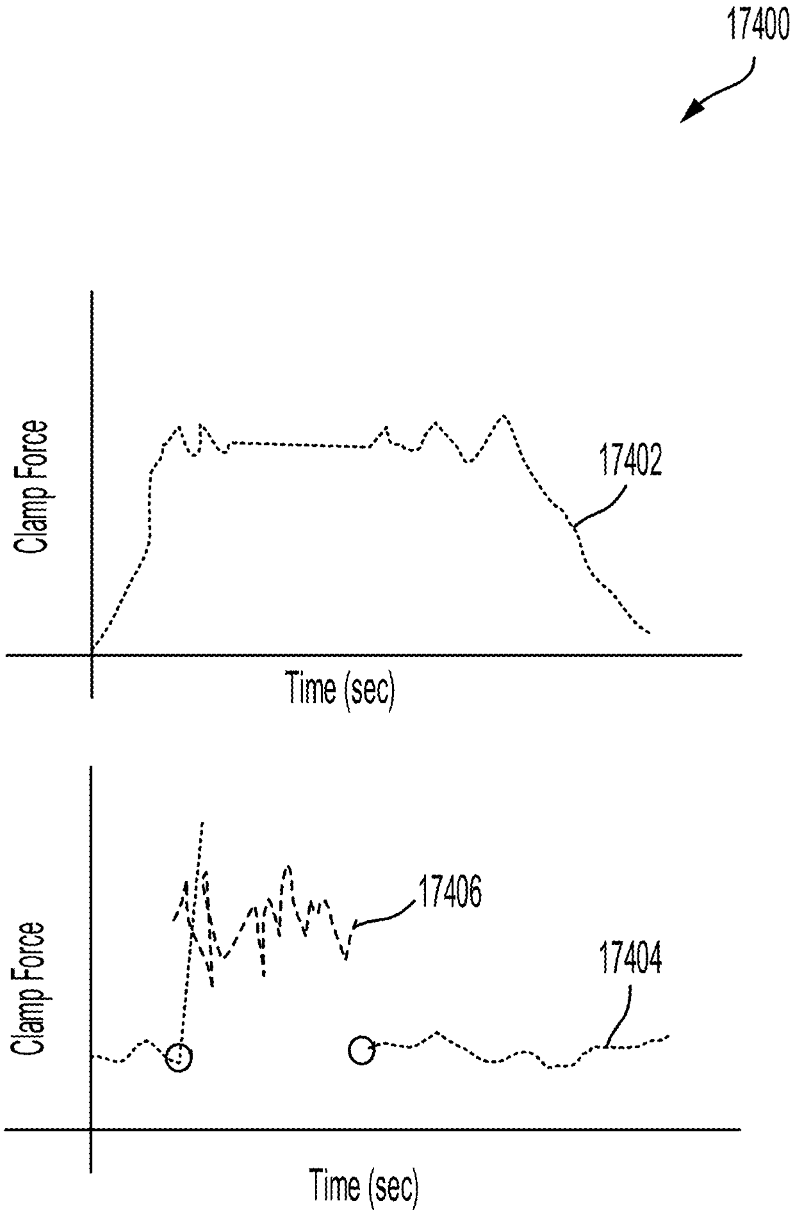

FIG. 106 shows a graphical representation of an end effector signal and noise, when the end effector clamps onto tissue and is in the process of firing, according to one aspect of this disclosure.

Figure 107:
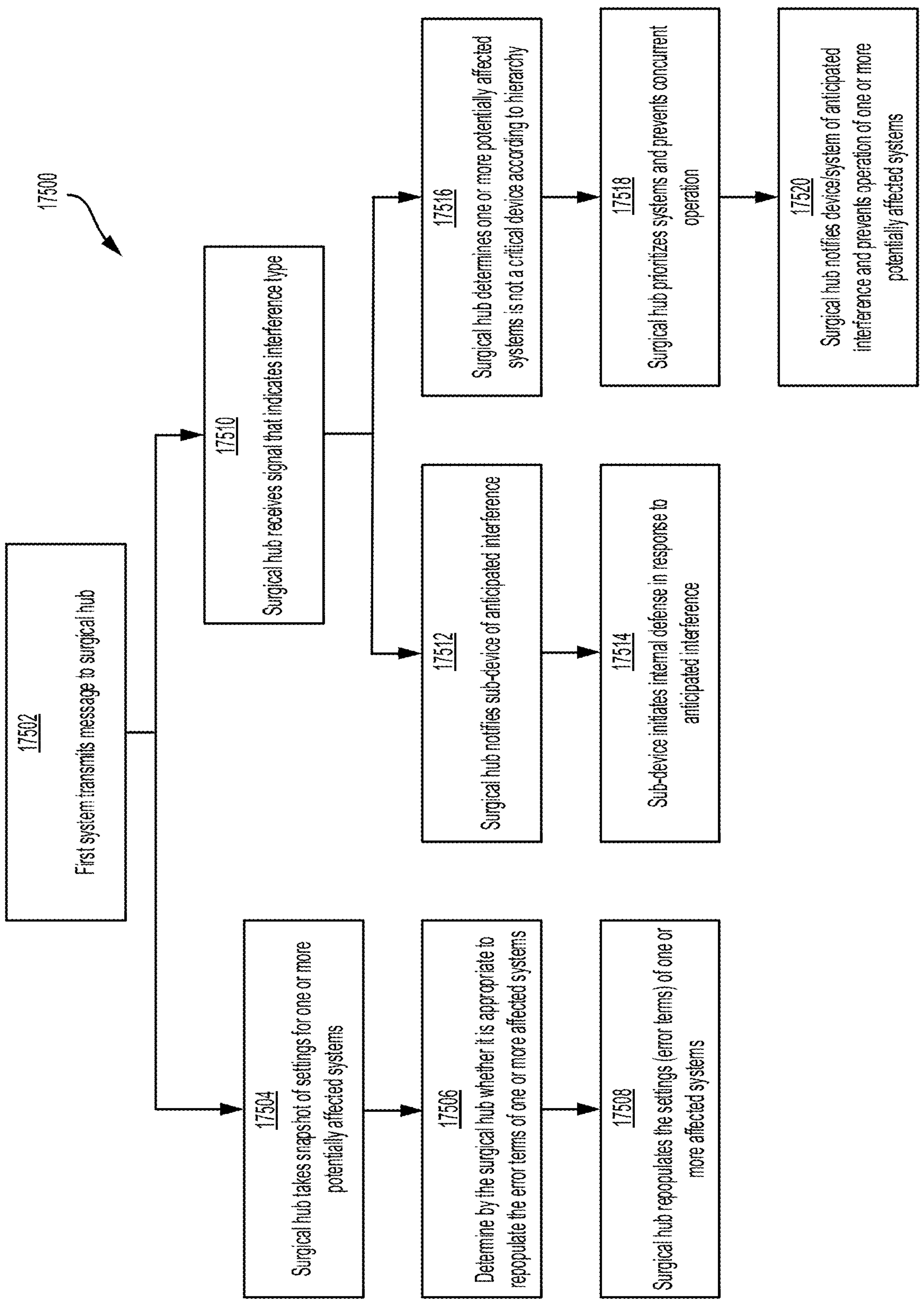

FIG. 107 shows a flow diagram of surgical hub responses based on the anticipation or detection of a trigger event, according to one aspect of this disclosure.

Figure 108:
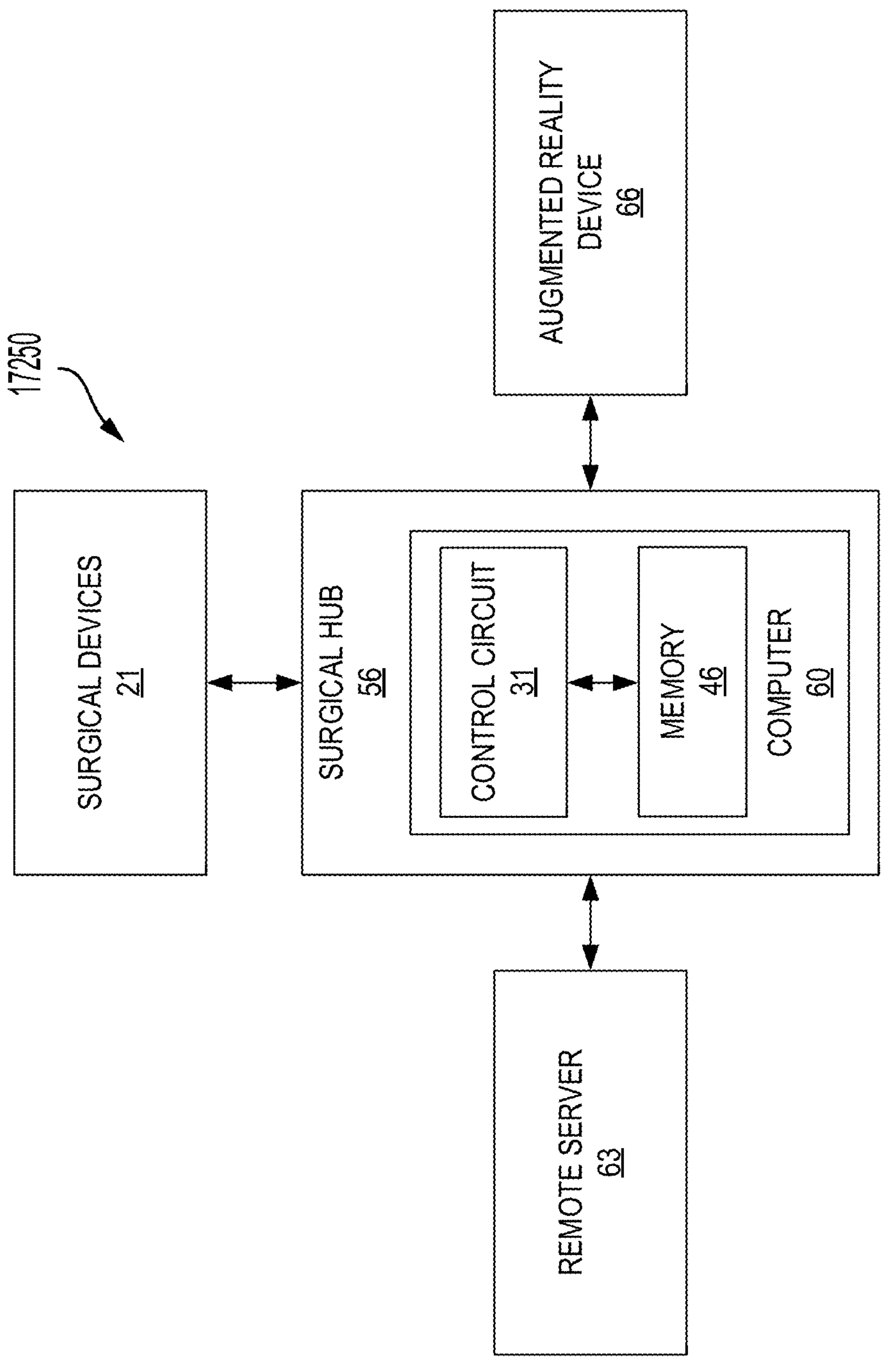

FIG. 108 shows a system for managing surgical device interaction during a surgical procedure, according to one aspect of this disclosure.

Figure 109:
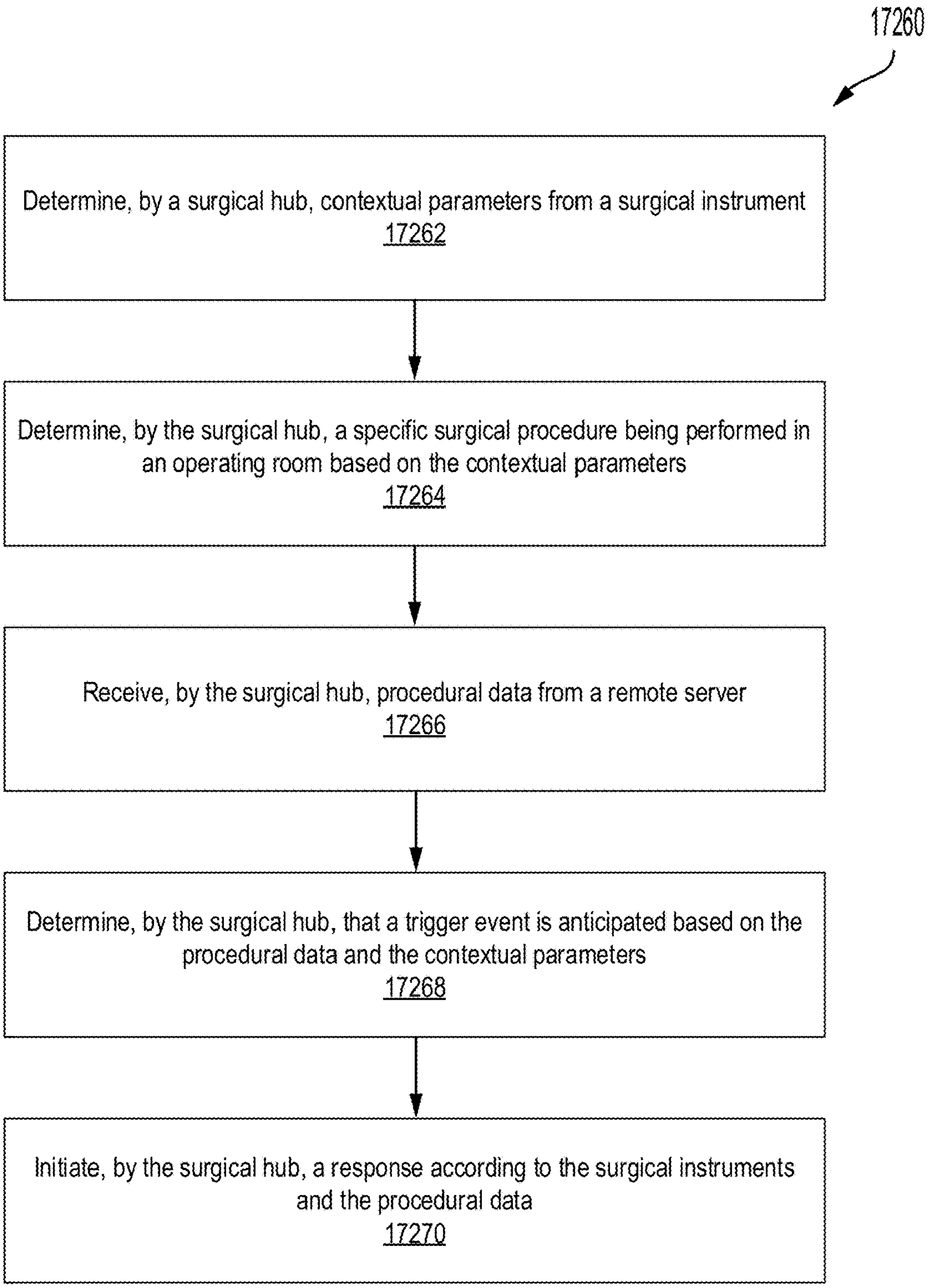

FIG. 109 is a logic diagram of a method for managing surgical device interaction during a surgical procedure, according to one aspect of this disclosure.

Figure 110:
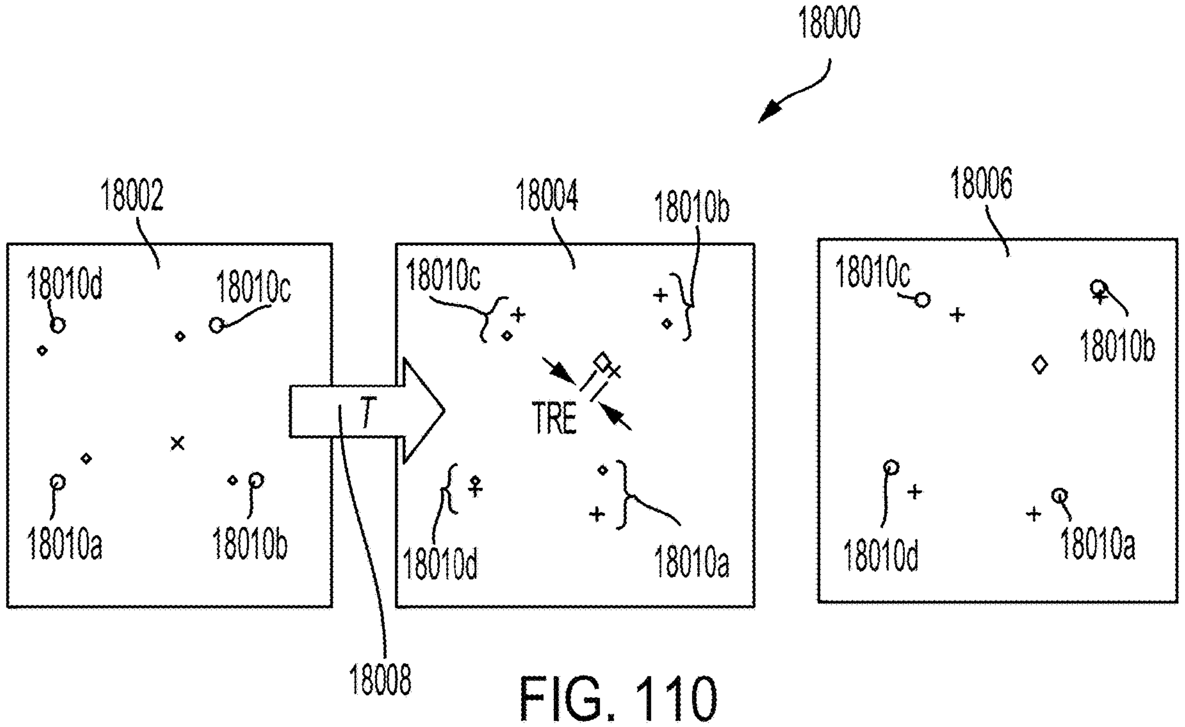

FIG. 110 shows a structural surface comprising a plurality of fiducial markers, according to one aspect of this disclosure.

Figure 111:
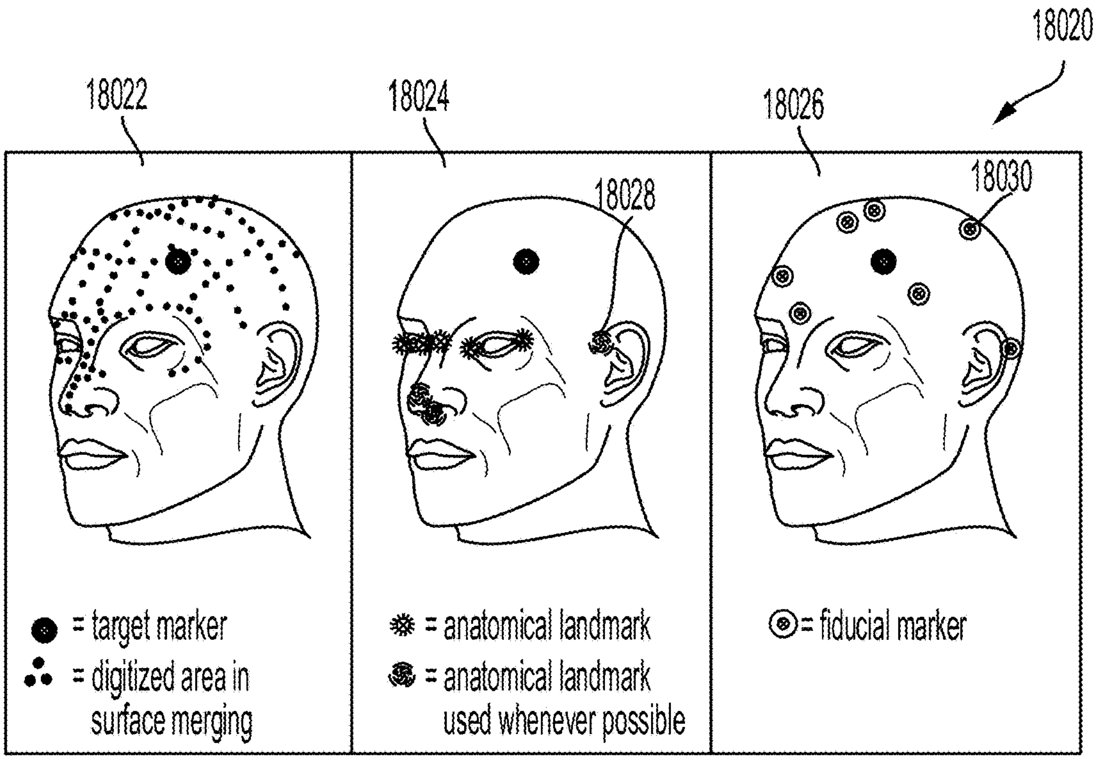

FIG. 111 shows a process for surface matching external structure of a patient with fiducial markers, according to one aspect of this disclosure.

Figure 112:
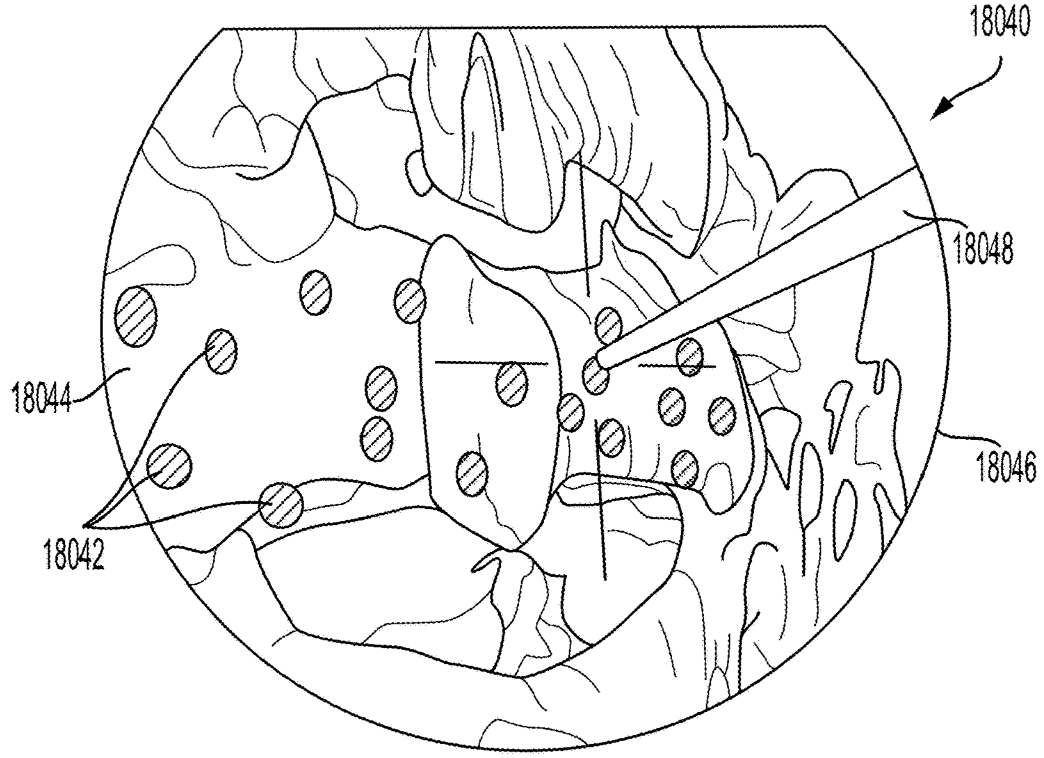

FIG. 112 shows a process for surface matching internal structure of a patient with fiducial markers, according to one aspect of this disclosure.

Figure 113:
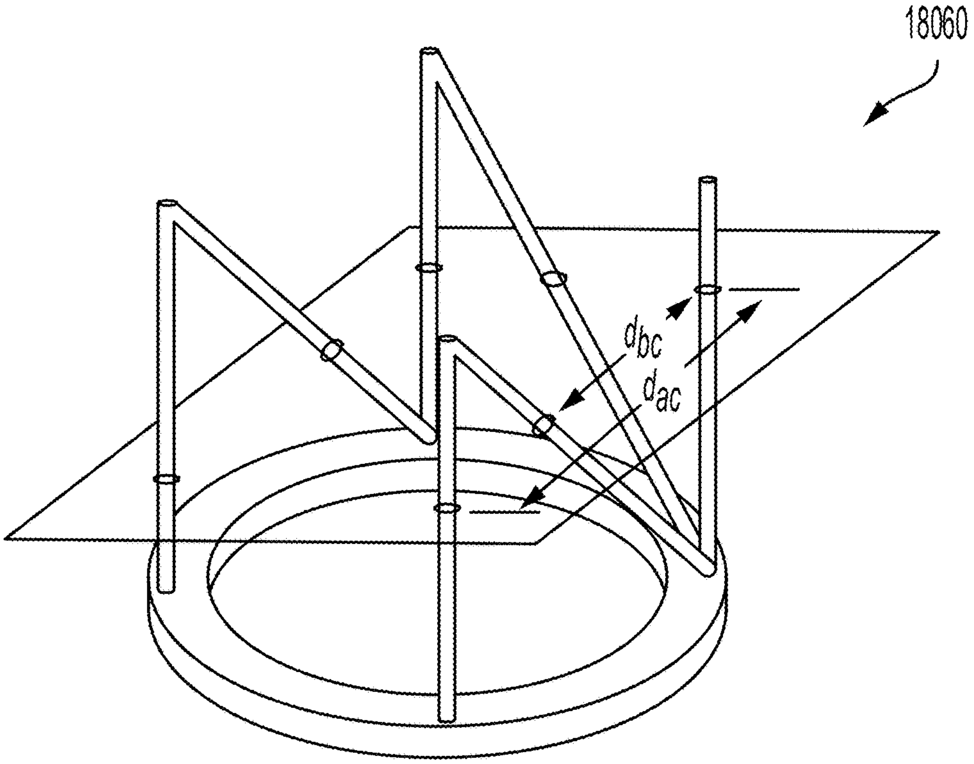

FIG. 113 shows a stereotactic frame external surgical alignment instruments to aid a surgeon in a surgical procedure, according to one aspect of this disclosure.

Figure 114:
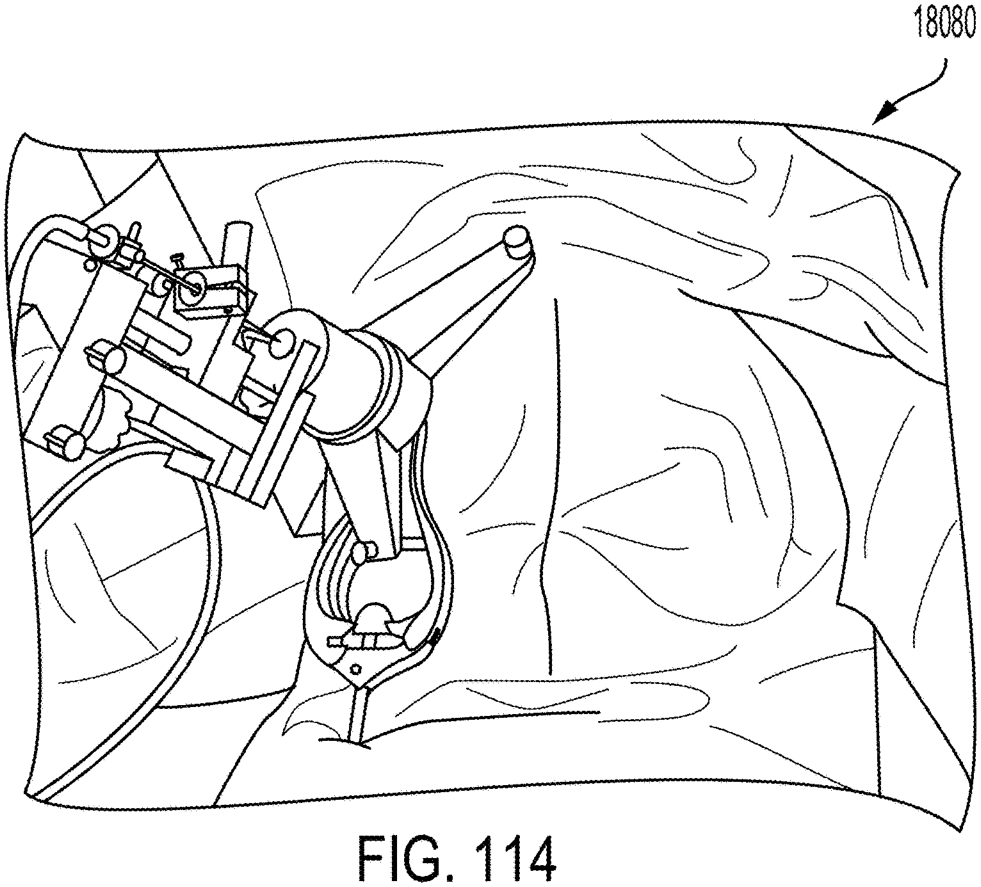

FIG. 114 shows a starfix platform external surgical alignment instruments to aid a surgeon in a surgical procedure, according to one aspect of this disclosure.

Figure 115:
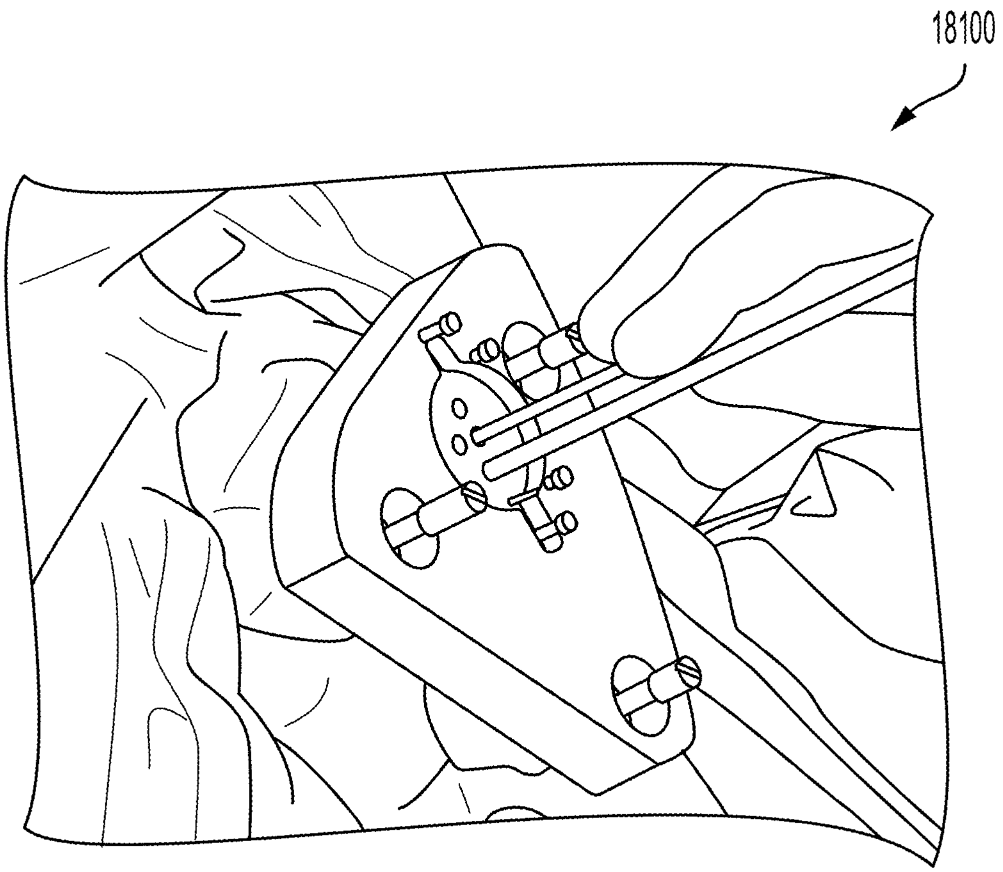

FIG. 115 shows a microtable external surgical alignment instruments to aid a surgeon in a surgical procedure, according to one aspect of this disclosure.

Figure 116:
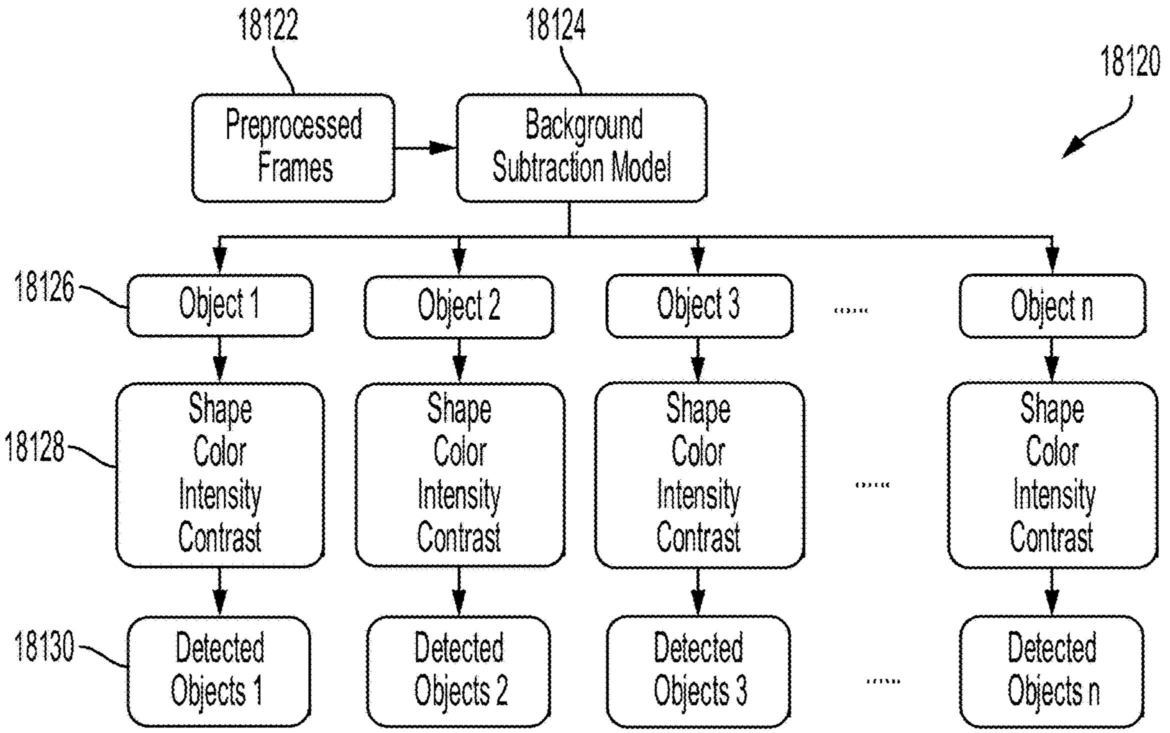

FIG. 116 shows a flow diagram for identifying objects based on a plurality of a registration parameters, according to one aspect of this disclosure.

Figure 117:
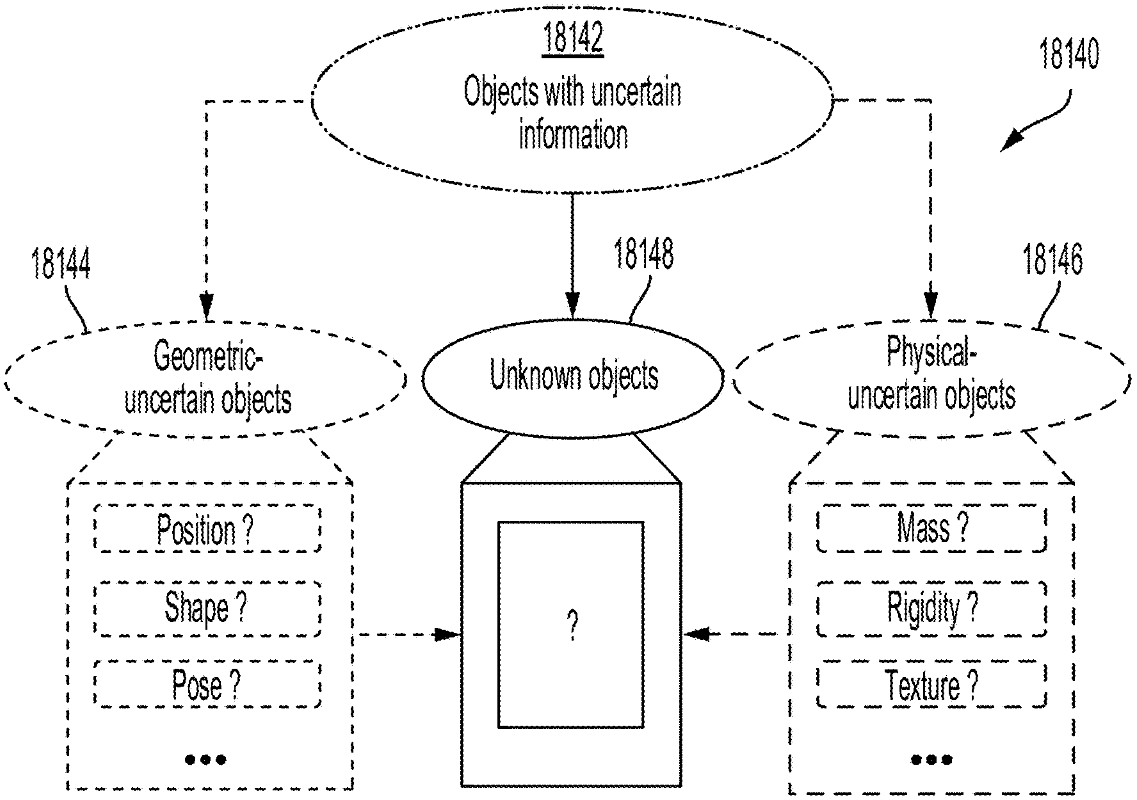

FIG. 117 shows a flow diagram for classifying unknown surgical instruments based on a partial information of known and unknown parameters, according to one aspect of this disclosure.

Figure 118:
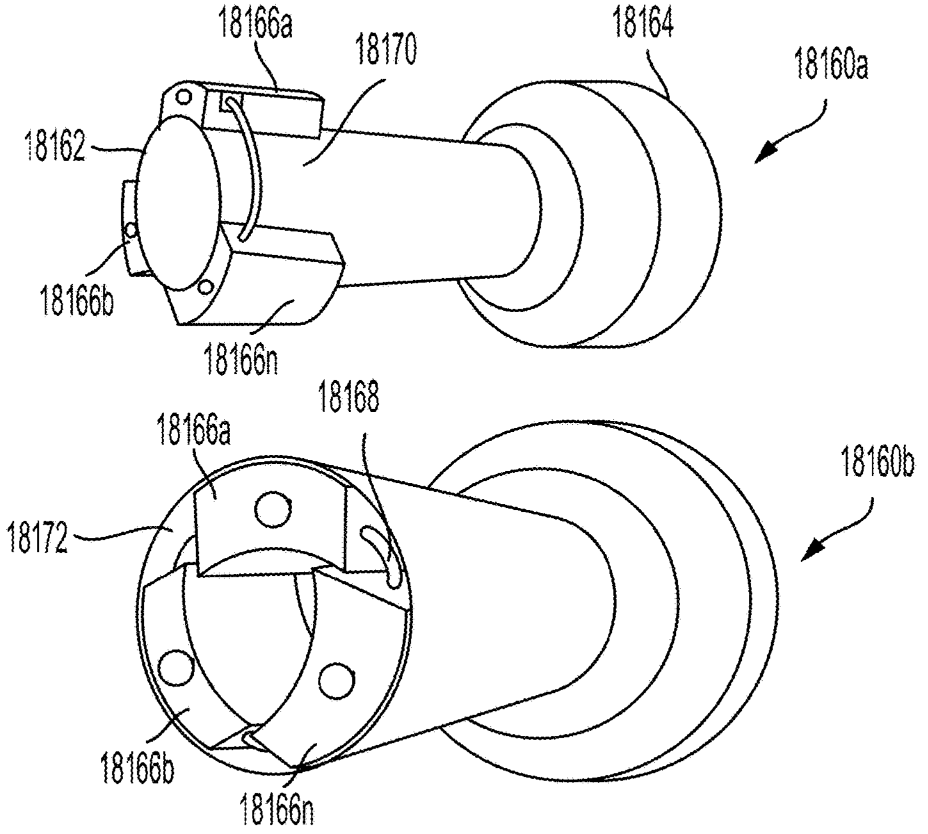

FIG. 118 shows a trocar comprising an internal camera system, according to one aspect of this disclosure.

Figure 119:
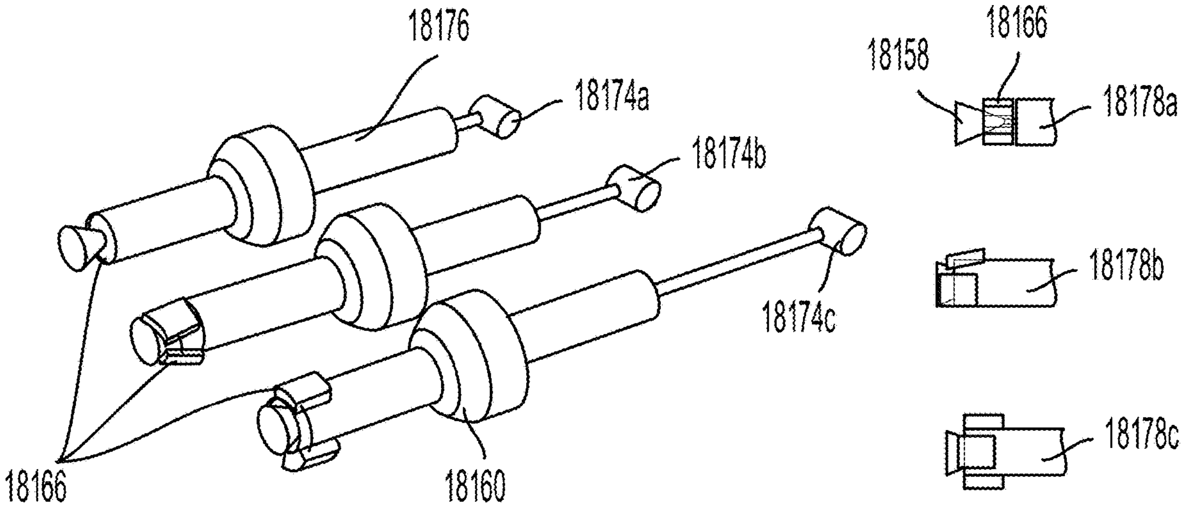

FIG. 119 shows a reusable installation tool, configured to insert into the proximal end of the trocar, deploy and retract the camera system around the outer diameter of the trocar, according to one aspect of this disclosure.

Figure 120:
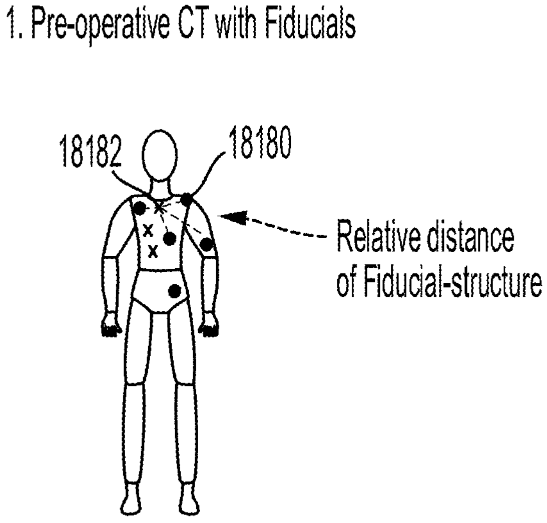

FIG. 120 shows a plurality fiducial markers tagged to areas of interest, in a pre-operative computerized tomography (CT) scan, according to one aspect of this disclosure.

Figure 121:
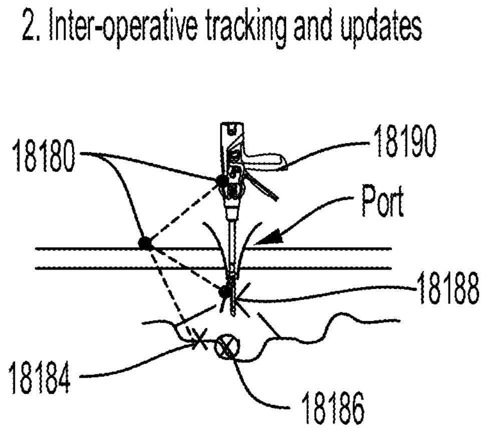

FIG. 121 shows a laparoscopic surgical procedure that utilizes a plurality of fiducial markers to aid a surgeon in locating a surgical site, according to one aspect of this disclosure.

Figure 122:
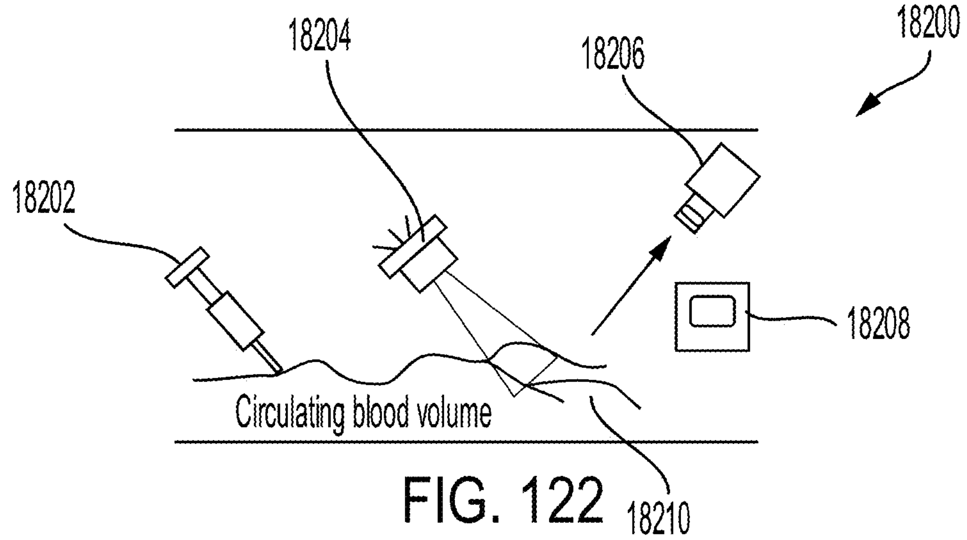

FIG. 122 shows a physical marker applied by injection into a vascular system of a patient with an indocyanine dye, according to one aspect of this disclosure.

Figure 123:
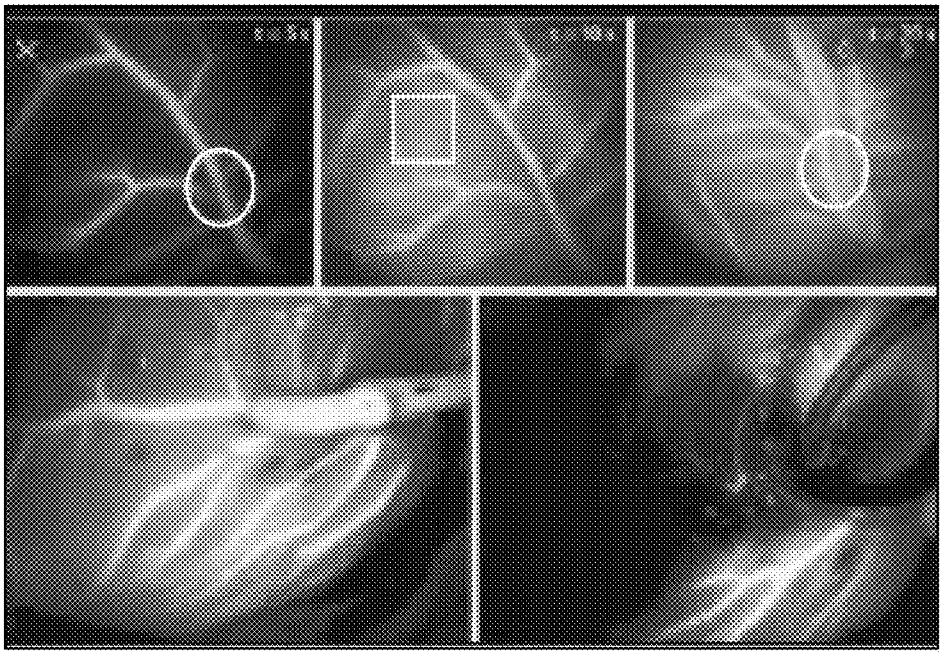

FIG. 123 further shows exemplary tissue injected with a dye and illuminated to show vasculature, according to one aspect of this disclosure.

Figure 124:
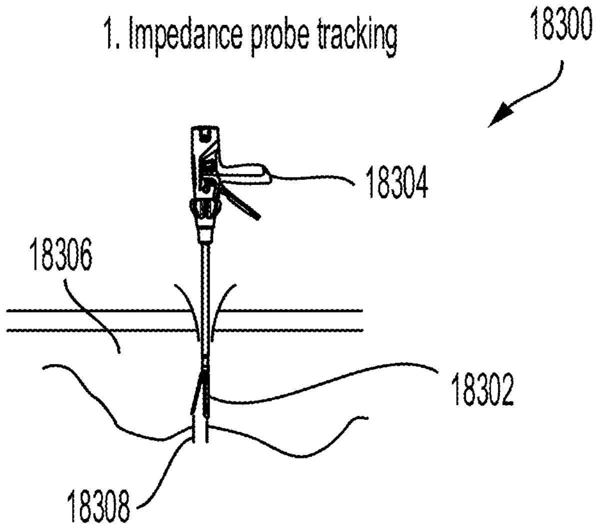

FIG. 124 shows a system configured to monitor the change in pressure or fluid in a body cavity according to an impendence measurement by a probe, according to one aspect of this disclosure.

Figure 125:
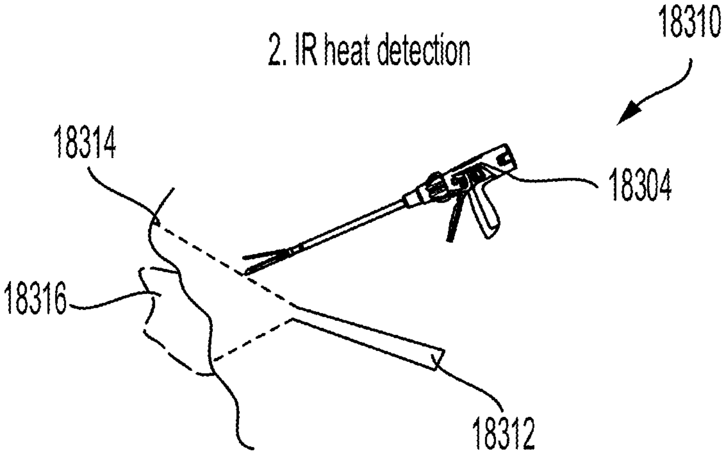

FIG. 125 shows an infrared (IR) heat detection system comprising an IR camera system configured direct IR light on a treated region of tissue and identify a temperature difference in a surgical environment, according to one aspect of this disclosure.

Figure 126:
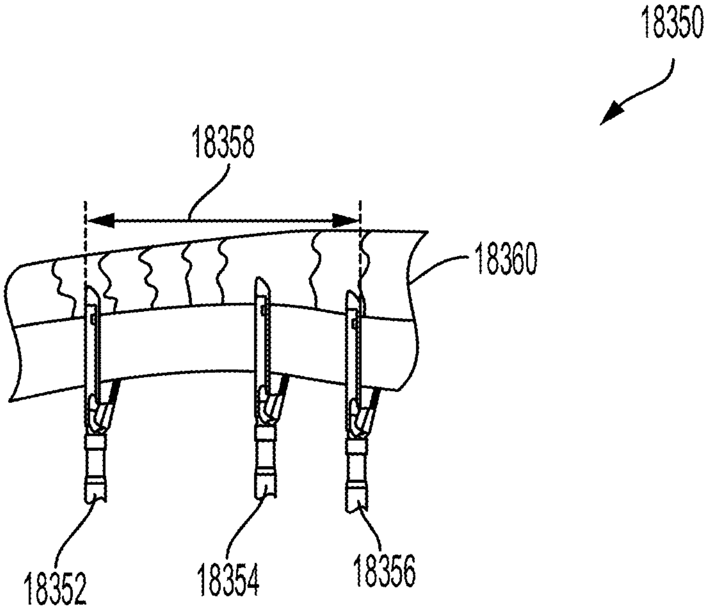

FIG. 126 shows a surgical procedure employing three end effectors configured to grasp and transect tissue, according to one aspect of this disclosure.

Figure 127:
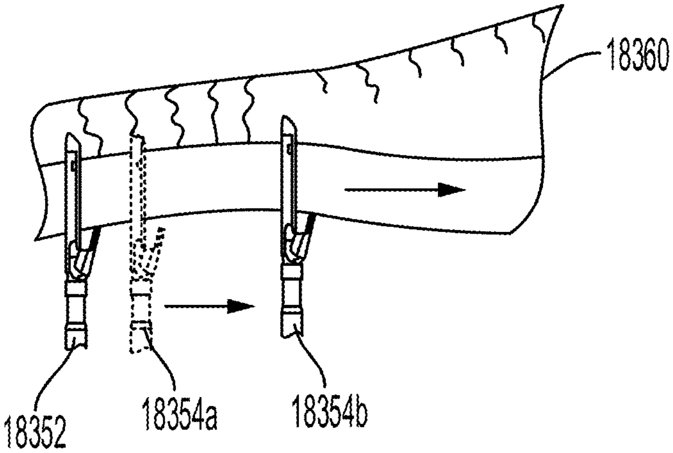

FIG. 127 shows the third end effector sliding along the tissue from a first position to a second position, according to one aspect of this disclosure.

Figure 128:
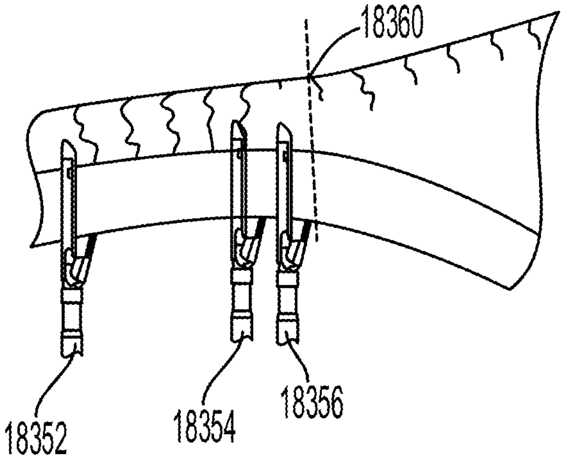

FIG. 128 shows the third end effector positioned adjacent to the second end effector, according to one aspect of this disclosure.

Figure 129:
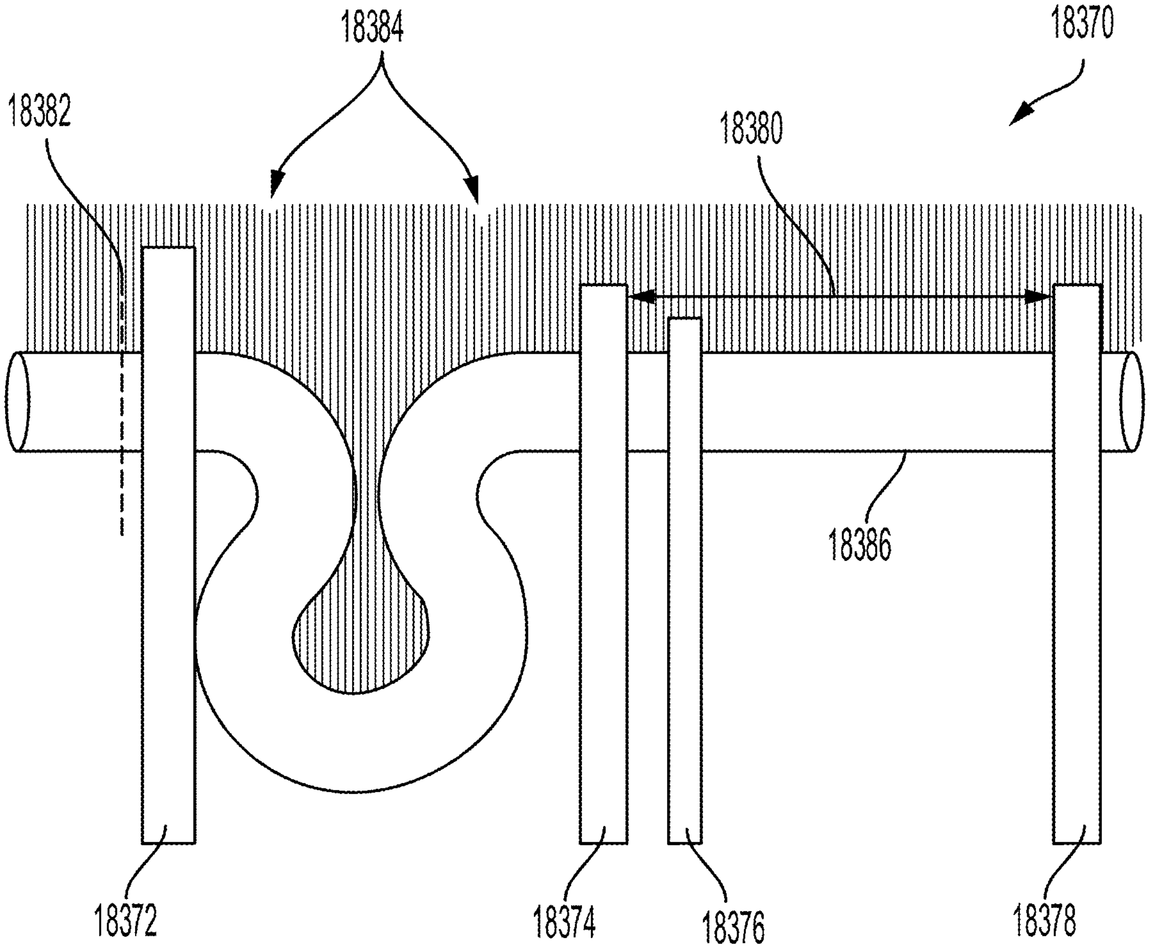

FIG. 129 shows a surgical procedure comprising three static clamps and a dynamic clamp configured to transfer tissue between stationary, according to one aspect of this disclosure.

Figure 130:
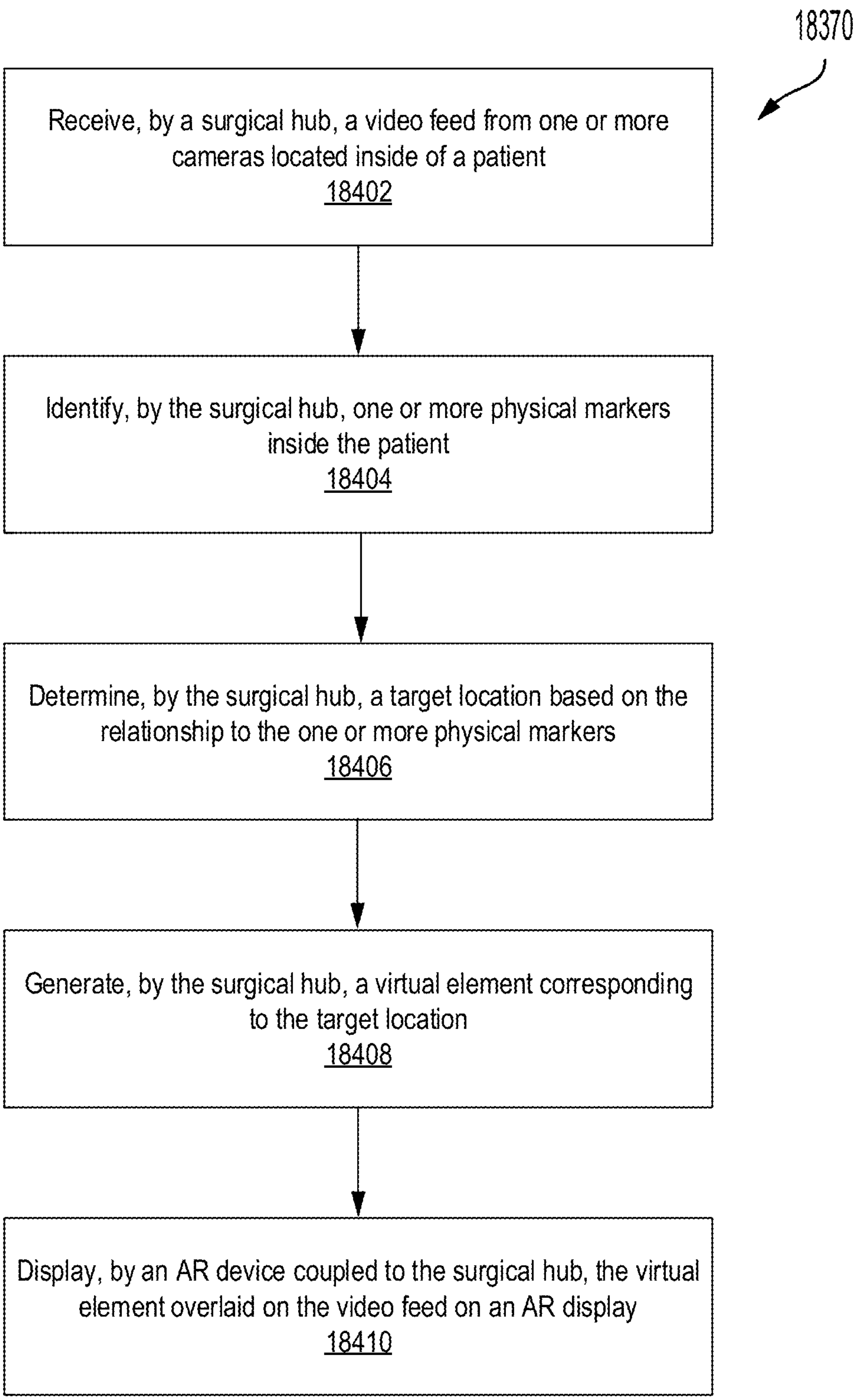

FIG. 130 shows a logic diagram of a method for displaying a surgical location inside of a patient, according to one aspect of this disclosure.

Figure 131:
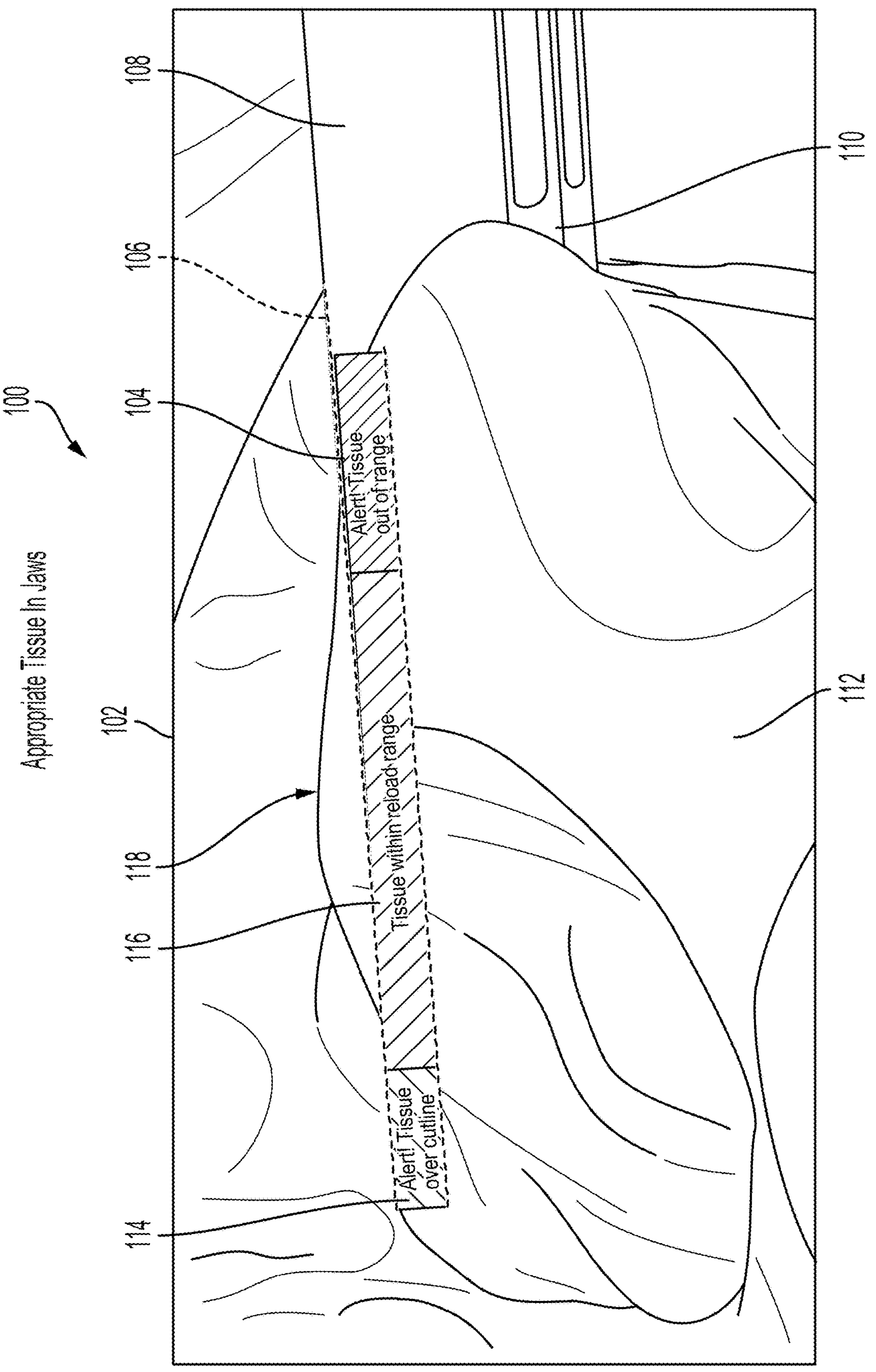

FIG. 131 is an augmented image of a live feed of a surgical area visualized through a laparoscopic camera during a minimally invasive surgical procedure indicating appropriate tissue captured between jaws of a surgical instrument end effector as a tissue aspect, according to one aspect of this disclosure.

Figure 132:
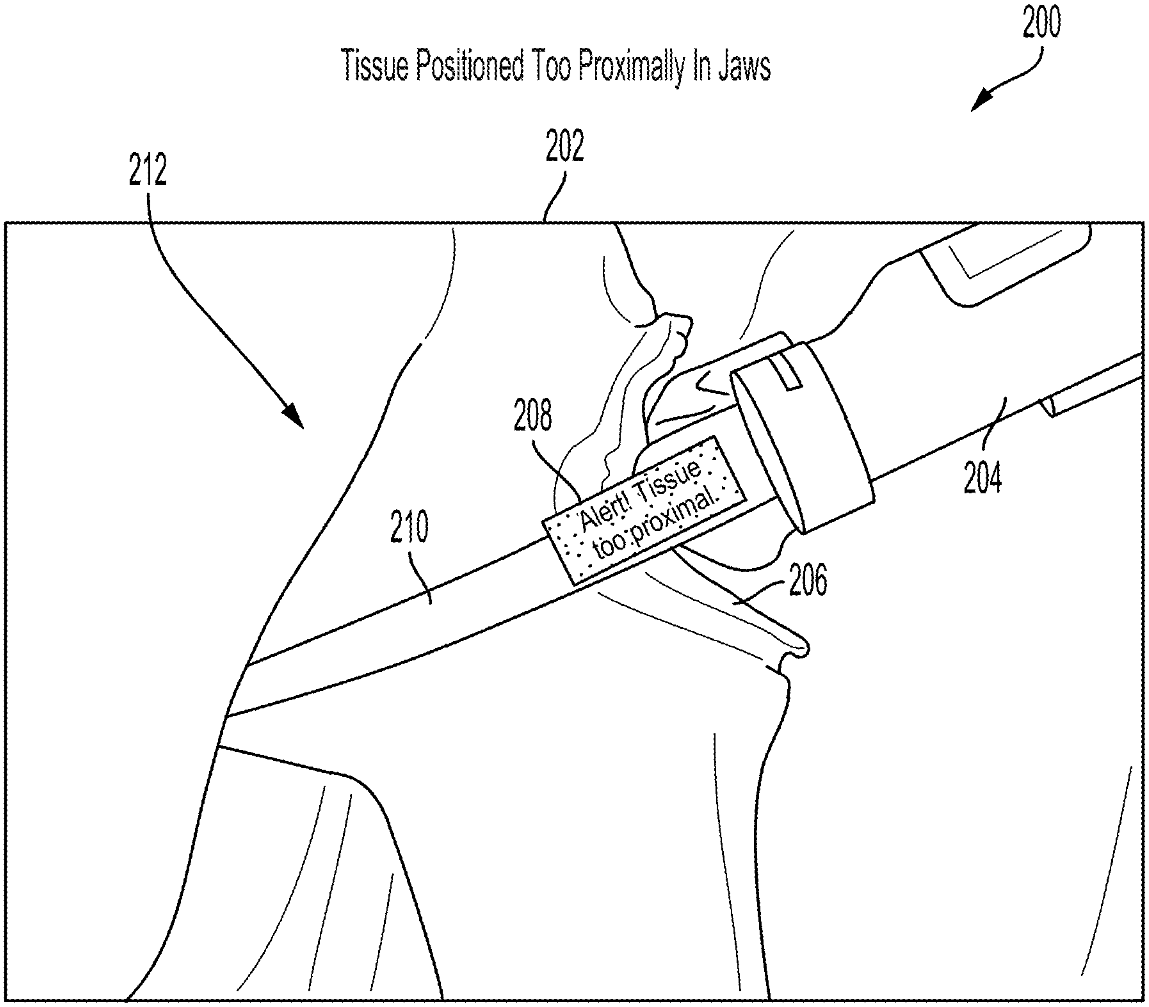

FIG. 132 is an augmented image of a live feed of a surgical area visualized through a laparoscopic camera during a minimally invasive surgical procedure indicating tissue position proximally captured between of a surgical instrument end effector as a tissue aspect, according to one aspect of this disclosure.

Figure 133:
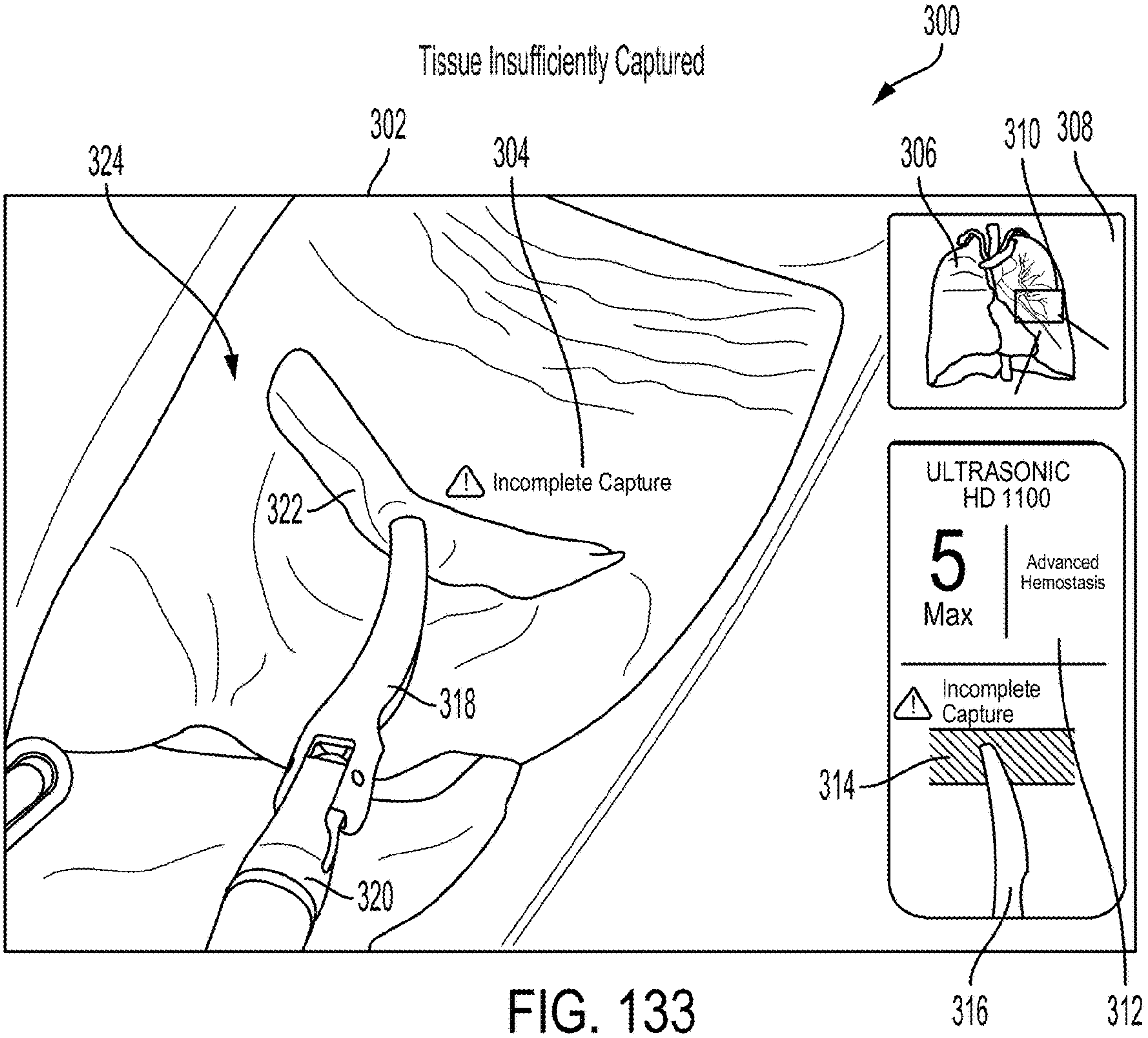

FIG. 133 is an augmented image of a live feed of a surgical area as visualized through a laparoscopic camera during a minimally invasive surgical procedure indicating tissue insufficiently captured between jaws of a surgical instrument end effector as a tissue aspect, according to one aspect of this disclosure.

Figure 134:
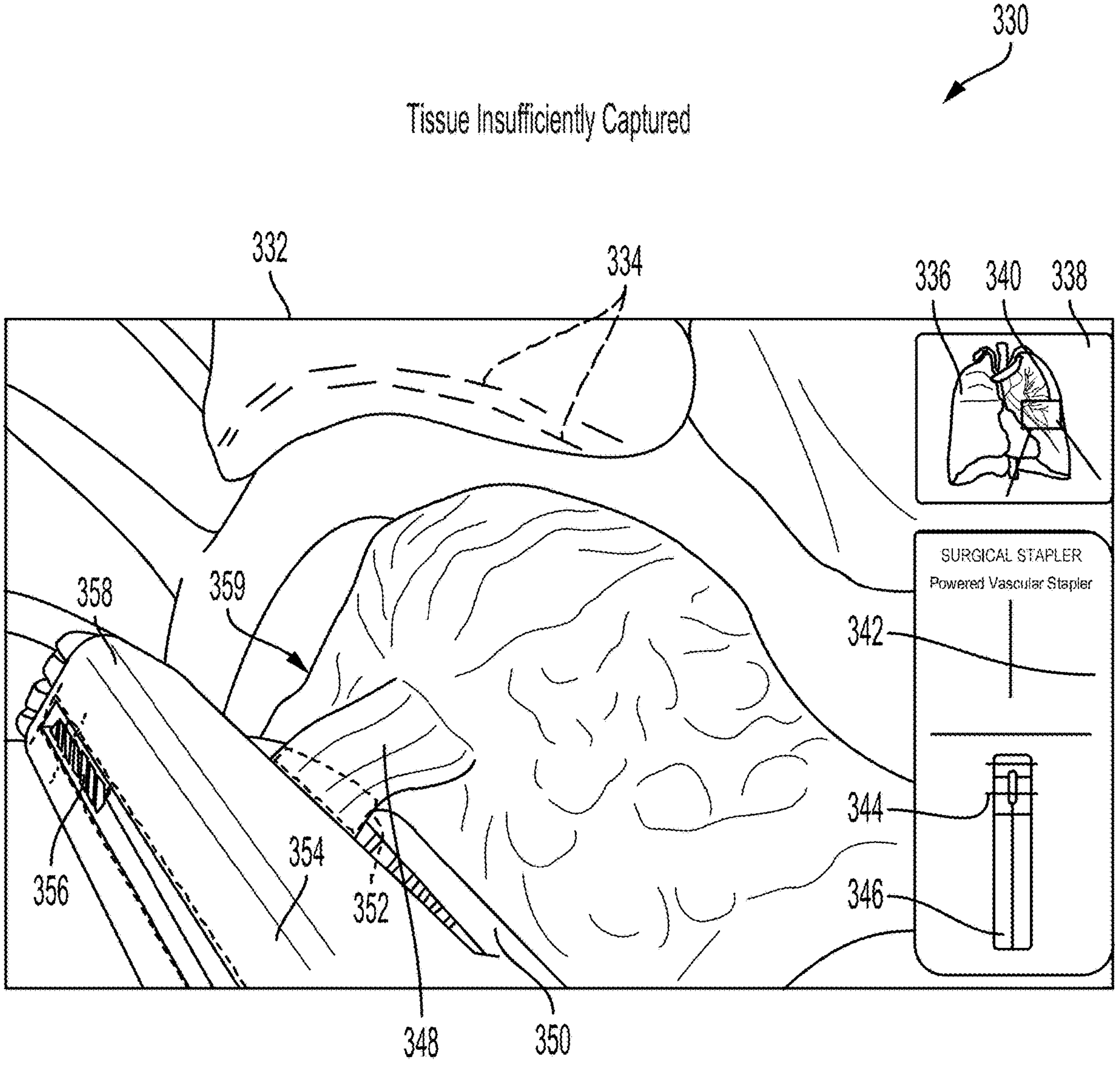

FIG. 134 is another augmented image of a live feed of a surgical area as visualized through a laparoscopic camera during a minimally invasive surgical procedure indicating tissue insufficiently captured between jaws of a surgical instrument end effector as a tissue aspect, according to one aspect of this disclosure.

Figure 135:
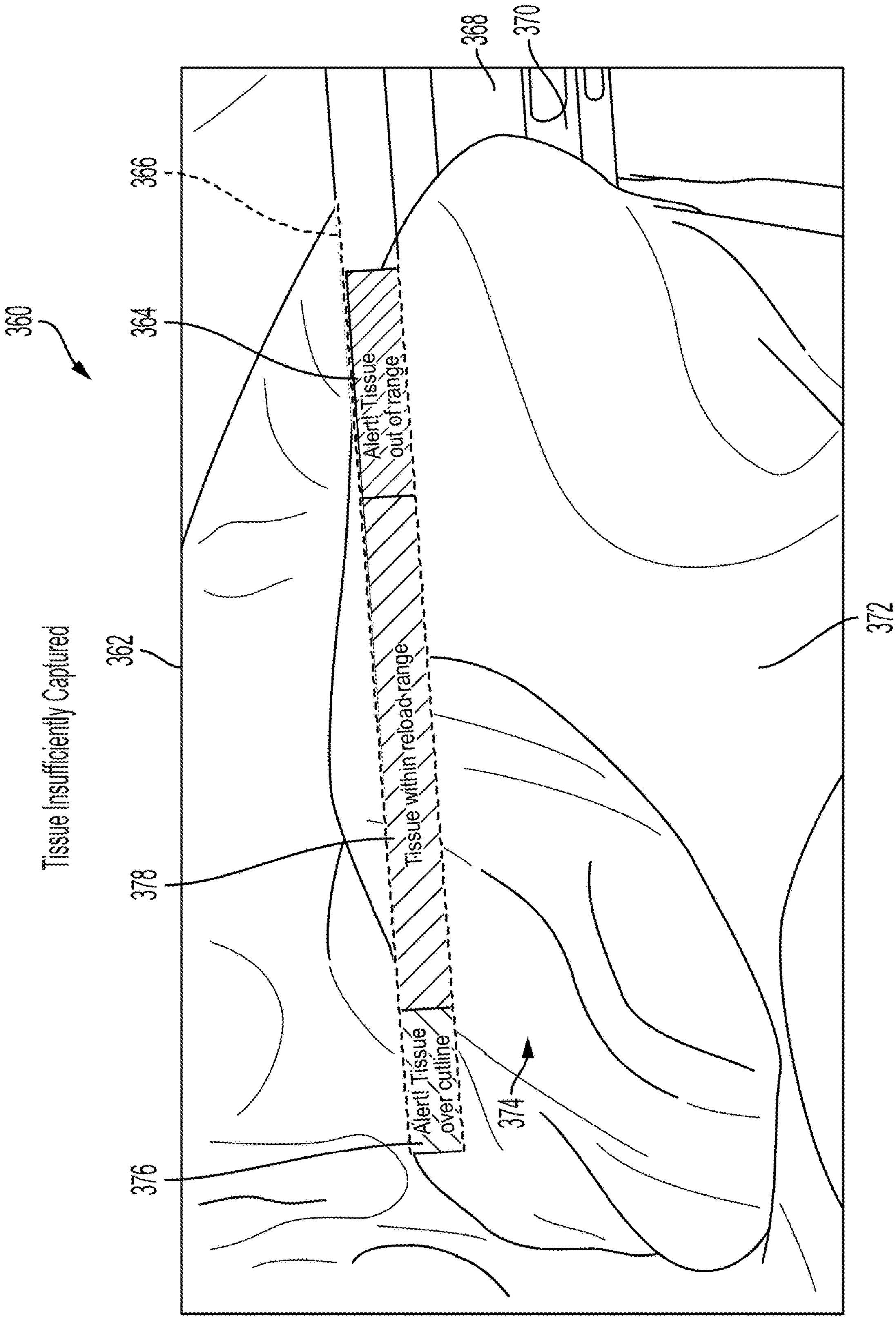

FIG. 135 is another augmented image of a live feed of a surgical area as visualized through a laparoscopic camera during a minimally invasive surgical procedure indicating tissue insufficiently captured between jaws of a surgical instrument end effector as a tissue aspect, according to one aspect of this disclosure.

Figure 136:
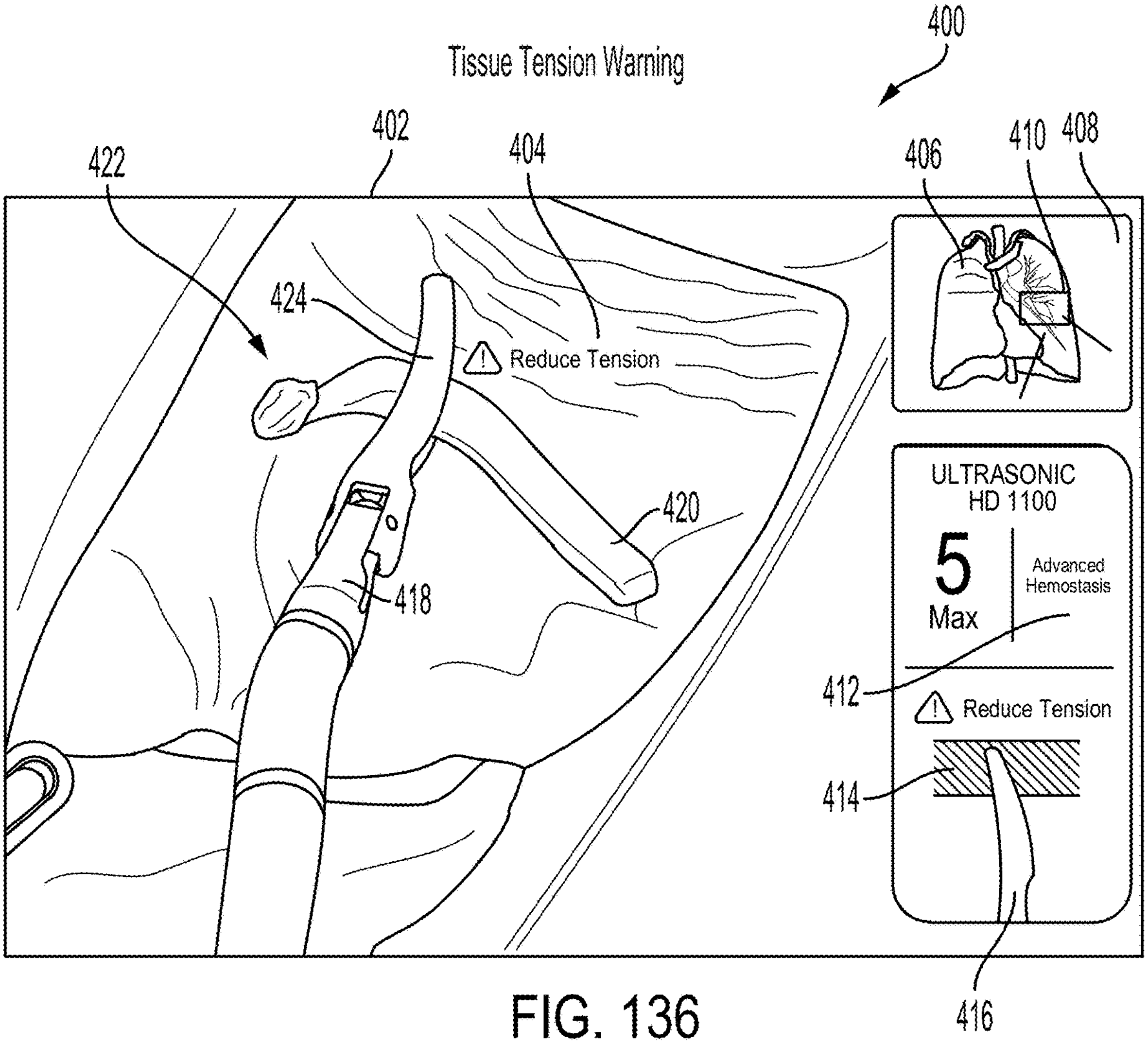

FIG. 136 is an augmented image of a live feed of a surgical area as visualized through a laparoscopic camera during a minimally invasive surgical procedure indicating tissue tension as a tissue aspect, according to at least one aspect of this disclosure.

Figure 137:
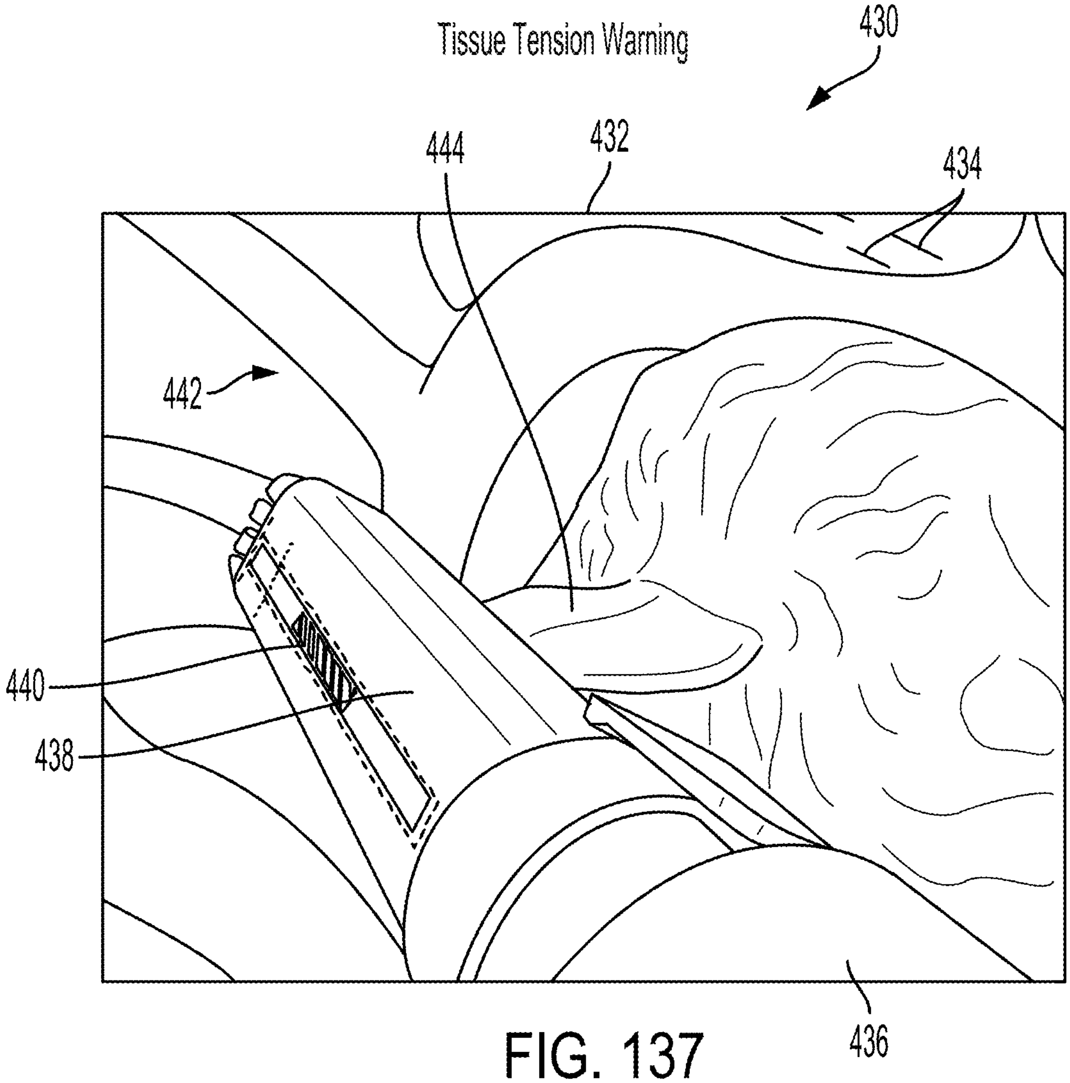

FIG. 137 is another augmented image of a live feed of a surgical area as visualized through a laparoscopic camera during a minimally invasive surgical procedure indicating tissue tension as a tissue aspect, according to one aspect of this disclosure.

Figure 138:
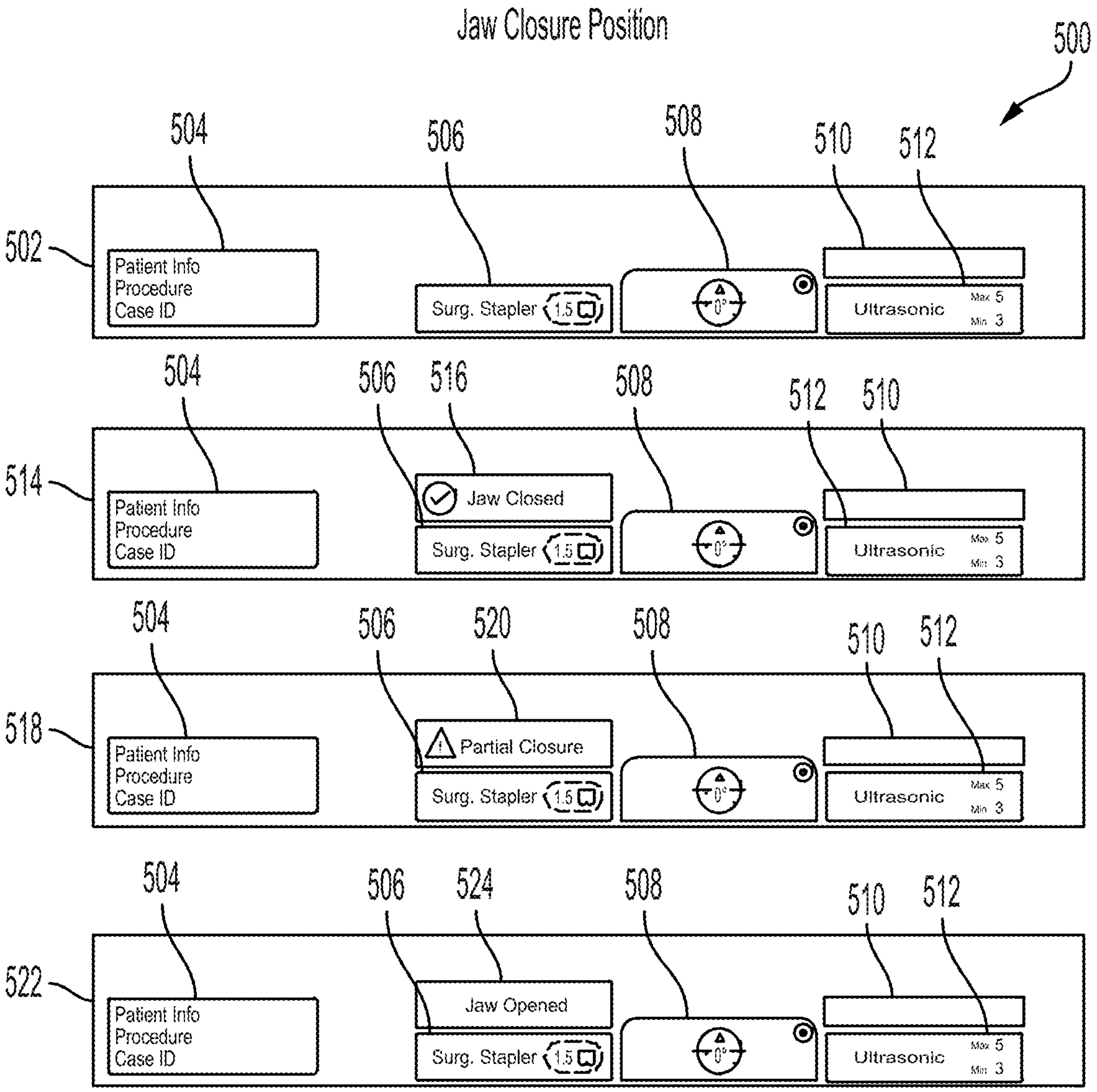

FIG. 138 is a plurality of graphic images indicating jaw closure position as an operational aspect of a surgical instrument as shown in FIGS. 131-138, according to one aspect of this disclosure.

Figure 139:
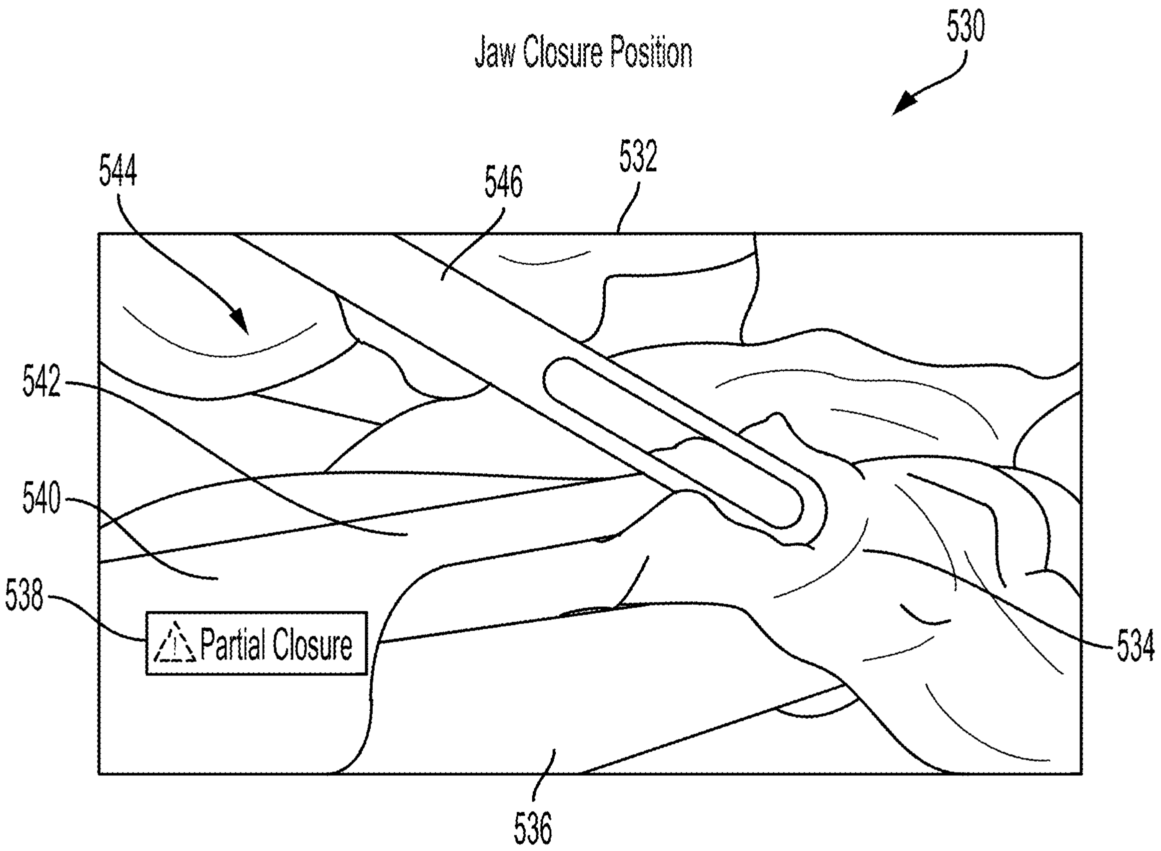

FIG. 139 is an augmented image of a live feed of a surgical area as visualized through a laparoscopic camera during a minimally invasive surgical procedure indicating jaw closure position as an operational aspect of a surgical instrument, according to one aspect of this disclosure.

Figure 140:
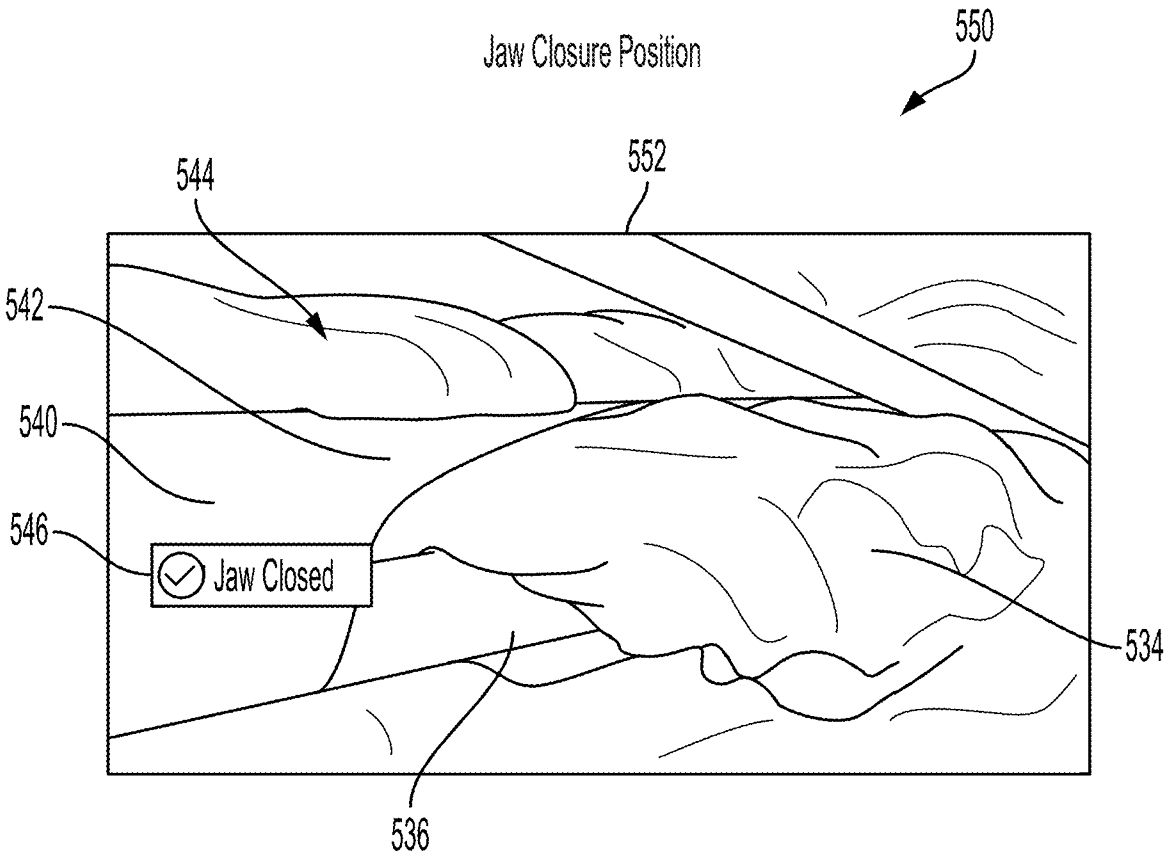

FIG. 140 is an augmented image of a live feed of the surgical area shown in FIG. 139 showing a fully closed surgical instrument end effector and a graphical alert overlay showing jaw closed position superimposed on the end effector, according to one aspect of this disclosure.

Figure 141:
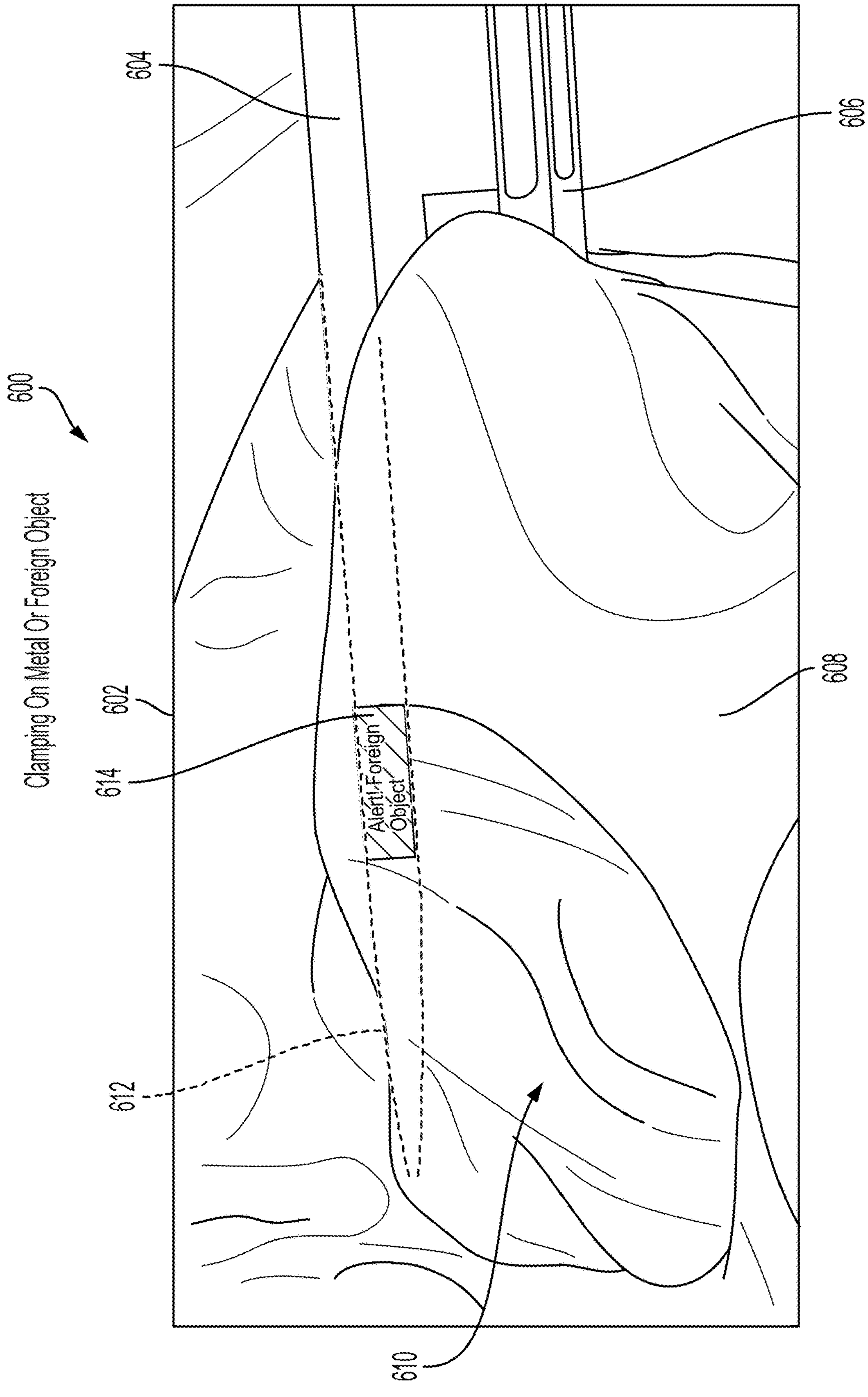

FIG. 141 is an augmented image of a live feed of a surgical area as visualized through a laparoscopic camera during a minimally invasive surgical procedure indicating clamping on metal or foreign object as an operational aspect of a surgical instrument, according to one aspect of this disclosure.

Figure 142:
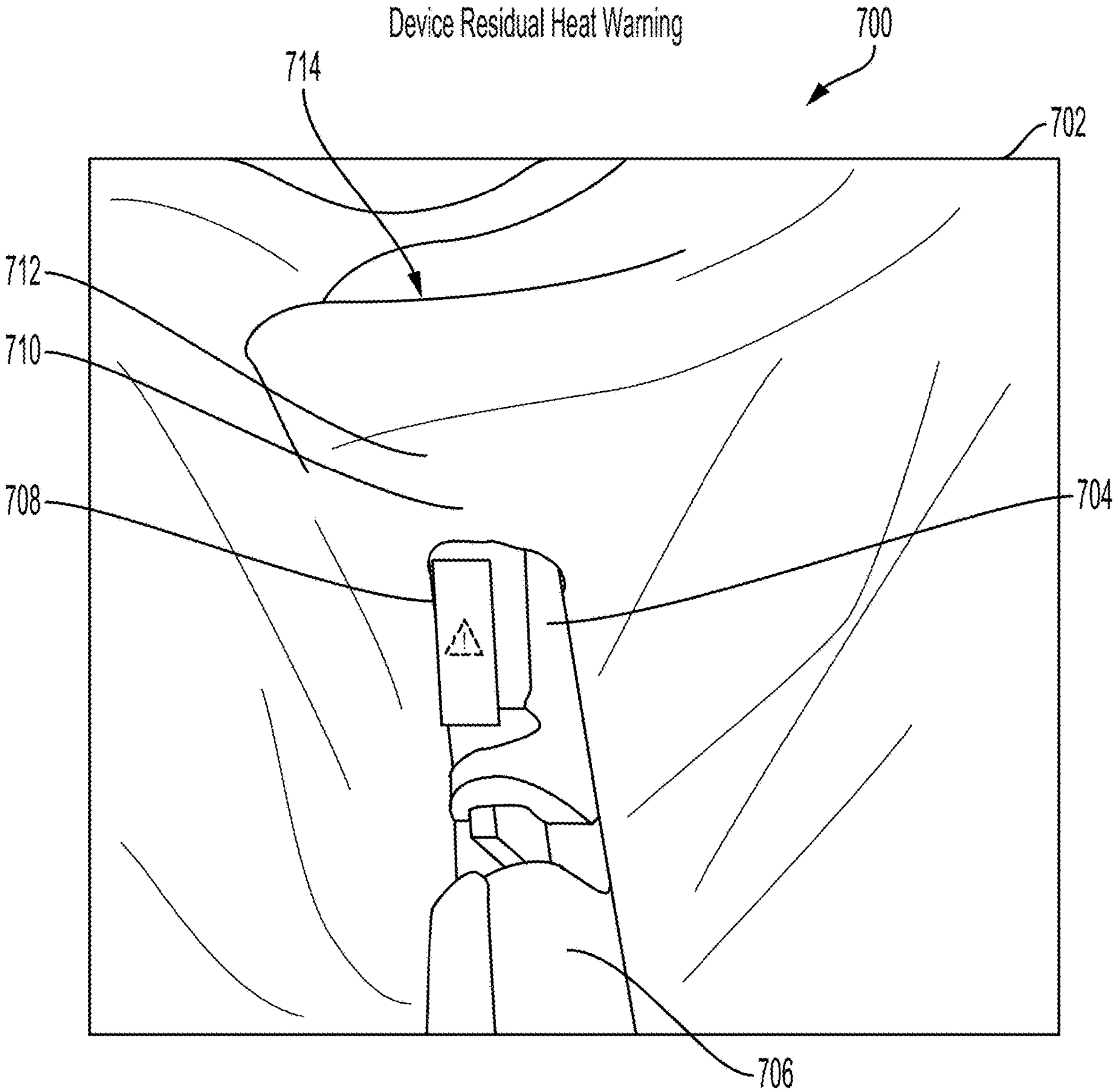

FIG. 142 is an augmented image of a live feed of a surgical area as visualized through a laparoscopic camera during a minimally invasive surgical procedure indicating device residual heat warning where overheating is an operational aspect of a surgical instrument, according to one aspect of this disclosure.

Figure 143:
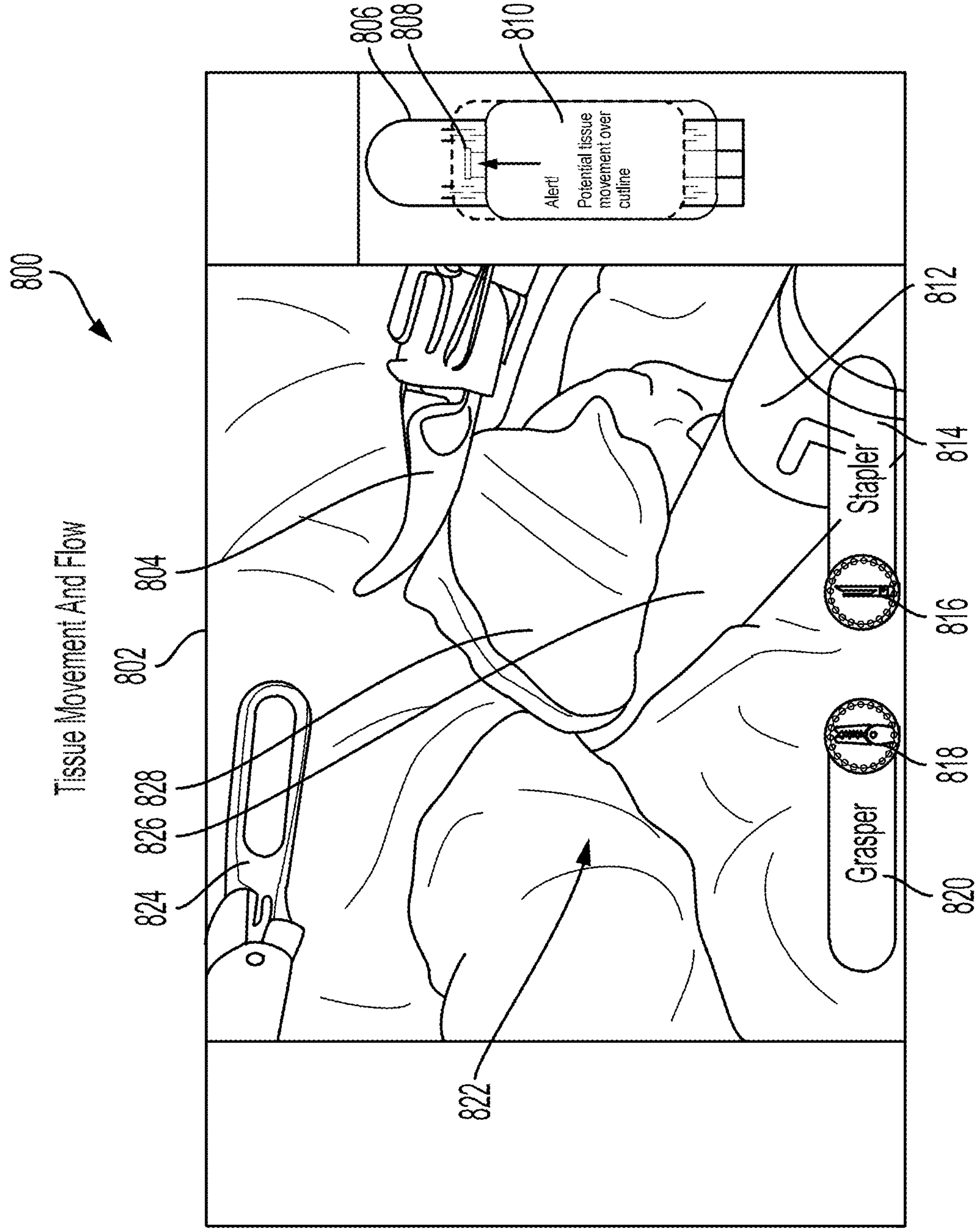

FIG. 143 is an augmented image of a live feed of a surgical area as visualized through a laparoscopic camera during a minimally invasive surgical procedure indicating tissue movement and flow is a tissue aspect, according to one aspect of this disclosure.

Figure 144:
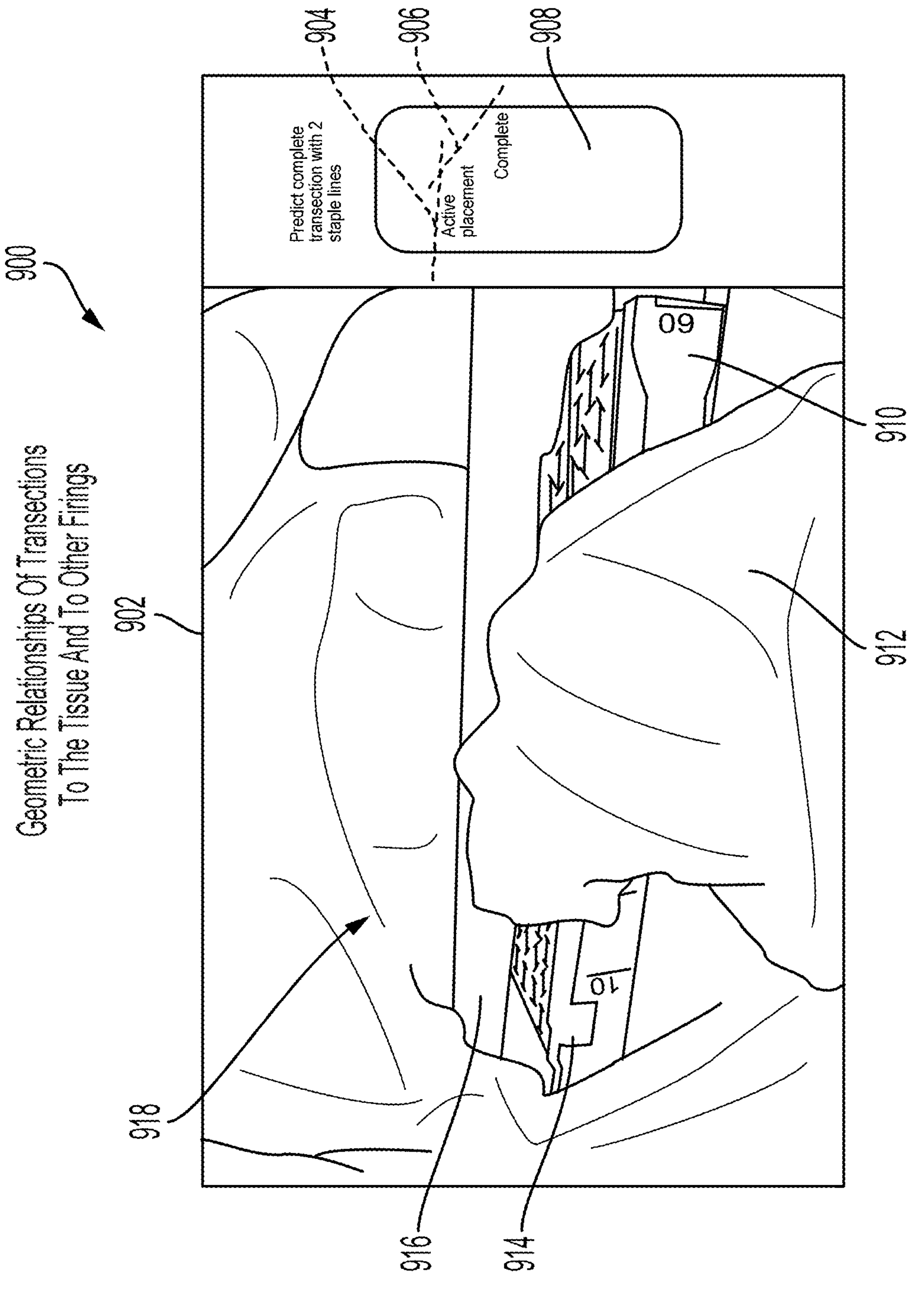

FIG. 144 is an augmented image of a live feed of a surgical area as visualized through a laparoscopic camera during a minimally invasive surgical procedure indicating the geometric relationship of the transections to tissue and other firings is a tissue aspect, according to one aspect of this disclosure.

Figure 145:
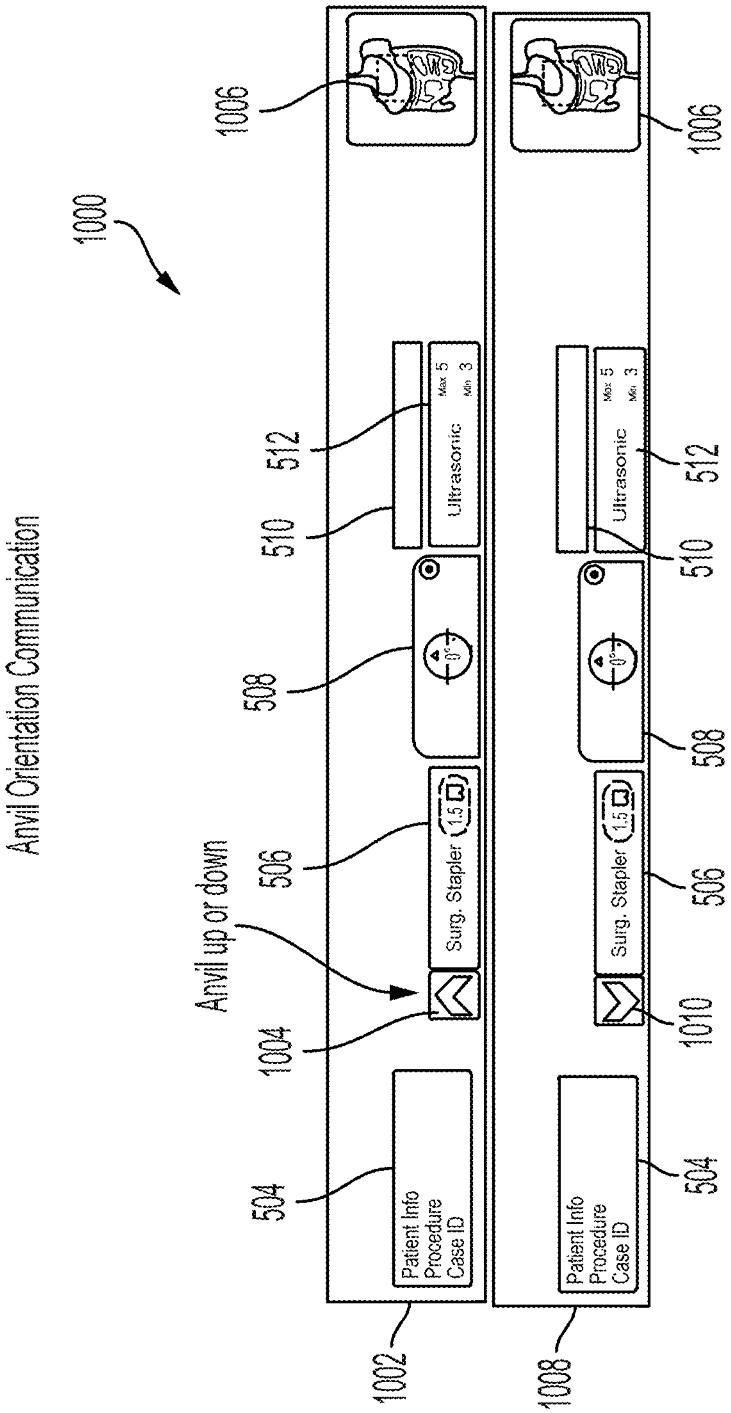

FIG. 145 is an image showing anvil orientation communication as an operational aspect of a surgical instrument, according to one aspect of this disclosure.

Figure 146:
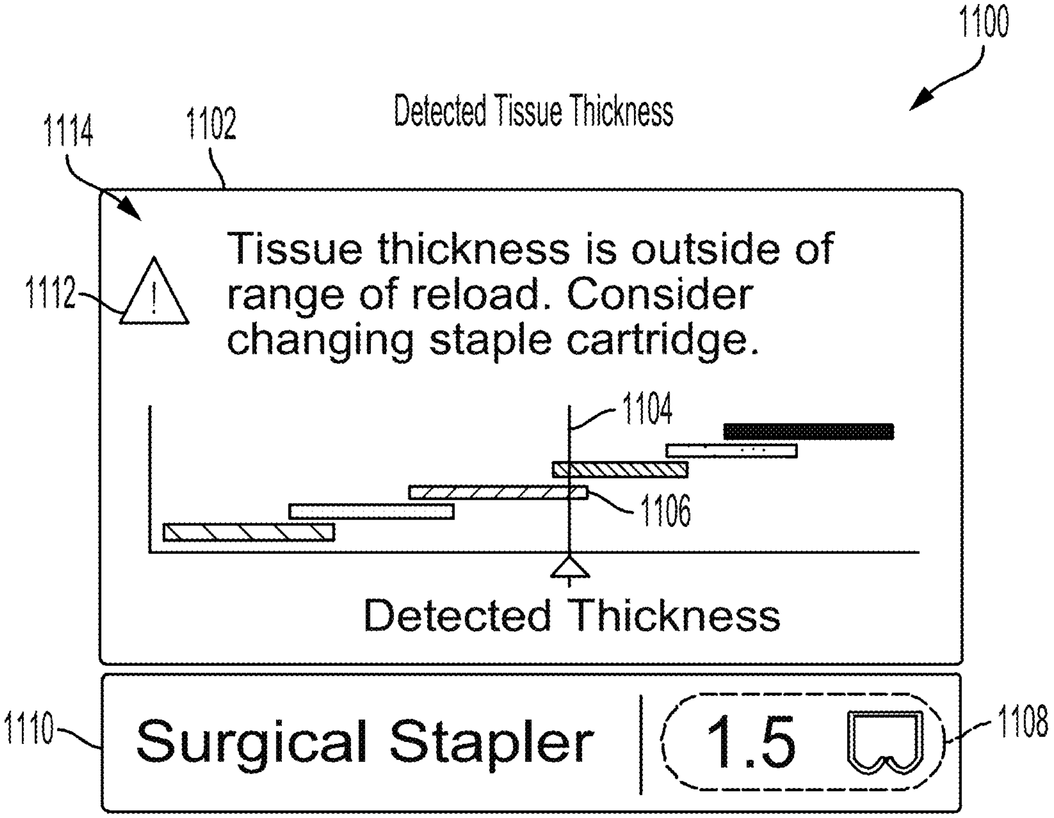

FIG. 146 is an image showing detected tissue thickness in the jaws of a surgical instrument end effector where tissue thickness is a tissue aspect, according to one aspect of this disclosure.

Figure 147:
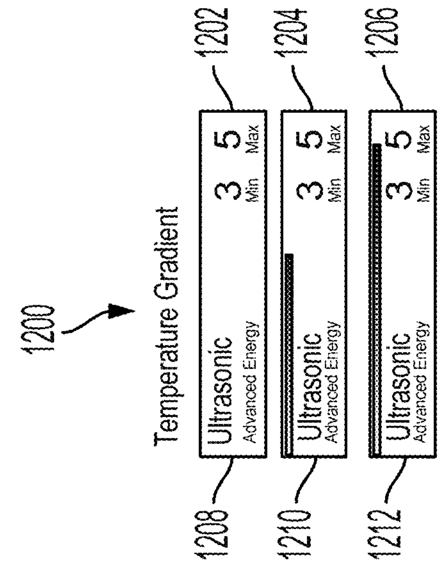

FIG. 147 is an image of temperature gradient display graphics for an ultrasonic instrument, according to one aspect of this disclosure.

Figure 148:
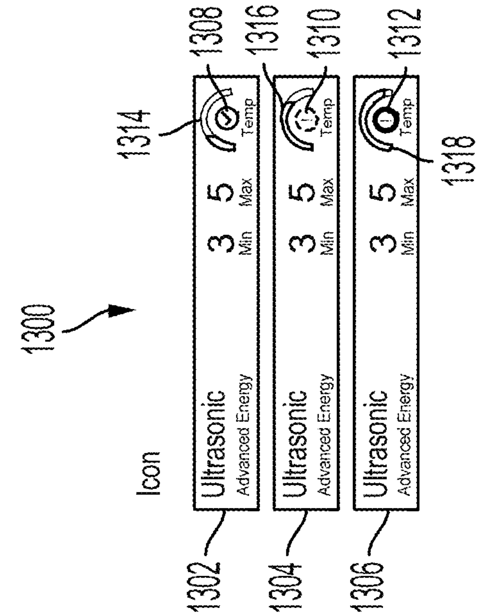

FIG. 148 is an image of temperature icon display graphics for an ultrasonic instrument, according to one aspect of this disclosure.

Figure 149:
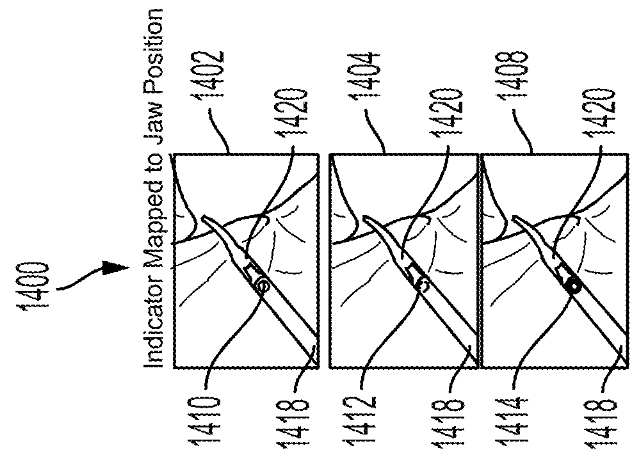

FIG. 149 is an image of an ultrasonic blade temperature graphic elements mapped to an end effector jaw position, according to one aspect of this disclosure.

Figure 150:
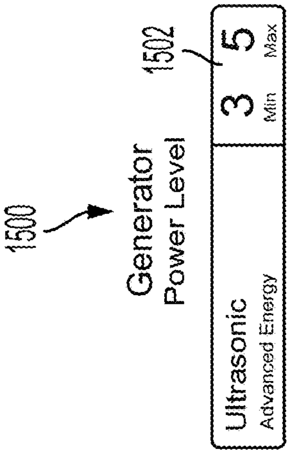

FIG. 150 is an image of an ultrasonic generator power level display graphic, according to one aspect of this disclosure.

Figure 151:
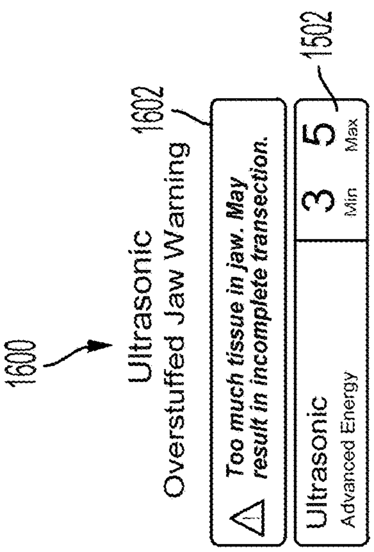

FIG. 151 is an image of an ultrasonic generator power level display graphic with a pop-up warning graphic indicating that the ultrasonic end effector jaw is overstuffed, according to at aspect of this disclosure.

Figure 152:
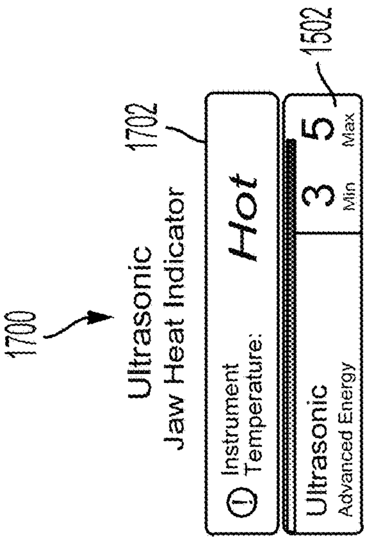

FIG. 152 is an image of an ultrasonic generator power level display graphic with a pop-up warning graphic indicating ultrasonic end effector jaw heat, according to one aspect of this disclosure.

Figure 153:
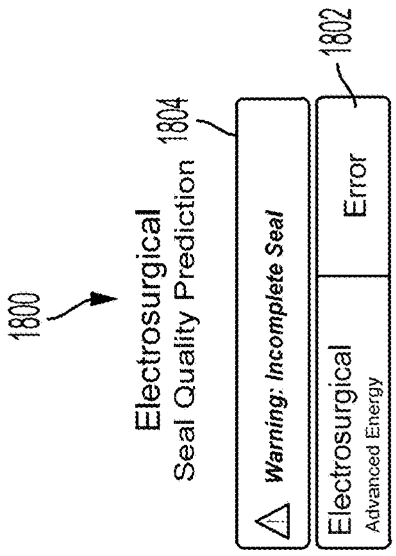

FIG. 153 is an image of an electrosurgical generator display graphic with a pop-up warning graphic indicating electrosurgical seal quality prediction, according to one aspect of this disclosure.

Figure 154:
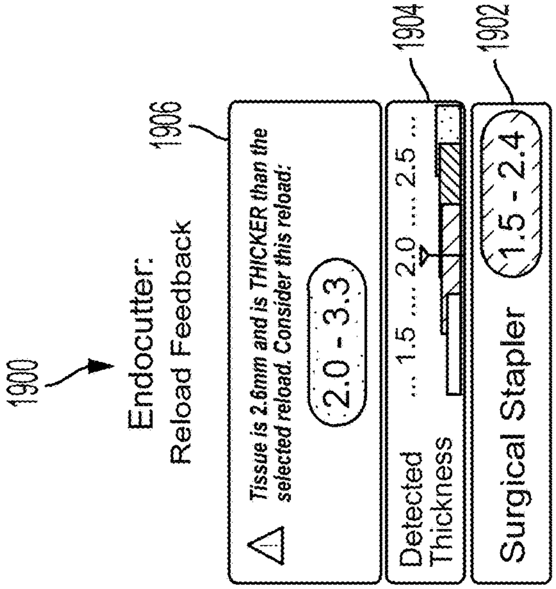

FIG. 154 is an image of a surgical stapler reload feedback, according to one aspect of this disclosure.

Figure 155:
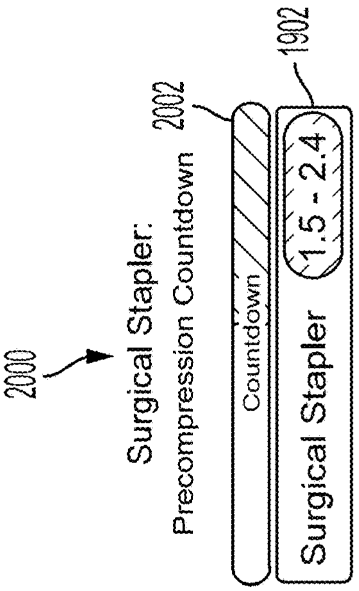

FIG. 155 is an image of a surgical stapler precompression countdown, according to one aspect of this disclosure.

Figure 156:
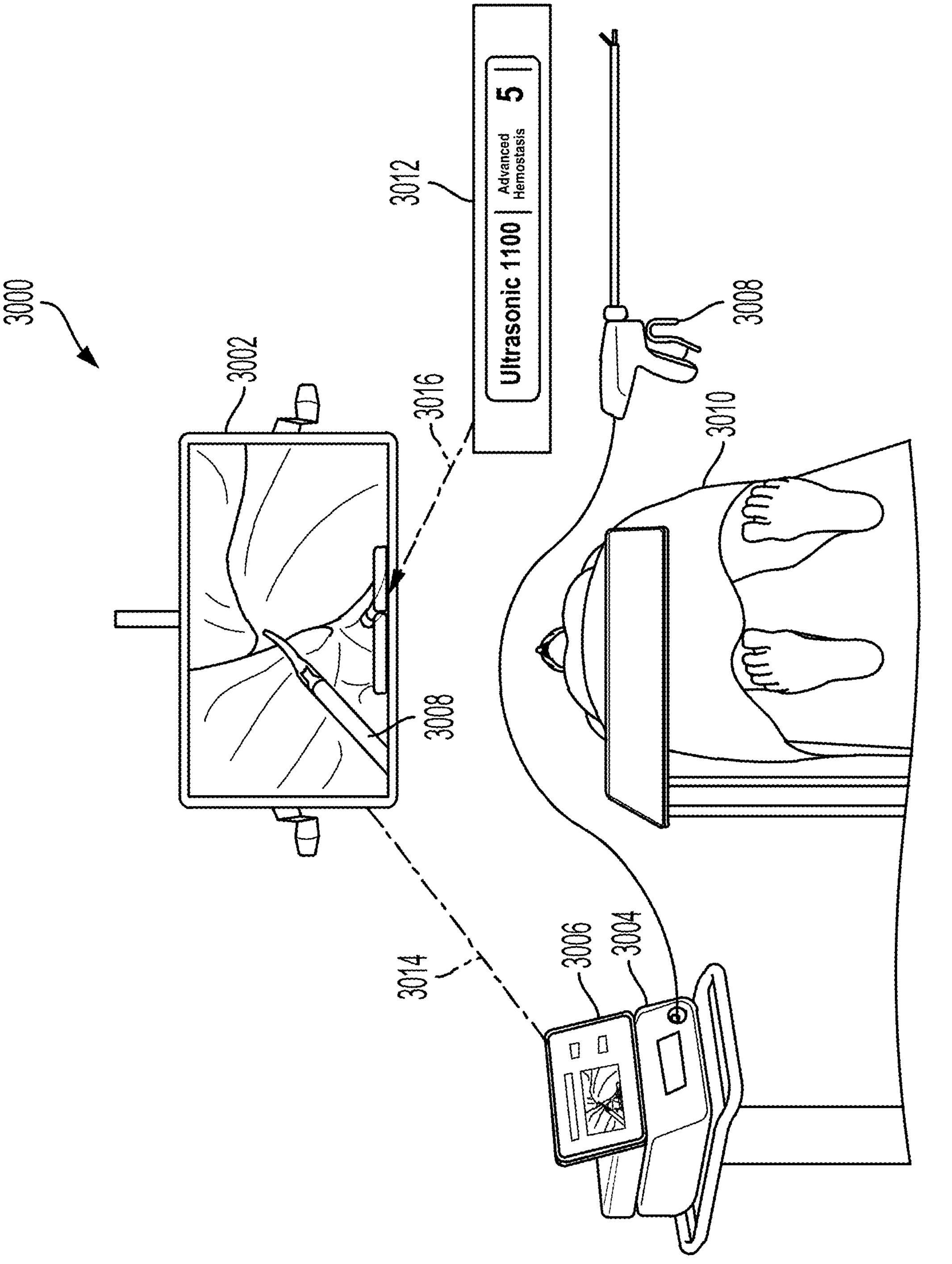

FIG. 156 is a system diagram of a surgical suite comprising a surgical monitor with intraoperative data display of a surgical area, according to one aspect of this disclosure.

Figure 157:
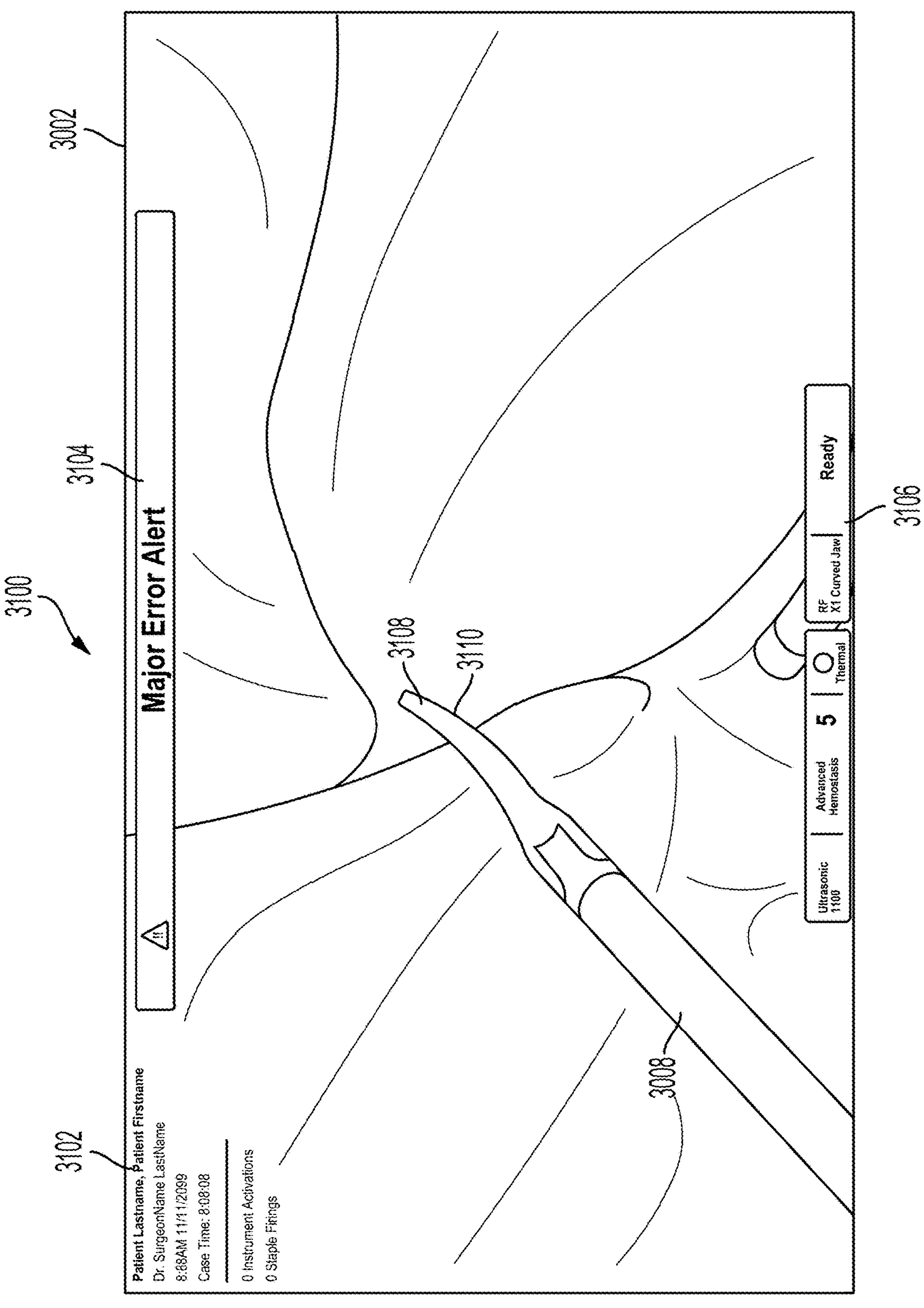

FIG. 157 is an augmented image of a live feed of a surgical area as visualized through a laparoscopic camera during a minimally invasive surgical procedure displayed on an intraoperative data display, according to one aspect of this disclosure.

Figure 158:
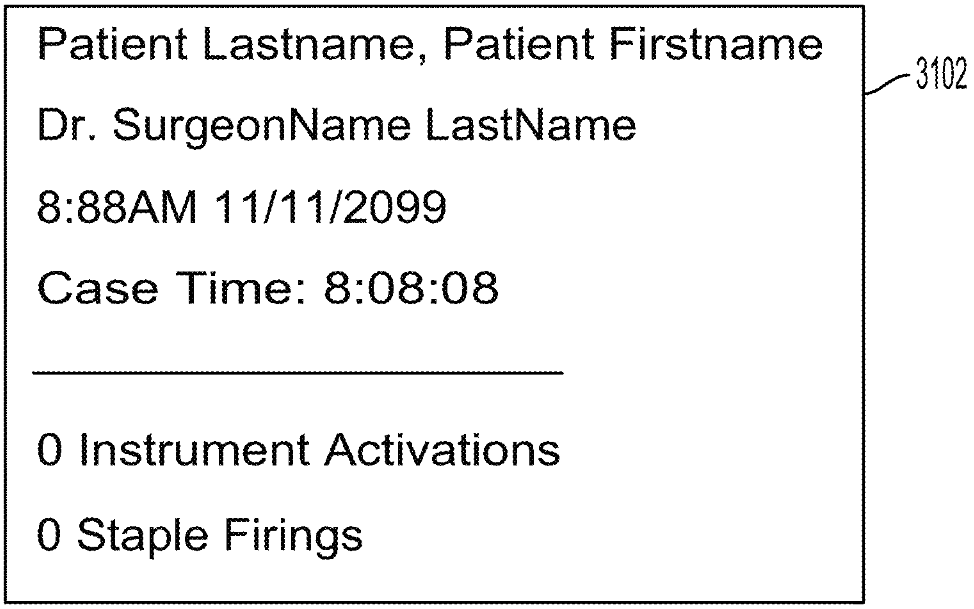

FIG. 158 is a detailed view of the case information panel overlay shown in FIG. 157, according to one aspect of this disclosure.

Figure 159:
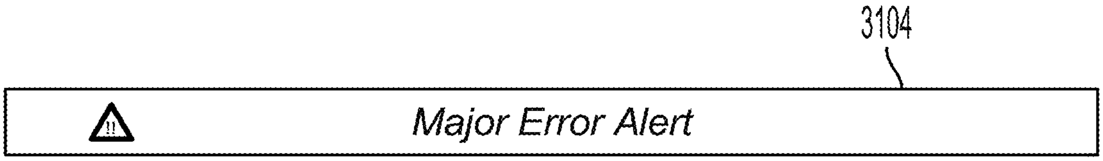

FIG. 159 is a detailed view of the systems notifications panel overlay shown in FIG. 157, according to one aspect of this disclosure.

Figure 160:
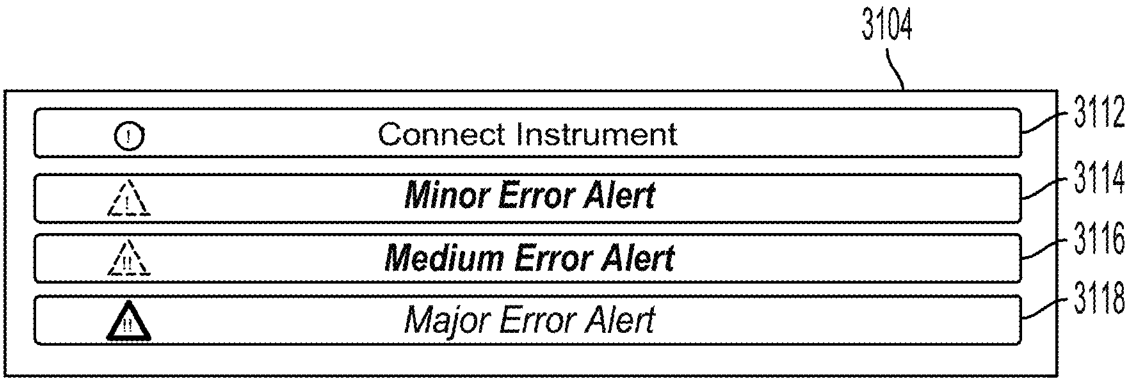

FIG. 160 is an image of several examples of systems notifications panel overlays, according to one aspect of this disclosure.

Figure 161:
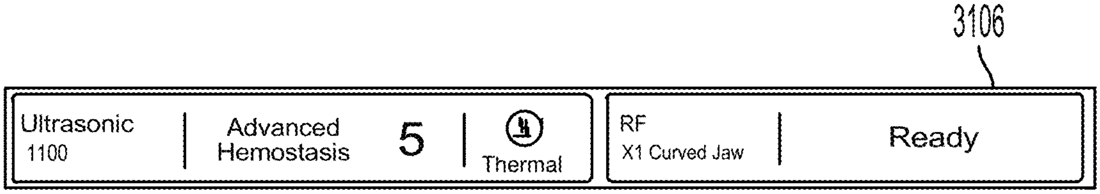

FIG. 161 is a detailed view of the device panels overlay shown in FIG. 157, according to one aspect of this disclosure.

Figure 162:
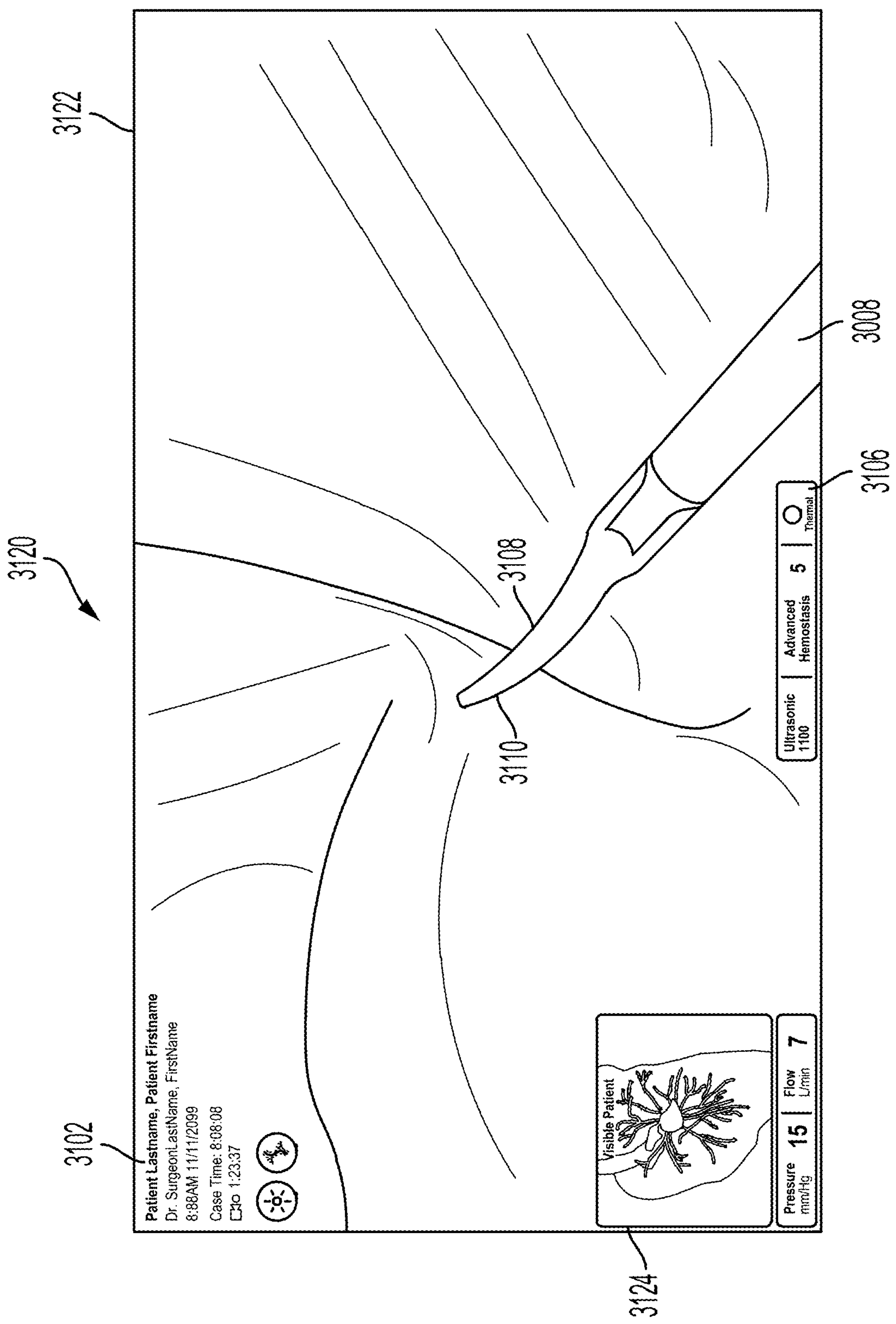

FIG. 162 is an augmented image of a live feed of a surgical area as visualized through a laparoscopic camera during a minimally invasive surgical procedure displayed on an intraoperative data display, according to one aspect of this disclosure.

Figure 163:
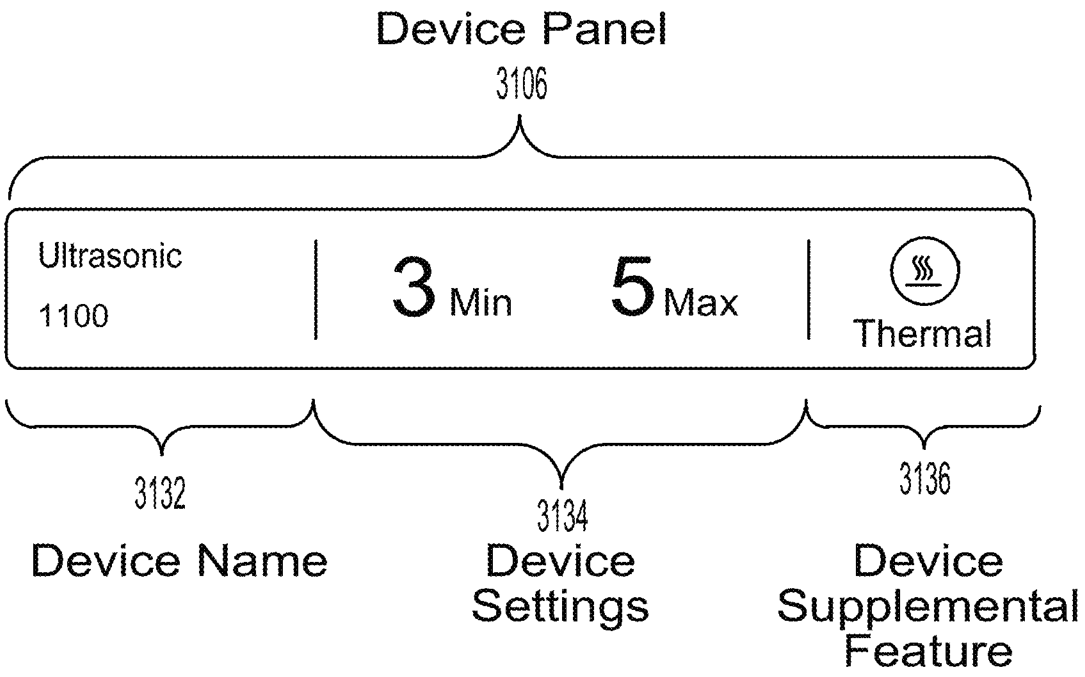

FIG. 163 is a schematic view of an energy device image panel architecture, according to one aspect of this disclosure.

Figure 164:
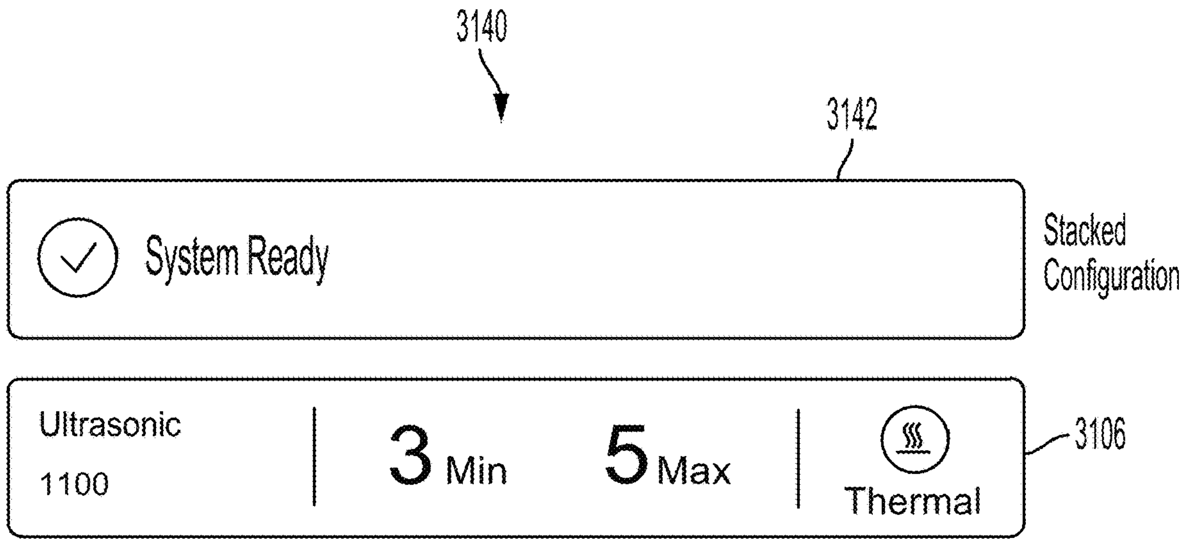

FIG. 164 is an image of supplemental device alerts/warning/information in a stacked configuration, according to one aspect of this disclosure.

Figure 165:
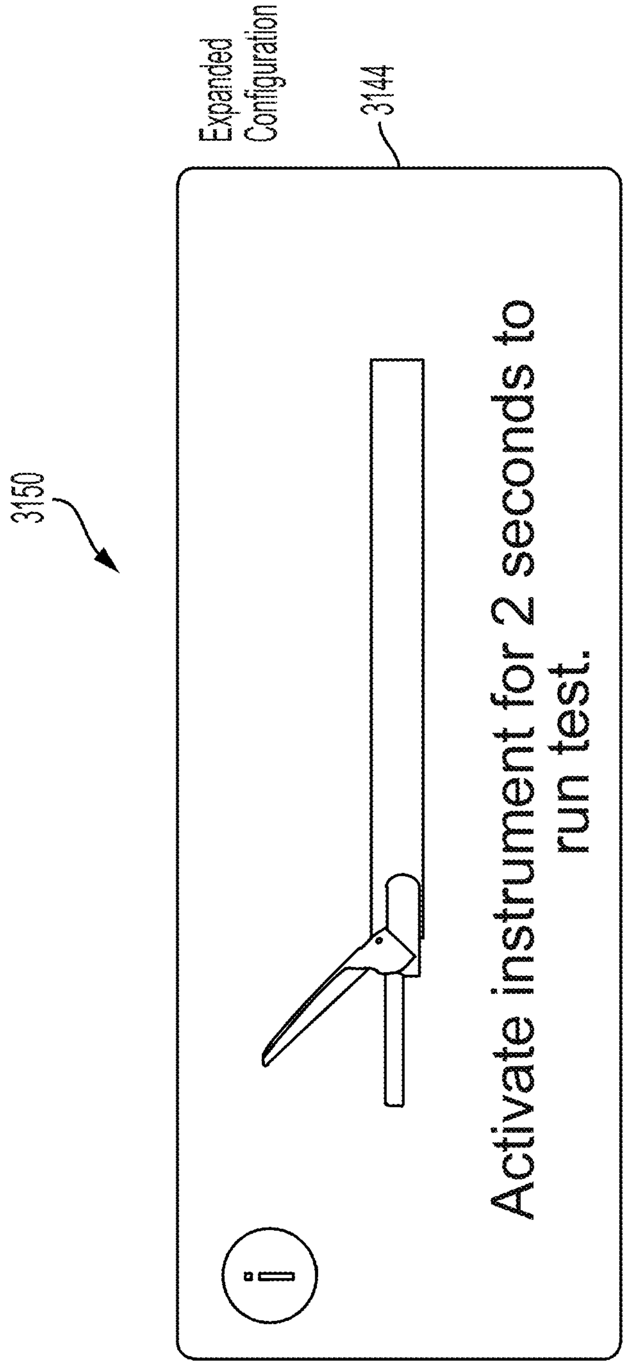

FIG. 165 is an image of supplemental device alerts/warning/information in an expanded configuration, according to one aspect of this disclosure.

Figure 166:
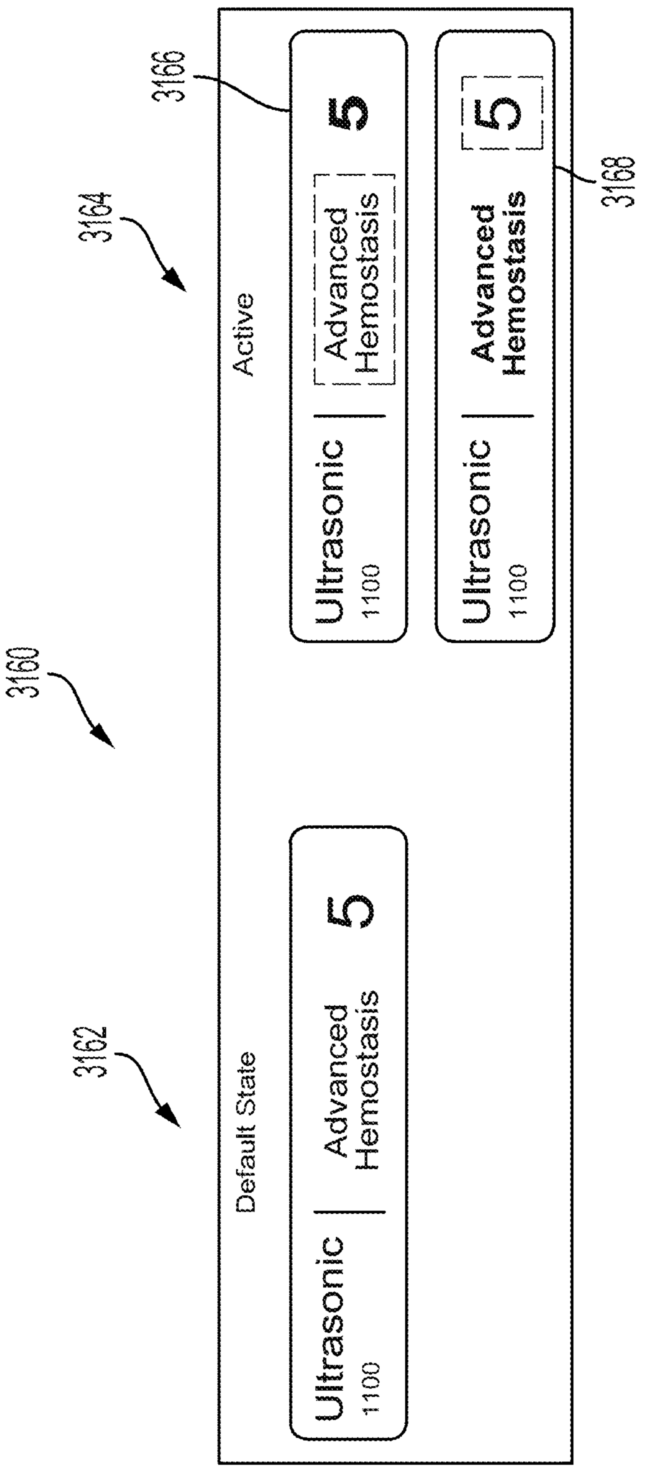

FIG. 166 is an instrument state image panel showing how instrument panel states change dynamically to show state changes such as device activation or power level adjustment, according to one aspect of this disclosure.

Figure 167:
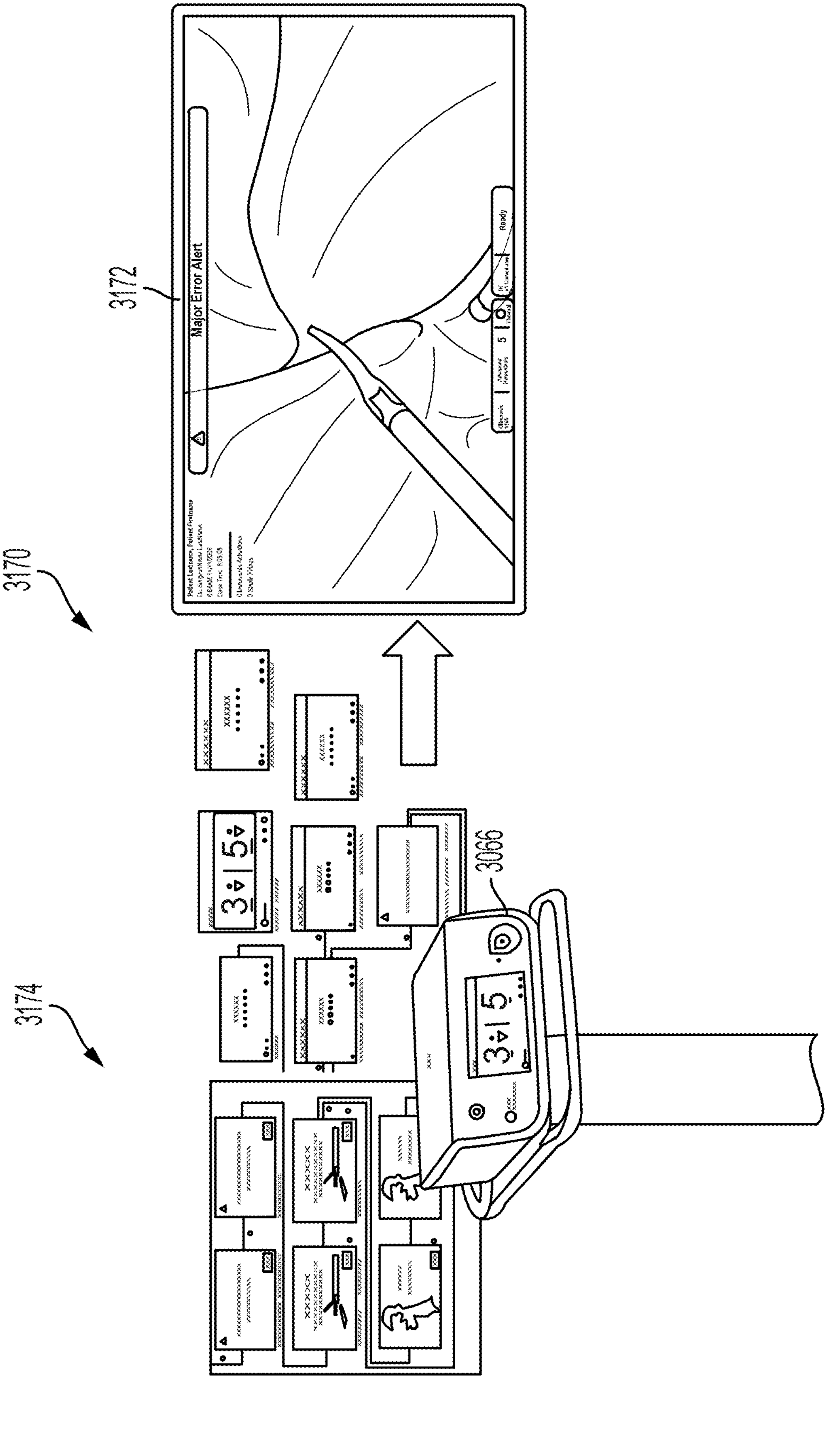

FIG. 167 is a system diagram of translating generator alerts and warnings to a laparoscopic monitor and displayed on a local interface, according to one aspect of this disclosure.

Figure 168:
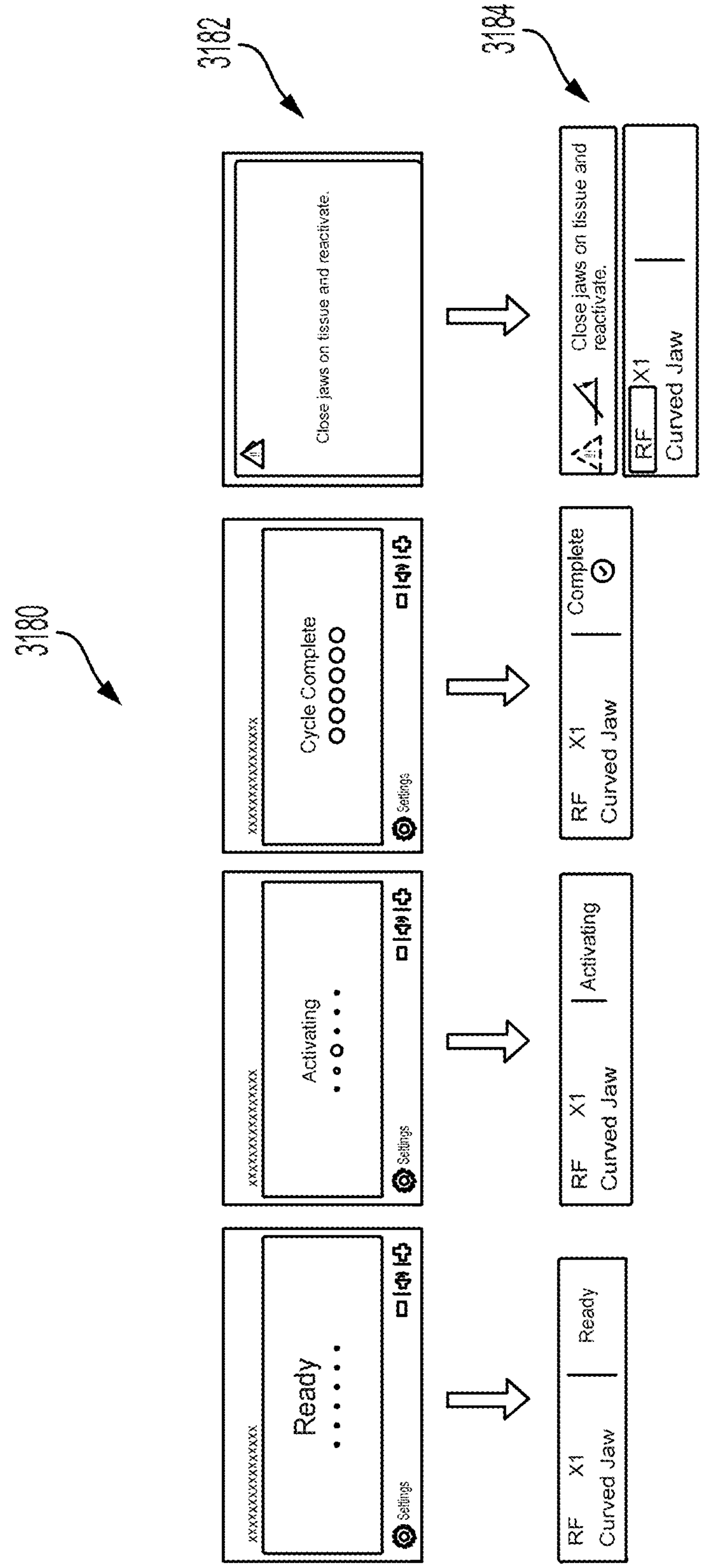

FIG. 168 is a diagram of a series of screens of existing alerts shown on a current generator that are transmitted to a surgical hub, which then displays them as a series of screens on a local interface, according to one aspect of this disclosure.

Figure 169:
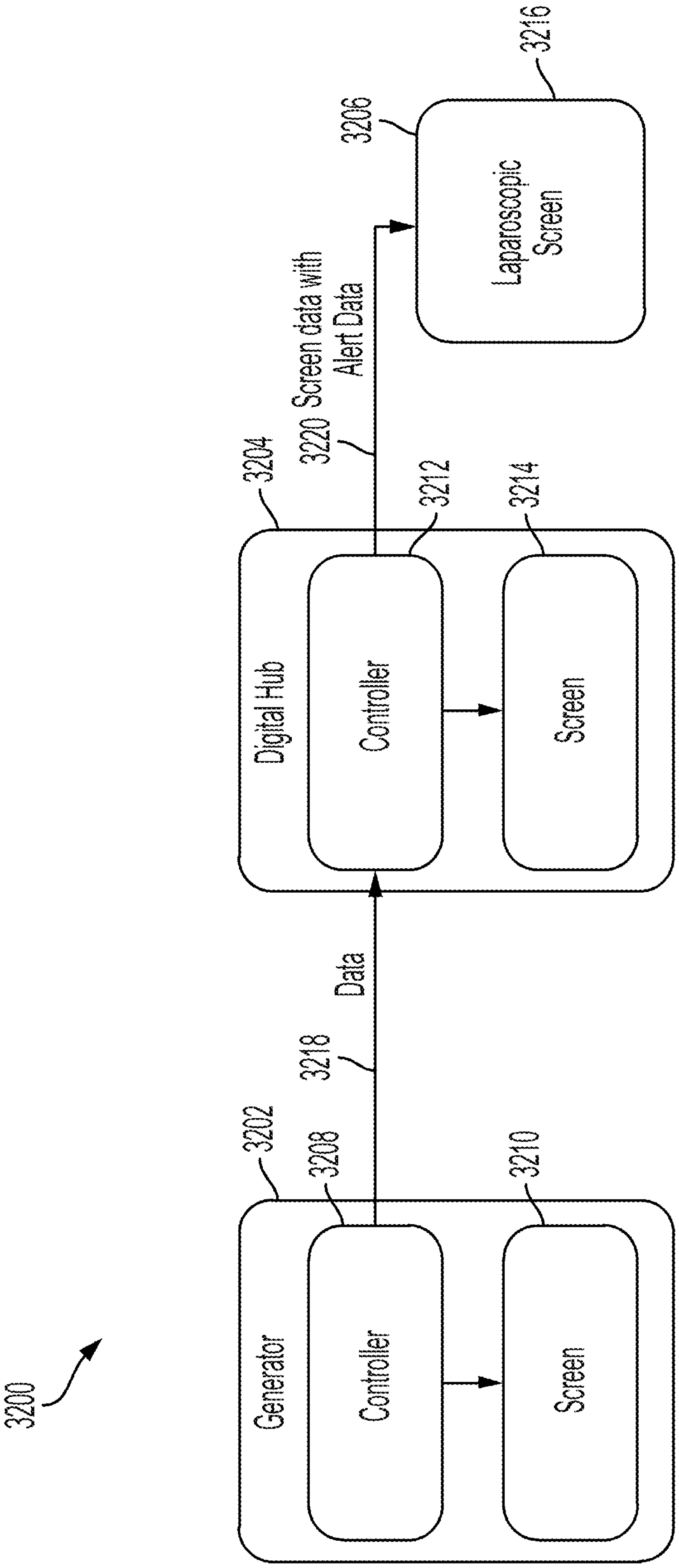

FIG. 169 is a schematic diagram of a system comprising a generator in communication with a digital hub, which then displays screen data and alert data on a local interface such as a laparoscopic screen, according to one aspect of this disclosure.

Figure 170:
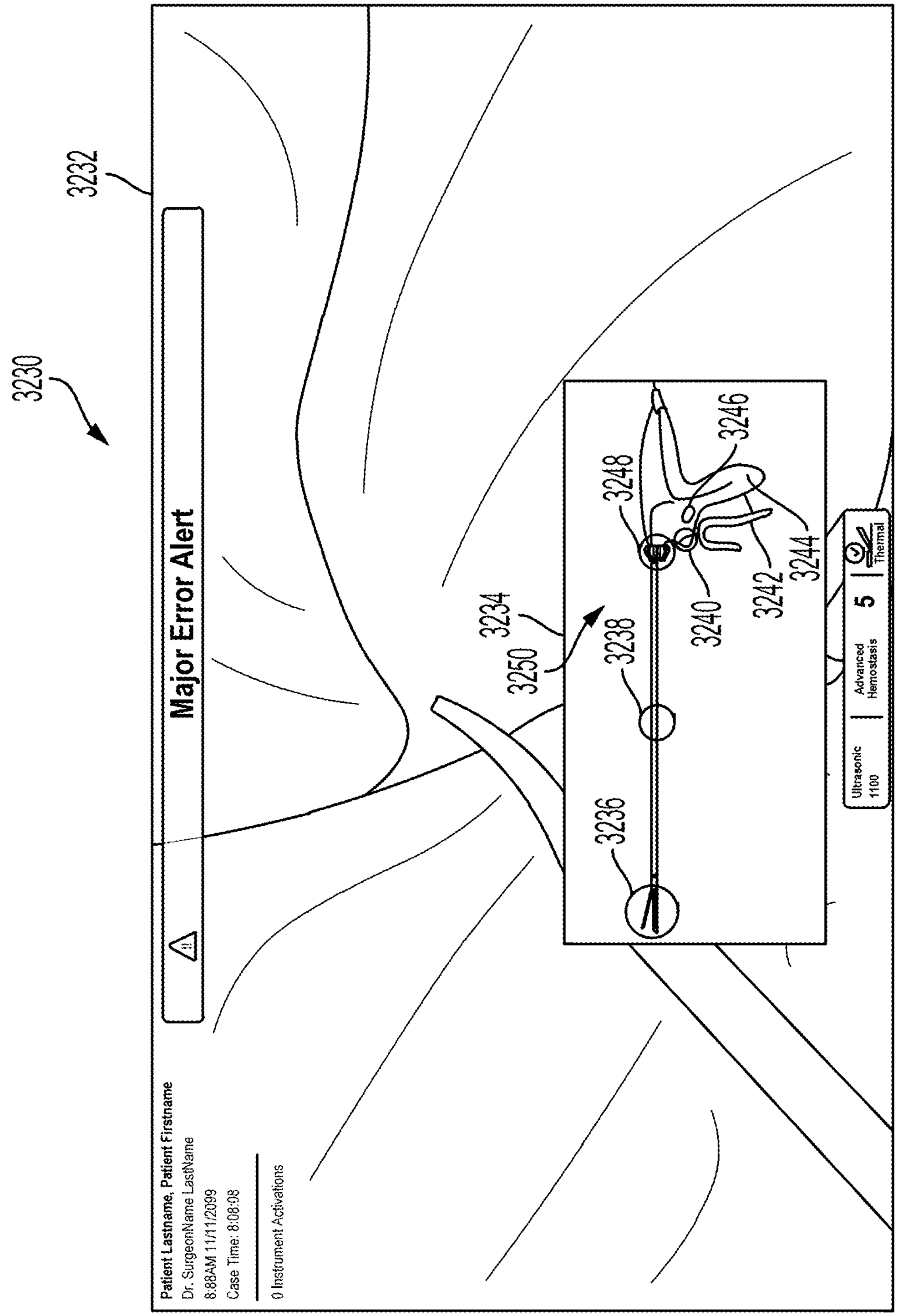

FIG. 170 is an augmented image of a live feed of a surgical area as visualized through a laparoscopic camera during a minimally invasive surgical procedure displayed on an intraoperative data display, according to one aspect of this disclosure.

Figure 171:
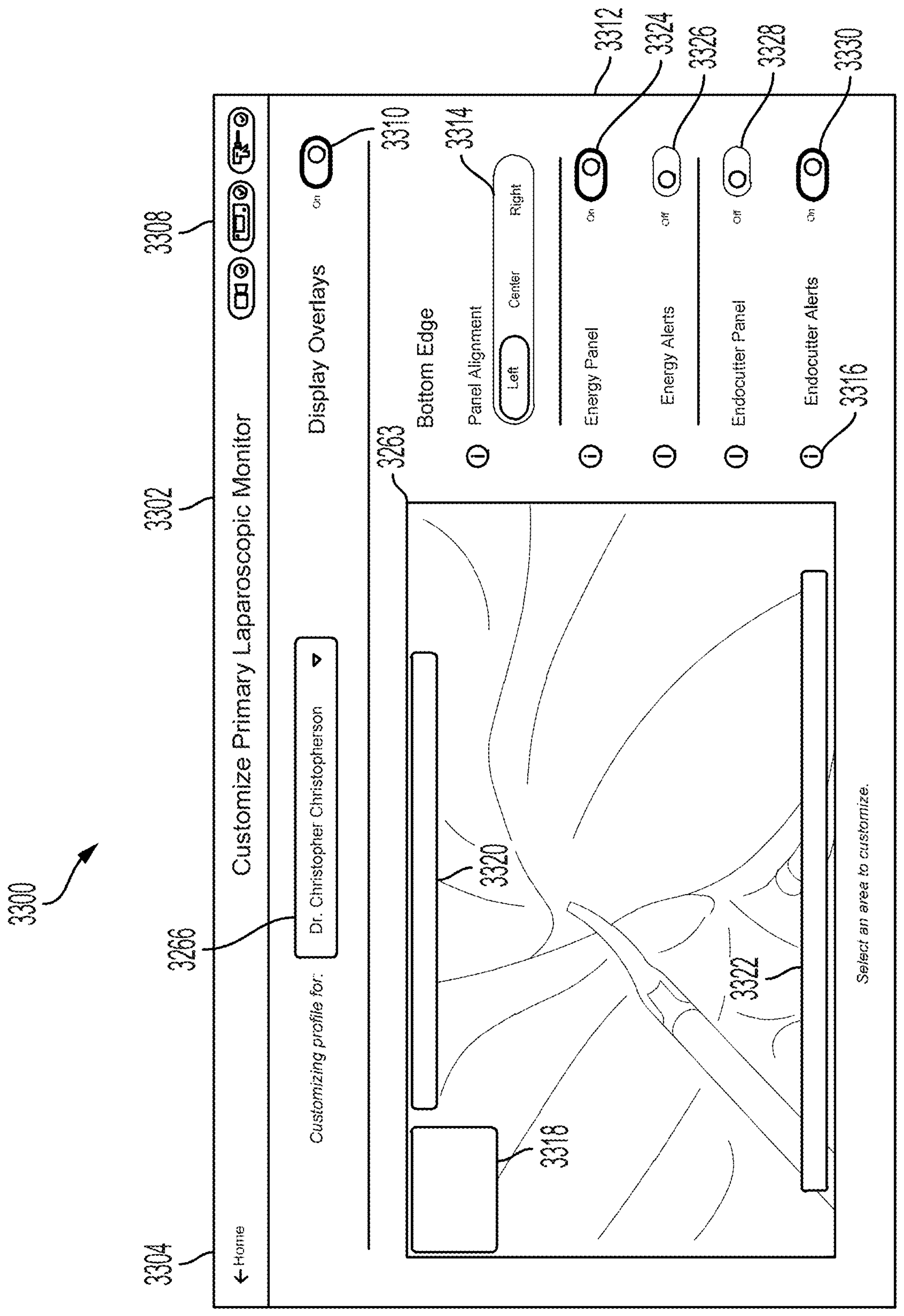

FIG. 171 is a display screen showing an intraoperative data display comprising a secondary bottom edge configurable panel, according to one aspect of this disclosure.

Figure 172:
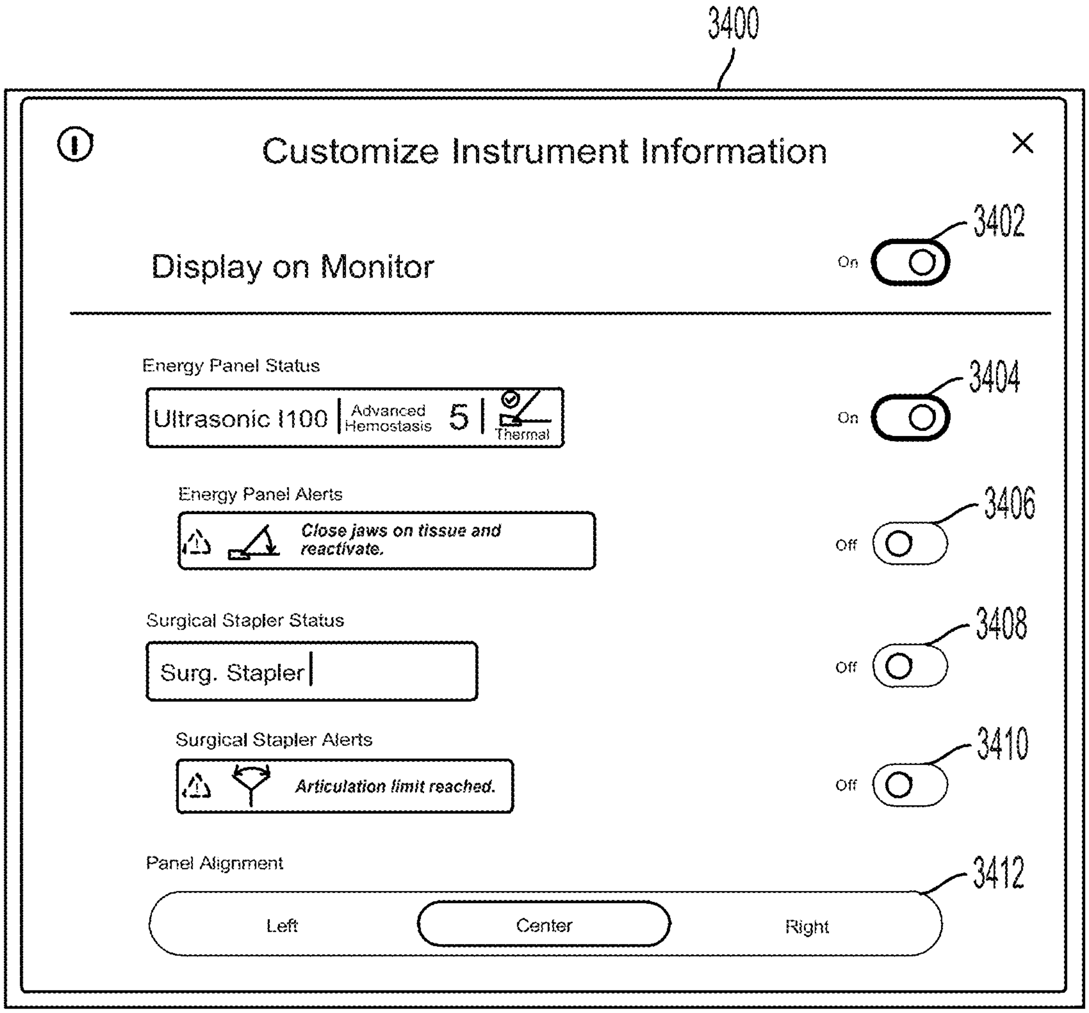

FIG. 172 is an alternative bottom edge configurable panel, according to one aspect of this disclosure.

Figure 173:
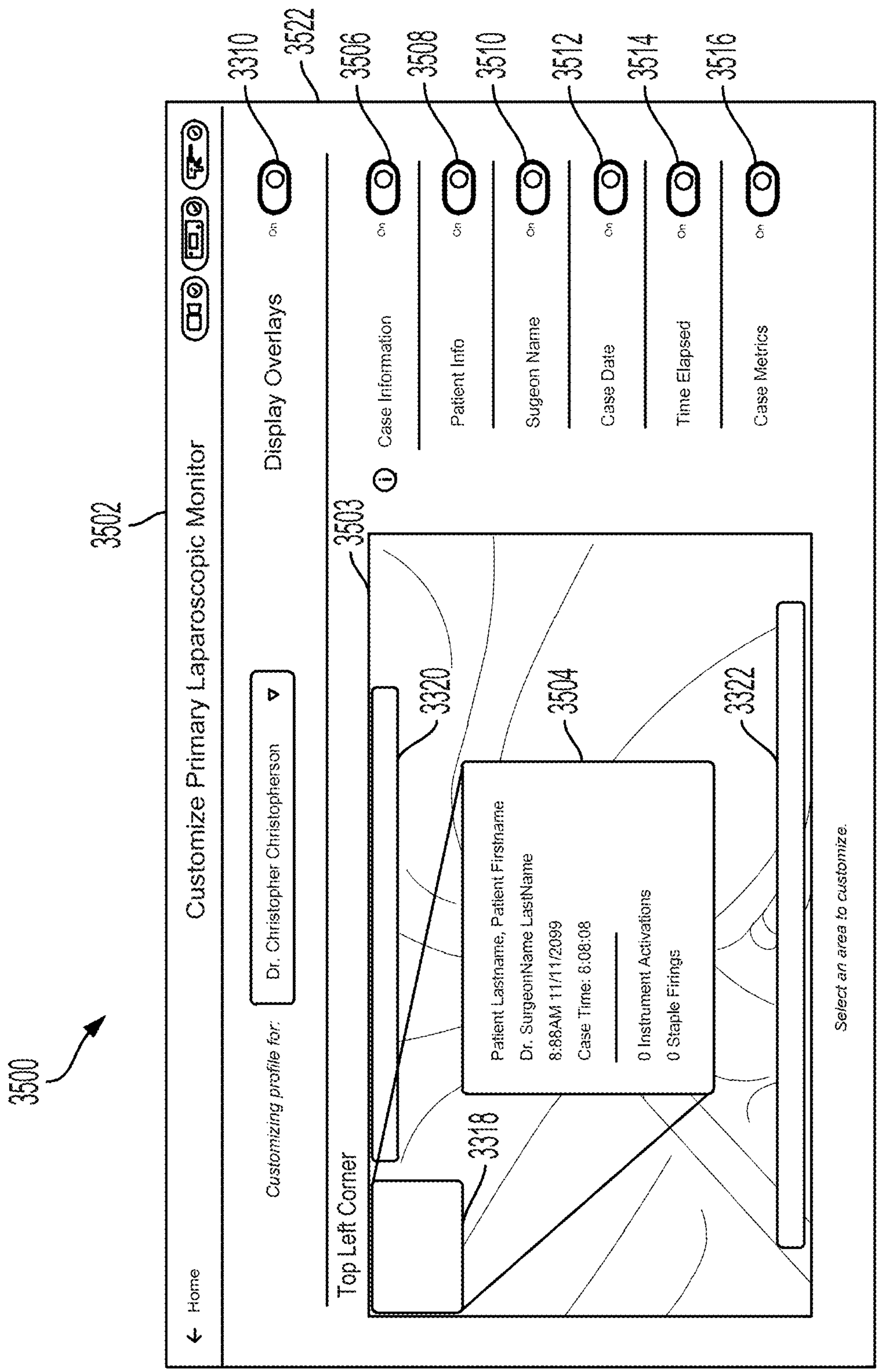

FIG. 173 is a display screen showing an intraoperative data display comprising a secondary top left corner configurable panel, according to one aspect of this disclosure.

Figure 174:
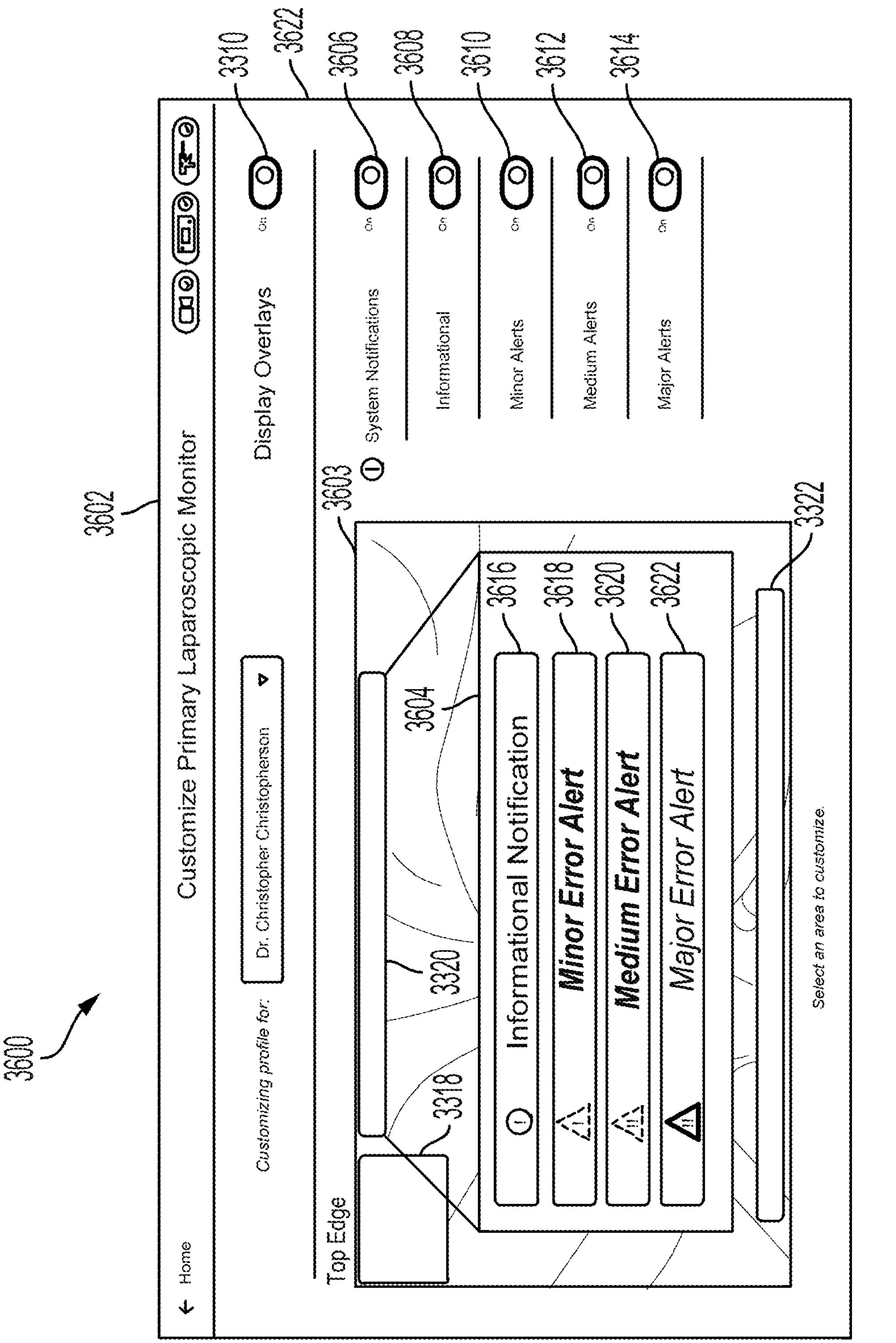

FIG. 174 is a display screen showing an intraoperative data display comprising a secondary top center configurable panel, according to one aspect of this disclosure.

Figure 175:
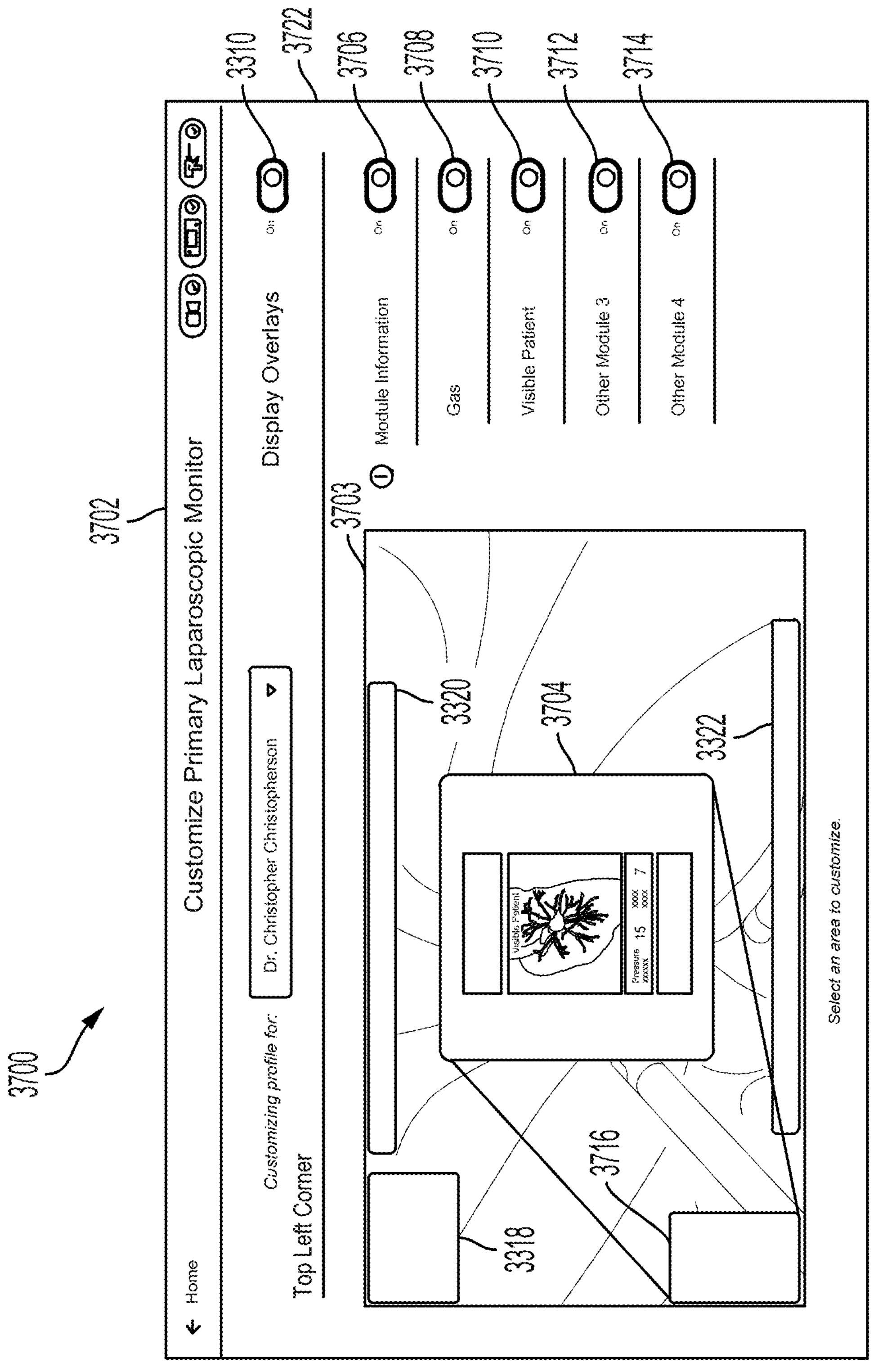

FIG. 175 is a display screen showing an intraoperative data display comprising a secondary side edge configurable panel, according to one aspect of this disclosure.

Figure 176:
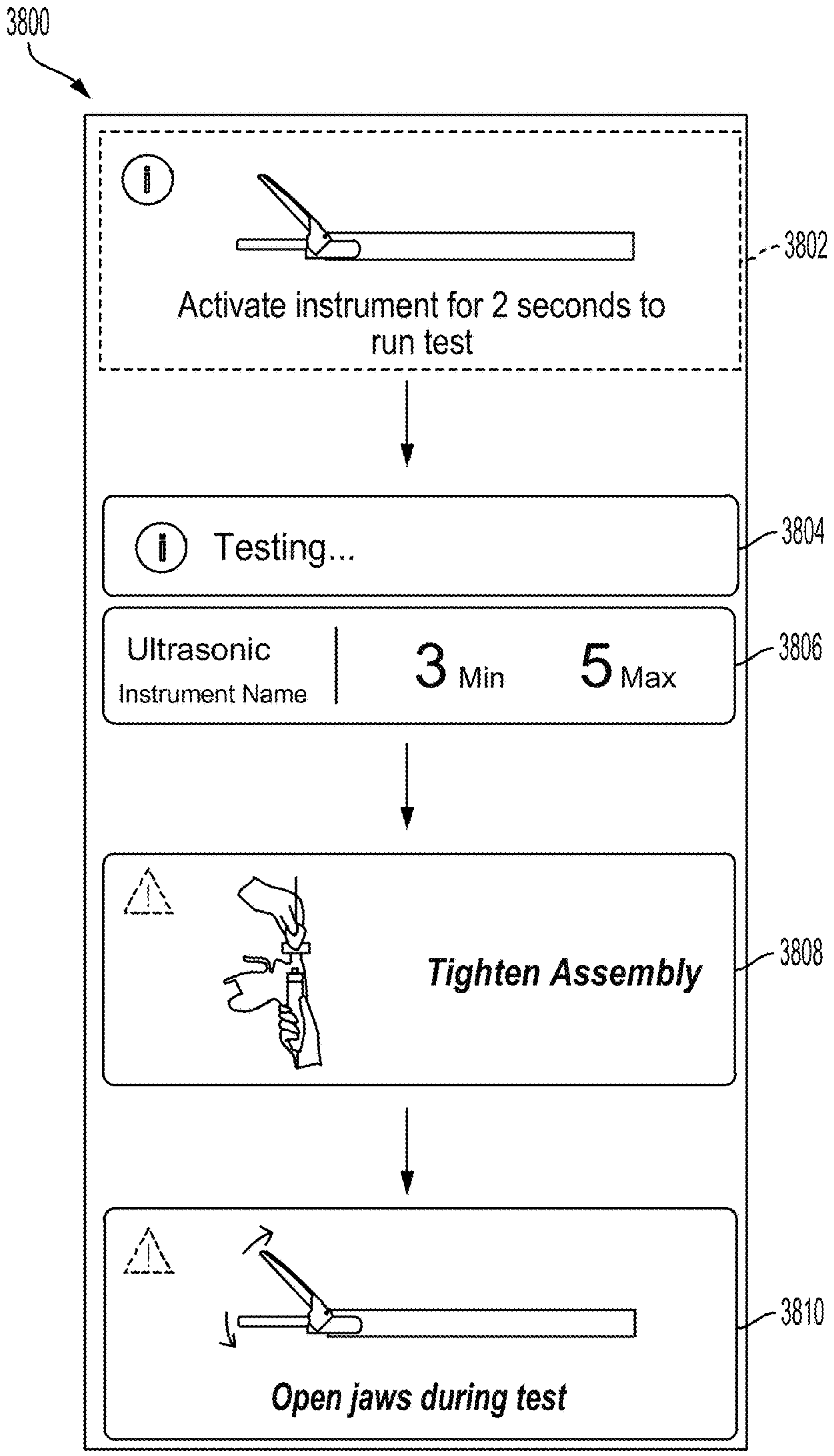

FIG. 176 is a series of image panels displaying device troubleshooting information, according to one aspect of this disclosure.

Figure 177:
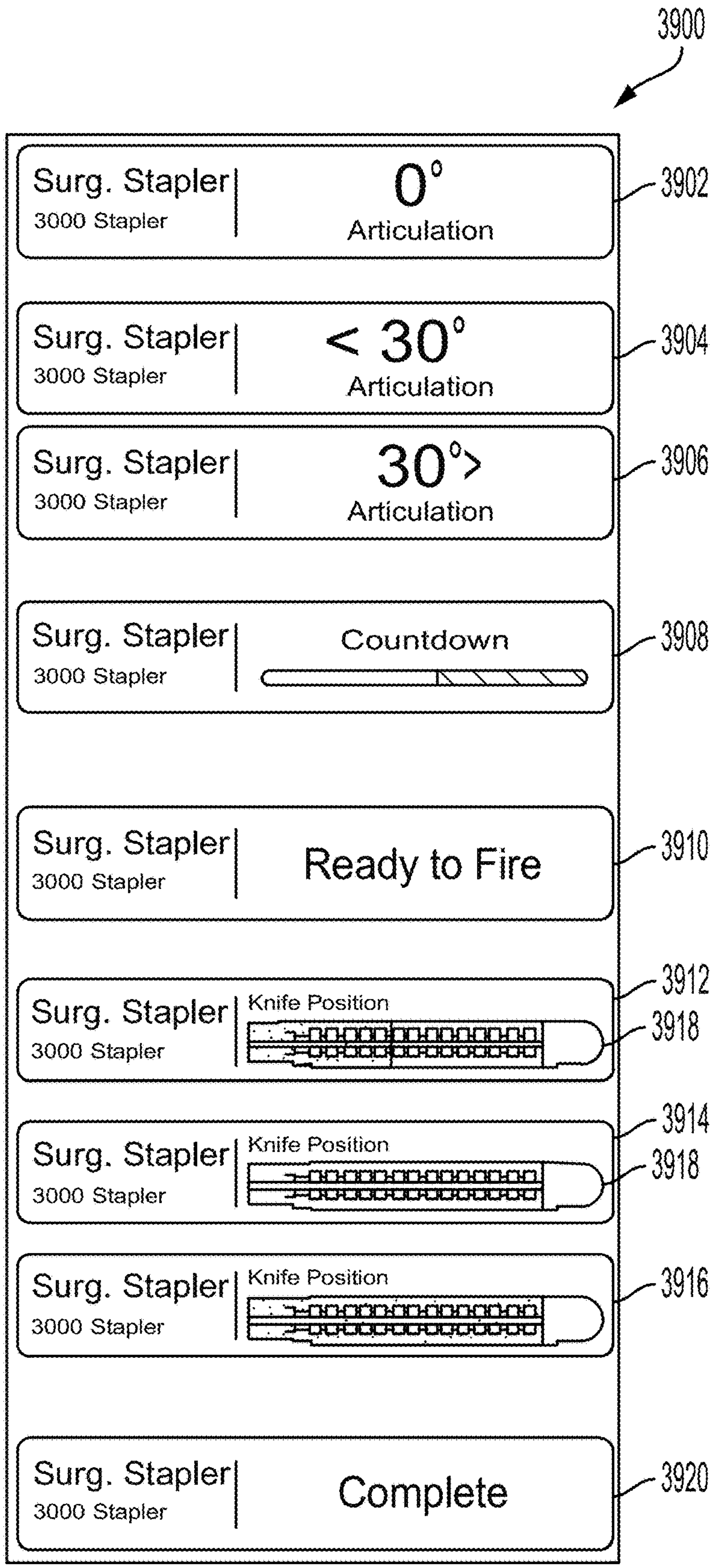

FIG. 177 is a series of image panels displaying articulating surgical stapler features, according to one aspect of this disclosure.

Figure 178:
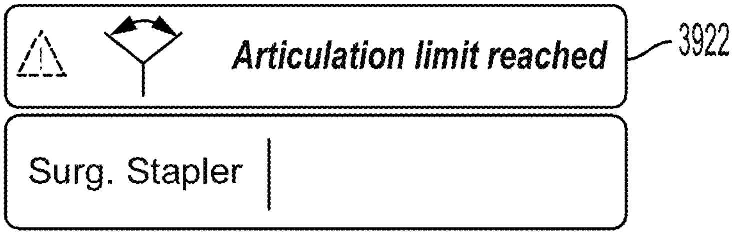

FIG. 178 is an alert/warning/information image panel displaying that the articulation limit has been reached, according to one aspect of this disclosure.

Figure 179:
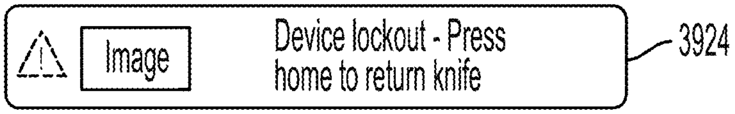

FIG. 179 is an alert/warning/information image panel displaying that the device is in lockout mode, according to one aspect of this disclosure.

Figure 180:
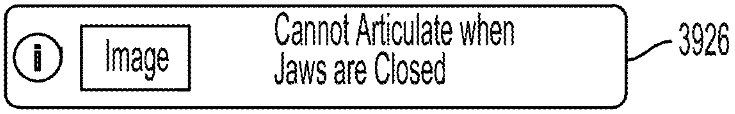

FIG. 180 is an alert/warning/information image panel displaying that the device cannot articulate when jaws are closed, according to one aspect of this disclosure.

Figure 181:
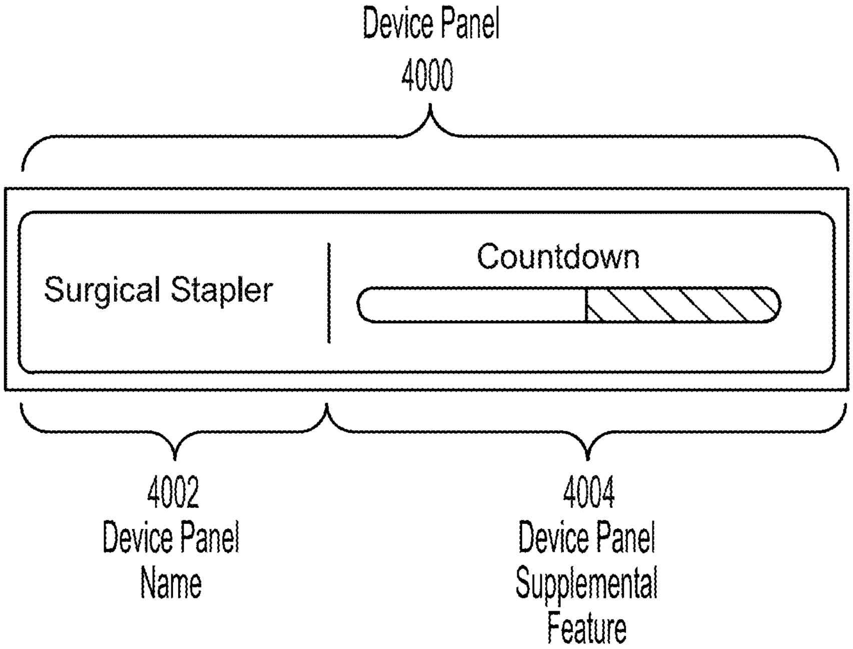

FIG. 181 is a device image panel showing articulating surgical stapler features, according to one aspect of this disclosure.

Figure 182:
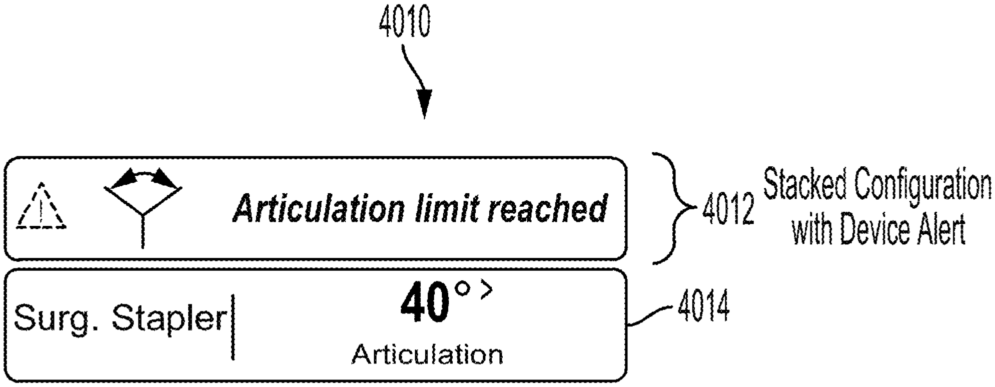

FIG. 182 is a stacked alert/warning/information image panel displayed in a stacked configuration with device alert displaying that the articulation limit has been reached, according to one aspect of this disclosure.

Figure 183:
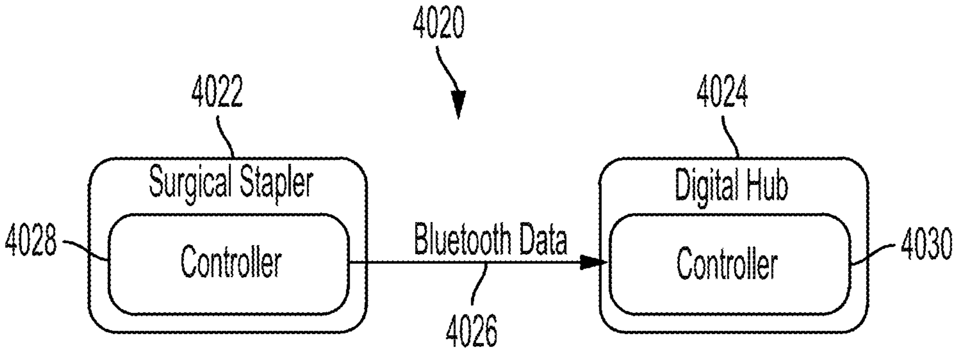

FIG. 183 is a schematic diagram of a system comprising a surgical stapler in communication with a digital hub over Bluetooth to execute an algorithm for the countdown timer image panel shown in FIGS. 176 and 180, according to one aspect of this disclosure.

Figure 184:
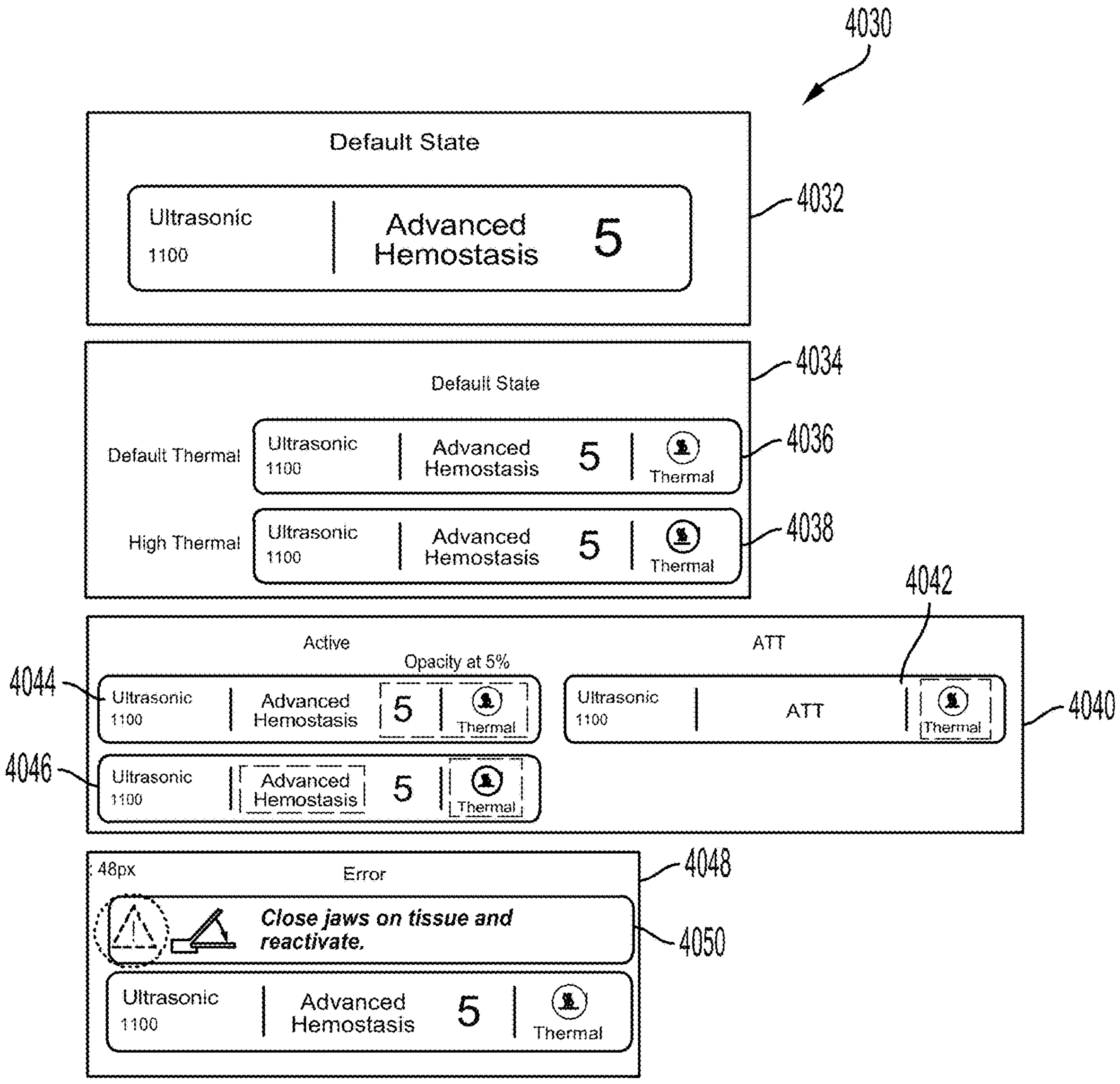

FIG. 184 is a series of device image panels/alerts displaying ultrasonic instrument features, according to one aspect of this disclosure.

FIG. 185 is a chart describing pairing a surgical stapler instrument, according to one aspect of this disclosure.

Figure 186:
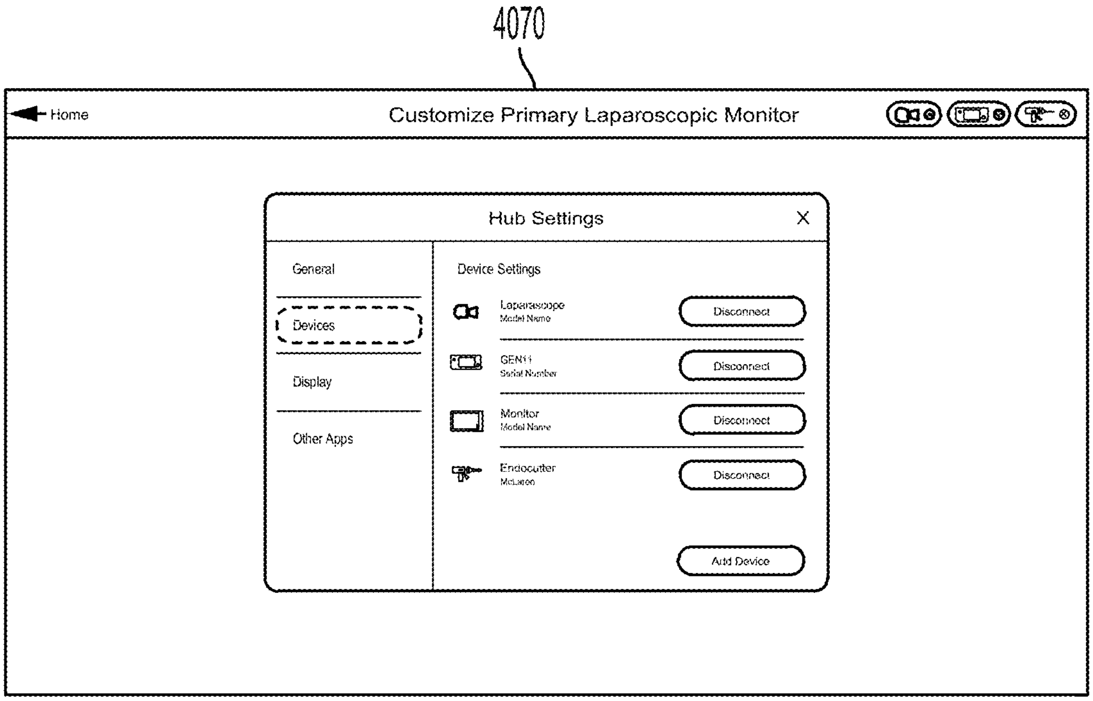

FIG. 186 is an image of a screen displaying pairing devices information, according to one aspect of this disclosure.

Figure 187:
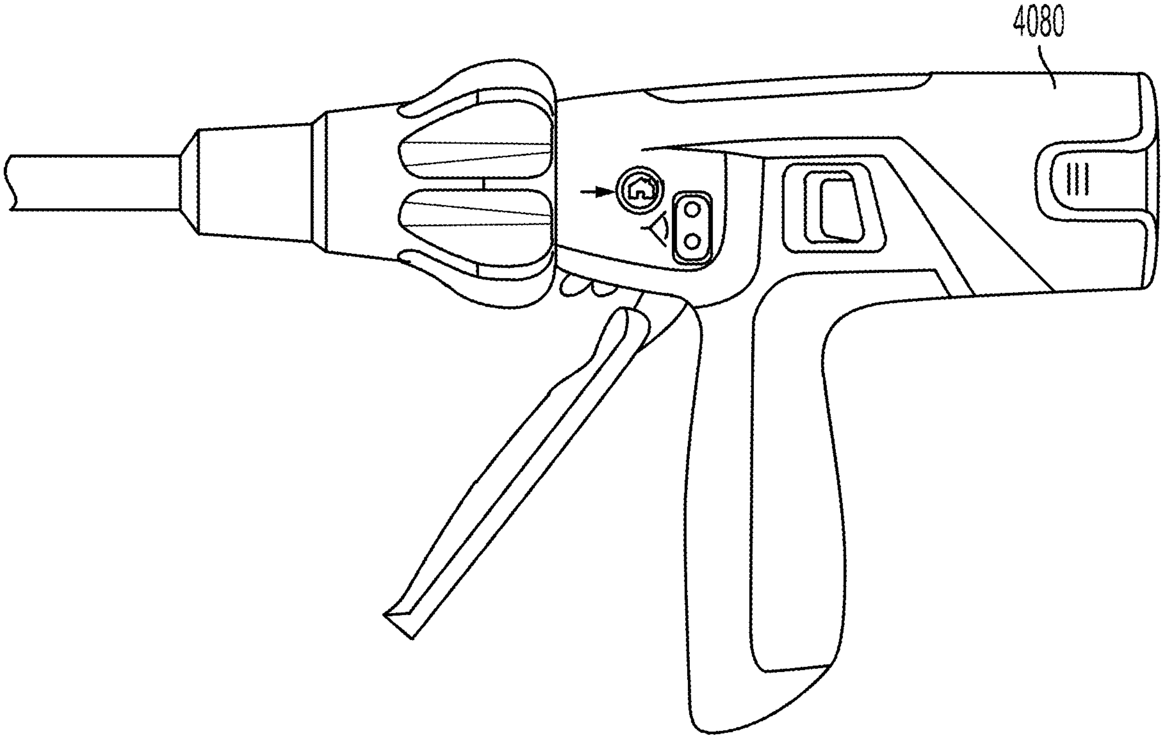

FIG. 187 is an image of a wireless surgical device comprising a unique identifier for pairing wireless devices, according to one aspect of this disclosure.

Figure 188:
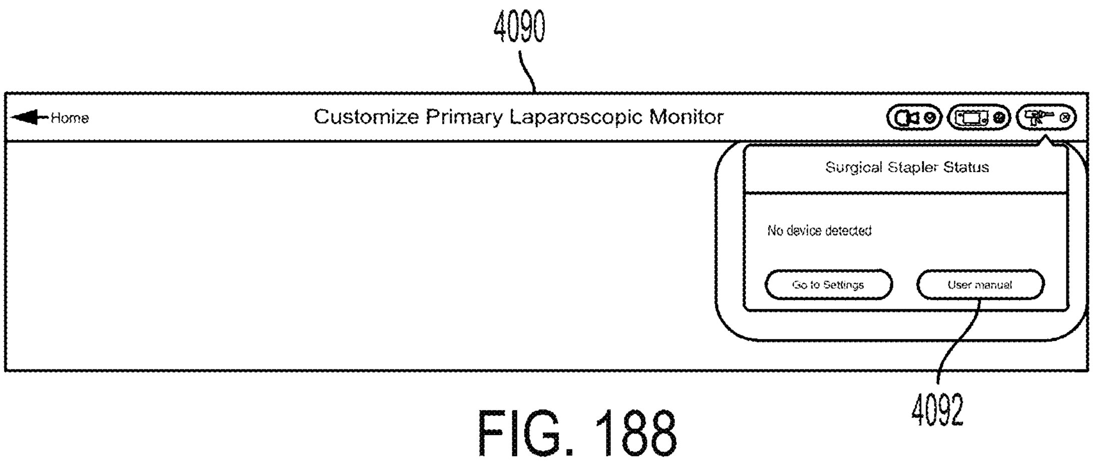

FIG. 188 is an image of a screen displaying a link to optimal device performance (ODP) guide images or other electronic instructions for use (e-IFU), according to one aspect of this disclosure.

Figure 189:
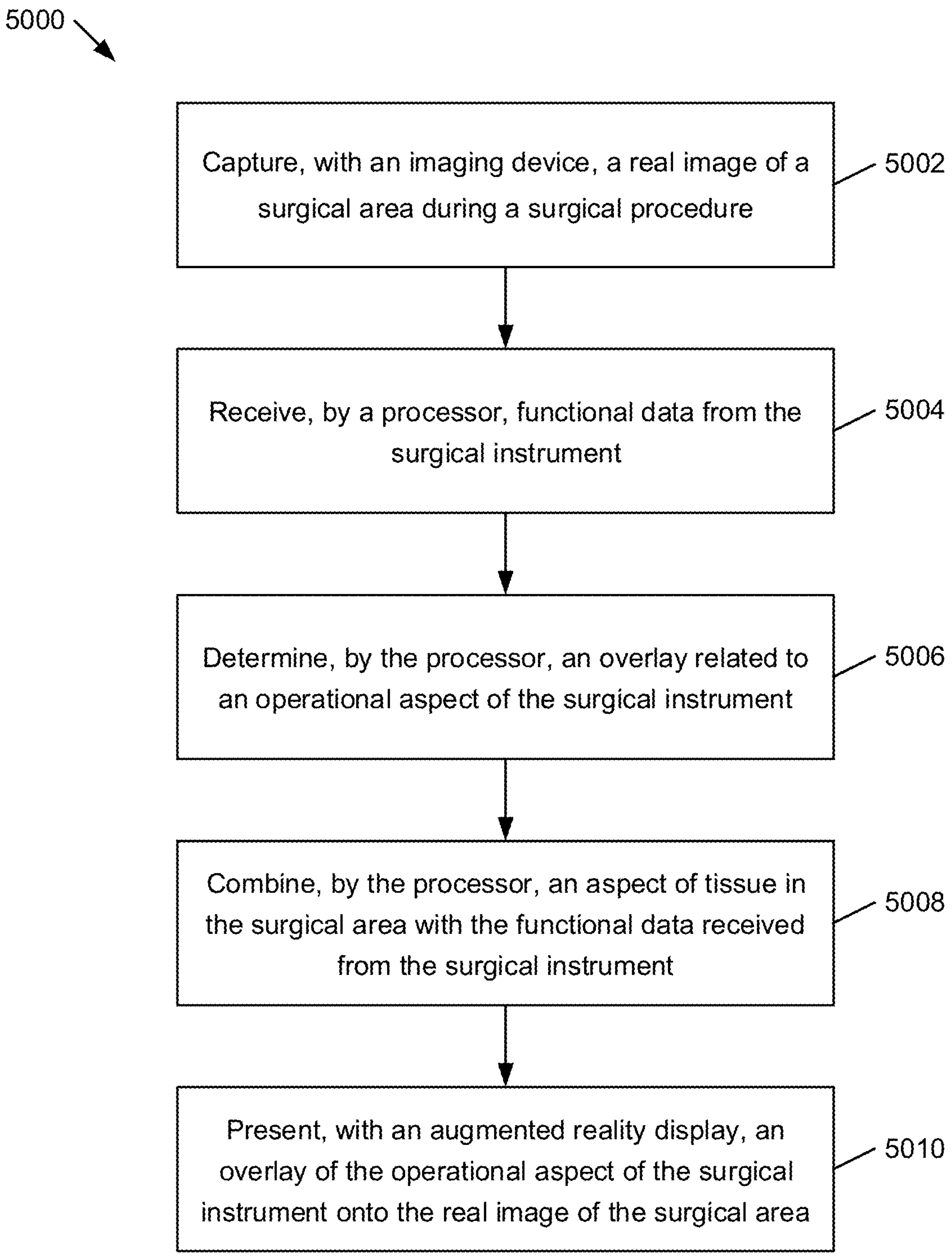

FIG. 189 is a diagram of an augmented reality method employing a surgical instrument and an augmented reality display for use during a surgical procedure, according to one aspect of this disclosure.

Figure 190:
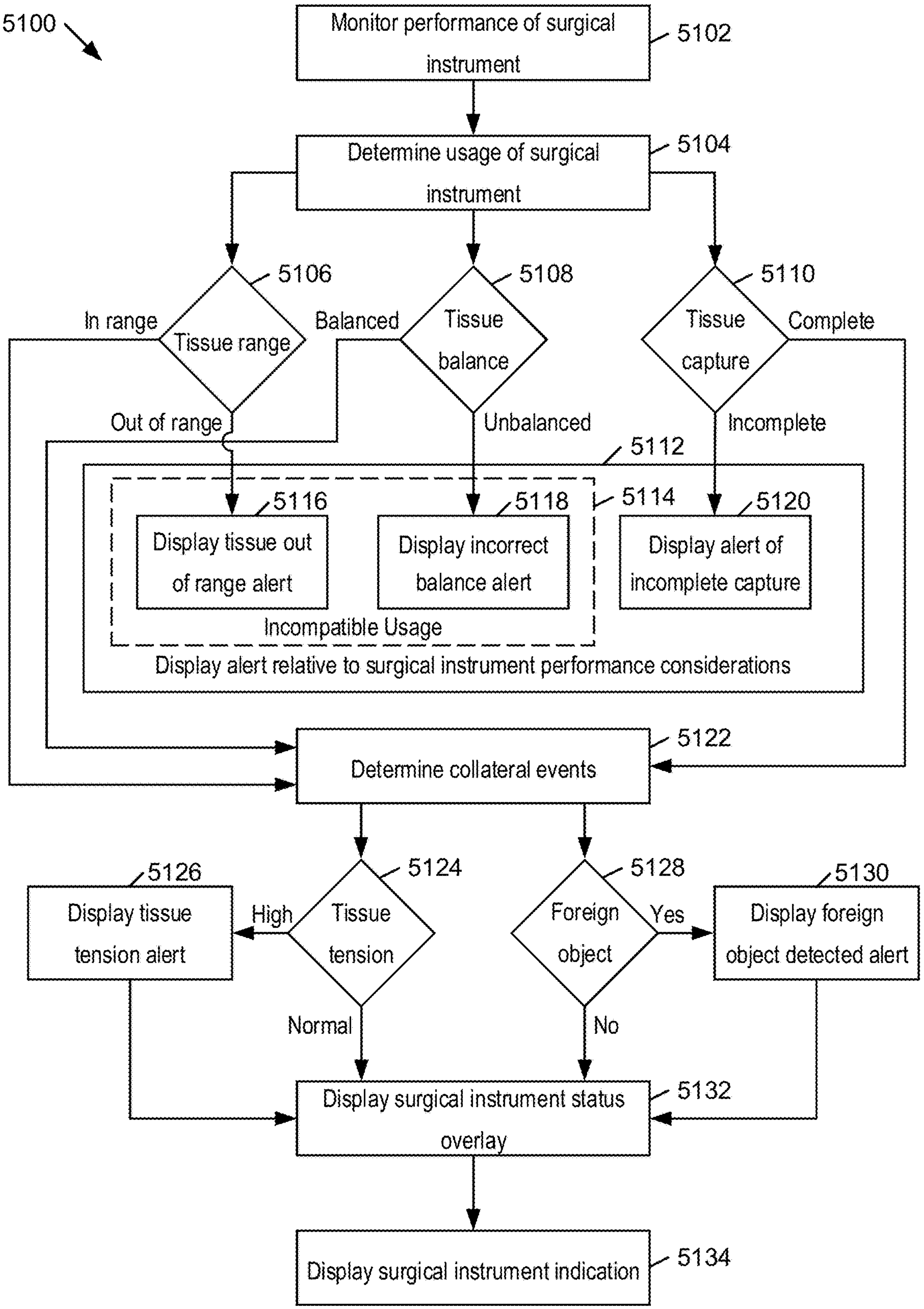

FIG. 190 is a diagram of an augmented reality method employing a surgical instrument and an augmented reality display for use during a surgical procedure, according to one aspect of this disclosure.

Figure 191:
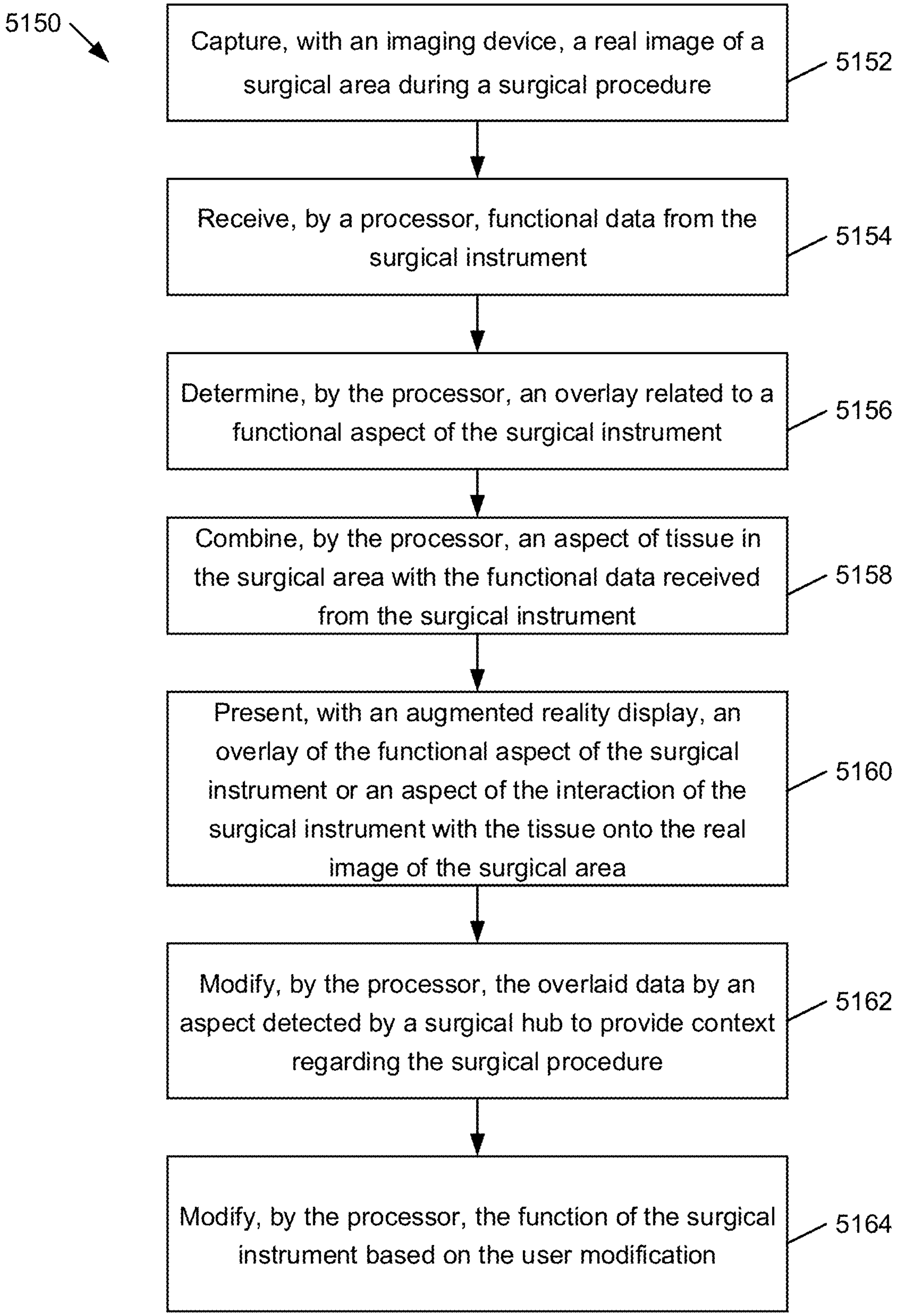

FIG. 191 is a diagram of an augmented reality method employing a surgical instrument and an augmented reality display for use during a surgical procedure, according to one aspect of this disclosure.

Figure 192:
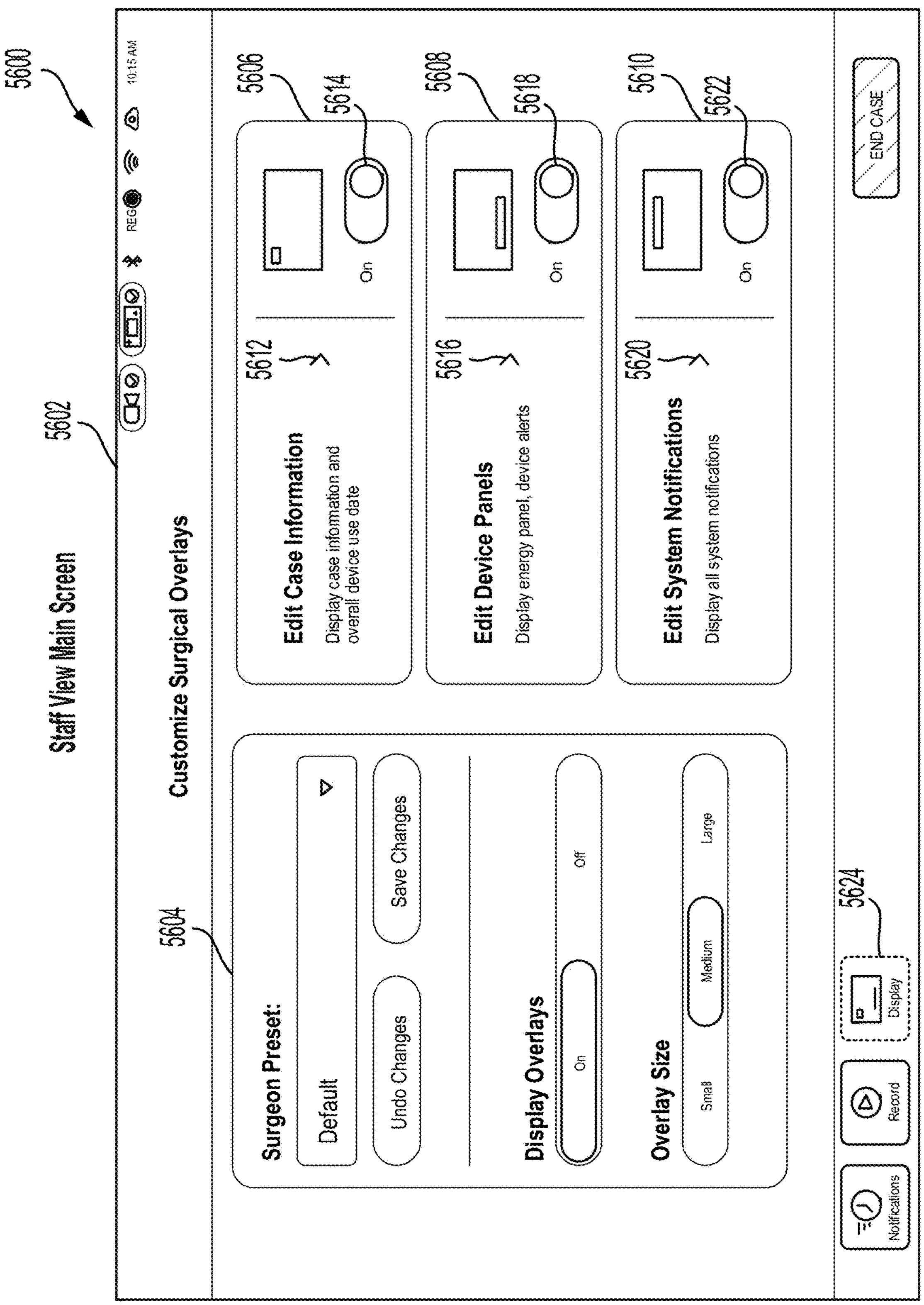

FIG. 192 is an image of a staff view screen displaying customized overlays information, according to one aspect of this disclosure.

Figure 193:
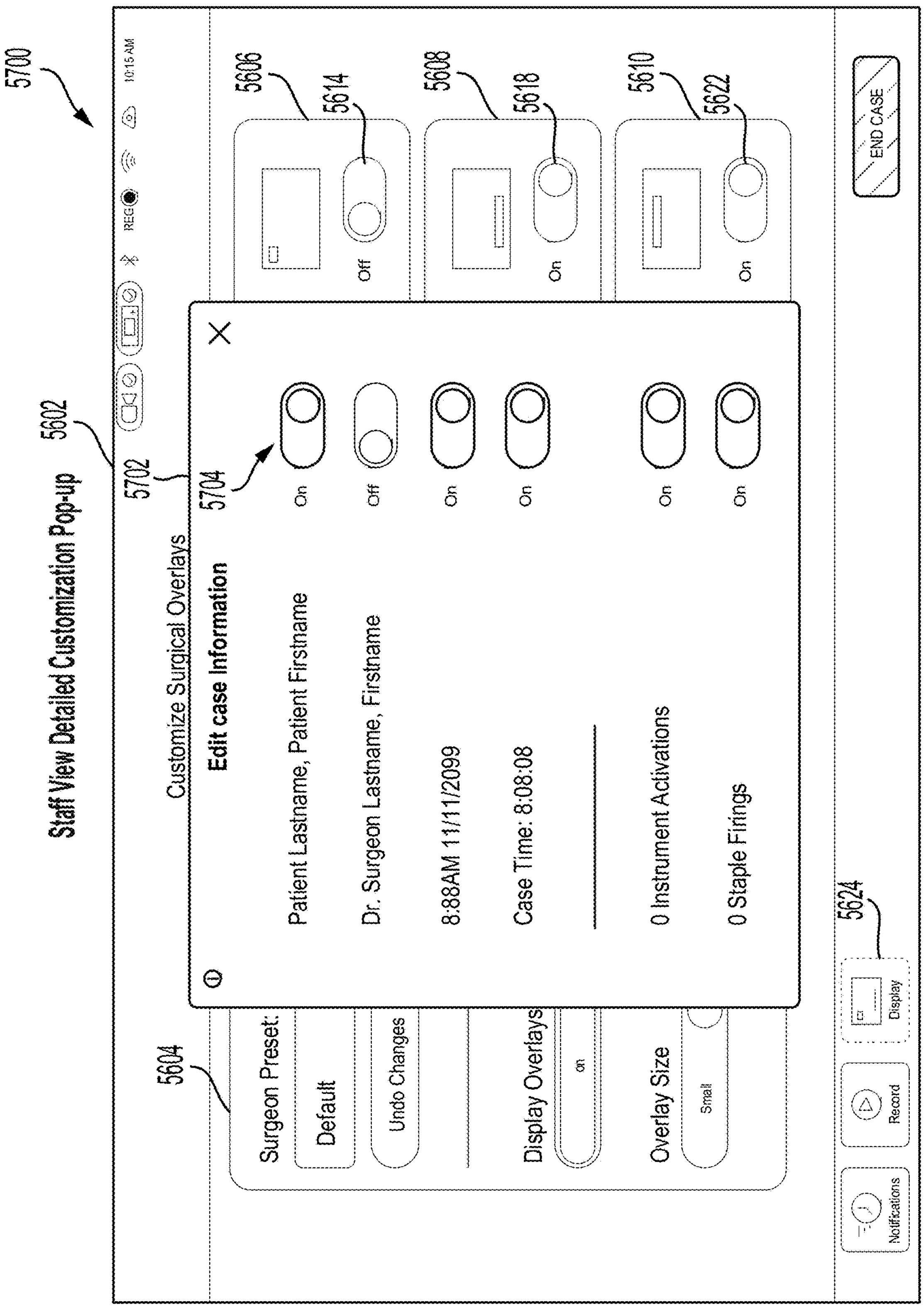

FIG. 193 is an image of a staff view screen displaying detailed customization pop-up information, according to one aspect of this disclosure.

Figure 194:
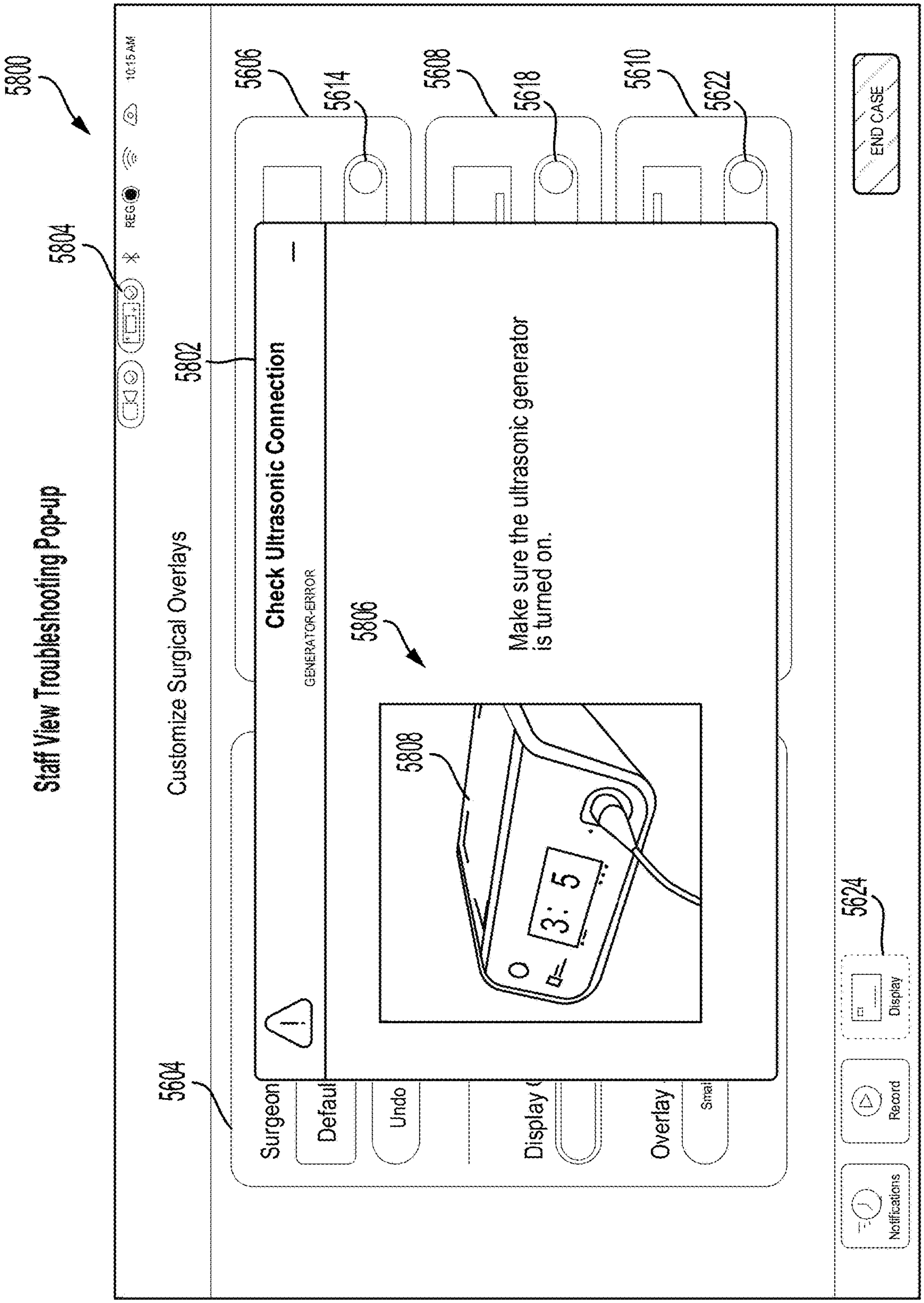

FIG. 194 is an image of a staff view screen displaying staff view troubleshooting pop-up information, according to one aspect of this disclosure.

Figure 195:
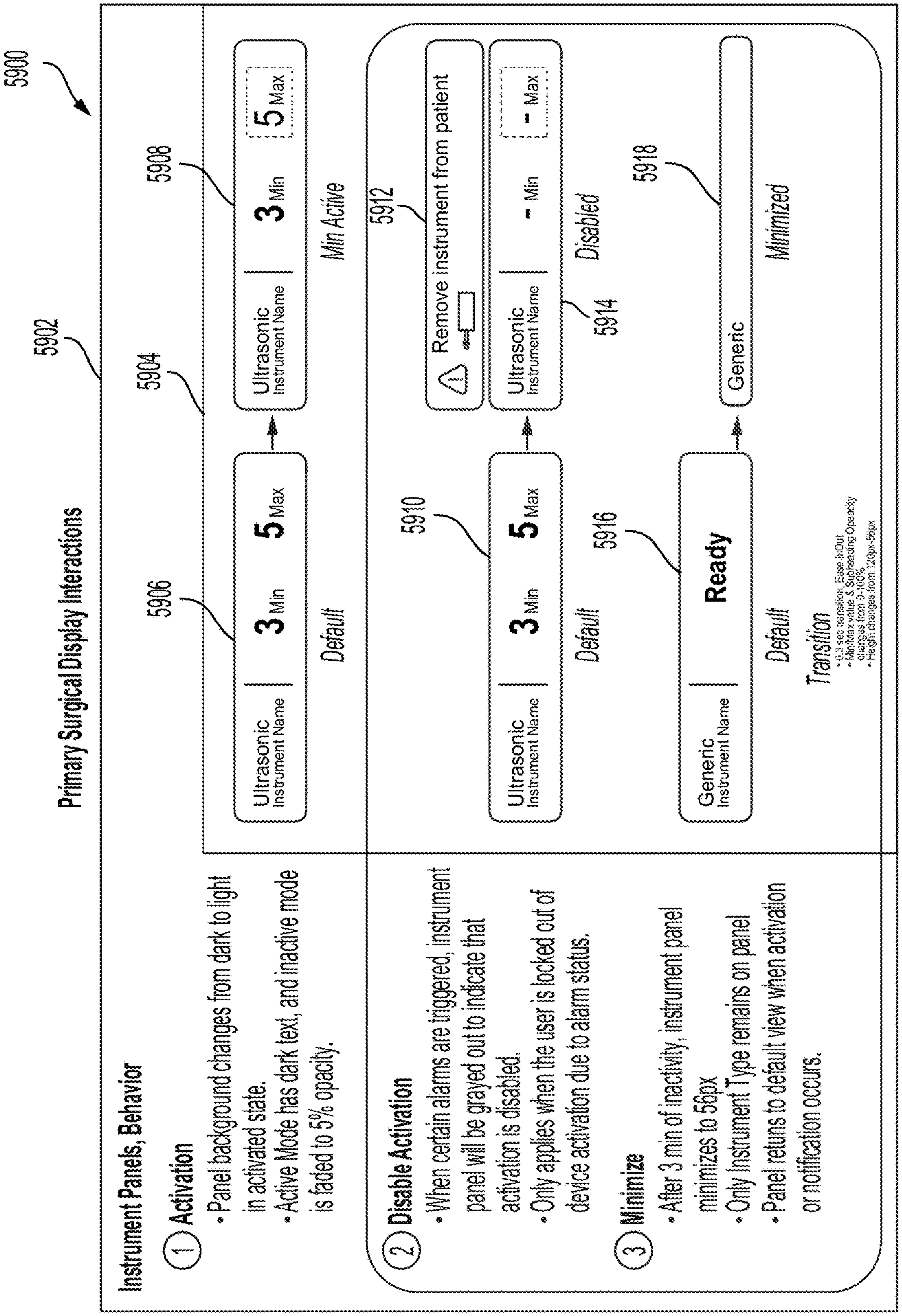

FIG. 195 is an image of a primary surgical display interactions screen displaying primary surgical display interactions, according to one aspect of this disclosure.

Figure 196:
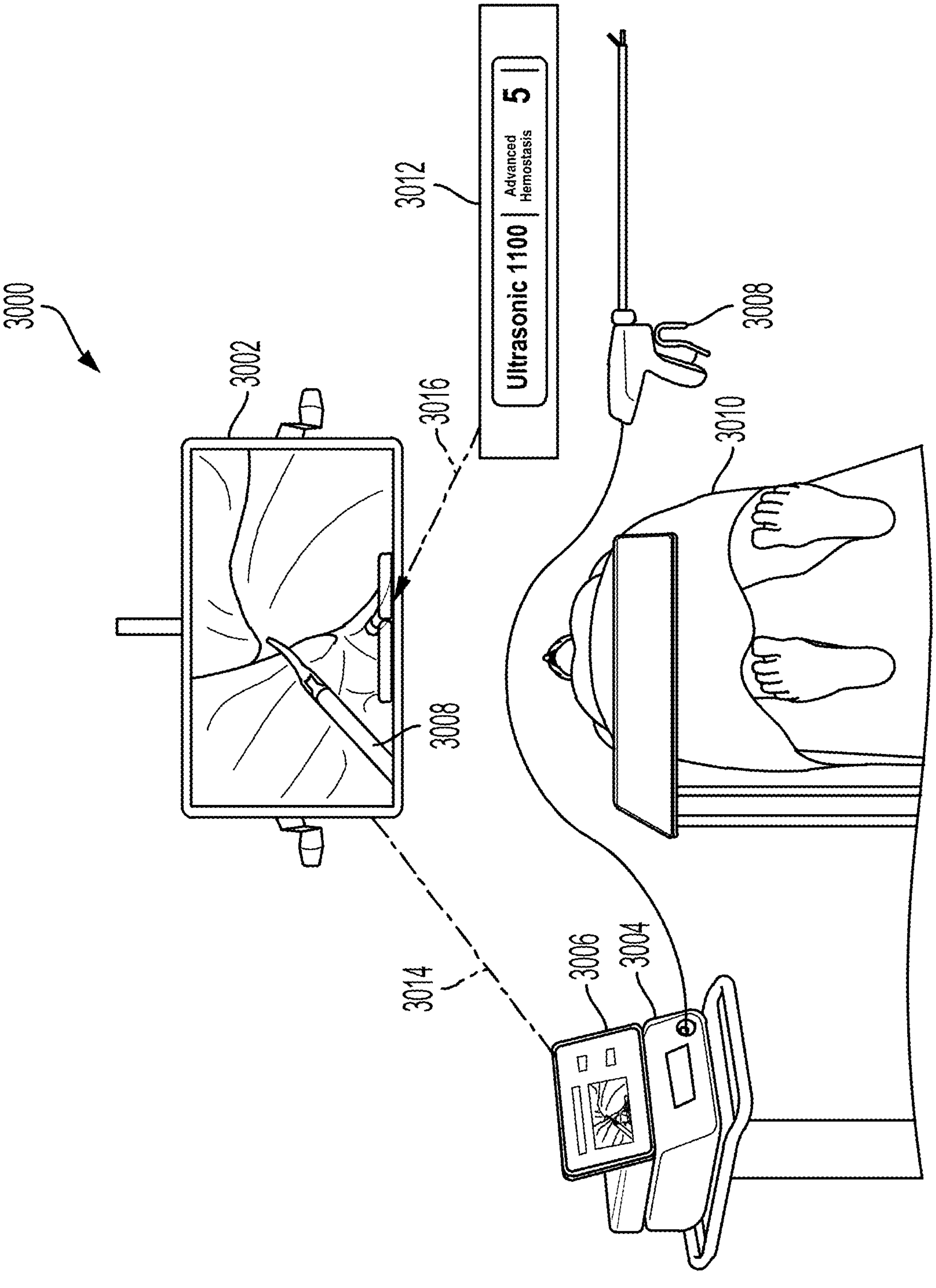

FIG. 196 is a system diagram of a surgical suite comprising a surgical monitor with intraoperative data display of a surgical area, according to one aspect of this disclosure.

Figure 197:
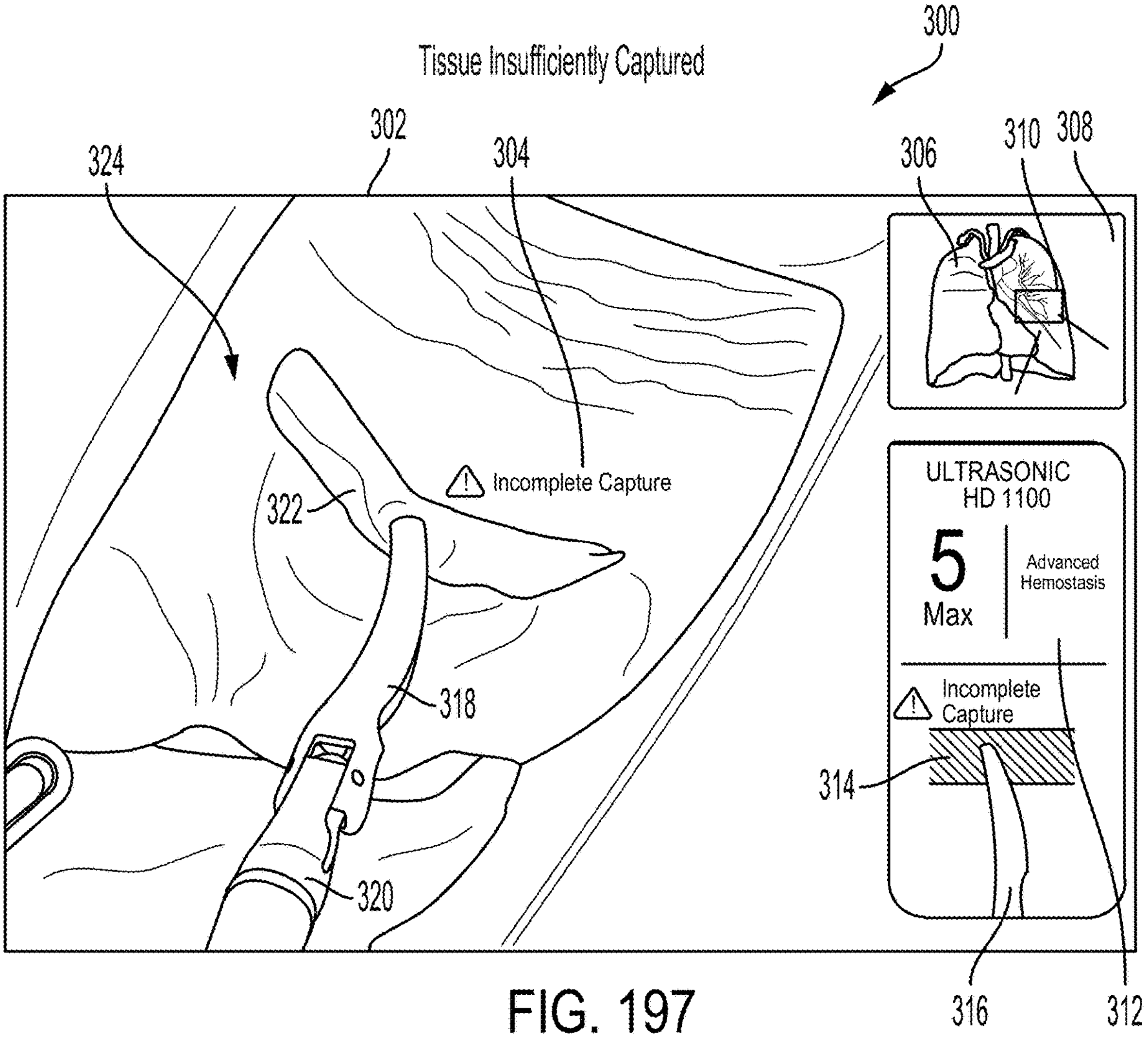

FIG. 197 is an augmented image of a live feed of a surgical area as visualized through a laparoscopic camera during a minimally invasive surgical procedure indicating tissue insufficiently captured between jaws of a surgical instrument end effector as a tissue aspect, according to one aspect of this disclosure.

Figure 198:
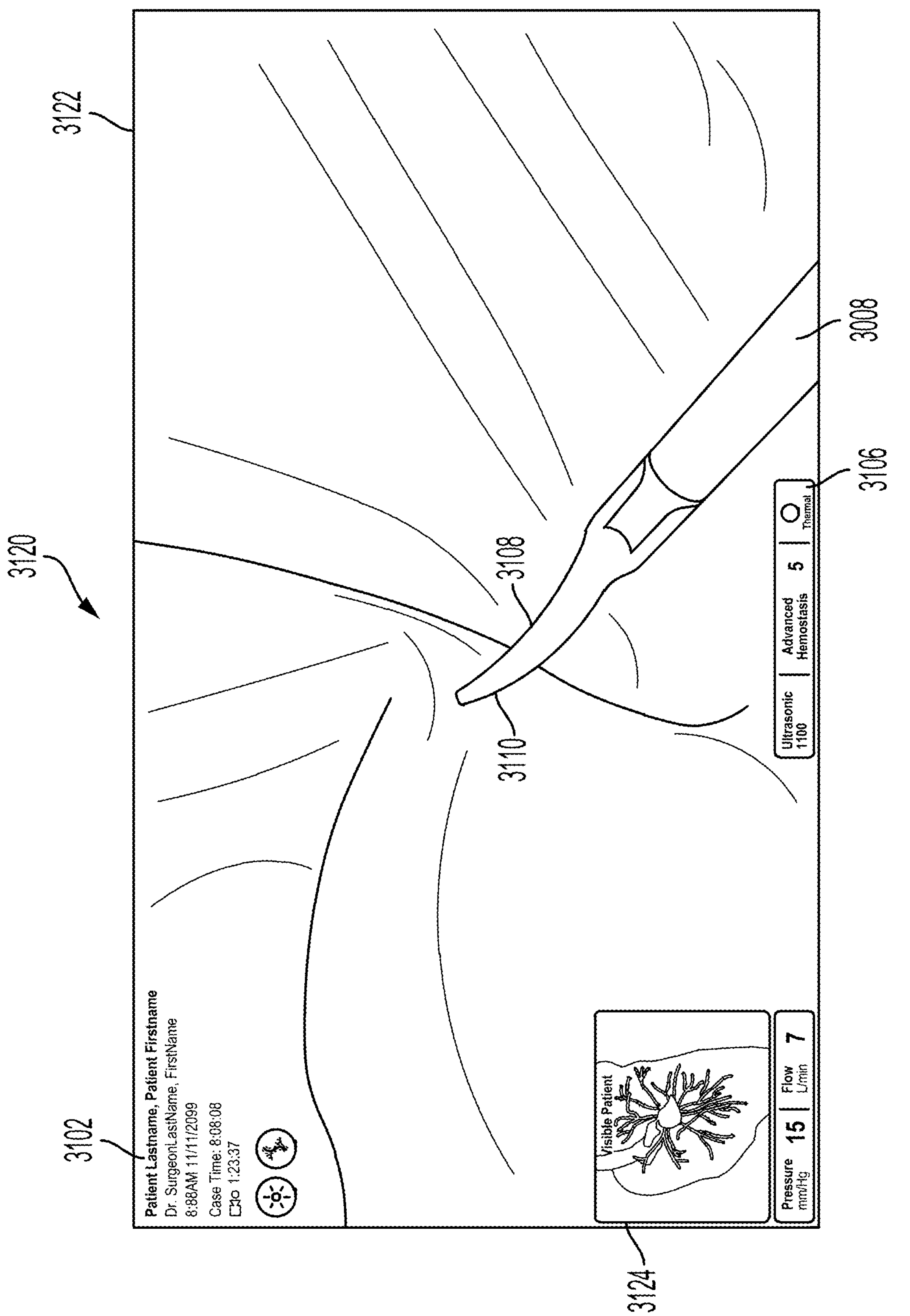

FIG. 198 is an augmented image of a live feed of a surgical area as visualized through a laparoscopic camera during a minimally invasive surgical procedure displayed on an intraoperative data display, according to one aspect of this disclosure.

Figure 199:
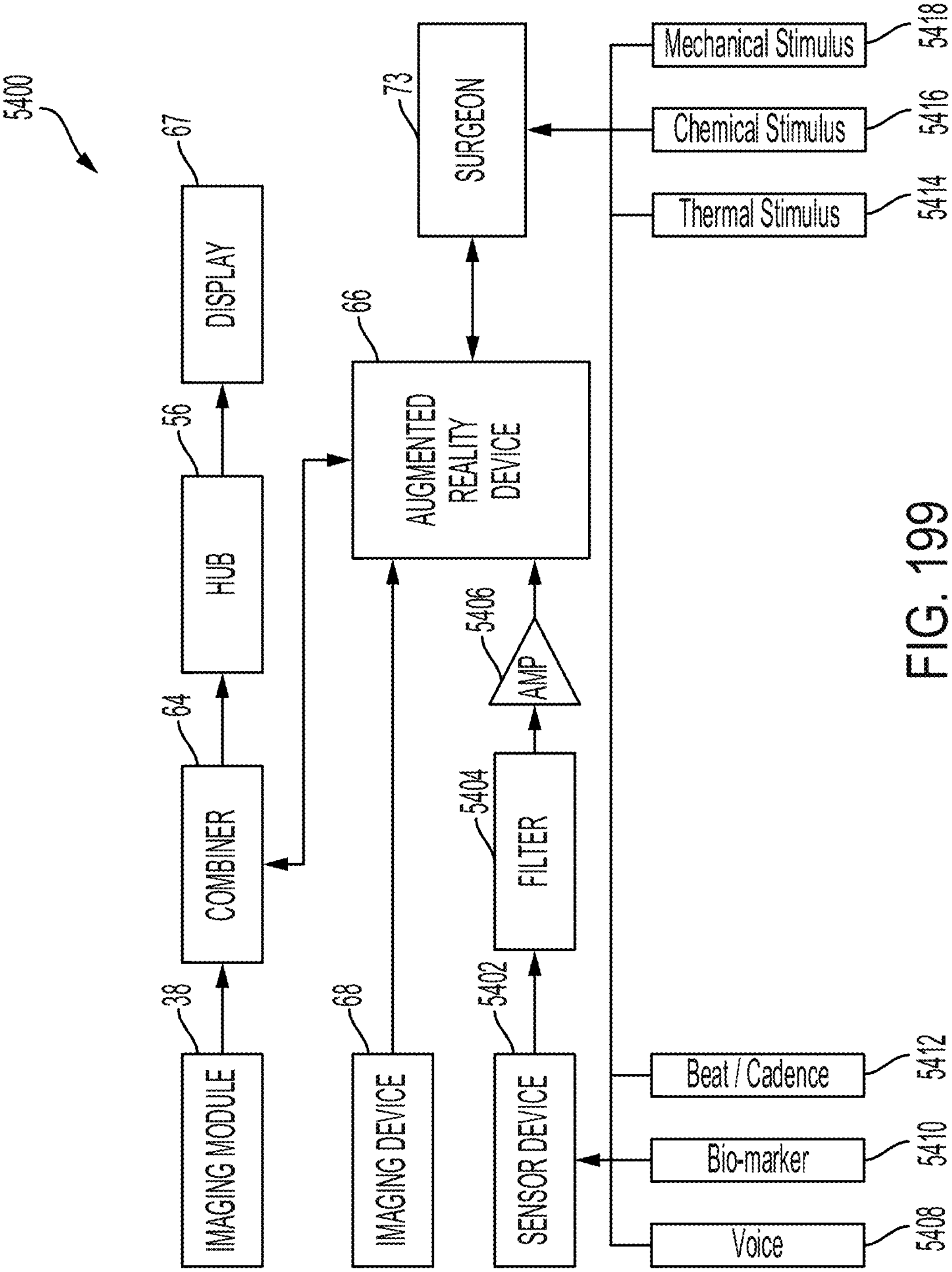

FIG. 199 illustrates an augmented reality system comprising an intermediate signal combiner positioned in the communication path between an imaging module and a surgical hub display, according to one aspect of this disclosure.

Figure 200:
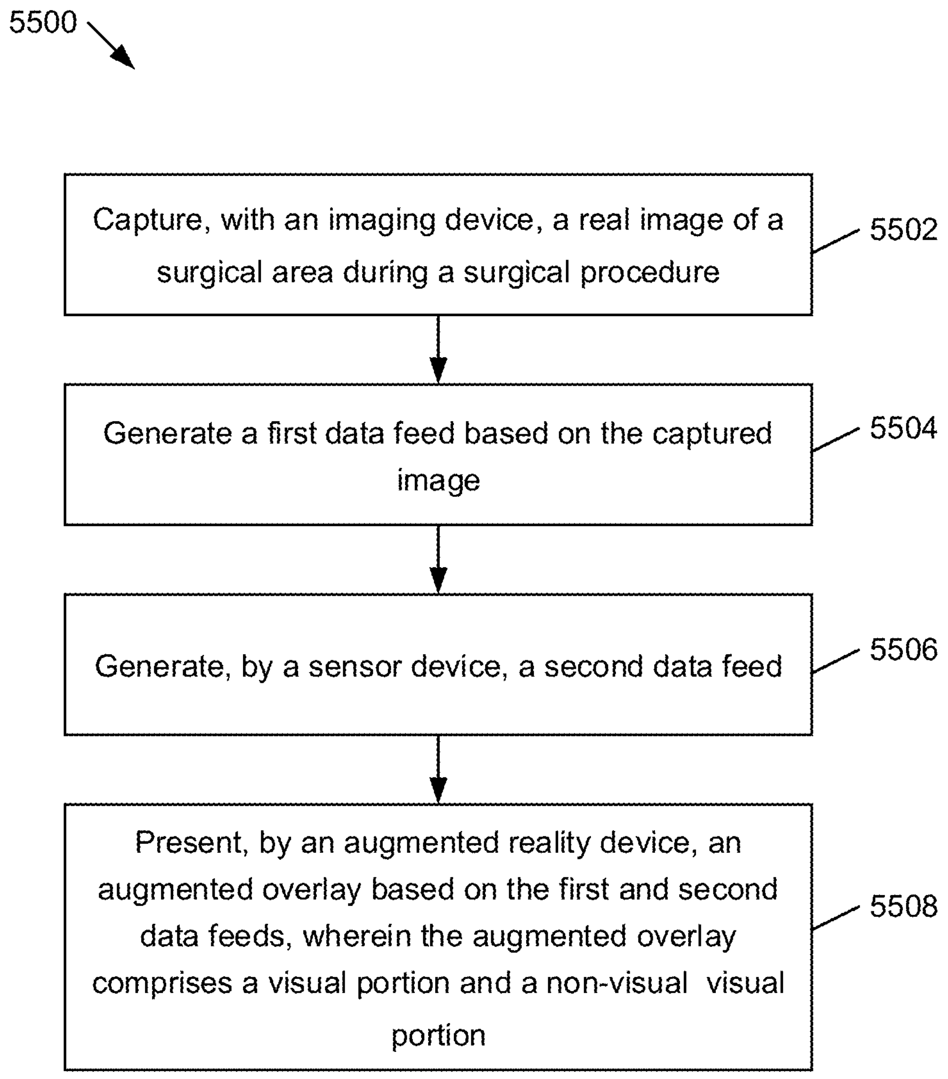

FIG. 200 illustrates a method of presenting an augmented overlay during a surgical procedure, according to one aspect of this disclosure.

Corresponding reference characters indicate corresponding parts throughout the several views. The exemplifications set out herein illustrate various disclosed embodiments, in one form, and such exemplifications are not to be construed as limiting the scope thereof in any manner.

DESCRIPTION

Applicant of the present application owns the following U.S. patent applications filed concurrently herewith, the disclosures of each of which is herein incorporated by reference in its entirety:

- U.S. patent application Ser. No. 17/688,597, titled Utilization of surgical data values and situational awareness to control the overlay in surgical field view;
- U.S. patent application Ser. No. 17/688,605, titled SELECTIVE AND ADJUSTABLE MIXED REALITY OVERLAY IN SURGICAL FIELD VIEW;
- U.S. patent application Ser. No. 17/688,615, titled RISK BASED PRIORITIZATION OF DISPLAY ASPECTS IN SURGICAL FIELD VIEW;
- U.S. patent application Ser. No. 17/688,626, titled SYSTEMS AND METHODS FOR CONTROLLING SURGICAL DATA OVERLAY;
- U.S. patent application Ser. No. 17/688,633, titled SYSTEMS AND METHODS FOR CHANGING DISPLAY OVERLAY OF SURGICAL FIELD VIEW BASED ON TRIGGERING EVENTS;
- U.S. patent application Ser. No. 17/688,638, titled CUSTOMIZATION OF OVERLAID DATA AND CONFIGURATION;
- U.S. patent application Ser. No. 17/688,641, titled INDICATION OF THE COUPLE PAIR OF REMOTE CONTROLS WITH REMOTE DEVICES FUNCTIONS;
- U.S. patent application Ser. No. 17/688,646, titled COOPERATIVE OVERLAYS OF INTERACTING INSTRUMENTS WHICH RESULT IN BOTH OVERLAYS BEING EFFECTED;
- U.S. patent application Ser. No. 17/688,651, titled ANTICIPATION OF INTERACTIVE UTILIZATION OF COMMON DATA OVERLAYS BY DIFFERENT USERS;
- U.S. patent application Ser. No. 17/688,653, titled MIXING DIRECTLY VISUALIZED WITH RENDERED ELEMENTS TO DISPLAY BLENDED ELEMENTS AND ACTIONS HAPPENING ON-SCREEN AND OFF-SCREEN.
- U.S. patent application Ser. No. 17/688,655, titled SYSTEM AND METHOD FOR TRACKING A PORTION OF THE USER AS A PROXY FOR NON-MONITORED INSTRUMENT;
- U.S. patent application Ser. No. 17/688,656, titled UTILIZING CONTEXTUAL PARAMETERS OF ONE OR MORE SURGICAL DEVICES TO PREDICT A FREQUENCY INTERVAL FOR DISPLAYING SURGICAL INFORMATION;
- U.S. patent application Ser. No. 17/688,660, titled COOPERATION AMONG MULTIPLE DISPLAY SYSTEMS TO PROVIDE A HEALTHCARE USER CUSTOMIZED INFORMATION;
- U.S. patent application Ser. No. 17/688,663, titled INTRAOPERATIVE DISPLAY FOR SURGICAL SYSTEMS;
- U.S. patent application Ser. No. 17/688,667, titled ADAPTATION AND ADJUSTABILITY OR OVERLAID INSTRUMENT INFORMATION FOR SURGICAL SYSTEMS; and
- U.S. patent application Ser. No. 17/688,671, titled MIXED REALITY FEEDBACK SYSTEMS THAT COOPERATE TO INCREASE EFFICIENT PERCEPTION OF COMPLEX DATA FEEDS.

Applicant of this application owns the following U.S. patent applications, the disclosure of each of which is herein incorporated by reference in its entirety:

- U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Publication No. US-2019-0200981-A1;
- U.S. patent application Ser. No. 16/209,453, titled METHOD FOR CONTROLLING SMART ENERGY DEVICES, now U.S. Patent Publication No. US-2019-0201046-A1.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to onscreen displays for surgical systems for a variety of energy and surgical stapler based medical devices. Energy based medical devices include, without limitation, radio-frequency (RF) based monopolar and bipolar electrosurgical instruments, ultrasonic surgical instruments, combination RF electrosurgical and ultrasonic instruments, combination RF electrosurgical and mechanical staplers, among others. Surgical stapler devices include and combined surgical staplers with electrosurgical and/or ultrasonic devices. Aspects of the ultrasonic surgical devices can be configured for transecting and/or coagulating tissue during surgical procedures, for example. Aspects of the electrosurgical devices can be configured for transecting, coagulating, sealing, welding and/or desiccating tissue during surgical procedures, for example. Aspects of the surgical stapler devices can be configured for transecting and stapling tissue during surgical procedures and in some aspects, the surgical stapler devices may be configured to delivery RF energy to the tissue during surgical procedures. Electrosurgical devices are configured to deliver therapeutic and/or nontherapeutic RF energy to the tissue. Elements of surgical staplers, electrosurgical, and ultrasonic devices may be used in combination in a single surgical instrument.

In various aspects, the present disclosure provides onscreen displays of real time information to the OR team during a surgical procedure. In accordance with various aspects of the present disclosure, many new and unique onscreen displays are provided to display onscreen a variety of visual information feedback to the OR team. According to the present disclosure, visual information may comprise one or more than one of various visual media with or without sound. Generally, visual information comprises still photography, motion picture photography, video or audio recording, graphic arts, visual aids, models, display, visual presentation services, and the support processes. The visual information can be communicated on any number of display options such as the primary OR screen, the energy or surgical stapler device itself, a tablet, augmented reality glasses, among others, for example.

In various aspects, the present disclosure provides a large list of potential options to communicate visual information in real time to the OR team, without overwhelming the OR team with too much visual information. For example, in various aspects, the present disclosure provides onscreen displays of visual information to enable the surgeon, or other members of the OR team, to selectively activate onscreen displays such as icons surrounding the screen option to manage a wealth of visual information. One or a combination of factors can be used to determine the active display, these may include energy based (e.g., electrosurgical, ultrasonic) or mechanical based (e.g., staplers) surgical devices in use, the estimated risk associated with a given display, the experience level of the surgeon and the surgeons' choice among other things. In other aspect, the visual information may comprises rich data overlaid or superimposed into the surgical field of view to manage the visual information. In various aspects described hereinbelow, comprise superimposed imagery that requires video analysis and tracking to properly overlay the data. Visual information data communicated in this manner, as opposed to static icons, may provide additional useful visual information in a more concise and easy to understand way to the OR team.

In various aspects, the present disclosure provides techniques for selectively activating onscreen displays such as icons surrounding the screen to manage visual information during a surgical procedure. In other aspects, the present disclosure provides techniques for determining the active display using one or a combination of factors. In various aspects, the techniques according to the resent disclosure may comprise selecting the energy based or mechanical based surgical device in use as the active display, estimating risk associated with a given display, utilizing the experience level of the surgeon or OR team making the selection, among other things.

In other aspects, the techniques according to the present disclosure may comprise overlaying or superimposing rich data onto the surgical field of view to manage the visual information. A number of the display arrangements described by the present disclosure involve overlaying various visual representations of surgical data onto a livestream of a surgical field. As used herein the term overlay comprises a translucent overlay, a partial overlay, and/or a moving overlay. Graphical overlays may be in the form of a transparent graphic, semitransparent graphic, or opaque graphic, or a combination of transparent, semitransparent, and opaque elements or effects. Moreover, the overlay can be positioned on, or at least partially on, or near an object in the surgical field such as, for example, an end effector and/or a critical surgical structure. Certain display arrangements may comprise a change in one or more display elements of an overlay including a change in color, size, shape, display time, display location, display frequency, highlighting, or a combination thereof, based on changes in display priority values. The graphical overlays are rendered on top of the active display monitor to convey important information quickly and efficiently to the OR team.

In other aspects, the techniques according to the present disclosure may comprise superimposing imagery that requires analyzing video and tracking for properly overlaying the visual information data. In other aspects, the techniques according to the present disclosure may comprise communicating rich visual information, as opposed to simple static icons, to provide additional visual information to the OR team in a more concise and easy to understand manner. In other aspects, the visual overlays may be used in combination with audible and/or somatosensory overlays such as thermal, chemical, and mechanical devices, and combinations thereof.

The following description is directed generally to apparatuses, systems, and methods that provide an augmented reality (AR) interactive experience during a surgical procedure. In this context, images of a surgical field and surgical instruments and other objects appearing in the surgical field are enhanced by overlaying computer-generated visual, auditory, haptic, somatosensory, olfactory, or other sensory information onto the real world images of the surgical field, instruments, and/or other objects appearing in the surgical field. The images may be streamed in real time or may be still images. Augmented reality is a technology for rendering and displaying virtual or "augmented" virtual objects, data, or visual effects overlaid on a real environment. The real environment may include a surgical field. The virtual objects overlaid on the real environment may be represented as anchored or in a set position relative to one or more aspects of the real environment. In a non-limiting example, if a real world object exits the real environment field of view, a virtual object anchored to the real world object would also exit the augmented reality field of view.

A number of the display arrangements described by the present disclosure involve overlaying various visual representations of surgical data onto a livestream of a surgical field. As used herein the term overlaying comprises a translucent overlay, a partial overlay, and/or a moving overlay. Moreover, the overlay can be positioned on, or at least partially on, or near an object in the surgical field such as, for example, an end effector and/or a critical surgical structure. Certain display arrangements may comprise a change in one or more display elements of an overlay including a change in color, size, shape, display time, display location, display frequency, highlighting, or a combination thereof, based on changes in display priority values.

As described herein AR is an enhanced version of the real physical world that is achieved through the use of digital visual elements, sound, or other sensory stimuli delivered via technology. Virtual Reality (VR) is a computer-generated environment with scenes and objects that appear to be real, making the user feel they are immersed in their surroundings. This environment is perceived through a device known as a Virtual Reality headset or helmet. Mixed reality (MR) and AR are both considered immersive technologies, but they aren't the same. MR is an extension of Mixed reality that allows real and virtual elements to interact in an environment. While AR adds digital elements to a live view often by using a camera, an MR experience combines elements of both AR and VR, where real-world and digital objects interact.

In an AR environment, one or more computer-generated virtual objects may be displayed along with one or more real (i.e., so-called "real world") elements. For example, a real-time image or video of a surrounding environment may be shown on a computer screen display with one or more overlaying virtual objects. Such virtual objects may provide complementary information relating to the environment or generally enhance a user's perception and engagement with the environment. Conversely, the real-time image or video of the surrounding environment may additionally or alternatively enhance a user's engagement with the virtual objects shown on the display.

The apparatuses, systems, and methods in the context of this disclosure enhance images received from one or more imaging devices during a surgical procedure. The imaging devices may include a variety of scopes used during non-invasive and minimally invasive surgical procedures, an AR device, and/or a camera to provide images during open surgical procedures. The images may be streamed in real time or may be still images. The apparatuses, systems, and methods provide an augmented reality interactive experience by enhancing images of the real world surgical environment by overlaying virtual objects or representations of data and/or real objects onto the real surgical environment. The augmented reality experience may be viewed on a display and/or an AR device that allows a user to view the overlaid virtual objects onto the real world surgical environment. The display may be located in the operating room or remote from the operating room. AR devices are worn on the head of the surgeon or other operating room personnel and typically include two stereo-display lenses or screens, including one for each eye of the user. Natural light is permitted to pass through the two transparent or semi-transparent display lenses such that aspects of the real environment are visible while also projecting light to make virtual objects visible to the user of the AR device.

Two or more displays and AR devices may be used in a coordinated manner, for example with a first display or AR device controlling one or more additional displays or AR devices in a system with defined roles. For example, when activating display or an AR device, a user may select a role (e.g., surgeon, surgical assistant, nurse, etc., during a surgical procedure) and the display or AR device may display information relevant to that role. For example, a surgical assistant may have a virtual representation of an instrument displayed that the surgeon needs to perform for a next step of a surgical procedure. A surgeon's focus on the current step may see different information displayed than the surgical assistant.

Although there are many known onscreen displays and alerts, this disclosure provides many new and unique augmented reality interactive experiences during a surgical procedure. Such augmented reality interactive experiences include visual, auditory, haptic, somatosensory, olfactory, or other sensory feedback information to the surgical team inside or outside the operating room. The virtual feedback information overlaid onto the real world surgical environment may be provided to an operating room (OR) team, including personnel inside the OR including, without limitation, the operating surgeon, assistants to the surgeon, a scrub person, an anesthesiologist and a circulating nurse, among others, for example. The virtual feedback information can be communicated on any number of display options such as a primary OR screen display, an AR device, the energy or surgical stapler instrument, a tablet, augmented reality glasses, device etc.

Figure 1:
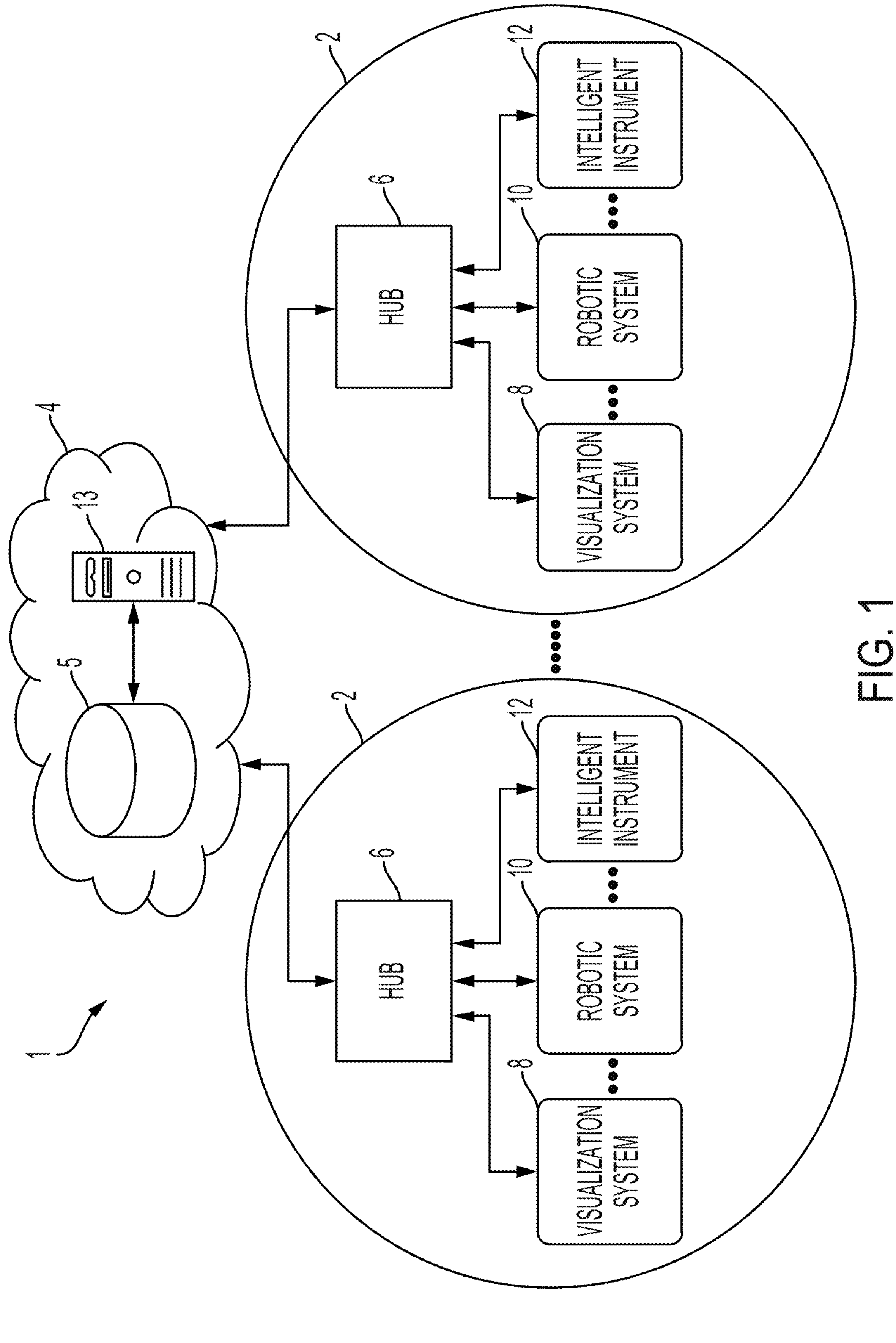
FIG. 1 is a block diagram of a computer-implemented interactive surgical system, according to one aspect of this disclosure.

FIG. 1 depicts a computer-implemented interactive surgical system 1 that includes one or more surgical systems 2 and a cloud-based system 4. The cloud-based system 4 may include a remote server 13 coupled to a storage device 5. Each surgical system 2 includes at least one surgical hub 6 in communication with the cloud 4. For example, the surgical system 2 may include a visualization system 8, a robotic system 10, and handheld intelligent surgical instruments 12, each configured to communicate with one another and/or the hub 6. In some aspects, a surgical system 2 may include an M number of hubs 6, an N number of visualization systems 8, an O number of robotic systems 10, and a P number of handheld intelligent surgical instruments 12, where M, N, O, and P are integers greater than or equal to one. The computer-implemented interactive surgical system 1 may be configured to provide an augmented reality interactive experience during a surgical procedure as described herein.

Figure 2:
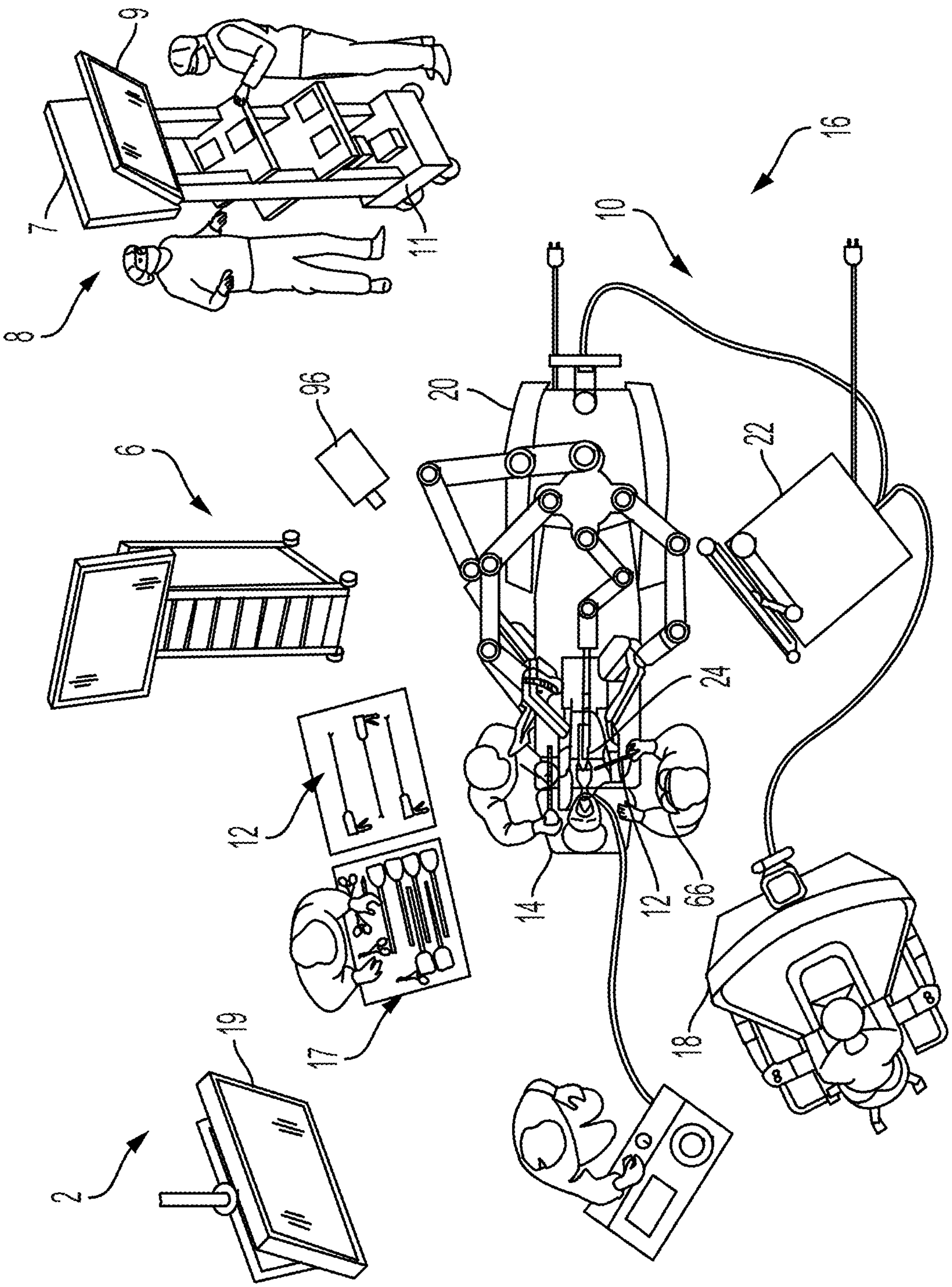
FIG. 2 is a surgical system being used to perform a surgical procedure in an operating room, according to one aspect of this disclosure.

FIG. 2 depicts an example of a surgical system 2 to perform a surgical procedure on a patient lying down on an operating table 14 in a surgical operating room 16. A robotic system 10 is used in the surgical procedure as a part of the surgical system 2. The robotic system 10 includes a surgeon's console 18, a patient side cart 20 (surgical robot), and a surgical robotic hub 22. The patient side cart 20 can manipulate at least one removably coupled surgical tool 17 through a minimally invasive incision in the body of the patient while the surgeon views the surgical site through the surgeon's console 18 or an augmented reality (AR) device 66 worn by the surgeon. An image (e.g., still or live streamed in real time) of the surgical site during a minimally invasive procedure can be obtained by a medical imaging device 24. The patient side cart 20 can manipulate the imaging device 24 to orient the imaging device 24. An image of an open surgical procedure can be obtained by a medical imaging device 96. The robotic hub 22 processes the images of the surgical site for subsequent display on the surgeon's console 18 or the AR device 66 worn by the surgeon, or other person in the surgical operating room 16.

The optical components of the imaging device 24, 96 or AR device 66 may include one or more illumination sources and/or one or more lenses. The one or more illumination sources may be directed to illuminate portions of the surgical field. One or more image sensors may receive light reflected or refracted from tissue and instruments in the surgical field.

In various aspects, the imaging device 24 is configured for use in a minimally invasive surgical procedure. Examples of imaging devices suitable for use with this disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope. In various aspects, the imaging device 96 is configured for use in an open (invasive) surgical procedure.

In various aspects, the visualization system 8 includes one or more imaging sensors, one or more image-processing units, one or more storage arrays, and one or more displays that are strategically arranged with respect to the sterile field. In one aspect, the visualization system 8 includes an interface for HL7, PACS, and EMR. In one aspect, the imaging device 24 may employ multi-spectrum monitoring to discriminate topography and underlying structures. A multi-spectral image captures image data within specific wavelength ranges in the electromagnetic spectrum. Wavelengths are separated by filters or instruments sensitive to particular wavelengths, including light from frequencies beyond the visible light range, e.g., IR and ultraviolet. Spectral imaging can extract information not visible to the human eye. Multi-spectrum monitoring can relocate a surgical field after a surgical task is completed to perform tests on the treated tissue.

FIG. 2 depicts a primary display 19 positioned in the sterile field to be visible to an operator at the operating table 14. A visualization tower 11 is positioned outside the sterile field and includes a first non-sterile display 7 and a second non-sterile display 9, which face away from each other. The visualization system 8, guided by the hub 6, is configured to utilize the displays 7, 9, 19 to coordinate information flow to operators inside and outside the sterile field. For example, the hub 6 may cause the visualization system 8 to display AR images of the surgical site, as recorded by an imaging device 24, 96 on a non-sterile display 7, 9, or through the AR device 66, while maintaining a live feed of the surgical site on the primary display 19 or the AR device 66. The non-sterile display 7, 9 can permit a non-sterile operator to perform a diagnostic step relevant to the surgical procedure, for example.

Figure 3:
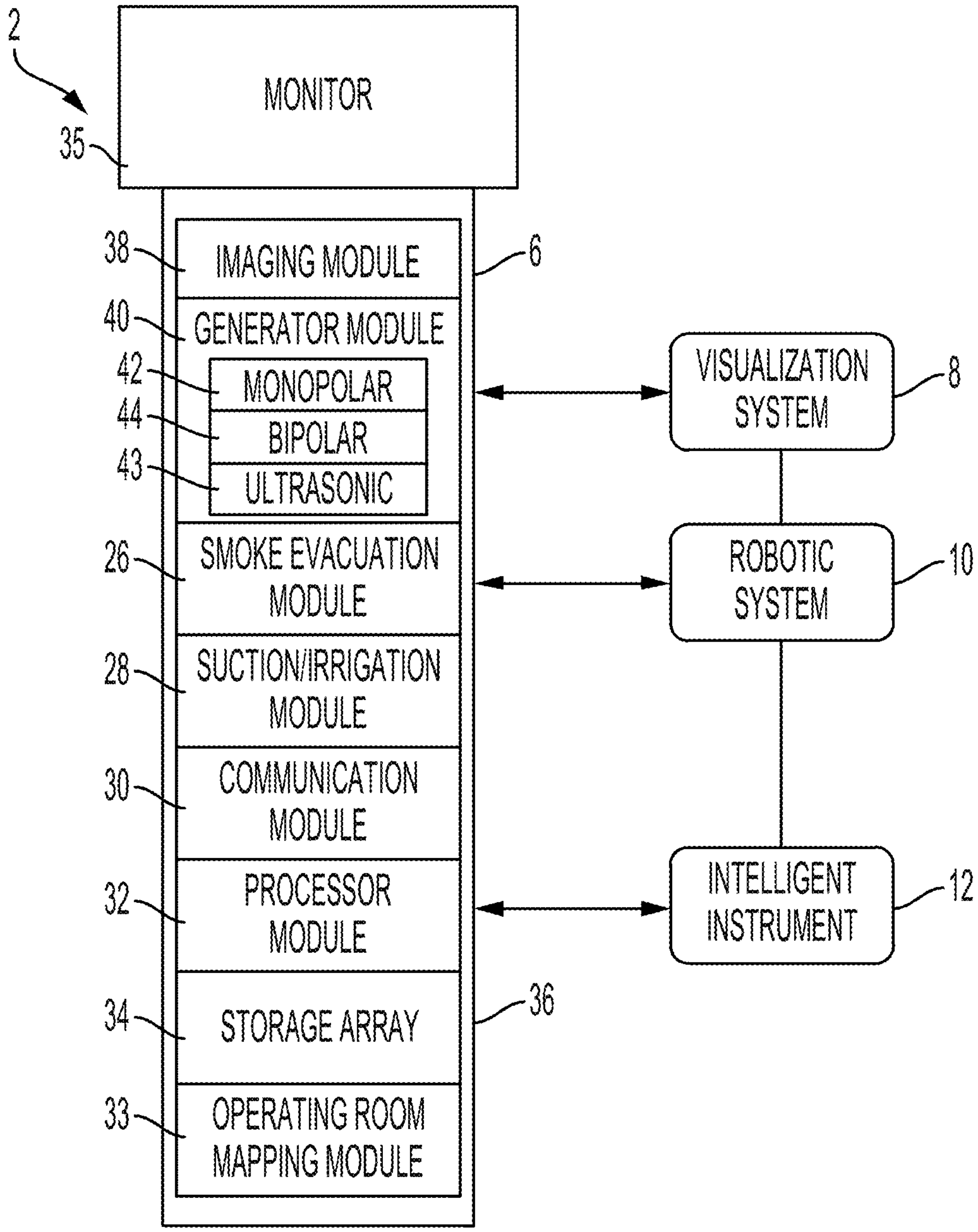
FIG. 3 is a surgical hub paired with a visualization system, a robotic system, and an intelligent instrument, according to one aspect of this disclosure.
Figure 10:
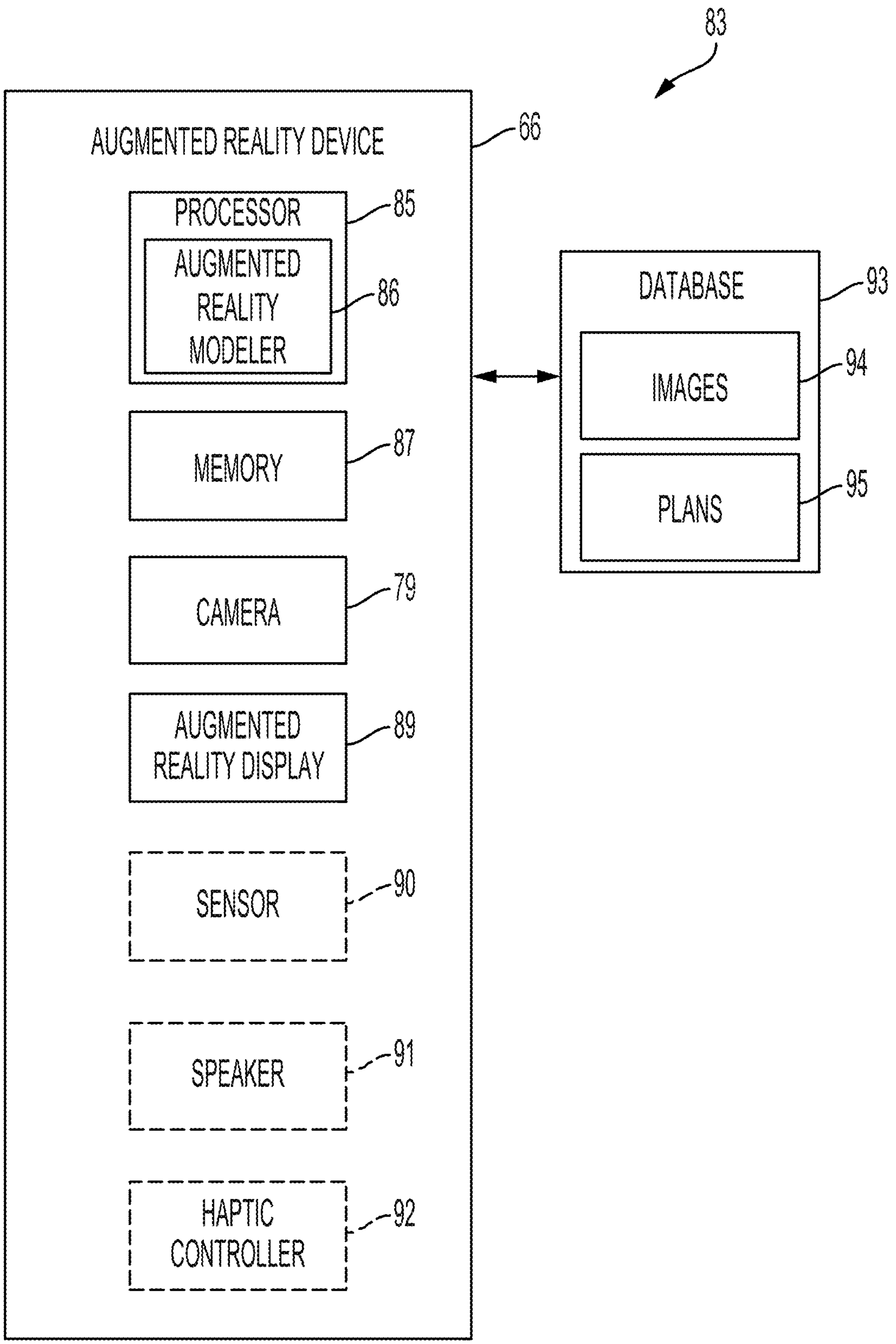
FIG. 10 illustrates a system for augmenting surgical instrument information using an augmented reality display, according to one aspect of this disclosure.

FIG. 3 depicts a hub 6 in communication with a visualization system 8, a robotic system 10, and a handheld intelligent surgical instrument 12. The hub 6 includes a hub display 35, an imaging module 38, a generator module 40, a communication module 30, a processor module 32, a storage array 34, and an operating room mapping module 33. The hub 6 further includes a smoke evacuation module 26 and/or a suction/irrigation module 28. In various aspects, the imaging module 38 comprises an AR device 66 and the processor module 32 comprises an integrated video processor and an augmented reality modeler (e.g., as shown in FIG. 10). A modular light source may be adapted for use with various imaging devices. In various examples, multiple imaging devices may be placed at different positions in the surgical field to provide multiple views (e.g., non-invasive, minimally invasive, invasive or open surgical procedures). The imaging module 38 can be configured to switch between the imaging devices to provide an optimal view. In various aspects, the imaging module 38 can be configured to integrate the images from the different imaging devices and provide an augmented reality interactive experience during a surgical procedure as described herein.

Figure 4:
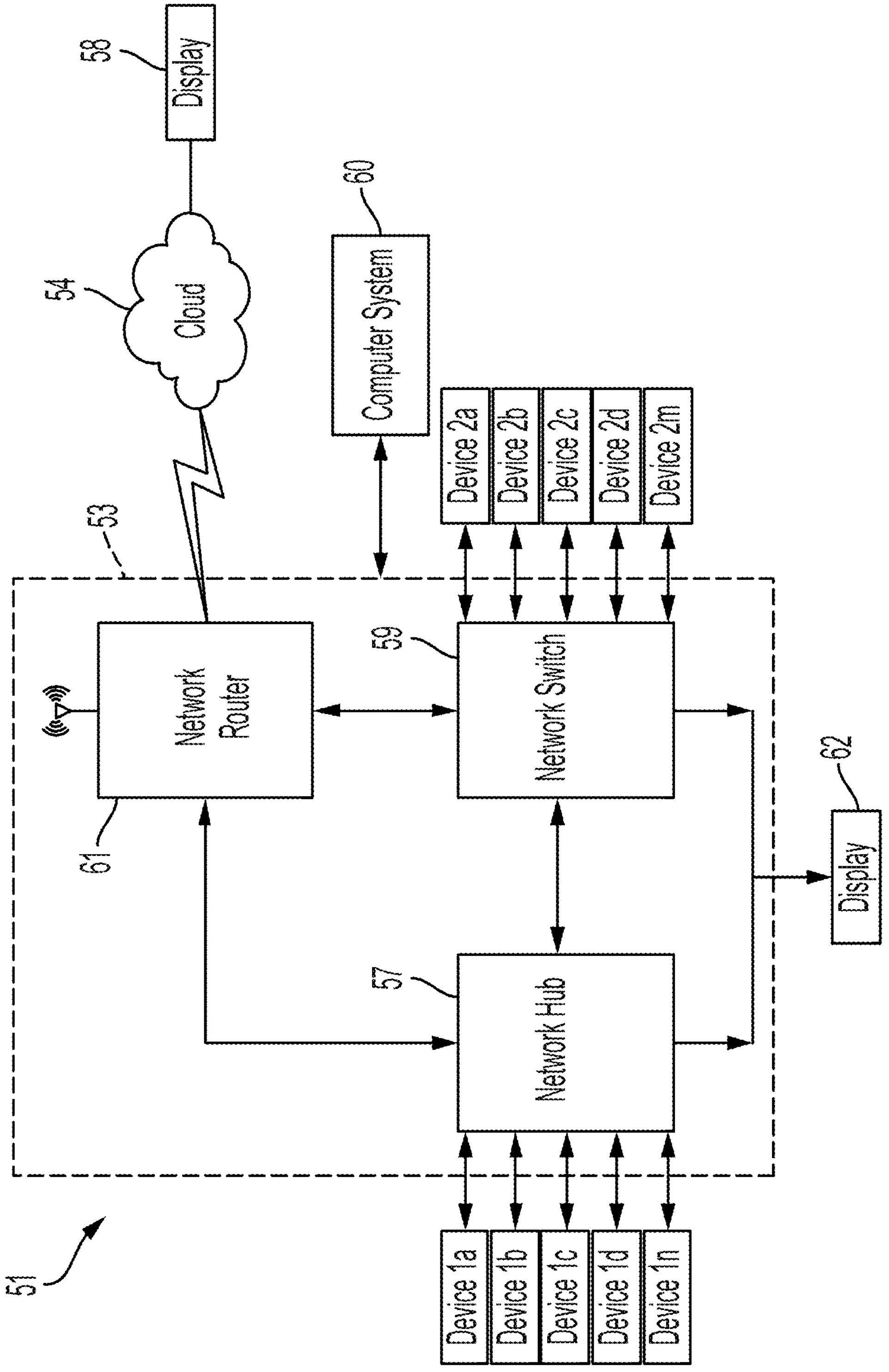
FIG. 4 illustrates a surgical data network comprising a modular communication hub configured to connect modular devices located in one or more operating theaters of a healthcare facility, or any room in a healthcare facility specially equipped for surgical operations, to the cloud, according to one aspect of this disclosure.

FIG. 4 shows a surgical data network 51 comprising a modular communication hub 53 configured to connect modular devices located in one or more operating theaters/rooms of a healthcare facility to a cloud-based system. The cloud 54 may include a remote server 63 (FIG. 5) coupled to a storage device 55. The modular communication hub 53 comprises a network hub 57 and/or a network switch 59 in communication with a network router 61. The modular communication hub 53 is coupled to a local computer system 60 to process data. Modular devices 1*a*-1*n* in the operating theater may be coupled to the modular communication hub 53. The network hub 57 and/or the network switch 59 may be coupled to a network router 61 to connect the devices 1*a*-1*n* to the cloud 54 or the local computer system 60. Data associated with the devices 1*a*-1*n* may be transferred to cloud-based computers via the router for remote data processing and manipulation. The operating theater devices 1*a*-1*n* may be connected to the modular communication hub 53 over a wired channel or a wireless channel. The surgical data network 51 environment may be employed to provide an augmented reality interactive experience during a surgical procedure as described herein and in particular providing augmented images if the surgical field to one or more than one remote display 58.

Figure 5:
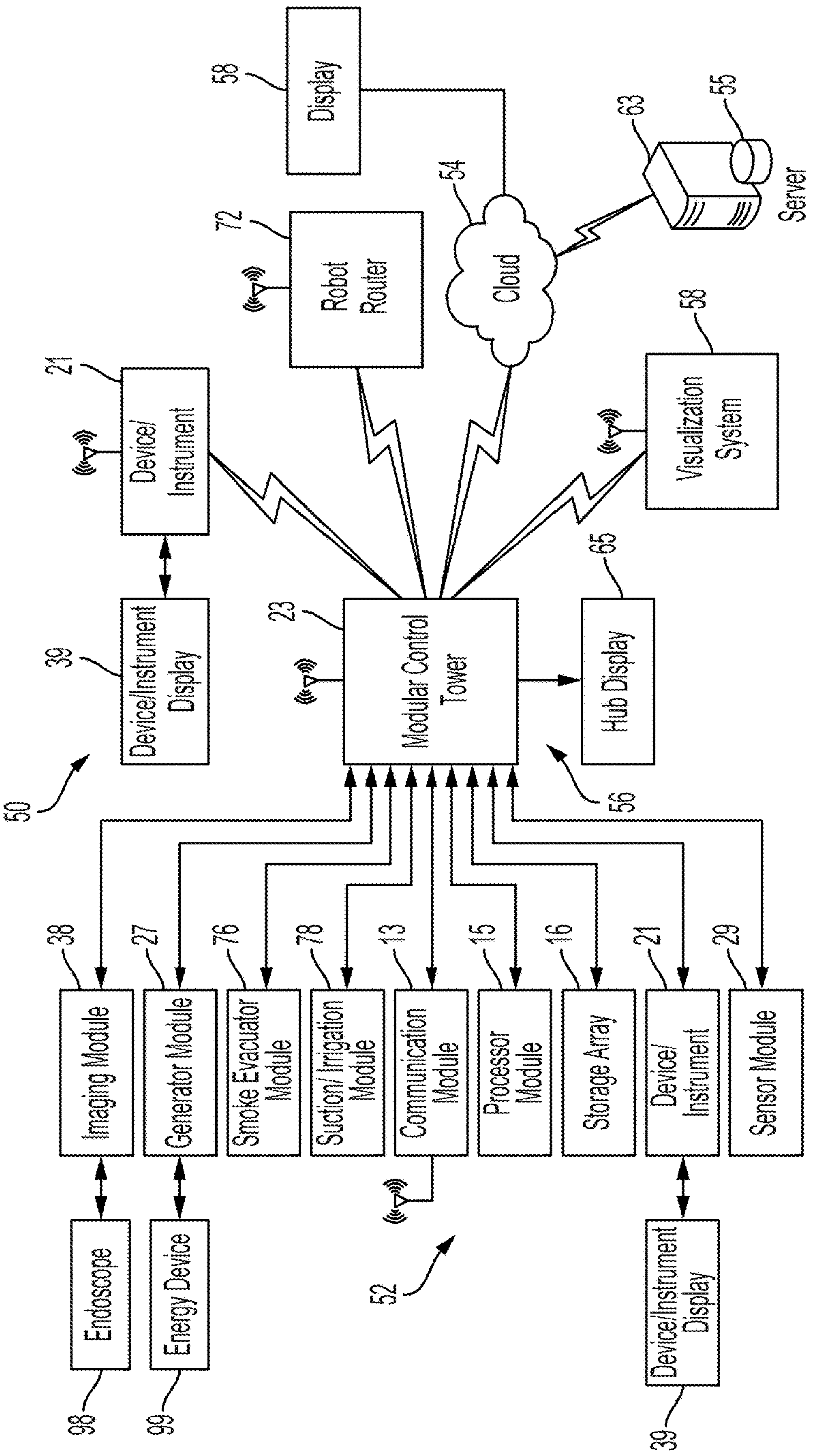
FIG. 5 illustrates a computer-implemented interactive surgical system, according to one aspect of this disclosure.
Figure 6:
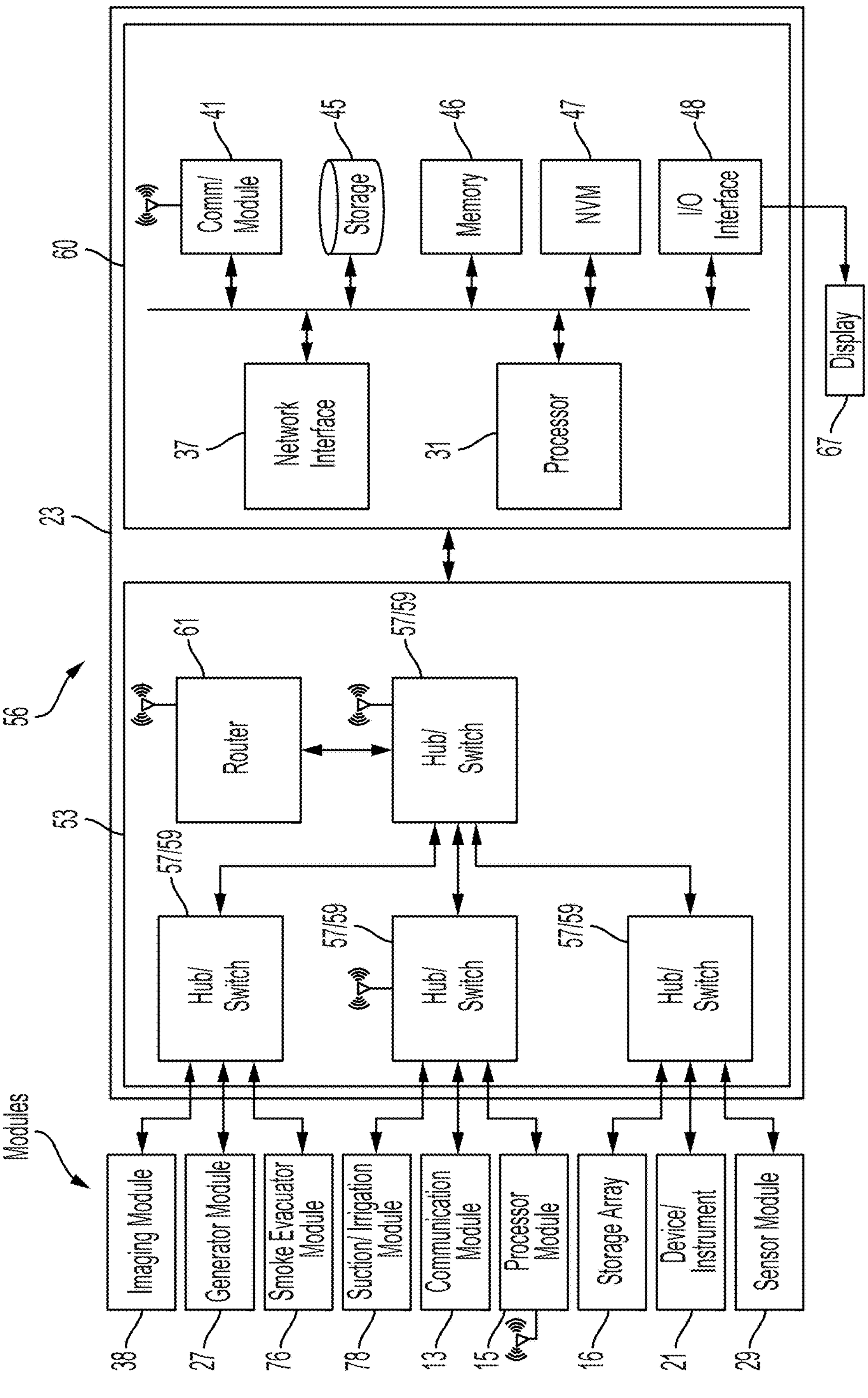
FIG. 6 illustrates a surgical hub comprising a plurality of modules coupled to the modular control tower, according to one aspect of this disclosure.

FIG. 5 illustrates a computer-implemented interactive surgical system 50. The computer-implemented interactive surgical system 50 is similar in many respects to the computer-implemented interactive surgical system 1. The computer-implemented interactive surgical system 50 includes one or more surgical systems 52, which are similar in many respects to the surgical systems 2. Each surgical system 52 includes at least one surgical hub 56 in communication with a cloud 54 that may include a remote server 63. In one aspect, the computer-implemented interactive surgical system 50 comprises a modular control tower 23 connected to multiple operating theater devices such as, for example, intelligent surgical instruments, robots, and other computerized devices located in the operating theater. As shown in FIG. 6, the modular control tower 23 comprises a modular communication hub 53 coupled to a computer system 60.

Back to FIG. 5, the modular control tower 23 is coupled to an imaging module 38 that is coupled to an endoscope 98, a generator module 27 that is coupled to an energy device 99, a smoke evacuator module 76, a suction/irrigation module 78, a communication module 13, a processor module 15, a storage array 16, a smart device/instrument 21 optionally coupled to a display 39, and a sensor module 29. The operating theater devices are coupled to cloud computing resources such as server 63, data storage 55, and displays 58 via the modular control tower 23. A robot hub 72 also may be connected to the modular control tower 23 and to the servers 63, data storage 55, and displays 58. The devices/instruments 21, visualization systems 58, among others, may be coupled to the modular control tower 23 via wired or wireless communication standards or protocols, as described herein. The modular control tower 23 may be coupled to a hub display 65 (e.g., monitor, screen) to display augmented images received comprising overlaid virtual objects on the real surgical field received from the imaging module 38, device/instrument display 39, and/or other visualization systems 58. The hub display 65 also may display data received from devices connected to the modular control tower 23 in conjunction with images and overlaid images.

FIG. 6 illustrates a surgical hub 56 comprising a plurality of modules coupled to the modular control tower 23. The modular control tower 23 comprises a modular communication hub 53, e.g., a network connectivity device, and a computer system 60 to provide local processing, visualization, and imaging of augmented surgical information, for example. The modular communication hub 53 may be connected in a tiered configuration to expand the number of modules (e.g., devices) that may be connected to the modular communication hub 53 and transfer data associated with the modules to the computer system 60, cloud computing resources, or both. Each of the network hubs/switches 57, 59 in the modular communication hub 53 may include three downstream ports and one upstream port. The upstream network hub/switch 57, 59 is connected to a processor 31 to provide a communication connection to the cloud computing resources and a local display 67. Communication to the cloud 54 may be made either through a wired or a wireless communication channel.

The computer system 60 comprises a processor 31 and a network interface 37. The processor 31 is coupled to a communication module 41, storage 45, memory 46, non-volatile memory 47, and input/output interface 48 via a system bus. The system bus can be any of several types of bus structure(s) including the memory bus or memory controller, a peripheral bus or external bus, and/or a local bus using any variety of available bus architectures.

The processor 31 comprises an augmented reality modeler (e.g., as shown in FIG. 10) and may be implemented as a single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHZ, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 60 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

In various aspects, the computer system 60 of FIG. 6, the imaging module 38 and/or visualization system 58, and/or the processor module 15 of FIGS. 4-6, may comprise an image processor, image-processing engine, graphics processing unit (GPU), media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

Figure 7:
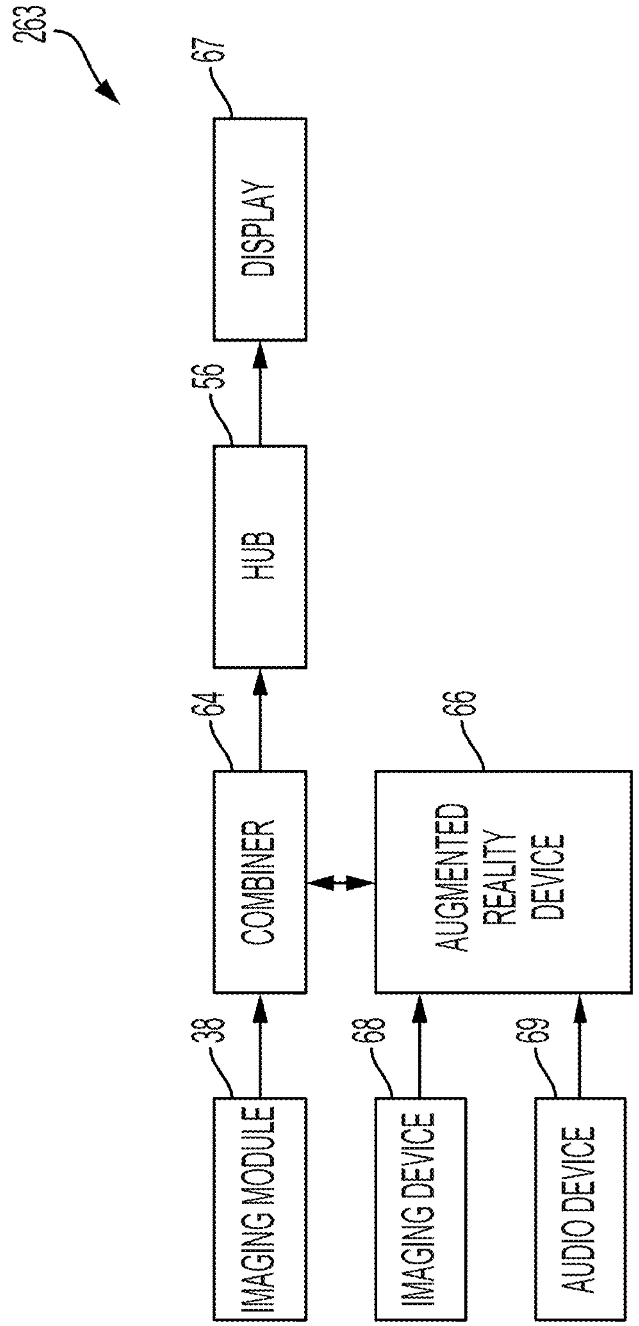
FIG. 7 illustrates an augmented reality (AR) system comprising an intermediate signal combiner positioned in the communication path between an imaging module and a surgical hub display, according to one aspect of this disclosure.

FIG. 7 illustrates an augmented reality system 263 comprising an intermediate signal combiner 64 positioned in the communication path between an imaging module 38 and a surgical hub display 67. The signal combiner 64 combines audio and/or image data received from an imaging module 38 and/or an AR device 66. The surgical hub 56 receives the combined data from the combiner 64 and overlays the data provided to the display 67, where the overlaid data is displayed. The imaging device 68 may be a digital video camera and the audio device 69 may be a microphone. The signal combiner 64 may comprise a wireless heads-up display adapter to couple to the AR device 66 placed into the communication path of the display 67 to a console allowing the surgical hub 56 to overlay data on the display 67.

Figure 8:
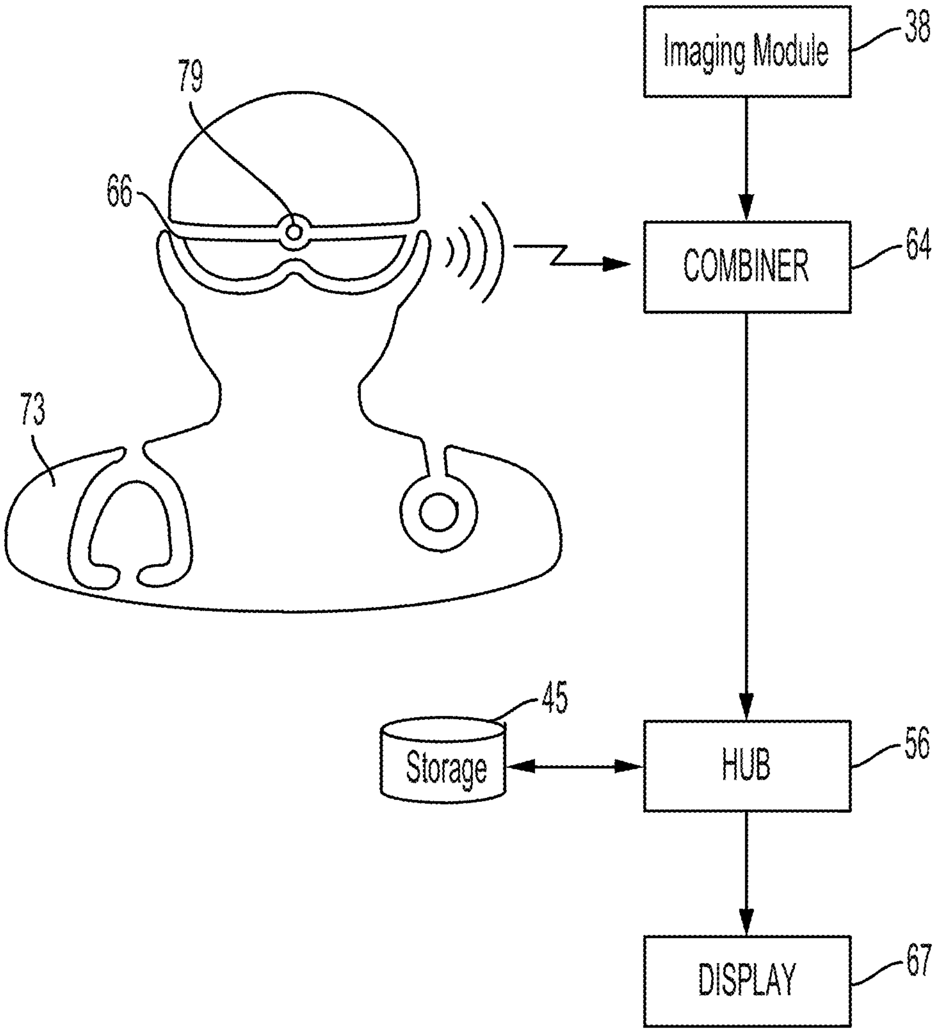
FIG. 8 illustrates an augmented reality (AR) system comprising an intermediate signal combiner positioned in the communication path between an imaging module and a surgical hub display, according to one aspect of this disclosure.

FIG. 8 illustrates an augmented reality (AR) system comprising an intermediate signal combiner positioned in the communication path between an imaging module and a surgical hub display. FIG. 8 illustrates an AR device 66 worn by a surgeon 73 to communicate data to the surgical hub 56. Peripheral information of the AR device 66 does not include active video. Rather, the peripheral information includes only device settings, or signals that do not have same demands of refresh rates. Interaction may augment the surgeon's 73 information based on linkage with preoperative computerized tomography (CT) or other data linked in the surgical hub 56. The AR device 66 can identify structure-ask whether instrument is touching a nerve, vessel, or adhesion, for example. The AR device 66 may include pre-operative scan data, an optical view, tissue interrogation properties acquired throughout procedure, and/or processing in the surgical hub 56 used to provide an answer. The surgeon 73 can dictate notes to the AR device 66 to be saved with patient data in the hub storage 45 for later use in report or in follow up.

The AR device 66 worn by the surgeon 73 links to the surgical hub 56 with audio and visual information to avoid the need for overlays, and allows customization of displayed information around periphery of view. The AR device 66 provides signals from devices (e.g., instruments), answers queries about device settings, or positional information linked with video to identify quadrant or position. The AR device 66 has audio control and audio feedback from the AR device 66. The AR device 66 is able to interact with other systems in the operating theater and have feedback and interaction available wherever the surgeon 73 is viewing. For example, the AR device 66 may receive voice or gesture initiated commands and queries from a surgeon, and the AR device 66 may provide feedback in the form of one or more modalities including audio, visual, or haptic touch.

Figure 9:
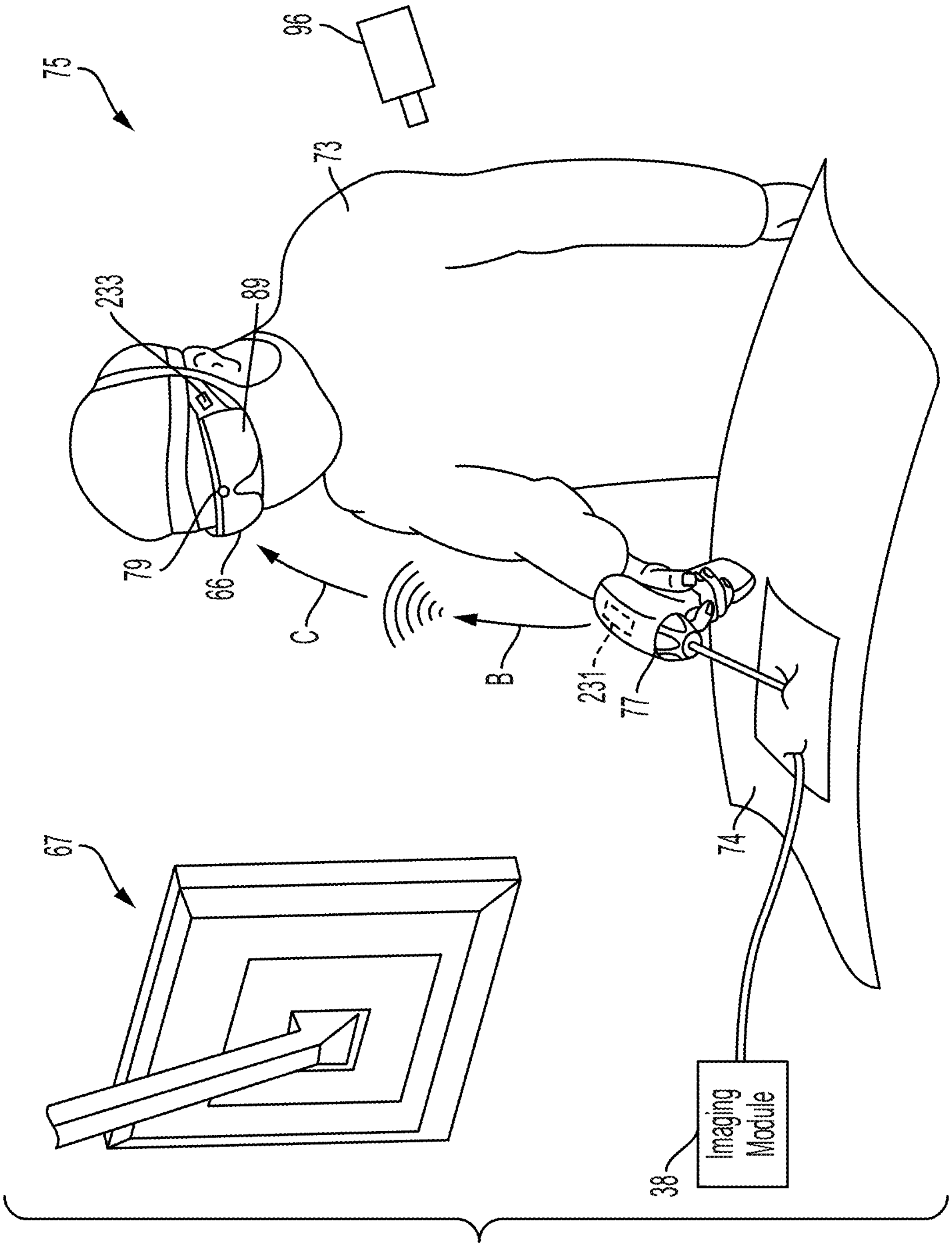
FIG. 9 illustrates an augmented reality (AR) device worn by a surgeon to communicate data to the surgical hub, according to one aspect of this disclosure.

FIG. 9 illustrates a surgeon 73 wearing an AR device 66, a patient 74, and may include a camera 96 in an operating room 75. The AR device 66 worn by the surgeon 73 may be used to present to the surgeon 73 a virtual object overlaid on a real time image of the surgical field through augmented reality display 89 or through the hub connected display 67. The real time image may include a portion of a surgical instrument 77. The virtual object may not be visible to others within the operating room 75 (e.g., surgical assistant or nurse), though they also may wear AR devices 66. Even if another person is viewing the operating room 75 with an AR device 66, the person may not be able to see the virtual object or may be able to see the virtual object in a shared augmented reality with the surgeon 73, or may be able to see a modified version of the virtual object (e.g., according to customizations unique to the surgeon 73) or may see different virtual objects.

A virtual object and/or data may be configured to appear on a portion of a surgical instrument 77 or in a surgical field of view captured by an imaging module 38, an imaging device 68 during minimally invasive surgical procedures, and/or the camera 96 during open surgical procedures. In the illustrated example, the imaging module 38 is a laparoscopic camera that provides a live feed of a surgical area during a minimally invasive surgical procedure. An AR system may present virtual objects that are fixed to a real object without regard to a perspective of a viewer or viewers of the AR system (e.g., the surgeon 73). For example, a virtual object may be visible to a viewer of the AR system inside the operating room 75 and not visible to a viewer of the AR system outside the operating room 75. The virtual object may be displayed to the viewer outside the operating room 75 when the viewer enters the operating room 75. The augmented image may be displayed on the surgical hub display 67 or the augmented reality display 89.

The AR device 66 may include one or more screens or lens, such as a single screen or two screens (e.g., one per eye of a user). The screens may allow light to pass through the screens such that aspects of the real environment are visible while displaying the virtual object. The virtual object may be made visible to the surgeon 73 by projecting light. A virtual object may appear to have a degree of transparency or may be opaque (i.e., blocking aspects of the real environment).

An AR system may be viewable to one or more viewers, and may include differences among views available for the one or more viewers while retaining some aspects as universal among the views. For example, a heads-up display may change between two views while virtual objects and/or data may be fixed to a real object or area in both views. Aspects such as a color of an object, lighting, or other changes may be made among the views without changing a fixed position of at least one virtual object.

A user may see a virtual object and/or data presented in an AR system as opaque or as including some level of transparency. In an example, the user may interact with the virtual object, such as by moving the virtual object from a first position to a second position. For example, the user may move an object with his or her hand. This may be done in the AR system virtually by determining that the hand has moved into a position coincident or adjacent to the object (e.g., using one or more cameras, which may be mounted on the AR device 66, such as AR device camera 79 or separate 96, and which may be static or may be controlled to move), and causing the object to move in response. Virtual aspects may include virtual representations of real world objects or may include visual effects, such as lighting effects, etc. The AR system may include rules to govern the behavior of virtual objects, such as subjecting a virtual object to gravity or friction, or may include other predefined rules that defy real world physical constraints (e.g., floating objects, perpetual motion, etc.). The AR device 66 may include a camera 79 on the AR device 66 (not to be confused with the camera 96, separate from the AR device 66). The AR device camera 79 or the camera 96 may include an infrared camera, an infrared filter, a visible light filter, a plurality of cameras, a depth camera, etc. The AR device 66 may project virtual items over a representation of a real environment, which may be viewed by a user.

The AR device 66 may be used in the operating room 75 during a surgical procedure, for example performed by the surgeon 73 on the patient 74. The AR device 66 may project or display virtual objects, such as a virtual object during the surgical procedure to augment the surgeon's vision. The surgeon 73 may view a virtual object using the AR device 66, a remote controller for the AR device 66, or may interact with a virtual object, for example, using a hand to "interact" with a virtual object or a gesture recognized by the camera 79 of the AR device 66. A virtual object may augment a surgical tool such as the surgical instrument 77. For example, the virtual object may appear (to the surgeon 73 viewing the virtual object through the AR device 66) to be coupled with or remain a fixed distance from the surgical instrument 77. In another example, the virtual object may be used to guide the surgical instrument 77, and may appear to be fixed to the patient 74. In certain examples, a virtual object may react to movements of other virtual or real-world objects in the surgical field. For example, the virtual object may be altered when a surgeon is manipulating a surgical instrument in proximity to the virtual object.

The augmented reality display system imaging device 38 capture a real image of a surgical area during a surgical procedure. An augmented reality display 89, 67 presents an overlay of an operational aspect of the surgical instrument 77 onto the real image of the surgical area. The surgical instrument 77 includes communications circuitry 231 to communicate operational aspects and functional data from the surgical instrument 77 to the AR device 66 via communication communications circuitry 233 on the AR device 66. Although the surgical instrument 77 and the AR device 66 are shown in RF wireless communication between circuits 231, 233 as indicated by arrows B, C, other communication techniques may employed (e.g., wired, ultrasonic, infrared, etc.). The overlay is related to the operational aspect of the surgical instrument 77 being actively visualized. The overlay combines aspects of tissue interaction in the surgical area with functional data from the surgical instrument 77. A processor portion of the AR device 66 is configured to receive the operational aspects and functional data from the surgical instrument 77, determine the overlay related to the operation of the surgical instrument 77, and combine the aspect of the tissue in the surgical area with the functional data from the surgical instrument 77. The augmented images indicate alerts relative to device performance considerations, alerts of incompatible usage, alerts on incomplete capture. Incompatible usage includes tissue out range conditions and tissue incorrectly balanced within the jaws of the end effector. Additional augmented images provide an indication of collateral events including indication of tissue tension and indication of foreign object detection. Other augmented images indicate device status overlays and instrument indication.

FIG. 10 illustrates a system 83 for augmenting images of a surgical field with information using an AR display 89, according to one aspect of this disclosure. The system 83 may be used to perform the techniques described hereinbelow, for example, by using the processor 85. The system 83 includes one aspect of an AR device 66 that may be in communication with a database 93. The AR device 66 includes a processor 85, memory 87, an AR display 89, and a camera 79. The AR device 66 may include a sensor 90, a speaker 91, and/or a haptic controller 92. The database 93 may include image storage 94 or preoperative plan storage 95.

The processor 85 of the AR device 66 includes an augmented reality modeler 86. The augmented reality modeler 86 may be used by the processor 85 to create the augmented reality environment. For example, the augmented reality modeler 86 may receive images of the instrument in a surgical field, such as from the camera 79 or sensor 90, and create the augmented reality environment to fit within a display image of the surgical field of view. In another example, physical objects and/or date may be overlaid on the surgical field of view and/or the surgical instruments images and the augmented reality modeler 86 may use physical objects and data to present the augmented reality display of virtual object s and/or data in the augmented reality environment. For example, the augmented reality modeler 86 may use or detect an instrument at a surgical site of the patient and present a virtual object and/or data on the surgical instrument and/or an image of the surgical site in the surgical field of view captured by the camera 79. The AR display 89 may display the AR environment overlaid on a real environment. The display 89 may show a virtual object and/or data, using the AR device 66, such as in a fixed position in the AR environment.

The AR device 66 may include a sensor 90, such as an infrared sensor. The camera 79 or the sensor 90 may be used to detect movement, such as a gesture by a surgeon or other user, that may be interpreted by the processor 85 as attempted or intended interaction by the user with the virtual target. The processor 85 may identify an object in a real environment, such as through processing information received using the camera 79. In other aspects, the sensor 90 may be a tactile, audible, chemical, or thermal sensor to generate corresponding signals that may combined with various data feeds to create the augmented environment. The sensor 90 may include binaural audio sensors (spatial sound), inertial measurement (accelerometer, gyroscope, magnetometer) sensors, environmental sensors, depth camera sensors, hand and eye tracking sensors, and voice command recognition functions.

The AR display 89, for example during a surgical procedure, may present, such as within a surgical field while permitting the surgical field to be viewed through the AR display 89, a virtual feature corresponding to a physical feature hidden by an anatomical aspect of a patient. The virtual feature may have a virtual position or orientation corresponding to a first physical position or orientation of the physical feature. In an example, the virtual position or orientation of the virtual feature may include an offset from the first physical position or orientation of the physical feature. The offset may include a predetermined distance from the augmented reality display, a relative distance from the augmented reality display to the anatomical aspect, or the like.

In one example, the AR device 66 may be an individual AR device. In one aspect, the AR device 66 may be a Hololens 2 AR device manufactured by Microsoft of Redmond, Wash. This AR device 66 includes a visor with lenses and binaural audio features (spatial sound), inertial measurement (accelerometer, gyroscope, magnetometer), environmental sensors, depth camera, and video camera, hand and eye tracking, and voice command recognition functions. It provides an improved field of view with high resolution by using mirrors to direct waveguides in front of wearer's eyes. Images can be enlarged by changing angles of mirrors. It also provides eye tracking to recognize users and adjust lens widths for specific users.

In another example, the AR device 66 may be a Snapchat Spectacles 3 AR device. This AR device provides the ability to capture paired images and recreate 3D depth mapping, add in virtual effects, and replay 3D videos. The AR device includes two HD cameras to capture 3D photos and videos at 60 fps—while four built-in microphones record immersive, high-fidelity audio. Images from both cameras combine to build out a geometric map of the real world around the user to provide a new sense of depth perception. Photos and videos may be wirelessly synchronized to external display devices.

In yet another example, the AR device 66 may be a Glass 2 AR device by Google. This AR device provides inertial measurement (accelerometer, gyroscope, magnetometer) information overlaid on lens (out of view) to supplement information.

In another example, the AR device 66 may be an Echo Frames AR device by Amazon. This AR device does not have cameras/displays. A microphone and speaker are linked to Alexa. This AR device provides less functionality than a heads-up display.

In yet another example, the AR device 66 may be a Focals AR device by North (Google). This AR device provides notification pusher/smartwatch analog; inertial measurement, screen overlay of information (weather, calendar, messages), voice control (Alexa) integration. This AR device provides basic heads-up display functionality.

In another example, the AR device 66 may be an Nreal AR device. This AR device includes spatial sound, two environmental cameras, a photo camera, IMU (accelerometer, gyroscope), ambient light sensor, proximity sensor functionality. A nebula projects application information on lenses.

In various other examples, the AR device 66 may be any one of the following commercially available AR devices: Magic Leap 1, Epson Moverio, Vuzix Blade AR, ZenFone AR, Microsoft AR glasses prototype, EyeTap to create collinear light to that of the environment directly into the retina. A beam splitter makes the same light seen by the eye available to the computer to process and overlay information, for example. AR visualization systems include HUD, contact lenses, glasses, virtual reality (VR) headsets, virtual retinal display, on in operating room displays, and/or smart contact lenses (bionic lenses).

Multi-user interfaces for the AR device 66 include virtual retinal displays such as raster displays drawn directly on retinas instead of on a screen in front of the eye, smart televisions, smart phones, and/or spatial displays such as Sony spatial display systems.

Other AR technology may include, for example, AR capture devices and software applications, AR creation devices and software applications, and AR cloud devices and software applications. AR capture devices and software applications include, for example, Apple Polycam app, Ubiquity 6 (Mirrorworld using Display.land app)—users can scan and get 3d image of real world (to create 3D model). AR creation devices and software applications include, for example, Adobe Aero, Vuforia, ARToolKit, Google ARCore, Apple ARKit, MAXST, Aurasma, Zappar, Blippar. AR cloud devices and software applications include, for example, Facebook, Google (world geometry, objection recognition, predictive data), Amazon AR Cloud (commerce), Microsoft Azure, Samsung Project Whare, Niantic, Magic Leap.

Situational awareness is the ability of some aspects of a surgical system to determine or infer information related to a surgical procedure from data received from databases and/or instruments. The information can include the type of procedure being undertaken, the type of tissue being operated on, or the body cavity that is the subject of the procedure. With the contextual information related to the surgical procedure, the surgical system can, for example, improve the manner in which it controls the modular devices (e.g., a robotic arm and/or robotic surgical tool) that are connected to it and provide contextualized information or suggestions to the surgeon during the course of the surgical procedure.

Figure 11:
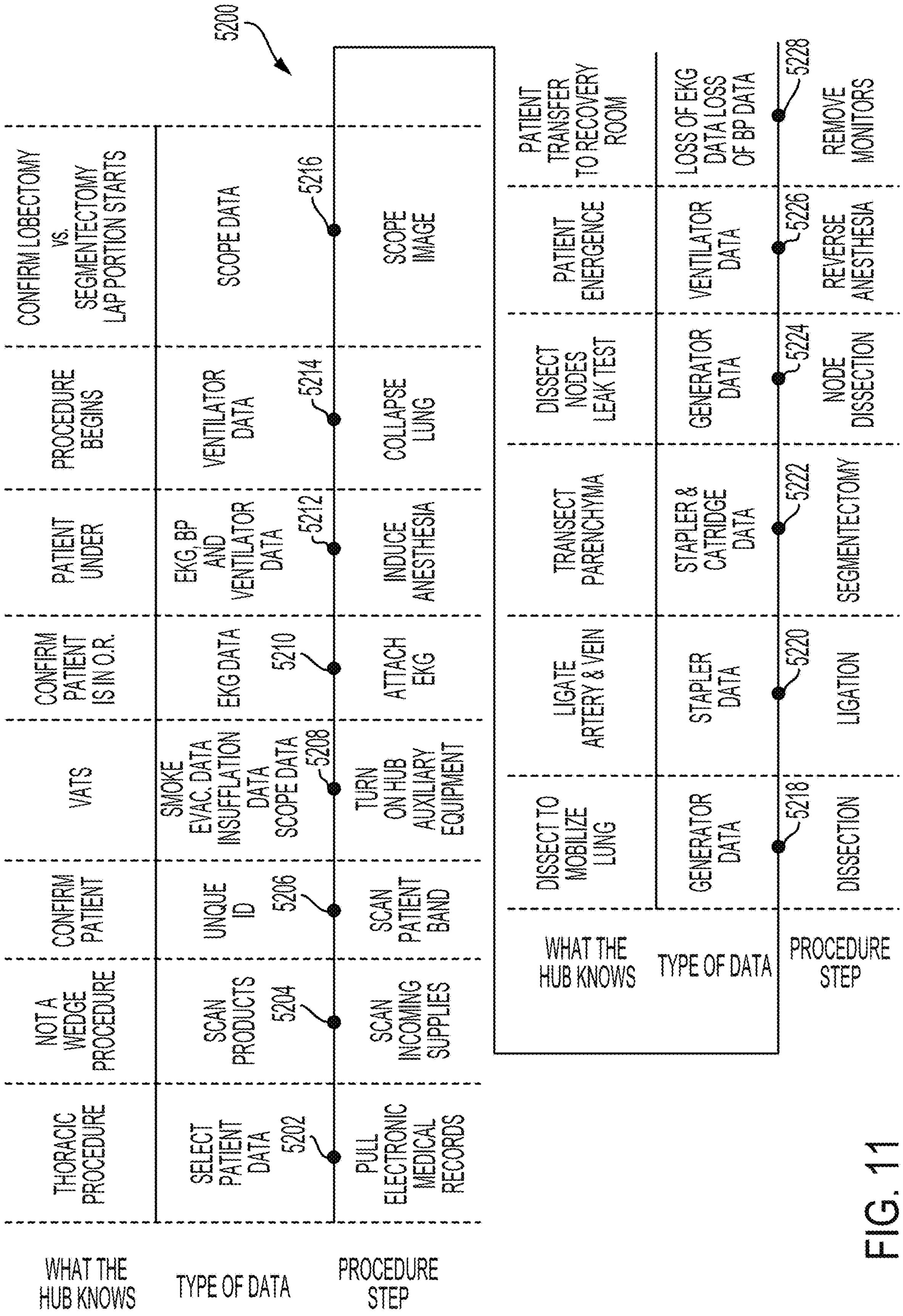
FIG. 11 illustrates a timeline of a situational awareness surgical procedure, according to one aspect of this disclosure.

FIG. 11 illustrates a timeline of a situational awareness surgical procedure. FIG. 11 illustrates a timeline 5200 of an illustrative surgical procedure and the contextual information that a surgical hub 5104 can derive from the data received from the data sources 5126 at each step in the surgical procedure. The timeline 5200 depicts the typical steps that would be taken by the nurses, surgeons, and other medical personnel during the course of a lung segmentectomy procedure, beginning with setting up the operating theater and ending with transferring the patient to a post-operative recovery room. The situationally aware surgical hub 5104 receives data from the data sources 5126 throughout the course of the surgical procedure, including data generated each time medical personnel utilize a modular device 5102 that is paired with the surgical hub 5104. The surgical hub 5104 can receive this data from the paired modular devices 5102 and other data sources 5126 and continually derive inferences (i.e., contextual information) about the ongoing procedure as new data is received, such as which step of the procedure is being performed at any given time. The situational awareness system of the surgical hub 5104 is able to, for example, record data pertaining to the procedure for generating reports, verify the steps being taken by the medical personnel, provide data or prompts (e.g., via a display screen) that may be pertinent for the particular procedural step, adjust modular devices 5102 based on the context (e.g., activate monitors, adjust the FOV of the medical imaging device, or change the energy level of an ultrasonic surgical instrument or RF electrosurgical instrument), and take any other such action described above.

First 5202, the hospital staff members retrieve the patient's EMR from the hospital's EMR database. Based on select patient data in the EMR, the surgical hub 5104 determines that the procedure to be performed is a thoracic procedure.

Second 5204, the staff members scan the incoming medical supplies for the procedure. The surgical hub 5104 cross-references the scanned supplies with a list of supplies that are utilized in various types of procedures and confirms that the mix of supplies corresponds to a thoracic procedure. Further, the surgical hub 5104 is also able to determine that the procedure is not a wedge procedure (because the incoming supplies either lack certain supplies that are necessary for a thoracic wedge procedure or do not otherwise correspond to a thoracic wedge procedure).

Third 5206, the medical personnel scan the patient band via a scanner 5128 that is communicably connected to the surgical hub 5104. The surgical hub 5104 can then confirm the patient's identity based on the scanned data.

Fourth 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices 5102 can automatically pair with the surgical hub 5104 that is located within a particular vicinity of the modular devices 5102 as part of their initialization process. The surgical hub 5104 can then derive contextual information about the surgical procedure by detecting the types of modular devices 5102 that pair with it during this pre-operative or initialization phase. In this particular example, the surgical hub 5104 determines that the surgical procedure is a VATS procedure based on this particular combination of paired modular devices 5102. Based on the combination of the data from the patient's EMR, the list of medical supplies to be used in the procedure, and the type of modular devices 5102 that connect to the hub, the surgical hub 5104 can generally infer the specific procedure that the surgical team will be performing. Once the surgical hub 5104 knows what specific procedure is being performed, the surgical hub 5104 can then retrieve the steps of that procedure from a memory or from the cloud and then cross-reference the data it subsequently receives from the connected data sources 5126 (e.g., modular devices 5102 and patient monitoring devices 5124) to infer what step of the surgical procedure the surgical team is performing.

Fifth 5210, the staff members attach the EKG electrodes and other patient monitoring devices 5124 to the patient. The EKG electrodes and other patient monitoring devices 5124 are able to pair with the surgical hub 5104. As the surgical hub 5104 begins receiving data from the patient monitoring devices 5124, the surgical hub 5104 thus confirms that the patient is in the operating theater.

Sixth 5212, the medical personnel induce anesthesia in the patient. The surgical hub 5104 can infer that the patient is under anesthesia based on data from the modular devices 5102 and/or patient monitoring devices 5124, including EKG data, blood pressure data, ventilator data, or combinations. Upon completion of the sixth step 5212, the pre-operative portion of the lung segmentectomy procedure is completed and the operative portion begins.

Seventh 5214, the patient's lung that is being operated on is collapsed (while ventilation is switched to the contralateral lung). The surgical hub 5104 can infer from the ventilator data that the patient's lung has been collapsed. The surgical hub 5104 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth 5216, the medical imaging device 5108 (e.g., a scope) is inserted and video from the medical imaging device is initiated. The surgical hub 5104 receives the medical imaging device data (i.e., still image data or live streamed video in real time) through its connection to the medical imaging device. Upon receipt of the medical imaging device data, the surgical hub 5104 can determine that the laparoscopic portion of the surgical procedure has commenced. Further, the surgical hub 5104 can determine that the particular procedure being performed is a segmentectomy, as opposed to a lobectomy (note that a wedge procedure has already been discounted by the surgical hub 5104 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 5104), and monitoring the types of visualization devices utilized.

For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device 5108, the surgical hub 5104 can thereby determine the specific type of surgical procedure being performed and/or the technique being used for a particular type of surgical procedure.

Ninth 5218, the surgical team begins the dissection step of the procedure. The surgical hub 5104 can infer that the surgeon is in the process of dissecting to mobilize the patient's lung because it receives data from the RF or ultrasonic generator indicating that an energy instrument is being fired. The surgical hub 5104 can cross-reference the received data with the retrieved steps of the surgical procedure to determine that an energy instrument being fired at this point in the process (i.e., after the completion of the previously discussed steps of the procedure) corresponds to the dissection step.

Tenth 5220, the surgical team proceeds to the ligation step of the procedure. The surgical hub 5104 can infer that the surgeon is ligating arteries and veins because it receives data from the surgical stapling and cutting instrument indicating that the instrument is being fired. Similarly to the prior step, the surgical hub 5104 can derive this inference by cross-referencing the receipt of data from the surgical stapling and cutting instrument with the retrieved steps in the process.

Eleventh 5222, the segmentectomy portion of the procedure is performed. The surgical hub 5104 infers that the surgeon is transecting the parenchyma based on data from the surgical instrument, including data from a staple cartridge. The cartridge data may correspond to size or type of staple being fired by the instrument. The cartridge data can indicate the type of tissue being stapled and/or transected for different types of staples utilized in different types of tissues. The type of staple being fired is utilized for parenchyma or other tissue types to allow the surgical hub 5104 to infer that the segmentectomy procedure is being performed.

Twelfth 5224, the node dissection step is then performed. The surgical hub 5104 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 5104 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Upon completion of the twelfth step 5224, the incisions and closed up and the post-operative portion of the procedure begins.

Thirteenth 5226, the patient's anesthesia is reversed. The surgical hub 5104 can infer that the patient is emerging from the anesthesia based on the ventilator data (i.e., the patient's breathing rate begins increasing), for example.

Lastly, fourteenth 5228, the medical personnel remove the various patient monitoring devices 5124 from the patient. The surgical hub 5104 can thus infer that the patient is being transferred to a recovery room when the hub loses EKG, BP, and other data from the patient monitoring devices 5124. The surgical hub 5104 can determine or infer when each step of a given surgical procedure is taking place according to data received from the various data sources 5126 that are communicably coupled to the surgical hub 5104.

In addition to utilizing the patient data from EMR database(s) to infer the type of surgical procedure that is to be performed, as illustrated in the first step 5202 of the timeline 5200 depicted in FIG. 11, the patient data can also be utilized by a situationally aware surgical hub 5104 to generate control adjustments for the paired modular devices 5102.

Surgical displays (e.g., displays 7, 9, 19, 35, 62, 65, 66, 67, and 89) play an important function within the operating room, by provide useful information to a clinician (e.g., surgeon, surgical staff) that can used to, among other things, assess the progress of a surgical procedure, determine subsequent steps to take in the surgical procedure, monitor patent vital signs, etc. The displays need to be large enough such that this information being provided can be seen, yet not so large as to be overbearing and obstruct workflow or movement in a crowded operating room.

For example, an imaging device, such as one of the many imaging devices described elsewhere herein, is used to capture a livestream of a surgical field during a surgical procedure. A display shows this livestream captured by the imaging device such that the clinician can view the surgical field during the surgical procedure.

During the course of the surgical procedure, information that is relevant to or associated with the surgical procedure can be overlaid onto the livestream on the display. For example, an electrocardiogram (EKG) monitors a patient's heart rate during the surgical procedure and the monitored heart rate is overlaid on the livestream such that the clinician can ensure that the patient is stable.

Various other sensors, detectors, modules, etc. monitor other parameters over the course of the surgical procedure and information associated with these parameters can also be overlaid onto the display. However, some overlaid information may be of more significance than other overlaid information. As an example, when a clinician is manipulating tissue with an end effector of a surgical instrument, information regarding how much force is being applied to the tissue with the end effector is relevant to monitor so as to ensure the tissue isn't being unintentionally damaged.

However, owing the amount of information being overlaid on the display, more important information, such as a force being applied to the tissue, may be overlooked or missed by the clinician. This abundance of competing information can cause the surgeon to become overwhelmed with information that may be detrimental to their ability to adequately perform the surgical procedure, which can prove costly to the patient. Accordingly, there is a need to prioritize, control and/or limit the amount of data that is being overlaid on the display.

Figure 12:
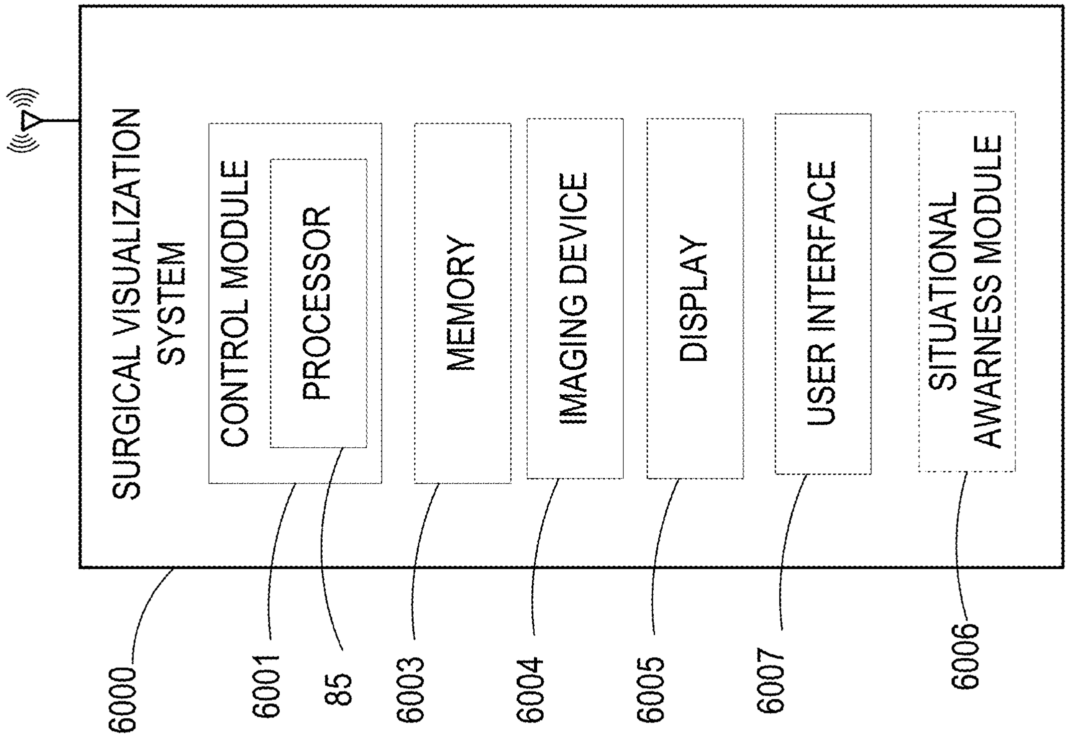
FIG. 12 illustrates a surgical visualization system, according to one aspect of this disclosure.

FIG. 12 illustrates a surgical visualization system 6000, according to one aspect of this disclosure. Various components of the surgical visualization system 6000 are similar in many respect to components of other systems described elsewhere in the present disclosure and, as such, are not repeated herein at the same level of detail for brevity. In some implementations the system 6000 is a standalone system. In other implementations, the system 6000 is integrated in, or used in conjunction with, the computer-implemented interactive surgical system 1.

The surgical visualization system 6000 includes a control module 6001 configured to perform various techniques described herein, for example, by using one or more processors or processing circuitry such as the processor 85. In some implementations, the system 6000 can include, be used in conjunction with, or be communication with the augmented reality device 84, for example. The system 6000 may further include storage medium such as, for example, a memory 6003, an imaging device 6004 such as, for example, the camera 88, and a display 6005. The system 6000 may further include one or more speakers 91, haptic controllers 92, and/or sensors 90 (see FIG. 10). The display 6005 can include, for example, the AR display 89, a VR display, a projector, a heads-up display, a screen, and/or any other suitable device for portraying visual content.

In some implementations, the system 6000 is incorporated into the computer-implemented interactive surgical system 50, for example. In some implementations the system 6000 is in operable communication with one or more hubs, systems, networks, servers, and/or databases that can deliver surgical data to the system 6000. For example, the system 6000 can be in operable communication with cloud 54 that may include a remote server 63, robot hub 72, surgical hub 56, devices/instruments 21, and/or modular control tower 23 via wired or wireless communication standards or protocols, as described herein. In some implementations, the system 6000 includes a situational awareness module 6006 similar to that described in connection was the surgical hub 5104. The situational awareness module 6006 can be trained to extrapolate contextual information about a surgical procedure based on a multitude of perioperative data received through sensor input and/or user input.

Figure 13:
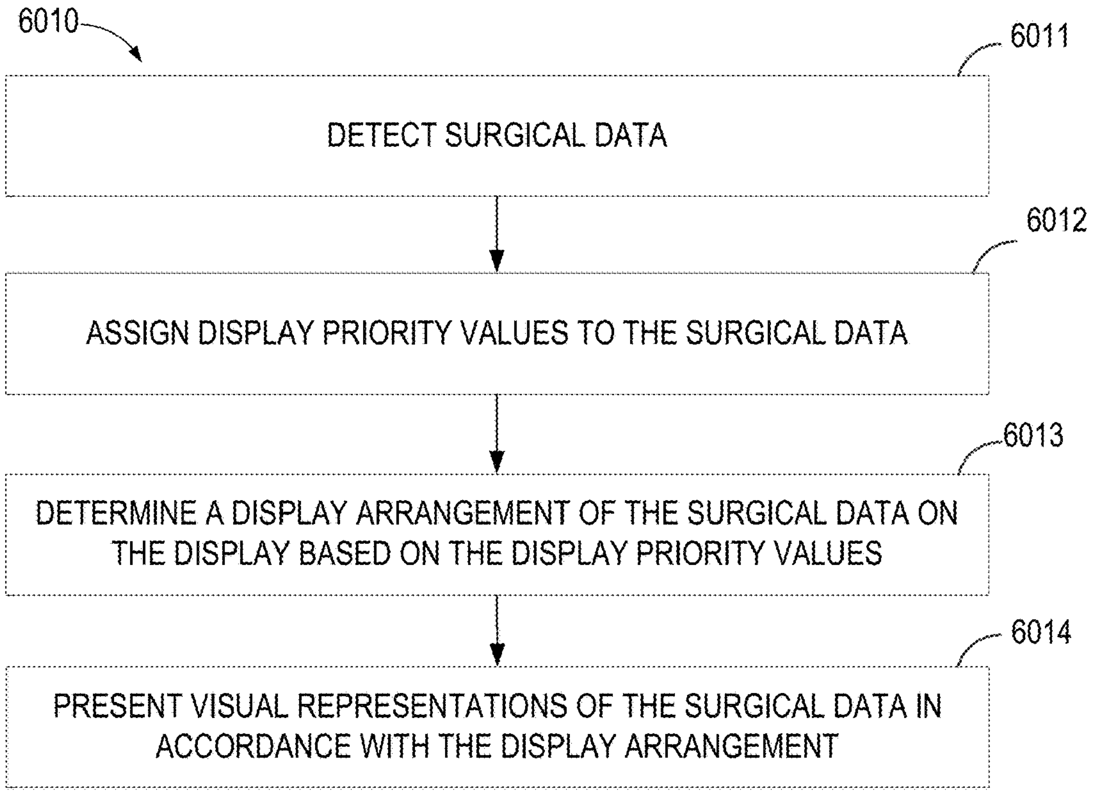
FIG. 13 is a logic diagram showing operations of an example method for determining a display arrangement of surgical data competing for presentation onto a display, according to one aspect of this disclosure.

FIG. 13 is a logic diagram showing operations of an example method 6010 for determining a display arrangement of surgical data competing for presentation onto a display such as the display 6005. The method 6010 includes detecting 6011 surgical data, assigning 6012 display priority values, or display priority statuses, to the surgical data, and determining 6013 a display arrangement of the surgical data on the display based on the display priority values. The method 6010 may further include presenting 6014, by displaying, or overlaying onto the livestream of the surgical field, for example, visual representations of the surgical data in accordance with the display arrangement.

In some implementations, the surgical data is detected 6011 by the control module 6001. The surgical data can be detected 6011 by receiving the surgical data from one or more sources such as, for example, components of the computer-implemented interactive surgical system 1 via one or more wireless and/or wired communication interfaces. In at least one example, the surgical data may include data received from one or more of the surgical instrument 21. In another example, the surgical data includes contextual information ascertained by the situational awareness module 6006.

In certain exemplifications, the surgical data comprise control data, biomarker measurements, and/or other operational indicators of operations and/or outcomes associated with a surgical instrument 21. In certain exemplifications, the surgical data can be any data indicative of a higher propensity of malformed staples and poorly sealed tissue. In certain instances, the surgical data can be associated with tissue flow, clamping force, firing force, among other tissue and/or instrument parameters, which can be monitored and displayed to the clinician in multiple ways in real time to allow for adjustments to the firing process or to alert the surgeon of a potentially malformed staple region.

In some implementations, the display priority values are assigned based on the surgical data and/or contextual information regarding the surgical procedure developed by the situational awareness module 6006. In some implementations, the display priority values are assigned based on a triggering event, a condition, or a characteristic of the surgical data. In some implementations, assigning 6012 a display priority value includes changing a previously-assigned display priority value. For example, the detection of a triggering event, a condition, and/or a characteristic of the surgical data may cause a change in previously-assigned display priority value to a higher value or a lower value.

In certain exemplifications, the processor 85 employs a predetermined equation and/or formula in determining the display priority values of the surgical data. Various relevant factors can be considered and assigned different weights in calculating the display priority values. Additionally, or alternatively, one or more databases or tables listing surgical data and corresponding display priority values can be utilized by the processor 85 in assigning the display priority values.

In various implementations, the assigned 6012 display priority values comprise various levels of display priority such as, for example, a low display priority level, a medium display priority level, and/or a high display priority level. In some implementations, the display priority values are display priority statuses such as, for example, a high priority status, a neutral priority status, and/or a low priority status.

Figure 14:
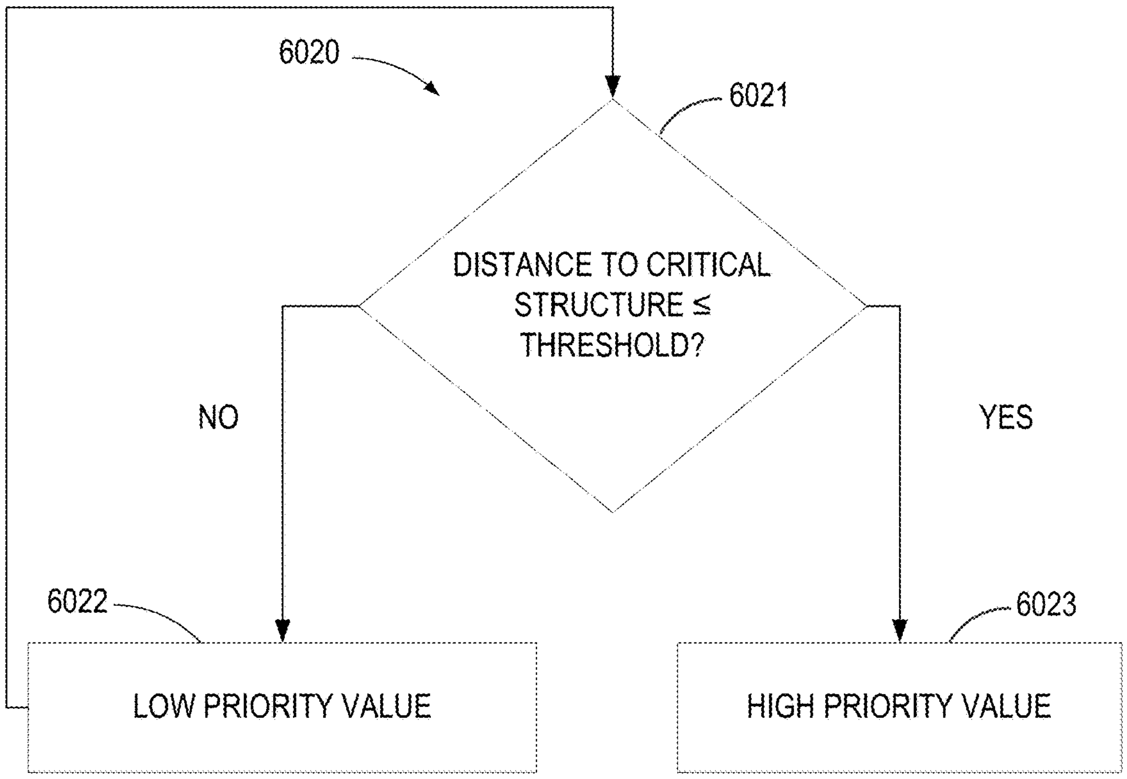
FIG. 14 is a logic diagram showing operations of an example method 6020 for determining display priority values of the surgical data detected 6011, in accordance with the method of FIG. 13.

FIG. 14 is a logic diagram showing operations of an example method 6020 for determining display priority values of the surgical data detected 6011, in accordance with the method 6010 of FIG. 13. In certain implementations, the display priority values depend on the surgical data. In the illustrated example, a display priority value is assigned based on proximity of a surgical instrument being utilized in the surgical procedure to a critical anatomical structure associated with the surgical procedure. The display priority value is based on a relationship between the received proximity data and a predetermined proximity threshold. For example, if 6021 the distance between the surgical instrument and the anatomical structure is greater than the predetermined threshold, the proximity data is assigned 6022 a low display-priority value. If 6021, however, the distance is less than or equal to the predetermined proximity threshold, the proximity data is assigned 6023 a high display-priority value.

In some implementations, the system 6000 employs the situational awareness module 6006 to identify the type of the surgical procedure to be performed. The type of surgical procedure can be determined from a user input, for example. Alternatively, or additionally, it can be determined from an inventory list of devices selected for use with the surgical procedure, which are unique to, or characteristic of, the surgical procedure type. The system 6000 may further identify a critical structure associated with the surgical procedure from a database and/or a user input, for example. In some implementations, the system 6000 can detect the critical structure in a livestream of the surgical field as captured by the imaging device. Moreover, the system 6000 may further detect a surgical instrument 21 in the surgical field, and may track proximity of the surgical instrument 21 to the critical structure. A display priority value of the proximity data can be determined, as discussed in connection with FIG. 14.

In some implementations, identification of the critical structure and/or the surgical instrument in the livestream of the surgical field can be attained through various suitable object recognition, object tracking, object labeling, and/or other image processing techniques such as one discussed in U.S. patent application Ser. No. 16/729,807, titled STRUCTURED MULTI SPECTRAL COMPUTATIONAL ANALYSIS, which is incorporated by reference in its entirety. For example, previously-stored images of the surgical instruments and/or the critical structure can be utilized to identify surgical instruments and/or critical structures in the surgical field.

A low anterior resection (LAR) surgical procedure is a common surgery for rectal cancer. This procedure involves the removal of the rectum. The colon is then attached to the remaining section of the rectum to allow for normal bowel movement. A circular stapler is generally used in a low LAR procedure. Initially, as the surgeon begins to set up the structures to create the anastomosis, certain parameters such as parameters of tissue tension and anastomosis tissue pressure are not relevant, and can be distracting if overlaid or emphasized too soon on the livestream. In certain instances, to avoid the distraction and/or reduction of the display space available for the livestream, such parameters are overlaid and/or emphasized onto the display 6005 per a display arrangement in accordance with the method 6010.

In some implementations, display priority values are assigned to the parameters of tissue tension and anastomosis tissue pressure based on a triggering event associated with the relevance of the parameters to the surgical procedure. The triggering event can, for example, be the detection of a connection of the anvil of the circular stapler to the circular stapler trocar. The detection can be achieved automatically by employing one or more object recognition, object tracking, object labeling, and/or other image processing algorithms of the livestream and/or through one or more sensors in the anvil and/or the trocar that are triggered by the connection or the proximity of the anvil to the trocar, for example.

In some implementations the triggering event is associated with an increased criticality or risk level. In certain instances, the triggering event can yield a warning and/or an immediate pausing of a surgical activity such as, for example, pausing the staple firing of a surgical instrument 21. The triggering event can yield a transition to a pending failure mode, for example, where a series of instructions are provided to remedy, or reduce, the cause of the failure. As described below in greater detail, the triggering event can be, for example, a buttress plowing, tissue cutting without tissue sealing, and/or broken anvil. In some implementations, these triggering events are visually detected automatically through object recognition, object tracking, object labeling, and/or other suitable image processing techniques of image frames of the livestream, for example, or through various suitable wired and/or wireless communication schemes.

In some implementations, the failure mode is caused by buttress plowing, a condition that may occur where a buttress is utilized in a tissue stapling by a surgical instrument 21. In response to detecting the buttress plowing, the control module 6001, for example, causes the surgical instrument 21 to stop a firing sequence of the surgical instrument. For example, the control module 6001 may communicate a firing-stop command to the surgical instrument 21 through a wireless, or wired, interface. Additionally, the control module 6001 may cause a warning, and/or a series of instructions that remedy the failure by applying tension to tissue during firing, for example, to be displayed, or overlaid onto a livestream of the surgical field.

Alternatively, the failure can be caused by detecting tissue cutting without tissue sealing. For example, the control module 6001 may detect a failure of staples to be deployed into tissue grasped by an end effector of the surgical instrument 21, as a cutting member of the surgical instrument 21 is advanced, which leads to a tissue cutting without tissue sealing failure. In response to detecting the failure, the control module 6001 may cause a warning, and/or a series of instructions that remedy the failure, to be displayed, or overlaid onto a livestream of the surgical field. The instructions may suggest clamping surrounding blood supply, preparing a material to stop bleeding before releasing the tissue from the jaws of the end effector of the surgical instrument 21.

Figure 15:
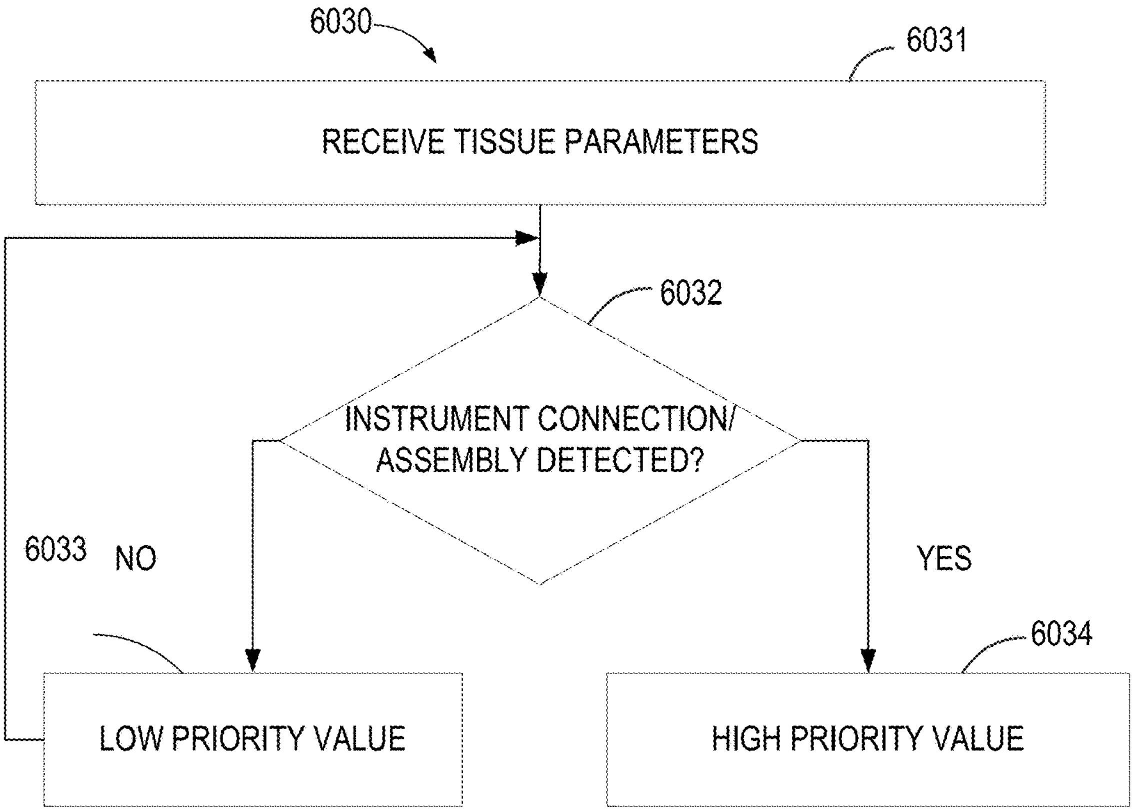
FIG. 15 is a logic diagram showing operations of a method for determining display priority values of tissue tension and/or pressure parameters within a surgical anastomosis, according to one aspect of this disclosure.

FIG. 15 is a logic diagram showing operations of an example method 6030 for determining display priority values of tissue tension and/or pressure parameters within a surgical anastomosis. The method 6030 includes receiving 6031 the tissue parameters and assigning display priority values to the parameters based on a triggering event such as the detection of a connection between the anvil and the trocar of the circular stapler. For example, if 6032 the trocar-anvil connection is not detected, a low display-priority value is assigned 6033 to the parameters. If 6032, however, the trocar-anvil connection is not detected, a high display-priority value is assigned 6034 to the parameters.

While the method 6030 provides an example that utilizes detection of the connection of components of a circular staple as a triggering event for determining display priority values, the connection of other components of other instruments 21 can be utilized as triggering events for determining display priority values. For example, the attachments of a cartridge reload, an end effector, and/or a shaft can represent a triggering event for determining display priority values. In some implementations, the assembly of surgical instrument components, surgical robotic components, and/or any suitable surgical systems can be utilized as triggering events for determining display priority values.

Figure 16:
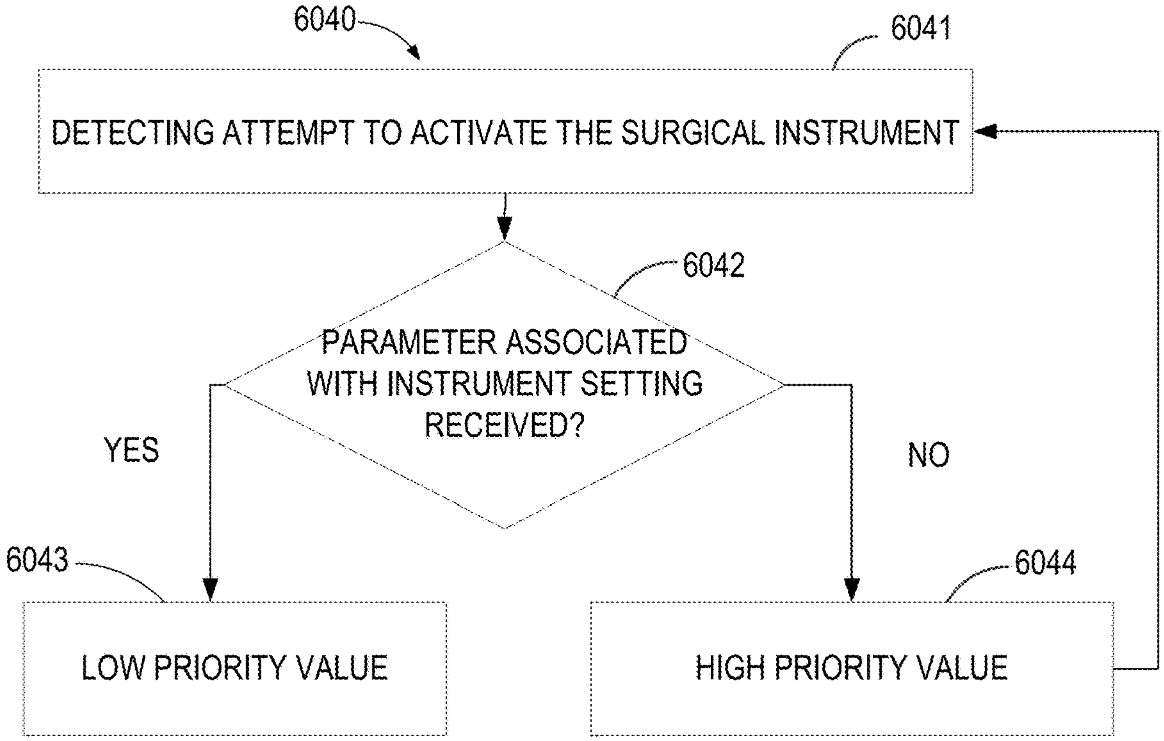
FIG. 16 is a logic diagram showing operations of a method for determining display priority values based on a triggering event, according to one aspect of this disclosure.

FIG. 16 is a logic diagram showing operations of an example method 6040 for determining display priority values based on a triggering event. In the illustrated example, the triggering event is an activation of a surgical instrument 21 prior to receiving a parameter needed to perform an adjustment of a setting of the surgical instrument 21 for optimal operation thereof. In some implementations, the system 6000 can be configured to detect the surgical instrument 21 in the livestream of the surgical field, and await a user input of the required parameter.

In some implementations, the parameter can be a required user input. The parameter can be associated with a tissue characteristic or a disease state. Certain device settings can be adjusted, prior to utilizing the device to treat a tissue, based on the condition of the tissue and/or a disease state. These adjustments may include lowering a firing speed for a surgical stapling instrument to better ensure a seal. For surgical energy device, the surgeon may adjust the power in response to the new tissue characteristics, for example, to provide a better seal of the tissue.

As illustrated in FIG. 16, the method 6040 includes detecting 6041 an attempt by the user to activate the surgical instrument 21. If 6042 the needed parameter is received, a low display-priority value is assigned 6043. If 6042, however, the trocar-anvil connection is not detected, a high display-priority value is assigned 6044 to the parameters.

In some implementations, the parameter is a sensor parameter, which can be an internal sensor of the surgical instrument 21, or any other sensor, configured to measure a parameter needed for proper operation of the surgical procedure. The detection of a triggering event, such as activation of the surgical instrument 21 prior to receiving the parameter, may cause the system 6000 to assign a high priority value to visual content, for example in the form of an overlay, requesting a permission to ignore, or proceed without, the missing parameter, or requesting entry of the missing parameter, for example.

In some implementations, the triggering event is a sensor parameter that deviates from an acceptable predetermined range or threshold. The sensor parameter can be a tissue impedance parameter measureable by a surgical instrument grasping tissue in the surgical field, for example by performing impedance spectroscopy. If the grasped tissue is highly saturated with saline, the measured tissue impedance will deviate from an acceptable predetermined range or threshold, triggering the system 6000 to assign a high display-priority value to a warning regarding the detected deviation, a user override request and/or a user override request.

In some implementations, the triggering event can be a detection of a mismatch between a selected surgical instrument 21 and the surgical procedure to be performed by the surgical instrument 21. The mismatch can be detected by the system 6000 and/or the computer-implemented interactive surgical system 1, for example. The type of the surgical procedure and an inventory list of surgical instruments 21 to be utilized in the surgical procedure can be entered through a user interface and/or can be detected through object recognition, object tracking, object labeling, and/or other suitable image processing techniques of image frames of the livestream, for example, or through various suitable wired and/or wireless communication schemes. The situational awareness module 6006 may compare the inventory list detected or entered by the user to a previously-stored inventory list that is historically associated with the surgical procedure type detected or entered by the user. The detection of a mismatch causes the system 6000 to assign a high display-priority value to a warning regarding the mismatch, a user override request, and/or a confirmation request.

In at least one example, detecting the selection of a circular stapler for use in a hysterectomy causes the system 6000 to assign a high display-priority value to a warning regarding the mismatch, a user override request, and/or a confirmation request. The system 6000 may require the staff to confirm the need for the circular stapler or to eliminate it from the current active list or correct the procedural plan mismatch.

In some implementations, the triggering event can be the detection of incompatible components of a surgical instrument assembly. Various surgical instruments 21 utilize interchangeable components such as, for example, interchangeable cartridges, reloads, end effectors, shafts, handles, motors, and/or batteries. Utilizing incompatible components may cause the surgical instrument 21 to function improperly, which may cause harm to the patient and/or interfere with the surgical procedure outcome. They system 6000 may assign display priority values based on the detection of incompatible components.

The computer-implemented interactive surgical system 1 can detect incompatible components through authenticity checks or integrity checks. Unsuccessful authenticity and/or integrity validations can indicate incompatible components. In certain implementations, various components are equipped with sensors that can detect a proper connection indicating a proper compatibility between connected components. In such implementations, sensor signals, or the lack thereof, can indicate incompatible components.

In at least one example, upon installation of an interchangeable component in a surgical instrument 21, the surgical instrument 21 may interrogate the interchangeable component for identification information that can be compared to recognized identification information stored in a database, for example. The database can be kept on a storage medium of the surgical instrument 21, a hub 22, and/or the remote server 13 of the cloud-based system 4, for example. Failure to authenticate the identification information causes the system 6000 to assign a high display-priority value to a warning regarding the incompatible components, a user override request, and/or a confirmation request. The computer-implemented interactive surgical system 1 may also inhibit certain capabilities of the surgical instrument 21, or lockout the surgical instrument 21, to protect the patient and/or the surgical procedure outcome.

In some implementations, the triggering event is a detection of a tissue condition such as a biological anomaly that can negatively affect a proper use of a surgical instrument 21 in the surgical procedure under standard settings. For example, an extremely high Body Mass Index "BMI" necessitates adjustments to various settings of surgical instruments 21 in a sleeve gastrectomy. The BMI level can be detected by the situational awareness module 6006, for example, from perioperative data.

Detection of a BMI level that deviates from an acceptable predetermined threshold may cause the system 6000 to assign a high display-priority value to a warning regarding the BMI level, a user override request, and/or a confirmation request. Moreover, the system 6000 may further assign a high display-priority value to a recommended surgical instrument setting such as, for example, a lower firing speed of a surgical stapler utilized in the sleeve gastrectomy. The system 6000 and/or the computer-implemented interactive surgical system 1 can be configured to automatically determine the recommended surgical instrument setting based on perioperative data.

In various aspects, determining 6013 a display arrangement of the surgical data on the display 6005 includes changing a characteristic of a visual representation of the surgical data. In some implementations, the surgical data can be in the form of a sensor reading that can be overlaid onto the livestream of the surgical field on the display 6005. The sensor reading can be highlighted in a color that changes in accordance with the significance of the sensor parameter reading to the surgical procedure. In some implementations, the sensor reading can be visually represented in a first color, while the sensor reading is within normal bounds of a predetermined standard, and the sensor reading can be visually represented in the second color, different from the first color, while the sensor reading is outside the normal bounds.

For example, the sensor reading can be a temperature reading that can be visually represented in a green color while the temperature reading is less than, or equal, to a predetermined temperature threshold. If the temperature reading exceeds the predetermined threshold, the temperature reading can then be visually represented in a yellow, or red, color, for example, indicative of the significance of the current temperature to the surgical procedure.

In some implementations, the change in the characteristic of the visual representation of the surgical data can be a gradual transition. For example, the temperature reading can be gradually transitioned from yellow to red as the temperature rises to reflect the severity of the change in the temperature. In some implementations, other characteristics of the visual representation can also be changed such as, for example, size, shape, display time, display location, display three dimensional arrangement (e.g., foreground, background), display blinking, highlighting, and/or font.

In various aspects, determining 6013 a display arrangement of the surgical data on the display 6005 includes removing, or changing, a characteristic of the visual representation of the surgical data in a manner that reflects a reduction in significance and/or an inactive status, for example. In some implementations, the surgical data comprises a temperature of a surgical energy device utilized to seal tissue in the surgical field of a surgical procedure. In response to activation of the surgical energy device, a visual representation of the temperature is overlaid onto the livestream of the surgical field on the display 6005. The visual representation signifies that the surgical energy device is "hot", in an effort to provide a warning for careful handling of the surgical energy device while in the active status. In some implementations, the visual representation may comprise a characteristic indicative of a high-priority status to ensure grabbing the attention of a clinician using the surgical energy device and/or other OR staff.

As the clinician uses the surgical energy device, the visual representation of the temperature may be assigned a lower-priority status, even though the surgical energy device continues to be hot. This is in order to reduce distraction to the clinician and/or shift the clinician's attention to another visual representation of higher-priority surgical data. For example, the visual representation of the temperature can be changed to a neutral color, reduced in size, and/or changed into a different shape.

Once the surgical energy device is inactive, if the temperature is at, or exceeds, a predetermined threshold, a high-priority status is reassigned to the temperature causing its visual representation to change providing a warning to draw attention or highlight that even inactive the surgical energy device is still above a temperature threshold that could cause injury. In response to the temperature dropping below the predetermined threshold, the visual representation of the temperature is changed again to a lower-priority status. In some implementations, the temperature of the surgical energy device can be monitored using one or more temperature sensors on, or near, an end effector of the surgical energy device. The sensor readings can be communicated wirelessly, or through a wired communication, to the system 6000.

In various aspects, determining 6013 a display arrangement of the surgical data includes transferring a visual representation of the surgical data between a first display and a second display. The transfer permits the system 6000 to timely present surgical data to an appropriate user at an appropriate time and location. In some implementations, the first display is a set-up display, nurse display, or preparation display, and the second display is a surgical field or surgeon display such as, for example, a display 6005. In such implementations, the transfer can be triggered by a detection of the completion of the setup. In certain instances, a user input can indicate the completion of the setup, which triggers the transfer. The setup may include checking surgical devices against an inventory list to ensure presence of the surgical devices necessary to perform the surgical procedure. The setup may further include testing the surgical devices to ensure successful wireless communication operation, and/or any other suitable testing.

In some implementations, the control module 6001 is configured to assign a high display-priority value to the surgical data at the first display and a low display-priority value to the same surgical data at the second display until the detection of a triggering event. In response to the detection, the control module 6001 is configured to assign a low display-priority value to the surgical data at the first display and a high display-priority value to the same surgical data at the second display. The switching of priorities causes the surgical data to be transferred to the second display. In some implementations, the switching causes a visual representation of the surgical data to be dimmed out at the first display, and to appear at the second display. Then, after a predetermined time period has passed, the visual representation of the surgical data can be completely removed from the first display.

Figure 17:
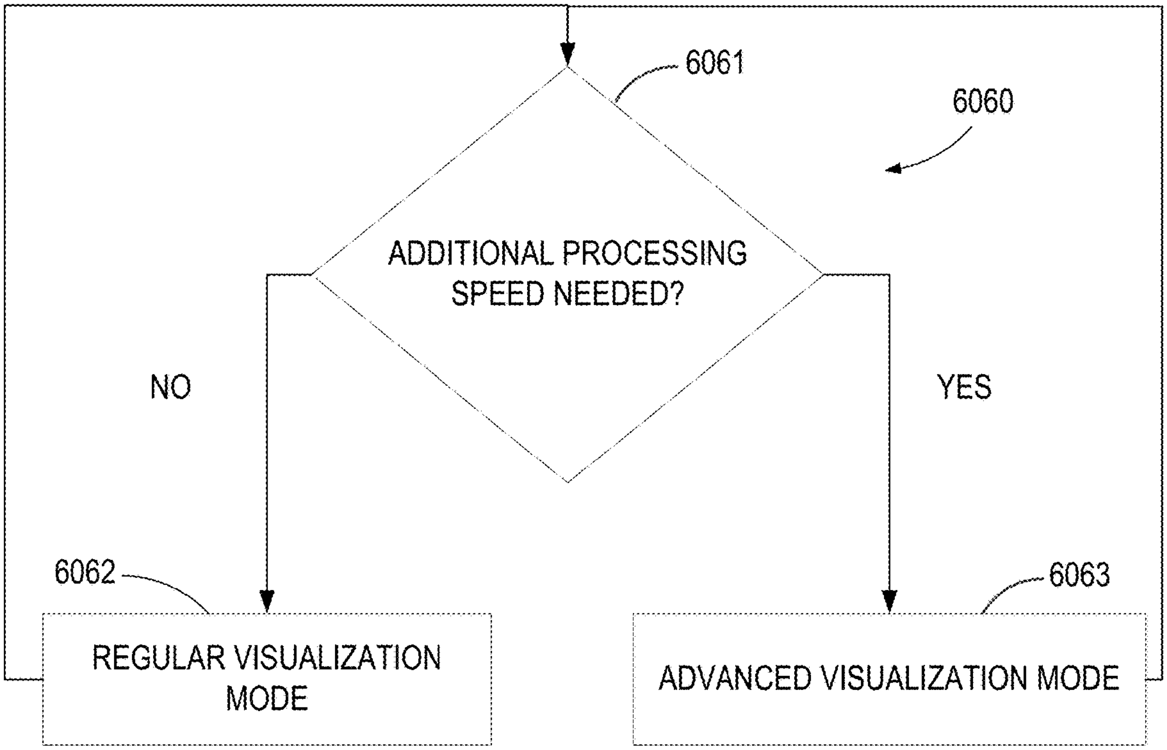
FIG. 17 is a logic diagram showing operations of a method, according to one aspect of this disclosure.

In various aspects, a determined 6013 display arrangement may require additional processing capabilities such as, for example, one that involves developing a spectral view and/or tacking a surgical end effector in the surgical field and overlaying surgical data on the surgical end effector. FIG. 17 is a logic diagram showing operations of an example method 60600 for responding to a need for additional processing speed during a surgical procedure performed by the computer-implemented interactive surgical system 1. In instances where additional processing capabilities are needed 6061, the control module 6001 may utilize a field programmable gate array (FPGA). Additional high speed calculations for key variables can be assigned to the FPGA in an advanced visualization mode 6063, for example, as illustrated in a method 6060 in FIG. 17. When the advanced visualization mode 6063 is enabled, the FPGA is dynamically re-purposed to maximize visualization (e.g., spectral) processing capabilities. After completion of the high speed calculations, the FPGA can be returned to normal operation, in a regular visualization mode 6062.

In some implementations, a transfer between the regular visualization mode 6062 and the advanced visualization mode 6063 can be triggered by the surgical task. The control module 6001 may detect an upcoming, or current, surgical task based on contextual information generated by the situation awareness module 6006. The control module 6001 may consult a database, which can be stored in the memory 6003, for the visualization mode associated with the surgical task. If the surgical task requires an advanced visualization mode 6063, the control module 6001 repurposes the FPGA to aid in the high speed calculations associated with the advanced visualization mode 6063. When the surgical task is completed, the control module 6001 then triggers a return to the regular visualization mode 6062, effectively switching the FPGA to performing regular tasks.

In certain implementations, detecting 6011 the surgical data includes receiving two separate surgical data competing for a user's attention. For example, detecting 6011 the surgical data can include receiving a first surgical data and a second surgical data, wherein the first surgical data and the second surgical data are both relevant to the current surgical task and/or are associated with one, or more, active surgical devices. In such implementations, the method 6010 can include assigning 6012 display priority values to the first surgical data and second surgical data based on their comparative criticality to the success of the surgical and/or severity of failures that can be caused by ignoring them. For example, if the first surgical data comprises a higher criticality than the second surgical data, the method 6010 assigns 6012 a higher display-priority value to the first surgical data than the second surgical data. Additionally, or alternatively, if a first failure associated with the first surgical data is more severe than a second failure associate with the second surgical data, the method 6010 assigns 6012 assigns a higher display-priority value to the first surgical data than the second surgical data.

In some implementations, display priority values and corresponding criticalities and/or failure severities associated with various surgical data can be stored in any suitable format, e.g., a table or a database, in a storage medium such as the memory 6003. The processor 85 of the control module 6001 can be configured to assign 6012 display priority values based on such stored information.

Additionally, or alternatively, display priority values can be assigned 6012 based on predetermined user preferences and/or user-specific surgical context. In some implementations, surgical data associated with an active surgical instrument 21 can be selectively displayed onto a display associated with a clinician using the surgical instrument 21. Accordingly, the method 6010 may include assigning 6012 different display priority values to the same surgical data for different displays.

In one exemplification, a surgical data associated with a first surgical device, being utilized by a clinician, is simultaneously assigned 6012 a high display-priority value with respect to a first display selected by, or otherwise associated with, the clinician, and a low display-priority value with respect to other displays not selected by, or associated with, the clinician. In another exemplification, a first surgical data associated with a first surgical device, being utilized by a clinician, is assigned a high display-priority value with respect to a first display selected by, or otherwise associated with, the clinician, while a second surgical data associated with a second surgical device, not being utilized by the clinician, is assigned a low display-priority value with respect to the first display.

In various instances, the control module 6001 receives contextual information from the situational awareness module 6006 that can be utilized in the aforementioned pairing of surgical data of a particular surgical device with a display associated with a clinician using the surgical device. The contextual information can be generated by the situational awareness module 6006 based on perioperative data.

In some implementations, a database or table may store the pairing information. In other instances, the clinician may wear a unique identifier that can be detected by the surgical device when the clinician holds the surgical device. When a positive identification is made, the control module 6001 can then assign high display-priority values to surgical data associated with the surgical device with respect to a display selected, or otherwise associated, with the clinician. In one exemplification the unique identifier can be an RFID in the clinician's glove, which is detected by a corresponding RFID scanner in the handle of the surgical device.

In certain instances, such as during a colorectal procedure, the system 6000 is configured to automatically switch a display (e.g., display 6005) from showing a first livestream of a first surgical field to a second livestream of a second surgical field. The automatic switching can be triggered by the completion of a surgical task in a surgical procedure. In one example, a predetermined surgical cue, indicative of the completion of the surgical task, can be utilized as a trigger for the automatic switching between the livestreams. The predetermined surgical cue may include, for example, detecting a completion of a staple firing into tissue by a surgical instrument 21, detecting a completion of a tissue sealing by a surgical instrument 21, and/or detecting the release of a tissue from the jaws of an end effector of a surgical instrument 21, for example by opening the jaws.

The predetermined surgical cue may also include detecting an activation of a surgical instrument 21 followed by a deactivation of the surgical instrument 21, which indicates completion of a surgical task by the surgical instrument 21. In some implementations, the control module 6001 leverages readings from one or more sensors of the surgical instruments 21 and/or other components of the computer-implemented interactive surgical system 1 to detect the predetermined surgical cue. In some exemplifications, predetermined surgical cue is detected based on contextual information generated by the situational awareness module 6006.

In a colorectal procedure a clinician uses a circular stapler and a liner stapler to complete various tasks of the procedure. The colorectal procedure involves operating at two discrete surgical fields, an internal surgical field where diseased tissue is excised and an external surgical field where the circular stapler is utilized. In some implementations, the first livestream focuses on the internal section where tissue excision is taking place, and the second livestream focuses on the external section where the circular stapler is applied. In such implementations, the automatic switching can be triggered by completion of the tissue excision by the linear stapler, which can be detected by deactivation of linear stapler and/or removal of the linear stapler from the first surgical field, for example. The control module 6001 may employ various object recognition, object tracking, and/or object labeling algorithms, and/or other image processing techniques of image frames of the livestream, for example, to detect removal of the linear stapler from the surgical field.

Figure 18:
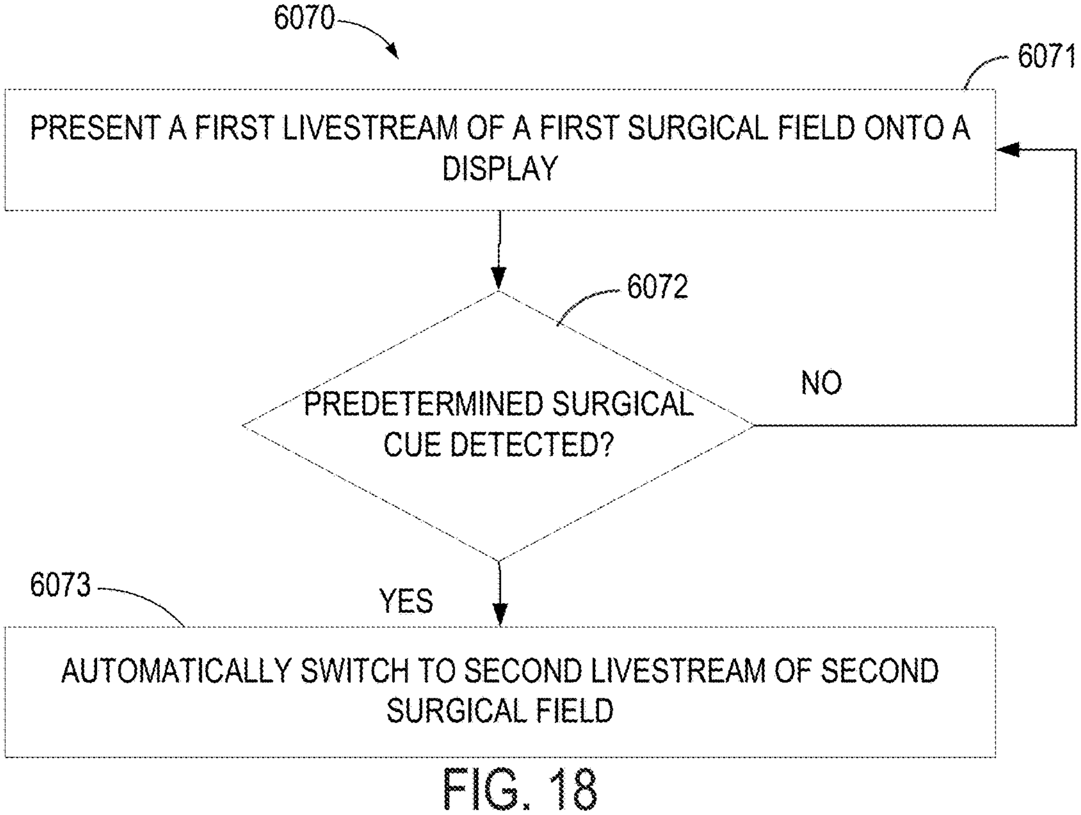
FIG. 18 is a logic diagram showing operations of a method for automatic switching between livestreams of surgical fields in a surgical procedure, according to one aspect of this disclosure.

FIG. 18 is a logic diagram showing operations of an example method 6070 for automatic switching between livestreams of surgical fields in a surgical procedure. In some implementations, the method 6070 can be executed by the computer-implemented interactive surgical system 1, for example. The method 6070 includes presenting 6071 a first livestream of a first surgical field onto a display (e.g., display 6005). If 6072 a predetermined surgical cue, indicative of completion of a surgical task at the first surgical field is detected, automatically switch 6073 from presenting the first livestream of the first surgical field onto the display to presenting a second livestream of the second surgical field onto the display. In some exemplifications, the second surgical field is associated with a second surgical task that follows the first surgical task in the surgical procedure.

During a surgical procedure, various components of the computer-implemented interactive surgical system 1 may compete for available system resources such as power, current, and/or processing resources. Additionally, or alternatively, the operation of certain components of the computer-implemented interactive surgical system 1 may interfere with, or negatively affect, the operation of other components of the computer-implemented interactive surgical system 1. Various methods and systems are described herein to ensure the components function successfully by maintaining a balance in system resources and/or components operations.

Figure 19:
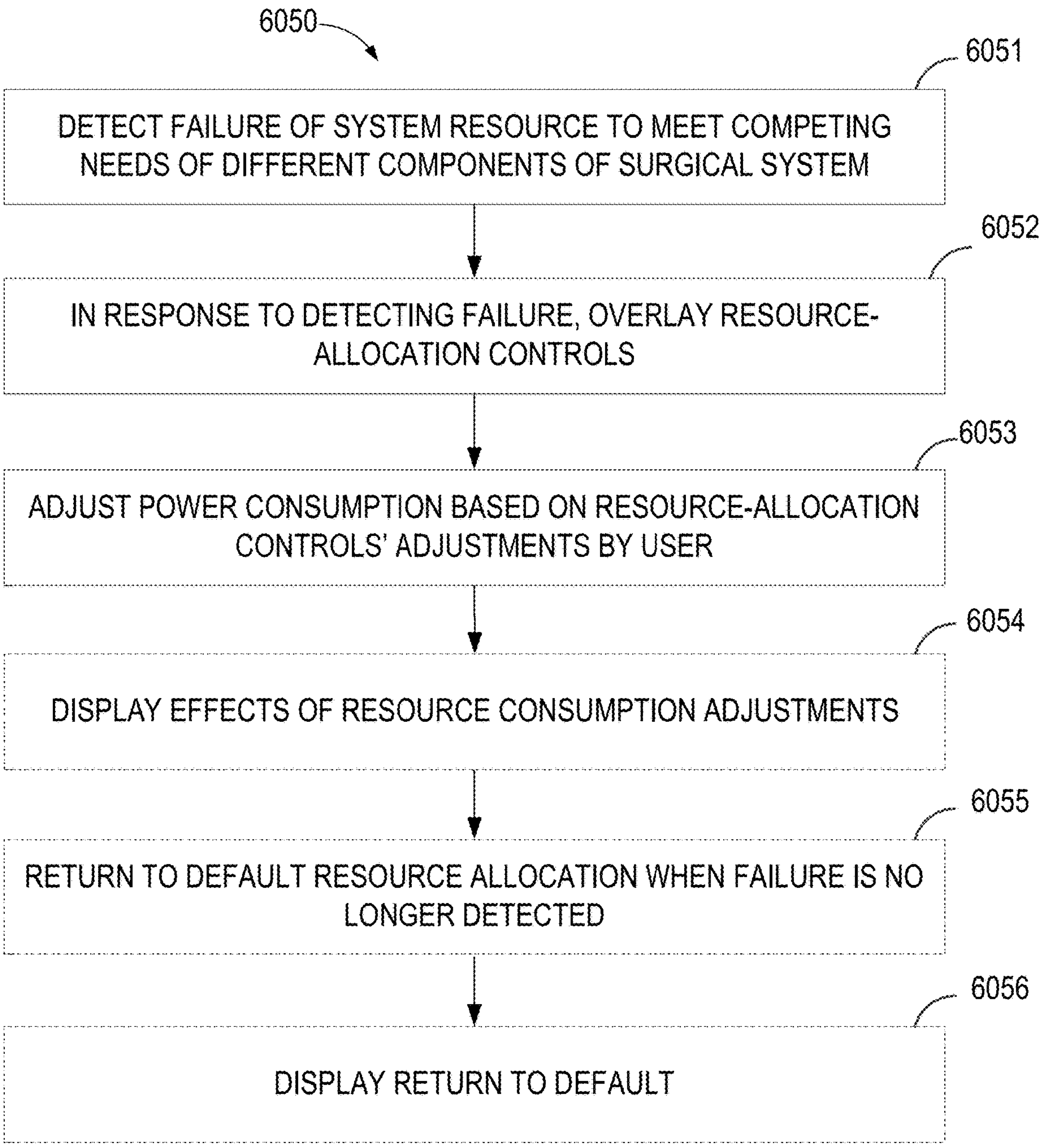
FIG. 19 is a logic diagram showing operations of a method for balancing system resources during a surgical procedure, according to one aspect of this disclosure.

FIG. 19 is a logic diagram showing operations of an example method 6050 for balancing system resources during a surgical procedure performed by the computer-implemented interactive surgical system 1. The method 6050 includes detecting 6051 a failure of a system resource to meet competing needs of different components of the computer-implemented interactive surgical system 1. The method 6050 further includes displaying resource-allocation controls of the system resource, in response to detecting the failure, for example by overlaying 6052 the resource-allocation controls on a livestream of a surgical field of the surgical procedure. Additionally, the method 6050 may further include displaying recommended adjustments to the resource-allocation controls.

Further to the above, the method 6050 includes adjusting 6053 power consumption of one or more of the different components based on resource-allocation controls' adjustments by the user. The method 6050 may further include returning 6055 to a default resource allocation, or removing resource consumption restrictions, when the failure is no longer detected. The method 6050 may further include displaying 6054 visual content representative of the effects of the adjustments to resource allocations and/or displaying 6056 visual content representative of a return to a default mode, for example by overlaying the visual contents onto a livestream of a surgical field on a display of the computer-implemented interactive surgical system 1.

In some implementations, detecting 6051 the failure includes reaching and/or exceeding a predetermined threshold such as, for example, a power threshold, a current threshold, a processing threshold, and/or a maximum utilization threshold. The predetermined threshold can be selected to ensure that detecting 6051 the failure is achieved prior to reaching a point where power consumption is beyond available power resources to avoid malfunctions during the surgical procedure. In some implementations, the predetermined threshold is stored in a storage medium such as the memory 6003, which is accessed by the processor 85 and compared to a monitored value (e.g., total consumption, consumption rate).

In some implementations, the failure is detected 6051 when the control module 6001 detects competing tasks being performed during a surgical procedure with a total estimated resource consumption (e.g., power consumption) or a resource consumption rate at, or greater than, the predetermined threshold. In some implementations, the failure is detected 6051 when the control module 6001 detects a simultaneous utilization of multiple components of the computer-implemented interactive surgical system 1 with a total estimated resource consumption (e.g., power consumption) or a resource consumption rate at, or greater than, the predetermined threshold. In one example, a database, stored for example in the memory 6003, may include a listing of resource consumption estimates associated with various components of the computer-implemented interactive surgical system 1 and/or various tasks performed by the computer-implemented interactive surgical system 1. The processor 85 may calculate a resource consumption value based on the information in the database, and compare the calculated value to the predetermine threshold for the purpose of determining whether the failure is detected 6051.

In some implementations, the system resource is power and the components of the computer-implemented interactive surgical system 1 competing for the power resource are the system 6000, or any other visualization system of the computer-implemented interactive surgical system 1, and the generator 27. During a surgical tissue sealing procedure, for example, the computer-implemented interactive surgical system 1 can be configured to perform two tasks that collectively require a power consumption that reaches, or exceeds, the predetermined threshold. The first task can be a visualization task, e.g., providing a spectral view, of the surgical field, and the second task can be energizing a surgical energy device to seal tissue grasped by the surgical energy device in the surgical field, for example. The generator module 27 can be configured to power the surgical energy device to seal the tissue by application of therapeutic energy to the tissue.

In such implementations, the failure is detected 6051 by monitoring power consumption by the system 6000 and the generator module 27. If the power consumption reaches and/or exceeds a predetermined threshold, the control module 6001 issues a user alert by causing an overlay 6052 of power-allocation controls onto the livestream of the surgical field on the display 6005. The control module 6001 may then adjust power consumption in accordance with the user adjustments of the power-allocation controls.

In certain instances, the control module 6001 reduces power requirements of one or more systems to implement the user adjustments. For example, the control module 6001 may reduce the brightness of the display 6005 in response to a user input that selects a reduction of power allocation to the system 6000 in favor of maintaining power allocation to the generator module 27. Additionally, or alternatively, the control module 6001 may slow, delay, or suspend certain tasks, such as secondary image processing tasks, performed by the system 6000 in response to a user input that selects a reduction of power allocation to the system 6000 in favor of maintaining power allocation to the generator module 27.

In certain instances, the user adjustments of the power-allocation controls can favor power allocation to the system 6000 over the generator module 27. This may occur where the user is at a critical step that requires optimal visualization, for example sealing a vessel, and where an adequate operation of the energy device can still be achieved at a lower power level, perhaps by increasing tissue sealing time. In such instances, the control module 6001 may cause the surgical energy device and/or the generator module 27 to adjust one or more of their settings to reduce power draw in favor of the system 6000.

In some implementations, the control module 6001 automatically intercedes to make the power allocation adjustments, in response to detecting the failure, without user input. In such implementations, the control module 6001 only alerts the user to the changes caused by the automatic changes to the power consumption. For example, the control module 6001 may overlay on the livestream on the display 6005 an alert to a change in brightness of the display 6005 and/or a temporary suspension of an overlay of visual content such a surgical data overlay due, for example, to the temporary suspension of the image processing yielding the overlay. The overlay can be reintroduced upon completion of tissue sealing by the surgical energy device. Alternatively, the overlay can be intermittently displayed rather than being continuously displayed to reduce power consumption of the system 6000 in favor of the generator module 27.

In some implementations, the user adjustments to the power-allocation controls are implemented via one or more active discrete current limiting circuits that are configured to prevent one or more systems from exceeding a max fuse limit threshold, for example.

In some implementations, the system resource is power and the components of the computer-implemented interactive surgical system 1 competing for the power resource are the system 6000, or any other visualization system of the computer-implemented interactive surgical system 1, and the smoke evacuator module 26 (FIG. 3). During a surgical tissue sealing procedure, for example, the computer-implemented interactive surgical system 1 can be configured to perform two tasks that collectively require a power consumption that reaches, or exceeds, the predetermined threshold. The first task can be a visualization task, e.g., providing a spectral view, of the surgical field, and the second task can be extracting smoke from the surgical field, for example. The smoke is a byproduct of the tissue sealing process by an energy device.

In such implementations, if the failure is detected 6051, the control module 6001 may then issue a user alert, for example by causing an overlay 6052 of power-allocation controls onto the livestream of the surgical field on the display 6005, as discussed previously. The control module 6001 may then adjust power consumption in accordance with the user adjustments of the power-allocation controls. In certain instances, the control module 6001 may recommend an adjustment of the smoke evacuation module 26 to a lower setting, for example by overlaying visual content representing the recommended adjustment onto the livestream of the surgical filed on the display 6005. Additionally, the control module 6001 may also cause visual content representative of slowdown of the smoke evacuation to be overlaid. Presenting such visual contents in the manner indicated affords a user of the surgical energy device an opportunity to slow down the sealing process by adjusting the surgical energy device to a lower setting that produces less smoke. When the additional power requirements of the system 6000 ceases, for example due to a completion of the image processing associated with the spectral view, the control module 6001 causes an overlay of visual content representative of an alert to inform the user that the smoke evacuation module 26 is returning to its original setting.

In various instances, methods similar to the method 6050 can be implemented to address other failures, e.g., overheating and/or noise, which can negatively influence a surgical procedure performed using the computer-implemented interactive surgical system 1. In such instances, failure detection can be achieved based on readings of one or more internal and/or external sensors of one or more components of the computer-implemented interactive surgical system 1. The sensor readings can then be compared to predetermined thresholds to detect a failure. For example, an overheating failure can be detected if one or more temperature sensor readings are at, or greater, than a predetermined temperature threshold. In response to the failure, the control module 6001 may overlay virtual controls onto a livestream of the surgical field of the surgical procedure on the display 6005, thereby presenting the user with an opportunity to change settings of one or more of the components of the computer-implemented interactive surgical system 1 to address the overheating. Similar methods can be utilized to address noise levels.

In various instances, the display arrangement, in accordance with the method 6010, includes a segmentation of the display 6005 to accommodate visual representations of the surgical data. Size, shape, display time, display location, display three dimensional arrangement (e.g., foreground, background), display blinking, highlighting, and/or font of concurrently displayed segments can depend on a number of factors including the nature, complexity, and/or criticality of the surgical data. In some implementations, pairing information of surgical data configured to be displayed simultaneously can be provided in a database or table stored on a storage medium such as the memory 6003. The processor 85 of the control module 6001 may determine whether multiple surgical data are to be displayed simultaneously based on the stored information.

In some implementations, visual representations of two different surgical data are configured to be displayed simultaneously in a segmented mode onto the display 6005, but only one of the visual representations is ready for display. In such implementations, the unready visual representation can be represented as a blank area in its assigned segment. Additionally, as described supra, the control module 6001 can be configured to repurpose FPGA for additional processing speed to aid in readying the unready visual representation. Alternatively, the unready visual representation can be displayed at a lower quality to ensure that the surgical data are displayed simultaneously.

In certain instances, visual representations of multiple surgical data are configured to be displayed simultaneously, for example in the segmented mode, onto the display 6005, but the system 6000 lacks sufficient processing capabilities to simultaneously display all of the different surgical data. In response to detecting a deficiency in its processing capabilities, the system 6000 may prioritize the display of higher priority surgical data over lower priority surgical data, based on assigned display-priority values of the surgical data, for example.

In other instances, the display issue can be a lack of sufficient display area at the display 6005 to simultaneously display visual representations of multiple surgical data in the segmented mode. In such instances, a display arrangement implemented by the control module 6001 may comprise a picture-in-picture type display arrangement, wherein a first visual representation is displayed inside a second visual representation. In other words, the first visual representation may appear in the foreground, and may be smaller in size than the second visual representation appearing in the background. Additionally, through any suitable user interface 6007, the clinician may toggle between the two visual representations by selectively causing one of the visual representations to move to the foreground, and the other to the background. The control module 6001 can be configured to detect a lack of sufficient display area based on a predetermined display size of the display 6005, and a calculated display size of the visual representations of the surgical data. In some implementations, a predetermined equation can be utilized in the calculation. In other instances, where the visual representations are the same, or similar, in size, the lack of sufficient display is detected where the number of visual representations of the surgical data is equal to, or greater than, a predetermined threshold.

In various instances, the display arrangement, in accordance with the method 6010, comprises a transition between display modes such as, for example, a static, or passive, display mode and a dynamic, or active, display mode. In some implementations, the control module 6001 is configured to transition a visual representation of a surgical data from the static mode to the dynamic mode. The control module 6001 can be configured to implement the transition in response to a predetermined trigger such as, for example, a change in the priority, criticality, and/or risk associated of the surgical data. For example, a surgical data initially assigned 6012 a low display priority value can be displayed, or overlaid onto a livestream of a surgical field, in a static display mode that is later transitioned into an active display mode due to an increase in the display priority value of the surgical data to a higher display priority value.

Further to the above, in some implementations, the static mode includes displaying, or overlaying, a static visual representation of the surgical data associated with a surgical instrument 21 onto a side, or corner, of a display 6005, for example. In contrast, the active mode may include overlaying an active visual representation of the surgical data onto a part of the surgical instrument 21 in the livestream of the surgical field and/or moving highlighted areas in the static visual representation, for example. In various implementations, the static display mode differs from the active display mode in one or more of size, shape, display time, display location, display three dimensional arrangement (e.g., foreground, background), display blinking, highlighting, and/or font, for example.

In some implementations, the transition from the static display mode to the active display mode is based on an actuation of, or activation of, a surgical instrument 21, which signals a technique sensitive step that requires a real-time dynamic display. For example, the actuation of, or activation of, a surgical instrument 21 in a subsequent staple firing into the tissue, which requires a specific angle of firing with respect to a previous firing, can trigger a transition into the active display mode. First, certain display elements such as visual representations of the surgical data (e.g., various firing and/or tissue parameters) can be displayed, or overlaid, in the static display mode. Then, in response to the actuation of, or activation of, a surgical instrument 21, in a subsequent firing, the control module 6001 causes a transition into the dynamic display mode, where display elements are highlighted and/or moved, for example. In various instances, the subsequent firing that triggers the transition involves a staple firing that also deploys a tissue adjunct (e.g., tissue thickness compensator).

In some implementations, the control module 6001 is configured to cause display elements in the static display mode to become smaller in size, become less highlighted, and/or disappear overtime. Various operational parameters of a surgical instrument 21 can initially be presented in the dynamic display mode, then transitioned into the static display mode, as the significance level of such parameters changes. In certain exemplifications, certain display elements are assigned predetermined locations onto a display 6005, for example, in the static display mode, which are then changed in the active display mode.

In some implementations, a visual representation of surgical data, e.g., a biomarker, is presented in a static display mode, e.g., solid color not highlighted, while values associated with the biomarker remain within a predetermined range, or below a predetermined threshold. If, however, the values move beyond the predetermined range, or beyond the predetermined threshold, the visual representation of the surgical data can be transitioned into the dynamic display mode by causing certain display elements of the visual representation to change in size, shape, display time, display location, display three dimensional arrangement (e.g., foreground, background), display blinking, highlighting, and/or font, for example.

Figure 19A:
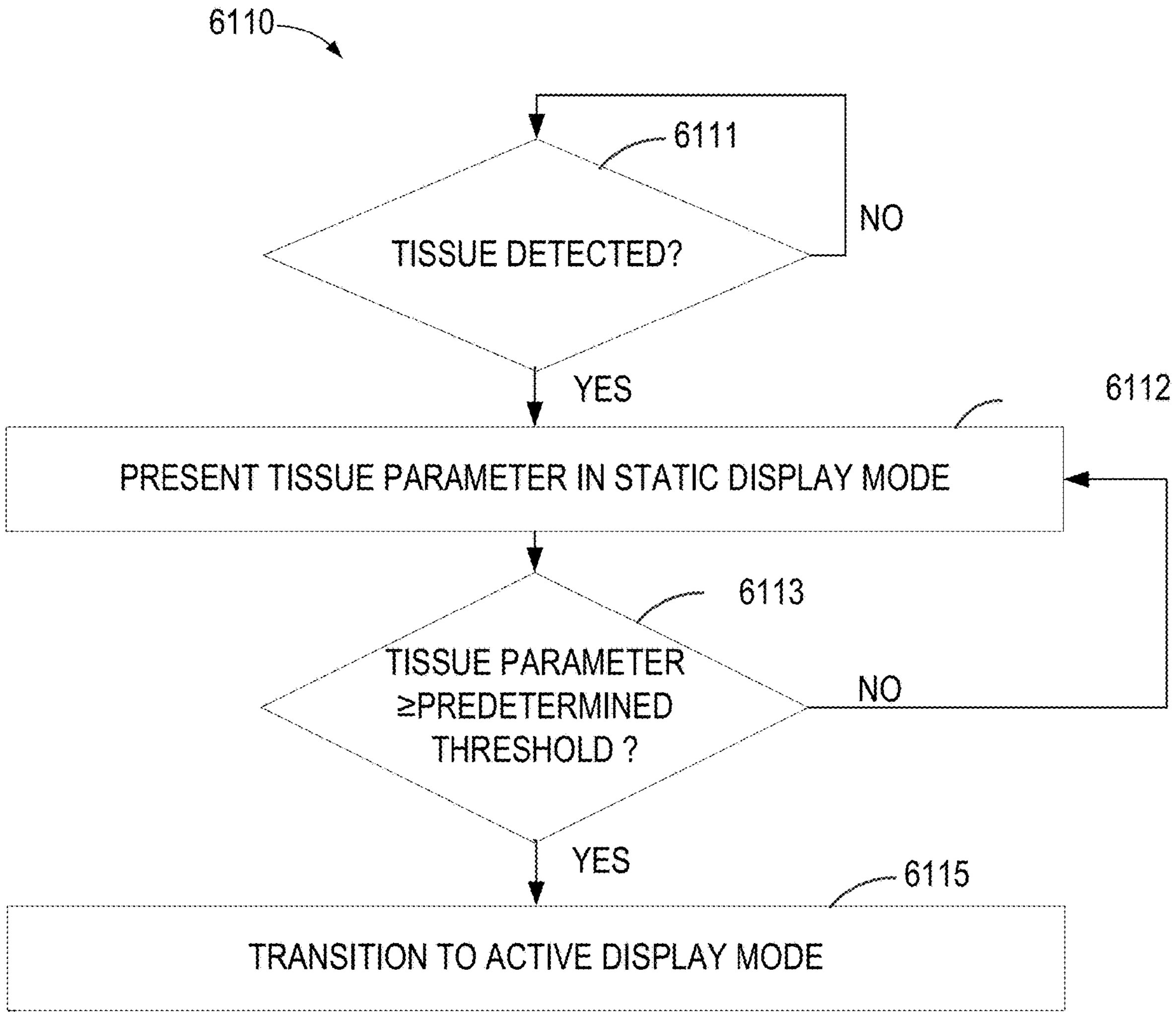
FIG. 19A is a logic diagram showing operations of a method for transitioning between the static display mode and the active display mode based on the surgical data, according to one aspect of this disclosure.

FIG. 19A is a logic diagram showing operations of an example method 6110 for transitioning between the static display mode and the active display mode based on the surgical data. In some implementations, the method 6110 can be executed by the computer-implemented interactive surgical system 1, for example. In the illustrated example, the surgical data comprises a tissue parameter. The tissue parameter is tissue impedance. Other tissue parameters such as, for example, tissue thickness, tissue pressure, tissue conductance, and/or tissue compression can be similarly presented.

Further to the above, the method 6110 includes detecting 6111 tissue between the jaws of an end effector of a surgical instrument 21. In certain instances, tissue detection 6111 can be achieved automatically through object recognition, object tracking, and/or object labeling algorithms, and/or other image processing techniques of image frames of the livestream, for example. Alternatively, the surgical instrument 21 can be configured to detect 61111 the presence of the tissue between the jaws based on signal readings of one or more sensors in the jaws. For example, a tissue can be detected 6111 when a non-therapeutic signal passed through the tissue yields an acceptable tissue impedance.

In response to detecting 6111 the tissue, the method 6110 presents 6112 the tissue parameter in the static display mode, for example, by displaying, or overlaying onto a livestream of the surgical field, a visual representation of the tissue parameter. If 6113, however, the tissue parameter reaches, or exceeds, a predetermined threshold, or becomes outside a predetermined range, the method 6110 further causes a transition 6115 of one or more display elements of the visual representation of the tissue parameter to the active display mode.

In some implementations, the surgical instrument 21 is an energy device configured to seal tissue grasped by the end effector of the surgical instrument 21. At the outset of the treatment, upon detecting 6111 the tissue, tissue impedance is presented in the static display mode. The surgical instrument 21 may communicate to the control module 6001, through a wired, or wireless, interface, surgical data indicative of the tissue impedance to display onto the display 6005, for example, in the static display mode. As energy application to the tissue commences, the tissue impedance changes. If, however, the tissue impedance reaches, or exceeds, a predetermined threshold, or becomes outside a predetermined range, this can be an indication of an immersion of the end effector in a fluid, an electrical short, or merely a low impedance tissue. In any event, a transition 6115 to the active display mode is triggered to alert the clinician to investigate.

In various instances, the control module 6001 determines various surgical information associated with a surgical procedure such as, for example, steps of the surgical procedure, surgical instruments 21 to be utilized in each step, and various risks and/or techniques associated with each of step. Such determination can be based on contextual information generated by the situational awareness module 6006, for example. The control module 6001 can then cause the surgical information to be displayed, or overlaid onto a surgical field of the surgical procedure, in a display arrangement utilizing one or more of the methods described by the present disclosure. For example, a current step, the surgical instruments 21 associated with the current step, risks associated with the current step and/or techniques associated with the current step can be presented in the active display mode, while previous and/or following steps are presented in the static display mode. When a following step becomes a current step, it is transitioned into the active display mode.

Further to the above, the transition 6115 from the static display mode to active display mode can be employed to reflect changes to a procedure plan, reflecting a new layout, for example. In various instances, the surgical information can be segmented for presentation by the control module 6001 into stages of access, separation and/or mobilization, resection, and/or repair and/or augmenting relevant data to surgeon, for example.

In various instances, the transition of a visual representation of a surgical data between the static display mode and the active display mode is based on changes in the use of a surgical instrument 21 linked to, or associated with, the surgical data. The surgical data can be initially presented in the static display mode. If, however, a predetermined change is detected in the use of the surgical instrument 21, a transition of the visual representation of the surgical data to the active display mode is affected.

Figure 19B:
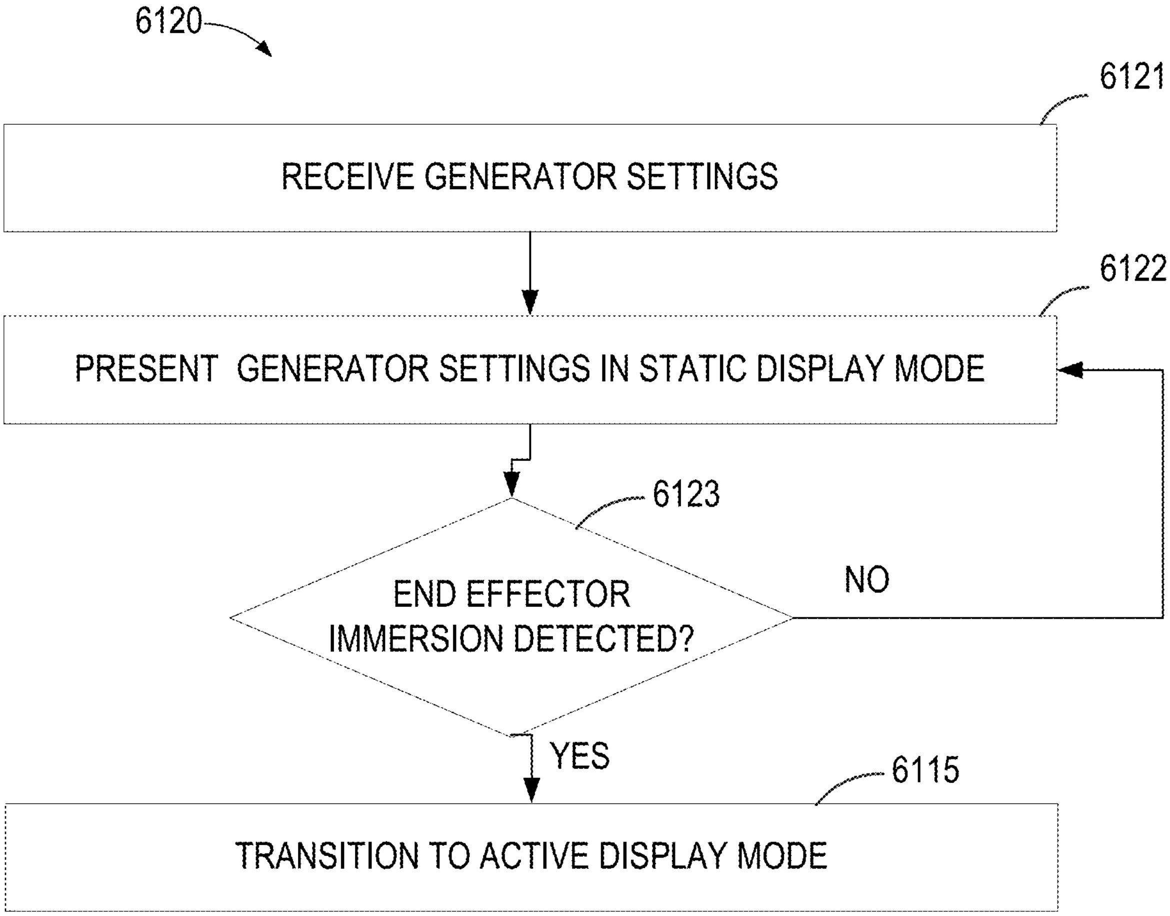
FIG. 19B is a logic diagram showing operations of a method for transitioning of a visual representation of a surgical data between the static display mode and the active display mode, according to one aspect of this disclosure.

FIG. 19B is a logic diagram showing operations of an example method 6120 for transitioning of a visual representation of a surgical data between the static display mode and the active display mode. The transition is based on, or triggered by, changes in the use of a surgical instrument 21 linked to, or associated with, the surgical data. In some implementations, the method 6120 can be executed by the computer-implemented interactive surgical system 1, for example.

In the illustrated example, the surgical instrument 21 is an ultrasonic surgical instrument configured to coagulate tissue grasped by its end effector in a surgical procedure. The surgical instrument 21 is utilized with a generator in preset generator setting that are received 6121 by the control module 6001 for display, or overlay onto a surgical field of the surgical procedure. The method 6120 further includes presenting 6122 the preset generator settings in the static display mode. If 6123, however, during the surgical procedure, an immersion of the end effector in blood is detected due to an attempted coagulation of a blood vessel that is semi-immersed in blood, for example, new generator settings are presented in the active display mode. The new generator settings may comprise an increase in the transducer power level in response to the end effector immersion in blood. The display, or overlay onto the livestream of the surgical field, of the new generator settings alerts the user of the surgical instrument 21, and affords an opportunity for the user to adjust the position of the end effector if the increased power levels are not desirable.

In some implementations, detecting the immersion of the end effector in blood is achieved by one or more sensors. In one example, a non-therapeutic current can be passed. If a short circuit is detected, the short circuit is indicative of the immersion in blood. In response, surgical data indicative of the immersion is communication wirelessly, or through a wired interface, to the control module 6001.

In various instances, a display arrangement in accordance with the method 6010 includes initially presenting a visual representation of the surgical data in the static display mode. Then the method 6010, in response to a change in a status of a surgical instrument 21 associated with the surgical data, causes a change in one or more display elements of the visual representation such as, for example, values associated with the surgical data. The changes includes, for example, encountering a staple cartridge lockout, activation of an advanced energy device, a transition between an open and a closed configuration of an end effector of a surgical instrument 21.

As described previously, the change in the one or more values associated with the surgical data can be performed in the static display mode. Alternatively, in some implementations, the change can be accompanied by a transition from the static display mode to the active display mode to provide an additional alert. Such implementations include, for example, various adaptation techniques such as, for example, pausing to allow for tissue creep and/or tissue compression, detecting unbalanced tissue in the jaws of an end effector of the surgical instrument 21, and/or detecting that the clamp of the jaws is inducing inappropriate tissue tension.

In various instances, a display arrangement in accordance with the method 6010 includes a transition from a first dynamic display mode to a second dynamic display mode, wherein the second dynamic display mode comprises, or represents, a higher priority, risk, and/or criticality than the first dynamic display mode. In one example, blood pressure is tracked during a surgical procedure via a blood pressure monitoring device that may communicate its readings to the control module 6001, for example, using a wireless, or wired, interface. A visual representation of the blood pressure can then be presented in a first dynamic display mode, due to the importance of the blood pressure data. If, however, during the surgical procedure, an increase is detected in blood pressure data beyond acceptable limits, a transition is made to elevate the blood pressure data to a second dynamic display mode, for example, to ensure an appropriate alert is delivered.

In various implementations, one or more characteristics of visual representations of surgical data such as, for example, the size, shape, display time, display location, display three dimensional arrangement (e.g., foreground, background), display blinking, highlighting, and/or font of the visual representations can be based on the assigned 6012 display-priority values. In certain instances, the assigned 6012 display-priority values can yield a display arrangement with a display conflict. For example, determining a display arrangement based on assigned display priority values may yield more than one visual representation of the surgical data with the same location on a display 6005, for example.

Figure 20:
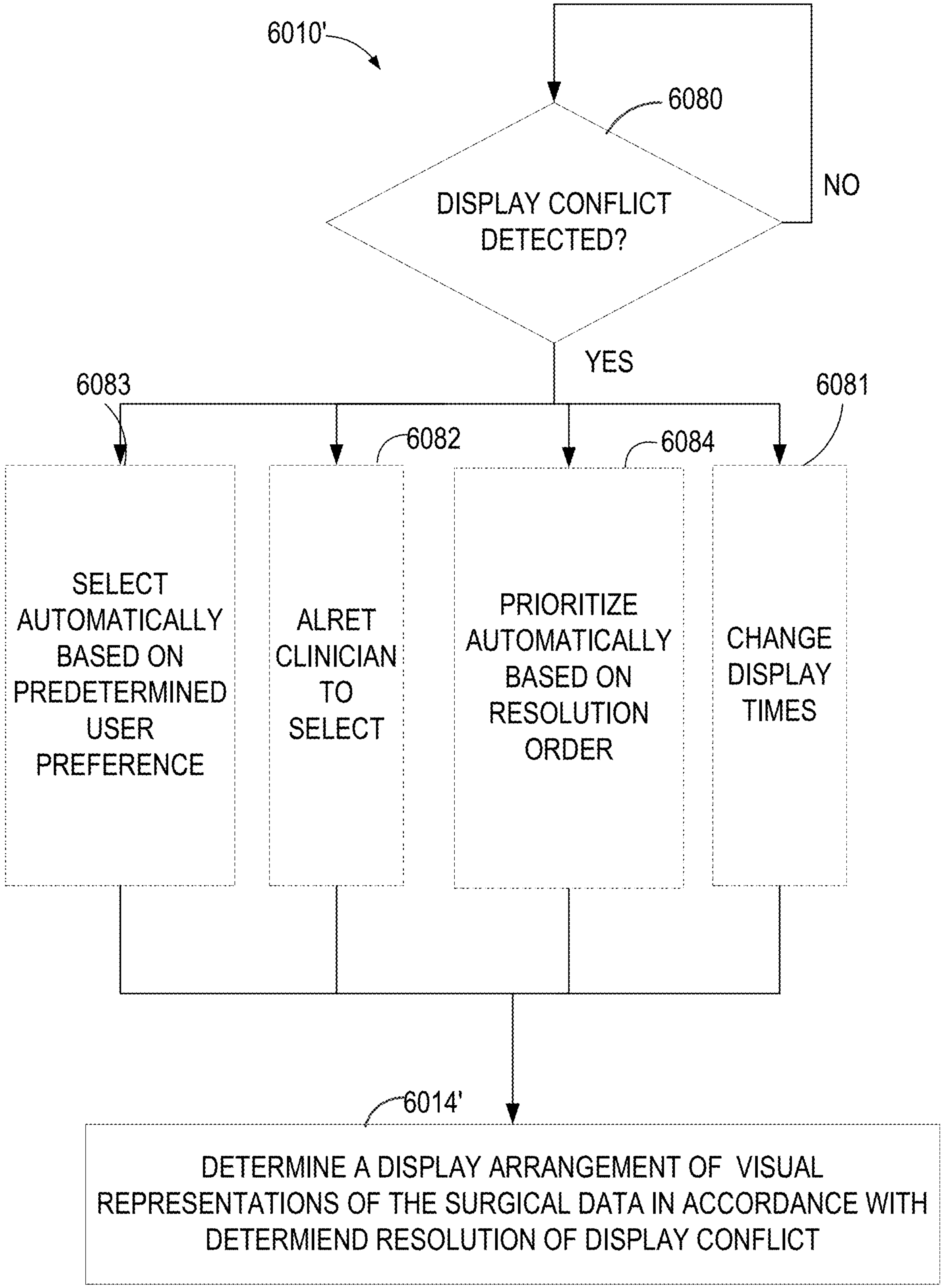
FIG. 20 is a logic diagram showing operations of a method for resolving display conflicts in a display arrangement, according to one aspect of this disclosure.

FIG. 20 is a logic diagram showing operations of an example method 6010' for resolving display conflicts in a display arrangement. The method 6010' is similar in many respects to the method 6010. Common details between the two methods are not repeated herein for brevity. In certain instances, as illustrated in FIG. 20, a detected 6080 display conflict can be resolved by changing 6081 one or more display times of competing visual representations to resolve the conflict. Alternatively, the clinician can be made aware of the conflict, and can be offered a choice, on the display 6005, to select 6082 between the different surgical data. Alternatively, the selection 6083 can be made automatically based on a predetermined preference of the clinician, which can be based on user-input or contextual information generated by the situational awareness module, for example 6006.

In some implementations, detecting 6080 a display conflict between a first surgical data and a second surgical data includes retrieving, by the processor 85, for example, display priority information for the first surgical data and the second surgical data from the memory 6003, for example. The processor 85 may then compare the display priority information of the first surgical data and the second surgical data to determine whether a display conflict is detected 6080.

In certain implementations, the control module 6001 is configured to respond to a detected 6080 display conflict by simultaneously showing visual representations of competing surgical data that are smaller in size than a default size, for example. A clinician is permitted to select between the visual representations though a user interface 6007, for example. In response, the control module 6001 removes the unselected visual representation, and increases the size of the selected visual representation to the default size.

In certain implementations, a detected 6080 display conflict can be resolved by automatically prioritizing 6084 based on a resolution order determined based on the surgical data presenting the display conflict. In some implementations, the resolution order is determined based on an order of the surgical steps associated with the surgical data and/or urgencies of risks and/or issues reported by the surgical data.

In certain exemplifications, a display conflict is detected 6080 between a first surgical data and a second surgical data, both presenting high priority issues and/or risks. Moreover, a second resolution associated with the second surgical data cannot be performed until a first resolution associated with the first surgical data is implemented. In such exemplifications, a first visual representation of the first surgical data is automatically prioritized 6084 over a second visual representation of the second surgical data based on the resolution order.

In certain exemplifications, a display conflict may arise between a first surgical data associated with a lockout preventing actuation of a surgical instrument 21 and a second surgical data associated with a suboptimal tissue thickness of a tissue being treated by the surgical instrument. In such exemplifications, a predetermined resolution order can be employed to resolve the conflict in favor of the lockout, since the tissue thickness issue, while a high priority, cannot be resolved while the surgical instrument 21 is in a lockout state.

In certain instances, the resolution order can be stored on a storage medium (e.g., the memory 6003) in the form of a database, a table, or any other suitable form. The stored information can list various surgical data and corresponding resolution order. The processor 85 may consult the stored information to identify a resolution order between competing surgical data to resolve a display conflict. In some implementations, the resolution order is based on an order of surgical tasks that will be initiated, or completed, based on the competing surgical data.

In some exemplifications, the control module 6001 may receive first surgical data indicating that a detected staple cartridge (e.g., one loaded onto a surgical instrument 21) has been previously fired. A controller of the surgical instrument 21 may interrogate the staple cartridge by requesting firing information stored on a chip of the staple cartridge, for example, and may determine that the staple cartridge has been previously fired based on the retrieved firing information. First surgical data comprising the firing information can then be communicated to the control module 6001, wirelessly or through a wireless communication. In addition, the control module 6001 may receive second surgical data associated with a closure of the end effector of the surgical instrument 21 onto a tissue being stapled in a surgical procedure involving the surgical instrument 21 that is loaded with the previously-fired staple cartridge. For example, the second surgical data may relate to tissue thickness and/or tissue position between jaws of the end effector.

Further to the above, the control module 6001 detects 6080 a display conflict as the first surgical data, previously-fired staple cartridge, and the second surgical data, end effector closure onto tissue, both comprise high priority statuses. To determine a display arrangement of visual representations of the first and second surgical data onto the display 6005, for example, the processor 85 checks a resolution order information stored on a storage medium (e.g., the memory 6003) in the form of a database, a table, or any other suitable form. In the present example, the first issue, previously-fired staple cartridge, presented by the first surgical data, must be resolved before a second issue, end effector closure onto tissue, presented by the second surgical data. This is because resolving the end effector closure onto tissue is immaterial if the previously-fired staple cartridge cannot be used to treat the tissue.

Once the display conflict is resolved, the method 6010' proceeds with displaying 6014' visual representations of the first surgical data and second surgical data in accordance a display arrangement selected based on the resolution order. For example, a first visual representation of the first surgical data can be displayed prior to a second visual representation of the second surgical data. Other suitable display arrangements, as described elsewhere in the present disclosure, can be employed.

In various aspects, a surgical procedure involves stapling a tissue using a surgical instrument 21 such as, for example, a surgical stapler. The surgical procedure typically includes positioning an end effector of the surgical instrument 21 in a surgical field, and actuating the end effector to grasp tissue between jaws of the end effector. The jaws place the grasped tissue under compression. Since the tissue comprises water, the grasped tissue gradually changes in response to being compressed by the jaws of the end effector in process known as tissue creep, until the tissue reaches the steady state. Moreover, the gap between the jaws and the tissue thickness may also change until the tissue reaches the steady state. Also, tissue flow, or tissue motion, may occur until the tissue reaches the steady state. In some implementations, for a successful stapling, the tissue is allowed a wait-time to achieve the steady state. Parameters associated with the previously-described tissue changes such as wait-time parameters, tissue-thickness parameters, and/or instrument gap parameters are important for properly assessing when a tissue steady-state is reached.

Figure 21:
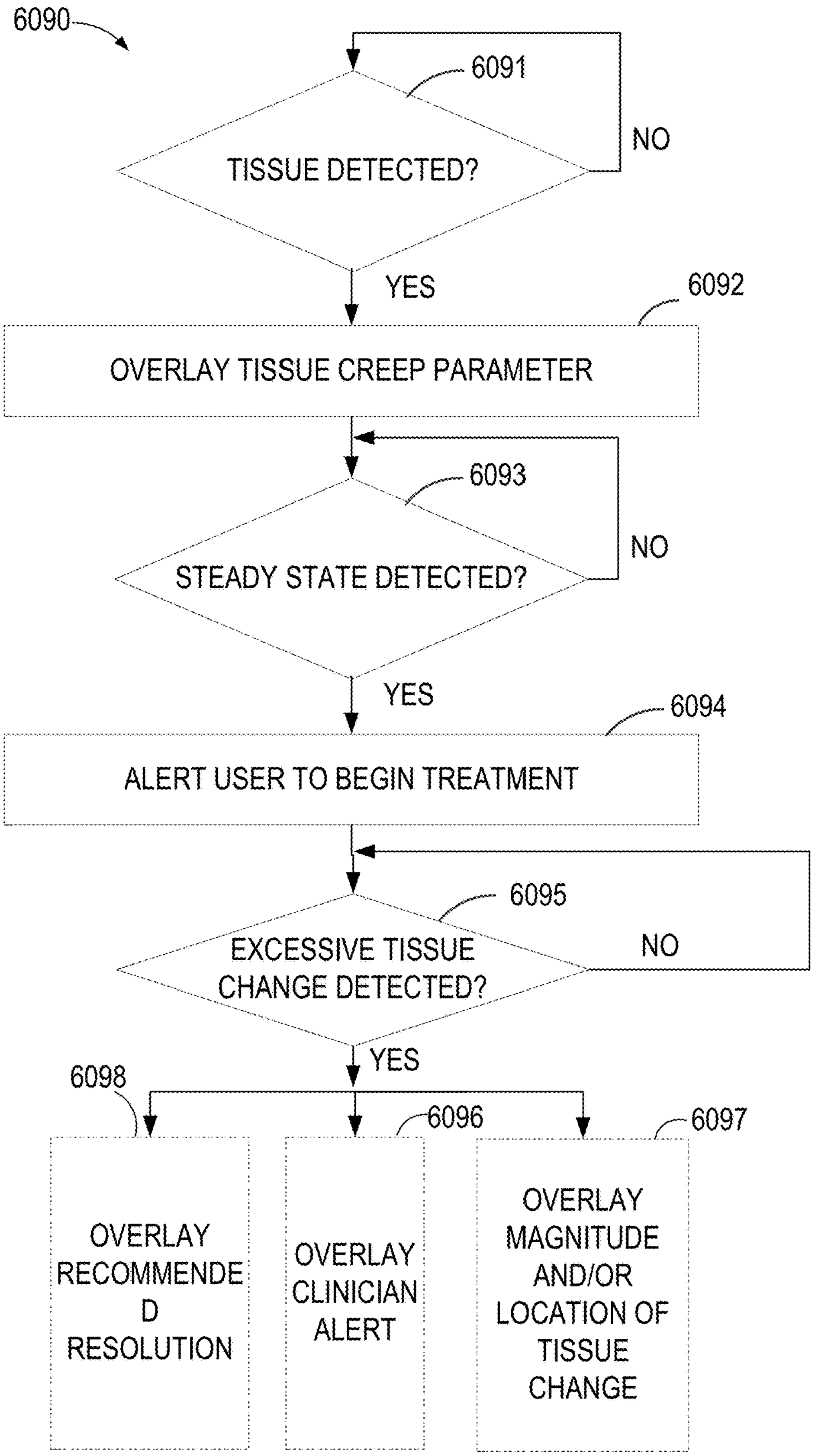
FIG. 21 is a logic diagram showing operations of a method for addressing tissue changes in a surgical procedure that employs a surgical instrument, according to one aspect of this disclosure.

FIG. 21 is a logic diagram showing operations of an example method 6090 for addressing tissue changes (e.g., tissue creep, tissue flow, tissue compression) in a surgical procedure that employs a surgical instrument 21. In some implementations, the method 6090 includes detecting 6091 tissue between the jaws of an end effector of the surgical instrument 21. In certain instances, tissue detection 6091 can be visually achieved automatically through object recognition, object tracking, and/or object labeling algorithms, and/or other image processing techniques of image frames of the livestream, for example. Alternatively, the surgical instrument 21 can be configured to detect 6091 the presence of the tissue between the jaws based on signal readings of one or more sensors in the jaws. For example, a tissue can be detected 6091 when a non-therapeutic signal passed through the tissue yields an acceptable tissue impedance.

In response to detecting 6091 the tissue, the method 6090 may display, or overlay 6092 onto a livestream of the surgical field, at least one parameters of tissue change (e.g., tissue creep, tissue flow, tissue compression) and/or parameters of the surgical instrument gap distance between the jaws of the end effector, and/or wait-time. In certain implementations, the method 6090 further includes alerting 6094 the user of the surgical instrument 21 when the steady state has been reached to begin tissue treatment. In certain instances, the steady state is detected 6093 based on one or more of the tissue change parameters and/or one or more of the surgical instrument parameter. For example, the steady state can be detected 6093 when one or more of the tissue flow, tissue creep, tissue thickness, tissue compression, gap distance between the jaws of the end effector, and/or wait-time is at, or beyond, a predetermined threshold. Alternatively, the steady state can be detected 6093 If a rate of change of one or more of the tissue flow, tissue creep, the tissue thickness, tissue compression, gap distance between the jaws of the end effector, and/or wait-time is less than, or equal, to a predetermined threshold. Additionally, or alternatively, the steady state can be automatically visually detected 6093 based on object recognition, object tracking, and/or object labeling algorithms, and/or other image processing techniques that may monitor, for example, a change in the tissue.

Figure 26:
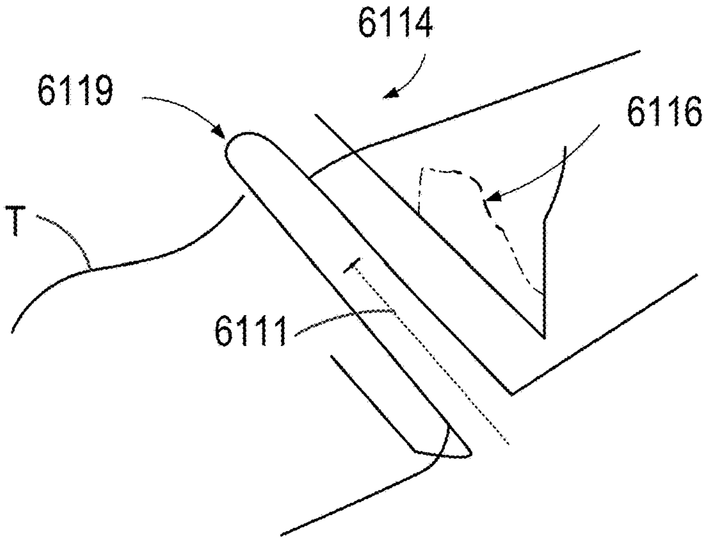
FIG. 26 illustrates a display arrangement, in accordance with methods of the present disclosure.

In some implementation, the method 6090 further includes automatically monitoring tissue change visually during the application of a treatment by the surgical instrument 21 by utilizing one or more suitable object recognition, object tracking, and/or object labeling algorithms, and/or other image processing techniques of image frames of the livestream, for example. In certain instances, the treatment can, for example, be the firing of staples into the grasped tissue. If 6095, during firing, the tissue change reaches an excessive level, the method 6090 may further include displaying, or overlaying 6096, an alert to the clinician. In certain instances, the method 6090 includes displaying, or overlaying 6097, a visual representation of the location and/or magnitude of the excessive tissue change, as illustrated in FIG. 26, for example. In some implementations, tissue change is automatically monitored visually by tracking size, location, color, and/or movement of one or more tissue targets of in the grasped tissue, for example.

The method 6090 may also include displaying, or overlaying 6098, a recommended resolution such as, for example, adjusting one or more parameters of the surgical instrument 21 such as one or more closure parameters (e.g., jaw clamping, jaw pressure, distal tip load) and/or firing parameters (e.g., firing speed, I-beam speed). In certain instances, the recommended resolution can be additional wait-time. In certain instances, the surgical instrument 21 is an ultrasonic instrument, and the recommended resolution is one that decreases a distal tip load of the end effector. In other instances, the surgical instrument 21 is a surgical stapler, and the recommended resolution is one that increases a distal tip load of the end effector.

In various instances, the tissue change, e.g., tissue flow, is affected, at least in part, by a tension suffered by the tissue grasped between the jaws. In certain instances, the tissue tension is due to a movement such as a rotation of the end effector from a neutral positon while grasping the tissue. In such instances, the overlaid 6098 resolution can be in the form of a recommended adjustment to a rotational position of the end effector. Excessive tissue tension can be automatically observed by utilizing one or more suitable object recognition, object tracking, and/or object labeling algorithms, and/or other image processing techniques of image frames of the livestream, for example.

In some implementations, position and/or orientation of the end effector can be determined using one or more sensors including an accelerometer, a gyro, a relative position sensor, and/or a three-dimensional magnetic sensor. In some implementations, the sensors can generate position information characterizing one or more position changes. The position information can be transmitted via a wired or wireless interface to the control module 6001.

In some implementations, the accelerometer may be a single, double, or triple axis accelerometer. The accelerometer may be employed to measure proper acceleration that is not necessarily the coordinate acceleration (rate of change of velocity). Instead, the accelerometer may see the acceleration associated with the phenomenon of weight experienced by a test mass at rest in the frame of reference of the accelerometer. Additionally, or alternatively, position and/or orientation of the end effector can be automatically observed by utilizing one or more suitable object recognition, object tracking, and/or object labeling algorithms, and/or other image processing techniques of image frames of the livestream, for example.

In response to detection of a tissue tension of the tissue grasped by the jaws of an end effector, the control module 6001 may display, or overlay onto the livestream of the surgical field, visual representations of the tissue tension, its magnitude, and/or the rotational orientation responsible for the tissue tension. In some implementations, as illustrated FIGS. 22A-22C, visual representations 6100, 6101, 6102 of tissue tension may provide positional information of the end effector in three dimensional space, for example. In some implementations, the positional information of the end effector is represented by a first axis (e.g., x-axis) extending centrally and longitudinally through the end effector, a second axis (e.g., y-axis) perpendicular to the first axis and extending in first plane with the first axis, and a third axis (z-axis) perpendicular to the first axis and extending in a second plane with the first axis, wherein the first plane intersects the second plane at the first axis.

Figure 22C:
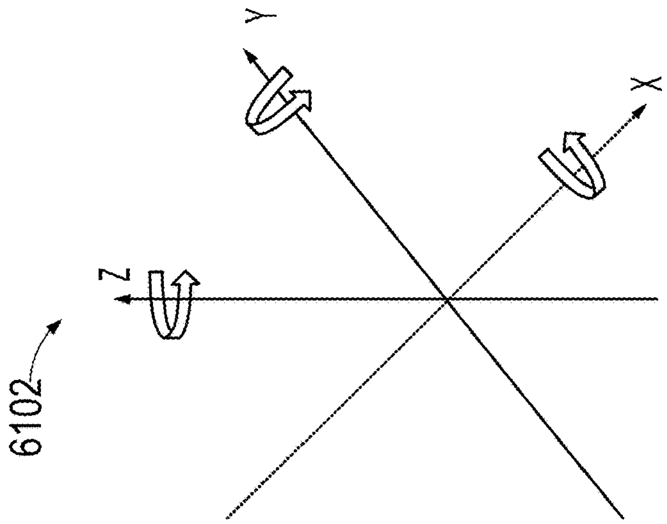
FIGS. 22A, 22B, 22C illustrate display arrangements, according to one aspect of this disclosure.
Figure 22B:
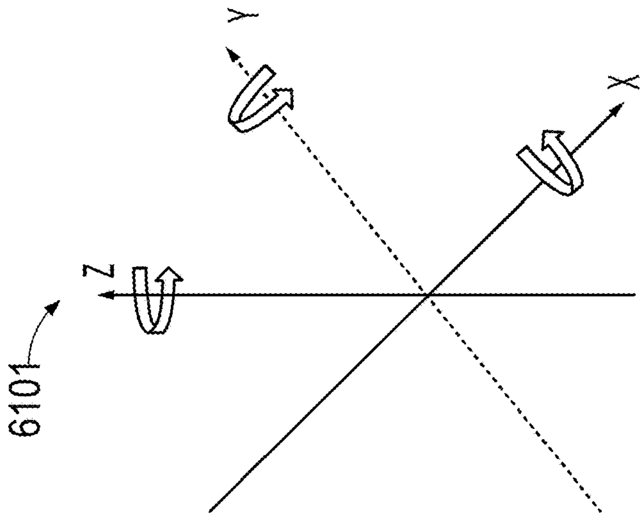
Figure 22A:
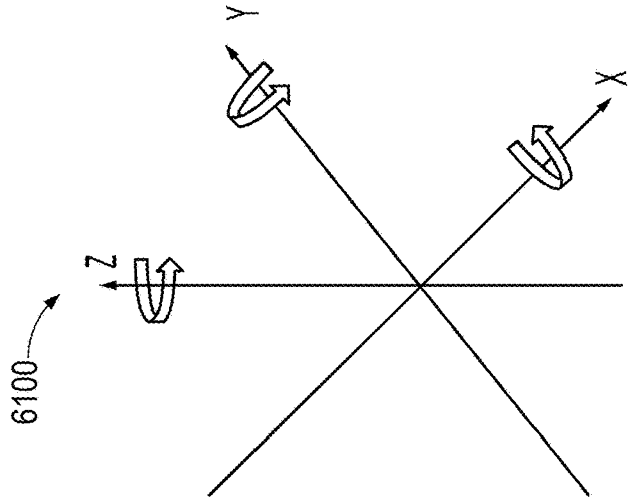

Each of the coordinate axes can be presented in a first form (e.g., color, shape, size), while the end effector is in a neutral state with respect to the coordinate axes, as illustrated in FIG. 22A. In response to detecting an excessive deviation from the neutral state about one or more coordinate axes, the control module 6001 causes the one or more coordinate axes to change to a second form different than the first form. In other instances, the excessive deviation from the neutral state can be a first deviation, and can be based on a first predetermined threshold or range, while a second deviation can be more excessive than the first deviation, and can be based on a second predetermined threshold or range different than the first predetermined threshold or range, for example. In such instances, the neutral state can be presented in the first form, the first excessive deviation can be presented in the second form, and the second excessive deviation can be presented in a third form different than the first form and the second form. In certain implementations, the first form includes a green color, the second form includes a yellow color, and the third form includes a red color.

In illustrated example, a first excessive deviation from the neutral state is detected about the y-axis. In response, the control module 6001 causes the y-axis to be switched from the first form to the second form, while the x-axis and the z-axis remain in the first form, as illustrated in FIG. 22B. In the illustrated example, the first excessive deviation is greater than, or equal, to the first predetermined threshold. Then, as illustrated in FIG. 22C, a second excessive deviation, greater than or equal to the second predetermined threshold, is detected about the x-axis, while the first excessive deviation about the x-axis has been remedied. In response, the control module 6001 causes the Y-axis to return to the first form, and the x-axis to be changed to the third form.

In various instances, different deviations (e.g., the first and second excessive deviations) from the neutral state may comprise different severities, and can be presented in different forms indicative of the severities. For example, a first excessive deviation can be presented by a yellow color, while a second excessive deviation, more severe than the first excessive deviation, can be presented in a red color. In some implementations, deviations from the neutral state are determined based on ranges of angles of rotation about one or more of the coordinate axes. For example, the neutral state with respect to a first axis is detected where an angle of rotation of the end effector with respect to the first axis meets a range of about A°, the first excessive deviation is detected where an angle of rotation of the end effector with respect to the first axis meets a range of about +B°, and the second excessive deviation is detected where an angle of rotation of the end effector with respect to the first axis meets a range of about +C°. In the illustrated example, A, B, and C are integers, wherein A is less than B, and B is less than C.

Figure 23A:
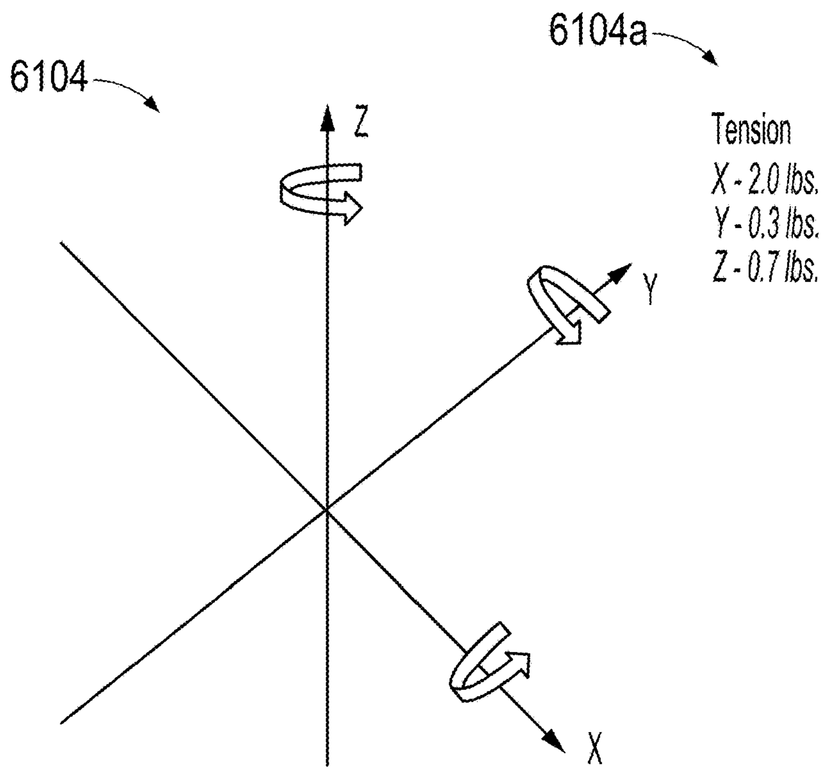
FIGS. 23A and 23B illustrate display arrangements, according to one aspect of this disclosure.
Figure 23B:
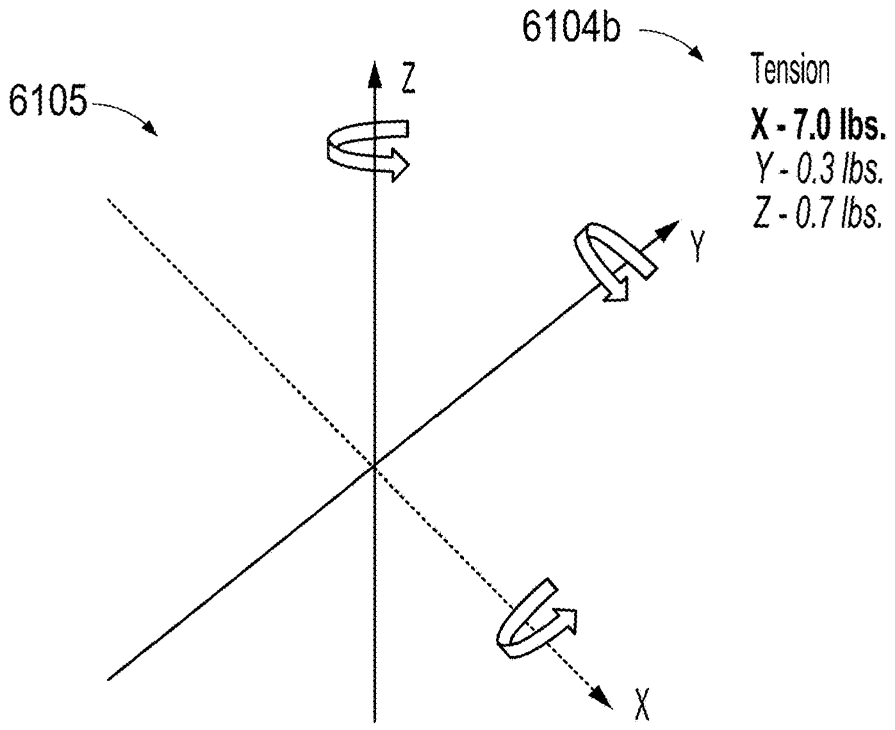

Referring to FIGS. 23A-23B, in some implementations, visual representations 6104, 6105 of the tissue tension may further include tissue tension measurements 6104*a*, 6105*a* associated with each of the coordinate axes. The control module 6001 may cause the tissue tension measurements to change form (e.g., color, size, and/or shape) in response to an excessive deviation in tissue tension (e.g., from 2.0 lbs. to 7.0 lbs.).

Figure 24:
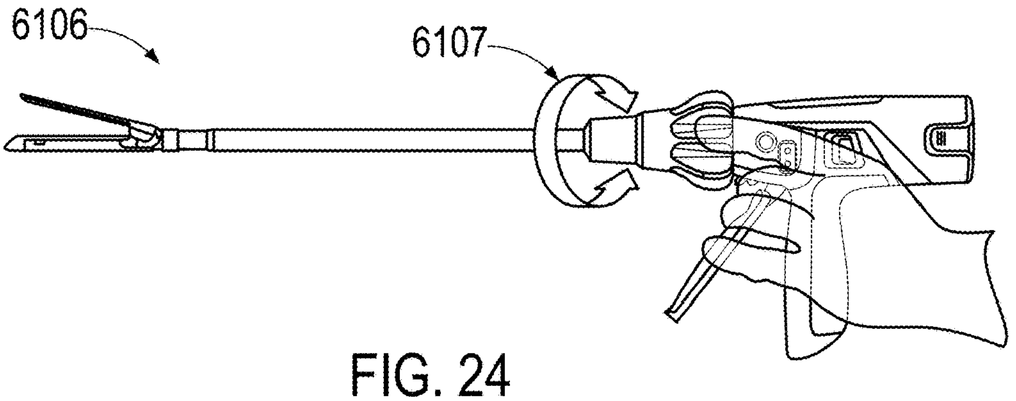
FIG. 24 illustrates a display arrangement, according to one aspect of this disclosure.

In some implementations, the control module 6001 may further cause a recommendation to be displayed, or overlaid onto the livestream of the surgical field, to address an excessive tissue tension. In some exemplifications, as illustrated in FIG. 24, the recommendation comprises a visual representation 2106 showing the surgical instrument 21 with an arrow 6107 representing the recommended rotation to transition the end effector of the surgical instrument 21 to the neutral state.

FIGS. 24-30 illustrate various display arrangements determined 6013 based on surgical data detected 6011, in accordance with the method 6010 and/or any other suitable method of the present disclosure. The display arrangements illustrated in FIGS. 24-30 are represented in the context of a surgical instrument 21 configured to staple and cut tissue. However, in other implementations, one or more of the display arrangements illustrated in FIGS. 24-30 can be similarly utilized with other surgical instruments in other types of surgical procedures.

A number of the display arrangements described by the present disclosure involve overlaying various visual representations of surgical data onto a livestream of a surgical field shown on a display such as, for example, the display 6005. As used herein the term overlaying comprises a translucent overlay, a partial overlay, and/or a moving overlay. Moreover, the overlay can be positioned on, or at least partially on, or near an object in the surgical field such as, for example, an end effector and/or a critical surgical structure. Certain display arrangements may comprise a change in one or more display elements of an overlay including a change in color, size, shape, display time, display location, display frequency, highlighting, or a combination thereof, based on changes in display priority values.

Figure 25:
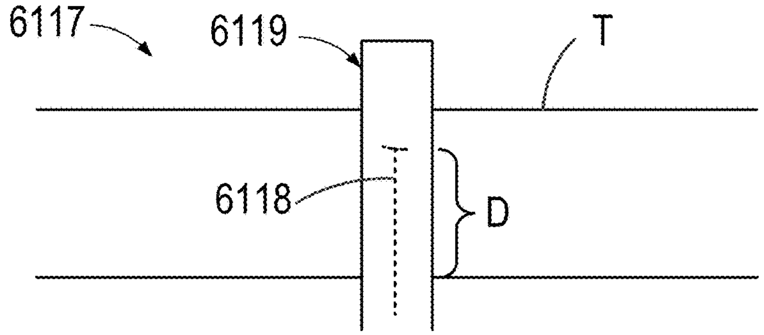
FIG. 25 illustrates a display arrangement, according to one aspect of this disclosure.

FIG. 25 illustrates a display arrangement 6117 that includes a mixed reality view presented by the control module 6001, for example, on a display 6005, for example. The display 6005 shows a livestream of a surgical field during a surgical procedure that utilizes a surgical instrument 21 to staple and cut tissue T grasped by an end effector 6119 of the surgical instrument 21. In the illustrated example, the display arrangement 6117 overlays a transection progress line 6118, or a staple firing progress line, on a channel of the end effector 6119. Moreover, the display arrangement 6117 overlays a distance D traveled by a firing member, or a cutting member, onto the channel of the end effector 6119 to aid a clinician in following the firing progress of the surgical instrument 21.

In some implementations, the control module 6001 detects a change in one or more parameters of the tissue grasped by the end effector 6119 and/or parameters of the surgical instrument 21, beyond a predetermine threshold, or beyond a predetermine range, for example. In at least one implementation, the parameter change is a change in firing speed equal to, or less than, a predetermined threshold. For example, the control module 6001 may receive surgical data indicative of the parameter change through a wired, or wireless, communication interface with the surgical instrument 21 and/or a surgical hub 6 (FIG. 1). In response to detecting the parameter change, the control module 6001 may cause a change in the transection progress line 6118, or a staple firing progress line, on a channel of the end effector 6119, including a change in color, size, shape, display time, display location, display frequency, highlighting, or a combination thereof.

Additionally, or alternatively, in response to detecting the parameter change, the control module 6001 may cause an overlay of a virtual channel, overlaid onto the end effector 6119, to change at least one color, size, shape, display time, display location, display frequency, highlighting, or a combination thereof, in accordance with a magnitude of the change, in accordance with a value of the parameter, or in accordance with a risk level associated with the parameter change.

FIG. 26 illustrates a display arrangement 6114 that is presented by the control module 6001, for example, on a display 6005, for example, in accordance with methods of the present disclosure. The display 6005 shows a livestream of a surgical field during a surgical procedure that utilizes a surgical instrument 21 to staple and cut tissue T grasped by an end effector 6119 of the surgical instrument 21. In the illustrated example, the display arrangement 6117 overlays a tissue marker 6116 indicative of tissue flow onto the tissue T. Excessive tissue flow can be detected as described in connection with the method 6090 of FIG. 21, for example. In the illustrated example, the display arrangement 6114 combines an overlay of the transection progress line 6118 and the tissue marker 6116. Other display arrangements may only comprise the tissue marker 6116.

FIGS. 27A-27C illustrate a display arrangement 6130 that provides a visual representation 6131 of surgical data, according to one aspect of this disclosure. In some implementations, the display arrangement 6130 is presented by the control module 6001, for example, on a display 6005, for example, in accordance with methods of the present disclosure. In the illustrated example, the display arrangement 6130 presents a visual representation 6132, in the form of a translucent overlay 6133, indicative of a tissue flow during a firing sequence of a surgical instrument 21. During the firing sequence, the surgical instrument 21 is configured to deploy staples into a tissue T grasped by an end effector of the surgical instrument 21, and concurrently cut the tissue T. In the illustrated example, the display arrangement 6130 is presented in a dynamic display mode, wherein a change in a display element 6132 (FIG. 27A), 6133' (FIG. 27B), 6133" (FIG. 27C) of the visual representation 6131 is depicted.

The display element may track the tissue flow across the width of the end effector. Different locations can be presented in different forms (e.g., colors, shapes, and/or sizes), wherein the different forms represent different levels of tissue flow in the different locations. In the illustrated example, the display element 6132 represents an acceptable tissue flow condition, and the display element 6132' represents a low risk tissue flow condition. On the contrary, the display element 6132''' represents a high risk tissue flow condition.

Referring to FIGS. 28 and 29, in some implementations, a display arrangement 6140 is presented by the control module 6001, for example, on a display 6005, for example, in accordance with methods of the present disclosure. The display 6005 shows a livestream of a surgical field during a surgical procedure that utilizes a surgical instrument 21 to staple and cut tissue T grasped by an end effector 6141 of the surgical instrument 21. In the illustrated example, the display arrangement 6140 overlays a performance parameter plot 6142 (FIG. 29) with history trace as a function of a firing member, cutting member, and/or knife position. The plot 6142 is overlaid adjacent to the end effector 6141, for example.

The plot 6142 presents risk severity associated with one or more parameters 6146 monitored during a firing sequence of the surgical instrument 21 such as, for example, an anvil gap, a tissue load, a firing speed, and/or a motor speed. Moreover, the plot 6142 further provides multiple thresholds, e.g., three thresholds 6143, 6144, 6145, each representing a severity level (e.g., low, medium, high) to provide a clinician with a visual indicator as to the severity of the risk associated with the measured parameter 6146.

Additionally, or alternatively, the display arrangement 6140 can be configured to utilize a color plot 6147 to present surgical data associated with a tissue parameter (e.g., tissue pressure, tissue compression, tissue flow, tissue thickness) of the tissue T. The tissue parameter values can be represented in different colors (e.g., green, yellow, red or light shading, intermediate shading, dark shading) that are in accordance with the values relations to one or more predetermined thresholds. In the illustrated example, green represents tissue portions with acceptable values, yellow represents tissue portions with low risk values, and red represents tissue portions with high risk values. The color plot 6147 provides a convenient and quick risk assessment tool that aids a clinician in determining whether to commence and/or continue a firing sequence, for example.

In various implementations, the tissue parameter values are measured by sensors dispersed in multiple locations across the width and along the length of the end effector 6141, for example. The tissue parameter values are then represented by coloring (e.g., green, yellow, red or light shading, intermediate shading, dark shading) areas on the color plot 6147 commensurate with the locations of the sensors on the end effector 6141, for example. FIG. 30 illustrates a display arrangement 6150 that provides a visual representation of surgical data, according to one aspect of this disclosure. In some implementations, the display arrangement 6150 is presented by the control module 6001, for example, on the display 6005, for example, in accordance with methods of the present disclosure. In some implementations, the display arrangement 6150 is overlaid onto a livestream of a surgical field of a surgical procedure that utilizes a surgical instrument 21 to staple and cut tissue.

In some implementations, the display arrangement 6150 includes a simulated cross-sectional overlay 6152 an end effector 6153 of the surgical instrument 21 showing, and matching, positions and motions of one or more end effector components in real time, for example. Increased visualization can help the clinician better understand current statuses and risk-based feedback from the surgical instrument 21 (e.g., Clamping loads too high, force to fire too high, wait-time needed, etc.).

In the illustrated example, the simulated overlay 6152 shows staples 6156, staple drivers 6154, and a firing member (e.g., sled 6155) configured to motivate the staple drivers 6154 to deploy staples 6156 into tissue. The position of the firing member in the simulated overlay 6152 mirrors the position of the firing member in the end effector 6153, and is indicative of the progress of the firing sequence, in real time. Moreover, in the illustrated example, the simulated overlay 6152 shows simulated tissue (ST), which can be presented in a manner reflective of tissue flow in areas where tissue flow is detected. While the illustrated example, only presents one row of staples 6156, in other examples, multiple rows can be shown.

In some implementations, the firing sequence is shown by the simulated overlay 6152 in a dynamic display mode. Moreover, the staple formation can, in some instances, be predicted based on one or more determined parameters such as, for example, tissue type, patient parameters, tissue flow, closure force, tissue creep stability, anvil gap, etc. For example, the control module 6001 may employ a predetermined equation, a database, and/or a table to predict the staple formation.

In the illustrated example, the display arrangement 6150 further includes a staple formation overlay 6157. The control module 6001 can be configured to predict staple formation, and update the staple formation overlay 6157 in real time, for example.

FIG. 31 is a logic diagram showing operations of an example method 6160 for risk-based manipulation of a display arrangement during a surgical procedure, according to one aspect of this disclosure. In some implementations, the method 6120 can be executed by the computer-implemented interactive surgical system 1, for example. In some implementations, the method 6160 is performed by a surgical system including a surgical instrument 21 configured to staple and cut tissue in a surgical field of a surgical procedure. The surgical system further includes a control module 6001, an imaging device 6004, and a display 6005 configured to show a livestream of the surgical field. The livestream is captured by the imaging device 6004, for example.

In some implementations, the method 6160 includes detecting 6161 a surgical risk, assigning 6162 a severity level to the surgical risk, and determining 6163 a display arrangement based on the severity level, wherein the display arrangement comprises overlaying an alert feature on the livestream. In some implementations, the method 6160 further includes presenting 6164 visual representations of the surgical risk, in accordance with the display arrangement.

In some implementations, the surgical risk is detected 6161 by the control module 6001. The surgical risk can be detected 6161 based one surgical data received from one or more sources such as, for example, components of the computer-implemented interactive surgical system 1 via one or more wireless and/or wired communication interfaces. In at least one example, the surgical data may include data received from one or more of the surgical instruments 21. In another example, the surgical data includes contextual information ascertained by the situational awareness module 6006.

In certain exemplifications, the surgical data comprise control data, biomarker measurements, and/or other operational indicators of operations and/or outcomes associated with a surgical instrument 21. In certain exemplifications, the surgical data can be any data indicative of a higher propensity of malformed staples and/or poorly sealed tissue. In certain instances, the surgical data can be associated with tissue flow, clamping force, firing force, among other tissue and/or instrument parameters, which can be monitored and displayed to the clinician in multiple ways in real time to allow for adjustments to the firing sequence or to alert the surgeon of a potentially malformed staple region.

In certain exemplifications, the processor 85 employs predetermined equations and/or formulas in determining the severity level of the surgical risk. Various relevant factors can be considered, and can be assigned different weights in calculating the severity level. Additionally, or alternatively, one or more databases or tables listing surgical data and corresponding severity levels can be utilized by the processor 85 in assigning 6162 the severity level. In various implementations, the assigned 6162 severity level comprises, for example, a low severity level, a medium severity level, or a high severity level.

FIG. 32 illustrates an implementation of a display arrangement 6170, according to one aspect of this disclosure. In some implementations, the display arrangement 6170 is determined based on a severity level of the surgical risk detected 6161 in the method 6160, for example. In the illustrated example, the display arrangement 6170 includes overlaying, by the control module 6001, an alert feature 6171 in response to detecting 6161 the surgical risk. The alert feature 6171 is overlaid onto a livestream of a surgical field 6179 during the surgical procedure. In the illustrated example, the livestream of the surgical field 6179 shows an end effector 6172 of the surgical instrument 21 configured to manipulate a surgical structure 6178.

In the illustrated example, the alert feature 6171 is overlaid onto the livestream in a corner area, away from the end effector 6172 and/or away from any critical surgical structures, so as to not hinder a clinician's view of the surgical field. In other exemplifications, the alert feature 6171 can be moved to, or initially overlaid onto, a central area of the livestream, closer to the end effector 6172 and/or any critical surgical structures, for example, to signify a higher severity of the surgical risk.

Further to the above, the display arrangement 6170 includes a change in the alert feature 6171, in response to a user reaction. In the illustrated example, the change to the alert feature 6171 includes replacing the alert feature 6171 with information 6173 associated with the surgical risk. The information 6173 can include details about the surgical risk and/or recommended solutions.

In the illustrated example, the user reaction is a transition of the end effector 6172 between an open configuration and a closed configuration. In other implementations, the user reaction may include any other suitable gesture or motion by the end effector 6172. In yet other implementations, the user reaction may include a hand gesture or motion and/or eye gesture or motion, for example.

In other examples, the user reaction can be a compounded user reaction or a multi-factor reaction to ensure that incidental actions by the user will not be construed by the control module 6001 as user reactions for the purposes of manipulating the alert feature 6171. In some implantations, a user reaction recognizable by the control module 6001 may include two components such as, for example, an end effector gesture or motion followed by an eye movement of the user or a hand movement of the user.

In some implementations, as illustrated in FIG. 33, a display arrangement 6170', which is similar in many respects to the display arrangement 6170, includes a different user reaction. In the illustrated example, the user reaction includes hovering the end effector 6172 over the alert feature 6171.

In some implementations, the user reaction is automatically detected through object recognition, object tracking, object labeling, and/or other suitable image processing techniques of image frames of the livestream, for example, or through various suitable wired and/or wireless communication schemes. Additionally, or alternatively, the user reaction can be automatically detected by receiving information, via suitable wired and/or wireless communication schemes, indicative of a user reaction. For example, a camera may monitor a body motion or a body gesture of the user such as, for example, a hand wave, an eye stare or a double blink. In another example, a clinician's glove can be tracked via one or more suitable sensors positioned on the glove. Sensor readings indicative of a predetermined hand motion, indicative of a predetermined user reaction, can be communicated to the control module 6001.

In some implementations, the display arrangement 6170 includes changing the alert feature 6171 based on a change in the severity of the surgical risk. The change can be implemented in a dynamic display mode, for example. In some exemplifications, the change to the alert feature 6171 includes a change in at least one of color, size, shape, display time, display location, display frequency, highlighting, or a combination thereof, in accordance with the severity level of the surgical risk. In some implementations, the alert feature 6171 is in the form of an alert icon, which changes color based on the severity level of the surgical risk, for example.

In some implementations, as illustrated in FIG. 34, a display arrangement 6170", which is similar in many respects to the display arrangement 6170, includes positioning the alert feature 6171 in a location that interferes with a clinician's view of a critical surgical structure 6178, to signify a high severity surgical risk, for example. Nonetheless, the display arrangement 6170" permits a user to move the alert feature 6171 away from the critical surgical structure 6178, by hovering the end effector 6172 over the alert feature 6171. In response to detecting that the end effector 6172 and the alert feature 6171 occupy the same location, the control module 6001 causes the alert feature to move to a different location on the livestream of the surgical field 6179, for example.

In other examples, a predetermined user reaction such as, for example, closing and opening the jaws of the end effector 6172 once, or twice, simulates grabbing the alert feature 6171. Moreover, the end effector 6172 can be moved to a corner of the display 6005, for example, causing the grabbed alert feature 6171 to move with it. A pause over the new location can signifies dropping the alert feature at the new location. Other suitable gestures and/or motions can be adopted to signify a user reaction to move the alert feature 6171 away from the critical surgical structure 6178. In some implementations, in a dynamic mode for example, the control module 6001 may automatically cause an alert feature 6171 to move away from an end effector 6172 and/or a critical surgical structure 6178, after an initial deployment that is determined to be less than, or equal to, an end effector 6172 and/or a critical surgical structure 6178, for example.

In various implementations, gestures and/or motions by the end effector 6172 can be automatically observed by utilizing one or more suitable object recognition, object tracking, and/or object labeling algorithms, and/or other image processing techniques of image frames of the livestream of the surgical field 6179, for example. In various instances, the end effector 6172 is visually recognized based on a characteristic reflectivity, color, and/or shaped. Additionally, or alternatively, gestures and/or motions by the end effector 6172 can be detected through sensor readings of sensors in the surgical instrument 21.

In some implementations, a change in the alert feature 6171, in response to the user reaction, includes a motion of the alert feature 6171 away from the end effector 6172 and/or a critical surgical structure 6178. In some exemplifications, the control module 6001, for example, is configured to track the positions of the end effector 6172 and/or the critical surgical structure 6178 with respect to the position of the alert feature 6171 on the display 6005. In addition, the control module 6001, for example, is configured to automatically change the position of the alert feature 6171 based on at least one of the positions of the end effector 6172 and the critical surgical structure 6178 to facilitate a clear view of the end effector 6172 and/or the critical surgical structure 6178.

In some implementations, the control module 6001, for example, is configured to correlate the alert feature 6171 to a source of the risk represented by the alert feature 6171. The correlation provides a clinician with an indication as to the nature of the risk without having to expand the alert feature 6171 to view details of the risk, for example. The correlation can be achieved through a common display characteristic such as, for example, a common color highlight and/or a common blink frequency. For example, where the risk is associated with a surgical instrument 21 comprising an end effector 6172 in the surgical field, the alert feature 6171 and the end effector 6172 can both be highlighted with a common color, for example. Additionally, or alternatively, the correlation can be achieved by causing the surgical instrument 21 to provide a sound and/or a haptic feedback that coincides with the presence of the alert feature 6171 on the display 6005, for example. Additionally, or alternatively, the correlation can be achieved by overlaying one or more color coded bubbles and/or arrows, separate from the alert feature 6171, which point to the end effector 6172, indicating that the risk represented by the alert feature 6171 is associated with the surgical instrument 21.

In some implementations, a display arrangement associated with a particular surgical instrument task, or a surgical step, can be changed in response to a detected completion of the surgical instrument task, or surgical step. For example, a surgical procedure such as a surgical sleeve procedure involves a predetermined number of firings of a surgical instrument 21 configured to staple and cut tissue. Each firing in the firing sequence deploys staples from a staple cartridge into the tissue. The staple cartridge is then replaced with a new staple cartridge for the following firing in the firing sequence. The control module 6001 can be configured to detect the number of firings by the surgical instrument 21, and to continue overlaying surgical data associated with the firing of the surgical instrument 21 until the predetermined number of firings is reached. In response to detecting the completion of the firings, the control module 6001 causes the overlay of the surgical data associated with the firing of the surgical instrument 21 to be collapsed or removed from the display 6005.

In some implementations, detecting the completion of the surgical instrument task, or surgical step, can be automatically achieved visually through object recognition, object tracking, object labeling, and/or other suitable image processing techniques of image frames of the livestream, for example, or through input from the surgical instrument 21 and/or a surgical hub 6, for example, via various suitable wired and/or wireless communication schemes.

In various instances, one or more functions of the aforementioned methods are executed by one or more components of the computer-implemented interactive surgical system 1 such as, for example, one or more components of the surgical visualization system 6000, for example. In certain instances, the components executing the one or more functions of the aforementioned methods communicate through wireless and/or wired communication interfaces. In various instances, a memory of the computer-implemented interactive surgical system 1, e.g., memory 6003, stores program instructions that, when executed by a processor (e.g., processor 85), cause the processor to effect one or more functions of the aforementioned methods. While the aforementioned functions are described in discrete methods, in some implementations, some functions of the aforementioned methods can be combined in any suitable form to yield different methods that yield different program instructions for execution by one or more components of the computer-implemented interactive surgical system 1, for example.

In various instances, to perform tracking, in accordance with one or more aspects of the present disclosure, an algorithm analyzes sequential video frames and outputs the movement of targets between the frames. Example algorithms include target representation and localization algorithms and filtering and data association algorithms. Target representation and localization algorithms include Kernel-based tracking and/or Contour tracking, for example. Filtering and data association algorithms include Kalman filters and Particle filters, for example.

In view of the foregoing problems associated with competing amounts of overlaid information, the present disclosure provides a control system that can control and/or limit the amount of data that is being overlaid on the display. In some aspects the system 6000, can monitor and/or control an amount of information that is being overlaid on a display, such as display 6005, such that the amount of overlaid information does not cause strain or overwhelm the surgical staff. In various embodiments, the system 6000 can control the amount of overlaid information by comparing the overlaid information to a distraction threshold. The distraction threshold can be a user defined threshold, a predefined threshold stored in a memory, such as memory 6003, a threshold based on the size of the display, or combinations thereof.

In some aspects, the distraction threshold can be based on the size of the display such that the distraction threshold of one display is different than a distraction threshold of a second display that is larger than the first display. In some embodiments, the distraction threshold can be based on a combination of user provided inputs at an input interface and predefined inputs stored in the memory 6003. In one aspect, the distraction threshold can be defined as a threshold amount of information that can cause a user to become overwhelmed with the amount of information overlaid on the display. In several embodiments, the distraction threshold can vary from user to user according to, among other things, a user's experience, a user's age, a user's eye sight, a user's comfort level, or combinations thereof.

In some embodiments, the distraction threshold can be defined as a percentage of the viewable area of the display, such as the screen of a monitor or the lens of a wearable device, like AR device 66, as examples. For example, the system 6000 can calculate a size of the viewable area of the display and set the distraction threshold as a percentage of the calculated area. In some example embodiments, the distraction threshold can be 10% of the calculated area, 25% of the calculated area, 50% of the calculated area, or 75% of the calculated area, as examples. In some embodiments, the percentage of the calculated area to be used as the distraction threshold can be user provided by the user via an input interface (such as at a keyboard of a computer), stored in the memory 6003, based on standard industry practices, based on an experience level of the user, or combinations thereof.

In various embodiments, the system 6000 can monitor the area occupied by overlaid information and adjust the amount of overlaid information when the total area occupied by overlaid information reaches or exceeds the distraction threshold. In some aspects, the system 6000 can receive a signal from a sensor that causes information to be overlaid on the display.

The system 6000 can determine the area that the overlaid information will occupy on the display prior to overlaying the information thereon. In some aspects, the area the overlaid information will occupy is predefined and stored in the memory 6003. In some aspects, the area the overlaid information will occupy is variable and will vary based on available space on the display. In some aspects, the area the overlaid information will occupy is based on a user provided input. In some example embodiments, a user can provide inputs to the system 6000 providing sizes of certain types of information to overlay on the display. Once the system 6000 determines the area that the overlaid information will occupy on the display, the system 6000 can evaluate whether or not to overlay the information on the display, as explained in more detail below.

In various embodiments, the system 6000 can track the total area occupied, or to be occupied, by the overlaid information on the display and compare the tracked area to the distraction threshold. In one example embodiment, the system 6000 can evaluate the display and determine that a first amount of information is currently overlaid on the display. The system can evaluate the first amount of information and determine that the first amount of information occupies a total area that is less than the distraction threshold. The system can then receive a signal from, as an example, an EKG that is indicative of a patient's heart rate. The system 6000 can determine the area of the display that will be occupied by the overlaid heart rate information based on, for example, a predefined area stored in the memory 6003. The system 6000 can then add the determined area to be occupied by the overlaid heart rate information to the total area already overlaid on the display. If the combined area is less than the distraction threshold, the system 6000 can overlay the heart rate information onto the display with no adjustment to the already overlaid information. If the combined area reaches or exceeds the distraction threshold, the system 6000 can take a positive action such that the overlaid information on the display does not exceed the distraction threshold, as discussed in more detail below.

In some aspects, the system 6000 can determine whether adding new overlaid information to the display will cause the distraction threshold to be reached or exceeded prior to overlaying the new overlaid information. By determining whether or not the distraction threshold is reached or exceeded prior to overlaying the new information, the system 6000 can prevent the display from overwhelming the OR personnel viewing the display, even if only momentarily. In the event the system 6000 determines that adding new overlaid information will not cause the amount of information to reach or exceed the distraction threshold, the system 6000 can proceed with overlaying the new information knowing that the distraction threshold will not be reached or exceeded. In the event the system 6000 determines that overlaying new information will cause the amount of information on the display to reach or exceed the distraction threshold, the system 6000 can take a positive action prior to overlaying the new information, such as removing overlaid information from the display, adjusting the overlaid information already on the display (such as by changing the size, as an example), among many other positive actions, as will be described in more detail herein below. By taking a positive action prior to overlaying the information, the system 6000 ensures that the distraction threshold isn't reached or exceeded on the display, even if only momentarily.

In some aspects, the system 6000 can take a positive action to reduce, control, or maintain the amount of information overlaid on the display such that the overlaid information does not reach or exceed the distraction threshold. In various embodiments, a situational awareness module, such as situational awareness module 6006, can determine, based on various sensors, such as sensor 90, imaging modules, such as imaging device 6004, or inputs, as described elsewhere herein, steps of the surgical procedure that have recently been completed, steps that are currently being performed, or steps that are soon to be completed, as examples, and prioritize and remove overlaid information according to these determined steps In one aspect, the system 6000 can prioritize the information overlaid, or to be overlaid, and remove information that is deemed less relevant or important. In some aspects, information can. be deemed less relevant, or irrelevant, when little to no information regarding a surgical step is being received by the situation awareness module 6006. In some aspects, information can be deemed more relevant or important when the situational awareness module is actively receiving updated data associated with the information to be overlaid. In some aspects, priority of information can be stored in a memory, such as memory 6003. In some aspects, priority can be based on industry standards, user preference, user experience, the type of surgical procedure being performed, or combinations thereof.

In one example embodiment, the system 6000 can receive data from an RF or ultrasonic generator indicating that an energy instrument is being fired. The situational awareness module 6006 can infer that the surgeon is in the process of dissecting patient tissue utilizing the energy instrument and, therefore, prioritize overlaying information associated with this step of the surgical procedure, such as measured impedance of the tissue, measured temperature of the tissue, measured energy output by the generator, as examples. In the event the amount of overlaid information reaches or exceeds the distraction threshold, the system 6000 can remove, or adjust, overlaid information that is deemed less relevant to the determined step of the surgical procedure currently being performed. In the above-reference embodiment, the situational awareness module 6006 can identify that no inputs indicative of a surgical stapling operation are currently being received, and therefore, information regarding surgical stapling steps can be removed from the display. In some aspects, the system 6000 can receive information that the situational awareness module 6006 deems irrelevant to the current step of the surgical procedure, and therefore, the system 6000 can choose to not overlay this information on the display. In one example embodiment, a surgeon can be performing a surgical stapling operation on patient tissue. During the stapling operation, the system 6000 can detect, via a temperature sensor, a change in the temperature level of the tissue. The system 6000 can determine that the change in temperature is less relevant, or irrelevant, to the surgical stapling procedure and therefore, cannot overlay this information on the display.

In various embodiments, when the system 6000 determines that overlaid information is to be removed from the display, or the system 6000 deems information irrelevant, or less relevant, to overlay on the display, the system 6000 can overlay the information onto a secondary display such that the information is still visible to the surgical staff. In one aspect, the OR can have primary display where the most relevant information is displayed and a secondary display where secondary information is displayed. Removed and/or less relevant information can removed from the primary display and overlaid onto the secondary display such that this information is still available, if necessary. In some example embodiments, the surgical staff can determine that information on the secondary display is more relevant than determined by the system. Accordingly, the surgical staff can provide an input to the system, such as at an input interface, like a keyboard, that shifts the information from the secondary display to the primary display. Similarly, the surgical staff can determine that information on the primary display is less relevant than determined by the system. Accordingly, the surgical staff can provide an input to the system, such as at an input interface, that shifts the information from the primary display to the secondary display. This provides the surgical staff with the ability to manually shift priorities of information in real-time during the surgical procedure.

In one aspect, the system 6000 can adjust the amount of information overlaid based on user provided inputs. For example, a user can provide inputs to the system 6000 that can be used when determining what information to overlay and what information to remove. In one example embodiment, the user can assign priority levels to types of information prior to, or during, a surgical procedure that the system 6000 can then use when determining what information to remove or adjust. In one example embodiment, the system 6000 can assign priority levels to overlaid information based on predefined parameters associated with the user, such as the user's experience level, the user's age, the user's eye sight, the user's preferences, as examples. In another example embodiment, the user can provide inputs to the system 6000 instructing the system which information to never to overlay, or only overlay in certain scenarios, as determined by the situational awareness module. In another example embodiment, the user can provide inputs to the system 6000 instructing the system which information to always overlay, regardless of the scenario. As one example, a user can instruct the system to always overlay the patient's heart rate. In such embodiments, even if the patient's heart rate is determined to be less relevant for the current surgical step, the information will not be removed from the display. In other such embodiments, if the patient's heart rate is determined to be less relevant by the system 6000, but the user instructs that the heart rate information remain overlaid, the system can, instead, change a size of the heart rate overlay, or change a position on the display of the heart rate overlay, as explained in more detail herein below.

In some aspects, the system 6000 can adjust overlaid information in combination with, or in the alternative to, removing overlaid information from the display. In some embodiments, the system 6000 can adjust a size of a portion of the overlaid information on the display. In one aspect, the system 6000 can increase a size of relevant information, such as information deemed relevant by the situational awareness module, user provided inputs, predefined inputs, or combinations thereof. Increasing the size of the information can include increasing the total area occupied by the overlaid information on the display or increasing the font size of the overlaid information, as examples. In one aspect, the system can decrease a size of information that is deemed less relevant, such as information deemed less relevant by the situational awareness module, user provided inputs, predefined inputs, or combinations thereof. Decreasing the size of the information can include decreasing the total area occupied by the overlaid information on the display or decreasing the font size of the overlaid information, as examples. In some embodiments, the system 6000 can adjust a weight of a portion of the overlaid information on the display, such as by bolding or unbolding information based on their relevance.

In some embodiments, the system 6000 can adjust a position of a portion of the overlaid information on the display. In one aspect, the system 6000 can adjust the position by positioning more relevant or important information in a readily visible area of the display, such as near the center of the display, or near the area on the livestream where the surgeon is currently working, as examples. In one aspect, the system 6000 can adjust the position by positioning less relevant or less important information in a less-readily visible area of the display, such as on the corners or sides of the display, or an area away from where the surgeon is currently working in the livestream, as examples.

In some example embodiments, when the system 6000 is determining which overlaid information to remove such that the overlaid information remains below the distraction threshold, the system 6000 can consider adjustments already made to overlaid information when determining what information to remove. In one example embodiment, the system 6000 can receive a signal indicative of new information to overlay on the display. The system 6000 can determine that the new information is relevant (according to a determination from the surgical awareness module) and overlaying the same will cause the distraction threshold to be reached or exceeded, and therefore, the system 6000 needs to remove or adjust information on the display to accommodate the new relevant information. When assigning priority or relevancy levels to information already overlaid (such as based on user input or the determined step of the surgical procedure being performed, as example), the system 6000 can evaluate whether certain portions of the overlaid information have already been adjusted. In one example embodiment, that system 6000 can determine that the overlaid patient's heart rate information has already been reduced in size and repositioned to a corner of the display. In some embodiments, the system 6000 can determine that the patient's heart rate, having already been lowered in priority (having been already twice adjusted), can be removed from the display. In some other embodiments, the system 6000 can determine that the patient's heart rate has already been adjusted twice, and therefore, the system 6000 should evaluate whether other information on the display can be adjusted before deciding to remove the patient's heart rate information.

In some aspects, the system 6000 can assign an amount to which information can be adjusted before being removed from the display. In various embodiments, a user can assign degrees of adjustment that can done before information is removed from the display. In one example embodiment, a user can instruct the system 6000 that information can be reduced in size until it occupies a lower threshold area of the display, such as 10% of the display. Once the system 6000 determines that the information needs to be reduced in size such that it occupies less than the threshold area of the display, such as 5% of the display, the system 6000 can instead remove the information. The above-provided degrees of adjustment allow the system 6000 to confidently remove information from the display such that portions of the display are not occupied by information only occupying small amount of the display.

In some embodiments, the system 6000 can provide auditory feedback to a surgeon or members of the OR while completing a task rather than overlaying information, or constantly adjusting overlaid information, on the display. In one aspect, for a tissue manipulation task, rather than having a visual on the display, the system 6000 can provide an auditory signal as feedback to minimize distractions on the display. In one example embodiment, the task can be to navigate tissue and/or a surgical instrument to a target location. The target location can be provided on the display. The system 6000, using the imaging device 6004, position sensors, accelerometers, a visualization system, any number of position tracking systems provided by the present disclosure, or combinations thereof, can be used to track the location of the tissue and/or the surgical instrument and provide an auditory tone as the task is being completed (i.e., as the tissue and/or surgical instrument is navigated to the target area). In various embodiments, the visualization system can be similar to visualization systems described in U.S. Pat. No. 11,000,270, U.S. Patent Application Publication No. 2020/0015900, U.S. Patent Application Publication No. 2020/0015899, U.S. Pat. No. 11,259,793, U.S. Patent Application Publication No. 2020/0015924, U.S. Patent Application Publication No. 2020/0015898, U.S. Patent Application Publication No. 2020/0015906, U.S. Patent Application Publication No. 2020/0015907, U.S. Pat. No. 10,925,598, U.S. Patent Application Publication No. 2020/0015914, and U.S. Patent Application Publication No. 2020/0015902, which are hereby incorporated by reference in their entireties herein.

In one example embodiment, the auditory feedback module can increase a volume, a speed, or a combination thereof, as the target area is being approach by the tissue and/or surgical instrument. In another example embodiment, the auditory feedback module can decrease a volume, a speed, or a combination thereof, as the tissue and/or surgical instrument is moved away from the target area. In another example embodiment, the auditory feedback module can provide an auditory tone that informs the surgeon that the target area is being completed. In another example embodiment, the auditory feedback module can provide an auditory signal indicative of the task being completed. In one aspect, the system 6000 can provide the auditory tones, via the auditory feedback module, without adjusting the overlaid information on the display, so as to minimize distractions thereon while completing the task.

By providing auditory tones in lieu of constantly updating information on the display, additional value is provided to the OR staff as the staff that is not focused on the display that the surgeon was looking at could provide indication that they completed the job and they need to be ready for the next step. For example, for a task involving stapling tissue, an auditory tone indicating that the stapler has been fired can notify the nurse that the surgical stapler is ready to handoff and to be replaced with a new staple cartridge for the next staple firing. This can eliminate the need for the surgeon to ask for the reload and keep focus on the surgical site.

As referenced above, the system 6000 can adjust or control the amount of information on the display based on, among other things, an experience level of the user. In one aspect, a user can provide their experience level to the system via an input interface and the system can retrieve parameters associated with the information to overlay according to the provided input. In one example embodiment, the user can provide a numerical input to the system that corresponds to their experience level (i.e., an input of '1' corresponds to a surgeon with 5+ years of experience, an input of '2' corresponds to a surgical resident, an input of '3' corresponds to a medical student, as examples.). In other example embodiments, the user can manually enter their years of experience. In other example embodiments, the user can enter their level of education. In other example embodiments, the user can enter the number of times in which they've performed the particular surgical procedure. In other example embodiments, the user can provide a confidence level associated with the particular surgical procedure. Based on the provided input, the system 6000 can retrieve, from the memory 6003, predefined parameters associated with the provided experience. In some aspects, the predefined parameters can include a distraction threshold, as explained elsewhere herein, to be used during a surgical procedure. In one example embodiment, a surgeon with several years of experience can have a higher distraction threshold than compared to a medical student, who requires may more information, but also requires less distractions to maintain their focus. In other aspects, the predefined parameters can include types of data to overlay during the course of a surgical procedure. In one example embodiment, for a less experienced user, the information to be overlaid could indicate anatomy overlays, warnings, steps for use of each step of the surgical procedure, confirmation that steps were completed, contradictions to expected results or steps of the surgical procedure, as examples. In another example embodiment, a more experienced user may not require certain overlays, such as anatomical overlays, warnings, confirmation that steps were completed, as examples, and therefore, these overlays will not be provided.

In various embodiments, the system 6000 can control what information is being overlaid based on surgical devices that are actively being used by the surgeon or the staff. In some aspects, the system 6000 can determine what surgical devices are actively being used based on data received from sensors and modules within the OR. In one example embodiment, the system can determine an energy device is actively being used based on data received from the generator module 40. In one example embodiment, the system can determine a vacuum module is actively being used based on data received from the smoke evacuation module 26. In one example embodiment, the system can determine a suction or irrigation module is actively being used based on data received from the suction/irrigation module 28. In one example embodiment, the system can determine a surgical device is actively being used based on data received from the sensor module 29. In one example embodiment, the system can determine a surgical device is actively being used based on data received from an imaging module 25. In one example embodiment, the system can determine a surgical device is actively being used based on inferences made from the situational awareness module. In one example embodiment, the system can determine that a device is actively being used based on the system receiving a signal indicative of a pairing occurring between a user-worn identifier and a surgical instrument, as explained in U.S. Pat. No. 10,758,310, which is hereby incorporated by reference in its entirety herein. In various embodiments, the system 6000 can determine what surgical devices are being actively used based on various sensors, modules, and input devices described herein, alone or in combination with each other. Once the system 6000 has determined what surgical devices are actively being used, the system 6000 can prioritize information associated with these surgical devices when deciding what information to overlay on the display. In one aspect, when the system 6000 determines a surgical device 6000 is actively being used, the surgical system can assign a higher priority level to information associated with the actively used surgical device when compared to information associated with other surgical devices that are not actively being used.

In various embodiments, the system 6000 can evaluate, determine, and control what information is overlaid on the display based on a series of predetermined conditions, user provided conditions, or conditions stored in a memory. In one aspect, when determining what information should be overlaid, the system 6000 can analyze inputs from various modules, sensors, and user input devices and determine what information to overlay based on what information would be useful to the surgeon, what condition or states of operation would the surgeon want to track, and what surgical jobs require conformation in the surgeon's mind that are worth tracking, among others. In one example embodiment, after the completion of a staple firing stroke with a surgical stapling device, the system 6000 can determined, based on the series of predetermined conditions, user provided conditions, and/or conditions stored in a memory, that the surgeon would want to inspect the staple line to ensure that the stapling stroke with successful. At this point, the display could zoom into the completed staple line to give the surgeon an optimal view, gray out or minimize everything else, or provide any necessary overlays to determine if the staple firing stroke was successful. With these predefined conditions, the system 6000 can determine that the focus at the present time should be on the task that was completed, therefore prioritizing information associated with the completion of this task and deprioritizing information irrelevant to the present task. The above-provided example could drive priority to the center of the display to ensure that no relevant information associate with the task is overlooked or missed by the surgeon.

In various embodiments, the system 6000 can assign priority on what information to overlay and what overlaid information to adjust or remove based on tasks associated with the surgical procedure being completed. In one example embodiment, the system 6000 can provide an overlay to confirm that a reload has been installed correctly, such a replacement surgical staple cartridge being reloaded into a surgical stapler. In another example embodiment, the system 6000 can provide an overlay indicating that a knife in a cutting instrument has reached its intended position, such as the end of stroke position, the beginning on stroke position, a middle of the stroke position, or any number or positions along the cutting path. In various embodiments, when the system 6000 determines that a tissue cutting step is to be accomplished (by way of inputs from any number of sensors, modules, user input interfaces, or by way of the situational awareness module, as examples), the system 6000 can overlay a trajectory of the intended staple line position to ensure that the staple line is captured between the jaws of the surgical cutting instrument. In various embodiments, the system 6000 can determine that tissue is being grasped by a surgical device and overlay a determined tissue thickness for a clinician's reference. In addition, the system 6000 can determine that a surgical stapling procedure is to be performed on the captured tissue (by way a user input or a situational awareness module, as examples) and overlay the appropriate staple reload to be used to staple the captured tissue.

In various embodiments, the system 6000 can assign priority on what information to overlay and what overlaid information to adjust or remove based on the criticality of the step of the surgical procedure being completed. In one example embodiment, when the system 6000 determines that tissue is being manipulated by a surgical device, the system 6000 can determine that it is critical to monitor the amount of force being applied to the tissue to ensure that the tissue isn't damaged. Accordingly, the system 6000 can drive priority toward overlaying information relating to the amount of force being applied to the tissue, which can be measured, by example, using a force sensor within the jaws of the tissue manipulator. In one example embodiment, when the system 6000 determines that tissue is being cut and stapled by a surgical stapling device, the system 6000 can determine that it is critical to overlay multiple pieces of information on the display, such as the position of the jaws, the thickness of the tissue, the pressure being applied to the tissue, a clock to ensure a sufficient amount of time was allowed for fluids to egress out of the clamped tissue being firing the surgical stapler, the firing force applied by the surgical staple, and/or the flow of tissue, as examples. The criticality of parameters associated with certain tasks of a surgical procedure can be predetermined, vary from user to user, such as based on experience level, preference, etc., or a combination thereof.

FIG. 35 illustrates a logic diagram showing operations of an example method 9000 for determining a display arrangement of surgical data competing for presentation onto a display, such as the display 6005, that is showing a livestream of a surgical field. In one aspect, the livestream can be captured by an imaging device, such as imaging device 6004, that is imaging a surgical field. The imaging device can be operably coupled to a control system, such as system 6000, which is also operably coupled to the display. The control system can transmit the livestream of the surgical field from the imaging device to the display such that surgical personnel can view the livestream on the display.

In various embodiments, the method 9000 includes overlaying 9005, on the livestream, a first amount of information associated with the surgical procedure being performed. In one aspect, the control system can receive inputs from various modules, sensors, user input devices, a situational awareness module, as examples, and overlay information associated with these inputs on the display.

In various embodiments, the method 9000 further includes detecting 9010 an event configured to cause the first amount of information being overlaid to increase to a second amount of information being overlaid. In one example embodiment, the situational awareness module can determine that a surgical stapling step is about to occur, which would drive the control system to overlay information associated with the surgical stapling step. Various other events that would cause the amount of information overlaid on the display are described elsewhere herein.

In various embodiments, the method 9000 further includes comparing 9015 the second amount of information to a distraction threshold. In one aspect, as described elsewhere herein, the distraction threshold can be predetermined, user provided, vary from user to user, as examples. In one example embodiment, the control system can evaluate the amount of area that the second amount of information would occupy on the display and compare this to the distraction threshold to determine if the distraction threshold will be reached or exceeded. As one example, the control system can determine that the second amount of information will occupy 60% of the viewable area of the display and the distraction threshold is defined as 50% of the viewable area of the display.

In various embodiments, the method 9000 further includes adjusting 9020 the second amount of information to a third amount of information based on the comparison, wherein the third amount of information is less than the distraction threshold. Continuing from the above provided example embodiment, the control system can determine that the second amount of information will occupy 60% of the viewable area of the display, which is greater than the 50% distraction threshold. Accordingly, the control system can adjust the overlaid information to ensure that the distraction threshold is not reached or exceeded. In one example embodiment, the control system can evaluate the information currently overlaid on the display and remove information that is determined to be irrelevant, or less relevant, based predetermined conditions, user provided conditions, or combinations thereof. In another example embodiment, the control system can evaluate the information currently overlaid on the display and adjust the information that is determined to be irrelevant, or less relevant, based predetermined conditions, user provided conditions, or combinations thereof. This adjustment could be changing a size thereof, a weight thereof, a position thereof, or combinations thereof, as described in greater detail elsewhere herein. In another example embodiment, the control system can evaluate the information currently overlaid on the display and both remove and adjust information that is determined to be irrelevant, or less relevant, based predetermined conditions, user provided conditions, or combinations thereof.

In various embodiments, the method 9000 can further include overlaying 9025, on the livestream, the third amount of information based on the second amount of information being adjusted. In one aspect, once the control system has determined an adjust to be made that will cause the overlaid information to not reach or exceed the distraction threshold, the control system can then adjust the overlaid information according to the determined adjustment. Continuing from the above-provided example embodiment where the second amount of overlaid information was to be 60% of the display, the control system can adjust the projected overlaid information such that only 45% of the display will be occupied by overlaid information, which is less than the 50% distraction threshold.

FIG. 36 illustrates a logic diagram showing operations of an example method 9100 for determining a display arrangement of surgical data competing for presentation onto a display, such as the display 6005, that is showing a livestream of a surgical field. In one aspect, the livestream can be captured by an imaging device, such as imaging device 6004, that is imaging a surgical field. The imaging device can be operably coupled to a control system, such as system 6000, which is also operably coupled to the display. The control system can transmit the livestream of the surgical field from the imaging device to the display such that surgical personnel can view the livestream on the display.

In various embodiments, the method 9100 includes overlaying 9105, on the livestream, a first amount of information associated with the surgical procedure being performed. In one aspect, the control system can receive inputs from various modules, sensors, user input devices, a situational awareness module, as examples, and overlay information associated with these inputs on the display.

In various embodiments, the method 9100 further includes determining 9110 a step of a surgical procedure being performed. In one aspect, the step of the surgical procedure can be determined by any number of inputs provided to a situational awareness module, such as data received from any number of sensors, modules, user inputs, or combinations thereof. Other examples for determining steps associated with a surgical procedure being performed as described elsewhere herein.

In various embodiments, the method 9100 further includes adjusting 9115 the overlaid information according to the determined step of the surgical procedure being performed. In one aspect, the control system can adjust a portion of the information currently overlaid on the display to assist the surgical personnel in completing the surgical task. In one example embodiment, the situational awareness module can determine that a tissue manipulation step is being performed on tissue, and therefore, the control system can adjust portions of the overlaid information that are relevant or irrelevant to the tissue manipulation step.

In one example embodiment, the control system can adjust the overlaid information by adjusting positions of the overlaid information on the display (i.e., moving overlaid information toward the center of the display, toward the edges of the display, toward or away from the spot in which the current step of the surgical procedure is being performed, as examples). In one example embodiment where tissue manipulation is occurring, overlaid information associated with force applied to the tissue can be moved toward the center of the display while information associated with tissue stapling operations can be moved to the edge of the display.

In one example embodiment, the control system can adjust the overlaid information by adjusting a size of the overlaid information on the display (i.e., increasing a front size of the information, decreasing a font size of the information, increasing the total area occupied on the display by the information, or decreasing a total area occupied on the display by the information, as examples). In one example embodiment where tissue manipulation is occurring, overlaid information associated with force applied to the tissue can increase from occupying 10% of the viewable area of the display to 20% of the viewable area of the display while information associated with tissue stapling operations can be decreased from occupying 20% of the viewable area of the display to 10% of the viewable area of the display.

In one example embodiment, the control system can adjust the overlaid information by adjusting a weight of the overlaid information on the display (i.e., bolding or unbolding information, as examples). In one example embodiment where tissue manipulation is occurring, overlaid information associated with force applied to the tissue can be bolded while information associated with tissue stapling operations can be unbolded.

In one example embodiment, the control system can adjust the overlaid information by adding or removing overlaid information on the display. In one example embodiment where tissue manipulation is occurring, the control system can detect that nothing is being overlaid on the display regarding pressure applied to the clamped tissue (determined, for example, by a force sensor in the jaws of the tissue manipulator). The control system can adjust the display to overlay information regarding the force applied to tissue, while also removing information relating to a tissue stapling operation.

In one aspect, the above-described adjustments can be made while also considering a distraction threshold. For example, the system 6000 can determine what kinds of adjustments to be made based on both the determined step of the surgical procedure and the distraction threshold such that the distraction threshold is not reached or exceeded. In the event that an adjustments will cause the distraction threshold to be reached or exceeded, the system can take an alternative adjustment. In one example embodiment, the control system can determine that adding information relevant to the surgical procedure will cause the distraction threshold to be reached or exceeds, and therefore, the control system can cause information less relevant to be decreased in size or removed from the display so as to avoid exceeding the distraction threshold. Any variety or combination of adjustments described herein above can be made such that relevant information is provided to the user without exceeding a distraction threshold, thus overwhelming the user with information.

FIG. 37 illustrates a logic diagram showing operations of an example method 9200 for determining a display arrangement of surgical data competing for presentation onto a display, such as the display 6005, that is showing a livestream of a surgical field. In one aspect, the livestream can be captured by an imaging device, such as imaging device 6004, that is imaging a surgical field. The imaging device can be operably coupled to a control system, such as system 6000, which is also operably coupled to the display. The control system can transmit the livestream of the surgical field from the imaging device to the display such that surgical personnel can view the livestream on the display.

In various embodiments, the method 9200 includes overlaying 9205, on the livestream, information associated with the surgical procedure being performed. In one aspect, the control system can receive inputs from various modules, sensors, user input devices, a situational awareness module, as examples, and overlay information associated with these inputs on the display. Other examples for determining steps associated with a surgical procedure being performed as described elsewhere herein.

In various embodiments, the method 9200 can further includes receiving 9210 an input signal that corresponds to a parameter associated with a user performing the surgical procedure. In one aspect, a surgeon, prior to or during the surgical procedure, can provide an input to the control system, such as at a keyboard or a computer, an audible command, or combinations thereof. In one aspect, the input can correspond to the identity of the user, the user's experience level, the user's age, the use's eye sight, the user's preferences, or combinations thereof, as examples.

In various embodiments, the method 9200 can further includes adjusting 9215 the overlaid information according to the parameter associated with the user. In one aspect, the parameter associated with the user can be the user's experience level. In some embodiments, the user can manually enter their experience level. In one aspect, the experience level can include a number of years of experience, a comfort level with the procedure, a position within the hospital (surgeon, resident, intern, as examples), or combinations thereof. In some embodiments, the control system can adjust the overlaid information according to this experience level. In one example embodiment, a first user with a first level of experience can have a first amount of information overlaid on the display and a second user with a second level of experience can have a second amount of information that is different than the first amount of experience overlaid on the display. In another example embodiment, a first user with a first level of experience can have a first type of information overlaid on the display and a second user with a second level of experience cannot have the type of information overlaid on the display. In some embodiments, a first user with a first level of experience can have a first amount of information and a first type of information overlaid on the display and a second user with a second level of experience can have a second amount of information that is different than the first amount of experience, as well as not have the first type of information, overlaid on the display. The control system can adjust the overlaid information according to the experience level such that user's with less experience can have more information, or more focused information, overlaid on the display, whereas user's with more experience can have less information, or only certain types of information, overlaid on the display.

Although all types of information can be valuable to the surgical staff at some point of the surgical procedure, when everything is important nothing is important. The above-provided disclosure allows surgical staff to be presented with meaning, relevant information on a display without being overwhelmed with large sums of information that cause surgical personnel to become distracted or lose focus during a surgical procedure.

In view of the foregoing problems associated with competing amounts of information to be overlaid on a display, the present disclosure provides a system, such as system 6000, that can monitor, sense, and/or detect the occurrence of triggering events that occur before, during, or after a surgical procedure so as to control the information that is overlaid on the display. In one aspect, triggering events can be events detected by the system, via any number of sensors, systems, or module described elsewhere herein, that can initiate changes in the information that is overlaid on the display. In various embodiments, detection of a triggering event can cause information to be added to the display, removed from the display, or adjusted on the display, such as moving the information to a different position on the display or adjusting a size that the information occupies on the display, as examples, and will be described in greater detail elsewhere herein.

In one aspect, the system can detect recognition based triggers, via a surgical visualization system, such as visualization system 8, and update overlaid information on the display accordingly. In various embodiments, the visualization system 8 can be similar to visualization systems described in U.S. Pat. No. 11,000,270, U.S. Patent Application Publication No. 2020/0015900, U.S. Patent Application Publication No. 2020/0015899, U.S. Pat. No. 11,259,793, U.S. Patent Application Publication No. 2020/0015924, U.S. Patent Application Publication No. 2020/0015898, U.S. Patent Application Publication No. 2020/0015906, U.S. Patent Application Publication No. 2020/0015907, U.S. Pat. No. 10,925,598, U.S. Patent Application Publication No. 2020/0015914, and U.S. Patent Application Publication No. 2020/0015902, which are hereby incorporated by reference in their entireties herein.

In one aspect, recognition based triggers can be, for example, objects (surgical instruments, surgical implants, surgical structures, organs, tissue, etc.) with predefined and/or identifiable sizes, shapes, patterns, colors, arrangements, or any other identifiable features that are unique to the object. In various embodiments, the system can include a memory, such as memory 6003, that stores data associated with the object therein, such as images and/or parameters associated with the objects, for comparison against objects that are captured by an imaging device, such as imaging device 6004, during a surgical procedure. In one aspect, the memory can store two-dimensional images of the objects therein, such as top views, bottom views, side views, isometric views, or any other suitable two-dimensional view of the object, as examples. In one aspect, the memory can store three-dimension models, such as CAD models, of the objects therein so that any number of image views are available to the system for comparison. In one aspect, the three-dimensional models can be generated using pre-operative imaging techniques, such as CT scans or MRI scans, using visualization system 8.

In one example embodiment, the system can identify, via the imaging device, an object in a livestream. The system can compare an image of the object and parameters thereof (color, dimensions, etc.) that can be identified by the system to the images and parameters stored in the memory to determine if the object is a known object. In the event of a match, or at least a substantial match, the system can overlay information on the display associated with the object identified in the livestream.

In one example embodiment, the imaging device can capture a natural surface feature, such as the incisura angularis of the stomach, in a livestream. The system can transmit a visual representation of the livestream to a display such that the natural surface feature can be seen by the surgical staff. The system can further compare the image and determined parameters of the natural surface feature to images and parameters stored in the memory to determine if the natural surface feature is a known natural surface feature. In the event of a positive identification of the natural surface feature, the system can overlay information on the display associated with the natural surface feature. In one aspect, the information associated with the natural surface feature can be stored in the memory. In one aspect, the overlaid information can be overlaid on top of the natural surface feature on the display. In one aspect, the overlaid information can be overlaid near the natural surface feature on the display such that the overlaid information is readily seen, but does not obstruct the view of the natural surface feature on the display. In one aspect, the overlaid information can be overlaid in a predetermined location on the display designated for positive identifications in the livestream, such as a corner of the display.

In one aspect, as described above, the object in the livestream can be a natural surface feature. In one aspect, the object in the livestream can be a surface feature of a surgical instrument, such as a surgical staple cartridge. In one aspect, the object in the livestream can be a marker, such as a barcode, an emblem, a pattern, or the like. In one aspect, the object in the livestream can be any number of objects that the system can compare to images and parameters of the objects stored in the memory.

In one aspect, the system can overlay information on the display based on a partial identification on an object in the livestream. In one aspect, the system can identify objects in the livestream that meet a threshold acceptance limit and overlay information on the display if the threshold acceptance limit is reached or exceeded. In one aspect, the threshold acceptance limit can be predefined, stored in a memory, user defined, based on industry standards, or combinations thereof. In the event that the threshold acceptance limit is not reached, the system can not overlay information on the display.

In one example embodiment, the system can identify a portion of a staple cartridge in the livestream. In one aspect, the staple cartridge could be obstructed, or partially out of frame, on the livestream, such that only the portion of the staple cartridge is visible. The system can compare the viewable portion of the staple cartridge to images and parameters of staple cartridges stored in the memory. In one aspect, parameters of the staple cartridge can be color of the cartridge, viewable/identifiable dimensions of the cartridge, such as distance between staple cavities or the length of the elongate slot that the cutting knife traverses, the number of staple cavities, or any other identifiable parameter associated with the staple cartridge. In the event the system determines that that the portion of the staple cartridge reaches or exceeds a threshold acceptance limit compared to a surgical staple cartridge stored in the memory, as will be described in more detail below, the system can overlay information on the display based on the determination.

In some embodiments, a threshold acceptance limit can be defined as a percentage of the image or parameters thereof stored in the memory that has been identified in the livestream. In one example embodiment, the system can identify a portion of a staple cartridge in the livestream. The system can analyze the image and determine that 75% of a staple cartridge stored in the memory has been identified on the object from the livestream. In one embodiment, the system can have, for example, a threshold acceptance limit of 50%, which has been exceeded by the comparison between the object in the livestream and the images stored in the memory. Accordingly, information associated with the staple cartridge can be overlaid on the display. In various embodiments, the threshold acceptance limit can be stored in a memory, be user defined, vary from user to user, be based on standard industry practices, or combinations thereof.

In some embodiments, the threshold acceptance limit can be defined as a threshold number of parameters that have been identified based on a comparison of the object identified in the livestream and an object stored in the memory. In one example embodiment, the system can identify a portion of a staple cartridge in a livestream. The system can identify various parameters of the staple cartridge, such as the color, the spacing between staple cavities, known marks thereon, or any other identifiable feature of the staple cartridge. The system can identify these parameters and compare the same to parameters stored in the memory, such as parameters stored in a look-up table. In one aspect, the threshold acceptance limit can be set to 3 matches between the object identified in the livestream and an object stored in the memory. In the event that the system determines that the threshold acceptance limit has been reached or exceeds (such as identifying the color of the staple cartridge, identifying the staple cavity spacing, viewing a known emblem thereon, as an example), the system can overlay information on the display according to the match. In various embodiments, the threshold acceptance limit can be a combination of a percentage of an object identified in the livestream and a number of parameters of the object that have been identified. In one example embodiment, the threshold acceptance limit can be 50% of the object in the livestream matching an object stored in the memory and 3 parameters matching the object stored in the memory.

In one aspect, the system can overlay a confidence level associated with the identified match. As described herein above, the system can identify partial matches in the livestream and overlay information when a threshold acceptance limit has been reached or exceeded. In the event of a partial match, the system can overlay a confidence level, or percentage, with the overlaid information. In one example embodiment, a staple cartridge stored in a memory can have 8 parameters associated therewith, but the threshold acceptance limit is set to only 3 matches. In the event that the system identifies 3 positive matches of the 8 parameters in the staple cartridge in the livestream, the system can overlay information about the staple cartridge on the livestream. In addition, the system can overlay a note identifying that the overlay is based on 3 of 8 parameters being identified, i.e., not a complete match. By overlaying a confidence level, surgical personnel viewing the display can utilize their own judgement on whether or not they agree with the determination. In various embodiments, the system can include a user interface that allows the surgical staff to accept or decline the overlaid information, thereby giving the staff the ability to remove the overlaid information if they disagree with the assessment or do not require the overlaid information.

In various embodiments, the system can overlay information on the livestream according to the identified object on the livestream. In one aspect, the system can overlay markers identifying various regions or features of the object based on a positive identification. In one example embodiment, when the system identifies the object as being the stomach, the system can overlay markers pointing to the greater curvature, the lesser curvature, the incisura angularis, as examples. In one aspect, the system can overlay a segmented overlay on the object identifying various regions of the object. In one example embodiment, the system can identify the stomach and overlay a segmented overlay that identifies the fundus, the body, the pyloric antrum, the pyloric canal, and the duodenum, as examples.

In one aspect, the system can overlay directional information on the livestream based on a positive identification. In one example embodiment, in the event the system identifies the incisura angularis, the system can overlay directional arrows that assist a surgeon in finding other areas of the stomach, such as the greater curvature, or other organs in the patient, such as the intestines. In one aspect, the directional arrows can be based on both the identified object, as well as the orientation or angle, at which the object was identified. In some aspects, the directional arrows can be based on a determined step of the surgical procedure. In one example embodiment, in the event the current step of the surgical procedure requires the surgeon to be looking at the greater curvature, but the surgeon is currently looking at the incisura angularis, the system can overlay a directional arrow indicating what direction the surgeon need go in order to reach the greater curvature.

In one aspect, the system can overlay information regarding known parameters or features of the object. In one example embodiment, the system can identify a green surgical staple cartridge in the livestream. In the event of a positive identification, the system can overlay parameters on the livestream associated with the identified staple cartridge, such as the size of the staples, the staple material, the tissue thickness intended for use with the identified staple cartridge, and combinations thereof, as examples.

In one aspect, the system can overlay information on the display according to an identified orientation of the object identified in the livestream. In one example embodiment, the system can identify an object in the display, based on a comparison of the object to data associated with objects stored in the memory. In one embodiment, the system can identify that the object is being viewed at a first orientation, such as a side view of the object, and trigger a first overlay adjustment. In another embodiment, the system can identify that the object is being viewed at a second orientation, such as a top view of the object, and trigger a second overlay adjustment that is different than the first overlay adjustment. In one embodiment, the system can identify that the object is being viewed at a first orientation, such as at a 30 degree angle relative to an upright position thereof, and trigger a first overlay adjustment. In another embodiment, the system can identify that the object is being viewed at a second orientation, such as at a 15 degree angle relative to an upright position thereof, and trigger a second overlay adjustment that is different than the first overlay adjustment.

In one aspect, the system can include interactive sensors and the triggering event can be a user interacting with the interactive sensor. In various embodiments, the interactive sensor can be an audible sensor and the triggering event can be the system identifying, via the audible sensor, a known sound, word, phrase, or the like, that can be stored in the memory. In one example embodiment, a surgeon can say "re-focus" and the system can detect the word, via the audible sensor, and update the overlaid information on the display based on the identified word. In various embodiments, the triggering event can be based on predefined movements captured by the imaging device. In one aspect, the predefined movements can be stored in a memory and compared to movements captured by the imaging device. In one example embodiment, the surgeon can move an end effector of a surgical instrument in a circular motion, the system can detect the circular motion in the livestream, and update the overlaid information on the display, based on the detected motion. In various embodiments, the adjustment that the system makes to the overlaid information according to the detected interaction can be stored in the memory. In one example embodiment, a surgeon can say "clear" and the system can determine, based on data stored in the memory, that "clear" means that the surgeon wants all overlaid information on the display to be removed.

In some aspects, the adjustment that the system makes to the overlaid information according to the detected interaction can be based on an identified step of the surgical procedure. In various embodiment, a situational awareness module, such as situational awareness module 6006, can determine a step of the surgical procedure being performed, based on one or more inputs received by the system. Based on the interaction provided by the user and the determined step of the surgical procedure, the system can adjust the overlaid information on the display accordingly. In one example embodiment, the surgeon can provide an audible command, such as a sound, to the system. The system, via the situational awareness module, can determine that a particular step of a surgical procedure is being performed. The system can compare the sound to sounds stored in the memory. In one aspect, the memory can store various executable instructions to perform based on both the detected sound and the determined step of the surgical procedure. In one aspect, a certain sound can cause a first adjustment to the overlaid information for one determined step and a second adjustment to the overlaid information for a second determined step, where the first and second adjustments are different. In various embodiment, an audible command can cause the same adjustment to the overlaid information independent of the determined step of the surgical procedure.

In one aspect, the system can detect location based triggers that cause overlaid information on the display to be adjusted. In various embodiments, the system can include various sensors and visualization systems, such as those described elsewhere herein, that can track and/or determine positions of various components and/or individuals associated with the surgical procedure. In one aspect, the system can utilize GPS for determining positions of various components and/or individuals. In one aspect, the system can include a digital compass for determining positions of various components and/or individuals. In one aspect, the system can include sensors for measuring velocity data and acceleration data (such as an accelerometer, as an example) for determining positions of various components and/or individuals. In one aspect, the components and individuals for tracking can include position sensors that are capable of being tracked by the system. The above-provided position tracking techniques can be used alone and in combination with each other for the purposes of identifying positions of components and/or individuals within or outside of the OR.

In one example embodiment, a surgeon can be working thru a colorectal sigmoidectomy mobilization using a surgical cutting device and viewing a livestream thereof on a display. The system can detect, via any number of position tracking techniques, as referenced above, when the end effector of the surgical cutting device is approaching the transection point of the blood supply. Based on the system detecting that the end effector is approaching, or has reached, the transection point, the system can adjust the display to overlay information to aid in the upcoming step of the mobilization. As one example, the system can overlay the location and directionality of the blood flow and to where the blood feeds based on inputs from a surgical visualization system to the system, thereby aiding in the visualization of the next step of the procedure.

In various embodiments, the system can detect, via any number of position tracking techniques, as referenced above, a position of an individual, or a group of individuals, within or outside of the OR and adjust the overlaid information on the display based on their detected position(s). In one aspect, the system can monitor a position of an individual, such as a nurse, within the hospital, that has a display, such as a wearable AR device 66, as an example. Although the proceeding discussion will be in the context of the wearable AR device, it should be understood that any other display described herein can be used in the alternative to achieve the same results. In various embodiments, instead of an AR device 66, the nurse could have a tablet, a cell phone, or any other portable display, as examples.

In various embodiments, the system can detect the position of the individual with the portable device relative to any number of locations. In one aspect, the system can detect when the individual is approaching, or has arrived, at a location, and adjust the information overlaid on the AR device 66 accordingly. In one example embodiment, when the nurse wearing the AR device 66 arrives at a location, such at the door of a stock room, the system can overlay information on the lens of the AR device associated with the stock room. In one embodiment, the system can overlay what room is behind the door. In one embodiment, the system can overlay what surgical equipment is stored in the stock room. In one embodiment, the system can overlay if the stock room includes required equipment for a surgical procedure, based on a detected step of the surgical procedure by the system. In various embodiments, the system can overlay any amount of information useful to the individual for retrieving desired pieces of equipment for a surgical procedure. In one aspect, the system can overlay information based on a detected step of a surgical procedure, such as directional information indicating where certain pieces of equipment can be obtained for completing the step of the surgical procedure. In various embodiments, the system can overlay information based on a user input, such as a verbal command, inquiring if a certain piece of equipment can be found at the identified location. Information regarding locations, such as what equipment can be found at the locations, can be stored in a memory.

In various embodiments, the system can determine steps of a surgical procedure that are being performed, or are soon to be performed, and adjust the overlaid information on the AR device according to the determination. In one example embodiment, the system can determine, via the situational awareness module, that a surgical stapling step is soon to be performed and a particular type of staple cartridge will be required. The system can overlay, on a nurse's AR device, as an example, that the particular type of staple cartridge will soon be needed. The system can further overlay on the AR device, for example, where the staple cartridge can be found, what the staple cartridge looks like, a model number of the staple cartridge, or any other suitable identifying information that would aid the nurse in acquiring the staple cartridge. The system can further overlay, on the AR device, directional information to aid the nurse in finding the staple cartridge. In one example embodiment, the system can overlay information as to where the staple cartridge can be found, such as a room number, a shelf number, a bin number, or any other suitable descriptive information as to where the staple cartridge can be found. In one example embodiment, the system can utilize position tracking techniques, such as GPS, and overlay directional arrows on the lens of the AR device to visually direct the nurse to where the staple cartridge can be retrieved. In one aspect, the system can overlay highlights on key features to aid in retrieving the staple cartridge. In one example embodiment, when the door of the stock room that the staple cartridge is stored in comes into the field of view of the AR device, the system can highlight the door to inform the nurse that the staple cartridge can be found behind the highlighted door. Any combination of the above-referenced embodiments can be used in combination with each other to aid in identifying a location of desired equipment.

In various other embodiments, the AR device can adjust the overlaid information based on the surgical procedure, the determined surgical steps of the surgical procedure, the surgeon's preferences, user inputs, such as physical or verbal inputs, or combinations thereof. In one example embodiment, when a nurse enters a stock room wearing the AR device, the system can adjust the overlaid information to point to, or highlight, pieces of equipment based on the surgical procedure, the determined surgical steps of the surgical procedure, the surgeons preferences, user inputs, such as physical or verbal, or combinations thereof. In one aspect, the system can adjust the overlaid information to highlight pieces of equipment in the stock room that are currently missing from the OR that are needed, or will be needed, for the surgical procedure. In one aspect, the system can adjust the overlaid information based a verbal request from the nurse inquiring on where a particular piece of equipment is located. Based on the request, the system can adjust the overlaid information accordingly. In one aspect, the system can highlight the requested item brighter, or more intensely, than the other highlighted items in the stock room. In another example embodiment, the system could unhighlight everything except for the requested piece of equipment.

In various embodiments, the system can track the location of the AR device and change the relevance of triggering events based on the location thereof. In one aspect, a first user can be wearing a first AR device and be at a first location and a second user can be wearing a second AR device and be at a second location. In one example embodiment, a triggering event can be detected that would cause the system to adjust the overlaid information. The system can detect that the first user is associated with the triggering event and that the second user is unassociated with the triggering event. In one aspect, the system can detect that the first user is within a certain distance at which the triggering event occurred and the second user is outside the certain distance at which the triggering event occurred. Based on the determination, the system can update the overlaid information of the first AR device, but not on the second AR device. In one example embodiment, a surgeon can be performing a surgical procedure wearing an AR device and a nurse can be retrieving a piece of equipment wearing an AR device. When the nurse arrives at the stock room (location based triggering event), the system can adjust information overlaid on the nurses AR device, while maintaining what is overlaid on the surgeons AR device. This selective adjustment in overlaid information prevents displays from being adjusted where the overlaid information may be of little or no value to particular individuals.

In various embodiments, the system can adjust information overlaid on the display based on any number of triggering events as detected by a visualization system, such as any number of the visualization systems described here. In one aspect, the system can adjust the overlaid information based on a determination of who is holding a particular surgical device. In one aspect, the system can adjust the overlaid information based on a particular surgical device coming into the field of view of the visualization system. In one aspect, the system can adjust the overlaid information based where a surgical device is relative to the patient. In one example embodiment, when a particular surgical device comes within a threshold distance of a patient, as determined by any number of inputs, such as the visualization system, position sensors, or any other position tracking techniques described herein, the system can adjust the display to overlay information related to the surgical device. In one example embodiment, when a particular surgical device exits a threshold distance of a patient, as determined by any number of inputs, such as the visualization system, position sensors, or any other position tracking techniques described herein, the system can adjust the display to remove overlaid information related to the surgical device. In one example embodiment, when a particular surgical device reaches a threshold distance of a patient, as determined by any number of inputs, such as the visualization system, position sensors, or any other position tracking techniques described herein, the system can adjust the display to add overlaid information related to the surgical device.

In various embodiments, the system can adjust information overlaid on the display based on determined prioritizations for surgical tasks. In one aspect, the system can determine a step of the surgical procedure, using for example, a situational awareness module, and adjust the importance, or the occurrence, of triggering events based on the determination. In one example embodiment, the system can determine, using the situational awareness module, that a surgical stapling step is being performed, or is to be performed. The system can monitor triggering events during the surgical stapling step and determine if adjustments to the overlaid information are required according to their determined relevance with the surgical stapling step. In one aspect, a triggering event, such as excess force being applied to the tissue being stapled, can be detected. The system can determine that the excess force is relevant to the current step of the surgical procedure and update overlaid information on the display accordingly. In one aspect, a triggering event, such as temperature of the tissue exceeding a temperature threshold, can be detected. The system can determine that the excess temperature is less relevant to the current step of the surgical procedure and can choose to not update the overlaid information based on the determination. In various embodiments, relevance of triggering events for steps of a surgical procedure can be stored in a memory, be used defined, be based on industry standards, or a combination thereof. In one aspect, when the system determines that information is less relevant to the current step of the surgical proceed, the system can overlay the information on the display, but adjust how much of the display the information overlays. In one example, when the system detects a triggering event that is less relevant the surgical step currently being performed. The system can overlay information associated with the step on the display, but overlay the information 50% of the size at which the overlaid information would normally occupy. In other embodiments, the system can overlay information associated with the step on the display, but position the information at a less readily visible portion of the display, such as in a corner or on an edge of the display.

In various embodiments, the system can adjust information overlaid on the display based on the criticality of the data to a user that is operating a surgical device. In one embodiment, the surgeon can utilize a surgical stapler to staple tissue. The system can detect excess force applied to the tissue, which the system deems critical, based on data stored in a memory, and adjust a display associated with the surgeon, such as an AR device 66, such that the excess force detection is made known to the surgeon utilizing the surgical stapler.

In various embodiments, the system can adjust information overlaid on the display based on the detection of a certain type of surgical device being used by a user. In one aspect, the system can adjust the overlaid information to inform the user of issues related to the particular surgical device being used so that the user can proceed knowing the potential failure points. As one example, the system can adjust the overlaid information to inform the user of how potential misuse of the surgical device can cause secondary failures, such as failures to other surgical devices. In various embodiments, this data can be stored in a memory. In various embodiments, this data can be accessible from a cloud-based system, such as cloud-based system 4.

In various embodiments, the system can adjust information overlaid on the display by moving information from a first display to a second display. In one aspect, the system can detect the occurrence of a triggering event that can cause a change in the overlaid information on a primary display in the OR. In various embodiments, this change in the overlaid information can be changing a size of a portion of the information, a weight of a portion of the information, a position of a portion of the information, removing overlaid information, adding overlaid information or combinations thereof. In one aspect, as a result of the adjustment, the system can move information deemed less relevant, such as less relevant to a particular surgical step being performed, from the first display to a second display, thereby keeping the information available to the surgical staff, but on a display that may not be the primary focus on the surgical staff.

In various embodiments, the system can adjust information overlaid on the display based on a detection that a triggering event was induced by a surgical instrument utilized by a particular user. In some aspects, the system can determine what surgical devices are actively being used by what surgical personnel based on data received from sensors, modules, and/or visualization systems within the OR. In one example embodiment, the system can determine an energy device is actively being used based on data received from the generator module 40. In one example embodiment, the system can determine a surgical device is actively being used based on data received from the sensor module 29. In one example embodiment, the system can determine a surgical device is actively being used based on data received from an imaging module 25, or any number of visualization systems described elsewhere herein. In one example embodiment, the system can determine a surgical device is actively being used based on inferences made from the situational awareness module. In one example embodiment, the system can determine that a device is actively being used based on the system receiving a signal indicative of a pairing occurring between a user-worn identifier and a surgical instrument, as explained in U.S. Pat. No. 10,758,310, which is hereby incorporated by reference in its entirety herein. In various embodiments, the system can determine what surgical devices are being actively used based on various sensors, modules, and input devices described herein, alone or in combination with each other.

In various embodiments, the system can detect triggering events that originate from surgical instruments actively controlled by a user and update the overlaid information on the display accordingly. In one example embodiment, the system can detect that a surgeon is actively using a tissue manipulator to manipulate tissue at a surgical location. The system can detect a tissue tension that exceeds a tissue tension threshold and determine that the tension was induced by the tissue manipulator associated with the surgeon. Based on the detected event and instrument origination, the system can adjust the overlaid information on the display, such as a wearable AR device worn by the surgeon.

In various embodiments, the system can detect triggering events that originate from outside of an active surgical instrument controlled by a user and update the overlaid information on the display accordingly. In one example embodiment, a liver retractor that is unassociated with a surgeon can be deployed and fixated to the liver while the surgeon is actively using two instruments for dissection of the liver. Based on the interaction of the two actively used instruments by the surgeon, a tissue tension in the liver can be induced due to the fixated retractor that exceeds a tension threshold. The system can detect the induced tissue tension by the retractor, such as using a visualization system, and adjust the overlaid information on the display, such as an AR device worn by the surgeon, despite the tissue tension event being induced by a component that is unassociated with the surgeon. Accordingly, the system can update the information on the AR device according to events that are induced by instruments, or actions, associated with or unassociated with a particular user.

In various embodiments, the system can adjust information overlaid on the display based on the detection of a risk event. In one aspect, a risk event can be an event that has at least some likelihood of causing an outcome that is unfavorable with regard to the surgical procedure. In one example embodiment, the risk event can be a detection of a particular type of device being used for a particular step of a surgical procedure. In another example embodiment, the risk event can be the end effector of a surgical instrument coming within a threshold distance of a critical structure, such as an artery, a vein, or a tumor, as examples, within the patient. In one example embodiment, the risk event can be the system detecting that a certain staple cartridge has been installed in a stapling device that is improper for the determined step of the surgical procedure. In some embodiments, the risk event can be an end effector of a surgical instrument articulating too far from an intended position. In any aspect, a detection of a risk event can cause the system to overlay a warning, or a corrective step, on the display explaining the detected risk event and possible remedies to avoid the risk event.

In various embodiments, the system can adjust information overlaid on the display based on the detection of an event that originates from outside of the field of view. In one aspect, an imaging device can capture a livestream of a surgical field and transmit the livestream to a display for the surgical staff to view. An event can be induced, or originate, from outside of the livestream of the surgical field, that would require the attention, or reaction, or a surgeon. In one example embodiment, a surgeon can be manipulating tissue that is visible in the surgical field on the display. As a result of the tissue manipulation, a portion of the tissue outside of the surgical field could tear as a result of a threshold tension being inadvertently applied to the tissue. The system can detect the tear, via, for example, a visualization system, and alert the surgeon that the tissue tear has occurred outside of the surgeon's field of view. This allows the surgeon to reposition the imaging device to the location of the tear and take appropriate action. In one aspect, the system can overlay directional information informing the surgeon where to look to find the event that originated outside of the field of view.

In various embodiments, the system can detect a triggering event that can cause an adjustment to the overlaid information on a wearable display. In some aspects, in addition to adjusting the overlaid information on the wearable display, the system can also adjust the overlaid information on various other displays in the OR such that individuals not wearing wearable AR devices can also view the adjusted overlays. In one example embodiment, the system can detect a triggering event that causes overlaid information on an AR device to be adjusted. In addition, the system can adjust the overlaid information on other displays in the OR, such as display 19, for surgical personnel not wearing AR devices 66 to view.

In various embodiments, the system can adjust the overlaid information on the display in any number of ways. In one example embodiment, upon occurrence of a triggering event, the system can overlay information regarding the state of a device accordingly to any number of sensors. In one example embodiment, upon occurrence of a triggering event, the system can overlay information regarding the heat or thermal profile of a device, which could be detected by temperature sensors. In one example embodiment, upon occurrence of a triggering event, the system can overlay information regarding a direction in which the imaging device should be moved to adjust the surgical field of view thereof. In one example embodiment, upon occurrence of a triggering event, the system can overlay information regarding danger areas, such as areas of tissue that should be avoided in order to avoid potential damage to the patient. In one example embodiment, upon occurrence of a triggering event, the system can overlay information regarding a state of the tissue as determined by any number of sensors. In one example embodiment, upon occurrence of a triggering event, the system can overlay information regarding external implants detected by the system, such as clips or staples implanted in a patient.

In various embodiments, the system can detect the occurrence of a packaging housing a surgical component being opened and adjust overlaid information on the display accordingly. In one example embodiment, the system can detect a packaging being opened that includes a surgical staple cartridge reload. The system can overlay information associated with the component within the packaging, such as implications for secondary packaging, such as staple retainers. In some aspects, the system can overlay information on the display such as a parameters associated with the component that is within the package, such as staple size, staple material, or intended tissue thickness to be stapled with the cartridge, as examples.

In various embodiments, the system can detect a surgical step of a surgical procedure and adjust the overlaid information accordingly. In one aspect, the system can detect a surgical step that subsequently requires a disposal step, such as disposing of an old surgical staple cartridge in an instrument and replacing the instrument with a new cartridge. In one example embodiment, the system can detect the completion of a stapling stroke and overlay instructions to the surgical staff that the cartridge needs to be removed and replaced. In one aspect, the overlaid information can further identify the type of replacement cartridge to utilize to complete the subsequent staple firing stroke. In various embodiments, the system can overlay information regarding where the surgical staple cartridge can be disposed.

In various embodiments, the system can adjust overlaid information based on monitored parameters associated with a patient reaching or exceeding a parameter threshold. In one aspect, any number of sensors or systems can monitor parameters associated with a patient, such as heart rate, and adjust the overlaid information accordingly. In one aspect, the system can monitor a value of various parameters and compare the values to parameters thresholds that are stored in a memory. In the event the value of the parameter reaches or exceeds a parameter threshold, the system can adjust the overlaid information to information the user of the occurrence of the threshold being reached or exceeded such that subsequent action can be taken. In some embodiments, the system can overlay corrective actions on the display that can aid in dropping the value of the parameter below the parameter threshold. In various embodiments, the system can monitor a rate of change of a parameter associated with a patient and adjust the overlaid information based on the rate of change reaching or exceeding a rate of change threshold.

In various embodiments, the system can detect an occurrence of a triggering event by detecting an accumulation of partial triggering events and comparing the accumulated events to a triggering event threshold. In one aspect, the system can set a triggering event count and count the number of occurrences of partial triggering events. In one example embodiment, the system can set the triggering event count to 0 at the start of a surgical procedure. In another example embodiment, the system can set the triggering event count to 0 at the start of a particular step of a surgical procedure. In one aspect, the system can rest the triggering event count back to 0 at the end of completed steps of the surgical procedure. In some embodiments, the triggering event count can be set to a value other than 0, such as 1, 2, 3, or any other suitable integer. In various embodiments, the system can set the triggering event count based on a user input, input from a situational awareness module based on a detected step of a surgical procedure, or combinations thereof.

In one aspect, the system can detect partial triggering events, adjust the triggering event count based on the occurrences of the partial triggering events, and adjust the overlaid information on the display based on the triggering event count reaching or exceeding a triggering event threshold. In one example embodiment, the system can set the triggering event threshold to 3 partial triggering events. The system can set the triggering even count to 0 at the onset of a detected tissue manipulation step. The system can detect tissue tensions induced in the manipulated tissue against a tension threshold and add 1 to the triggering event count at each occurrence of the tension threshold being reached or exceeded. In the event the triggering event count reaches or exceeds the triggering event threshold, the system can adjust the overlaid information on the display accordingly, such as issuing a warning to the surgical staff or providing corrective actions to ensure the tension threshold is not reached or exceeded.

The ability to detect and count partial triggering events enables the system to track events that, in isolation, may be minor or inconsequential, but an accumulation of which could lead to an event that is major or consequential. For example, in the above-referenced tissue manipulation step, inducing tissue tension that exceeds a tension threshold in isolation may not overly harm the patient tissue, but multiple occurrences could result in torn, or damaged tissue.

In various embodiments, the partial triggering events could include additive triggering events that add to the triggering event count and negative triggering events that subtract from the triggering event count. In the above-described example embodiment regarding tissue tension induced by a tissue manipulator, tissue tension induced by the tissue manipulator can be an additive triggering even that adds 1 to the triggering event count. In some aspects, the system can track an amount of time that has elapsed since the occurrence of the last additive triggering event and compare the elapsed time to a threshold time. In the event that another additive triggering event is not induced by the time the elapsed time searches the threshold time, the system can detect this as a negative triggering event and subtract 1 from the triggering event count. In various embodiments, negative triggering events can be any event that diminishes, or takes away, from the impact caused by an additive triggering event. In one example embodiment, an additive triggering event can be a temperature threshold being reached or exceeded and a negative triggering event can be applying a temperature that is below the temperature threshold that cools the heated tissue. In other example embodiments, negative triggering events can be administering a drug, such as an injection, that negates, or takes away from, the impact caused by a positive triggering event.

In various embodiments, the additive and negative partial triggering events can have different weights. In one aspect, a first type of additive triggering event can add 1 to the triggering event count while a second type of additive triggering event can add 2 to the triggering event count. In one aspect, a first type of negative triggering event can subtract 1 from the triggering event count while a second type of negative triggering event can subtract 2 from the triggering event count. Any number of weights can be assigned to the partial triggering events, such as 1 to n, where n is the triggering event threshold (i.e., an additive triggering event count with a weight n will cause the triggering event threshold to be reached upon an occurrence thereof). The weights can be user defined, stored in a memory, be based on industry standards, or combinations thereof. In various embodiments, the partial triggering events can be values other than integers, such as 0.5, 1.5, or 1.8, as examples.

The ability to add and subtract from the triggering event count enables the system to track events that, in isolation, may be minor or inconsequential, but an accumulation of which could lead to an event that is major or consequential (additive triggering event). However, the system can also detect events that minimize, or diminish, the additive triggering events, and therefore, can take away from the triggering event count (negative triggering event). For example, in the above-referenced tissue manipulation step, inducing tissue tension that exceeds a tension threshold in isolation may not overly harm the patient tissue, but multiple occurrences could result in torn, or damaged tissue (additive triggering event). However, during the course surgical procedure that may last several hours, exceeding the tension threshold may be expected to occur a number of times that is greater than the triggering event threshold. This number of occurrence happening over a long period of time, however, may not result in serious harm to the tissue. Accordingly, the system can subtract from the triggering event count (negative triggering event) so as to maintain the triggering event count below the triggering event threshold and prevent the overlaid information to be adjusted where it may not be necessary.

In various embodiments, the system can detect cancelation triggering events that can cause the triggering event count to be reset. In one embodiment, the system can detect the number of occurrence in which tension is induced in tissue that exceeds a tension threshold during a step of the surgical procedure. The system can detect that the current tissue manipulation step of the surgical procedure has concluded and that a new step of the surgical procedure is occurring. Accordingly, the system can detect the completion of the tissue manipulation step as a cancelation triggering event, which resets the triggering event count, such as resetting the count back to 0.

In various embodiments, the system can monitor a plurality of triggering events that can have differing triggering event thresholds. In one embodiment, a first triggering event can have a first triggering event threshold, such as the system detecting 3 partial triggering events, and a second triggering event can have a second triggering event threshold, such as the system detecting 4 partial triggering events. In one aspect, having different triggering event thresholds allows the system to monitor partial triggering events that can have varying degrees of severity.

In various embodiments, the additive triggering events can be the same, or similar, additive triggering events. In one example embodiment, the triggering event threshold can be reached when the system detects the occurrence of the same three partial triggering events, such as tension in tissue reaching or exceeding a tension threshold. This allows the system to monitor for a specific type of event associated with a triggering event threshold and adjust the overlaid information in the event the specific type of event occurs a threshold number of times.

In various embodiments, the additive triggering events can be different additive triggering events. In one example embodiment, the triggering event threshold can be reached when the system detects the occurrence of three different types of additive triggering events, such as tension induced in tissue reaching a tension threshold, force applies to the tissue reaching a force threshold, and heat applied to the tissue reaching a temperature threshold. This allows the system to monitor different events that, on their own, may be inconsequential, but in combination, could damage the tissue. Therefore, the triggering event threshold can be reached upon the occurrence of multiple, independent partial triggering events, which can therefore cause the system to adjust the overlaid information on the display.

FIG. 38 illustrates a logic diagram showing operations of an example method 10000 for determining a display arrangement of surgical data competing for presentation onto a display, such as the display 6005, that is showing a livestream of a surgical field. In one aspect, the livestream can be captured by an imaging device, such as imaging device 6004, that is imaging a surgical field. The imaging device can be operably coupled to a control system, such as system 6000, which is also operably coupled to the display. The control system can transmit the livestream of the surgical field from the imaging device to the display such that surgical personnel can view the livestream on the display.

In various embodiments, the method 10000 includes overlaying 10005, on the livestream, information associated with the surgical procedure. In one aspect, the control system can receive inputs from various modules, sensors, user input devices, a situational awareness module, as examples, and overlay information associated with these inputs on the display.

In various embodiments, the method 10000 includes detecting 10010 an occurrence of a triggering event. In one aspect, the triggering event can be any number of the triggering events described by the present disclosure that can result in the system adjusting overlaid information on the display.

In various embodiments, the method 10000 includes adjusting 10015 the overlaid information based on the occurrence of the triggering event. In one example embodiment, the adjustment can be the control system overlaying overlay information on the display associated with the triggering event. Any number of adjustments to the overlaid information can be made as described by the present disclosure.

FIG. 39 illustrates a logic diagram showing operations of an example method 10100 for determining a display arrangement of surgical data competing for presentation onto a display, such as the display 6005, that is showing a livestream of a surgical field. In one aspect, the livestream can be captured by an imaging device, such as imaging device 6004, that is imaging a surgical field. The imaging device can be operably coupled to a control system, such as system 6000, which is also operably coupled to the display. The control system can transmit the livestream of the surgical field from the imaging device to the display such that surgical personnel can view the livestream on the display.

In various embodiments, the method 10100 includes overlaying 10105, on the livestream, information associated with the surgical procedure. In one aspect, the control system can receive inputs from various modules, sensors, user input devices, a situational awareness module, as examples, and overlay information associated with these inputs on the display.

In various embodiments, the method 10100 further includes setting 10110 a triggering event count. In one aspect, the system can set the triggering event count to a value, such as 0, at the onset, or the beginning, of a step of the surgical procedure. In one aspect, the system can set the triggering event count to a value, such as 0, at the onset, or beginning, of the surgical procedure.

In various embodiments, the method 10100 further includes detecting 10115 partial triggering events. In one aspect, the system can detect partial triggering events, such as tissue tension reaching or exceeding a tension threshold, temperature of tissue reaching or exceeding a temperature threshold, or force applied to tissue reaching or exceeding a temperature threshold, as examples. The system can detect partial triggering events using any number of sensors, modules, imaging systems, or combinations thereof, as described elsewhere herein.

In various embodiments, the method 10100 further includes adjusting 10120 the triggering event count based on an occurrence of a partial triggering events. In one aspect, the system can index the triggering event count up 1 when an additive triggering event is detected. In one aspect, the system can index the triggering event count down 1 when a negative triggering event is detected. In one aspect, the system can reset the triggering event count back to the initial triggering event count, such as 0, upon the detection of a cancelation triggering event.

In various embodiments, the method 10100 further includes adjusting 10125 the overlaid information based on the triggering event count reaching or exceeding a triggering event threshold. In one aspect, the system can compare the triggering event count to a triggering event threshold and adjust the overlaid information based on the determination that the triggering event threshold has been reached or exceed. In one aspect, in the event of the triggering event threshold being reached or exceeded, the system can overlay a warning on the display indicating that the triggering event threshold has been reached or exceeded.

FIG. 40 illustrates a logic diagram showing operations of an example method 10100 for determining a display arrangement of surgical data competing for presentation onto a display, such as the display 6005, that is showing a livestream of a surgical field. In one aspect, the livestream can be captured by an imaging device, such as imaging device 6004, that is imaging a surgical field. The imaging device can be operably coupled to a control system, such as system 6000, which is also operably coupled to the display. The control system can transmit the livestream of the surgical field from the imaging device to the display such that surgical personnel can view the livestream on the display.

In various embodiments, the method 10200 includes overlaying 10205, on the livestream, information associated with the surgical procedure. In one aspect, the control system can receive inputs from various modules, sensors, user input devices, a situational awareness module, as examples, and overlay information associated with these inputs on the display.

In various embodiments, the method 10200 further includes determining 10210 a step of the surgical procedure. In one aspect, the system can determine a step of the surgical procedure, such as a step currently taking place, or that is soon to take place, based on any number of inputs provided to the system. In one aspect, the system can determine the step of the surgical procedure using a situational awareness module that can receive various amount of information from sensors, modules, and devices, for the purposes of determining the step of the surgical procedure.

In various embodiments, the method 10200 further includes detecting 10215 an occurrence of a triggering event. In one aspect, the triggering event can be any number of the triggering events described by the present disclosure that can result in the system adjusting overlaid information on the display.

In various embodiments, the method 10200 further includes adjusting 10120 the overlaid information based on the occurrence of the triggering event and the step of the surgical procedure. In one example embodiment, the system can determine that an upcoming step of the surgical procedure is a surgical stapling operation and the triggering event is the completion of a step of the surgical procedure. The system can adjust the display to overlay information about the upcoming step of the surgical procedure, such as the type of staple cartridge that is needed to complete the step of the surgical procedure. In another example embodiment, the system can determine that the currently step of the surgical procedure is a tissue manipulation step and the triggering event is a force being applied to the tissue reaching or exceeding a force threshold. The system can adjust the display to overlay information related to the threshold being reached or exceeded, such as informing the user that less pressure should be applied.

Customization of Overlaid Data and Configuration

Augmented Reality Display of Non-Visible Procedure Steps

It may be understood that a computer-implemented interactive surgical system may include one or more surgical systems and a cloud-based system. The cloud-based system may include a remote server coupled to a storage device. Each surgical system includes at least one surgical hub in communication with the cloud. For example, the surgical system may include a visualization system, a robotic system, and one or more handheld intelligent surgical instruments, each configured to communicate with one another and/or the hub. The surgical hub may dynamically determine which devices are in use and the locations of those devices relative to each other and to critical structures and anatomy as identified by the system. Based on the position of these devices, the patient anatomy, and procedural step in the operating room, the augmented reality displays may be updated to depict one or more auxiliary augmented reality views. Such auxiliary augmented reality views may consist of views within the surgical field which the surgeon cannot see in the primary fields of view. In one aspect, such auxiliary augmented reality views may depict anatomical structures that are hidden in the primary field of view by other tissues. In another aspect, such auxiliary augmented reality views may depict views of a handheld intelligent surgical instrument from a secondary point of view (for example an underside view of the handheld intelligent surgical instrument).

It may be recognized that the computer-implemented interactive surgical system is constantly acquiring device position and usage data during the procedure. The interactive surgical system may also continually receive visual tracking or imaging information of the various intelligent surgical instruments or other devices in relation to the patient's anatomy. The surgical system may also retain the imaging information throughout the surgical procedure. The surgical system, through connections to the cloud-based system, may also retain imaging information of the patient's anatomy from previous surgical procedures.

The computer-implemented interactive surgical system may determine the state of the intelligent surgical instruments based on device movement while such devices are in use. Such movement data may be obtained from the intelligent device itself, for example, based on a three-axis accelerometer disposed within the device. Alternatively, the movement data may be obtained from a visualization device that can optically track the motion of the surgical instrument. The interactive surgical system may also include anatomical image recognition algorithms configured to receive imaging data of an anatomical structure and to determine its nature and location. The combination of the motion of the surgical device and the determination of the anatomical structures around the surgical device may be used by the interactive surgical system to identify the current step of the surgical procedure.

In some aspects, the interactive surgical system may use the imaging data regarding the surgical device obtained from the visualization device, to determine if the surgical device is the proper device for the current step in the surgical procedure. The augmented reality device may provide a virtual object as a warning, such as an icon or a text box, overlaying an image of the surgical device in the augmented reality display to provide a warning to the surgical device user that the device is not correct for that procedure.

At steps in which the surgeon is unable to see certain portions of an end effector of an intelligent surgical device, the augmented reality display may include a secondary view generated to show the surgeon the position of the device that cannot be seen in the current fields of view. As an example, FIG. 41A depicts a surgical display 11000 obtained from a surgical imaging device during a laparoscopic sleeve gastrectomy procedure in which a portion of the fundus of a patient's stomach is removed. FIG. 41A depicts the patient's stomach 11002 while a surgeon uses a stapler 11004 to staple an interior edge of the stomach 11002 together and cut the remaining stomach portion 11003 away. As can be observed, the surgical display 11000 depicts a top surface 11006 of the end effector of the stapler 11004. The surgeon may wish to see the bottom side of the stapler 11004 prior to firing the staples, in order to assure that both edges of the resected stomach are sealed together. The surgeon may not wish to rotate the stapler 11004 while it is clamped to the stomach 11002 to see the back side of the device prior to firing. Such a rotation of the stapler 11004 may result in pulling the tissue in ways that may compromise the stapling function. FIG. 41B depicts an augmented reality image 11012 comprising the surgical display 11000 along with a virtual secondary view 11010 overlaid thereon. The virtual secondary view 11010 may include an augmented reality depiction of a side view 11014 of the stapler. The augmented reality depiction of the side view 11014 of the stapler may depict a side view 11016 of a portion of the patient's stomach grasped by a lower jaw 11018 of the stapler. In this manner, the virtual secondary view 11010 can permit the surgeon to visualize the underside of the stapler and see the underside without having to excessively manipulate the tissue.

In some aspects, the augmented reality image 11012 may display information in addition to the imaging views not available to the surgeon (such as the side view 11014 of the stapler and the side view 11016 of the portion of the patient's stomach). For example, the virtual secondary view 11010 may also include visual indicators 11020 regarding the status of the procedure or tissue. For example, a warning 11021 may be depicted indicative of tissue status. In another example, a device status indicator 11022 may indicate a status of the present operation of the stapler.

In one aspect, the virtual secondary view 11010 may be created using predictive modeling of the patient based on previous anatomical images of the patient or images of similar anatomical portions of other patients undergoing the same surgical procedure. In another aspect, the virtual secondary view 11010 may be created from real-time images obtained from a secondary camera used during the procedure. In one example, the surgeon may request the virtual secondary view 11010 from the interactive surgical system through the use of a gesture or spoken command. The interactive surgical system may issue an alert to the surgeon to adjust a position of the secondary camera position so that the auxiliary view can be created.

In another aspect, the virtual secondary view 11010 may be used to identify and display critical anatomic structures at all times during the surgical procedure. As an example, such a persistent secondary view may be used to maintain an image of a tumor disposed on an organ of interest on a display device throughout the surgical procedure. Such a persistent display may allow the surgeon to toggle between overlaying this view on the image of the current procedure and having it as a secondary view on the side of the display.

Predictive Analytics And AI Learning By Procedure-Display Power For Active Devices It may be understood that a computer-implemented interactive surgical system may include one or more surgical systems and a cloud-based system. The cloud-based system may include a remote server coupled to a storage device. Each surgical system includes at least one surgical hub in communication with the cloud. For example, the surgical system may include a visualization system, a robotic system, and one or more handheld intelligent surgical instruments, each configured to communicate with one another and/or the hub. The surgical hub may dynamically determine which devices are in use and the locations of those devices relative to each other and to critical structures and anatomy as identified by the system. Additionally, computer-implemented interactive surgical system and/or cloud-based system may include an artificial intelligence ("AI") system configured to monitor data that is pulled from previous cases of the same procedure type and import data from the current case. Cloud-based data specific to the surgeon operating in a specific surgical case (and/or all completed surgical cases of this type) along with device position data, may permit the AI system to recognizes the current procedure step, and use this information to predict the next step of the procedure. Using this prediction, the augmented reality display may be updated to present the predicted next action to be taken and/or predicted outcomes based on previous cases.

The computer-implemented interactive surgical system may determine the state of the intelligent surgical instruments based on device movement while such devices are in use. Such movement data may be obtained from the intelligent device itself, for example, based on a three-axis accelerometer disposed within the device. Alternatively, the movement data may be obtained from a visualization device that can optically track the motion of the surgical instrument. The interactive surgical system, or the AI system, may also include anatomical image recognition algorithms configured to receive imaging data of an anatomical structure and to determine its nature and location. The combination of the motion of the surgical device and the determination of the anatomical structures around the surgical device may be used by the interactive surgical system to identify the current step of the surgical procedure.

It may be recognized that the computer-implemented interactive surgical system is constantly acquiring device position and usage data during the procedure. The interactive surgical system may also continually receive visual tracking or imaging information of the various intelligent surgical instruments or other devices in relation to the patient's anatomy. The surgical system may also retain the imaging information throughout the surgical procedure. The surgical system, through connections to the cloud-based system, may also retain imaging information of the patient's anatomy from previous surgical procedures, or imaging information from a different patient's anatomy from related surgical procedures.

In one aspect, data may be sent to a cloud data source configured to store in memory all prior procedural data from additional Hub connected cases. The data may be mined and analyzed to predict the most likely next step to be taken by the surgeon. Non-limiting examples of predictive modeling may use one or more of classification models, regression models, and Markov chain models. The prior procedural data may include imaging data and data obtained from the specific devices while they are used in the procedure. Device dependent data may include, for example, power levels, timing parameters, staple types, device position and orientation data, along with other operational parameters. The surgical cases that are analyzed may encompass any number of related or identical procedures. In some instances, only related cases completed by a specific surgeon performing the procedure may be analyzed. In one aspect, the surgeon performing the current procedure may have an option to choose which prior case(s) should be analyzed as being relevant to the case at hand for making predictive recommendations.

Using the surgeon-specified prediction, the tracked position and orientation of surgical devices in use, and patient anatomy, the augmented reality display may be updated to show a prediction of the next surgical action (for example a predicted position of a stapler for its next stapling operation). It may be recognized that the augmented reality display may be shown on any display device within the operating room or outside of it. In some aspects, the augmented reality display may be displayed on a main or primary display in the operating room. Alternatively, the augmented reality display may be displayed on one or more alternative displays, for example tablet devices, secondary monitors, or even a display device associated with a specific intelligent surgical device such as a device generator display. This prediction may be accompanied with additional device specific recommendations such as predicted staple reload size based on the patient's anatomy, or suggesting the use of a buttress material to reduce leakage based on observations from previous stapler operations, patient disease state, or similar.

Other augmented reality displays may include recommendations related to the use of additional surgical devices that can be used to complete the procedure with improved outcomes. By tracking the procedural steps during an on-going surgical procedure, and comparing those to previously obtained data stored in the cloud system, the intelligent surgical system may also adjust the communication prioritization among the intelligent surgical devices within the hub network. Thus, based on surgical history, a second intelligent surgical device that will be needed after the use of first surgical device may have its communication stream prioritized in anticipation of its use. For example, after all Stapler firings are completed in a gastric sleeve procedure, the communication stream from a needle driver may be prioritized over other devices.

As an example, FIG. 42A depicts a surgical display 11000 obtained from a surgical imaging device during a laparoscopic sleeve gastrectomy procedure in which a portion of the fundus of a patient's stomach is removed, similar to the depiction of FIG. 41A. FIG. 42A depicts the patient's stomach 11002 while a surgeon uses a stapler 11004 to staple an interior edge of the stomach 11002 together and cut the remaining stomach portion 11003 away. As can be observed, the surgical display 11000 depicts a top surface 11006 of the end effector of the stapler 11004 at a particular location on the stomach 11002. The surgeon may be uncertain regarding how or where to position the stapler 11004 for the next staple-and-cut operation FIG. 42B depicts an augmented reality image 11030 comprising the surgical display 11000 along with a predicted or recommended placement of the stapler 11032. In some aspects, the augmented reality image 11030 may display ancillary information 11034 in addition to the predicted or recommended placement of the stapler 11032. For example, the ancillary information 11034 may include recommendations 11036 for changes in device operating parameters, such as the type of stapler to be used by the stapler. The recommendation may include statistical data regarding the success rate of the new operating parameters in similar surgeries. In another example, the ancillary information 11034 may also include one or more warnings 11038 regarding the status of the tissue being manipulated by the surgical device. The warnings 11038 may include recommended remediation steps that can be used to address the issue. As an example, the warning 11038 may indicate that a staple line is stressing the tissue which may lead to tearing or incomplete healing at the staple line. A recommendation may be given to suggest the use of a buttress material to help seal the tissue.

FIG. 43 is a logic diagram 11500 depicting a method by which an interactive surgical system may receive surgical procedure information and suggest next procedural steps. In a first step in the process 11510, a surgeon has completed a surgical step A. The data related to surgical step A may be sent 11512 from a communication hub to a cloud-based data source. An artificial intelligence engine in the cloud-based data source may predict 11514 the next step in the surgical procedure, and transmit that data to the communication hub. The communication hub may then predict 11516 a location in the surgical field and the surgical devices that may be used by means of displaying one or more virtual objects on an augmented reality display. The communication hub may then communicate 11518 with the cloud data source to determine a best surgical outcome of the predicted step, location, and device, based on parameters associated with the patient. These parameters may be compared to similar patient statistics, surgical information, and surgical device characteristics in the cloud-based database. The hub may communicate 11520 parameters related to the use, orientation, location, and device parameters to the surgeon as virtual objects displayed on her or his associated augmented reality display device. The surgeon may then complete 11522 the recommended next surgical step. The method may continue in this manner for each subsequent set in the surgical procedure.

Association Instrument And User-Hub/Network Sensing Of Devices And Interactions It may be recognized that the computer-implemented interactive surgical system is constantly acquiring device position and usage data during the procedure. The interactive surgical system may also continually receive visual tracking or imaging information of the various intelligent surgical instruments or other devices in relation to the patient's anatomy. The surgical system may also retain the imaging information throughout the surgical procedure. The surgical system, through connections to the cloud-based system, may also retain imaging information of the patient's anatomy from previous surgical procedures, or imaging information from a different patient's anatomy from related surgical procedures.

The augmented reality interactive surgical system comprises a plurality of data connected intelligent surgical devices. The surgical system can dynamically determine which devices are in use and where those devices are located in space relative to each other and to critical structures and anatomy as identified by the system. Based on the locations of these devices and the preferences/position of the user, the system may prioritize data communication. Data communication prioritization may be enabled for devices proximate to critical structures, and may include increased alert sensitivity at critical procedural steps and/or around specific anatomy. In response to the data communication prioritization, the augmented reality display(s) may be quickly updated to inform the surgeon or other members of the operating room staff of device position, high risk areas, and other sensitive locations.

Via spatial tracking, the interactive surgical system can adapt the augmented reality display to fit procedural steps, such as highlighting critical structures when instruments are nearby, or setting an alert if instruments are too close to each other. Thus, the augmented reality information is constantly tracked by the system, but information is only displayed at the times that it is important to the surgeon. For example, augmented reality visualization of hidden structures may not always be enabled, but may be triggered by a position of the intelligent medical devices. In this manner, the surgeon can proceed with the surgery as normal until high risk areas are identified, or a risk of un-intended injury is present. Under such circumstances, the augmented reality visualization may be enabled and the surgeon is notified of any impending issues.

In one example, the interactive surgical system may recognize the position of a critical anatomical structure, such as the ureter, that may not be otherwise visible to the surgeon. For example, an artificial intelligence module in the cloud system may include anatomical models that may take images of the surgical field and predict or estimate the position of near-by or underlying anatomical structures. Although the ureter may not be readily visible, an image of the ureter may appear as an augmented reality virtual object on one or more augmented reality displays. In one option, such augmented reality virtual objects might be displayed when the system detects/predicts that the end effector of a connected device has come within a specified distance to this critical structure.

In another example, an augmented reality virtual object may include a highlighting superimposed on a display of an end effector of an ultrasound instrument if the temperature reaches a certain level and the instrument is close to the wall of the bowel.

Alternative display options might be based on surgeon preference. Some options could include persistent display of the augmented reality visualization of the critical structure. Alternatively, the display of the augmented reality visualization of the critical structure may be enabled only during a certain portion of the procedure, or only when energy devices are in use. These visualization options may rely on a combination of monitoring device position relative to patient anatomy (via the scope, scans, as examples), processing this information in the interactive surgical system, and enabling the desired augmented reality display based on surgical context.

As an example, FIG. 44A depicts a surgical display 11040 obtained from a surgical imaging device during a laparoscopic procedure. The procedure may include the use of an ultrasonic cutter 11042 and an auxiliary tissue clamp 11044. The surgeon may wish to grasp a piece of tissue 11046 with the tissue clamp 11044 and resect a portion of it using the ultrasonic cutter 11042. The surgeon may be unaware that a portion of the patient's ureter lies close beneath the tissue 11046.

FIG. 44B depicts an augmented reality image 11050 comprising the surgical display 11040 along with an augmented reality virtual object 11056 presenting an outline of the ureter underlying the tissue to be resected. In some aspects, the augmented reality image 11050 may display ancillary information 11057 in addition to augmented reality virtual object 11056. For example, the ancillary information 11057 may include a tissue related warning 11058 that the ultrasonic cutter 11052 or the auxiliary tissue clamp 11054 is too close to the position of the ureter. The ancillary information 11057 may include a device related warning 11059 that the ultrasonic cutter 11052 may be too close to the position of the auxiliary tissue clamp 11054.

The augmented reality displays may be used to provide any related guidance to a surgeon related to the procedure or the device being used in the procedure. For example, a surgeon-in-training (such as a surgical resident) may receive a greater amount of feedback in a user training mode if the interactive surgical system determines that the surgeon=in-training lacks experience based on the surgeon's skill history. The amount of feedback presented may be graded based on a "training curve" related to the skill level of the surgeon, and may be accelerated if the surgeon displays an improvement in the learned skills. The feedback may be tailored to present guidance in areas needing skill improvement. The individualized feedback may be based on data and images stored in the cloud system for the individual surgeon based on past performance and surgical experience and the recorded use by the surgeon of the device during past surgeries. Examples of surgical outcomes that may indicate a need for skill improvement may include bleeding at the surgical site, double burns for cauterized tissue, or tissue tagging.

The augmented reality displays may also be used to recommend specific devices to a surgeon during a procedure. Improved, or updated devices may be recommended to replace the surgical device being used during the procedure. Information may be provided in the augmented reality display indicating how such an improved device may be used in the present surgery. The augmented reality display may also provide statistics regarding the outcomes of similar surgeries performed with the recommended device compared to the outcomes of surgeries using the present device.

Linked Users To Form An AR Ecosystem

It may be recognized that the computer-implemented interactive surgical system is constantly acquiring device position and usage data during the procedure. The interactive surgical system may also continually receive visual tracking or imaging information of the various intelligent surgical instruments or other devices in relation to the patient's anatomy. The augmented reality interactive surgical system comprises a plurality of data connected intelligent surgical devices and one or more display devices configured to provide the members of the surgical team information related to the surgical operations, the patient status, and the operation of the intelligent surgical devices used throughout. The surgical system can dynamically determine which devices are in use and where those devices are located in space relative to each other and to critical structures and anatomy as identified by the system.

In some aspects, each member of a surgical team may be associate with on one or more display devices to provide information related to the surgical proceedings. Each display device may display images obtained from one or more imaging devices along with augmented reality virtual objects overlaid on the imaging data. The display associated with any member of the surgical team may be customized to the functional role of that surgical team member. For example, the display of a member of the surgical team may be customized to include virtual objects associated with a device or instrument controlled by the member of the surgical team. The interactive surgical system may monitor the instruments and devices under the control of each surgical team member within the operating room. The data displayed on each display device may be dependent on which user has control of a surgical device and the surgical role of the user. The displayed information for a user may change as instruments or devices enter or leave their control. For example, the surgical system may track instrument exchanges between surgeons or between surgeons and nurses. The augmented reality displays may adjust the nature, type, and/or positions of the virtual objects in the augmented reality displays associated with the affected surgical team members. For example, virtual objects associated with control of a surgical device may disappear from a display associated with one surgical team member as she or he relinquishes control of the surgical device. Similarly, virtual objects associated with control of the surgical device may appear on a display associated with a second surgical team member as she or he accepts control of the surgical device.

In some aspects, the intelligent surgical system may be capable of determining an in-situ and an extracorporeal aspect of the instruments in use and the associated user in control of the instruments. The surgical system may also be able to associate actions occurring outside the body with motions occurring inside the body to verify correct correlation of the two facets.

As disclosed above, each member of the surgical team may have associated with her/himself display device configured to display augmented reality displays customized to the activity and role of the surgical team member. Such displays may include any appropriate type of display, including a primary or main operating room display, one or more auxiliary operating room displays, displays associated with one or more tablet devices, a laptop display, smart phone displays, or displays associated with individual surgical devices such as patient monitoring devices or anesthesia delivery/monitoring devices. The purpose of each of these devices is to provide information customized to the functional role of the individual.

Not only is a display customized to a specific surgical team member, but the team member may be able to modify her or his display to show the display of another member of the team, such as by swiping a touch activated screen, the use of a hand gesture, or by a verbal command. In this manner, the team member may be able to "pull" the display from another team member's display device. Alternatively, some team members may have authority to "push" their own display onto the display device of other members of the surgical team.

In some aspects, each member may not have a physical display device. Instead, multiple members of the surgical team may rely on a shared or common display device. In this circumstance, the customization experience may be derived from a wearable image filtering device such as glasses, a heads-up display, or contact lenses. The common display device may display an image including the virtual objects associated with all of the members of the surgical team. The virtual objects may be color coded or otherwise visually encoded so that each member of the surgical team may be able to view only those virtual objects associated with her or him by using a wearable image filtering device. The wearable image filtering devices may filter an image displayed on a common display device based on color filtering, polarization filtering, or time filtering of a rapidly changing imaging. Color and polarization filtering may allow a user to see only light emitted at preselected wavelengths or polarization states. Time filtering may coordinate the timing of a blanking condition of the wearable filter with the time a specific image is displayed on the common display device. Color filter contact lenses or goggles may be used for rapid prototyping and information gathering on information level. Alternatively, zoom feature or UV light activation options may be incorporated in the wearable filters.

The interactive surgical system may also manage the priority of the communications among and between the members of the surgical team and/or with the hub or cloud system.

Thus, communications arising from functions or activities deemed critical to the procedure at any specified time may have priority over communications that may, for example, be associated with routine patient monitoring. These communications may be prioritized among the members of the surgical team. Thus, relevant data generated by critical devices being used during a specific portion of a procedure may be communicated directly to all relevant members of the surgical team to convey device useful information. In one non-limiting example, a surgeon may always needs to know if an ultrasonic blade is hot but an anesthesiologist may only need to know when the hot blade comes in contact with a critical anatomical structure. In this case, the anesthesiologist may be notified by vibrational feedback associated with the temperature of the ultrasonic blade only when a critical anatomical structure is contacted with by hot blade. The surgeon may receive tactile feedback—for example, a light vibrational response—from the hot blade and receive notification/light vibration when the blade is close to critical structures overall. As another example, devices and/or procedures that result in difficulty with hemostasis may be prioritized. Data specific portion of the procedure that may be necessary to monitor hemostasis—type and source of blood flow, for example—may be shared among the surgical team.

While each member of the surgical team may have her or his own customized augmented reality display, under some circumstance, the individual display options may be overridden. As one example, during emergency situations, everyone may see the same display or gets the same prioritized alerts based on detected situation. Every member of the surgical team may get a standard non-negotiable master settings or view that is standard. However, each individual may add additional settings and preferences to the standard image.

In some aspects, communications between specific members of the surgical team may be prioritized to result in pairing information with specific members for direct communication. In one example, a head surgeon can share what she or he is seeing and her or his display/wearable preferences may be extend to specifically chosen members of the surgical team. For example, the head surgeon may "push" her or his display to a surgical resident who can thus see or feel the same things as the head surgeon. A ping system with a wearable device may notify other surgical team members to switch over their respective augmented reality displays. As one example, a surgeon or physician assistant may ping an anesthesiologist to switch to their view/preferences to that of the surgeon. It may be understood that a surgical team member thus pinged may decline the invitation if a higher priority task is at hand.

The surgical system may initiate a communication pairing with an intelligent surgical device and subsequently associate a user of the device with the device while it is active. It is disclosed above that an intelligent surgical device may be controlled by a member of surgical team. The interactive surgical system may recognize the associating of the person with the device after the interactive surgical system has established a communication pairing with the device itself. The system may first determine that the device is located within the surgical suite. The system may then recognize when the device is removed from its sterile packaging, thereby becoming passively selectable for use by a member of the team. Once a surgical team member begins to handle the device, the interactive surgical system may then recognize the status of the intelligent device as being actively selected and the system may then recognize a control or associating between the device and the surgical team member.

Monitoring Device-User Interactions And Changes In Display Needs

The interactive surgical system may determine a task of a member of the surgical team based on one or more of the situational awareness of the intelligent surgical instrument status, the team member's functional role, and the step in the procedure. The situational awareness may be used to adapt the augmented reality virtual object display information based on the task at hand.

In one non-limiting example, the surgeon may deploy a loaded stapler positioned on the organ to transect. The augmented reality display may include a virtual object displaying information related to one or more of a force-to-fire (FTF), a wait time, and a tissue tension detected, as well as a cartridge color, status, and stroke location of the intelligent medical device. Once the firing is complete, the surgeon could release the tissue, close, and remove the device. Since the device now has an expended cartridge, the augmented reality display could indicate the inability of the stapler to be used again until reloaded. The augmented reality display may use a colored virtual object as an overlay over an image of the stapler to indicate that it is not available for additional use until the staples are reloaded. As the stapler is handed off to the scrub nurse, the virtual object representing the stapler could be transferred to the nurse's augmented reality display. At the same time, the virtual object representing the stapler could be removed from the surgeon's augmented reality display to indicate that control of the device has been passed to the nurse. The nurse's augmented reality display could then indicate fired state of the stapler, and indicate the steps needed to reload the instrument with a fresh unfired cartridge. Such virtual objects may include indications regarding buttons of the stapler to press, their order, and a suggestion of the next cartridge color based on the awareness of the procedure plan and the step in which the intelligent medical instrument is currently in-between. In some aspects, the nurse's augmented reality display could also link up to other displays to show where the needed cartridge is located and even a compatibility of the cartridge being loaded with the device and the procedure.

In some aspects, the interactive surgical system may track multiple aspects of an operating room procedure. In some examples, the interactive surgical system may track the use and control of the multiple intelligent surgical devices used during the procedure, the location and activities of the surgical team members, and the disposition of the equipment and patient within the confines of the operating rom itself. Additional trackable aspects that the interactive surgical system may include surgical access points and register them with patient, instrument location, orientation, or status, or missing or misplaced equipment. In some additional aspects, the interactive surgical system may identify surgical procedural steps in process. The surgical system may display virtual objects with a background highlight on one or more augmented reality displays to indicate a critical or time sensitive step or to indicate that a particular step is at a higher risk level than the others.

In some aspects, the interactive surgical system may track the skills or capabilities of members of the surgical team in the operating room. In addition, the interactive surgical system may track the individual locations of the members of the surgical team in the operating room as well as their functions. The locations of personnel entering and exiting the operating room may also be tracked. The interactive surgical system may monitor the surgical staff motions, interactions, and movement within the operating room to improve the layout. Aspects related to the use of the intelligent surgical devices may be tracked, for example the hand dominance of a team member using such a device, or the placement on a table of the surgical device before or after use to optimize efficiency.

FIG. 45 depicts the various aspects associated with a surgical procedure that may be tracked by the interactive surgical system, and which may be analyzed to develop optimization strategies. Data related to the patient may include patient location, and pre- and post-surgical scheduling. Materiel data may include lists and location of consumable products, such as gauze and wipes, and their management in the hospital supply chain. Location related data may include not only the operating room, but ancillary rooms such as storage facilities and work locations. Control matters may include rules, regulations, and laws related to hospital business practices, medical, political, economic, and legal constraints on the practice. Functional data are all data related to the individual steps, processes, and subprocesses involved in the surgical procedure. Flow data encompass the actual sequence of procedures and processes including models. Operational data relate to the application of various pieces of surgical equipment, along with devices and tools. Informational matters include all data acquired during the procedure, documents, and data models of the procedure. Finally, organizational data may include human resources data from the hospital, including staff identification, surgical roles, and organizational models of the hospital itself.

FIG. 46 depicts aspects of an operating room 11100 which may be modeled for tracking purposes. The operating room 11100 depicted may merely be representative of operating rooms in general, and the layout may be adapted to any real-world example of an operating room. The operating room 11100 has an access 11102 through which the patient, surgical team members, and equipment may enter. The operation room may have an exit 11116 through which used equipment may flow for disposal or recycling. There may be a central surgical theater 11118 comprising the sterile zone 11108 for the patient and the surgeons and an anesthesia zone 11110 for the anesthesiologist and nurse anesthetist. The central surgical theater 11118 may also include the location of any surgical robots involved with the surgery. Surrounding the central surgical theater 11118 may be a circulation zone 11106 where nurses, technicians, and other personal may move so as not to disturb the surgical procedure carried out in the surgical theater 11118. A charting area 11104 where clinical notes may be taken may be accessible through the circulation zone 11106. There may be a perimeter corridor 11112 outside of the operating room 11100 which may include a scrub station 11114 for the surgical team members to wash their hands and put on their personal protective gear.

The interactive surgical system may track postural changes in the members of the surgical team, such as rocking back and forth while standing. Such postural activities may be an indication of an increase in the fatigue level of a member of the surgical team. In response, the interactive surgical system may display a virtual object on the augmented reality display associated with the fatiguing member of the surgical team. The interactive surgical system could alert support staff to potentially allow a break to the current staff or surgeon by displaying an appropriate virtual object on their respective augmented reality displays. In one aspect, the virtual object may be an indicator of the fatigue status of the team member. An example of such a virtual objection warning of surgical member fatigue 11060 is depicted in FIG. 47.

As part of the ability of the interactive surgical system to track multiple aspects of an operating room procedure, the interactive surgical system may include optimization algorithms to improve performance during a surgical procedure. Such optimizations may include an optimization of right surgical tool used at right time such as determining that all of the required surgical tools are available and conveniently placed before start of the procedure. The system may determine an optimize operating room layout of equipment, an optimized patient placement, or an optimize access to equipment or operating room doors.

Upon procedure completion, the interactive surgical system could analyze and propose variations to the operating room flow to minimize areas of inefficiency. This analysis can impact the procedural planning of all future comparable surgeries. This analysis can be tailored for each unique operating. Operating room size, shape, number of staff, entrance and exit placement, locations of supplies within the operating room and external materials needed to come into the operating room may all be analyzed by the interactive surgical system in view of the movements and actions of the surgical team members during the surgery and the outcome of the surgery. The interactive surgical system could run multiple scenarios virtually to determine an "optimal" workflow. Future similar procedures could use the updated flow to gain efficiency and lower fatigue. For example, improved logistics and surgical efficiency may be indicated by enabling virtual objects on the augmented reality display. Such virtual objects may include graphical overlays over images of device layout, equipment locations, and patient layout to visualize the flow and utilization of the products.

Some exemplary illustrations of optimized operating rooms are depicted in FIG. 48A, FIG. 48B, and FIG. 48C. Each illustration 11200*a,b,c* depicts possible organization of components of an operating room including one or more support zones 11202*a,b,c*, a transition zone 11204*a,b,c* (comparable to the circulation zone 11106 in FIG. 46), and one or more supply zones 11206*a,b,c*. The anesthesiology zone is illustrated at 11208*a,b,c*, and the surgical table 11210*a,b,c* is located in the central surgical theater (11118 in FIG. 46). In these depictions, the surgical table 11210*a,b,c* is subdivided into a right table zone, a left table zone, an a foot zone.

After surgery is complete, an overlay is projected to indicate what disposal method should be used for the various instruments and materials in the operating room. In some instances, batteries may be directed to their own waste stream. Used medical devices or disposable portions of intelligent medical devices could be directed to the medical waste disposal area. Unused material could be directed back into stock or to stay within the operating room. Packaging for the medical devices, or medical disposables may be tracked to ensure proper recycling, reuse or disposal.

Customization Of The Virtual Object Data Based On Device Ownership And Task Needs In some aspects, an augmented reality display may be customized by its associated user to enable the display of a virtual object related to an intelligent surgical instrument under the user's control. The interactive surgical system may monitor a state of an intelligent surgical instrument under the control of each member of the surgical team within the operating room. The interactive surgical system may then control the display of one or more virtual objects on an augmented reality display associated with the surgical team member that is a result of both the device under control of the surgical team member and the task or situation in which the team member is acting.

The interactive surgical system could track which surgical team member is using which augmented reality display device. This could include traditional monitors, but also could include augmented reality glasses, wearables, secondary displays, displays on instruments, and capital equipment control displays. Then, using its understanding of the instruments being used by the surgical team member, the interactive surgical system could adjust the displays with virtual objects useful to the task at hand onto the display associated with the surgical team member. In one aspect, such virtual objects may be displayed on an augmented reality display of the surgical team member in control of the intelligent surgical device. Alternatively, such virtual objects may be displayed on augmented reality displays of several or all of the members of the surgical team. This could be occurring with all users in the OR and all the instruments and displays they are each using simultaneously. In some aspects, the virtual objects may appear. as colored highlights surrounding the images of the surgical equipment. The highlights may appear as outlines or colored overlays displayed over the images of the surgical equipment. Other virtual objects may include auxiliary window displays containing text messages or secondary images of tissue visible in the surgical field. In some other aspects, the auxiliary window displays may include images derived from models calculated by the artificial intelligent module in the cloud system. These models may include images of tissue hidden from view in the surgical field or alternative views of the intelligent medical instruments used by the surgeon.

In some aspects, an augmented reality display may be customized by its associated user to enable the display of a virtual object related to a status of an intelligent surgical device under the control of the associated user or of another surgical team member. The status may include that the device is powered, that it is performing one of several types of functions, a power level of the device, a status of auxiliary components such as staples, error conditions, and similar functional states.

In some aspects, an augmented reality display may be customized by its associated user to enable the display of a virtual object related to an event, such as the application of another surgical device to a patient. The virtual object may display a counter or timer such as a linear counter or a circular counter. The timer may be used to time the event.

In some aspects, an augmented reality display may be customized by its associated user to enable the display of a virtual object related to status of a paired device. In one example, the virtual object may be a highlight overlaid on a stapler having a color or intensity related to the energy level of the stapler. In some examples, the highlight may be applied to the augmented reality display only when the stapler is controlled by the surgeon associated with the display device.

In some aspects, an augmented reality display may be customized by its associated user to enable the display of a virtual object related to a status of active devices. An intelligent surgical device located within the operating room may be in active communication (actively paired) with the interactive surgical system, the communication hub, the cloud system, or other equipment. The surgical device may or may not be in active use by the surgeon, but may merely be located mayo stand, ready for use. A device in active use by a surgeon may be one currently being used or held by the surgeon. A device in use by a surgeon may be a device currently performing some action with the surgeon in the surgical field.

In some aspects, a virtual object related to a status of active device may disappear from the display after a fixed time of non-use. In some aspects, a virtual object related to a status of active device may display device related information only when the device is in active use or in use.

In some aspects, an augmented reality display may be customized by its associated user based on the user inputs or request to enable the display. Depending on the technical capabilities of the augmented reality display, the input may be received from a keyboard, a mouse, a verbal command, a gesture, a tactile input on a touch sensitive screen, a stylus, or any other means of information input.

It may be understood that multiple augmented reality display devices may be used within the operating room. One or more main, wide-screen displays may be available for all of the members of the surgical team to use. Alternatively, other display types of devices may be associated by the interactive surgical system with each of the members of the surgical team. Such devices may include one or more laptop devices, tablet devices, or wearable devices such as augmented reality head-sets. A tablet display device may be different from the larger display devices within the standard OR. If the interactive surgical system determines or the user indicates they are using the tablet screen, the virtual objects displayed on the augmented reality display devices may be adjusted to adapt to the smaller screen either in display location, aspect ratio, color, or other visual design aspects. The user can determine what virtual objects are present and which ones should be excluded.

The surgical team member may interact with a portion of the augmented reality display with which they are associated to determine where a particular virtual object is displayed. In other aspects, the surgical team member may scan, photograph, or input a classifier that would designate the display of the overlay, configuration, or location. In other aspects, a surgical team member may interact with a portion of the augmented reality display via a separate device, such as a wearable device in order to identify a predetermined configurations or inputs to customize the layout of the augmented reality display associated with the user. In other aspects, an audio or visual source of a user may be coupled with the instruments in their control. In some other aspects, virtual objects that show linked or interactive displays of multiple instruments may be displayed on multiple augmented reality displays or together on a main or primary operating room display, along with a summary that is more detailed than each of the independent displays individually.

While an individual member of the surgical team may be able to customize the display of virtual objects on their associated augmented reality display, the displayed information for a specific surgical team member may change as intelligent surgical instruments enter or leave their control. In some aspect, the interactive surgical system tracks instrument exchanges and changes in ownership between members of the surgical team and may adjust the augmented reality displayed data based on the ownership change. Further, the interactive surgical system is capable of determining the in-situ and extracorporeal aspects of the instruments in use and the associated user in control of the instruments. The interactive surgical system can relate actions occurring outside the body with motions occurring inside the body to verify correct correlation of the two facets.

Indication of the Couple Pair of Remote Controls with Remote Devices Functions

Device And User Specific Augmented Reality Display

In some aspects, the information displayed by an augmented reality display device may depend on the user and the device being used. In particular, the specific views and overlaid virtual objects depicted in the augmented reality display may be determined based on data specific to the user and data specific to an intelligent medical device. Data specific to the user may includes their experience level with the use of the intelligent medical device along with their specific experience with the current procedure. This data may be incorporated in surgical team member personnel data stored in the cloud system. Data specific to the intelligent medical device may include all relevant manufacturing and model data and history of use. In some aspects, the device specific data may be included in one or more memory devices disposed within the intelligent medical device. In other aspects, the device specific data—such as history of use—may in medical device data stored in the cloud system. The combination of the user specific data and the intelligent medical device specific data may be used to determine the user's level of experience with the device and the proficiency as measured by past uses of the same or a similar device.

In some aspects, based on user/device data, the augmented reality display device can be configured to display the information in a "Training mode". In this mode, the augmented reality virtual objects can include displays or alerts such as safety alerts (for example, possible bleeding, high tissue tension), as well as alerts on suboptimal technique (for example double burns, tissue tagging). The alerts can be specific to the user's assessed skill history and provide guidance where skill needs improvement. For example, a new ultrasonic device user might have a history of overfilling the jaw which might result in incomplete cuts. In some aspects, augmented reality displaying warnings against overfilled jaws may accelerate learning specific to insertion of tissue in the jaw. In contrast, an advanced user might become overconfident and tend to speed up the flow by pulling on the tissue. In such examples, augmented reality displaying warnings on tissue tension may alert on suboptimal technique that might cause bleeding.

The user might be using a competitor's device. The augmented reality interactive surgical system can then display features in a "Sales mode". The sales mode compares the user's use of the competitor's device to a baseline performance with comparable device and displays suggestions such as "This step could be x % faster, with y % less bleeding" if another device was used.

The nature of information displayed by augmented reality display devices may vary according to who is the user of the device. In one aspect, if the user of an intelligent surgical device may be an automated system (a robot), the information displayed by the augmented reality display devices may include general procedural metrics and alerts. In some examples, such procedural metrics and alerts may be displayed in the form of a dashboard that can be read by one or more members of the surgical team. Alternatively, for manual laparoscopic surgery, the augmented reality display may be more granular to the successive steps in the surgical procedure and may specifically relate to structures and operations visible in the surgical field. There may be a gradual progression between these two extremes.

Various forms of information may be entered by the user to the interactive surgical system. For example, the user may enter information via pressure sensors or contact points disposed on an intelligent medical device. For example, activation of these sensors or contact points may indicate that the device is closed. In another aspect, the user may provide warnings to the interactive surgical system by means of hand gestures that may sensed by the interactive surgical system via visualizing devices. These gestures may indicate that a next surgical step should not proceed (for example, that a tissue grasped by a set of jaw should not be cut with a knife).

The augmented reality display system may display information relative to a surgical procedure step, such as a procedure step ID indicator. The interactive surgical system may obtain the information regarding the procedure step from an analysis of images received as video streams from imaging systems (such as from one or more cameras). Artificial intelligence modules disposed in the cloud system may determine the information content based on the images from the camera video stream and the camera originating the video stream. As a result, the interactive surgical system may analyze the video data and display the information relative to the procedure step based on additional analysis using procedure planning software. In some aspects, the augmented reality display may be associated with a specific surgeon's way to perform procedure.

In some aspects, an extension of the user's virtual "location" may be to that of the end of the instrument being manipulated by the user. In additional aspects, the interactive surgical system may cooperatively cause an augmented reality trigger that would occur in the micro space at the end of the instrument when looking at the monitor or surgical site as well as the grosser macro-space of the patient and the equipment surroundings. For example, this may include image scaling from the micro to the macro spaces based on the tracking of where the user is looking. In one non-limiting example, the interactive surgical system may display information related to energy delivery by one intelligent surgical device, but also include information related to a tissue grasper when the grasper comes into the surgical site field of view.

Smart Trocar

Endoscopic tools, such as energy devices, can heat tissue to a temperature where damage can occur upon contact. A method is disclosed to warn the surgeon of high temperature for safe positioning of such energy devices could minimize the risk of tissue damage.

In one aspect, a trocar may be transmissive of infrared radiation. The interactive surgical system may also include a low-cost infrared sensor (either a video sensor or other optical sensor) with particular sensitivity to wavelengths consistent with temperatures that may harm tissue. The trocar would then be paired with the interactive surgical system or visualization system wirelessly. Additionally, the smart trocar could be a source of emergency lighting in the case of a light source failure. Further, the smart trocar may have a high intensity LED, a haptic motor, or a sound emission system (such as a piezoelectric annunciator) to alert the surgeon of the temperature hazard in the absence of a connected visualization system.

In some aspects, the smart trocar may have localization capabilities, to provide its location in the patient to the interactive surgical system. Technologies associated with such localization capabilities may include, without limitations, Bluetooth connectivity, magnetic field, and an infrared beacon.

As disclosed above, the augmented reality display may be adapted to display image and virtual objects consistent with the role and function of the various members of the surgical team. In some aspects, the brightness of a particular virtual object in an augmented reality display may be modulated or change to indicate, for example, a change in priority associated with the information of that virtual object. In another aspect, the change in display or virtual object brightness may be a means to differentiate an active but paused surgical device (capable of being active but currently passive) from active and in-use surgical device by being coupled to the console controllers (movable by a user selected to perform an operation). Thus, for example, an active but paused instrument may have a data display in the augmented reality display but have the reading un-highlighted, grayed or otherwise indicative of the passive or paused state of the instrument. The brightness of overlaid virtual objects associated with each of the multiple intelligent surgical devices may be used to establish which of the multiple intelligent surgical devices are used by the same user. The brightness of overlaid virtual objects associated with each of the multiple intelligent surgical devices may also be used to distinguish transfer of control of an instrument during hand-off during instrument exchanges. The brightness change may be used to track in real time which instruments are being used by a single user.

Methods Of Pairing A Device With A User/System

In one aspect, a user may initiate a communication pairing mode between an interactive medical system via a touch-screen disposed on a piece of capital equipment such as a modular energy supply or a hub communication module. The user may then depress one or more actuation devices such as rocker switches or buttons on the medical device to initiate the complementary part of pairing of the medical device with the intelligent medical system. During routine use of the intelligent medical device, these actuation devices may have alternative functions related to the specific operations of the medical device. Once the device is successfully paired, it may trigger user feedback via a haptic buzz and/or an on-screen display of the capital equipment. In one aspect, if the communication pairing is not successful, then the medical device may fail to trigger the haptic buzz, and the interactive medical system may eventually 'timeout' in its search for active devices. The user screen on the capital equipment may prompt the user to press the buttons simultaneously on that medical device in an attempt to initiate or re-initiate communication pairing. In another aspect, the user may push a button on the intelligent medical device and then remove the bailout door. The state of the bailout door may be detected by a Hall affect sensor.

In one aspect, the capital equipment comprising the interactive surgical system may identify multiple smart surgical devices, and the user is prompted with which device they would like to be able to connect. After an initial communication pairing, the surgical device may perform an authentication step which may include any security features needed to validate that the medical device is approved for use with the interactive surgical system.

In another aspect, an intelligent medical device may include an imaging device such as a display screen which could display a pairing code. During an initialization step for communication pairing, the user may enter the pairing code directly into the capital equipment of the interactive surgical system using a touch screen or a keyboard. Alternatively, the user may receive the pairing code on the user's assigned imaging device screen and simply select an icon to 'verify' the communication pairing through any one of a touch screen operation, a mouse click operation, or a keyboard entry operation.

In some aspects, an intelligent medical device may include a gyroscope or three-axis accelerometer to detect changes in the position and/or orientation of the device. The interactive surgical system may prompt the user to perform a series of motions with the medical device (for example, tilt the device forward, back, or similar) to validate the connection between the medical device and the surgical system. Additionally, these actions may be used to validate the integrity of the connection, as well as calibrate the gyroscope and/or accelerometer.

In another aspect, the camera of a laparoscopic device may be used to read a communication pairing code. For example, the user of the laparoscopic device may initiate a communication pairing mode on the interactive surgical system via a touchscreen button. Then, using the laparoscopic camera, the user may direct the camera at a pairing code. The laparoscopic device may then analyze to initiate active pairing between the two devices. In some aspects, the pairing code may be one of a QR code, barcode, a plaintext, an image, or any other visually recognizable mark. It may be understood that the laparoscopic device must be maintained in the sterile field during the visual pairing process. Alternatively, a Bluetooth® or other wireless QR code reader may be used, which may allow more flexibility with the location of the reader. Alternatively, other cameras located within the operating room may be engaged to capture the serial number and pair the intelligent surgical device with the interactive medical system.

In another aspect, an intelligent medical device can form a communication pair with the interactive surgical system via a near field communication ("NFC) reader/pick-up coil that is incorporated into a reusable grounding pad. In yet another aspect, communication between the interactive surgical system and the intelligent surgical device may be accomplished with the use of infra red communication means.

In some alternative aspects, a communication pairing code may be physically incorporate on a bulkhead of the interactive surgical system or on the intelligent medical device. Such physical incorporation may include a sticker displaying the pairing code, or the pairing code may be engraved on the body of the interactive surgical system or on the intelligent medical device In another aspect, a communication pairing code may be incorporated in or included with the packaging of the intelligent medical device. An example of the use of such packing associated pairing code may be found in FIG. 49, FIG. 50, and FIG. 51.

FIG. 49 is a perspective view of packaging 12000 for a wireless surgical instrument capable of RFID token-based pairing, in accordance with one aspect of the present disclosure. Included within packaging 12000 is a packaging container 12002, a surgical instrument 12004, and an RFID card 12006. Surgical instrument 12004 may be, for example, an ultrasonic surgical instrument, an RF electrosurgical instrument, or a multifunction surgical instrument. Further, RFID card 12006 is unique to surgical instrument 12004. A first side 12008 of RFID card 12006 includes an RFID symbol and an arrow instructing a user to flip the card over to a second side 12010. A second side 12010 of RFID card 12006 includes instructions for wirelessly pairing surgical instrument 12004 to a modular energy system or other component of the interactive surgical system. Specifically, the second side 12008 of RFID card 112006 includes a visual prompt 12012 instructing the user hold the card up to a display screen of a modular system (which has the effect of locating the card proximal to the RFID reader) to initiate pairing and a visual prompt 12014 instructing the user to follow instructions on the display screen to complete pairing.

FIG. 50 is a perspective view of a user holding RFID card 12006 proximal to a display screen 12024 of a modular energy system 12020. The modular energy system 12020 may be incorporated into the interactive surgical system. Further, modular energy system 12020 includes a header module 12022 and a display screen 12024. Display screen 12024 includes an RFID symbol 12026 that indicates the location of the RFID reader. FIG. 51 depicts a user locating RFID card 12006 proximal to RFID symbol 12026. This action causes modular energy system 12020 to begin searching for the surgical instrument 12004 for wireless pairing. This action also causes display screen 12024 to display illustrated instructions for wirelessly pairing surgical instrument 12004 to modular energy system 12020.

FIG. 51 is a perspective view of a display screen 12024 displaying illustrated instructions 12028 for wirelessly pairing surgical instrument 12004 to modular energy system 12020. The illustrated instructions 12028 displayed on the display screen 12024 may prompt the user to press a button on surgical instrument 12004 that causes the instrument to enter a pairing mode. In one aspect, placing surgical instrument 12004 in pairing mode causes it to connect to modular energy system 12020, completing the wireless pairing process. In another aspect, multiple steps may be required to pair surgical instrument 12004 to modular energy system 12020. In this case, illustrated instructions 12028 may prompt the user to complete each of the steps required to pair the instrument.

Aspects Of Pairing A Device With A User/System

In some aspects, a technology used for pairing an intelligent surgical device with an interactive surgical system may have additional functions. For example, an intelligent surgical device may be recognized by an interactive surgical system based on a radiofrequency identification (RFID) chip embedded in the device. In addition to providing an identifying token recognized by the system, the RFID chip may also provide data related to the manufacturing status of the device. Such status information may include a serial number, a lot number, or a manufacturing date of the medical device. The RFID chip may also include information related to any flaws or faults in the manufacturing and testing of the intelligent surgical device to indicate that the device is unusable. Such flaws may also be read from the RFID while the surgical device is being processed in the manufacturer's packaging line.

In some aspects, a geofence may be established for a certain functional area in a surgical suite, such as a Mayo stand, a charting table, or the entire Operating Room. Any device that is brought within the geofence area may automatically be paired with any other medical device that is already present within that same geofence area.

In some aspects, an intelligent medical device may automatically be paired with piece of capital equipment when simply brought in proximity thereto. Proximity may be defined based on a signal strength of a communication signal emitted by the surgical device. The signal strength may be used as a mechanism for determining the proximity of the device to the equipment. The capital equipment or other components of the interactive surgical system may pair only with the closest surgical device based on its signal strength. Alternatively, multiple devices may pair with the interactive surgical system, but the devices that are closest to the system components may be prioritized in their communication streams. In some aspects, an intelligent surgical device may reject the pairing process however. In some aspects, the pairing may not be automatic, but may still require an affirmative step by the surgical device user. Thus, the user may be required to issue an acknowledgement or respond to a prompt for additional action.

Although communication pairing between devices is typically accomplished over a wireless communication network, such as Bluetooth®, wired devices may also be suitably paired. For example, the MAC address of a wired device may be stored in an EEPROM on the device. The information from the EEPROM may be read by a pairing device, and then MAC address may be used to establish a secondary wireless Bluetooth® connection. Thus, the wired connection can be used as an indicator to the circuitry when the device is ready to be paired. In one non-limiting example, an energy device may include an additional Bluetooth® enabled processor to allow an auxiliary form of wireless communication. The auxiliary wireless communication may enable certain additional features in addition to those features already available over the wired connection. Such wireless enabled medical devices may still work adequately over the wired connection with interactive surgical systems that lack the additional wireless communication capability. As one example, the MAC address stored in the on board medical device EEPROM may be read by a power generator once the medical device is connected to it. Subsequently, the power generator may then establish the wireless pairing with the medical device.

Indication To Mitigate Confusion Of Paired Devices

It has been disclosed above that communication pairing between intelligent devices or an intelligent device and the interactive surgical system may permit close and repeatable control of the devices as well as a means for recording the device actions during a surgical procedure. Further, such communication pairing may permit information sharing among the members of the surgical team. It may be recognized that successful communication pairing is required to obtain these advantages. Therefore, it is necessary to have a mechanism to identify that each communication pairing is accurate and complete, and that improper pairing or the pairing of incorrect instruments may be avoided. Thus, an indication of pairing status to differentiate correct pairing and what devices are paired together is required.

It may be understood that incorrect device communication pairing may cause unintended surgical outcomes, delays in executing the surgical procedures, device lockout (the device does not function) or may result in a change the operation of the device. For example, a smart stapler and/or energy device, operating on its own, may have a defined performance. However, if such a device is paired to the interactive surgical system, it may receive additional feedback data from other devices. Such additional data may allow the smart surgical device to activate advanced performance functions and adjusted its functional algorithms based on the additional feedback. For example, tissue images from a laparoscopic imaging device may be analyzed by the interactive surgical system which can then provide additional details of the tissue type and/or disease state of the tissue to the smart stapler and/or energy device. The additional information may result in a increased or decreased clamping pressure and/or firing speed of the stapler, or a change in power level of the energy device. Additionally, improper communication pairing may alter the automation steps within the procedure plan based on an expected pairing with other devices and/or accessories. Additionally, smart surgical devices that are unable to pair with the rest of the surgical system may default to the control feature to allow the lowest risk of unintended tissue trauma, thereby reducing the optimized outcome of the procedure.

Several types of indicators may be used to notify a member of the surgical team of successful or ineffective communication pairing. Loss of communication pairing and/or registry of a device may occur when a user or system switches devices or device priorities.

In some aspects, an audible or haptic annunciator may be used to indicate the state of communication pairing. For example, a piezo-based speaker may be programmed to beep once when a first surgical device has been paired successfully to a second device. Alternatively, one or several small audible chirps may be used to indicate a successful communication pairing. In one example, a surgical device user may attempt to pair an intelligent surgical device with the interactive surgical system. Once the pairing process has completed, the device may issue three small chirps to signify that the device has completed the pairing process. If the device fails to pair, a different audible signal may be emitted. Such different audible signals may include, for example, a difference in number, frequency, decibel level, and/or tone of the audible signal. In one non-limiting example, the device user may attempt to pair the intelligent surgical device with the interactive surgical system, but the communication pairing was unsuccessful or rejected. The unsuccessfully paired device may emit a long, lower frequency chirp to signify that the pairing was not successful. Alternatively, no audible signal may be emitted by a device that has not successfully paired with another. In another example, a user may attempt to pair an intelligent surgical device, but the device may not have received the pairing command and therefore never entered the pairing mode. The device may therefore not emit any auditory signal since no pairing had been initiated. Different types of audible signals may represent different states of communication pairing. As one example, a chirp may indicate when a successful pairing has occurred, while a haptic buzz to indicate when unsuccessful pairing has occurred. Different auditory signals, or types of auditory signals may be used to indicate unidirectional versus bidirectional device-to-device pairing. In some aspects, communication pairing could use multiple or user selectable indications for each device. In other aspects, several different indicators may be used at the same time to show successful or unsuccessful pairing, such as a combination of a piezo and haptic buzz for acknowledgement of pairing.

In some aspects, a visual indicator may be used to indicate the status of communication pairing between intelligent surgical devices or a device and the interactive surgical system. An example of a visual indicator of communication pairing status may be in the form of an LED that flashes, or changes color when it is confirmed successful pairing. It may be understood that pre-existing device LEDs may be recruited to provide this additional information. For example, pre-existing, but not viewable, LEDs, on a device circuit board may be relocated to be visible to the user. For example, an opaque bailout door on a capital piece of equipment may be made translucent, thereby allowing visibility of the pre-existing LED's inside. In some aspects, multiple pairing devices to an interactive surgical system may be distinguished based on using a series of LEDs to show on the device what number device it is. In some other aspects, multiple color LEDs may be used to signify different states. Thus, different colored LEDs may correspond to the pairing status/number of the device. For example, a specific colored LED may be associated with the communication pairing of a first device, while a second specific colored LED may be associated with a second device. In some alternative aspects, a series of colored dots may indicate if the device is paired or not. The user can then decide if data should be used from a device based on its indicator color. In some aspects, the color associated with the pairing state of a device may correspond to the actual data color. In some aspects, one or more augmented relay displays may display colored virtual objects having the same color as the various LEDs associated with the pairing of the devices. In this manner, multiple members of the surgical team may be made aware of the status of the communication pairings. Each surgical device may have a multi-color LED as does each instrument and control system. The same displayed color may be displayed on mutually paired devices.

In some aspects, a combination of visual signal color and other effects may be used to differentiate the pairing statuses of two intelligent surgical devices or a surgical device and an interactive surgical system. FIG. 52 illustrates a group of visual indicia 12100 and their associated status characteristics. Thus, for example, when pairing mode is initiated, a red LED and a blue LED may flash in an alternating matter. A flashing blue LED may indicate that the receiving mode is in process of connecting, while a solid blue LED may indicate that the receiving mode has connected. Similarly, a flashing red LED may indicate that the transmitting mode is in process of connecting, while a solid red LED may indicate that the transmitting mode has connected. The red or blue LEDs may flash rapidly (around once every 0.5 seconds, as an example) to indicate that no connection has been made, or that the first medical device is actively searching for its communication partner. Additional colors may be used to indicate other statuses. Thus, a yellow LED may be used to indicate that the communication pairing connection is not stable (for example, has low bandwidth). A blinking yellow LED may indicate that the pairing has an error other than bandwidth.

In some aspects, a smart battery pack on an intelligent device may serve as a location to implement the LED functionality for displaying the pairing status. In a related aspect, a light ring on the back of a smart battery pack could be used in this manner. A smart battery pack would not necessarily require buttons for activation. In some examples, a battery powered intelligent surgical device may initiate a pairing process with another device when the battery pack is inserted into the surgical device. The pairing process may be maintained for a fixed amount of time until communication pairing is accomplished, or the device times-out with no response.

As noted above, two medical devices or a medical device and an interactive surgical system may indicate the successful formation of a communication pair. In some aspects, the interactive surgical system may depict an augmented reality display on a display device, in which the augmented reality display may indicate the communication pairing status of the various devices. For example, the interactive surgical system may display a virtual object overlaid on images of paired devices and may also show which devices are currently paired together, for example using color coding. In some aspects, interactive surgical system may request a member of the surgical team to confirm the current pairing as depicted in the augmented reality display. It may be understood that the augmented reality display may be displayed on any of the display devices in the operating room, including a main surgical display, auxiliary surgical display, or displays associate with tablet or laptop computers assigned to individual members of the surgical team.

In some aspects, two devices may not completely form a communication pairing. In other aspects, two devices may form a communication pair in error. In some aspects, the interactive surgical system may initially exclude a device from forming a communication pair if that device does not support footswitch triggering as part of its functions. An augmented reality display may depict an image of the non-triggerable device with a virtual object such as a partially opaque or grayed out overlay. A user would then be aware that such devices are not available for communication pairing. The interactive surgical system could initiate a test to ensure that the surgeon has the correct device that is paired to a foot switch. For example, the interactive surgical system could signal for the person setting the system up to depress the clamping system on the device. The interactive surgical system may decode which device is indicative as being active. The interactive surgical system could then prompt the user to verify if this device is one to have an external triggering control. If yes, the user could depress the foot switch to signal acknowledgement; if no, the interactive surgical system may gray out the current device on the augmented reality display device by using a partially gray virtual object overlay. In one example, an operating room may include a set of footswitches that are wirelessly attached to the interactive surgical system. In addition, there may be a wirelessly connected linear stapler and two energy devices also connected through the surgical system. In some aspects, multiple medical devices may be paired to a single foot petal. Prior to the procedure, all devices may require an initial pairing with the accessories within the system, for example surgical staplers, ultrasound devices, monopolar and bipolar RF energy devices, and accessories foot petals.

In one aspect, during the initial setup of the devices within the operating room, all of the intelligent devices and resources may form predefined communication pairs. In some aspects, communication priority of the device being used is set by the primary active interface with the foot petal. In another aspect, communication priority of the various devices may be determined by structural or hierarchical criteria. Thus, devices used during high risk or critical stages of the surgical procedure may be assigned higher communication priorities. In some aspects, a lead surgeon of the surgical procedure may be identified by one or more cameras disposed throughout the operating room. A device used by or held by the surgeon—and visible in the camera's field of view—may also be assigned a high communication priority based on the importance of the surgeon during the procedure. Alternatively, a device not visible in the camera's field of view may be considered to have a low communication activity or may not even be considered active. In some aspect, the user of the device may select the communication priority for a device based on a priority list of devices. The user may also choose to indicate which device is a primary device. As each surgical item is added to the communication network within the operating room, a user may be required to confirm that it should be paired with one or more other devices in the operating room. Alternatively, as each surgical item is added to the communication network within the operating room, one or more components of the interactive surgical system may determine if a smart surgical device should be paired or not. In some other aspects, communication priority or communication pairing for a given surgical device may be determined by the surgical plan which may be entered into the memory of the interactive surgical device or may be determined by the artificial intelligence module in the cloud system.

In some aspects, all of the instruments used during a surgical procedure may be present within the operating room and form necessary communication pairs during an initiation protocol. In some alternative aspects, new instruments may be brought into the operating room after the procedure has started, and they will need to pair with other devices within the existing communication network. As one example, a new device may need to be brought into the procedure due to a failure of a device currently in use. In some aspects, one or more devices may issue a type of warning to notify the surgical team members that a new device has entered the operating room. Warnings may include visual warnings on one or more medical devices or audio warning on one of more devices. Additionally, a warning may appear as a virtual object displayed on a primary augmented reality display device. The virtual object may be overlaid on an image of the new device. The surgical member who may assume control of the new device may acknowledge the receipt of the warning. As one example, if the new medical device is to be activated by a foot switch—with which it will pair—the surgical team member may touch or activate the foot switch in acknowledgment. Alternatively, a surgical team member may acknowledge a new clamping device by activating the clamping trigger or closing the jaws to acknowledge the device. If the user does not activate or otherwise acknowledge the new device, an alternative may be considered active. In yet another example, a user may acknowledge the receipt of the communication warning by activating an icon on a primary surgical display screen, a control tablet, or generator or device screen. Such activation may include a making a hand gesture, touching a touch active screen, or using a mouse or keyboard for data entry in another device.

Pairing Information Displayed At The Request Of The System Or User

Information about pairing status between surgical devices or an intelligent surgical device and an interactive surgical system may be displayed on any number of displays or at the request of the interactive surgical system or the user. Communication pairing between devices may be accomplished through wireless (inaudible) signal transmission, for example using the Bluetooth® bandwidth. In alternative aspects, the communication may occur over a high frequency (or radio frequency RF) band. This communication band may be received by capital equipment in the operating room which may be in a frequency band that may not disturb individuals within the operating room.

In some aspects, wireless communication between devices may be initiated by the issuance of a “preamble” or “syncword” by the initiating device. For example, an intelligent surgical device may be powered up and start transmitting its “preamble,” which the receiver may cross-correlate or convolute with other signals to identify appropriate devices. Essentially, the transmitter of an intelligent surgical device may emit a wireless fingerprint specific to that device, which has characteristics identifiable by the transceiver. The receiver may use an internal mathematical function to “merge” the preamble signal with another signal in order to identify appropriate transmitters. FIG. 53 depicts how a receiving device may use a convolution function 12200*a*, a cross-correlation function 12200*b*, or an autocorrelation function 12200*c* to identify a particular transmitting surgical device. In some aspects, the initiating or transmitting device may transmit a preamble defined by a function f. In one aspect, the receiving device may store a second pairing syncword function g. The receiving device may then use the appropriate mathematical functions-convolution, cross-correlation, or autocorrelation—on both f and g to obtain resulting functions that may specifically identify the transmitting device.

In some aspects, the transmitted syncword f may include transmitting device identifiable information such as a model number and/or serial number. Alternatively, the syncword f may be a random data string. The transmitter radio may be a hardware defined radio to create a modular platform to randomize the preamble signal. Alternatively, transmitter radio may be a software defined radio to create a modular platform to randomize the preamble signal. Depending on the communication protocol used, the syncwords may be composed of wireless data packets.

In some alternative aspects, the transmitting or initiating device may transmit both the fand g syncwords for the receiving device to decode. In some aspects, the two syncwords may be transmitted using the same carrier frequency. In other aspects, each syncword may be transmitted using a unique carrier frequency. In one example, the initiating device may transmit syncword f over a 2.4 GHz channel, and transmit syncword g over a 5.0 GHz cannel. In this example, the receiving device may need multiple physical receivers, each tuned to the appropriate carrier frequency, in order to detect the two syncwords. This particular example suggests that the transmitter and receiver are each tuned to specific carrier frequencies. Alternatively, the transmitter and receiver may each be tuned to specific carrier frequencies bands. In some aspects, each individual type of smart surgical device may be configured or tuned in manufacturing to a specific carrier frequency based on a unique identifier number The use of one or more syncwords or preamble data packets to initiate communication pairing may provide additional information regarding the device attempting to form the communication pair. Additionally, the use of syncwords may improve device communication security. In one aspect, a periodic synchronization key may be embedded within the “preamble” data to add security to wireless communication channel. As an example, within the initial “preamble” message, the transmitter could tell the receiver a new “preamble” will occur after x transmissions or t time. This security measure may prevent preamble decryption as a “listening/sniffing” device may only be able to understand a portion of the message (for example the f preamble or syncword) before having to re-identify the new signal pattern. In this manner, a medical device using a “preamble” to re-initiate appropriate wireless communications for added security. For medical devices that are enabled to receive communication packets within a defined frequency band, the transmitting device may use frequency hopping techniques to mask the synchronization signals.

In some aspects, the transmitting device may combine multiple registers to show what device is able to be connected to. In other aspects, the syncword may be broadcasted on the same service or multiple services, and the device could pair automatically. In some additional aspects, the interactive surgical system may record the series of syncwords transmitted to maintain a record of the communication pairing.

The use of multiple initialization sequences for communication pairing may not be limited to wireless transmission packets. In some aspects, the initialization sequences may be encoded in multiple barcodes or other optically identified markers. For example, a reusable shaft of an intelligent surgical device may have a first bar code inscribed on it, and a disposable end effector (for example a 60 mm end-effector) may have a second barcode engraved on it. The bar codes may be read separately and combined through a mathematical function to result in a single, initialization code.

In some aspects, two devices may be incorrectly or improperly paired. As an example, a robotic procedure could have multiple energy devices and multiple energy generators which both communicate with a control device for example a wireless foot pedal control. The foot pedal could be paired to an incorrect handpiece control for the specific user in control of the foot pedal. In this case, the incorrect wireless device would need to be unpaired from the initial device and then re-paired to the correct device. Additionally, it would also need to provide some indication of what control is paired to what handpiece.

In some aspects, communication pairing may be verified to prevent pairing errors. Pairing errors may be displayed by the augmented reality display device as a virtual object, such as an overlay, on an image of the devices involved. In some aspects, an initial faulty pairing may be severed and re-established if a connectivity error is detected. In some aspects, pairing faults may be recorded and communicated to administrative levels of the surgical system for later analysis. Aspects of such faults may include the nature of the fault, its frequency, and other aspects related to the pairing fault or failure.

In another aspect, a hand-held intelligent surgical device may include a radio frequency identification device (RFID) in its handle. The surgeon using the device may have an RFID reader in the surgical gloves, which may be in communication with the interactive surgical system. In this manner, the surgical system may be made aware of the specific device being handled by the surgeon.

Cooperative Overlays of Interacting Instruments which Result in Both Overlays being Effected

Cooperative Overlays of Interacting Instruments

Having described a general implementation of the various surgical systems, surgical hubs, communication systems, augmentation systems, and augmented reality devices disclosed herein, such as surgical systems 1, 2, 50, 52, surgical hubs 6, 56, 5104, communication system 63, augmentation system 83, and AR devices 66, 84, the disclosure now turns to describe various other implantations of the systems, hubs, and devices. For the sake of brevity, various details and implementations of the systems, hubs, and devices being described in the following sections, which are similar to the various systems, hubs, and devices described above, are not repeated herein. Any aspect of the systems, hubs, and devices described below can be brought into and/or be implemented by the above systems, hubs, and devices.

Multiple surgical instruments are often present in the operating room (OR) during a surgical procedure. The surgical instruments present can have different functionalities, different operating parameters, and different intended uses. For example, depending on the surgical procedure or step of the surgical procedure that is being performed, it is often desirable, or even required, to use multiple surgical instruments simultaneously. Thus, some of the surgical instruments in the OR during a surgical procedure may be intended to be use simultaneously and/or in close proximity to one another. For example, a circular stapling instrument may be intended to be used with a specific anvil device. As another example, a buttress device may be intended to be used with a specific type of endo-cutter instrument. As yet another example, a staple cartridge may be intended to be used with a specific type of surgical stapling instrument. Moreover, the simultaneous use of multiple surgical instruments may be associated with various recommended functionalities that are not available when the instruments are not used in combination.

However, in other instances, some surgical instruments present in the OR are not intended to be used simultaneously or in close proximity to one another (e.g., because the use of various combinations of surgical instruments may cause one or more the instruments to malfunction). For example, using a metallic instrument in proximity to an energy device could cause arcing from the energy device to the metallic instrument. As another example, using a metallic instrument in proximity to an energy device could cause a change in the normal thermal spread of the energy device leading to incomplete seals or device failure. As yet another example, a staple cartridge may be counterfeit and therefore should not be used with a specific surgical stapling instruments. Furthermore, whether or not surgical instruments should be used together may depend on the specific type of surgical instrument being used and the specific surgical procedure that is being performed.

Given the wide variety of combinations of different types surgical instruments that may be present in the OR and the wide variety of different surgical procedures that may be performed, it may be difficult for OR staff to keep track of which combinations of surgical instruments are associated with various functionalities, which combinations of surgical instruments should be used simultaneously and/or in close proximity to one another, and which combinations of surgical instruments should not be used simultaneously and/or in close proximity to one another. Accordingly, there is a need for apparatuses, systems, and methods for determining the presence and/or use of various combinations surgical instruments within the OR, for identifying additional functionality that may available based on the determined combination, for determining that surgical instruments are intended to be used proximately to one another, and/or for determining that surgical instruments are not intended to be used proximately to one another.

Moreover, in cases were multiple surgical instruments are used simultaneously during a surgical procedure or a step of a surgical procedure, the surgical instruments are often interacting with each other and/or with a common object within the surgical field. For example, a surgical grasping device may be used to hold or stabilize tissue while an endo-mechanical surgical device is used to cut the same tissue. As explained above, augmented reality (AR) devices may be used to display virtual objects, data, or visual effects overlaid on images of a surgical field. Thus, in the case of the exemplary surgical grasping device and endo-mechanical surgical device, an AR device may be used to display overlays with information related to each surgical devices' individual interactions with the tissue (e.g., force exerted on the tissue). However, when multiple surgical instruments are interacting with each other and/or a common object, the interaction often results in some combined effect that is different than the effect caused by any one of the individual surgical instruments. Knowledge of this combined effect may be useful to aid OR staff during the performance of the surgical procedure. Thus, in addition to the need for apparatuses, systems, and methods for determining the presence and/or use of various combinations surgical instruments within the OR, there is also a need for apparatuses, systems, and methods for displaying cooperative AR overlays based on interactions between multiple surgical instruments.

Apparatuses, systems, and methods for determining the presence and/or use of various combinations surgical instruments within the OR are disclosed herein. Also disclosed herein are apparatuses, systems, and methods for determining the functionality that may available based on a determined combination of surgical instruments that are present and/or in use during a surgical procedure. As described above, various surgical system configurations may be implemented to communicatively couple multiple surgical instruments within an OR (e.g., operating theater) to one or more surgical hubs. For example, referring again to FIGS. 5 and 6, a computer-implemented interactive surgical system 50 can include at least one surgical hub 56 communicatively coupled to multiple operating theater devices (e.g., multiple surgical instruments 21, 98, 99, etc. within the OR). The surgical hub 56 can be configured to determine the combination of specific surgical instruments that are connected thereto (instrument types, instrument models, instrument settings and functionality, etc.) and/or the combination of specific surgical instruments that are present with a specific OR. Further, the surgical hub 56 can be configured to determine the combination of specific surgical instruments that are being used for a given surgical procedure. It should be noted that although surgical system 50 and surgical hub 56 are referenced in this section as an exemplary surgical system and surgical hub, any of the surgical systems and hubs disclosed herein can be configured to determine the presence and use of specific combinations of surgical instruments.

In various aspects, the connection and/or activation of specific surgical instruments and/or specific combinations of surgical instruments can enable functionality related to the hub and/or the surgical instruments. In one aspect, the connection and/or activation of a specific surgical instrument (surgical device) can enable functionality on the hub. In another aspect, the connection and/or activation of a specific combination of surgical instruments can enable functionality on the hub. The hub functionality may be enabled based on information stored within a memory of the surgical instrument or instruments that are connected thereto. Moreover, the hub functionality enabled may involve unlocking additional modes and/or features that can be executed by the hub. These additional modes and/or features may be related to the specific instrument or combination of instruments that, by connection to the surgical hub, enabled the hub functionality. For example, a specific surgical instrument such as a specific model and/or revision of an energy device may contain information mapped within its electrically erasable programmable read-only memory (EEPROM) that is read upon connection to the surgical hub. The EEPROM-stored information may cause additional features and/or modes to be unlocked on the hub. As another example, the connection of the combination of a specific model of an energy device and a specific model of an endoscope may cause additional features and/or modes to be unlocked on the hub.

In another aspect, the connection and/or activation of a specific surgical instrument (surgical device) or a specific combination of surgical instruments can enable functionality on the surgical instrument and/or instruments. The instrument functionality enabled by the surgical hub may include configuring the surgical instrument and/or instruments by the surgical hub. For example, upon connection, the surgical hub may cause a surgical instrument to prompt the user to input a setting selection or a user profile related to the connected instrument or combination of instruments. The instrument functionality enabled by connection of a surgical instrument or combination of instruments to the surgical hub may include automatically updating a configuration of the surgical instrument and/or instruments based on setting of the surgical hub. For example, upon connection, based on the settings of the surgical hub, the surgical hub may cause a surgical instrument to include an additional button (e.g., a touch screen button). The additional button may relate to an additional operation or function of the instrument that is available based on the combination of surgical instruments connected to the surgical hub.

In yet another aspect, the connection and/or activation of a specific surgical instrument (surgical device) or a specific combination of surgical instruments can cause the hub to change a parameter of the surgical instrument and/or instruments. For example, connecting a specific combination of surgical instruments to the surgical hub may cause the hub to adjust a clamping pressure, knife speed, maximum articulation angle, and/or firing stroke setting of an end effector of one of the connected surgical instruments. Any of the surgical instrument parameters that are adjusted by the hub may be adjusted or customized by the user.

In yet another aspect, the connection and/or activation of a specific surgical instrument (surgical device) or a specific combination of surgical instruments can cause parameters of the surgical hub to be adjusted. For example, the surgical hub may include an algorithm for optimizing ideal and/or targeted firings and angles for a specific surgical procedure, such as a sleeve gastrectomy. The hub could be configured to update the algorithm depending on the specific surgical instrument that is activated during the procedure (e.g., the algorithm can be updated depending on whether the active linear endo-cutter is a 45 mm endo-cutter or a 60 mm endo-cutter).

FIG. 54 illustrates method 13000 for enabling functionality based on combinations of connected surgical devices, according to several non-limiting aspects of this disclosure. The method 13000 can include connecting 13002 a first surgical device to a surgical hub and connecting 13004 a second surgical device to the surgical hub. Further, the method 13000 can include identifying 13006, by the surgical hub, the combination of devices connected thereto based on the connection 13002 of the first surgical device and the connection 13004 of the second surgical device. The method 13000 can further include enabling 13008, based on the identified 13006 combination of devices connected to the surgical hub, functionality of the first surgical device, the second surgical device, the surgical hub, or a combination thereof.

Apparatuses, systems, and methods for determining that surgical instruments are intended to be used together (e.g., in proximity to one another) and for determining that surgical instruments are not intended to be used together are disclosed herein. As explained above, various surgical system configurations may be implemented to communicatively couple multiple surgical instruments within an OR (e.g., operating theater) to one or more surgical hubs. For example, referring again to FIGS. 5 and 6, a computer-implemented interactive surgical system 50 can include at least one surgical hub 56 communicatively coupled to multiple operating theater devices (e.g., multiple surgical instruments 21, 98, 99, etc. within the OR). The surgical hub 56 can be configured to determine the combination of specific surgical instruments that are connected thereto. Further, the surgical hub 56 can be configured to determine the combination of specific surgical instruments that are being used for a given surgical procedure. In one aspect, the surgical hub 56 may store information related to the intended uses of various types of surgical instrument and/or combinations of various types of surgical instruments. In another aspect, the surgical hub 56 may be in communication with a server or other device that stores information related to the intended uses of various types of surgical instrument and/or combinations of various types of surgical instruments. Thus, the surgical hub 56 can be configured to determine, based on the determined combination of surgical instruments connected thereto, that connected surgical instruments are intended to be used together and/or that connected surgical instruments are not intended to be used together. The surgical hub may provide a notification to one or more users (e.g., OR staff) based on the determination of whether or not the connected surgical instruments are intended to be used together. This notification may be in the form of an AR overlay.

However, some surgical instruments may not have the capability to connect to the surgical hub (e.g., surgical instruments may not be smart devices/instruments). Thus, in various aspects, any of the surgical instruments disclosed herein that are capable of connecting to the surgical hub may include sensors configured to detect and/or identify other surgical instruments The hub-connecting surgical instruments including sensors may be referred to hereinafter as "smart sensing instruments". In one aspect, the surgical hub may be configured to cause a smarting sensing instruments to send information related to instruments detected and/or identified by the smart sensing instrument to the surgical hub. The surgical hub may use this information to determine if the detected instruments are intended or are not intended be used with the smart sensing instrument. In another aspect, the surgical hub may use this information to enhance location data used to generate AR overlays related to the detected instruments.

In various aspects, surgical instruments, such as smart sensing instruments and/or instruments that cannot connect to the surgical hub, can include a proximity sensor to detect other instruments. In some aspects, the proximity sensor may be a proximity beacon of a first instrument that sends out a signal including a data set describing the first instrument's functions. A proximity sensor of second surgical instrument may read the incoming signal and determine, based on the data set, whether or not the first instrument and the second surgical instrument are intended to be used in proximity to one another. In one aspect, the second surgical instrument may provide a notification to OR staff based on the determination. In another aspect, the second surgical instrument may send data related to the determination to the surgical hub causing the surgical hub to provide a notification to one or more users (e.g., OR staff) indicating whether or not the first and second surgical instruments are intended to be used together. This notification may be in the form of an AR overlay.

In various aspects, some surgical instruments may include a proximity beacon that can send out a signal but cannot read incoming signals from other instruments. For example, the first surgical instrument described above may be a surgical grasper with a proximity beacon capable of sending out a signal but not capable of reading incoming signals. In this case, the second surgical instrument, for example, an energy device, may include a proximity beacon capable of reading the incoming signal from the first surgical instrument. Thus, the second surgical instrument may be configured to determine if the first and second instruments are intended to be used together.

FIG. 55 illustrates a method 13010 for determining whether or not multiple surgical instruments are intended to be used in proximity to one another, according to several non-limiting aspects of this disclosure. The method 13010 can include transmitting 13013, by a proximity beacon of first surgical device, a signal to a proximity beacon of a second surgical device. Further, the method 13010 can include connecting 13014 the second surgical device to a surgical hub. Yet further, in one aspect, the method 13010 can include determining 13016A, by the second surgical device, the surgical hub, or a combination thereof, that the first surgical device and the second surgical device are intended to be used proximately to one another. In another aspect, the method 13010 can include determining 13016B, by the second surgical device, the surgical hub, or a combination thereof, that the first surgical device and the second surgical device are not intended to be used proximately to one another. In some aspects, the method 13010 can also include providing 13018, by the second surgical device, the surgical hub, an AR device connected to the surgical hub, or a combination thereof, a notification to a user (e.g., OR staff) based on the determination 13016A and/or the determination 13016B.

In some aspects, the determination of whether or not multiple surgical instruments are intended to be used together may be based on an identification code of at least one of the instruments. For example, FIG. 56 illustrates a surgical instrument 13020 including an identification code 13022 as well as a corresponding identification code table 13026, in accordance with at least one non-limiting aspect of the present disclose. The identification code 13022 can be a set of characters printed or otherwise displayed on a surface 13024 of the instrument 13020. In one aspect, the identification code 13022 may be displayed on multiple surfaces of the instrument 13020 so that the identification code can be viewed from multiple angles (not shown in FIG. 56). The identification code 13022 may include five (5) binary characters 13028, wherein each specific type and/or model 13029 of surgical instrument is associated with a unique combination of the five binary characters. An identification code table 13026 can be used correlate the unique combination of five binary characters 13028 with the type and/or model 13029 of the surgical instrument. In one aspect, the identification code 13022 may be detected by an imaging device associated with an imaging module of the surgical hub (e.g., imaging device 24, 96, AR device 66 referenced with respect to FIG. 2; imaging module 38 referenced with respect to FIG. 3). In another aspect, a user (e.g., OR staff) may manually provide the identification code 13022 to the surgical hub. Thus, the surgical hub may be able to identify the surgical instrument 13020 based on the identification code 130222 and determine if the identified surgical instrument 13020 is intended to be used with other detected instruments.

In various aspects, apparatuses, systems, and methods for displaying cooperative AR overlays based on interactions between multiple surgical instruments are disclosed herein. As explained above, augmented reality (AR) devices (e.g., AR device 66) may be used to generate an image of a surgical field during a surgical procedure, for example, based on images of the surgical field captured by one or more imaging devices of a surgical system (e.g., imaging device 24, 96, AR device 66 referenced with respect to FIG. 2; imaging module 38 referenced with respect to FIG. 3). The image generated by the AR device can be a still image or a live feed of the surgical field. Further, the image of the surgical field generated by the AR device can sometimes be referred to hereinafter as an intraoperative display.

As explained in more detail above, the surgical systems and/or surgical hubs disclosed herein (such as surgical systems 1, 2, 50, 52, surgical hubs 6, 56, 5104) can be configured to cause the AR device to display a virtual objects, data, or visual effects overlaid on the intraoperative display. These virtual objects, data, and visual effects can be based on various attributes of a surgical instrument, for example, as the surgical instrument is performing a surgical procedure in the surgical field. In other words, the intraoperative display can display a virtual data overlay including objects, data, and/or visual effects related to the use of a surgical instrument in the surgical field. For example, the intraoperative display can display data related the effect a surgical instrument has on tissue as the surgical instrument interacts with tissue in the surgical field.

As also explained in more detail above, multiple surgical instruments may be used simultaneously when performing a surgical procedure. Further, the surgical hub and/or the individual instruments can be configured to detect the combination specific combination of surgical instruments are in use. In other aspects, the surgical hub and/or the individual instruments can be configured to detect an interaction between the combination of instruments. In one aspect, the detected interaction can include the surgical instruments interacting with each other. In another aspect, the detected interaction can include the instruments interacting with a common structure within the surgical field, such as, for example tissue. Thus, the intraoperative display can be configured to display a data overlay based on the interaction between the combination of surgical instruments.

In some aspects, the intraoperative display can be configured to display multiple data overlays based on the use of multiple instruments. For example, a first surgical instrument may be simultaneously present in the surgical field with a second surgical instruments. The surgical hub may receive data related to the operation of the first surgical instrument and data related to the operation of the second surgical instrument. The data related to the operation of the first surgical instrument can be used to display generate a first data overlay and data related to the operation of the second surgical instrument can be used to generate a second data overlay. The first data overlay and the second data overlay can be simultaneously displayed by the intraoperative display. Thus, a surgeon using the AR device may be able to simultaneously receive information related to both instruments.

In some aspects, multiple users (e.g., multiple OR staff members) may each be using an AR device. In other aspects, multiple users may each be using a surgical instrument. The surgical systems and/or surgical hubs disclosed herein can be configured to cause any combination of different AR devices to display any number and combination of different data overlays based on the use of multiple surgical instruments. For example, a first user may be using a first AR device generating a first intraoperative display. The surgical hub can be configured to link the first AR device to the first user. A second user may be using a second AR device generating a second intraoperative display. The surgical hub can be configured to link the second AR device to the second user. Further, the first user may be using a first surgical instrument and the second user may be using a second surgical instrument. The first interactive display can be configured to display a first data overlay based on the first instrument and a second data overlay based on the second instrument. Likewise, the second interactive display can be configured to display the first data overlay based on the first instrument and the second data overlay based on the second instrument. In another example, the first intraoperative display may only display the first data overlay based on the first user's use of the first instrument and not the second instrument. Thus, the data overlays displayed by each intraoperative display can be customized based on which user the AR device is linked to, the preferences of the user, the surgical instrument the user is using, or any combination thereof.

Moreover, as surgical instruments are used in combination, data related to various attributes of the combined use of the surgical instruments can be detected, calculated, and/or otherwise determined by the surgical hub, the individual instruments, other components of the surgical system, or a combination thereof. Thus, the intraoperative display can be configured to display a data overlay based on an attributed related to the combined use of the surgical instruments. This type of data overlay can sometimes be referred to herein as a cooperative data overlay. Attributes related to the combined use of surgical instruments can include, for example, a combined force exerted by the instrument, a distance between the instruments, a distance between the instruments and an object, a combined parameter of the instruments, or any other attribute that can be detected, calculated, or otherwise determined based on the interaction of multiple surgical instruments. The cooperative data overlay may be displayed with and combination of other data overlays.

FIGS. 57A and 57B illustrate an exemplary intraoperative display 13030 displaying an endo-cutter 13034 and a surgical grasper 13036 interacting with tissue 13038 in a surgical field 13032, in accordance with several non-limiting aspects of this disclosure. Referring now to FIG. 57A, the endo-cutter 13034 can be seen grasping the tissue 13038. This grasping action causes a tension force on the tissue 13038. In some aspects, the tension force can be determined by a surgical hub. Based on the interaction of the surgical grasper 13036 and the tissue 13038, a first data overlay 13040 is displayed by the intraoperative display 13030. The first data overlay 13040 includes a vector arrow depicting the tension force (5.7) and the direction of the tension applied to the tissue 13038 by the surgical grasper 13036. FIG. 57A also depicts an endo-cutter 13034 grasping the tissue 13038. This grasping action also causes a tension force on the tissue 13038 which, in some aspects, can be determined by a surgical hub. Based on the interaction of the endo-cutter 13034 and the tissue 13038, a second data overlay 13042 is displayed by the intraoperative display 13030. The second data overlay 13042 includes a vector arrow depicting the tension force (7.8) and the direction of the tension applied to the tissue 13038 by the surgical grasper 13036.

Referring now to FIG. 57B, a cooperative data overlay 13044 is displayed by the intraoperative display 13030. The cooperative data overlay 13044 includes a vector arrow depicting a combined tension force (13.5) and direction of the tension applied to the tissue 13038 by the combined interaction of the endo-cutter 13034 and the surgical grasper 13036. The combined tension force and direction of tension shown by the cooperative data overlay 13044 can be calculated or otherwise determined by the surgical hub. Thus, a user viewing the intraoperative display 13030 including the cooperative data overlay 13044, is able to easily visualize the combined effect that the endo-cutter 13034 and the surgical grasper 13036 are causing to the tissue 13038.

Figure 58A:
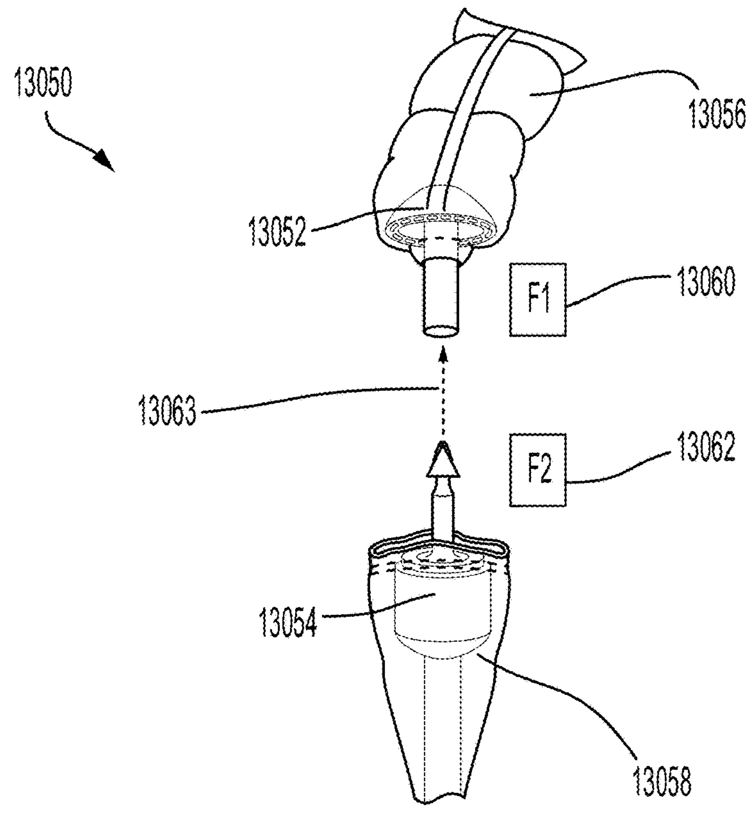

FIGS. 58A, 58B, 58C, and 58D illustrate an exemplary intraoperative display 13050 displaying the performance of an anastomosis procedure using an anvil 13052 and a device deck 13054, in accordance with several non-limiting aspects of this disclosure. Referring now to FIG. 58A, the anvil 13052 can be seen interfacing with a first section of a colon 13056. As the first section of the colon 13056 is advanced 13063 towards the device deck 13054, the anvil 13056 exerts a pulling force F1 on the surrounding tissue of the first section of the colon 13056. This force can be determined by the surgical hub. Based on the interaction of anvil 13056 and the first section of the colon 13056, a first data overlay 13060 is displayed by the intraoperative display 13050. The first data overlay 13060 can include graphic indicating the pulling force of the anvil 1352 on the first section of the colon 13056 as well as the directionality of the force. FIG. 58A also depicts device deck 13054 interfacing with a second section of a colon 13058. As the second section of the colon 13058 is advanced 13063 towards the anvil 13052, the device deck 13054 exerts a pulling force F2 on the surrounding tissue of the second section of the colon 13058. This force can be determined by the surgical hub. Based on the interaction of device deck 13054 and the second section of the colon 13058, a second data overlay 13062 is displayed by the intraoperative display 13050. The second data overlay 13062 can include graphic indicating the pulling force of the device 13060 on the second section of the colon 13058 as well as the directionality of the force.

Figure 58B:
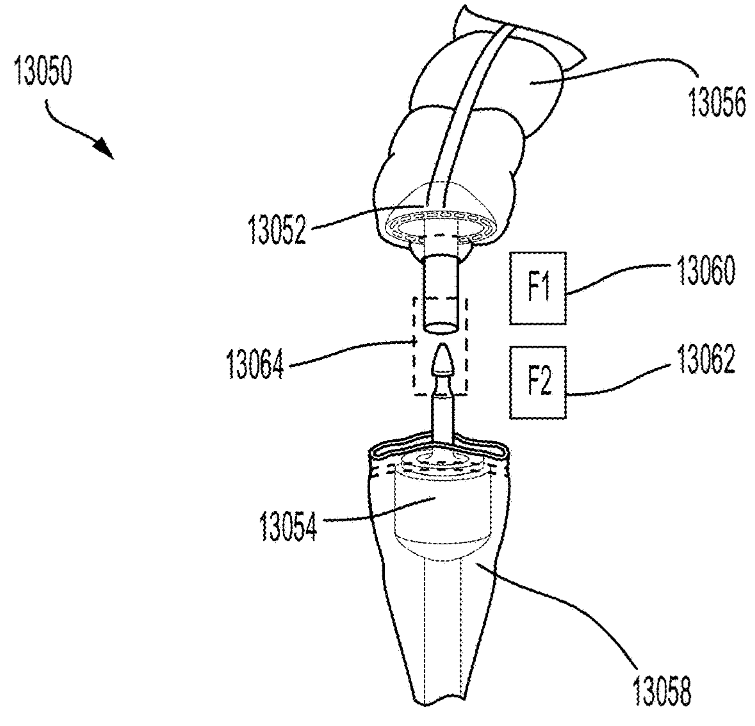

Referring now to FIG. 58B, the intraoperative display 13050 now depicts the anvil 13052 and the device deck 13054 as they are nearing attachment. The surgical hub can be configured to sense the proximity of the anvil 13052 and the device deck 13054. Further, the surgical hub can be configured to display a first cooperative overlay 13064 based on the sensed proximity. The first cooperative overlay 13064 can graphically indicate whether or not attachment between the anvil 13052 and the device deck 13054 has been achieved. For example, the first cooperative overlay 13054 as shown in FIG. 58B can indicate that attachment between the anvil 13052 and the device deck 13054 has not yet been achieved. The first data overlay 13060, the second data overlay 13062, and the first cooperative overlay 13064 can assist a user viewing the intraoperative display 13050. In some aspects, the intraoperative display 13050 can also include additional data overlays to indicate a predicted change in the forces applied to the colon tissue. In other aspects, the intraoperative display 13050 can include additional data overlays to indicate an optimal angle of approach. These data overlays may assist the user in achieving an optimal outcome of the anastomosis procedure.

Figure 58C:
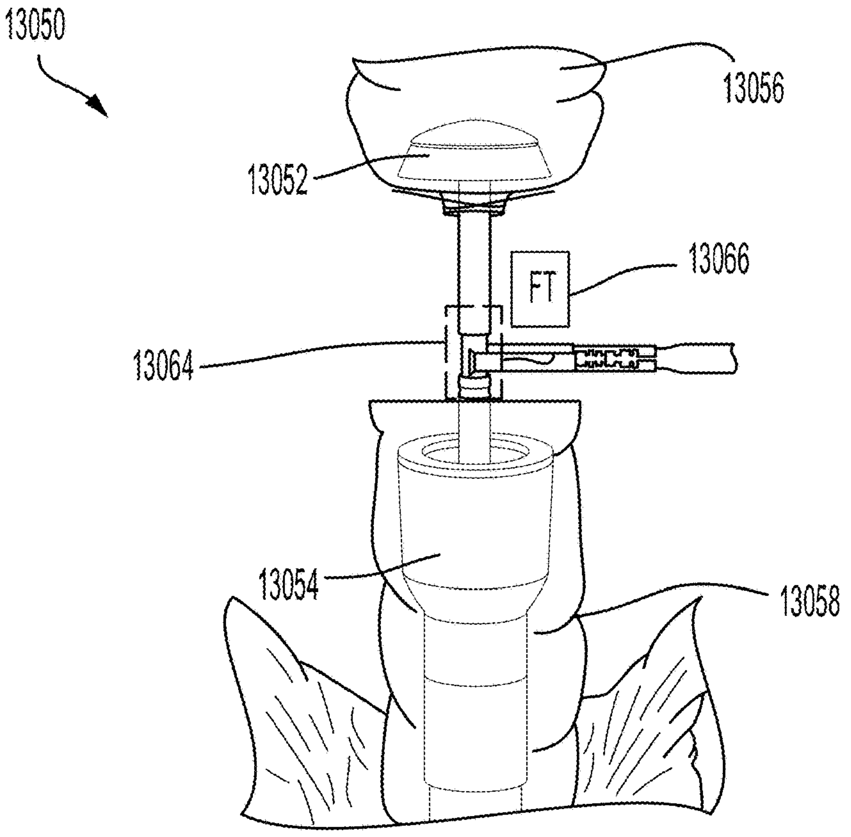

Referring now to FIG. 58C, the intraoperative display 13050 now depicts attachment of the anvil 13052 and the device deck 13054 by a device 13068. The surgical hub can be configured to determine this attachment. Based on the attachment, the first cooperative overlay 13064 now graphically indicates the attachment. As a result of the attachment, the intraoperative display 13050 now depicts a second cooperative overlay 13066. The second cooperative overlay 13066 can include a graphic indicating the combined pulling force FT of the anvil 13052 and the device deck 13054. In the non-limiting aspect of FIG. 58C, the attachment of the anvil 13052 and the device deck 13054 causes the first data overlay 13060 and the second data overlay 13062 to no longer be displayed by the intraoperative display. In other aspects, the first data overlay 13060 and the second data overlay 13062 may remain displayed upon attachment of the anvil 13052 to the device deck 13054.

Figure 58D:
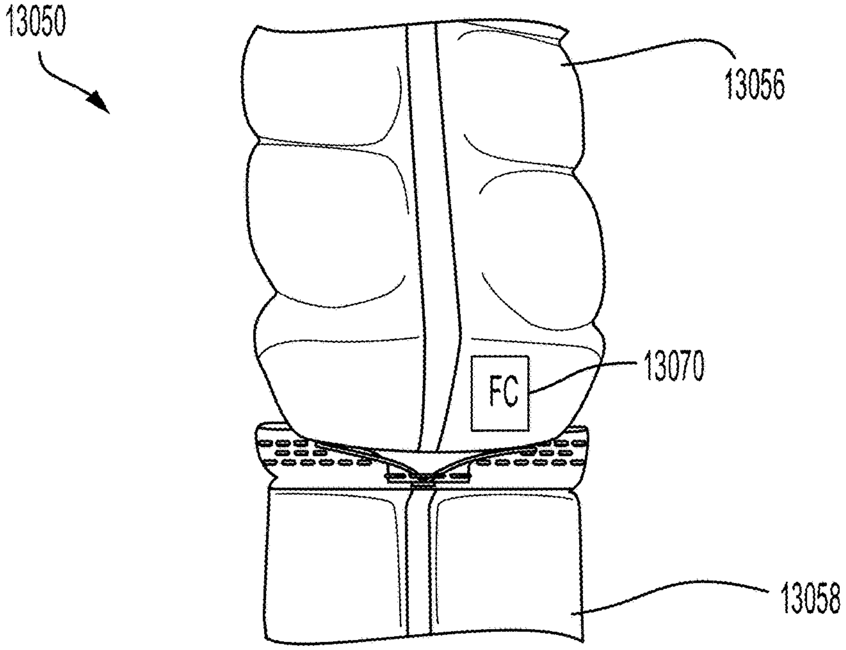

Referring now to FIG. 58D, the intraoperative display 13050 now depicts the compression of the first section of the colon 13056 and the second section of the colon 13058 during anastomosis. The surgical hub can be configured to determine the compression force FC on the first section of the colon 13056 and the second section of the colon 13058 during this portion of the procedure. The compression force can be a force caused by compression of the tissue between the anvil 13052 and the device deck 13054. Accordingly, the intraoperative display 13050 can display a third cooperative overlay 13070 that graphically depicts the compression force FC. The third cooperative overlay 13070 can be used by the user to ensure that there is a good seal and acceptable staple formation across the first section of the colon 13056 and the second section of the colon 13058.

FIG. 59 illustrates a method 13200 for displaying a cooperative overlay of interacting instruments, according to several non-limiting aspects of this disclosure. The method 13200 may be practiced by any combination of the surgical systems, surgical hubs, communication systems, augmentation systems, AR devices, any of the components thereof, and any other devices and systems disclosed herein, such as surgical systems 1, 2, 50, 52, surgical hubs 6, 56, 5104, communication system 63, augmentation system 83, and AR devices 66, 84.

In accordance with the method 13200, a first augmented reality display device may be communicatively coupled 13202 to a surgical hub. The first augmented reality device can generate 13204 a first intraoperative display of a surgical field. The first intraoperative display can display 13206 a first data overlay based on operation of a first surgical instrument. The first surgical instrument can interact 13208 with a second surgical instrument and, based on the interaction 13208 of the first and second surgical instrument, the first intraoperative display can display 13210 an indicator of the interaction.

In accordance with one aspect of the method 13200, the interaction 13208 of the first surgical instrument with a second surgical instrument can include the first surgical instrument and the second surgical instrument interacting with a common structure in the surgical field. In another aspect, the first intraoperative display can simultaneously display the first data overlay based on operation of the first surgical instrument and a second data overlay based on operation of the second surgical instrument. In yet another aspect, the first intraoperative display can display a cooperative data overlay based on the interaction of the first surgical instrument and the second surgical instrument. In yet another aspect, the interaction of the first surgical instrument and the second surgical with the common structure in the surgical field can include interacting the first surgical instrument and the second surgical instrument with tissue. Further, the first intraoperative display can display a combined force applied to the tissue by the first surgical instrument and the second surgical instrument.

In accordance with one aspect of the method 13200, a second augmented reality display device can be communicatively coupled to the surgical hub. The second augmented reality display device can generate a second intraoperative display of the surgical field. The second intraoperative display can display a second data overlay based on operation of the second surgical instrument. Further, the second intraoperative display can display an indicator based on the interaction between the first and second surgical instruments. In another aspect of the method 13200, the surgical hub can link the first surgical instrument and the first display device to a first user and link the second the surgical instrument and the second display device to a second user.

In accordance with one aspect of the method 13200, the surgical hub can identify that the first surgical instrument and the second surgical instrument are intended to be operated proximately to one another. In another aspect, the surgical hub can identify that the first surgical instrument and the second surgical instrument are not intended to be operated proximately to one another. In yet another aspect, a proximity sensor of the first surgical instrument can detect the second surgical instrument.

Anticipation of Interactive Utilization of Common Data Overlays by Different Users Having described a general implementation of the various surgical systems, surgical hubs, communication systems, augmentation systems, and augmented reality devices disclosed herein, such as surgical systems 1, 2, 50, 52, surgical hubs 6, 56, 5104, communication system 63, visualization system 8, augmentation system 83, imaging devices 24, 96 and AR devices 66, 84, the disclosure now turns to describe various other implantations of the systems, hubs, and devices. For the sake of brevity, various details and implementations of the systems, hubs, and devices described in the following sections, which are similar to the various systems, hubs, and devices described above, are not repeated herein. Any aspect of the systems, hubs, and devices described below can be brought into and/or be implemented by the above systems, hubs, and devices.

The operating room (OR) staff often includes a combination of members with different roles such as surgeons, anesthesiologists, nurse anesthetists, surgical technicians, residents, physician's assistants, etc. Throughout the course of a surgical procedure, staff members with varying roles may rely on different information in order to make decisions. Thus, if a staff member does not receive relevant information related to their role, it can result in critical errors related to the procedure.

To illustrate the importance of communicating relevant information to various OR staff members based on their role, two exemplary situations are provided below. The first exemplary situation relates to an abdominal perineal resection procedure performed by a surgical team and an anesthesiology team. During the procedure, the patient experienced some blood loss and the patient's surgical team was informed about the anesthesiology team's plan to transfuse the patient with a third unit of packed red blood cells. The surgical team members looked up in acknowledgement and continued surgery. Later on, a blood gas was drawn revealing the patient's hemoglobin (Hgb) level as 6.6 g/dL. Comparatively, at the start of the procedure, the patient's Hgb level was measured at 14.8 g/dL. When the surgical team was informed of the former Hgb measurement of 6.6 g/dL, the surgical team indicated that more bleeding should be expected. However, the surgical team did not indicate why they expected more bleeding. On three separate occasions, the attending anesthesiologist asked the surgical team for updates on the patient's surgical situation because the anesthesiology team was not able to keep up with the patient's blood, fluid, and resuscitation demands. Specifically, the amount and source of blood loss (e.g., arterial vs. venous vs. oozing), as well as the surgical team's plan to continue dissection despite continued bleeding, was not clearly communicated to the anesthesiology team. The patient's hemodynamics continued to worsen. As a result, the anesthesiology team initiated a massive transfusion protocol, a transesophageal electrocardiogram, and a rapid infuser. Additional anesthesia personnel were also called to assist. At this point, the surgical team finally disclosed to the anesthesiology team that the patient's iliac vein was nicked earlier in the surgery. Thus, as a result of the lack of real-time communication of relevant information from the surgical team, the anesthesiology team had dramatically underestimated how much blood loss the patient would suffer.

The second exemplary situation relates to an elective laparoscopic left nephrectomy procedure performed on a 43-year-old woman to remove a renal cell carcinoma. The OR staff included a surgical team lead by a head surgeon and an anesthesiology team lead by a head anesthesiologist. Both the head surgeon and head anesthesiologist agreed that the patient's risk for perioperative complications was low. The procedure proceeded as expected and the patient woke from anesthesia in stable condition. However, a few hours later, the patient developed a tense, distended abdomen. Further, the patient showed an elevated heart rate and low blood pressure. The head surgeon evaluated the patient and believed that the patient was experiencing internal bleeding. Thus, the head surgeon returned the patient to the OR.

Back in the OR, a massive transfusion of blood products was initiated. After induction of anesthesia, the patient's blood pressure dropped significantly. The anesthesiology team administered medications to try and improve the patient's blood pressure. Further, the surgical team opened the patient's abdomen and confirmed the presence of significant internal bleeding. At this point, a vascular surgeon was called to the room and the surgical staff worked to attempt to control the patent's bleeding. The head anesthesiologist continued to deliver blood products and escalated doses of blood pressure-augmenting medications. However, ST elevations on the patient's electrocardiogram indicated cardiac compromise. The head anesthesiologist communicated this information to surgical team members. The surgical team continued to try to identify the source of bleeding.

Eventually, the surgical team identified patient's inferior vena cava (IVC) as the source of the bleeding. However, the patient was experiencing cardiac arrest. In response, the surgical team stopped operating as the anesthesiology team attempted to resuscitate the patient. After 10 minutes of resuscitation attempts during which more than 100 units of blood products were administered, spontaneous circulation was achieved. Although the surgical team resumed operation, the head anesthesiologist was concerned about the patient's neurological status. Specifically, anesthetics had not been administered for several minutes suggesting the patient suffered a brain injury resulting from low blood pressure. The patient again began to experience cardiac arrest. Although the anesthesiology team attempted resuscitation, they eventually stopped because they believe the patient was moribund. The surgical team, however, requested that the anesthesiology team proceed with resuscitation as they attempted to control the patients IVC bleeding.

As can be appreciated from these two exemplary situations, the various surgical staff members can require different information, depending on their role, to proceed with decision making. For example, members of the anesthesiology team may need to monitor both neurosurgical-related and cardiac-related information. The neurosurgical-related information can include, for example, adequacy of oxygenation, deviation from expected hemodynamic parameters, blood loss, difficulties with hemostasis, relevant medical history of the patient (e.g., patient risk level), level of consciousness, brainstem reflexes, gaze, muscle tone, responses to pain, and the presence of adventitious movements in the eyes, face, or limbs. The cardiac-related information can include, for example, echocardiograph data, volume status, electrolyte levels, presence of acidosis, relevant medical history of the patient (e.g., patient risk level), patient position (e.g., during renal cell tumor removal), information from the surgical team, and intraabdominal pressure resulting from insufflation (e.g., related to risk of hypertension, increased myocardial workload, reduction in venous return, decreased preload, reduced end-diastolic volume). Thus, there is a wide variety of information that an anesthesiology team member may need to access during a surgical procedure. Likewise, surgical team members, and other members of the OR staff can have similarly extensive streams of information, specific to their role, that they may need to rely on during a surgical procedure. Accordingly, there is a need for apparatuses, systems, and methods for selectively presenting information based on a plurality of data streams to multiple users of a surgical system.

In various aspects, apparatuses, systems, and methods for selectively presenting information based on a plurality of data streams to multiple users of a surgical system are disclosed herein. In some aspects, the apparatuses, systems, and methods can include displaying interactive overlays to provide information customized for a specific user.

FIG. 60 depicts a surgical system 14000 configured to display interactive overlays for multiple users based on a plurality of data streams, according to several non-limiting aspects of this disclosure. The surgical system 14000 can include a surgical hub 14002 in communication with patient monitoring devices 14004, surgical devices/instruments 14006, tracking system 14008, and visualization system 14010. The surgical system 14000, surgical hub 14002, surgical devices/instruments 14006, and visualization system 14010 can be similar in many aspects, respectively, to any of the surgical systems, surgical hubs, surgical instruments/devices, and visualization systems described above, (e.g., surgical systems 1, 2, 50, 52; surgical hub 6, 56, 5104; device/instrument 21; visualization systems 8, 58). As explained above, surgical instruments may be communicatively connected to the surgical hub (e.g., device/instrument 21 can be connected to surgical hub 56 of FIG. 5). Thus, the surgical hub 14002 can be configured to receive instrument data from the surgical devices/instruments 14006 related to various sensed parameters and operational settings of the devices/instruments 14006. Based on the instrument data received by the surgical hub 14002, the surgical hub 14002 can determine operating parameters of the instrument. For example, based on instrument data received from the surgical devices/instruments 14006, the surgical hub 14002 can determine operating parameters such as speed, force, firing speed, firing force, activation status, power level, activation time, energy mode, and instrument settings.

Still referring to FIG. 60, the patient monitoring devices 14004 can be any type of device(s) configured to monitor aspects of a patent related to a surgical procedure. For example, referring again to the exemplary surgical situations discussed above, the patient monitoring devices 14004 can be configured to monitor aspects of the patient that may be used by a member of the anesthesiology team (e.g., oxygenation, hemodynamic parameters, blood loss, echocardiograph data, volume status, electrolyte levels, intraabdominal pressure resulting from insufflation, etc.). The surgical hub 14002 can be configured to receive patient monitoring data from the patient monitoring devices 14004.

The tracking system 14008 and/or the visualization system 14010 can be similar, in many aspects, to the tracking system 15006 and visualization system 15008 discussed in the aforementioned U.S. patent application Ser. No. 17/688,653 filed currently herewith, titled MIXING DIRECTLY VISUALIZED WITH RENDERED ELEMENTS TO DISPLAY BLENDED ELEMENTS AND ACTIONS HAPPENING ON-SCREEN AND OFF-SCREEN, the disclosure of which is herein incorporated by reference in its entirety. The tracking system 14008 can be configured to track the location, position, motion, and/or other attributes of various objects within the OR based on one or more different types of tracking methods. For example, the tracking system 14008 and/or visualization system 1400 can utilize any combination of imaging devices (e.g., cameras, visual and/or non-visual image sensors, etc.), structured light sensors, LIDAR (Light Detection and Ranging) sensors, floor sensors, acoustic sensors, fiducial markers, user/device sensors, and GPS (global positioning system) sensors to track the position, location, and/or movement of objects in the OR. The objects tracked by the tracking system can include OR staff members, surgical devices/instruments 14006, a patient, AR devices 66, equipment, etc. In some aspects, the surgical hub 14002 can be configured to receive data from the tracking system 14008 and/or visualization system 14010 to determine the relative position of tracked objects, interactions between tracked objects, and/or the proximity of tracked objects to each other.

In various aspects, the surgical hub 14002 can be communicatively coupled to a cloud 14012 that can include a remote server 14014 having data storage 14016. The cloud 14012, remote server 14014, and data storage 14016 can be similar in many aspects, respectively, to any of the clouds, remote servers, and data storage devices described herein, (e.g., cloud 54, remote server 63, data storage 55 of FIG. 5). In some aspects, data storage 14016 can store information related to a patient undergoing a surgical procedure. The patient information can include, for example, information related to a patient's medical history (e.g., patient risk level). The surgical hub can be configured to retrieve data from data storage 14016.

Accordingly, in some aspects, the surgical hub 14002 can be configured to receive a plurality of data streams related to a surgical procedure. The plurality of data streams related to a surgical procedure can include any combination of data received from patient monitoring devices 14004, surgical devices/instruments 14006, tracking system 14008, visualization system 14010, and/or server 14014.

Still referring to FIG. 60, the surgical hub 14002 can be communicatively connected to AR devices 66. As explained above, the AR devices 66 can be similar, in many aspects, to the AR device 84 disclosed with respect to FIG. 10. The surgical hub 14002 can cause the AR devices 66 to display information based on any of the plurality of data streams received from the patient monitoring devices 14004, surgical devices/instruments 14006, tracking system 14008, visualization system 14010, and/or server 14014. For example, the surgical hub 14002 can be configured to cause an AR device 66 to display an interactive overlay including information related to monitored aspects of a patient, surgical instrument operating parameters, tracked objects (e.g., device interactions), various captured images of a surgical field, etc. Thus, a user (e.g., an OR staff member) using the AR device 66 is able receive information related to a surgical procedure, in real time, based on at least some of the plurality of different data streams. The user can use this information to assist with decision making during the surgical procedure. Moreover, because of the real-time display of this information, the user may be able to more effectively make decisions that affect critical aspects of the surgical procure compared to other methods of communicating information in the OR.

In some aspects, the interactive overlays displayed by the AR device 66 can be customized based on the user who is using the AR device 66. Moreover, if multiple users are using different AR devices 66, the interactive overlays displayed by each of the different AR devices 66 can be customized based on each user. For example, as described in the exemplary surgical situations above, OR staff members can often include a surgical team and an anesthesiology team. The surgical team members and the anesthesiology team members may each be wearing AR devices 66. The surgical hub 14002 can be configured to cause the AR devices 66 worn by the surgical team to display a first interactive overlay customized based on the informational needs of the surgical team. The first interactive overlay can include information such as an operating parameter of a device that a surgical team member is using and/or patient information that is relevant to a step of a procedure that the surgical team is performing. Moreover, the surgical hub 14002 can be configured to cause the AR devices 66 worn by the anesthesiology team to display a second interactive overlay customized based on the informational needs of the anesthesiology team. The second interactive overlay can include information such as an operating parameter of a device that an anesthesiology team member is using and/or patient information relevant to a step of a procedure that the anesthesiology team is performing.

In some aspects, the control of a surgical device/instrument 14006 may transfer from a first user to a second user during a surgical procedure. For example, the first user may hand the surgical device/instrument 14006 to the second user. Prior to the handoff, the AR device 66 worn by the first user can display an overlay based on data related to the surgical device/instrument 14006. The tracking system 14008 can be configured to detect that the first user has transferred control of the surgical device/instrument 14006 to the second user. Based on data from the tracking system 14008 related to the detected transfer, the surgical hub 14002 can cause the interactive overlays displayed by the first user's AR device 66 and the second user's AR device 66 to update. For example, after the handoff, the AR device 66 worn by the second user can display an overlay based on the data related to the transferred surgical device/instrument 14006. Additionally, the AR device 66 worn by the first user may stop displaying the overlay based on the data related to the transferred surgical device/instrument 14006.

In some aspects, the informational needs of users may overlap. Accordingly, the overlays displayed by the various AR devices 66 of the surgical system 14000 can be based on at least some of the same information (i.e., can be based on at least some of the same data streams received by the surgical hub 14002).

In some aspects, the AR devices 66 of the surgical system 14000 can be linked to specific users by the surgical hub 14002. The term "linked," as used herein when referring to an AR device being linked to a specific user, can mean that the surgical hub 14002 has determined that the specific user is using the AR device. Linking a specific AR device 66 to a specific user can allow the surgical hub 14002 to cause the specific AR 66 to display customized overlays for the specific user.

In some aspects, the surgical hub 14002 can link an AR device 66 to a user based on information stored by the surgical hub 14002 and/or based on data stored by data storage 14016. In one aspect, data storage 14016 can be a data storage device of a hospital network or a manufacturer of the surgical system 14000. The data storage device 14016 can include information identifying OR staff members expected to be present for various types of procedures. Further, data storage 14016 may include information related to the hospital's scheduling system, such as which staff members are scheduled to be present during a procedure. Accordingly, the surgical hub 14002 can be configured to identify specific AR devices 66 that can be linked to the expected OR staff members. Thus, the surgical hub 14002 can cause the AR devices 66 to display overlays customized based on the roles of the expected OR staff members. For example, referring again to the second exemplary surgical situation described above, the data storage device 14016 can store information related to the OR staff members expected to perform the elective laparoscopic left nephrectomy procedure. The expected staff members can include a surgical team and an anesthesiology team. The surgical hub 14002 can identify specific AR devices 66 that should be worn by the staff members based on their respective roles.

In some aspects, the surgical hub 14002 can be configured to provide external notifications when the expected OR staff members change during a surgical procedure. In one aspect, these external notifications may be provided via an AR device or other type of display device used by a staff member in a different operating room or elsewhere in the hospital (e.g., surgical system 14000 can be similar to the surgical data network 51 if FIG. 4, with a modular communication hub 53 configured to connect modular devices located in one or more operating theaters/rooms of a healthcare facility). For example, referring again to the second exemplary surgical situation described above, a specialist, such as vascular surgeon, may be called into an OR based on specific events (e.g., unexpected uncontrollable bleeding) that occur during a surgical procedure. The surgical hub 14002 can be configured to detect the occurrence of the event (e.g., the surgical hub 14002 can be similar to the situationally aware surgical hub 5104 described above with respect to FIG. 11) and cause a notification to be derived to the relevant staff member, such as the vascular surgeon from the example above, indicating that the staff member is needed or may be needed for the procedure. In one aspect, the notifications may be bypassed. In another aspect, the notifications may be classified based on risk level and/or severity of the detected event. For example, depending on a risk level of the detected event, the surgical hub 14002 may cause an early warning notification to be delivered to an on-call specialist indicating that the specialist may be needed in the OR. In another aspect, the notification may enable a staff member who is not in the OR to view an image of the surgical field and/or other overlays that staff members who are present in the OR are viewing. For example, upon receiving a notification, an on call vascular surgeon who is not present in the OR, but who is wearing an AR device 66, may be able to cause the AR device 66 to display the same interactive overlay that is being displayed on an AR device 66 of a member of the surgical team who is performing the surgical procedure in the OR (e.g., allowing the vascular surgeon to view vitals, warnings, etc.).

In some aspects, the OR staff members may be able to customize the overlays that are displayed by their AR devices 66. For example, at the start of a procedure, the AR device 66 may display a menu with multiple functionality levels selectable by the user. In one aspect, the menu may include three functionality levels, wherein selecting the first level causes the display of an overlay related to overarching position of the staff member, wherein selecting the second level causes the display of perioperative data and/or information related to the patient history, and wherein selecting the third level causes the display of preferences and/or and or priorities of the user. The user may be able to adjust settings related to each of the selected levels.

In some aspects, the surgical hub 14002 can link an AR device 66 to a user based on data from the tracking system 14008. In one aspect, the tracking system 14008 can be configured to detect when a specific user picks up or otherwise takes control over a specific AR device. For example, as explained in more detail in the aforementioned U.S. patent application Ser. No. 17/688,653 filed currently herewith, titled MIXING DIRECTLY VISUALIZED WITH RENDERED ELEMENTS TO DISPLAY BLENDED ELEMENTS AND ACTIONS HAPPENING ON-SCREEN AND OFF-SCREEN, the disclosure of which is herein incorporated by reference in its entirety, the user may be wearing a user sensor (e.g., a smart glove) that is tracked by the tracking system 14008. The tracking system 14008 can detect the proximity of the user sensor to an AR device 66, and based on this detected proximity, the surgical hub 14002 can link the AR device 66 to the user. In another aspect, surgical hub 14002 can be configured to cause the linked AR device 66 to automatically display an overlay based on proximity of the tracked user sensor to a surgical device/instrument 14006. For example, the proximity of the user sensor to the surgical device/instrument 14006 (e.g., a surgical stapler) may cause the linked AR device 66 to display parameters of the surgical device/instrument 14006 (e.g., a power level, a type of staple cartridge installed therein, etc.).

In some aspects, upon linking an AR device 66 to a user by the surgical hub 14002, the surgical hub 14002 may cause an update to the settings of and/or overlays displayed by the AR device 66. For example, the surgical hub 14002 may determine that an AR device 66 is linked to a user with a specific experience level (e.g., a resident vs. an experienced surgeon). The surgical hub 14002 may cause the AR device 66 to display different levels of information depending on the experience level of the user. In another aspect, the surgical hub 14002 can select the information to display on the AR device 66 based on prior uses of the AR device 66 by a particular user (e.g., based on machine learning, based on the experience of the user with the AR device 66). In another aspect, a user can override the automatic linking of an AR device 66 to the user. In yet another aspect, a user can to manually link an AR device to the user (e.g., using controls included on the AR device 66).

FIG. 61 illustrates a method 14100 of displaying interactive overlays for multiple users of a surgical system, according to several non-limiting aspects of this disclosure. The method 14100 may be practiced by any combination of the surgical systems, surgical hubs, tracking systems, visualization systems, patient monitoring devices, surgical devices/instruments, AR devices, any of the components thereof, and any other devices and systems disclosed herein, such as surgical systems 1, 2, 50, 52, 14000, surgical hubs 6, 56, 5104, 14002, tracking system 14008, visualization systems 8, 14010, patient monitoring devices 14004, surgical devices/instruments 14006, and AR devices 66, 84.

In accordance with the method 14100, a surgical hub can receive 14102 a plurality of data streams related to a surgical procedure. A first augmented reality display device can communicably couple 14104 to the surgical hub. The surgical hub can link 14106 the first augmented reality display device to a first user. The first augmented reality display device can display 14108 a first interactive overlay customized for the first user based on at least one of the plurality of data streams.

In accordance with one aspect of the method 14100, a second augmented reality display device can communicably couple to the surgical hub. Further, the surgical hub can link the second augmented reality display device to a second user. The second augmented reality display device can display a second interactive overlay customized for the second user based on at least one of the plurality of data streams.

In accordance with another aspect of the method 14100, the first augmented reality display device and the second augmented reality device can simultaneously display the first interactive overlay and the second interactive overlay. In another aspect, the first interactive overlay and the second interactive overlay can be based on the same data stream of the plurality of data streams.

In accordance with another aspect of the method 14100, the first augmented reality display device and the second augmented reality device can respectively display the first interactive overlay and the second interactive overlay differently for the first user and the second user based on the respective preferences of the first user and the second user.

In accordance with another aspect of the method 14100, the first augmented reality display device can display the first interactive overlay based on a first data stream related to a first surgical instrument when the first user is using the first surgical instrument and the second augmented reality display device can display the second interactive overlay based on a second data stream related to a second surgical instrument when the second user is using the second surgical instrument. In yet another aspect, the first augmented reality display device can update the first interactive overlay to be based on the second data stream when the first user is using the second surgical instrument. In one aspect, the plurality of data streams can include the first data stream and the second data stream.

Decision Matrix For User Notification Based On Risk-Level Of Error And Surgeon Response As explained in detail above, the communication of information can be critical during the performance of a surgical procedure. Accordingly, augmented reality systems utilizing data streams from multiple sources, such patient monitoring devices, surgical devices/instruments, tracking systems, and other data storage devices, may rely on the seamless integration of interconnected systems for the collection, interpretation, and communication of these data streams between devices and OR staff throughout a procedure. However, there may be situations where data is erroneously communicated and/or where communication of a data stream is interrupted or lost. Accordingly, there is a need for apparatuses, systems, and methods for detecting errors and/or data communication issues and determining the appropriate actions to implement when errors and/or data communication issues arise. Moreover, there is a need for apparatuses, systems, and methods that are able to implement an action based on varying levels of risk associated with the criticality of the detected errors and/or based on OR staff members' responses to prior warnings.

Apparatuses, systems, and methods for detecting errors and/or data communication issues and determining the appropriate actions to implement when the errors and/or data communication issues are detected are disclosed herein. In various aspects, the apparatuses, systems, and methods can implement a decision matrix based on the type of errors detected. The decision matrix can trigger various actions, such as user notification, a system override, and a device lockout, based on the varying degrees of risk associated with the detected errors. The decision matrix may also trigger various actions based on prior responses of the user to similar detected errors.

FIG. 62 illustrates a method 14200 for detecting a device-related error and determining actions to implement based on the detected error, according to several non-limiting aspects of this disclosure. The method 14200 may be practiced by any combination of the surgical systems, surgical hubs, tracking systems, visualization systems, patient monitoring devices, surgical devices/instruments, AR devices, any of the components thereof, and any other devices and systems disclosed herein, such as surgical systems 1, 2, 50, 52, 14000, surgical hubs 6, 56, 5104, 14002, tracking system 14008, visualization system 8, 14010, patient monitoring devices 14004, surgical devices/instruments 14006, and AR devices 66, 84.

Referring primarily to FIG. 62, and also to FIG. 60, in accordance with the method 14200, the surgical hub 14002 can detect 14202 an alert related to the operation of a surgical device/instrument 14006. For example, the device/instrument 14006 may indicate that an operating parameter of the instrument is outside of an expected and/or recommended operating range. Next, the surgical hub 14002 may determine 14204 the detected alert is functioning properly. For example, the surgical hub 14002 can determine 14204 that the operating parameter of device/instrument 14006 is in fact outside of the recommended operating range. Upon determining 14204 that the detected alert if functioning properly, the surgical hub 14002 can cause AR device 66 to display 14206 an alert (e.g., an overlay) related to the detected error. For example, the AR device 66 may display an overlay instructing the user to take a specific action to address the detected error (e.g., waiting for a temperature of the instrument to return to the recommended operating range).

In another aspect of the method 14200, the surgical hub can determine 14204 that the detected alert is not functioning properly. Upon determining 14204 that the alert is not functioning properly, the surgical hub 14002 can determine 14208 whether the detected error is a low risk-level error. For example, the surgical hub 14002 may determine that the device/instrument 14006 is only generating erroneous data under a low risk condition (e.g., the instrument is only generating erroneously high temperature readings when the instrument is operating at low-temperature conditions). Upon determining 14208 that the detected error is a low risk-level error, the surgical hub 14002 can determine to not provide 14210 an alert to the user based on the detected error.

In another aspect, upon determining 14204 that the detected alert is not functioning properly, the surgical hub 14002 can determine 14212 whether the detected alert is a range-based high-risk error. For example, the surgical hub 14002 may determine that the device/instrument 14006 is generating erroneous data under a high-risk condition (e.g., the instrument is generating erroneously temperature readings when the instrument is operating at a high temperature, thereby causing a risk of overheating). Upon determining 14212 that the detected alert is a range-based high-risk error, the surgical hub 14002 can determine 14214 the frequency of the range-based high-risk error. For example, a range-based high-risk error may have a high frequency of error when the percentage of erroneous data generated by the device/instrument 14006 are above a predetermined threshold (e.g., 10%, 20%, 30%, 40%, 50%, 60%, 70%, 80%, or 90% of the erroneous readings generated by the instrument indicate that the operating parameter of the instrument is outside of the expected and/or recommended range). In various aspects, the frequency threshold may be determined 14214 based on a sampling rate of the data.

Upon determining 14214 that the range-based high-risk error is above a frequency threshold, the surgical hub 14002 can cause AR device 66 to display an alert (e.g., an overlay) related to the detected error and disable 14216 the surgical instrument/device 14006. For example, the surgical hub 14002 can cause the AR device 66 to display an overlay indicating that the instrument/device 14006 has been locked out due to errors related to the detected operating parameter. Conversely, upon determining 14214 that the range-based high-risk error is below a frequency threshold, the surgical hub 14002 can cause AR device 66 to display 14218 an alert (e.g., an overlay) related to the detected error. For example, the surgical hub 14002 can cause the AR device 66 to display an overlay instructing the user to verify the accuracy of the detected operating parameter via alternate means. In this aspect, the surgical hub 14002 may not lockout the surgical instrument/device 14006.

In another aspect of the method 14200, upon determining 14204 that the detected alert is not functioning properly, the surgical hub 14002 can determine 14220 whether the detected error is communication-related. A communication-related error can be caused by a loss of communication between the surgical hub 14002 and the surgical instrument 14006. In one aspect, upon determining 14220 that the detected alert is a communication-related error, the surgical hub 14002 can cause AR device 66 to display an alert (e.g., an overlay) related to the detected error. For example, the surgical hub 14002 can cause the AR device 66 to display an overlay indicating the loss of communication with the surgical instrument/device 14006. In another aspect, the surgical hub 14002 can disable 14222 the surgical instrument/device 14006, preventing further use of the instrument/device 14006.

Figure 63A:
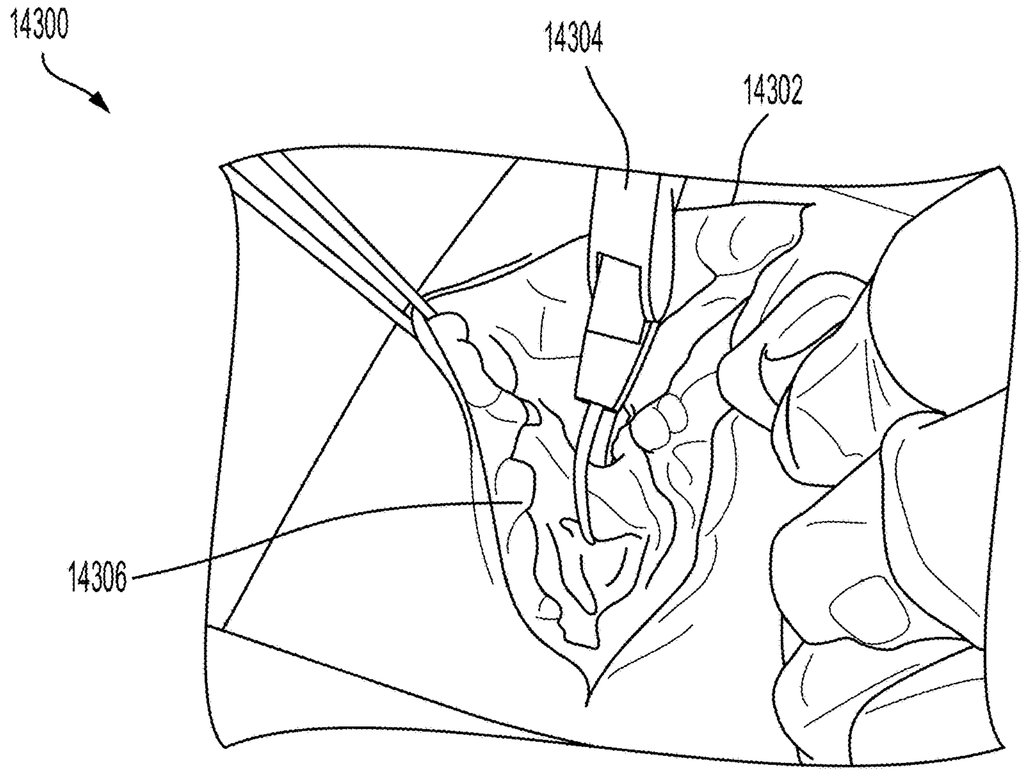

FIGS. 63A, 63B, 63C, 63D, 63E, and 63F illustrate an exemplary implementation of the method 14200 of FIG. 62 during a thyroidectomy procedure, according to several non-limiting aspects of this disclosure. Referring to FIG. 63A, a first step 14300 of the thyroidectomy procedure can include making an incision 14302 to gain access to underlying tissue 14306. The first step 14300 can also include using an ultrasonic energy device 14304 to dissect platysmal muscle in the underlying tissue 14306. At this point in the procedure, the blade of the ultrasonic energy device 14304 can begin to heat up from repeated use. Referring now to FIG. 63A and FIG. 60, the ultrasonic energy device 14304 can be a surgical instrument/device 14006 in communication with the surgical hub 14002. The surgical hub 14002 can receive data from the ultrasonic energy device 14304 related to the temperature of the blade.

Figure 63B:
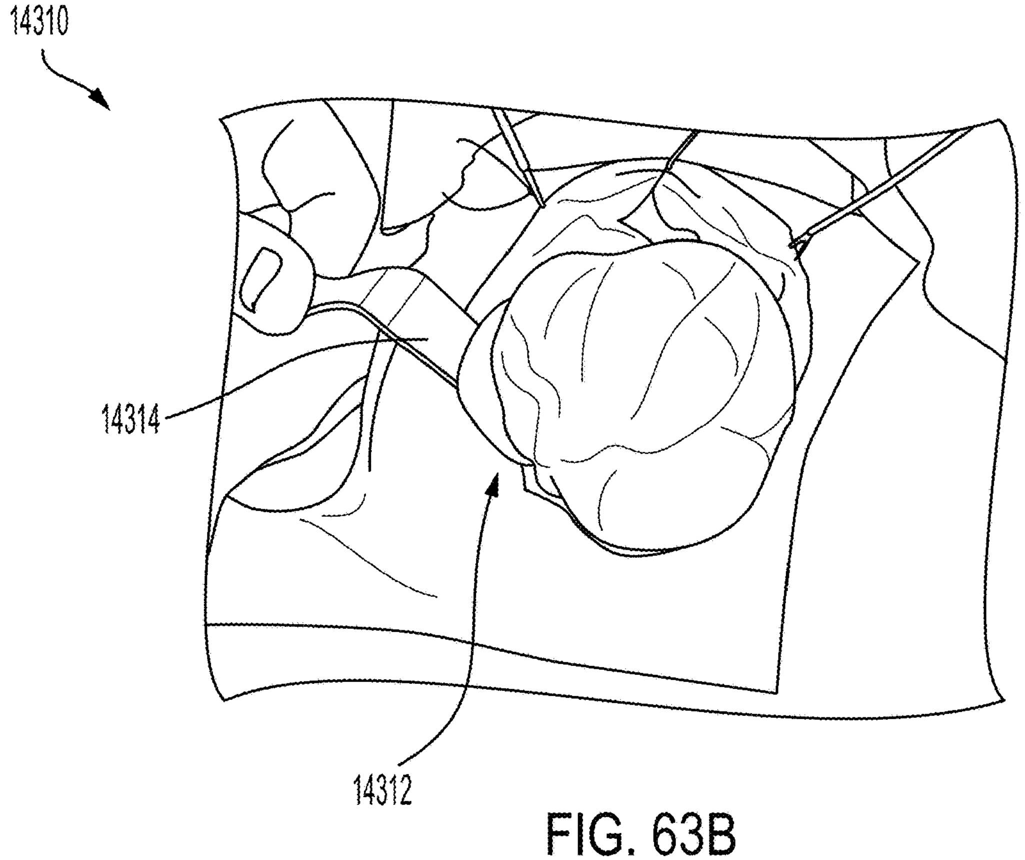

Referring now to FIG. 63B, a second step 14310 of the thyroidectomy procedure can include further dissecting strap muscles 14312. This second step 14310 may be performed using a blunt device 14314 (shown) or the ultrasonic energy device 14304 (not shown). Use of the ultrasonic energy device 14304 can cause the blade to continue to raise in temperature.

Figure 63C:
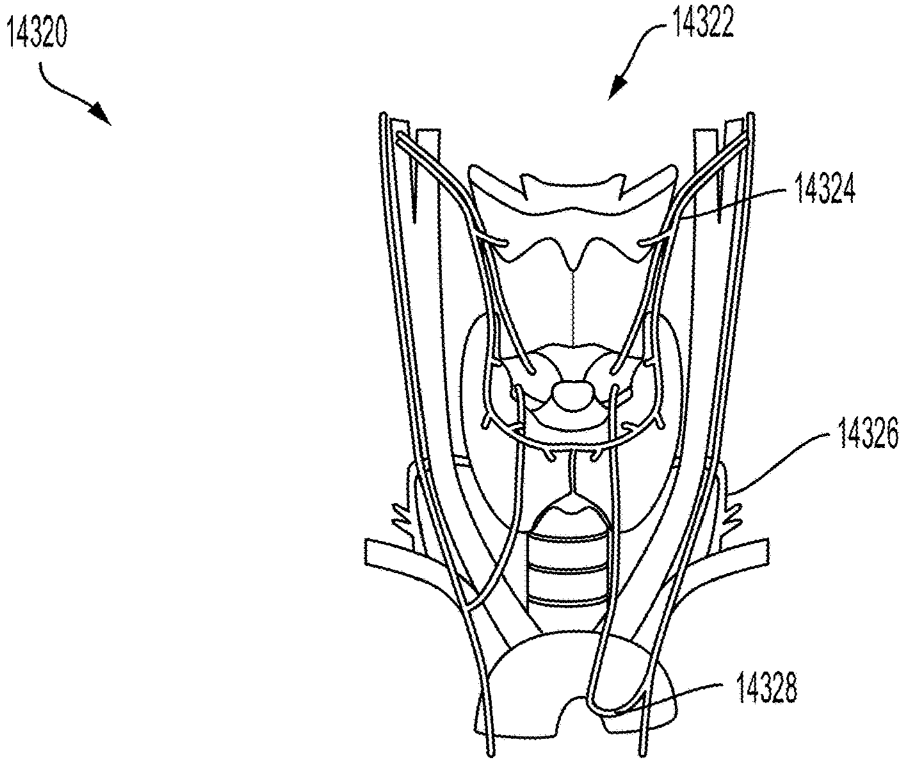
Figure 63D:
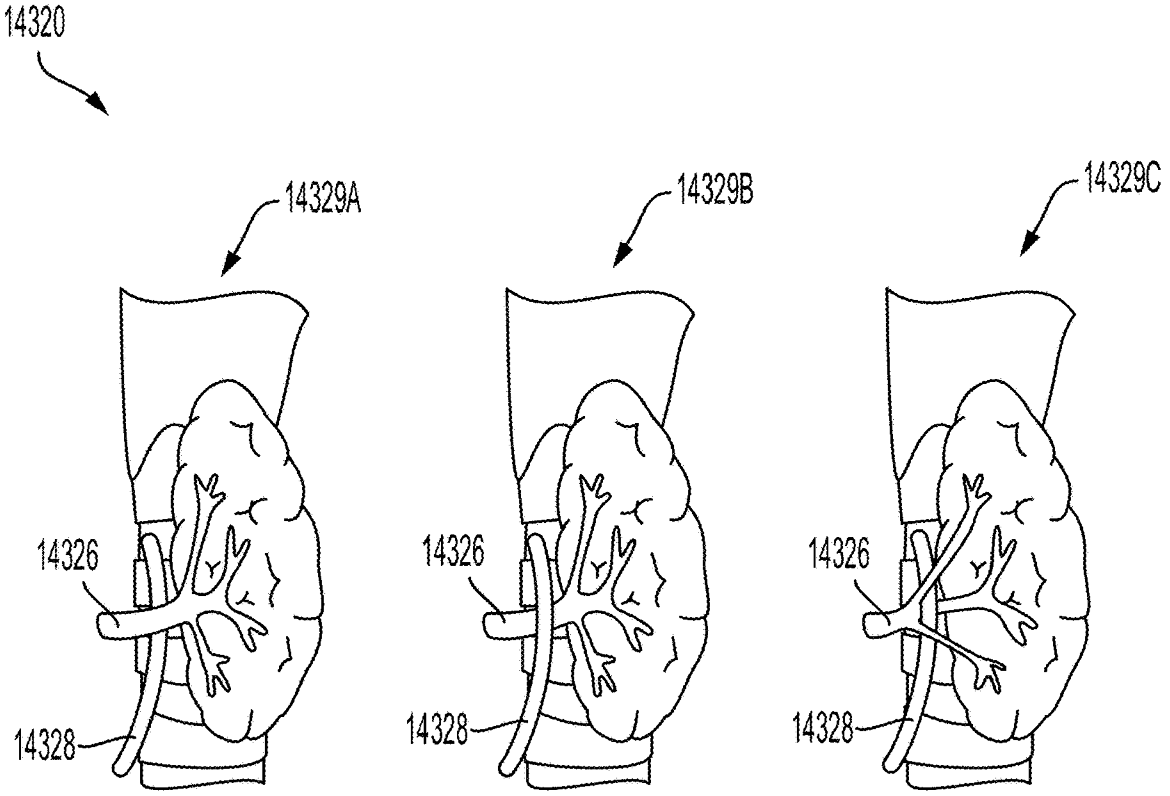

Referring now to FIGS. 63C and 63D, a third step 14320 of the thyroidectomy procedure can include identifying critical structures such as the superior thyroid artery 14324, the inferior thyroid artery 14326, and the recurrent laryngeal nerve 14328. FIG. 63C illustrates a schematic of an exemplary anatomy 14322 of the superior thyroid artery 14324, the inferior thyroid artery 14326 and the recurrent laryngeal nerve 14328. FIG. 63D illustrates how anatomies 14329A, 14329B, and 14329C can vary with different configurations of the recurrent laryngeal nerve 14328 with respect to the inferior thyroid artery 14326. The third step 14320 can be an importation step of the thyroidectomy procedure because it is generally critical that the recurrent laryngeal nerve 14328 not be damaged.

Figure 63E:
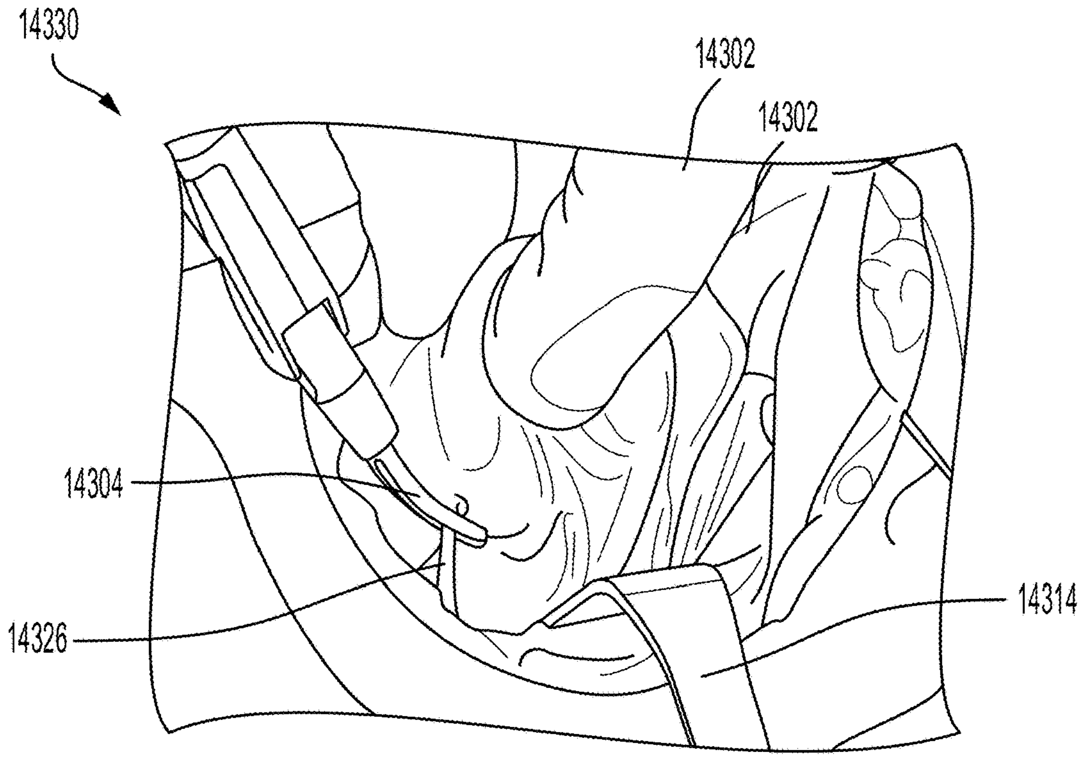

Referring now to FIG. 63E, a fourth step 14330 thyroidectomy procedure can include dividing the inferior thyroid artery 14326 using the ultrasonic energy device 14304. However, as mentioned above, the temperature of the blade of the ultrasonic energy device 14304 may continue to increase in temperature as it is used during the procedure. If the blade temperature overheats, the recurrent laryngeal nerve 14328 may be damaged. For example, a growing degree of lateral thermal spread occurs as heat builds at the blade. Activation of the ultrasonic energy device 14304 in tight spaces near the laryngeal nerve 14328 can cause damage to the nerve 14328. As another example, between activations, the surgeon may want to use the ultrasonic energy device 14304 to grasp and manipulate tissue. Doing so with a hot blade can cause damage to the laryngeal nerve 14328. As yet another example, between activations, in tight spaces, slight movement of the ultrasonic energy device 14304 can cause contact with the laryngeal nerve 14328. An inexperienced user may not anticipate tissue effects caused by the ultrasonic energy device 14304 when the user is not actively applying energy. Thus, it can be important for the ultrasonic energy device 14304 to communicate accurate temperature readings to the surgical hub. Moreover, if there is an error related to the temperature readings, the surgical hub may need to respond appropriately to avoid damage to the laryngeal nerve 14328.

Referring still to FIG. 63E, and also to FIGS. 60 and 62, upon receiving a hot blade notification from the ultrasonic energy device 14304, the surgical hub 14002 may implement the method 14200 for detecting device-related errors and determining actions to implement based on the detected error. For example, the surgical hub 14002 can detect 14202 a hot blade notification. If the surgical hub 14002 determines 14204 the detected alert is functioning properly, the surgical hub 14002 can cause AR device 66 to display an alert 14206 (e.g., an overlay) instructing the user to pause in order to cool off the blade of the ultrasonic energy device 14304. Once cool, the AR device 66 may indicate that the user can proceed without risk of damaging the laryngeal nerve 14328 because of a hot blade.

However, the surgical hub 14002 may determine 14208 the hot blade notification is a low risk-level error. For example, the surgical hub 14002 may determine that the ultrasonic energy device 14304 is only generating the hot blade notification when the blade is not actually overheating. In this case, the surgical hub 14002 can determine that no alert will be provided 14210 to the user.

Referring still to FIG. 63D, and also to FIGS. 60 and 162, the surgical hub 14002 may determine 14212 that the hot blade notification is a range-based high-risk error. For example, ultrasonic energy device 14304 may be generating abnormally high temperature readings. The surgical hub 14002 can determine 14214 whether to disable 14216 the ultrasonic energy device 14304 and alert the user or only alert 14218 the user based on the frequency of the high temperature readings.

Referring still to FIG. 63D, and also to FIGS. 60 and 62, the surgical hub 14002 may determine 14220 that the hot blade notification is based on a loss of communication with the ultrasonic energy device 14304. In this case, the surgical hub 14002 can 14222 disable (e.g., lockout) ultrasonic energy device 14304 and the cause AR device 66 to display an alert notifying the user of the communication loss. The lockout may be temporary, giving the blade of the ultrasonic energy device 14304 time to cool. Moreover, the duration of the temporary lockout may be based on the time it takes for the blade to cool.

Figure 63F:
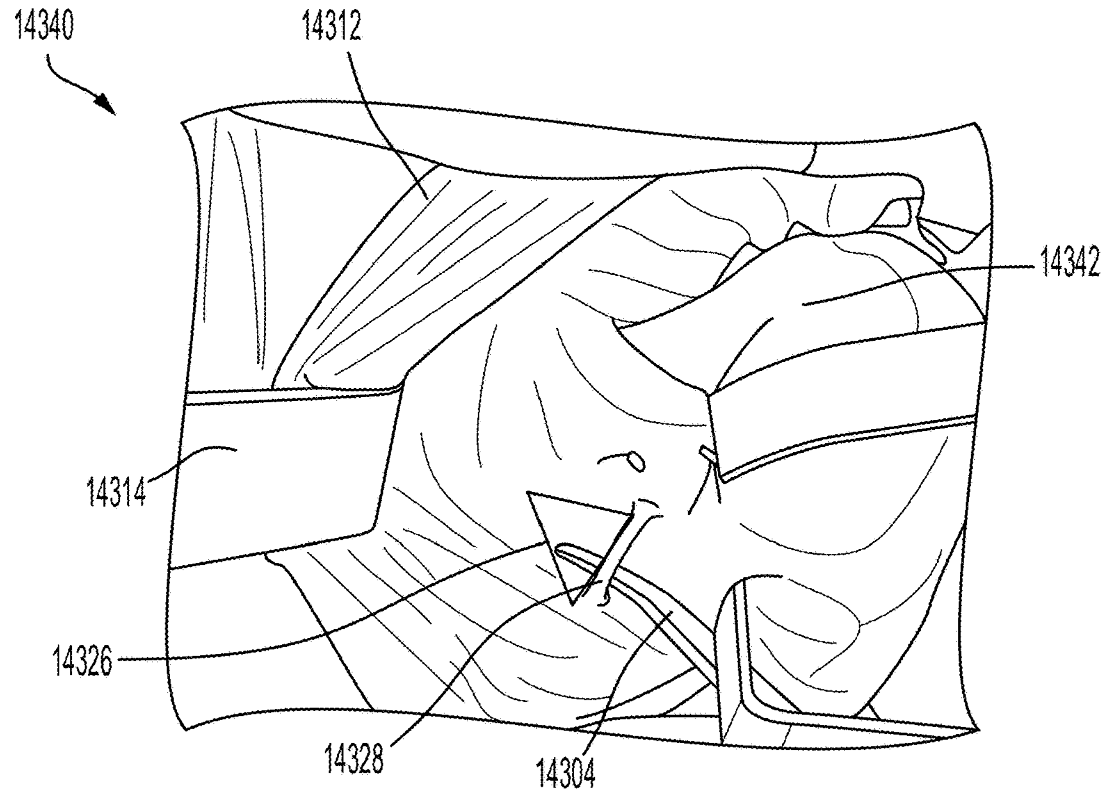

Referring now to FIG. 63F, after a hot blade notification has been addressed according to method 14200, the final steps 14340 of the thyroidectomy procedure can include rotating the thyroid lobe 14342 to gain access to the ligament of Berry and associated minor vasculature. Further, the thyroid may be removed, the wound may be irrigated, the strap muscles 14312 may be closed, and the skin may be closed.

Deployment Of Overlays And Managing Power Requirements

As explained in detail above, the communication of information can be critical during the performance of a surgical procedure. In some aspects, information may be communicated to users (e.g., OR staff members) via intraoperative displayed by wearable display devices (e.g., AR device 66, 84). In some aspects, the AR devices may be powered using battery power with a limited battery life. Thus, there may be a risk that an AR display device will lose power and/or have low power during a surgical procedure. Accordingly, there is a need for apparatuses, systems, and methods for managing power of AR devices.

In various aspects, apparatuses, systems, and methods for managing power of AR devices are disclosed herein. In some aspects, the power of AR devices (e.g., AR device 66, 84) may be managed by ensuring that a second AR device is available for a user in case a first AR device used by the user loses power. Referring again to FIG. 60, the surgical system 14000 can include a surgical hub 14002 in communication with AR devices 66. In one aspect, each AR device 66 in communication with the surgical hub 14002 can have the same capabilities (i.e., the same functionality). Moreover, as explained above, various AR devices 66 can display customized information based on the user that the device is linked to. Thus, in the case of a loss of power in a first AR device 66 worn by a first user (e.g., an AR device 66 worn by a surgeon), a second AR device 66 (e.g., a spare AR device 66, an AR device 66 worn by a different member of the OR staff) can be linked with the first user. For example, the first user can be associated with a first user profile implemented by AR devices 66. The user profile can include various setting and preferences of the first user. Upon the first AR device 66 losing power, the second AR device 66 can be linked to the first user, causing the second AR device to implement the profile of the first user. In some aspects, the linking of the second AR device 66 to the first user can be executed by the surgical hub 14002 using the various techniques described herein. In another, aspect the linking of the second AR device 66 to the first user may be executed by selecting the first user's profile on the second AR device 66 (e.g., via ID scan).

In some aspects, one or more of the AR devices 66 can display notifications indicating the remaining power available for the various AR devices 66 worn by OR staff. For example, a circulating nurse may receive a notification indicating that an AR device 66 linked to a surgeon is at low power. As another example, a circulating nurse may receive a notification indicating the power level of all of the AR devices 66 linked to OR staff members. In one aspect, the notifications may be listed based on a priority level of each of the OR staff members (e.g., ranked based on which OR staff members have the lowest power lever, ranked based on which OR staff members are most critical to the performing the surgical procedure, etc.). In another aspect, the notification may include an estimated time of the battery life remaining on the AR device(s) 66. Accordingly, the circulating nurse can identify which OR staff member may need a new AR device 66 based on the power level notifications and prepare to provide the OR staff member(s) with replacement AR devices 66.

In other aspects, the power of an AR device 66 may be managed by prioritizing functions executed by the AR device 66. In one aspect, the AR device 66 can be configured to have various levels of functionality. For example, an AR device 66 may be configured to have three levels of functionality, wherein level 1 functionality enables the display of information related to overarching position (e.g., full imaging and overlay functionality), wherein level 2 functionally enables the display of information related to perioperative data and/or patient history, and wherein level 3 functionality enables the display of information related to user preferences and/or priorities. Level 1 functionality can include level 2 and level 3 functionality. Further, level 2 functionality can include level 3 functionality.

In some aspects, the AR device 66 can be configured to allow a user to select the level of functionality of the AR device 66. For example, prior to the start of surgical procedure, a user may select level 1 functionality (e.g., full power mode). As the battery of the AR device 66 approaches a depletion, the AR device may be configured to adjust the functionality level, thereby conserving battery life. For example, the AR device 66 may be configured to enter a low power mode where only level 2 or level 3 functionality is enabled. In one aspect, in low power mode, the AR device 66 may only display standard vitals, emergency alerts, and/or displays related to level 2 and/or level 3 functionality. In another aspect, in low power mode, the user may no longer have the ability to use high-power-consuming functionality (e.g., swiping to view the AR displays of other users). Accordingly, the AR device 66 can be configured to mitigate situations were low and/or completely depleted power levels interrupt the delivery of information to the user of the device.

Multi-Level Pairing Methods To Ensure Device/System Security

Cyber security is often a concern in cases where various devices are connected wirelessly to a system. As explained in detail above, the various surgical systems described herein can include various smart devices (e.g., smart surgical instruments, patient monitoring devices, tracking devices, AR devices, etc.) that are wireless connected to a surgical hub. Thus, there is an opportunity for unauthorized devices to attempt to exploit the wirelessly capabilities of the surgical system. Moreover, the unauthorized communication between corrupt devices and various components of the surgical system could lead incorrect data being presented to OR staff members. If an OR staff member relies on this incorrect data, it could ultimately cause the OR staff member to make an incorrect decision during a surgical procedure. Accordingly, there is a need for apparatuses, systems, and devices for ensuring the secure pairing of various smart devices of the surgical system. Moreover, smart devices may be compromised and/or corrupted after the initial paring to the surgical system. Therefore, there is also a need for apparatuses, systems, and methods for verifying the secure and/or authenticated connection to paired smart devices.

Apparatuses, systems, and methods for ensuring the secure wireless paring of smart devices to a surgical system are disclosed herein. The smart devices discussed below can include any device disclosed herein that may be configured to wirelessly communicate with a surgical system (e.g., surgical instruments/devices 14006, AR devices 66, 84, etc.). Referring again to FIG. 60, a surgical system 14000 can include a surgical hub 14002, a tracking system 14008, a cloud 14012 including a server 14014, surgical devices/instruments 14006, and AR devices 66. In some aspects, and least some of the surgical devices/instruments 14006 and/or the AR devices 66 (sometimes collectively referred to herein as devices 14006, 66) can be configured to wirelessly pair with the surgical hub 14002. The surgical hub 14002 can be configured to classify the security level of the connection to the paired of a device 14006, 66 based on the technique that is used to pair the device 14006, 66. In one aspect, the classified security levels can include a high security level, a medium security level, and a low security level, with the high security level being more secure than the medium security level and the medium security level being more secure than the low security level.

In various aspects, a device 14006, 66 can be semi-automatically paired at an inventory level. Inventory level pairing can include the tracking system 14008 recognizing a device 14006, 66 as the OR is being populated (i.e., stocked) in preparation for a surgical procedure. For example, various imaging devices and/or other tracking techniques employed by the tracking system 14008 may automatically detect a device 14006, 66 as it enters the OR. The surgical hub 14002 may identify the device 14006, 66 based on data from the tracking system 14008. The surgical hub 14002 can be configured to cross reference the identified device 14006, 66 with data stored by the server 14014 (e.g., a hospital network server, a device manufacturer server) to retrieve a MAC (media access control) address associated with the identified device 14006, 66. Based on the MAC address, the surgical hub 14002 may begin to actively search for the identified device 14006, 66 for wireless pairing. In one aspect, as the device 14006, 66 is powered on (e.g., OR staff inserts a battery into the device 14006, 66), the surgical hub 14002 can automatically pair the device. In this aspect, the surgical hub 14002 may identify the pairing of the device 14006, 66 as a high security level pairing. In another aspect, OR staff may manually pair the device 14006, 66 to the surgical hub (e.g., using controls/buttons included on the device 14006, 66). In this aspect, the surgical hub 14002 may identify the pairing of the device 14006, 66 as a medium security level pairing.

In various aspects, a device 14006, 66 can be semi-automatically paired at a packaging level. Packaging level pairing can include scanning, by the surgical hub 14002 or a component thereof, a QR (quick response) code included on the packaging of a device 14006, 66. For example, OR staff may bring the device 14006, 66 into the OR in preparation for a surgical procedure. The device 14006, 66 may still be in its packaging from the manufacture (e.g., Tyvek packaging). The packaging can include a QR code to identify the device. In one aspect, the OR staff may scan the QR code using an imaging device associated with the surgical hub 14002. In another aspect, an imaging device of the tracking system 14008 may automatically scan the QR code. The surgical system 14002 can be configured to identify the device 14006, 66 based on the scanned QR code. Thus, the surgical hub 14002 may begin to actively search for the identified device 14006, 66 for wireless pairing. In one aspect, as the device 14006, 66 is powered on (e.g., OR staff inserts a battery into the device 14006, 66), the surgical hub 14002 can automatically pair the device. In this aspect, the surgical hub 14002 may identify the pairing of the device 14006, 66 as a high security level pairing. In another aspect, OR staff may manually pair the device 14006, 66 to the surgical hub (e.g., using controls/buttons included on the device 14006, 66). In this aspect, the surgical hub 14002 may identify the pairing of the device 14006, 66 as a medium security level pairing.

In various aspects, a device 14006, 66 can be semi-automatically paired at a device level. Semi-automatic device level pairing can include scanning, by the surgical hub 14002 or a component thereof, a QR (quick response) code included on the device 14006, 66. For example, OR staff may bring the device 14006, 66 into the OR in preparation for a surgical procedure and remove it from its packaging. In one aspect, the OR staff may scan the QR code using an imaging device associated with the surgical hub 14002. In another aspect, an imaging device of the tracking system 14008 may automatically scan the QR code. The surgical system 14002 can be configured to identify the device 14006, 66 based on the scanned QR code. Thus, the surgical hub 14002 may begin to actively search for the identified device 14006, 66 for wireless pairing. In one aspect, as the device 14006, 66 is powered on (e.g., OR staff inserts a battery into the device 14006, 66), the surgical hub 14002 can automatically pair the device. In this aspect, the surgical hub 14002 may identify the pairing of the device 14006, 66 as a high security level pairing. In another aspect, OR staff may manually pair the device 14006, 66 to the surgical hub (e.g., using controls/buttons included on the device 14006, 66). In this aspect, the surgical hub 14002 may identify the pairing of the device 14006, 66 as a medium security level pairing.

In various aspects, a device 14006, 66 can be manually paired at a device level. Manual device level pairing can include an OR staff member initiating paring of a device 14006, 66 with the surgical hub 14002 using controls and/or buttons included on the device 14006, 66. For example, as OR staff brings the device 14006, 66 into the OR in preparation for a surgical procedure, the staff may insert a battery into the device 14006, 66 or otherwise power on the device 14006, 66. Further, staff may initiate pairing of the device 14006, 66 to the surgical hub 14002 by using the controls and/or buttons included on the device 14006, 66. Upon recognizing that the device 14006, 66 is attempting to pair, the surgical hub 14002 can be configured to cause the device 14006, 66 to ask the user to conform the paring. In this aspect, the surgical hub 14002 may identify the pairing of the device 14006, 66 as a low security level pairing.

Apparatuses, systems, and methods for verifying the secure and/or authenticated connection to paired smart devices (device 14006, 66) are also disclosed herein. Various techniques may be implemented to verify and/or authenticate connected devices 14006, 66 after pairing, such as verifying duplicate data streams, checksum checking, "dummy" signal checking, data error threshold checking, and pre-procedure checking of data streams.

In some aspects, the device 14006, 66 may be authenticated after initial pairing by verifying duplicate data streams sent by the device 14006, 66. For example, the device 14006, 66 can be configured to wirelessly transmit duplicate data streams (e.g., duplicate packets sent multiple times) to the surgical hub 14002. The surgical hub 14002 can be configured to cross check each of the received data streams to verify device 14006, 66 authenticity.

In some aspects, the device 14006, 66 may be authenticated based on "dummy" signal checking. A dummy signal may refer to a signal sent by the device 14006, 66 that the surgical hub 14002 can compare to an expected signal to verify the authenticity of the device 14006, 66. In one aspect, the dummy signal can be sent by the device 14006, 66 on a predefined cadence. The surgical hub 14002 can authenticate the device if it receives the dummy signal at the expected predefined cadence. In another aspect, the predefined cadence may be adjusted to ensure data authenticity. In yet another aspect, the surgical hub 14002 can be configured to authenticate the device 14006, 66 based on the timing of received dummy signals and/or data included in the dummy signals. The surgical hub 14002 may index signals received by various devices 14006, 66 so that the security of the various devices 14006, 66 can be verified based on specific time points. In yet another aspect, the dummy signal expected by the surgical hub 14002 can be based on a signal received by the surgical hub 14002 from the device 14006, 66 upon initial pairing. For example, a device 14006, 66 may be initially paired to the surgical hub 14002 based on semi-automatically paired at a packaging level, as described above. Upon pairing, the device 14006, 66 may send an initial dummy signal that is stored by the surgical hub 14002. The surgical hub 14002 can compare subsequent dummy signals received from the device 14006, 66 to the initial dummy signal to authenticate the device 14006, 66. In another aspect, the dummy signal can include data derived from manufacturing calibration of the device 14006, 66. The data derived from manufacturing calibration of the device 14006, 66 could be stored by the device (e.g., by the devices EEPROM). In another aspect, the QR code on the packaging of the device could include data related to the dummy signal.

In some aspects, the device 14006, 66 may be authenticated after initial pairing by monitoring a data error rate of the data received from the device 14006, 66 by the surgical hub 14002. For example, the surgical hub 14002 can be configured to identify a device 14006, 66 as corrupted if the error rate of data received from the device 14006, 66 exceeds a data error rate threshold. In one aspect, the data error rate threshold can be predefined (e.g., six sigma). In another aspect, the data error threshold can be determined based on a risk level associated with the device 14006, 66. For example, each type of device may have a different error rate threshold. As another example, the error rate threshold may be based on the type of procedure the device is performing (e.g., based on wither critical structures are present in the surgical field, based on whether arteries are present in the surgical field, based on a location of the device, based on whether the device is performing a dissection and/or manipulating tissue). As yet another example, the error rate threshold may be based on a combination of the device type and the type or procedure the device is performing (e.g., an ultrasonic device performing a thyroidectomy may have a different error rate threshold compared to a device performing a PFS firing on a pulmonary artery or using a device being a grasper, etc.).

In some aspects, the device 14006, 66 may be authenticated by a pre-procedure check of the data stream received from the device 14006, 66 by the surgical hub 14002. For example, the device 14006, 66 may be an endo-cutter. Prior to the start of a surgical procedure, the surgical hub 14002 can require that the endo-cutter perform a test firing. Based on the data received by the surgical hub 14002 related to the test firing, the surgical hub 14002 can verify the authenticity of the connection between the endo-cutter (device 14006, 66) and the surgical hub 14002.

FIG. 64 illustrates a method 14400 for ensuring the secure wireless paring of smart devices to a surgical system, according to several non-limiting aspects of this disclosure. The method 14400 may be practiced by any combination of the surgical systems, surgical hubs, tracking systems, visualization systems, patient monitoring devices, surgical devices/instruments, AR devices, any of the components thereof, and any other devices and systems disclosed herein, such as surgical systems 1, 2, 50, 52, 14000, surgical hubs 6, 56, 5104, 14002, tracking system 14008, visualization system 8, 14010, patient monitoring devices 14004, surgical devices/instruments 14006, and AR devices 66, 84.

Referring primarily to FIG. 64, and also to FIG. 60, in accordance with the method 14400, a tracking system 14008 can detect 14402 a device 14006, 66. A surgical hub 14002 can wirelessly pair 14404 with the detected device 14006, 66. The surgical hub 14002 can determine 14406 a first or second security level of the wireless pairing, wherein the first security level is determined based on the detection 14002 of the device by the tracking system 14008 and an automatic wireless pairing of the detected device 14006, and wherein the second security level is determined on the detection 14002 of the device by the tracking system 14008 and a manual pairing of the detected device. Further, the surgical hub 14002 can authenticate 14408 a data stream transmitted by the detected device 14006, 66.

In accordance with one aspect of the method 14400, detecting 14002 the device 14006, 66 by the tracking system can include recognizing the device 14006, 66 as the OR is being populated. In another aspect of the method 14400, detecting 14002 the device 14006, 66 by the tracking system can include scanning a QR code included on packaging of the device 14006, 66. In yet another aspect of the method 14400, detecting 14002 the device 14006, 66 by the tracking system can include scanning a QR code included on the device 14006, 66.

QR Code System To Confirm Data Transmission Accuracy And Latency In Connected OR Devices As explained above, as devices and instruments gain the capability to connect within a digital OR ecosystem, concerns of data integrity (e.g., corrupt data being transmitted by devices) become more warranted. Moreover, in some aspects, the successful pairing of a device to a surgical hub does not preclude potentially faulty, corrupt, and/or delayed data being received by the surgical hub from the device. Simple approaches, such as checksums of data, may be employed to help ensure data authenticity and/or integrity. However, simple approaches can provide a false sense of data authenticity and integrity. For example, different permutations of bytes in a packet can generate the same checksum value. Thus, even though the checksum value appears to be authentic, the data received may actually be faulty, corrupt, etc. Accordingly, there is a need for apparatuses, systems, and methods for ensuring data authenticity and/or integrity after initial device pairing.

Apparatuses, systems, and methods for ensuring data authenticity and/or integrity after initial device pairing are disclosed herein. These apparatuses, systems, and methods can employ a two-part approach involving (i) the secure, initial pairing of a device to a surgical hub based on QR code and (ii) subsequent authentication of the pairing based on data transmitted to the surgical hub by the device at the initial pairing.

FIG. 65 illustrates a method 14500 for ensuring data authenticity and/or integrity after initial device pairing, according to several non-limiting aspects of this disclosure. The method 14500 may be practiced by any combination of the surgical systems, surgical hubs, tracking systems, visualization systems, patient monitoring devices, surgical devices/instruments, AR devices, any of the components thereof, and any other devices and systems disclosed herein, such as surgical systems 1, 2, 50, 52, 14000, surgical hubs 6, 56, 5104, 14002, tracking system 14008, visualization system 8, 14010, patient monitoring devices 14004, surgical devices/instruments 14006, and AR devices 66, 84.

Referring primarily to FIG. 65, and also to FIG. 60, in accordance with the method 14500, a QR code may be provided 14502 on a device 14006, 66 (e.g., on the device packaging, on the device itself). The QR code can include information such as a media access control (MAC) address and first unique authentication data that can be used to uniquely identify the device 14006, 66. A component of the surgical system 14000, such as the surgical hub 14002 or the tracking system 14008 can scan 14504 the QR code to retrieve the MAC address and the first unique authentication data. Further, the surgical hub 14002 can wirelessly pair 14506 with the device 14006, 66 upon powering the device. After pairing 14506, the device 14006, 66 can transmit 14508 second unique authentication data to the surgical hub 14002. The surgical hub 14002 can compare 14510 the first unique authentication data to the second authentication data.

Still referring primarily to FIG. 65, and also to FIG. 60, the surgical hub 14002 can be configured to determine 14512 various comparison outcomes based on the comparison 14510. Further based on the determination 14512 of the comparison outcome, the surgical hub 14002 can cause various actions 14514. In one aspect, surgical hub can determine 14516 that the second unique authentication data is accurate and received within a transmission time threshold. Accordingly, the surgical hub 14002 can be configured to inform 14518 a user of the device 14006, 66 that the device 14006, 66 has been authenticated (e.g., via an overlay on AR device 66) and allow the user to proceed with using the device 14006, 66.

In another aspect, surgical hub can determine 14520 that the second unique authentication data is accurate but is not received within a transmission time threshold. Accordingly, the surgical hub 14002 can be configured to 14522 alert the user of the device's 14006, 66 poor transmission speed (e.g., via an overlay on AR device 66).

In another aspect, surgical hub can determine 14524 that the second unique authentication data is inaccurate. Accordingly, the surgical hub 14002 can be configured to alert 14526 the user of the device 14006, 66 that the device 14006, 66 has not been authenticated (e.g., via an overlay on AR device 66) and lockout the device 14006, 66.

In another aspect, surgical hub can determine 14528 that the second unique authentication data has not been received. Accordingly, the surgical hub 14002 can be configured to 14530 alert the user of the device 14006, 66 that the device 14006, 66 has not been authenticated (e.g., via an overlay on AR device 66) and lockout the device 14006, 66.

Mixing Directly Visualized with Rendered Elements to Display Blended Elements and Actions Happening on-Screen and Off-Screen Having described a general implementation of the various surgical systems, surgical hubs, communication systems, augmentation systems, and augmented reality devices disclosed herein, such as surgical systems 1, 2, 50, 52, surgical hubs 6, 56, 5104, communication system 63, visualization system 8, augmentation system 83, imaging devices 24, 96 and AR devices 66, 84, the disclosure now turns to describe various other implantations of the systems, hubs, and devices. For the sake of brevity, various details and implementations of the systems, hubs, and devices described in the following sections, which are similar to the various systems, hubs, and devices described above, are not repeated herein. Any aspect of the systems, hubs, and devices described below can be brought into and/or be implemented by the above systems, hubs, and devices.

As explained above, augmented reality display devices and other types of display devices can be used to provide overlays of information to operating room (OR) staff during a surgical procedure. In some aspects, these overlays can include information related to the step of a procedure that the OR staff member is performing. Thus, the information displayed by the overlay may need to be based on a surgical instrument that the staff member is using or an area of the surgical field that the staff member is working in. However, during a surgical procedure, there are often multiple OR staff members interacting with a wide variety of surgical instruments and other objects. Moreover, surgeons, nurses, and assistants may all be working in and around the surgical field at various times. Thus, each staff member may move throughout the operating room and handle multiple surgical instruments, passing instruments to each other and setting instruments aside when they are not in use. Given the constantly changing situation in the OR, it can be difficult for surgical systems to track and organize the information that needs to be displayed to various staff members on various devices throughout the surgical procedure. Accordingly, there is a need for apparatuses, systems, and methods for tracking multiple users and objects within the OR so that relevant information can be properly displayed by various augmented reality and other display devices.

Furthermore, at various times during a surgical procedure, staff members, instruments, and other objects may pass in and out of the view of various imaging devices of the surgical system, such as imaging devices configured to capture an image of the surgical field. As a result, staff members relying on augmented reality and other display devices that are displaying the captured images of the surgical field may not be able to view a portion of an instrument that is actively being used. Thus, the staff member may not be able to accurately perceive important attributes of the instrument. For example, a surgeon performing a transection using an endo-cutter may not be able to view a portion of the endo-cutter as it passes outside of the field of view of an endoscope. Because of the obstructed view, the surgeon may not be able to perceive the articulation range of the endo-cutter's end effector. Or, in another example, the surgeon may not be able to perceive the position of the end effector. Thus, the surgeon may have trouble accurately performing the transaction. Accordingly, there is a need for apparatuses, systems, and methods for tracking attributes of surgical instruments outside of the field of view of an imaging device and displaying the tracked attributes using overlays on augmented reality devices and other display devices.

Yet further, at various times during a surgical procedure, surgical instruments and other objects may be outside of the field of view of various imaging devices. Thus, staff members relying on augmented reality and other display devices may not be able to perceive potential interactions of the surgical instrument and other objects outside of the field of view. For example, a surgeon may be using an energy device for a step of a surgical procedure. However, viewing a display device showing a live image of the surgical field captured by an endoscope, the surgeon may not be able to perceive that the energy device is in close proximity to a metallic instrument outside the field of view of the endoscope. Accordingly, there is a risk that the surgeon could activate the energy device in close proximity to the metallic instrument, causing a malfunction of the energy device (e.g., electric arcing). As another example, a surgeon attempting to perform a procedure using a circular stapler may be able to view a device deck of the stapler that is within the field of view of the imaging device but not be able to view an anvil that it outside of the field of view. Thus, the surgeon may have difficulty routing and manipulating tissue to optimize the attachment of the device deck and anvil. As yet another example, a surgeon operating a device may not be able to perceive potential collisions or unintended interactions between a surgical instrument and an object that is outside of the field of view of the imaging device. Accordingly, there is a need for apparatuses, systems, and methods for predicting interactions of surgical instruments with objects that are outside of the field of view of imaging devices and displaying attributes of the surgical instruments related to the potential interactions.

Real-Time Location Tracking Of Objects

In various aspects, apparatuses, systems, and methods for tracking multiple users and objects within the OR are disclosed herein. In some aspects, these apparatuses, systems and methods for tracking multiple users and objects can be employed to ensure that relevant information related to the tracked objects can be displayed to the specific user(s) using the various augmented reality and other display devices disclosed herein.

FIG. 66 depicts an example of a surgical system 15000 for tracking the location of objects within an OR, according to several non-limiting aspects of this disclosure. The surgical system 15000 can include a surgical hub 15002 in communication with a tracking system 15006 and at least one AR device 66. In some aspects, the tracking system 15006 can include a visualization system 15008. The surgical system 15000, surgical hub 15002, and visualization system 15008 can be similar in many aspects, respectively, to any of the surgical systems, surgical hubs, and visualization systems described above, (e.g., surgical systems 1, 2, 50, 52; surgical hub 6, 56, 5104; visualization systems 8, 58). In the non-limiting aspect of FIG. 66, the tracking system 15006 is in communication with the surgical hub 15002. In other aspects, the surgical hub can include a module comprising the tracking system 15006. The surgical hub 15002 can include an operating room mapping module 15004 configured to map the location and/or status of various objects within the OR based on data received from the tracking system 15006, as discussed in more detail below.

The tracking system 15006 can be configured to track the position and/or other attributes of various objects within the OR based on one or more different types of tracking methods. In one aspect, the tracking system 15006 (and/or the visualization system 15008) can include one or more imaging devices 15010. The imaging device(s) 15010 can be similar in many aspects to the imaging devices 24, 96, the AR device 66 and/or other imaging sensors described above with respect to visualization system 8. Thus, the imaging device(s) 15010 can include cameras and other types of visible and non-viable sensors for capturing images or otherwise tracking objects within the OR. For example, the imaging device(s) 15010 may employ visual, infrared, and/or other higher wavelength image recognition techniques to establish positional movements and locations of objects within the OR. Imaging device(s) 15010 may be placed in multiple locations throughout the operating room with overlapping fields of view such that images of objects within the OR can be captured and tracked from multiple angles. Further, multiple imaging devices 15010 may be implemented such that an object in the OR can be tracked by at least a second imaging device 15010 (e.g., a second camera 15010) when the object leaves the field of view of a first imaging device 15010 (e.g., a first camera 15010).

In another aspect, the tracking system 15006 can include one or more structured light sensors 15012 (e.g., structured light scanners) configured to track objects in the OR. The structured light sensor(s) 15012 can be configured to project a defined pattern of light, for example, from multiple angles in order to triangulate the position of objects within the OR based on distortion of the pattern caused by the objects. The structured light sensor(s) 15012 may be similar to and/or include devices such as Microsoft Kinect, Intel F200, Intel R200, and or Occipital Structure.

In another aspect, the tracking system 15006 can include one or more LIDAR (Light Detection and Ranging) sensors 15014 configured to track objects in the OR. In other aspects, sensors that use techniques similar to LIDAR may be employed by the tracking system 15006 to track objects in the OR.

In another aspect, the tracking system 15006 can include one or more floor sensors 15016 configured to track objects in the OR. The floor sensors 15016 can include weight sensors. In one aspect, the tracking system can include an array of floor sensors 15016 that are configured to determine where equipment is placed within the OR. For example, referring now to FIGS. 2 and 66, the floor sensors 15016 can be configured to determine the location and/or position of the operating table 14, surgeon's console 18, robotic hub 22, side cart 20, etc. In another aspect, the floor sensors 15016 can be configured to monitor the location and/or position of staff members within the OR.

The data generated by the floor sensors 15006 may be processed by the surgical hub 15002 and to make determinations related to various aspects of a surgical procedure. For example, a weight measured by the floor sensors 15006 could be used to determine if a device has been placed on a side cart or other piece of OR equipment (e.g., by recognizing a change in weight when the device is placed). As another example, the floor sensors 15006 can be used to detect fatigue of the OR staff based on their movements (e.g., swaying, weight distribution, etc.). As another example, the floor sensors can be used to track the weight of a patient during surgery. The patient weight may be verified by the surgical hub 15002 throughout a procedure for various reasons, such as to ensure that the dose of a drug administered to the patient is within an acceptable range for that patient's weight, as tracked by the tracking system 15006. As yet another example, the floor sensors 15016 can be used to track medical waste, devices, equipment, etc. that fall to the floor during a procedure.

Referring still to FIG. 66, in another aspect, the tracking system 15006 can include one or more acoustic sensors 15018 configured to monitor the position, location, and/or movement of objects in the OR. For example, the acoustic sensors 15018 may employ audio beaconing techniques, phase-coherent tracking, and/or time-of-flight triangulation to establish the positional movement of an object in the OR.

In another aspect, the tracking system 15006 can include one or more fiducial markers 15020. In one aspect, the fiducial markers 15020 can be any type of marker configured to assist in tracking the location, position, and/or movement of an object relative to the field of view of the imaging device(s) 15010 and/or relative to location, position and/or movement data tracked by any of the other devices/sensors of the tracking system 15006. For example, the fiducial marker(s) 15020 can include an RFID (radio frequency identification) chip configured to track the location and/or position of an object that the RFID chip is attached to. Thus, in some aspects, the fiducial markers(s) 15020 can be placed in and/or on a surgical device, operating room equipment, objects worn by OR staff, or any other object that may be tracked by the tracking system 15006. In some aspects, tracking of the fiducial markers 15020 by the tracking system 15006 can be triggered to start based on the occurrence of an event such as, for example, removal of an object (e.g., device) comprising the fiducial marker 15020 from its packaging, inserting a battery into an object (e.g., device) comprising the fiducial marker 15020, and/or when an object comprising the fiducial marker 15020 enters the OR. The fiducial markers 15020 can be used to assist in the generation of augmented reality overlays, as discussed in more detail below.

In another aspect, the tracking system 15006 can include one or more user/device sensors 15022 configured to identify and monitor the position, location, and/or movement of OR staff and/or devices within the OR. In one aspect, the user/device sensors 15022 can be included in devices or equipment worn by OR staff. The user/device sensors 15022 can include, for example, accelerometers, gyroscopes, and/or magnetometers to track the three-dimensional movements of OR staff and/or devices. In other aspects, user/device sensors 15022 can include, an RFID bracelet worn by OR staff. In one aspect, data from the user/device sensors 15022 can be used by the surgical hub 15002 and/or the tracking system 15006 to associate a device (e.g., surgical instrument) to a specific user within the OR at a given time during the surgical procedure. For example, the tracking system 15006 and/or the surgical hub 15002 may be configured to separately track the movements of OR staff and devices using multiple user/device sensors 15022. When the tracking system 15006 detects that a user/device sensor 15022 worn by an OR staff member is proximate to a user/device sensor 15022 associated with a surgical instrument, the surgical hub 15006 can identify that the OR staff member is associated (e.g., linked, using) the surgical instrument. Based on the identified association of the staff member and the instrument, the surgical hub 15002 can cause the generation of augmented reality overlays specific to the staff member and/or surgical instrument, as explained in more detail below with respect to FIGS. 66-68. In another aspect, the user/device sensors 15022 can be used to identify instruments and/or devices. The user/device sensors 15022 may include RFID tags to identify the specific type of device that is being used during a procedure. As one example, the user/device sensor 15022 can be an RFID tag on a trocar to identify the kind of trocar being used.

In another aspect, the tracking system 15006 can include one or more GPS (global positioning system) sensors 15024 that are tracked using GPS (e.g., satellite) tracking techniques to monitor the position, location, and/or movement of objects in the OR. It should be noted that although the tracking system 15006 of FIG. 66 is shown implementing tracking techniques including imaging device(s) 15010, structured light sensor(s) 15012, LIDAR sensor(s) 15014, floor sensor(s) 15016, acoustic sensor(s) 15018, fiducial marker(s) 15020, user/device sensor(s) 15022, and GPS 15024, the tracking system 15006 can be configured to use any combination of these techniques (e.g., including only some of these techniques). Further, in some aspects, other tracking techniques configured to track the location, position, movements, and/or other attributes of objects in the OR may be implemented by the tracking system 15006.

FIG. 67 illustrates a schematic side view of an exemplary implementation the tracking system 15006 in an operating room (OR) 15050, according to several non-limiting aspects of this disclosure. The OR 15050 can be any portion of an OR. For example, in some aspects, FIG. 67 can illustrate an overall side view of an OR 15050. In other aspects, FIG. 67 can illustrate a cross-sectional side view of a surgical field. The tracking system 15006 can include a first tracking device 15054 and a second tracking device 15056. The first tracking device 15056 and/or the second tracking device 15054 may be implemented using any combination of the tracking techniques referenced above with respect to FIG. 66 (e.g., imaging device(s) 15010, structured light sensor(s) 15012, LIDAR sensor(s) 15014, acoustic sensor(s) 15018, etc.). The first tracking device 15056 and the second tracking device 15054 may implement the same tracking technique or a different tracking technique.

Referring primarily to FIG. 67, and also to FIG. 66, in some aspects, the first tracking device 15054 and/or the second tracking device 15056 can be configured to track a first portion 15058 and a second portion 15060 of a target object 15062. The target object 15062 may be and object or area such as, for example, an object within the surgical field, an area within a sterile barrier, a patient, tissue, OR equipment, a surgical device, OR staff, etc. The first tracking device 15054 may be able to directly track 15055A, 15055B the first portion 15058 and the second portion 15060 of the target object 15062. For example the first tracking device 15054 may be a camera (e.g., imaging device 15010) with the first portion 15058 and the second portion 15060 of the target object 15062 directly 15055A, 15055B in a field of view of the camera. The second tracking device 15056 may be able to directly track 15057A the first portion 15058 of the target object 15062. However, the second tracking device 15056 may not be able to track 15057B the second portion 15060. For example, the second tracking device may be a camera (e.g., imaging device 15010) and the second portion 15060 may be outside of the field of view of the camera. This may be because an obstructing object 15064 (e.g., an OR staff member, a surgical instrument, tissue, etc.) is blocking the tracking 15057B of the second portion 15060 of the target object 15062. Despite the obstructing object 15064 blocking the tracking 15057B of the second portion 15060 of the target object 15062 by the second tracking device 15056, the tracking system 15006 can still track the second portion 15060 because the first tracking device 15054 is directly tracking 15055B the second portion 15060. Thus, the tracking system 15060 can be configured to have tracking devices tracking overlapping tracking areas (e.g., multiple imaging devices/systems with overlapping fields of view) so that target objects can be tracked when the target object or a portion of the target object is outside of the field of view of one of the tracking devices. Accordingly, the surgical hub 15002 is able to cause display devices to display information (e.g., images, overlays, notifications, etc.) related to the target object even when the target object or a portion thereof is outside of the field of view of one of the tracking devices.

Still referring primarily to FIG. 67, and also to FIG. 66, in other aspects, the first tracking device 15054 and/or the second tracking device 15056 may include a tracking device that is configured to directly 15055A, 15055B, 15057A and/or indirectly track 15057C, 15057D the first portion 15058 and the second portion 15060 of the target object 15062. For example, the second tracking device 15056 may be a device that implements a reflective tracking technique (e.g., an acoustic sensor(s) 15018) such that when an obstructing object 15064 prohibits direct tracking 15057B, the second tracking device 15056 can indirectly track 15057C, 15057D the target object 15062 (e.g., based on reflection using an object 15066). Thus, the tracking system 15060 can be configured to have tracking devices with overlapping tracking areas (e.g., including areas tracked using non-image techniques, reflective techniques, audio beaconing, GPS, RFID, etc.) to track the location, position, movement, and/or other attributes of a target object.

FIG. 68 illustrates a schematic plan view of an exemplary operating room map 15070 generated by the operating room mapping module 15004 of FIG. 66, according to at least one non-limiting aspect of the present disclosure. Referring primarily to FIG. 67, and also to FIGS. 66-69, the tracking system 15006 can transmit tracking data to an operating room mapping module 15004 of surgical hub 15002 generated using any combination of tracking techniques (e.g., imaging device(s) 15010, structured light sensor(s) 15012, LIDAR sensor(s) 15014, floor sensor(s) 15016, acoustic sensor(s) 15018, fiducial marker(s) 15020, user/device sensor(s) 15022, and GPS 15024). Based on the tracking data, the operating room mapping module 15004 can generate an operating room map 15070 of an operating room 15060. The map 15070 can include information related to the location, position, motion, and/or other attributes of multiple objects (e.g., 15072A-15072L) within the operating room 15060. For example, the objects 15072A-15072L of the map 15070 can correspond to various devices, equipment, OR staff, present in the operating room. The map 15070 can be updated in real-time based on tracking data from the tracking system 15006. In some aspects, the map 15070 may be displayed by any of the display devices disclosed herein. In other aspects, the surgical hub 15002 can determine the proximity and/or interaction of objects based on the map 15070.

Multi-User Track And Information Association

Referring to FIG. 66-68, in other aspects, augmented reality overlays and other notifications and alerts can be generated based on the location, position, and/or motion of objects (e.g., 15072A-15072L) as determined by the operating room mapping module 15004. In some aspects, users and devices can be tracked using the tracking system 15006 both based on the user/device sensors 15022 and other sensing techniques (e.g., imaging device(s) 15010, structured light sensor(s) 15012, LIDAR sensor(s) 15014, floor sensor(s) 15016, acoustic sensor(s) 15018, GPS 15024, etc.).

In some aspects, as mentioned above, user and device sensor data can be used by the surgical hub 15002 (e.g., the operating room mapping module 15004) and/or the tracking system 15006 to associate a device (e.g., surgical instrument) to a specific user within the OR at a given time during the surgical procedure. In this aspect, both active (wearables) and passive (cameras) tracking methods can be used by the tracking system 15006 and the operating room mapping module 15004 to map 15070 the location of devices and staff within the OR suite. For example, users (surgeons and OR other staff members) may wear gloves including user/device sensors 15022. In one aspect, the surgical hub 15002 can be configured to identify the gloves as linked to a user's right and left hands.

In some aspects, the operating room mapping module 15004 can be configured to associate users with specific locations within the operating room map 15070. For example, the operating room map 15070 may divide the OR 15060 into specific areas. Based on data from the tracking system 15006, the operating room mapping module 15004 can identify the user who has prioritization and/or control over a device. As a user exchanges a device (e.g., transfers physical control over a device to a different user), sensors (e.g., device/user sensors 15022) can detect the exchange, thereby enabling the surgical hub 15002 to identify which user is associated with the device. For example, gloves worn by the users may be configured with sensors tracking finger pressure and position. The surgical hub 15002 (e.g., the operating room mapping module 15004) can determine who has control over a device based on the glove sensor data, device sensor data, and/or data from imaging devices 15010 to calculate likelihoods of who is directing the device.

In various aspects, the surgical hub 15002 can cause any of the display and/or AR devices described herein (displays 7, 9, 19; AR devices 66, 84) to display notifications, alerts, and/or overlays based on data from the tracking system 15006, operating room mapping module 15004, and/or the surgical hub 15002. In one aspect, notifications can be displayed to one or more users based a determination by the operating room mapping module 15004 that a user has control over a surgical instrument. For example, an AR device that a surgeon is wearing can display a notification indicating that the surgeon has taken control over a surgical instrument handed to the surgeon by another OR staff member. As another example, both a first AR device that the surgeon is wearing and a second a AR device that the OR staff member is wearing can display the notification indicating that the surgeon has taken control over the surgical instrument from the OR staff member. In some aspects, whether or not a particular user's AR device displays a notification can be based on a priority level related to the data tracked by the tracking system 15006 and/or information determined by the surgical hub 15002.

In one aspect, a surgical device may be intended to be used by multiple users simultaneously. In this aspect, portions (e.g., sections) of the surgical device can be individually tracked by the tracking system 15006. For example, a circular stapling device can include device portion with a retractable trocar controllable by an adjustable knob. The circular stapling device can also include an attachable an anvil portion. The different portions of the circular staple device can be controlled by different users and separately tracked by the tracking system 15006. Based on data from the tracking system 15006, display devices (e.g., AR devices) associated with each user can be configured to display different overlays based the portion(s) of the device the user has control over. For example, a display associated with the user controlling the adjustable trocar can display an overlay based on the dialing pressure as the user adjusts the knob. The displays associated with both users may display a status of the anvil being attach to the trocar.

In some aspects, users may not be wearing a trackable sensor (e.g., user/device sensor 15022). The tracking system 15006 can be configured to track actions of the user and/or devices controlled by the user using passive tracking (e.g., using an imaging device 15010). For example, a nurse may not be wearing a trackable sensor. The nurse may perform reload of an endo-cutter with a staple cartridge. Specific cartridge types may be color coded. The reload exchange performed by the nurse can be detected based on a camera of the tracking system. Further, a notification based on the reload exchange detected by the camera can be displayed to the user who the surgical hub 15002 determined as last using the device (e.g., a surgeon wearing an active tracking device). The notification can include an overlay indicating the type of cartridge that was reloaded based on the color of the cartridge detected by the camera of the tracking system 15006. This tracking can enable the detection of potential mistakes, such as the loading of an incorrect type of staple cartridge into the endo-cutter. This tracking can also enable the issuance of warnings (e.g., display notifications) based on these detections. Further, this tracking can provide users with an awareness of actions that the users cannot directly observe.

FIG. 69 is a table 15100 of exemplary tracked object interactions determined by the surgical hub 15002 based on data generated by the tracking system 15006, according to at least one non-limiting aspect of the present disclosure. Each tracked object interaction 15102 is associated with a timestamp 15104 and a position 15106 of the object(s) during the interaction. Where applicable, the object interaction is associated with a glove ID 15108 and device ID 15110 based on the user and/or device involved in the object interaction (e.g., as determined based on user/device sensors 15022, imaging devices 15010, etc.). In cases where multiple portions of the device are tracked, the object interaction also includes a device portion identifier 15112. The table also includes a type of action 15114 that is determined by the surgical hub 15002 based on the tracked information associated with the object interaction(s). The table also includes the tracking source 15116 (e.g., imaging device(s) 15010 (cameras); user/device sensors 15022 (wearable)). Thus, based on data from the tracking system 15006, the surgical hub 15006 is able to identify various actions occurring during a surgical procedure, such as device handoffs, device operations, etc.

In various aspects, the information shown in the exemplary table of FIG. 69 can be stored in a non-relational database or in formats such as JSON arrays, thereby allowing additional information to be associate with an entry (e.g., stored by storage device 5 of FIG. 1; storage device 55 of FIG. 5, etc.). For example, detected object interactions may be entered into an even log comprising a variety of device-related information such as the timestamp, device position/rotation, equipment/device ID, and the determined action. In some aspects, the information can be associated with device-sensed data such as tracked forces/stresses, finger positions, and other relevant diagnostic data.

Off-Screen Interaction With Rendered Imagine That Are Created Based On Predictions In various aspects, apparatuses, systems, and methods for tracking attributes of surgical instruments outside of the field of view of an imaging device and displaying the tracked attributes using overlays on augmented reality devices and other display devices are disclosed herein. Referring again to FIG. 66, the surgical system 15000 can include a tracking system 15006 configured to visualize and/or track various objects within the operating room. As explained above, in some aspects, the tracking system 15006 can include a visualization system 15008 and one or more imaging devices 15010. The visualization system 15008 can be similar in many aspects to visualization systems 8, 58 described herein and the imaging device(s) 15010 can be similar in many aspects to the imaging devices 24, 96, the AR device 66 and/or other imaging sensors described herein. Thus, the visualization system 15008 can be configured to capture images (e.g., a live feed) of the surgical field during a surgical procedure. For example, the visualization system can capture an image of a surgical instrument in the surgical field as the surgical instrument is used to perform a step of a surgical procedure. The images captured by the visualization system 15008 can be displayed by any of the display devices disclosed herein, such as augmented reality (AR) display devices, to assist surgical staff during the surgical procedure.

As also explained above, in some aspects, the tracking system 15006 can utilize fiducial marker(s) 15020 to track various attributes of surgical devices. The fiducial markers 15020 can be any type of marker configured to assist in tracking the location, position, and/or movement of an object relative to the field of view of the imaging device(s) 15010 and/or relative to the location, position, and/or movements detected by other sensors/devices of the tracking system 15006. For example, the fiducial marker(s) 15020 can include an RFID (radio frequency identification) chip configured to track the location and/or position of an object that the RFID chip is attached to. Thus, in some aspects, the fiducial markers(s) 15020 can be placed in and/or on a surgical device, operating room equipment, objects worn by OR staff, or any other object that may be tracked by the tracking system 15006.

In various aspects, the surgical hub 15002 can be configured to cause a display of the surgical system 15000 (e.g., AR device 66) to display a captured image of an object in a surgical field based on the imaging device(s) 15010 overlaid with a graphic representing an attribute of the object determined based on the fiducial marker(s) 15020. In some aspects, the fiducial marker 15020 could be included on/in a surgical instrument. Based on the fiducial marker(s), the tracking system 15006 can be configured to identify the type of surgical instrument that is associated with the fiducial marker(s) 15020 and/or various other attributes of the surgical instrument.

In one aspect, the tracking system 15006 can detect a position and orientation of a fiducial marker 15020. The fiducial marker may be located on a first portion of the surgical instrument. Based on the detected position and orientation of the fiducial marker 15020, the surgical hub 15002 can determine the position and orientation of a second portion of the surgical instrument relative to the image of the surgical field captured by an imaging device 15010. Thus, the surgical hub 15002 can cause the AR device 66 to display a graphic related to the position and orientation of the second portion of the surgical instrument, overlaid on an image of the surgical field, based the fiducial marker 15020. In another aspect, the second portion of the surgical instrument may be outside of the field of view of the imaging device 15010. Therefore, the second portion of the surgical instrument cannot be observed based only on the image captured by the imaging device 15010. In this aspect, the graphic related to the second portion of the surgical instrument can be displayed by the AR device 66 as an overlay on representing the position and orientation of the second portion of the surgical instrument. Thus, a user viewing the AR device 66 can perceive the position and orientation of the second portion of the surgical instrument even when this portion of the surgical instrument is outside of the field of view of the imaging device 15010.

For example, an endo-cutter may include a fiducial marker 15020 on a handle of the endo-cutter. Based on the fiducial marker 15020, the surgical hub 15002 can determine a position of the end effector or the endo-cutter. A surgeon using the AR device 66 to view an image of the surgical field captured by an imaging device 15010 surgeon may be operating the endo-cutter. The end effector may not be within the field of view of the imaging device 15010. Therefore, to assist the surgeon in perceiving the position and orientation of the end effector, the AR device 66 can display a graphic related to the position and orientation of the end effector. This graphic can be, for example, a rendered image of the end effector or a graphic object that points to the position of the end effector.

In some aspects, the tracking system 15006 and/or the surgical hub 15002 can determine various other attributes of an object based on the fiducial marker 15020. In one aspect, the fiducial marker 15020 can be associated with a surgical instrument having defined range of motion (e.g., defined volume and/or area of operation, articulation range, rotational range, etc.). Therefore, based on the fiducial marker 15020, the surgical hub 15002 can determine the range of motion of the instrument relative to an image of the surgical field. For example, the endo-cutter referenced in the paragraph above can have an articulation range of motion and/or rotational range of motion. Thus, based on tracking of the fiducial marker 15020, the surgical hub 15002 can demine the range of motion of the endo-cutter and display an overlay graphic representing the determined range of motion relative to the image of the surgical field.

In some aspects, the tracking system 15006 and/or the surgical hub 15002 can use fiducial markers 15020 to verify the identity of an object, such as the identity and/or type of a surgical instrument. For example, as explained above, surgical instruments may be communicatively connected to the surgical hub (e.g., device/instrument 21 and surgical hub 56 of FIG. 5). Based on this connection, the surgical hub can be configured to identify the instrument. The identification can include the type of instrument (e.g., a 45 mm stapler, a 60 mm stapler, etc.). Thus, the tracking system 15006 and fiducial marker 15020 may be used as an alternate and/or redundant means of identifying the surgical instrument. In one aspect, identifying the instrument based on the fiducial marker 15020 can include determining if the instrument is active and/or available for use.

In some aspects, the tracking system 15006 and/or the surgical hub 15002 can use fiducial markers 15020 as markers within the OR to provide a zero reference point. In another aspect, fiducial markers 15020 may be positioned at various locations around the OR to provide a frame of reference that may be used by the tracking system 15006 and/or surgical hub 15002 to orient other objects tracked by the tracking system 15006. For example, fiducial markers 15020 can be placed on patients and/or instruments to determine the relative location of the patient and instruments to each other. As another example, fiducial markers 15020 can be placed on instruments to determine the proximity and/or relative distance of the instruments to each other. As yet another example, fiducial markers 15020 can be placed on instruments and other equipment within the operating room, such as a table or cart, to demine if the instrument has been placed on the table.

In some aspects, the tracking system 15006 and/or the surgical hub 15002 can use fiducial markers 15020 to detect potential accidents and/or safety concerns related to the movement of an object. The detected potential accidents and/or safety concerns could be displayed as notifications via an AR overlay. In one aspect, fiducial markers 15020 can be positioned at various portions to designate a zero reference point and/or safety zone. The tracking system 15006 can be configured to detect when an object is approaching the safety zone or when an object is outside of the safety zone. For example, a surgical procedure may involve the use of a robotic system in conjunction with a laparoscopic instrument. Fiducial markers 15020 can be positioned to designate a safety zone within which the robotic system can safely maneuver the laparoscopic instrument. The tracking system 15006 and/or surgical hub 15002 can be configured to identify that the laparoscopic instrument is outside of the safety zone and provide a warning to the user and/or adjust the operation of the robotic system.

FIGS. 70A and 70B illustrate exemplary intraoperative displays 15200 including an image of a surgical instrument 15204 in a surgical field 15202 and a graphic 15212, 15214 representing a portion 15210 of the surgical instrument 15204 outside of the field of view, according to at least one non-limiting aspect of the present disclosure. The intraoperative displays 15002 can be displayed by any of the display devices (e.g., AR device 66) disclosed herein. Referring primarily to FIGS. 70A and 70B and also to FIG. 66, the image of the surgical field 15202 can be captured by an imaging device 15010. Based on the image of the surgical field 15202 captured by the imaging device 15010, a first portion 15208 of the surgical instrument 15204 (e.g., a grasper portion) can be seen interacting with tissue 15206. However, a second portion 15210 of the surgical instrument 15204 (e.g., a shaft portion) is outside of the field of view of the imaging device 15010 and therefore cannot be seen in the image of the surgical field 15202. The surgical instrument 15204 can include a fiducial marker 15020 (not shown in FIGS. 70A and 70B). Based on the fiducial marker 15020, the tracking system 15006 and/or the surgical hub 15002 can determine a position of the second portion 15210 of the surgical instrument 15204 relative to the surgical field. Thus, the surgical hub 15002 can cause the intraoperative display 15200 to include a graphic 15212, 15214 representing the position of the second portion 15210. In the non-limiting aspect of FIG. 70A, the graphic 15212 is a rendered image 15212 of the second portion 15210 of the surgical instrument 15204. In the non-limiting aspect of FIG. 70B, the graphic 15214 is a graphical object representing the position of the second portion 15210 of the surgical instrument 15204 relative to the image of the surgical field 15202.

Accordingly, the surgical system 15000 can track attributes of surgical instruments and display the tracked attributes using overlays displayed by AR display devices (e.g., AR device 66) and other display devices disclosed here. OR staff members may be relying on augmented reality and other display devices displaying the images of the surgical field captured by imaging devices. Surgical system 15000 can enable staff members to perceive portions of surgical instruments that may be outside of the field of view of the imaging devices. Moreover, surgical system 15000 can allow OR staff members to more accurately perceive important attributes of the instrument that may not be viewable based on a single imaging device, such as a range of motion of the instrument and/or the position of the instrument relative to other tracked objects.

Prediction Of Interactions And Interrelationships Of Objects Not In The Field Of View In various aspects, apparatuses, systems, and methods for predicting interactions of objects that are outside of the field of view of imaging devices and displaying attributes of the object based on the predicted interactions are disclosed herein. Referring again to FIG. 66, the surgical system 15000 can include a tracking system 15006 configured to visualize and/or track various objects within the operating room. As explained above, in some aspects, the tracking system 15006 can include a visualization system 15008 and one or more imaging devices 15010. The visualization system 15008 can be similar in many aspects to visualization systems 8, 58 described above and the imaging device(s) 15010 can be similar in many aspects to the imaging devices 24, 96, the AR device 66 and/or other imaging sensors described above. Thus, the visualization system 15008 can be configured to capture images (e.g., a live feed) of the surgical field during a surgical procedure. For example, the visualization system can capture an image of a surgical instrument in the surgical field as the surgical instrument is performing a step of a surgical procedure. The images captured by the visualization system 15008 can be displayed by any of the display devices disclosed herein, such as augmented reality (AR) display devices, to assist surgical staff during the surgical procedure.

In some aspects, as explained above, surgical instruments may be communicatively connected to the surgical hub (e.g., device/instrument 21 can be connected to surgical hub 56 of FIG. 5). Thus, the surgical hub 15002 can be configured to receive instrument data from surgical instruments related to various sensed parameters and operational settings of the instruments. Based on the instrument data received by the surgical hub 15002, the surgical hub 15002 can determine operating parameters of the instrument. For example, based on instrument data received from the various surgical instruments disclosed herein, the surgical hub 15002 can determine operating parameters such as to speed, force, firing speed, firing force, activation status, power level, activation time, energy mode, etc.

In some aspects, the surgical hub 15002 can be configured to identify interactions and potential interactions of surgical instruments and other objects based on data from the tracking system 15006 and/or based on instrument data received from the surgical instruments. Moreover, the potential interactions of the surgical instrument and the other object(s) may not be perceivable based only on images captures by an imaging device 15010 of the visualization system 15008. Therefore, a user relying on a display device (e.g., AR device 66) displaying only captured images from an imaging device 15010 may not be able to accurately respond to the potential interaction. Therefore, to assist the user, the surgical hub 15002 can be configured to cause the display device to display various notifications and other graphical indicators (e.g., overlays) related to the interactions and/or potential interactions detected by the surgical hub.

In one aspect, based on data from the tracking system 15006, the surgical hub 15002 can detect collisions or potential collisions of tracked objects. For example, using any combination of the various tracking techniques disclosed herein (e.g., imaging device(s) 15010, structured light sensor(s) 15012, LIDAR sensor(s) 15014, floor sensor(s)

15016, acoustic sensor(s) 15018, fiducial marker(s) 15020, user/device sensor(s) 15022, and GPS 15024), the surgical hub 15002 can detect a potential collision between a portion of a surgical instrument and a critical structure within the surgical field. As another example, the surgical hub 15002 can be configured to detect a potential collision between multiple surgical instruments. As yet another example, the surgical hub 15002 can be configured to detect a potential collision between various other objects in the surgical field. The detected potential collisions and/or detected collisions may not be within the field of view of imaging device(s) 15010, and therefore, may not be viewable by OR staff. Based on the detected potential collisions and/or detected collisions, the surgical hub 15002 can cause display device (e.g., AR device 66) to display a notification, such as an overlay with information related to the collision. In one aspect, the notification can include a warning and/or other instructions for avoiding the collisions. In another aspect, the notification can include an overlay with a graphical representation of the objects involved in the collision. Accordingly, OR staff can perceive and act upon potential collisions and collisions that are not within the field of view of the imaging device(s) 15010.

In another aspect, based on data from the tracking system 15006, the surgical hub 15002 can detect unintended interactions of tracked objects. For example, similar to detecting potential collisions, the surgical hub 15002 can detect an unintended interaction between a portion of a surgical instrument and a critical structure within the surgical field. As another example, the surgical hub 15002 can detect an unintended interaction between multiple surgical instruments. As yet another example, the surgical hub 15002 can detect unintended interactions between various other objects in the surgical field. The detected unintended interactions may not be within the field of view of imaging device(s) 15010, and therefore, may not be viewable by OR staff. Based on the detected unintended interaction, the surgical hub 15002 can cause the display device (e.g., AR device 66) to display a notification, such as an overlay with information related to the unintended interaction, a warning and/or other instructions for avoiding the interaction, and/or an overlay with a graphical representation of the objects involved in the interaction. Accordingly, OR staff can perceive and act upon unintended interaction that are not within the field of view of the imaging device(s) 15010. In some aspects, the surgical hub 15002 can prevent the operation of instruments based on the detected unintended interaction.

For example, a user may be using a monopolar energy device. The tracking system 15006 and/or surgical hub 15002 may detect that the monopolar energy device is proximate to a metallic object (e.g., another surgical instrument, an object in the surgical field, etc.). The surgical hub 15002 can determine that there is a potential unintended interaction between the monopolar device and the metallic object because activating the monopolar device proximate to the metallic object may cause arcing. Based on the detected unintended interaction, the surgical hub 15002 may cause an AR display device 66 to display an overlay warning of the interaction. In another aspect, the surgical hub 15002 may prevent the activation of the monopolar energy device. In yet another aspect, the surgical hub 15002 can cause an overlay to be displayed instructing the user to redirect the energy direction to the intended therapeutic zone.

In some aspects, the notifications, warnings, and/or overlays displayed based on detected potential collisions, detected collisions, detected unintended interactions, and other detected interactions between objects can include attributes of an object involved in the interaction. The attributes of the object may be based on instrument data received by the surgical hub 15002 and/or based on tracking data from the tracking system 15006. For example, a force, speed, impact, and/or physical magnitude of interactions between objects may be displayed as overlays. In other aspects, the notifications, warnings, and/or overlays may include a graphic indicating a location of the interaction. Accordingly, a user viewing this graphic may adjust the field of view of an imaging device to view the interaction.

In another aspect, based on data from the tracking system 15006, the surgical hub 15002 can cause graphic overlays to be displayed by a display device (e.g., AR device 66) to assist a user performing a step of a surgical procedure. In one aspect, the overlay can include a graphical representation and/or indicator for an object that is outside of the field of view of an imaging device 15010 capturing an image of the surgical field. The graphic overlay can provide information related to the location and/or other attributes of the object that is out of view. For example, a surgeon may be performing a procedure using a circular stapler. The procedure may involve attaching a device deck of the stapler to a separate anvil portion. The device deck of the stapler may be within the field of view whereas the anvil may be outside of the field of view (e.g., outside of the field of view based on the camera angle, outside of the field of view because tissue is obstructing the view of the anvil, etc.). The surgical hub 15002 can cause the display device to display a rendered image or other graphical representation of the anvil (e.g., indicating the off-image position of the anvil, overlaying a rendered image of the anvil over the obstructing tissue, etc.). In another aspect, the surgical hub 15002 can cause the display device to display a directional indicator overlay showing the direction and/or route that tissue may be manipulated to optimize the attachment of the anvil to the device deck. Thus, the overlay can assist the surgeon in perceiving how objects outside of the field of view of the imaging device 15010 can be manipulated to more easily achieve a desired outcome of the step of the surgical procedure.

In another aspect, based on data from the tracking system 15006, the surgical hub 15002 can cause graphic overlays to be displayed by a display device (e.g., AR device 66) that may replace the need to use various instruments. For example, FIGS. 71A and 71B illustrate exemplary intraoperative displays 15300 showing the surgical field 15302 during the cutting of stomach tissue 15306, according to at least one non-limiting aspect of the present disclosure. The intraoperative displays 15000 can be displayed by any of the display devices (e.g., AR device 66) disclosed herein. Referring to FIG. 71A, a bougie tube 15310 has been inserted into the patient to provide a guide as a surgeon makes a cut line 15308 in the stomach tissue 15306 using an endo-cutter 15312, assisted by a surgical grasper 15304. Referring now to FIG. 71B, the bougie tube 15310 is no longer being used. Instead, in one aspect, a graphical overlay of a virtual bougie 15316 can be displayed by the intraoperative display 15300 to provide a guide to the surgeon for cutting the stomach tissue 15306. In another aspect, a graphical overlay of a cut-line guide 15314 can be displayed by the intraoperative display 15300 to provide a guide to the surgeon. Thus, the graphical overlay 15314, 15316 can replace the need to physically install the bougie tube 15310 in the patient.

FIG. 72 illustrates a method 15400 for mixed reality visualization of a surgical system, according to several non-limiting aspects of this disclosure. The method 15400 may be practiced by any combination of the surgical systems, surgical hubs, tracking systems, visualization systems, augmentation systems, AR devices, any of the components thereof, and any other devices and systems disclosed herein, such as surgical systems 1, 2, 50, 52, 15000, surgical hubs 6, 56, 5104, 15002, tracking system 15006, visualization system 8, 15008, communication system 63, augmentation system 83, and AR devices 66, 84.

In accordance with the method 15400, a first camera of a first visualization system can capture 15402 of an image of an object in a surgical field, wherein a first portion of the object is outside of a field of view of the first camera. A tracking system can track 15404 a position of a second portion of the object. A surgical hub can determine 15406 an attribute of the object based on the tracked position of the second portion of the object, wherein the attribute of the object is related to the first portion of the object outside of the field of view of the camera. An augmented reality display device can display 15408 the captured image of the object in the surgical field and a graphic based on the attribute of the object. In one aspect, the object can comprise a surgical instrument, patient issue, a user, or a combination thereof.

In accordance with one aspect of the method 15400, determining 15406 the attribute of the object based on the tracked position of the second portion of the object can include determining a position of the first portion of the object. Further, displaying 15408 the graphic can include the augmented reality display device displaying a rendered image of the first portion of the object.

In another aspect of the method 15400, the tracking system can include the visualization system. Further, the visualization system can include a second camera. Tracking 15404 the position of the second portion of the object can include the second camera capturing an image of the second portion of the object. The second portion of the object may be outside of the field of view of the first camera. In another aspect of the method 15400, tracking 15404 the position of the second portion of the object can include tracking the second portion of the object using a structured light sensor, a light detection and ranging (LIDAR) sensor, radio frequency identification (RFID), global position system (GPS) tracking, audio beaconing, non-visual light tracking, or a combination thereof.

In another aspect of the method 15400, the tracking system can track a position of a structure in the surgical field. Further, determining 15406 an attribute of the object based on the tracked position of the second portion of the object can include the surgical hub identifying an interaction of the first portion of the object and the structure. In one aspect, the augmented reality display device can display a graphic based on the position of the structure. In another aspect, displaying the graphic based on the position of the structure can include displaying an alert based on the identified interaction of the first portion of the object and the structure. In yet another aspect, displaying the graphic based on the position of the structure can include displaying a force of the interaction, a speed of the interaction, an indication of an impact of the first portion of the object and the structure, an energized condition of the object, a time, or a combination thereof.

In another aspect of the method 15400, the object can include a surgical instrument including a fiducial marker. In this aspect, tracking 15404 the position of the second portion of the object can include the tracking system tracking the fiducial marker. In another aspect, the surgical hub can determine a range of motion of the surgical instrument based on the tracked fiducial marker. Further, displaying 15408 the graphic can include the augmented reality display device displaying a rendered image representing the range of motion of the surgical instrument.

Displaying Device-Specific Information And Managing Devices Use Across Networks As explained throughout this disclosure, various devices and instruments can be used to perform surgical procedures. These devices can vary widely. For example, devices can have different device types and different device versions, each with different features and intended uses. In some cases, the features and intended uses of devices may be updated by the device manufacturer. Moreover, device manufacturers may develop new techniques for existing devices or release software updates related to device operation. In other cases, devices may be recalled by the manufacture. In yet other cases, counterfeit devices or counterfeit device components can exist that should not be used. Thus, there is an abundance of device identification-related information that OR staff members need to be aware of when using devices for surgical procedures.

Moreover, there is an abundance of device operation-related information that OR staff members must consider when using devices. For example, device performance may deteriorate over time based on repeated use. As another example, devices can be over-used or misused during the course of a surgical procedure. Yet further, devices may sense information that users may not be aware of or know how to easily access. Accordingly, there is a need for apparatuses, system, and methods for managing device-related information and for allowing users to easily access relevant device-related information.

In various aspects, apparatuses, systems, and methods for managing device-related information are disclosed herein. As explained above, devices and surgical instruments may be communicatively connected to a surgical hub (e.g., device/instrument 21 can be connected to surgical hub 56 of FIG. 5). Thus, the surgical hub can be configured to receive device-related information from various devices used with various surgical systems. Moreover, the surgical hub can be communicably coupled a hospital network and/or a network of the device manufacturer. For example, referring to FIG. 5, a computer-implemented interactive surgical system 50 can include one or more surgical systems 52 that include at least one surgical hub 56 in communication with a cloud 54 that may include a remote server 63. In one aspect, the cloud 54 and/or remote server 63 can be associated with a hospital network. The hospital network may be in communication with a device manufacturer database. In another aspect, the cloud 54 and/or remote server 63 can be associated with the device manufacturer database.

In some aspects, devices/instruments 21 connected to a surgical hub 56 can be authenticated based on communication with the hospital network and/or the device manufacturer database. The hospital network can be configured to determine if a connected device/instruments 21 is authorized. For example, a counterfeit device that is attempting to connect to a surgical hub 56 may not be authorized. In one aspect, the hospital network may communicate with a manufacturer database to determine that the counterfeit device is not authorized. As another example, a recalled device attempting to connect to the surgical hub 56 may not be authorized. A device/instrument 21 that is not authorized may be blocked from use, for example by the surgical hub 56.

In one aspect, the authorization of a device/instrument 21 of the device can be verified during a surgical procedure. In another aspect, the authorization of a device/instrument can be verified at a time the device/instrument 21 and/or components of the device (e.g., reload cartridges, replacement components) are stocked. In yet another aspect, the surgical hub 56 may be configured to allow a procedure to proceed even if a device/instrument 21 has not been authorized. For example, a procedure may be allowed to proceed without device/instrument authorization if the lack of authorization is due to the hospital network being down.

In some aspects, connected devices/instruments 21 can store information related to techniques for using the device, intended uses, and/or software updates. This information may be communicated to the surgical hub 56 and stored by the hospital network (e.g., server 63). In other aspects, information related to techniques for using the device, intended uses, and/or software updates may be accessed on the device manufacturer's database upon the connection of the device. Instructions and/or intended uses for device/instruments may be presented to the user of the device via a display device (e.g., AR device 66).

In some aspects, the hospital network and/or the device manufacturer database can store information related to recommended and/or intended device usage. This device usage information can be used to determine if a specific device/instrument 21 has exceeded a recommended use. For example, device usage information can include a maximum recommended usage during a specific period of time (e.g., a device may not be intended to be used for longer than a specified time period, a device may not be intended to be activated more than a specified number of times over a specific time period, etc.). As another example, device usage information can include a maximum recommended number of activations and/or maximum usage time over the course of the lifetime of the device. As another example, device usage information can include intended uses for a specific device/instrument 21. Based on this device usage information, the surgical hub 56 can be configured to alert a user (e.g., via a display device, such as AR device 66) of a detected overuse and/or misuse. In other aspects, the surgical hub 56 can be configured to prevent further use of a device based on device usage information stored by the hospital network and/or the device manufacturer database.

In various aspects, apparatuses, systems, and methods for allowing users to easily access relevant device-related information are disclosed herein. Referring still to FIG. 5, and also to FIG. 8, a user using a device/instrument 21 connected to the surgical hub 56 can request that a display device (e.g., hub display 65, instrument display 50, AR device 66, etc.) display device information related to the device/instrument 21. For example, the surgeon may provide a verbal prompt detected by a microphone associated with the surgical hub 56 to requesting that device information be displayed (e.g., the surgeon may say "show me information"). The user's request that device information be displayed can cause the surgical hub 56 to cause the display device to display information related to the device/instrument 21.

In various aspects, the information displayed related to the device/instrument 21 may include information related to the historic usage of the device and other information related to the current operation of the device. In some aspects, the information displayed can vary depending on the type of device. In one aspect, if the device/instrument 21 is an energy device, the information displayed can include, for example, a number of activations, a total time of activation, a residual temperature at the jaw, an estimated wearing condition of the device, device-specific calibration and/or characterization information which may affect the best usage, a device parameters of interest, or a combination thereof. In another aspect, if the device/instrument 21 is an endo-cutter, the information displayed can include, for example, a number of firings, estimated anvil decambering information, a high/low on tissue gap based on firing on test skin in build, device parameters of interest (e.g., maximum articulation angle, jaw temperature etc.), or a combination thereof. Thus, a user of the device may be able to easily determine if the device is nearing or has exceeded its recommended lifetime (e.g., based on the displayed usage history). The user may also be able to easily access important parameters related to the operation of the device to assist with decision making during a surgical procedure.

System and Method for Tracking a Portion of the User as a Proxy for Non-Monitored Instrument In view of the foregoing description of augmented reality (AR), mixed reality, and image overlay technology, the present disclosure may be configured to render and display augmented reality content on an AR headset, external display, or combination of one or more devices. Additionally, an external display may be configured to provide a split screen view that displays AR content and an unaugmented live feed of the surgical field.

The present disclosure describes a tracking system of operating room (OR) personnel and is configured to extrapolate the movement, position, orientation, and context of one or more of the active OR participants to determine the specific operation procedure in progress, the surgical instrument being used by the OR participant, and/or anticipated movement of the OR personnel. The system may further be configured to render a virtual element that includes an anticipated position of a surgical instrument, recommendations, guidance, warning, and surgical location information, as augmented reality (AR) content. The AR content is integrated in real-time with the live-feed of the surgical site, and aids the OR personnel in perioperative surgical procedures.

FIG. 73 is a diagram of an illustrative OR 16000 setup with a passive tracking camera system, according to one aspect of this disclosure. In various implementations, a, surgical hub 16001 can be communicably connected to one or more cameras 16002, surgical instruments 16010, displays 16006, overhead lights 16008, and other surgical devices within the OR 16000 via a communications protocol (e.g., Bluetooth), as described above. The cameras 16002 can be oriented in order to capture images and/or video of the surgical staff members 16003 and/or surgical instruments 16010 (or other surgical devices) within the OR 16000 during the course of a surgical procedure. The captured image(s) can include static images or moving images (i.e., video). The images of the surgical staff members 16003 and/or surgical instruments 16002 can be captured at a variety of angles and magnifications, utilize different filters, and so on. In one implementation, the cameras 16002 are arranged within the OR 16000 so that they can collectively visualize each surgical staff member 16003 performing the surgical procedure. Accordingly, the surgical hub 16001 can receive the captured image and/or video data from the cameras 16002 to visually analyze the surgical staff members 16003 and/or the surgical instruments 16010 during the surgical procedure. The image and/or video data can be processed utilizing a variety of machine vision, image processing, object recognition, and optical tracking techniques to track characteristics, properties, actions, and movements of the surgical staff members 16003 and/or the surgical instruments 16010.

The surgical hub 16001 (FIG. 73) can be configured to determine the position of a surgical instrument 16010, as shown in FIG. 74, based on the wrist angle of the surgical staff members 16003. In this particular implementation, the angle of the individual's wrist 16016 is defined as the angle α between the longitudinal axis 16014 of the surgical instrument 16010 being held by the surgeon and the longitudinal axis 16012 (i.e., the proximal-to-distal axis) of the individual's hand. In other implementations, wrist angle can be defined as the angle between the individual's hand and forearm, for example. The surgical hub 16001 may use the wrist angle α, along with other hand movements 16004 of the surgical staff members 16003 to track the movements of the surgical staff members 16003.

FIG. 75 shows a passive tracking system 16005 comprising one or more cameras 16002 configured to uniquely identify and differentiate surgical staff members in an operating room, such as Surgeon A, Surgeon B, Nurse A, Nurse B, Anesthesiologist, Technician, etc., The passive tracking system 16005 may use a number of different visual identifiers on a surgical glove 16018 to differentiate between the different surgical staff members including a pattern, color, ink, code (e.g., bar code or QR code), or combination of multiple identifiers. In one aspect, each surgical staff member in the operating room has a different color or pattern 16020*a*-16020*n* on their gloves 16018 that uniquely corresponds to the surgical staff member's identify. The color of the surgical glove 16018 is only detectable by the camera 16002 and is shown in color on the display 16006.

FIG. 76 shows an initialization sequence in a passive tracking system 16005. In one aspect, the surgical staff member's glove may comprise an identifier or a code 16022*a*, 16022*b*. The code 16022*a*, 16022*b* may be scanned or identified by the camera 16002 and sent to a surgical hub 16001 (FIG. 73) to associate an identifying glove color or pattern 16020*a*-16020*n* (as shown in FIG. 75), staff member identify, and left and right hand. The surgical hub 16001 records the identifying information associated with the code 16022*a*, 16022*b* and may associate the information with a surgical procedure, operating room, patient, or other surgical analytics. Each surgical staff member may be required to initializes their gloves 16018 upon entering the operating room or prior to surgery. The gloves 16018 are shown and identified on the display 16006.

The identifying characteristics on the gloves 16018 may be printed directly onto the gloves 16018 providing a sterile surface that is visible or invisible in the visible light spectrum. In various aspects, the identifying pattern may be comprise an invisible ink, optical fiducial marker, photosensitive tag printed directly onto the gloves, or retroreflective material. In one aspect, certain colors, patterns, or codes may be found distracting so it maybe preferred that the identifying pattern is invisible in the visible light spectrum.

FIG. 77 shows a directional pattern 16040 that may be used to differentiate between a left and right appendage or aid the passive tracking cameras 16002 in detecting movement. The different directional pattern 16040 may be associated with different staff members and may be printed on gloves, wristbands, and/or forearm bands to aid the passive tracking cameras 16002 in detecting movement.

FIG. 78 shows an identifying code 16022 on the dorsal side of a surgical glove 16018, detected by a thermal imaging or infrared (IR) camera 16002. The code 16022 may be printed on the back of the surgical glove 16018 with a thermal conductive material that allows heat the transfer from the surgical staff member in a specific pattern. Additionally, the colors or patterns may be visible to the surgical staff members to ensure that they have a matching pair of gloves. In another aspect, each glove 16018 is unique and associated with the staff member by the initialization sequence. The initialization sequence does not require that gloves are kept in pairs and may be pulled form a box of disposable gloves like traditional latex gloves.

In another aspect, FIG. 79 shows an identifying code 16022*a*, 16022*b* on both the dorsal side and palmar side a surgical glove 16018. By printing the identifying code on both sides of the glove 16018, the staff member can more quickly initialize their gloves 16018 in the initialization sequence increase the likelihood that one of the passive tracking cameras 16002 (FIGS. 75-76) is able to view the identifying code 16022*a*, 16022*b*.

Some tracking analysis may require more granular identification of the hand movement including the precise movement by each finger of the staff member. In one example, the surgical hub 16001 (FIG. 73) may track the hand-off of a surgical instrument from a first surgeon to a second surgeon, based on the tracked finger movement of the surgical staff members. FIG. 80 shows identifying QR codes 16022*a*, 16022*b* assigned to each finger 16024*a*-*j* of a surgical staff member glove 16018.

During a surgical procedure, multiple surgical staff members may be clustered in close proximity to the surgical site and impede the view of one or more of the passive tracking cameras 16002 (FIGS. 75-76). In order to mitigate this issue, the surgical hub 16001 (FIG. 73) may use the one or more cameras 16002 in a network configuration to track an identifier throughout the operating room. FIG. 81 shows a wrist-mounted camera 16026*a*, 16026*b*, . . . 16016*n* configured to monitor and track the finger and wrist movement of a single staff member. The wrist-mounted camera 16026*a*-*n* is communicably coupled to the surgical hub through a wired or wireless communication medium and may transmit data continuously or in periodic data dumps. The wrist-mounted camera 16026*a*-*n* comprises a sterile adjustable strap 16028 that houses the plurality of cameras 16026*a*-*n* along the wrist of the surgical staff member. The wrist-mounted camera 16026*a*-*n* may map the hand and finger movement based on a plurality of nodes 16030 that correspond to the joints in the hand. The wrist-mounted camera 16026*a*-*n* may be used with traditional surgical gloves or may be used with IR printed grids to that aid the cameras 16002 in tracking the node 16030 movement. However, there may be times that even the wrist-mounted camera 16026*a*-*n* is unable to see or identify certain granular measurements. An identifier or node 16030 obscured or not visible to the camera 16002 because it is covered by biological material. In some situations, the passive cameras 16002 may still be able to view the identifiers when they are printed with IR visible ink.

However, the passive tracking cameras 16002 (FIGS. 75-76) alone may not have enough resolution to pick up on detailed and granular hand movements 16004 (FIG. 74) that are required to measure certain parameters, such as force or finger strain. Additionally, the cameras 16002 may be visual obstructed and inhibited from recognizing certain movement 16004 that is necessary to identify the surgical instrument 16010 (FIG. 73), the procedure, or other movement of interest. In the present disclosure, various active tracking systems are suitable to measure and detect different levels of precision and reliability that may not be perceptible to the passive tracking cameras. In one aspect, a gyroscope or accelerometer (FIGS. 82-83) may be positioned on the back of (dorsal side) a surgical staff members' glove that can detect hand angles as the hand pivots and rotates. The surgical glove may further comprise a strain gauge (FIGS. 82-83) on the fingers of the glove to track finger movement of the surgical staff member and supplement the passive tracking date. Active sensors such as gyroscopes and strain gauges provide additional data points and allow the surgical hub to manage multiple user interactions in the same surgical space with greater accuracy. Additionally, the data gathered by these active sensors can be used to better quantify surgical staff member's interaction with the surgical devices. The surgical hub 16001 (FIG. 73) may be configure to receive active signals, passive signals, or a combination of both active and passive signals.

In various aspect, active sensors may be used to provide additional resolution (orientation and finger positioning) to passive tracking systems when multiple users are operating different aspects of a single device. For example, during a complex endoscopic procedures, one surgeon will be managing scope stabilization and visualization while another surgeon operates the tool through the working channel. It is common for multiple sets of hands to be in contact with the handle of the scope, and the passive system may not be able associate the actions performed by a set of hands with the corresponding user. With the addition of active systems such as strain gauges in the fingers, or gyroscopes in the glove, the surgical hub could identify which surgeon's hand is feeding or holding the tool, and which is stabilizing the scope due to the different finger shapes as well as hand orientations are required to perform each tasks. Finger shape and hand orientation could be characterized in depth to improve accuracy of predicting which users are performing particular tasks or operating certain devices while there are multiple users or devices in the same visual space.

FIG. 82 shows an active surgical glove 16118 comprising fiducial markers on each of the fingers 16124, a plurality of embedded strain gauge sensors 16132, and a gyroscope 16136 coupled to a control circuit 16140. The fiducial markers 16124 are used by passive tracking cameras track finger movement. The control circuit 16140 receives strain gauge measurements from each of the strain gauge sensors 16132, through a flexible wire 16134, as well as gyroscope data. The gyroscope may be embedded in a circuit or house coupled to the control circuit 16140. The control circuit 16140 may transfer active sensor data to the surgical hub 16001 (FIG. 73) through a wireless communication protocol or physically I/O communication port. The control circuit 16140 may be configured to transmit data in real-time via a wireless communication protocol, such as Bluetooth. In various aspects, the control circuit 16140 my dynamically adjust the transmission rate in order to manage power.

The control circuit 16140 may have an active identifier 16122, such as a QR code, RFID sensor, or other wireless communication, that allows the staff member to associate their identity with the active tracking data. Additionally, the surgical hub associates the fiducial markers 16124 with the user during the initialization sequence.

In various aspect, the surgical hub uses the passive tracking data to calibrate active sensors on gloves relative to surrounding environment, such that sensors in glove are aware of hand positions in space regardless of visual obstruction. For example, at the beginning of each surgery, a calibration sequence (FIGS. 75-76) can be performed to synchronize sensors in the gloves with the surrounding environment which includes other users in the room in addition to critical areas (patient bed, mayo stand, etc.). Each surgical staff member may scan a unique identifier (e.g., QR code, NFC, active RFID, passive RFID, etc.) in their gloves to uniquely correspond to the user and sensors in the system. During the calibration sequence, all users hold their hands into the field of view of the passive tracking system (e.g., cameras 16002 FIGS. 75-76) in various orientations, and unique identification markers on the gloves allow the vision system to identify the relative position of each user's glove. Throughout the procedure, as hands are blocked by devices, blood, or move in and out of the field of view, active sensors such as accelerometers and gyroscopes can be used to track hand positions and orientation of each users.

FIG. 83 show a single strain gauge sensor 16132 is relation to the tip of a finger. In various aspects, active sensor surgical glove comprises a least one strain gauge sensor 16132 per finger, and may include a strain gauge sensor 16132 at each joint in the hand. Due to the size of the strain gauge sensor 16132, they may be embedded into a flexible sterile material with little to no perceptible size by the surgeon. It will be appreciated that the surgical gloves do not impede the natural tactile feedback that is provided by traditional latex, nitrile, or other sterile materials used in surgical gloves.

FIGS. 84 and 85 show flexible circuits 16135 that may be used to connect the strain gauge sensors 16132 to the control circuit. FIG. 84 shows a flexible circuit that is printed into a sterile flexible material 16138 such as latex, nitrile, or other sterile materials used in surgical gloves. After use, the gloves may be sterilizes for a predetermined number of use cycles or may be disposable. Reusable gloves may be sterilized using heat or antiseptic solutions such as alcohol as long as the sterilization process does not breakdown the material of the gloves or damage the printed active sensor circuits.

FIG. 86 shows active fiducial markers 16144 connected to a control circuit 16140, printed directly on a sterile flexible material 16138. This allows stain gauge sensors 16132 and fiducial markers to be strategically placed on the surgical glove in order to track and locate fingers and hand movement.

FIG. 87 shows a piezoelectric ceramics power cell 16146 that harvests energy from movement and can be used to power the control circuit, strain gauge, gyroscope, accelerometer, and/or active fiducial markers. The active sensor gloves may comprise a plurality of piezoelectric ceramics power cells 16146 that convert low frequency movement (finger or wrist movement) into energy which is stored in a power source (e.g., battery or capacitor). A power cell 16146 comprises a flexible ceramic layer that captures the vibrations of movement as mechanical energy. The stretched power cell **16146*a* stretches when the sterile flexible material 16138 of the glove stretches, the flexible ceramic layer 16148 is released and vibrates with the motion of the hand. The stretched power cell 16146*a* is in the excitation state and returns to a static state un-stretched power cell 16146*b* when the sterile flexible material 16138 contracts. The change results in the vibration of the flexible ceramic layer 16148** and creates a small-amplitude voltage response that may be captured in an energy storage device.

FIG. 88 shows an active sensor glove 16118 with a removable housing 16150 that comprises the control circuit 16140 and the gyroscope 16136. The housing 16150 is a waterproof enclosure to protect electrical components such as the control circuit, gyroscope, accelerometer, and power source such as a rechargeable battery or super capacitor. The housing 16150 physically connects to the active sensor glove 16118 at a connection point 16142. The connection point 16142 allows power and data to pass between the housing and the active sensors on the glove 16118. After a surgical procedure, the removable housing is disconnected from the connection point 16142 so that the glove 16118 can be sterilized and the housing 16150 can be connected to an external power source to charge the internal power source.

In another aspect, the active sensors are removable from a passive glove 16018 with fiducial sensors 16024. FIG. 89 shows a removable active sensor harness 16252 comprising a plurality of embedded strain gauge sensors 16232 communicably coupled to a control circuit 16240 with flexible wires 16234, within a housing 16250. FIG. 90 shows an active sensor harness 16252 removed from a hand. After a surgical procedure, the surgical staff member may remove the active sensor harness 16252 so that it can be sterilized for subsequent use and may discard their gloves 16018. As shown in FIGS. 89-90, the passive glove 16018 includes a removable finger/glove strap 16254.

In various aspects, the strain gauge sensors 16132, 16232 provides additional data to track a surgical instrument hand-off between a first surgeon and a second surgeon. Tracking the hand-off helps a medical facility to monitor the device after the hand-off and ensure that the correct user is in control of the device. FIG. 91 shows a graphical representation of a surgical instrument hand-off 16300 between a first surgeon and a second surgeon. Surgeon A begins to hand-off the surgical instrument to Surgeon B, and Surgeon B reaches for and grabs the device at 16302. Both active and passive tracking systems determine that the surgical instrument passed from Surgeon A and Surgeon B.

In another example, Surgeon A begins to hand-off the surgical instrument to Surgeon B. However, Surgeon B started to grab the instrument but before making the hand-off, Surgeon A pulled the instrument away. Surgeon A regripped the instrument because they see some bleeding that needed to be cauterized. The passive tracking system had tracked Surgeon A's hand and the surgical instrument as it moved into proximity with Surgeon B to initiate the hand-off, and recognized that Surgeon B came into contact with the device, suggesting that the hand-off was complete. Using the passive tracking system alone may result in losing track of the instrument because Surgeon B never "initiated" the hand-off, yet the device is traveling back with the hands of surgeon A. The active tracking system can detect finger position as it relates to an opened or gripped hand, an additional level of confirmation can ensure that the device can only be assigned to a "gripping" user when outside of the transfer zone.

Active Tracking With EMG And MMG Signals

The present disclosure further describes active tracking of one or more surgical staff members by monitoring mechanomyogram (MMG) and/or electromyogram (EMG) signals, produced by muscles and tendons in the staff member's hands, wrists, and forearms. EMG sensors measure electrical current generated by a muscle during a contraction in response to neuromuscular activity. MMG sensors measure the change in mechanical energy observed on the surface of a muscle. MMG sensors may be used alternatively or additionally with EMG sensors. MMG signals may have a higher signal-to-noise ratio than the EMG signals, and may allow for more granular muscle activity measurements. The EMG and MMG sensors may be placed on the hands, wrists, and forearms to measure muscle movement, in place of, or in conjunction with the passive tracking system. The surgical hub can further synchronize the passive data and active data.

FIG. 92 shows a musculoskeletal view of human hands. The back or dorsal-side 16402 of the hand shows the extensor tendons 16406 and the front or palmar-side 16404 of the hand shows the flexor tendons 16408. The extensor 16406 and flexor tendons 16408 are complementary tendons that control the movement and force of each finger in the hands. Each finger is actuated by an individual extensor 16406 and flexor 16408 tendon that runs from the respective finger to through the wrist and to muscles in the forearm. The brain sends neuro signals to the muscles in the forearms to produce movement in the hands.

FIG. 93 shows the anterior 16410 and posterior 16412 side of a right arm. The brain sends electrical signals to the muscles in the forearms to control respective finger movement and force in each hand. Thus, the specific finger movement and force can be determined my measuring signals produced by the extensor and flexor tendons.

FIG. 94 shows a pair of wrist-mounted sensors 16502 communicably coupled to a surgical hub 16001 (FIG. 73). The sensors 16502 are configured to monitor EMG and/or MMG signals generated by extensor and flexor tendons as they pass through the flexor retinaculum and extensor retinaculum.

In another aspect, the active sensors may be mounted directly to the controlling muscles in the forearms. FIG. 95 shows a plurality of MMG sensors 16502 mounted directly to the muscles in the forearms. The sensors are placed according to the corresponding flexor and extensor tendon in the finger.

In another aspect, the active sensor may be a wireless sensor 16602 that adheres directly to the skin. FIG. 96 shows a flexible wireless sensor 16602 coupled to a flexible adhesive medium 16604 that adheres directly to the skin 16606. The wireless sensor 16602 may be placed over muscles to measure EMG or MMG signals or may be used by the passive tracking system to monitor specific movements of the staff member. The wireless sensor 16602 may communicably couple to the surgical hub, to wirelessly transmit active tracking data. A plurality of wireless sensors 16602 may come on an adhesive sheet, where all of the sensors are registered to the identity of a specific staff member.

FIG. 97 shows a graphical plot 16620 of five EMG channels corresponding the movement of four fingers and a thumb in a hand. The surgical hub receives the EMG signals and may plot the results so that the motion can be analyzed. Each channel is corresponds to one sensor and one finger, but may pick up movement from other fingers. The surgical hub plots the data to isolate and classify the movement and magnitude to a specific finger 16610-16618. The surgical hub may indicate periods when there is motion and no motion.

FIG. 98 shows a graphical plot 16640 of MMG signals corresponding to the movement and position of a hand. It is important to accurately place the MMG sensor because the MMG signal resolution is dependent on the proximity to the muscle. The graphical plot 16640 comprises 8 channels that correspond to different muscles to actuate coordinated movement.

FIG. 99 shows a model 16660 that correlates amplitude values for the maximal muscle contraction, measured in Vrms, and the percentage of maximal voluntary contraction (% MCV). In one aspect, a linear regression model may be used to correlate the MMG signals to force applied by a specific finger or combination of fingers.

FIG. 100 shows an active sensor sleeve 16800 comprising a plurality of active sensors 16802 that measure MMG and/or EMG signals. The sensor sleeve 16800 comprises an elastic form-fitting material 16804 that is configured to snuggly fit around the forearms of a surgical staff member. The active sensors 16802 correspond to different muscle movements in the forearm and indicate the overall movement, motion, and force of fingers and the hand. The sensors may be connected with an elastically deformable conduit wires that expand and contrast with the material 16804 of the sleeve. The sensor sleeve 16800 may be configured in different size range to fit different forearm sizes and ensure proper sensor positioning. The sleeve comprises a control circuit 16808 and power source 16806. The control circuit may be configured to store active data during the surgical procedure and transmit the data to a surgical hub at the end or transmit data in real-time to the surgical hub. The sleeve further comprises a plurality of active beacons 16810 that indicate the real-time position and the surgical staff member. Additionally sensors may include thermocouples 16812, pressure transducers 16814, and impedance electrodes 16816.

FIG. 101 shows three linear regression models that analyze EMG signals that evaluate muscle fatigue over time. Plot 16902, 16904, 16906 corresponds to a different surgeon. The linear fit slope correlates to the rate of muscle fatigue over time. The active signals may be used to evaluate and individual surgeon's technique or a surgical procedure. In this example, plot 16904 shows a smaller slope for Surgeon B, indicating that Surgeon B experienced less muscle fatigue in the contemporaneous interval as Surgeon A and Surgeon C. Additionally, the EMG signals may be used to similarly plot muscle stress over the duration of a surgical procedure.

FIG. 102 is a logic diagram of a method 17210 for tracking movement of operating room staff members, according to one aspect of this disclosure. With reference now also to FIGS. 73, 75, and 76, according to the method 17210 surgical hub 16001 receives 17212 contextual data from an external source. The contextual data comprises hand positions for surgical instruments used in a surgical procedure. The surgical hub 16001 identifies 17214 a first unique identifier associated with a first surgical staff member 16003 and a second unique identifier associated with a second surgical staff member 16003. The surgical hub 16001 receives 17216 passive tracking data from a camera system 16002 associated with the first surgical staff member 16003 and the second surgical staff member 16003. The passive tracking data is determined by fiducial markers. The surgical hub 16001 receives 17218 active tracking data from an active sensor associated with the first surgical staff member 16003 and the second surgical staff member 16003. The surgical hub 16001 determines 17220 that the first surgical staff member 16003 or the second surgical staff member 16003 is using a first surgical instrument 16010 that is not tracked by the surgical hub 16001. The surgical hub 16001 compares 17222 the passive tracking data and active tracking data to the hand positions for surgical instruments 16010 used in a surgical procedure. The surgical hub 16001 determines 17224 a specific surgical instrument 16010 corresponding to the passive tracking data and the contextual data. The surgical hub 16001 transmits **17226*a* virtual element to be displayed on an augmented reality device 66 (FIGS. 1-10**).

Accordingly, the present disclosure provides methods, systems, and devices that differentiate between a plurality of surgical staff members, in close proximity, working on the same tools, overlapping in the same spatial area, and/or obstructed from a direct line of sight of passive tracking cameras.

Utilizing Contextual Parameters of One or More Surgical Devices to Predict a Frequency Interval for Displaying Surgical Information The present disclosure provides a system, method, and device for displaying relevant augmented reality (AR) content to the surgical staff members without over-saturating the augmented display with virtual elements. The surgical staff members (e.g., doctors, nurses, surgeons, technicians, etc.) require AR content that is delicately balanced between displaying helpful information without distracting the surgeon. A surgical hub receives a plurality of inputs related to surgical environment and displays only necessary information to allow the surgeon to provide effective care to the patient.

In various aspects, the surgical hub generates virtual elements that are displayed in response to a triggered event or an evaluation of contextual parameter received by the situational awareness system (FIG. 11). The surgical hub may determine contextual information of the surgical procedure and environment including a current surgical procedure, an expected next step in the surgical procedure, and/or an active surgical instrument. The surgical hub evaluates the contextual information determine whether information is relevant, and provide necessary or emergency information to the surgeon. If the surgeon is inundated with information, they may begin to ignore notifications or have a difficult time distinguishing between monitored information and emergency notifications.

Additionally, the surgical hub may selectively display or update information at a refresh rate that is useful for the surgeon but not does create a lag, jitter, or delay. An essential component of AR content is that it is consumed by the user in real-time. Emergency notification must be immediately displayed and therefore processing lags and delays are unacceptable in a surgical environment. In order to prevent network and processing delays, certain traffic and virtual elements may be prioritized over others. In one aspect, certain parameters may be continuously monitored by the surgical hub, but only displayed in response to a predetermined threshold or a trigger event. The trigger event may include audible noise interference, low or high availability of bandwidth, and activation of a medical system, an unanticipated medical event, etc.

In various aspect, a trigger event may include an anticipated signal interruption that is the result of a surgical system, such as a mono-polar or bi-polar energy system. In response to the trigger event, the surgical hub may be configured to automatically display a warning on an AR device, or take remedial action and notify the surgical staff members through on an AR device.

In one aspect, the surgical hub may use redundant communication protocols for high resiliency communication. Redundant communication has a higher packet payload than a low weight packet like User Datagram Protocol (UDP), but comprises built-in redundancies to ensure packet receipt, such as checksum. The surgical hub may determine that a surgical device is connected to the surgical hub with an interference susceptible communication protocol, and suggests that the surgical device moves to a more resilient communication protocol, such as a low communication throughput Bluetooth. If the surgical device experiences interference during a communication transfer, the device can be rescanned after the procedure to initiate the transfer and confirm that the data received by the surgical hub was accurate.

In various aspects, the surgical hub evaluates a plurality of surgical systems and signal present during the surgical procedure to determine and prevent signal interference. FIG. 103 shows a graphical representation 17100 of frequency shifting response by a surgical hub 6, 56 (FIGS. 1-3, 5-8) to anticipated signal interference. Prior to the generation of signal 17106 by a first surgical device, the surgical hub may notify the surgical staff that a second surgical device produces signal 17104 that may experience interference or signal interruption during the use of the first surgical device. The surgical hub may prompt the second surgical device to shift communication signals to a different frequency, outside the frequency spectrum of the first surgical device. Additionally, if the surgical hub deems that the communication by the second surgical device is a critical communication, the surgical hub may automatically shift the frequency of signal 17104 to the frequency at 17102. In one example, the 2.4 gHz frequency band is commonly used for under IEEE 802.11 for wireless communication, but is also used by electromechanical equipment. A bio-polar or monopolar energy system by generate signal noise in the 2.4 ghz frequency band that results in high packet loss and thus, communication delay. In order to avoid signal interference and communication delay, the surgical hub by seek another frequency band such as the 5.0 gHz frequency band. The second surgical device may then be enable to dynamically channel hop or channel hop based on a trigger communication sent by the surgical hub. Prior to the beginning of the surgical procedure, the surgical hub may recognize a potential communication interference between two devices and may initiate the prompt at the outset of surgery or automatically enable channel hoping as a precaution.

The surgical hub receives contextual data that indicates the specific procedure that is to be performed, the surgical instruments that are used during the procedure, situations when the surgical instruments are surgical instruments must be activated, flexible time intervals when the instruments may be activated, the potential for interference due to instrument activation, and the type of interference. Based on this information, the surgical hub can automatically schedule the activation of surgical systems and communication to avoid an anticipated interference.

FIG. 104 shows a timeline 17200 of device activation and communication transmissions scheduled by a surgical hub 6, 56 (FIGS. 1-3, 5-8). The surgical hub may delay communication signals 17204*a* until after the activation of a surgical system at 17202*a*. The surgical hub repeats this sequence by delaying the communication of signals 17204*b*, until after the activation of the surgical system at 17202*b*. The surgical determines, based on a hierarchy of communication and device activation, that communication signal 17204 is a critical communication and all other devices are deactivated. Typically the surgical system 17202 would be activated, but is delayed for a critical communication. Upon the completion of the signal transmission 17204, the surgical system resumes activation at 17202*c*.

FIG. 105 shows a flow diagram 17300 to evaluate a plurality of factors and determine a hierarchy of communication and device activation. The surgical hub 6, 56 (FIGS. 1-3, 5-8) may determine 17302 a hierarchy based on the schedule of device activation in a surgical procedure and anticipated interference. The surgical hub also may prioritize certain communications, in real-time, based on critical factors (e.g., life and death situations). The surgical hub determines 17304 the type of interference that may inhibit the effectiveness of a device or system, and the degree for the interference to be perceptible. For example, the surgical hub 6, 56 determines 17304*b* if device is susceptible to the type of interference/noise that can be produced by the potential interference causing signal. The surgical hub 6, 56 uses tracking and position information to determine 17306 whether the first device is located or positioned within the body of the patient. For example, the surgical hub 6, 56 determines 17306*a* if the device is located inside the body of the patient. A surgical device may comprise proximity markers that allow a tracking system to determine the location of various ends of the device in relation to the patient and other devices. The proximity to the patient can indicate the active use, or imminent use of a device. The surgical hub 6, 56 may be configured to determine the proximal relationship between devices and system to evaluate the likelihood of interfering systems. The surgical hub 6, 56 determines 17308 the location or proximity of the first devices to the potential interference causing device. For example, the surgical hub 6, 56 determines 17308*a* if the device is located within a predetermined distance from potential interference causing device. Further, the surgical hub 6, 56 determines 17308*b* affected proximity based on interference/noise type generated by the potential interference causing device. The surgical hub 6, 56 can further evaluate a predetermine range that the inference can propagate. The surgical hub evaluates, based on the situation awareness system, the contextual parameters that indicate whether a communication or activation schedule is flexible. The surgical hub 6, 56 determines 17310 whether the first device is in active usage/currently performing function. For example, the surgical hub 6, 56 determines 17310*a* if the device is in active operation mode. Further, the surgical hub 6, 56 determines 17310*b* if change in location, position, user inputs, power level, indicate device is in active operation or will be in inactive operation.

Prior to the activation of a first surgical device, the first surgical device sends a communication to the surgical hub that a potential noise/interference inducing event is about to occur. In response to the communication, the surgical hub changes one or more settings to mitigate the anticipated interference. In one example, bi-polar and mono-polar ablation systems are used during the same surgical procedure. The activation of the mono-polar system will interfere with the impedance control of the bipolar system. If the bi-polar is already in-cycle and the mono-polar is activated, the surgical hub changes the bi-polar control loop to continue operating in the manner just prior to the activation, rather than prohibiting the combined use of both devices. When the interface stops, the bi-polar goes back to its normal closed loop use.

In another aspect, the surgical hub is configured to takes a snap shot of setting or present operations for all the surgical devices. The snap shot of settings is used as a precaution in case one or more of the surgical devices is required to re-setup and reconnect to the surgical hub. Additionally, the snapshot may be used to reestablish a network communication setup (e.g., SSID, network domain, wireless communication authorization) and potential sub-device settings (by retransmitting the data back to the devices).

FIG. 106 shows a graphical representation 17400 of an end effector signal and noise as the end effector clamps onto tissue and is in the process of firing. A mono-polar or microwave ablation system is activated and interferes with the internal function of the closed loop firing control of the end effector. Signal 17406 represents the interference signal. The microwave ablation system creates an RF overload or saturation event and can interfere with the control signal of the end effector. The mono-polar ablation system produces RF energy that could propagate noise up the metallic shaft into the contacts and cause a similar RF saturation event. Signal 17402 shows the desired result of the end effector and signal 17404 shows a failure in the control loop sensors and causes the end effector to stop. Once the interference event is finished, the surgical hub may repopulate the error term and rate cells of the PWM and enable the end effector to resume where it left off and finish the operation.

In various aspect, the surgical hub may determine that the repopulation of settings and error terms is prohibited. In one example, an ARM processor itself may be affected interference, not just the sub-function of a motor control, thus the surgical hub would prohibit repopulation. In another examples, the surgical hub determines that a predetermined amount of time has elapsed since the start of the interface, then the system could be reset rather than restarted. In other cases, the surgical hub may be required to initiate additional steps as part of the repopulation process. In the case of pulmonary artery or pulmonary vein transections, the system may require that the tissue is unclamped, checked, augmented, or reviewed prior to allows the end effector to complete the transection.

In various aspect, the surgical hub notifies sub-devices that could be affected directly by an anticipated interference event. The warning allows the sub-devices to prepare internal defenses for the anticipated interference. The internal defenses may include enabling noise filters that allow the device to continue to operate through periods of signal interference. The signal noise filters may be internal signal processing and built into the device.

In various aspect, the surgical hub comprises a noise receiver that monitors external noise and then communicates a warning to one or more surgical devices. External noise (e.g., audible, impedance, frequency, or other electrical signals) is sensed and generator/device signal (i.e., volume output, frequency output) may be adjusted according to a specific interference to compensate.

In various aspect, the surgical hub prohibits the combined activation or utilization of systems that have been identified to conflict or potentially interfere with one another. The surgical hub generates a warning and then inhibits any devices that could malfunction while being used while the noise event is in effect, according to a hierarchy of interference (FIG. 14). Additionally hierarchy factors include the prioritization of communication based on critical life support procedures, devices, and to maintain patient hemostasis (FIG. 105). The surgical hub prioritizes cooperative interaction of systems, such that the scheduling of communication and device activation is imperceptible to the surgical staff. Accordingly, critical communications and critical life support procedures may always be prioritized.

FIG. 107 shows a flow diagram 17500 of surgical hub responses based on the anticipation or detection of a trigger event. The surgical hub notifies 17502 one or more devices of a detected or anticipated interference. The surgical hub takes a snapshot 17504 of all device settings, and determines whether the device(s) are may be reset and repopulated without issue. If the devices permit, the surgical hub initiates 17508 a repopulation event. Additionally or alternatively, the surgical hub determines 17510 the type of interference, and notifies 17512 a sub-device system of the anticipated interference type. The sub-device responds by initiating 17514 a defense to the interference (e.g., channel hopping). The surgical hub may evaluate and determine 17516 the communication and activation of systems according to a hierarchy of critical systems. The surgical hub determines 17518 whether the systems may interact in cooperation for concurrent operation or the systems need to be prioritized for sequential operation. In response to the interference type and schedule of systems, the surgical hub prevents 17520 the operation of one or more systems.

In various aspects, the surgical hub determines a trigger event based on a change in force or motion exerted on tissue during a retraction. In response the surgical hub generates a preemptive warning that displays tissue tension or similar metrics that provide real-time measurements of the retraction, as a virtual element, on an AV display. Additionally, the surgical hub may display measurements of displacement and force in relation to the patient or the ground. This information is useful for the surgeon to balance the intended forces of gravity, tissue tension, and grip force without creating undue collateral damage, or forces that were not intended for adjacent connections.

In various aspects, the surgical hub may continuously monitor a plurality of surgical parameters including force, direction, and magnitude created by a surgical instrument on tissue. Additionally, the surgical hub may determine that a force meets or exceeds a predetermined threshold at a specific location. In response, the surgical hub may initiate the display of a virtual element.

The surgical hub is configured to continuously monitor the force exerted on one or more organs as part of a surgical procedure, wherein the organs are retracted to aid the surgeon's vision in a laparoscopic procedure. If an organ fails to remain retracted, the surgeon's vision may be impeded or damage may result to the organ. The surgical hub may employ a predictive algorithm to evaluate changes in position, movement, and force of the organs. The predictive algorithm may identify a likely increase in tissue tension that exceeds a predetermined amount, at a specific location, and automatically displays a warning to the surgeon.

A warning may be provided in the form of an alert, notification, audio or visual cues, or message on a display. Tissue tension created by a surgical instrument may be display in real-time on an OR display. The system is configured to measure and monitor the force, tension and/or change in force or tension as related to the patient and/or the ground. The system may detection the initiation of force, the time that the force was initiated, and compare to an expected amount of tension or force. Real-time display is configured to provide warnings when tissue tension exceeds an intended level to prevent unintended tissue damage and undue collateral consequences.

With reference now to FIGS. 108 and 109, the disclosure turns to description of a method 17260 for managing surgical device 21 interaction during a surgical procedure. The method 17260 shown in FIG. 109 may be practiced by the system 17250 shown in FIG. 108. According to the method 17260, a surgical hub 56 determines 17262 contextual parameters from a surgical environment. As shown in FIG. 108, and in more detail in FIG. 6, the surgical hub 56 comprises a computer 60 including a control circuit 31 (e.g., a processor) coupled to a memory 45, among other components. The surgical hub 56 determines 17264 a specific surgical procedure being performed in an operating room based on the contextual parameters. The surgical hub 56 receives 17266 procedural data from a remote server 63. The procedural data indicates steps and surgical instruments 21 associated with the specific surgical procedure. The surgical hub 56 determines 17268 that a trigger event is anticipated based on the procedural data and the contextual parameters. The surgical hub 56 initiates 17270 a response according to the surgical instruments 21 and the procedural data.

In other aspects of the method 17260, the surgical hub 56 may further determine a current procedural step of the surgical procedure. The current procedural step activates a first surgical device 21 and the surgical hub 56 determines that the first surgical device 21 is anticipated to interfere a communication of a second surgical device 21. Accordingly, the surgical hub 56 notifies the second surgical device 21 of the anticipated interference and enables an interference defense on the second surgical device 21. In one aspect, the interference defense enabled by the surgical hub 56 is a frequency shifting protocol configured to shift from a communication signal outside of an anticipated interference frequency band.

In other aspects of the method 17260, the surgical hub 56 may further determine a current procedural step of the surgical procedure. The current procedural step activates a first surgical device 21. The surgical hub 56 determines that the first surgical device 21 is anticipated to interfere a communication of a second surgical device 21. The surgical hub 56 determines that the first surgical device 21 and the second surgical device 21 are operable in a cooperative schedule. The surgical hub 56 may then activate the first surgical device 21 and in response to completing a first surgical device activation, the surgical hub may initiate a communication of the second surgical device 21.

In other aspects of the method 17260, the trigger event is associated with a change in force exhibited on tissue while the tissue is being retracted. The change in force is determined by the surgical hub 56 based on readings from the surgical device 21 and is based on exceeding a predetermine tissue tension. Further, according to the method 17260, the surgical hub 56 generates a virtual element to display on an augmented reality (AR) device 66. The virtual element provides monitoring information for the retracted tissue.

Cooperation Among Multiple Display Systems to Provide a Healthcare User Customized Information The present disclosure describes a method and system for tracking tissue, identifying marked areas of interest, and generate virtual element indicative of the areas of interest in an augmented reality environment.

Registration Of Physical Spatial Parameters

In various aspects, the patient may be virtually or physically tagged with fiducial markers to aid the surgeon in an operation. A surgical procedure may require that a patient undergoes a pre-operative fiducial marking process.

FIG. 110 shows an example of a structural surface 18000 comprising a plurality of fiducial markers. A plurality of points 18010*a-d* are identified and tagged to the structural surface 18000. A computing system, such as remote server 63 (FIG. 5) or the surgical hub 56 (FIG. 6) evaluates the structural surface and assigns fiducial marker 18010*a-d*, based on a target registration error (TRE) model 18008. The TRE model uses a sample data set to estimate the placement of fiducial markers 18010*a-d*. 18002 show an initial view of the structure surface 18000. 18004 shows the TRE model representation of the structural surface 18000. Transformation 18006 shows the resultant placement of fiducial markers 18010*a-d* of the structural surface 18000.

FIG. 111 shows a process 18020 for surface matching external structure of a patient with fiducial markers. A computing system, such as remote server 63 (FIG. 5) or the surgical hub 56 (FIG. 6) system generates 18022 an initial mapping of a surface based on a digital representation of the surface. The system uses facial recognition features such as eyes and the bridge of the nose to recognize 18024 a plurality of anatomic landmarks 18028 to map the surface and distance between points. Based on the determined distance between anatomic landmarks 18028, the system generates 18026 the fiducial markers 18030.

FIG. 112 shows a process 18040 for surface matching internal structure 18044 of a patient with fiducial markers 18042. The internal structure is displayed on an output display 18046 which allows a technician to tag areas of the internal structure 18044 with a stylus 18048. The fiducial markers 18042 may correspond to a path or the location of the surgical procedure.

FIGS. 113-115 show external surgical alignment instruments to aid a surgeon in a surgical procedure. FIG. 113 shows a stereotactic frame 18060, FIG. 114 shows a starfix platform 18080, and FIG. 115 shows a microtable 18100. The surgical hub 56 (FIG. 6) may register and catalog the dimensions of the external surgical aids and assign fiducial markers to a plurality of points on the surgical aids. The surgical hub 56 may then align fiducial markers of the external surgical alignment instruments with surface markers on the patient.

In various aspects, the surgical hub 56 (FIG. 6) is configured to track the location and position of surgical instruments 12 (FIGS. 1, 2), 21 (FIGS. 5, 6) in the operating room 16 (FIG. 2). The surgical instrument 12, 21 may comprise a plurality of fiducial markers, strategically placed on the external housing of the instrument 12, 21 to convey the special parameters of the instrument 12, 21. The fiducial markers may be used by a passive tracking system, in combination with an infrared (IR) light source. Additionally, the surgical instrument 12, 21 may comprise sensors that indicate when the surgical instrument 12, 21 is in use and when then surgical instrument 12, 21 in inside the patient. In one aspect, a trocar may comprises one or more internal patient sensors that indicate when the device is inserted into the body cavity. Once the trocar determines that the surgical instrument 12, 21 is inside the body cavity of the patient, the trocar may automatically or manually detect and track the location of another surgical instrument 12, 21. The trocar may comprise an internal camera system that identifies fiducial markers on other surgical instruments 12, 21. The internal camera system may receive commands to locate an end effector and tag an end effector with a marker in relation to the tip of the trocar. The tag provides a registration point that may be used to monitor the tip of the end effector throughout the surgical procedure, and may be associated with a virtual element that is rendered on an AR display 89 of an AR device 66 (FIG. 10). In situations when the tip of the end effector may be out of view of the internal camera system, the virtual element may continuously display the tracked position of the end effector tip, based on the tag.

Prior to a surgical procedure, all surgical instruments 12 (FIGS. 1, 2), 21 (FIGS. 5, 6) are cataloged according to a plurality of parameters including mass, size, length, shape, associated surgical procedures, hand positions for surgical procedures, etc. FIG. 116 shows a flow diagram for identifying objects based on a plurality of a registration parameters. In various aspects, the surgical hub receives physical characteristic of an object from one or more object detection cameras in an operating room. Camera provides 18122 raw imaging data of an object. The surgical hub performs 18124 image processing to remove the back of the image or fame and perform edge detection. Once the surgical hub performs the image processing, the surgical hub compares 18126 the detected object to a catalog of objects. The surgical hub reviews 18128 the properties of each object and determines 18130 the object the most closely fits the identified parameters of the image.

FIG. 117 shows a flow diagram 18140 for classifying unknown surgical instruments based on a partial information of known and unknown parameters. An object recognition system may implemented by the remote server 63 (FIG. 5) or the surgical hub 56 (FIG. 6). The object recognition system may be unable to affirmatively determine an object, but may have it narrowed down to a plurality of candidates. The system inputs 18142 partial object information and uses known parameters to evaluate the object. If the system determines physical characteristics of the object, it can perform 18144 the geometric-uncertain analysis. If the system determines geometric characteristics of the object, the system can perform 18146 the physical-uncertain analysis 18146. However, if the system does not have enough information, the system may require manual identification, and classifies the object as unknown 18148.

In various aspects, the surgical hub receives spatial and physical parameters associated with an operating room or an external environment. The physical parameters may be registered to a specific room or environment. In various aspect, an external environment may be classified according to certain features such as a sterile or non-sterile environment; pre-op, OR, or post-op room; and specific equipment in the room (e.g., MRI, CT scanner).

Trocar Comprising an Outer Diameter Mounted Camera System Keeps Port Free for Instruments and Increases Field of View The present disclosure further describes a camera system integrated into a trocar. The camera system allows for wide field of view of an internal surgical site and 3D mapping of fiducial markers during a laparoscopic procedure. Upon entry into the patient, the camera system is configured to deploy from a recessed position at the distal end of the trocar. In various aspects, the internal camera system is configured to keep the trocar ports free for surgical instruments and provide the surgical staff members with an increased view of the surgical environment.

FIG. 118 shows a trocar 18160 comprising an internal camera system 18166. The internal camera system 18166 comprises a plurality of cameras 18166*a-n* connected together with an elastic member 18168. The elastic connection 18168 allows the camera system 18166 to collapse together and fit through a passage defined in the center of the trocar. In various aspects, the camera system 18166 emits light in the non-visible spectrum allowing the cameras 18166*a-n* to detect various types of fiducial markers (e.g., IR fiducial markers). When the internal camera system 18166 is deployed at 18160*a*, the camera system 18166 attaches to the outer diameter 18170 of the distal end 18162 of the trocar 18160. When the trocar is inserted and removed from the body cavity of the patient, the internal camera system 18166 is in the retracted position 18160*b*. In the retracted position 18160*b*, the camera system 18166 recesses and attaches to the inner diameter 18172 of the distal end 18162 of the trocar 18160.

With reference to FIGS. 118 and 119, FIG. 119 shows a reusable installation tool 18176, configured to insert into the proximal end 18164 of the trocar 18160, deploy and retract the camera system 18166 around the outer diameter 18170 of the trocar 18160. The camera system 18166 is communicably coupled to a surgical hub 56 (FIG. 6) through a wired or wireless connection. In a wireless configuration, each camera 18166*a-n* may have its own power supply (e.g., rechargeable battery), the camera system 18166 may have a single external power supply that connects to each camera 18166*a-n* through an elastically deformable wired connection. In a wired configuration, the wired connection may be inserted externally to the trocar 18160, while the trocar 18160 is inserted, keeping the inner diameter of the trocar 18160 free for surgical instruments. The camera system 18160 may attach to the outer diameter of the trocar 18160 through a squeeze and friction of elastic connection, magnet in the case of a metal trocar, or a separate connection on the outer diameter of the trocar 18160.

FIG. 119 also shows a profile view 18178*a* of the installation plunger 18174*a* in a full depressed position. A conical distal end 18158 of the trocar 18160 releases the camera system 18166. The plunger 18174*b* is pulled in the proximal direction which causes the conical distal end 18158 to force the camera system along the outer diameter 18170 of the trocar 18160. As the plunger 18174*c* continues to retreat in the proximal direction, the camera system 18166 attaches to the outer diameter 18170 of the trocar 18160. The reusable installation tool 18176 is removed so that a laparoscopic surgical procedure may begin.

Fiducial Marker Based Pre-Operative Computerized Tomography (CT) Scans with Real-Time 3D Model Updates to Improve Sub-Procedure Tracking The present disclosure further describes a system configured to generate a 3D model for a surgeon to navigate through the internal tissue structure of a patient. The system identifies and marks target tissue or structure of interest in a pre-operative CT-scan. The system generates an initial 3D-model based on the CT-scan that is used by the surgeon to aid in their navigation of internal structure. The 3D-model may be continuously updated in real-time based on additional data points received intra-operatively. In one aspect, the system may determine the proximity of distance from a surgical instrument, and update the model to reflect the tissue movement or change in tissue location.

In various aspect, the system generates a 3D rendering of the internal tissue structure with virtual elements, and displays the 3D-model on an augmented reality display. The system may generate a live feed of the surgical environment or provide virtual elements, overlaid on top of a real world live feed of the surgical site. In various aspect, the 3D-model indicates areas of interest, areas to avoid. Additionally, the markers can indicate tissue that needs to be sealed or tissue that is difficult to find, such as pulmonary veins and pulmonary arteries.

FIG. 120 shows a plurality fiducial markers 18180 tagged to areas of interest, in a pre-op CT scan. The fiducial markers may be placed to create a centroid at a critical structure 18182. A centroid value is determined based on the relative distance between each of the fiducial markers in a set.

FIG. 121 shows a laparoscopic surgical procedure that utilizes a plurality of fiducial markers to aid a surgeon in locating a surgical site. The pre-operative determination of a critical structure 18184 is generally a close approximation of the structure location, but may not be the exact location. In various aspects, an internal camera may be used in conjunction with the fiducial markers to provide a real-time updated location of critical structure 18186, with an updated model or updated fiducial marker. In various aspects, fiducial markers are located on the surgical instrument 18190 and help provide an updated location 18186 based on a relationship between other points. The surgical instrument may further comprise an integrated mapping sensor 18188.

Tracking Tissue Movement And Position With Physical Markers In Laparoscopic Surgery The present disclosure further describes various methods and systems for marking and tracking tissue movement with physical markers. The tracking system comprises a camera system configured to detect and track the physical markers. In various aspect, the physical markers comprise magnetic ink, visible ink at visible light spectrums, invisible ink at invisible light spectrums, or other detectable ink by a camera system.

FIG. 122 shows a physical marker applied by injection into a vascular system of a patient with an indocyanine dye 18202. The dye 18202 is illuminated by a light source 18204 which allows a camera 18206 to capture and record the vascular structure of the tissue 18210. In one aspect, the light source 18204 may be a fluorescent light source. The camera system 18206 may use various light frequencies or lasers to visualize the dye 18202. The camera system 18206 is further configured to identify various overlaying paths of the ink and display a 3D rendering on an output display 18208. In various aspects, vasculature can be used like a fingerprint to unique identify structure and track the structure as it moves. Additionally, pre-op CT imaging may be used to help the system generate a 3D map of the structure. The dye also may be used to track organs and warn the surgical staff if they are about to grasp highly vascularized tissue. FIG. 123 further shows exemplary tissue injected with a dye and illuminated to show vasculature.

In various aspects, the light source 18204 may emit light at a wavelength outside of the visible spectrum such as IR. Additionally, the dye 18202 may comprise magnetic ink used as a marker to distinguish areas of interest inside and outside the field of view of the camera 18206. In one aspect, the dye 18202 may be splatter sprayed in a surgical area in a no-visible spectrum, such that the body can easily absorb the dye 18202. The splatter creates a unique pattern that allows the camera 18206 to easily track the location and movement of the tissue 18210.

Tracking Of Non-Fixed Physical Markers Inter-Operatively To Measure Anatomical Or Surgical Events The present disclosure further describes a system configured to track tissue or anatomical structure without physical fixed anatomical markers. Physical markers are typically used to track tissue or anatomical structure but there are situations that prevent the use of this method, such as tissue that was recently sealed. The system tracks tissue with non-fixed markers with temperature and impedance.

FIG. 124 shows a system 18300 configured to monitor the change in pressure or fluid in a body cavity according to an impendence measurement by a probe 18302. The probe 18302 is coupled to a surgical instrument 18304 and measures an impedance value based on a pressure created by fluid and/or gas in a body cavity 18306. A surgical hub 56 (FIG. 6) may be coupled to the surgical instrument 18304 and configured to determine whether there is a change in pressure in the body cavity 18306. The change in pressures indicates that there is a leak present in the body cavity 18306. The probe 18302 is configured to maintain a fixed gap to measure a change in pressure at a potential leak site 18308.

Additionally, the surgical hub 56 (FIG. 6) may notify the surgical staff members of a detected leak by generating a warning through AR content. In one aspect, a virtual element may be rendered on an AR display 89 of an AR device 66 (FIG. 10) that anchors to the location of the detected event. The virtual element may be identified with a contrasting color that is solid, flashing, or semi-transparent. The virtual element may be accompanied with a textual warning that identifies the type of event and/or the severity of the event.

FIG. 125 shows an infrared (IR) heat detection system 18310 comprising an IR camera system 18312 configured to direct IR light 18314 on a treated region of tissue 18316 and identify a temperature difference in a surgical environment 18304. In one aspect, the IR camera system 18312 may be configure to identify the location of a leak in a pressurized cavity due to the change in temperature of air surrounding the leak. The body cavity is pressurized with air at a temperature that is colder or warmer than the fluid in the peritoneal cavity. The IR camera system 18312 will observe a leak by seeing a gas at a temperature that is warmer or colder than the cavity. In response to a leak detection, the surgical hub 56 may notify the surgical staff members.

In one aspect, the IR camera system 18312 may determine that an area of tissue was recently sealed. The sealed tissue may be at a different temperature and allows the IR camera system 18312 to distinguish the sealed tissue as a sensitive treated area. The surgical hub 56 (FIG. 6) may render a virtual element that overlays on top of the treated area to indicate to a surgeon that the sealed tissue was recently treated and is a sensitive area.

The sealed tissue is identified based on a predetermined tissue temperature threshold at the time the tissue was sealed. The tissue temperature may slowly cool however, the IR camera system 18312 may mark the region with a non-fixed marker that is maintained even after the tissue temperature drops below the initial threshold temperature.

Motion Tracking System Configured To Control And Adjust Surgical Instruments To Prevent Excess Tension On Tissue The present disclosure further describes a tissue tracking system to prevent excess tension from being exerted on tissue. The system is configured to track markers applied to tissue at specific location that indicate motion, force, and tension. A surgical hub 56 (FIG. 6) may continuously monitor tissue tension and motion parameters. The surgical hub 56 may determine that tissue tension at a specific location has reached a predetermined threshold, and provides a notification to one or more AR devices 66 (FIG. 10).

FIG. 126 shows a surgical procedure 18350 employing three end effectors 18352, 18354, 18356 configured to grasp and transect tissue 18360. The tissue 18360 is initially grasped at two points by a first end effector 18352 and a second end effector 18356. An AR device 66 (FIG. 10) may indicate the initial positions that the end effectors 18352, 18356 should be located. The initial distance 18358 between the first end effector 18352 and the second end effector 18356 is determined based on a force applied to the tissue 18360. The second end effector 18356 is configured to transect the tissue 18360 and requires a third end effector 18354 to compensate for an increase in tissue tension.

FIG. 127 shows the third end effector 18354 sliding along the tissue from a first position **18354*a*** to a second position 18354*b*. The surgical staff members monitor the position of the third end effector 18354 so that it is properly positioned to compensate for increase in tension. In various aspects, an AR device 66 (FIG. 10) may highlight the tissue 18360 when it exceeds a predetermine tension threshold. The surgeon may reposition third end effector 18354 so that the tissue 18360 is no longer highlighted and indicates the tissue tension is back within the predetermine threshold. In various aspect the surgeon may receive feedback in a handle or joy stick to indicate when need to reposition and when the new position is satisfactory.

FIG. 128 shows the third end effector 18354 positioned adjacent to the second end effector 18356. Upon transection of the tissue 18360 by the second end effector, the tissue tension will be within a predetermined threshold, based on the initial distance 18358 (FIG. 127).

FIG. 129 shows a surgical procedure 18370 employing three static clamps 18372, 18274, 18378 and a dynamic clamp 18376 configured to transfer tissue between stationary clamps 18372, 18274, 18378. A first clamp 18372 is a stationary clamp configured to hold the end of the tissue 18386 and prevent tension or pulling from beyond a region of interest 18382. A second clamp 18374 and a third clamp 18378 are positioned according to a predetermined distance such that the tissue maintains a predetermined tension. The second clamp 18374 and the third clamp 18378 are stationary but may open and close to pull new tissue 18386 between the stationary distance 18380. A fourth clamp 18376 is a dynamic clamp and is configured to pull the tissue 18386 between the second 18374 and third clamp 18378, and reduce the tension between the first 18372 and second clamp 18374. The fourth clamp 18376 repositions the tissue 18386 to reduce excess tension at 18384, indicated by a graphical highlight. An AR device 66 (FIG. 10) may provide a similar highlight to indicate excess tissue tension.

FIG. 130 shows a logic diagram of a method 18400 for displaying a surgical location inside of a patient. According to the method 18400, a surgical hub 56 (FIG. 6) receives 18402 a video feed from one or more cameras located inside of a patient. The surgical hub 56 identifies 18404 one or more physical markers inside the patient. The surgical hub 56 determines 18406 a target location based on the relationship to the one or more physical markers. The surgical hub 56 generates 18408 a virtual element corresponding to the target location. An AR device 66 (FIG. 10) coupled to the surgical hub 56 (FIG. 6) displays 18410 the virtual element overlaid on the video feed on an augmented reality (AR) display 79 (FIG. 10).

In one aspect of the method 18400, the video feed is a wide angle view stitched together from at least two video feeds. In another aspect, according to the method 18400 one or more physical markers is visible under the illumination of a light source in outside of the visible spectrum. In another aspect of the method 18400, the one or more physical markers is a fiducial marker assigned in a pre-operative computerized tomography (CT) scan. In yet another aspect of the method 18400, the target location is continuously updated on an augmented reality (AR) device 66 (FIG. 10) in real-time.

Intraoperative Display for Surgical Systems

One aspect of the following disclosure describes various overlays of surgical instrument operational aspects or functions onto a live video stream of a surgical area as visualized through a laparoscopic camera surgical field of view during a minimally invasive surgical procedure. The overlay is related to the operation of one of the surgical instruments or devices being actively visualized. The overlays combine aspects of tissue/organ interaction with functional data received from surgical instruments used in the surgical procedure. Surgical instruments may include graspers, clamps, staplers, ultrasonic, RF, or combination of each of these instruments. In regard to graspers and clamps, aspects of tissue parameters may include incomplete capture of the tissue along with the status of the clamp or magnitude of the clamp. In regard to a surgical stapler, aspects of tissue parameters may include tissue capture location, tissue compression, clamping, or firing sufficiency of a surgical stapler. In regard to advanced energy devices, such ultrasonic or RF devices, aspects of tissue parameters may include impedance, cautery status, bleeding magnitude, and aspects of instrument function may include energy level, timing, clamp pressure, among others, for examples. The augmented images shown in FIGS. 131-195 hereinbelow may be viewed on a local display, a remote display, and/or an AR device as described hereinabove in connection with FIGS. 1-10. Although the augmented images are described as being visualized through a laparoscopic camera during a minimally invasive surgical procedure, the images may be captured during non-invasive and invasive (e.g., open) surgical procedures without limiting the scope of this disclosure in this context. These aspects are described hereinbelow.

FIGS. 131-195 describe various augmented images visualized through a laparoscopic camera during a minimally invasive surgical procedure. An augmented reality display system is used during a surgical procedure. The augmented reality display system comprises an imaging device to capture a real image of a surgical area during the surgical procedure, an augmented reality display to present an overlay of an operational aspect of a surgical instrument onto the real image of the surgical area, and a processor. The overlay is related to the operational aspect of the surgical instrument being actively visualized. The overlay combines aspects of tissue interaction in the surgical area with functional data from the surgical instrument. The processor is configured to receive the functional data for the surgical instrument, determine the overlay related to the operation of the surgical instrument, and combine the aspect of the tissue in the surgical area with the functional data from the surgical instrument. The augmented images indicate alerts relative to device performance considerations, alerts of incompatible usage, alerts on incomplete capture. Incompatible usage includes tissue out range conditions and tissue incorrectly balanced within the jaws of the end effector. Additional augmented images provide an indication of collateral events including indication of tissue tension and indication of foreign object detection. Other augmented images indicate device status overlays and instrument indication.

FIGS. 131-195 also describe functional overlays of instrument critical operations or parameters to clearly represent the surgical stapler, energy device, or aspects of its interaction. In one aspect, the overlaid data is adjusted by an aspect detected by the surgical hub to modify the overlay from the information merely detected by the source instrument to add context. In another aspect, the displays may be adjusted or modified by the user and as a result also result in modifications of the surgical instrument being monitored operation.

FIG. 131 is an augmented image 100 of a live feed of a surgical area 118 as visualized through a laparoscopic camera during a minimally invasive surgical procedure indicating appropriate tissue 112 captured between jaws 110 of a surgical instrument end effector 108. The operational aspect of the surgical instrument is clamping the tissue 112 between the jaws 110 of the end effector 108. The aspect of the tissue 112 is appropriate capture of the tissue 112 between the jaws 110 of the end effector 108. The laparoscopic field of view 102 of the surgical area 118 shows a surgical instrument end effector 108 grasping tissue 112 in its jaws 110. The augmented image 100 shows a virtual graphical alert overlay 106 superimposed on the anvil 110 of the end effector 108. The virtual superimposed graphical alert overlay 106 indicates the amount of tissue grasped in the end effector 108 jaws 110 to inform the OR team of staple cartridge reload selection for stapling, overloading tissue for energy, etc. A first superimposed alert 104 informs that the tissue 112 grasped with the jaws 110 at the proximal end of the end effector 108 is out of range. A second superimposed alert 116 informs that the tissue 112 grasped with the jaws 110 at the medial portion of the end effector 108 is within reload range. A third superimposed alert 114 informs that the tissue 112 grasped with the jaws at the distal end of the end effector 108 is over the cut line. The superimposed graphical alert overlay 106 apply to energy based surgical instruments, stapler based surgical instruments, manipulation tools, and the like.

FIG. 132 is an augmented image 200 of a live feed of a surgical area 212 as visualized through a laparoscopic camera during a minimally invasive surgical procedure indicating tissue 206 position proximally captured between jaws 210 of a surgical instrument end effector 204 as a tissue aspect. Aspects of the tissue include incorrectly captured or positioned tissue 206 between the jaws 210 of the end effector 204. The laparoscopic field of view 202 of the surgical area 212 shows the surgical instrument end effector 204 grasping tissue 206 between the jaws 210 of the end effector 204. The augmented image 200 shows a graphical alert overlay 208 superimposed on one of the jaws 210 of the end effector 204 to indicate that the tissue 206 is grasped excessively proximally 206 with the jaws 210 of the end effector 204. Although the superimposed alert 208 applies primarily to energy based surgical instruments, for example, similar alerts may be superimposed in surgical stapler instruments.

FIG. 133 is an augmented image 300 of a live feed of a surgical area 324 as visualized through a laparoscopic camera during a minimally invasive surgical procedure indicating tissue 322 insufficiently captured between the jaws 318 of a surgical instrument end effector 320 as a tissue aspect. The laparoscopic field of view 302 of the surgical area 324 shows a surgical instrument end effector 320 grasping tissue 322 with the jaws 318 of the end effector 320. The augmented image 300 shows a graphical alert overlay 304 superimposed on the image of the surgical area 324 to indicate insufficiently captured tissue 322 relative to the end of cut in the jaws 318 of the end effector 320.

The augmented image 300 also comprises a first sub image 308 showing a graphic image 306 of the general anatomy superimposed on or adjacent to the surgical field of view 302 and a reference frame 310 of the actual anatomy superimposed on or adjacent to the surgical field of view 302. The augmented image 300 also comprises a second sub image 312 showing the type of surgical instrument in use, the energy level if applicable, and the current surgical procedure. The second sub image 312 may be superimposed on or located adjacent to the surgical field of view 302. The augmented image 300 shows an ultrasonic surgical instrument being used in a surgical procedure at an energy level set to 5 Max to achieve advanced hemostasis. A graphic image 316 of the surgical instrument is shown superimposed on a graphic image 314 of the incomplete tissue capture alert overlay 304. Accordingly, the augmented image 300 provides several virtual objects that inform the OR team of insufficiently captured tissue 322 relative to the end of cut. The superimposed incomplete tissue capture alert overlay 304 applies to energy based surgical instruments as well as surgical stapler instruments, and the like.

FIG. 134 is another augmented image 330 of a live feed of a surgical area 359 as visualized through a laparoscopic camera during a minimally invasive surgical procedure indicating tissue 348 insufficiently captured between jaws 358 of a surgical instrument end effector 354 as a tissue aspect. The laparoscopic field of view 332 of the surgical area 359 shows a surgical instrument end effector 354 with insufficiently captured tissue 352 relative to the end of cut in the jaws 359, 358 of the end effector 354. The augmented image 330 shows a graphical alert overlay 352 superimposed on the tissue 348 to indicate incomplete tissue capture. In the illustrated example, a jaw 358, e.g., anvil, of the end effector 354 includes a series of light emitting diode (LED) indicators 356 to indicate the position of tissue 352 grasped with the jaws 350, 358 of the end effector 354. Also shown in the surgical field of view 332 are two rows of staples 334 in a previously stapled portion of tissue 352.

The augmented image 330 comprises a first sub image 338 showing a graphic image 336 of the general anatomy illustrated in the laparoscopic field of view 332 and a reference frame 340 of the actual anatomy shown in the laparoscopic field of view 332. The augmented image 330 comprises a second sub image 342 showing the type of instrument being used and the surgical procedure. In the illustrated example, a powered vascular surgical stapler is being used in a vascular surgical procedure. Also shown in the second sub image 342 is a graphic image of the stapler cartridge 346 of the powered surgical stapler and a graphic 344 superimposed on the graphic image of the stapler cartridge 346 to indicate the cut line of the powered surgical stapler.

FIG. 135 is another augmented image 360 of a live feed of a surgical area 374 as visualized through a laparoscopic camera during a minimally invasive surgical procedure indicating insufficiently captured tissue 372 between jaws 370 of a surgical instrument end effector 368 as a tissue aspect. The laparoscopic field of view 362 of a surgical area 374 shows a surgical instrument end effector 368 with insufficiently captured tissue 372 relative to the end of cut in the jaws 370 of the end effector 368. The augmented image 360 shows a graphical alert overlay 366 superimposed on the anvil of the end effector 368 to indicate incomplete tissue capture. A first superimposed alert 364 informs that the tissue 372 grasped at the proximal end of the jaws 370 of the end effector 368 is out of range. A second superimposed alert 378 informs that the tissue 372 grasped at the medial portion of the jaws 370 of the end effector 368 is within reload range. A third superimposed alert 376 informs that the tissue 372 grasped at the distal end of the jaws 370 in the end effector 368 is over the cut line.

FIG. 136 is an augmented image 400 of a live feed of a surgical area 422 as visualized through a laparoscopic camera during a minimally invasive surgical procedure indicating tissue 420 tension as a tissue aspect. The laparoscopic field of view 402 shows tissue 420 grasped between the jaws 424 of a surgical instrument end effector 418. The augmented image 400 shows a graphical alert overlay 404 superimposed in the surgical area 422 and a coloration of the tissue 420 to warn that the grasped tissue 420 is under tension. The superimposed tissue tension alert 404 and coloration of the tissue 420 grasped with the jaws 424 of the end effector 418 informs that the grasped tissue 420 is under tension. The superimposed tissue tension alert overlay 404 and coloration of tissue 420 under tension applies to energy based surgical instruments, surgical stapler instruments, as well as manipulation tools.

The augmented image 400 comprises a first sub image 408 showing a graphic image 406 of the general anatomy illustrated in the laparoscopic field of view 402 and a reference frame 410 of the actual anatomy shown in the laparoscopic field of view 402. The augmented image 400 also comprises a second sub image 412 showing the type of surgical instrument in use, the energy level being applied, if applicable, and the current surgical procedure. The augmented image 400 shows an ultrasonic surgical instrument being used in a surgical procedure at an energy level of 5 Max to achieve advanced hemostasis. A graphic image 416 of the surgical instrument is shown superimposed on a graphic image 414 of the reduce tension alert overlay 404. Accordingly, the augmented image 400 provides several options for informing the OR team to reduce the tension of the captured tissue 420 relative to the end of cut. The superimposed reduce tension alert overlay 404 applies to energy based surgical instruments as well as surgical stapler instruments, and the like.

FIG. 137 is another augmented image 430 of a live feed of a surgical area 442 as visualized through a laparoscopic camera during a minimally invasive surgical procedure indicating tissue 444 tension as a tissue aspect. The laparoscopic field of view 432 shows a surgical instrument end effector 436 grasping tissue 444 between the jaws 438 of the end effector 436. In the augmented image 430, coloration is added to the grasped tissue 444 to indicate that the grasped tissue 444 is under tension. Tissue 444 grasped with the jaws 438 of the end effector 436 is colored to indicate that the tissue 444 is under tension. Also shown in the laparoscopic field of view 432 are rows of previously applied staples 434. Also shown is a set of LEDs 440 to indicate the position of the tissue 444 grasped with the jaws 438 of the end effector 436.

FIG. 138 is a plurality of graphic images 500 indicating jaw closure position as an operational aspect of a surgical instrument as shown in FIGS. 131-137. The plurality of graphic images 500 comprise static graphics and alerts overlaid on the image of the surgical area and/or overlaid on the jaw of the end effector itself. The superimposed graphic images 500 apply to energy based surgical instruments, stapler based surgical instruments, manipulation tools, and the like.

A first image 502 comprises a first graphical overlay 504 showing the Patient Information, Procedure, and Case ID. A second graphical overlay 506 informs the type of surgical stapler instrument under use in the surgical procedure, e.g., a surgical stapler with a closed staple height of 1.5 mm as shown. A third graphical overlay 508 informs of the degree of articulation of the surgical stapler A fourth graphical overlay 510 is a pop-up error display. Finally, a fifth graphical overlay 512 informs of the energy surgical instrument under use in the surgical procedure, e.g., ultrasonic instrument operating between energy levels of 3 Min to 5 Max.

A second image 514 includes all of the graphical overlays 506, 508, 510, 512 explained in the description of the first image 502 with the addition of a sixth graphical overlay 516 that informs of the jaw of the surgical stapler being closed.

A third image 518 includes all of the graphical overlays 506, 508, 510, 512 explained in the description of the first image 502 with the addition of a sixth graphical overlay 520 that informs of the jaw of the surgical stapler being partially closed.

A fourth image 522 includes all of the graphical overlays 506, 508, 510, 512 explained in the description of the first image 502 with the addition of a sixth graphical overlay 524 that informs of the jaw of the surgical stapler being open.

FIG. 139 is an augmented image 530 of a live feed of a surgical area 544 as visualized through a laparoscopic camera during a minimally invasive surgical procedure indicating jaw 536, 542 closure position as an operational aspect of a surgical instrument. The laparoscopic field of view 532 shows a partially closed surgical instrument end effector 540 with tissue 534 grasped between the jaws 536, 542 of the end effector 540 and a tissue manipulation tool 546 used to assist the tissue grasping process. The augmented image 530 shows a graphical alert overlay 538 superimposed on the end effector 540 indicating partial closure.

FIG. 140 is an augmented image 550 of a live feed of the surgical area 544 shown in FIG. 139 showing a fully closed surgical instrument end effector 540 and a graphical alert overlay 546 showing jaw closed position superimposed on the end effector 540. The laparoscopic field of view of the surgical area 544 shows tissue 534 grasped in the jaws 536, 542 of the end effector 540.

FIG. 141 is an augmented image 600 of a live feed of a surgical area 610 as visualized through a laparoscopic camera during a minimally invasive surgical procedure indicating clamping on metal or foreign object as an operational aspect of a surgical instrument. The laparoscopic field of view 602 of the surgical area 610 shows the surgical instrument end effector 604 clamped on a metal or foreign object embedded in the tissue 608. The augmented image 600 shows a graphical alert overlay 614 superimposed on a graphical overlay 612 of an upper jaw 606 of the end effector 604 showing a foreign object clamped between the jaws of the end effector 604.

FIG. 142 is an augmented image 700 of a live feed of a surgical area 714 as visualized through a laparoscopic camera during a minimally invasive surgical procedure indicating device residual heat warning where overheating is an operational aspect of a surgical instrument. The laparoscopic field of view of the surgical area 714 shows a surgical instrument end effector 706 with tissue 710 clamped between an ultrasonic blade 710 and a clamp arm 704. The end effector 706 shows a hot ultrasonic blade 710. The augmented image 700 includes a graphical alert overlay 708 superimposed on the hot ultrasonic blade 710. The graphical alert overlay 708 warns the user that the ultrasonic blade 710 is building up residual heat, which will be transferred to the surrounding tissue 712 captured between the ultrasonic blade 710 and a clamp arm 704 pivotally coupled thereto.

FIG. 143 is an augmented image 800 of a live feed of a surgical area 822 as visualized through a laparoscopic camera during a minimally invasive surgical procedure indicating tissue 828 movement and flow as a tissue aspect. The laparoscopic view of the surgical area 822 shows the movement and flow of tissue 828 relative to tissue graspers 804, 824 and a surgical instrument end effector 812 with the tissue 828 grasped in the jaws 824 of the end effector 812 and the jaws of the tissue graspers 804, 824. The augmented image 800 shows graphical images 814, 820 overlaid on surgical area 822. The first graphical image 814 includes an icon 816 of a surgical stapler and text identifying the surgical instrument as a "stapler." The second image 820 includes an icon of a grasper 818. A sub image 810 alerts the OR team (e.g., the surgeon) of potential tissue movement over the cutline 808 displayed over an outline of the stapler cartridge 806.

FIG. 144 is an augmented image 900 of a live feed of a surgical area 918 as visualized through a laparoscopic camera during a minimally invasive surgical procedure indicating the geometric relationship of the transections to tissue 912 and other firings as a tissue aspect. The laparoscopic view of the surgical area 918 shows a surgical instrument end effector 910 and the geometric relationships of transections to the tissue 912 grasped between the jaws 914, 916 of the end effector 910 and to other firings. The augmented image 900 shows graphical images overlaid on the surgical area 918. A sub image 908 includes graphics that predict a complete transection with two staple lines shown graphically as active placement staple line 904 and complete staple line 906.

FIG. 145 is an image 1000 indicating anvil orientation communication as an operation as an operational aspect of a surgical instrument. A first image 1002 shows all of the graphical overlays 504, 506, 508, 510, 512 of the explained in the description of the first image 502 shown in FIG. 138 with the addition of an anvil up/down indicator graphic 1004. In the illustrated example, the up/down indicator graphic 1004 shows that the anvil is in the up (e.g., open) position. Another image 1006 illustrates the anatomy. A second image 1008 shows all of the graphical overlays 504, 506, 508, 510, 512 of the explained in the description of the first image 502 shown in FIG. 138 and the image 1006 of the anatomy with the addition of an anvil up/down indicator graphic 1010. In the illustrated example, the up/down indicator graphic 1010 shows that the anvil is in the down (e.g., closed) position.

FIG. 146 is an image 1100 indicating detected tissue thickness in the jaws of a surgical instrument end effector where tissue thickness is a tissue aspect. The image 1100 shows a graphic screen 1102 with text 1114 that tissue thickness is outside of range of reload with a recommendation to consider changing staple cartridge ad a warning icon 1112. The graphic screen 1102 shows a detected thickness marker 1104 positioned along a scale 1106 that shows detected tissue thickness. The graphic screen 1102 also shows the type of surgical instrument in use. The type of surgical instrument in use is a surgical stapler 1110 with a closed staple height 1108 of 1.5 mm.

FIG. 147 is an image 1200 of temperature gradient display graphics 1202, 1204, 1206 for an ultrasonic instrument. The first, second, and third display graphic 1202, 1204, 1206 may be overlaid on a surgical area of a surgical field of view displayed on a display as described in FIGS. 131-146, informs of the instrument type, minimum and maximum output energy levels, and displays temperature gradient elements 1208, 1210, 1212 on a portion of the display graphic 1202, 1204, 1206. In the first display graphic 1202 the ultrasonic instrument is either off or the ultrasonic blade temperature is running at a normal temperature and a "green" gradient bar is not displayed or barely visible. In the second display graphic 1204 a temperature gradient element 1210 "heat map bar" ranging from green to yellow shows that the ultrasonic blade is approaching a temperature above normal. In the third display graphic 1206 a temperature gradient element 1212 "heat map bar" ranging from green to red shows that the ultrasonic blade temperature is above normal in an overheated state.

FIG. 148 is an image 1300 of temperature icon display graphics 1302, 1304, 1306 for an ultrasonic instrument. The first, second, and third display graphics 1302, 1304, 1306 may be overlaid on a surgical area of a surgical field of view displayed on a display as described in FIGS. 131-146, informs of the instrument type, minimum and maximum output energy levels, and displays temperature green, yellow, and red icons 1308, 1310, 1310 on a portion of the display graphic 1302, 1304, 1306. In the first display graphic 1302 the ultrasonic instrument is operating in a normal condition and the temperature of the ultrasonic blade is in a normal range as shown by green icon 1308 and also shown by the green semicircular temperature meter element 1314. In the second display graphic 1304 the yellow temperature icon 1310 shows that the ultrasonic blade is approaching a temperature above normal as also shown by the yellow semicircular temperature meter element 1316. In the third display graphic 1306 a red temperature icon 1312 shows that the ultrasonic blade temperature is above normal and is in a overheated state as shown by the red semicircular temperature meter element 1318.

FIG. 149 is an image 1400 of ultrasonic blade temperature graphic elements 1410, 1412, 1414 mapped to an end effector 1418 jaw 1420 position. The first, second, and third display graphic elements 1410, 1412, 1414 may be overlaid on the jaw 1420 of an ultrasonic end effector 1418 in a surgical area of a surgical field of view displayed on a display as described in FIGS. 131-146. The first temperature graphic element 1410 shows that the ultrasonic blade is operating in a normal range as shown by the green temperature graphic element 1410. The second temperature graphic element 1412 shows that the ultrasonic blade is approaching a heated temperature state as shown by the yellow temperature graphic element 1412. The third temperature graphic element 1414 shows that the ultrasonic blade is in an overheated temperature state as shown by the red temperature graphic element 1414.

FIG. 150 is an image 1500 of an ultrasonic generator power level display graphic 1502. The display graphic 1502 informs of the generator type and minimum and maximum power levels. One or more graphic elements of the image 1500 may be overlaid on the jaw of the ultrasonic end effector or anywhere in the surgical area in the surgical field of view displayed on a display as described in FIGS. 131-146.

FIG. 151 is an image 1600 of an ultrasonic generator power level display graphic 1502 with a pop-up warning graphic 1602 indicating that the ultrasonic end effector jaw is overstuffed. The pop-up warning graphic 1602 may include the language to show that too much tissue is in the jaw and may result in an incomplete transection. One or more graphic elements of the image 1600 may be overlaid on the jaw of the ultrasonic end effector or anywhere in the surgical area in the surgical field of view displayed on a display as described in FIGS. 131-146.

FIG. 152 is an image 1700 of an ultrasonic generator power level display graphic 1502 with a pop-up warning graphic 1702 indicating ultrasonic end effector jaw heat. The pop-up warning graphic 1702 may include the language to show that the instrument temperature is hot and in one aspect, the word hot may be shown in red. One or more graphic elements of the image 1700 may be overlaid on the jaw of the ultrasonic end effector or anywhere in the surgical area in the surgical field of view displayed on a display as described in FIGS. 131-146.

FIG. 153 is an image 1800 of an electrosurgical generator display graphic 1802 with a pop-up warning graphic 1802 indicating electrosurgical seal quality prediction. The pop-up warning graphic 1804 may include the language Warning: Incomplete Seal and the electrosurgical generator display graphic 1802 may include the language Error to show that an incomplete seal is predicted. One or more graphic elements of the image 1800 may be overlaid on the jaw of the electrosurgical end effector or anywhere in the surgical area in the surgical field of view displayed on a display as described in FIGS. 131-146.

FIG. 154 is an image 1900 of a surgical stapler reload feedback. The image 1900 comprises a first display graphic 1902 indicating a suitable tissue thickness range for the surgical stapler in use. In the illustrated example, the suitable surgical stapler tissue thickness range is 1.5 mm-2.4 mm. A second display graphic 1904 shows the detected tissue thickness. In the illustrated example, the detected tissue thickness is 2.6 mm. A third pop-up display graphic 1906 shows that the tissue thickness is 2.6 mm and is thicker than the selected reload and provides a suggestion to consider a reload in the range of 2.0 mm-3.3 mm. The image 1800 may be overlaid on the jaw of the electrosurgical end effector or anywhere in the surgical area in the surgical field of view displayed on a monitor or screen. One or more graphic elements of the image 1900 may be overlaid on the jaw/anvil of the surgical stapler end effector or anywhere in the surgical area in the surgical field of view displayed on a display as described in FIGS. 131-146.

FIG. 155 is an image 2000 of a surgical stapler precompression countdown. The image 2000 comprises a first display graphic 1902 as shown in FIG. 154 indicating the surgical stapler tissue thickness range of 1.5 mm-2.4 mm. A second pop-up display graphic 2002 shows a surgical stapler precompression countdown element to show the time remaining in the precompression phase of the surgical stapler operation. One or more graphic elements of the image 2000 may be overlaid on the jaw/anvil of the surgical stapler end effector or anywhere in the surgical area in the surgical field of view displayed on a display as described in FIGS. 131-146.

The following description provides an intraoperative display for surgical systems to provide adaptation and adjustability or overlaid instrument information. One aspect provides functional overlay of instrument critical operations or parameters to clearly represent a surgical stapler or energy device or aspects of each of its interaction with tissue during a surgical procedure. Overlaid data may be adjusted by aspects detected by the surgical hub to modify the overlay from the information merely detected by the source instrument to add context. The displays may be adjusted or modified by the user and as a result also result in modifications of the instrument being monitored operation.

FIGS. 156-188 describe an intraoperative display system for use during a surgical procedure. The system comprises a surgical monitor with an intraoperative data display of a surgical area. An advanced energy generator is coupled to an advanced energy surgical instrument. The advanced energy surgical instrument employs radio frequency (RF) energy and ultrasonic energy during a surgical procedure on a patient. A surgical hub is coupled to the advanced energy generator and to the surgical monitor. The surgical hub provides a live feed of the surgical area to the surgical monitor to display the live feed of the surgical area by the intraoperative data display. The intraoperative data display displays a view of the surgical area including the advanced energy surgical instrument grasping tissue and a panel overlay that displays information specific to the advanced energy surgical instrument.

One aspect, the intraoperative data display shows an end effector of the surgical instrument grasping tissue and a panel overlay displaying case information, systems notifications, or device panels, or any combination thereof, overlaid over the live surgical feed. A location, opacity, size and placement of the panel overlay is customized. The panel overlay is configured to be turned on or off individually or turned on/off as a group. The panel overlay is further configured to change dynamically to show state changes such as device activation or power level adjustment. The panel overlay depicts optimal device performance (ODP) guide images or other instructions for use (IFU)/informational sources.

In various aspects the panel overlay comprises at least one of data input information from capital equipment, generators, insufflator, smoke evacuator, electronic health record, laparoscope, computer, surgical devices, wired and wirelessly connected devices, surgeon profile preferences that may be saved, recalled or edited, or any combination thereof. The panel overlay may include case information including at least one of Patient Name, Surgeon Name, Case Time, or Instrument Activations, or combinations thereof. The panel overlay may include system notifications including at least one of connect instrument status, minor error alert, medium error alert, or major error alert, or any combination thereof. The panel overlay may include information associated with the surgical instrument connected to the system to provide advanced hemostasis. The panel overlay may include a visible patient panel overlay. The panel overlay may include a device panel overlay comprising at least one of device name, device settings, or device supplemental features, or any combination thereof. The panel overlay may include a plurality of panel overlays in a stacked configuration. The panel overlay may include a plurality of panel overlays in an expanded configuration. The panel overlay may display device troubleshooting information. The panel overlay may display at least one of alerts, warnings, device information, or device features, or any combination thereof.

In another aspect, the intraoperative data display comprises a secondary configurable panel. The secondary configurable panel changes dynamically based on the selected customized laparoscopic overlay fields displayed in the surgical field of view of a live surgical feed area of the intraoperative data display. The customized laparoscopic overlay fields comprise at least one of a bottom edge panel, a top left corner panel, a top center panel, or a side edge panel, or any combination thereof.

FIG. 156 is a system diagram 3000 of a surgical suite comprising a surgical monitor with intraoperative data display 3002 of a surgical area. An advanced energy generator 3004 is coupled to a surgical hub 3006 and to an advanced energy surgical instrument 3008. The advanced energy surgical instrument 3008 employs RF energy and ultrasonic energy during a surgical procedure on a patient 3010. The surgical hub 3006 provides a live feed 3014 of the surgical area, which is displayed by the intraoperative data display 3002. The intraoperative data display 3002 displays a view of the surgical area including the advanced energy surgical instrument 3008 grasping tissue and a panel overlay 3012 that displays information specific to the advanced energy surgical instrument 3008.

FIG. 157 is an augmented image 3100 of a live feed of a surgical area as visualized through a laparoscopic camera during a minimally invasive surgical procedure displayed on an intraoperative data display 3002. The laparoscopic field of view shows an end effector 3108 of a surgical instrument 3008 grasping tissue 3110. The augmented image 3100 shows three panel overlays displaying case information 3102, systems notifications 3104, and device panels 3106 overlaid over the live surgical feed.

The panel overlays 3102, 3104, 3106 are displayed on the live surgical feed. The location, opacity, size and placement of the panel overlays 3102, 3104, 3106 can be customized. The panel overlays 3102, 3104, 3106 may be turned on or off individually or turned on/off as a group. The panel overlays 3102, 3104, 3106 may be opaque or have varying levels of transparency. The panel overlays 3102, 3104, 3106 may include data input information from capital equipment, generators, insufflator, smoke evacuator, electronic health record, laparoscope, computer, surgical devices, wired and wirelessly connected devices. Surgeon profile preferences may be saved, recalled or edited. In other aspects, general screen settings including overall screen settings and fonts for panel overlay 3102, 3104, 3106 sizing may be configurable based upon surgeon preferences via a staff console. The panel overlays 3102, 3104, 3106 features on all screen displays may be enables/disabled, or bypassed through a dedicated physical switch, for example.

FIG. 158 is a detailed view of the case information panel overlay 3102 shown in FIG. 157. The case information panel overlay 3102 may be selectively enabled/disabled via the staff console. Specific details of the case information panel overlay 3102 including Patient Name, Surgeon Name, Case Time, Instrument Activations, etc., may be selectively enabled/disabled based on the staff console settings Other aspects of the case information panel overlay 3102 may include, for example, enabling the screen at the start of the surgery and disabling the screen after a specific criteria is met (surgery time elapsed number of device activations, etc.).

FIG. 159 is a detailed view of the systems notifications panel overlay 3104 shown in FIG. 157. The systems notifications panel display overlay 3104 may comprise a warning symbol that may be variable based on the severity of the warning/alert/information. The message may be potentially based on any combination of: connected capital equipment, connected devices (medical, wired, wireless, etc.), or surgical hub device (this device). The notification disappears based on notification dwell time or alert status resolution.

FIG. 160 is an image of several examples of systems notifications panel overlays 3104. The systems notifications panel overlays 3104 may include connect instrument 3112, minor error alert 3114, medium error alert 3116, and major error alert 3118, for example.

FIG. 161 is a detailed view of the device panels overlay 3106 shown in FIG. 157. The example device panels overlay 3106 shown in FIG. 161, displays information associated with a combination ultrasonic/RF instrument connected to the system 3000 (FIG. 156) to provide advanced hemostasis. The device panels overlay 3106 provide a Thermal indication and a Ready indication, for example.

In various aspects, the device panels overlay 3106 provides a visual concept influenced by the Ottava framework and may be selectively enabled/disabled via the staff console. The staff console also can selectively enable/disable individual panels such as, for example, energy and surgical stapler. In one aspect, the device panels overlay 3106 only appears if a relevant instrument is connected to the system 3000 (FIG. 156). The device panels overlay 3106 are not visible if nothing is connected to the system 3000 (FIG. 156). The space occupied by the device panels overlay 3106 is configurable (e.g., left, center, right aligned). The device panels overlay 3106 also may be configured to display connectivity to handheld instruments. In other aspects, the device panels overlay 3106 may be configurable in the space along the top/bottom of the display. The device panels overlay 3106 may display multiple instrument devices connected simultaneously. In one aspect, the device panels overlay 3106 may display information only for devices which are actively being used by the surgeon such that connected, but inactive device displays are hidden.

In one aspect, the size of the device panels overlay 3106 may be configurable based on the features that are enabled, such as the Thermal example described herein. These features may be enabled or disabled based upon intrinsic device design (e.g., future models), as well as enabled/disabled by the surgeon, or paid subscription.

FIG. 162 is an augmented image 3120 of a live feed of a surgical area as visualized through a laparoscopic camera during a minimally invasive surgical procedure displayed on an intraoperative data display 3122. showing an end effector 3108 of a surgical instrument 3008 grasping tissue 3110 and a screen with a visible patient panel overlay 3124, according to one aspect of this disclosure. The visible patient panel overlay 3124 may require an additional application to display content. The intraoperative data display 3122 also displays the case information panel overlay 3102 and the device panels overlay 3106. In the illustrated example, the systems notifications panel overlay 3104 is hidden.

FIG. 163 is a schematic view of an energy device image panel 3106 architecture. In one aspect, the energy device image panel 3106 includes a device name 3132, device settings 3134, and device supplemental features 3136, for example.

FIG. 164 is an image 3140 of supplemental device alerts/warning/information in a stacked configuration. The supplemental device alerts/warnings/information display may be stacked. The supplemental device alerts/warnings/information display also may be stacked vertically to cover the main device panel, or may be expanded horizontally. As shown in the example of FIG. 164, the energy device panel overlay 3106 is stacked vertically below a system ready 3142 display.

FIG. 165 is an image 3150 of supplemental device alerts/warning/information in an expanded configuration. The supplemental device alerts/warnings/information display may be expanded. The expanded display 3144 may be expanded vertically or horizontally. As shown in the example of FIG. 165, the expanded display 3144 provides additional information about the instrument device. As shown in the example is FIG. 165, the expanded display 3144 shows an image of a surgical instrument and the instructions to activate the instrument for 2 seconds t run test.

FIG. 166 is an instrument state image panel 3160 showing how instrument panel states change dynamically to show state changes such as device activation or power level adjustment. The left side 3162 of the instrument state image panel 3160 shows the default state of the instrument. The right side 3164 of the instrument state image panel 3160 shows the active state of the instrument. In the example shown in FIG. 166, a first panel 3166 on the right side 3164 of the instrument state image panel 3160 shows a dynamic change in the instrument activation and a second panel 3168 of the right side 3164 on the instrument state image panel 3160 shows a dynamic change in the instrument power level.

FIG. 167 is a system diagram 3170 of translating generator 3066 alerts and warnings 3174 to a laparoscopic monitor 3172 and displayed on a local interface.

FIG. 168 is a diagram 3180 of a series of screens 3182 of existing alerts shown on a current generator that are transmitted to a surgical hub, which then displays them as a series of screens 3184 on a local interface.

FIG. 169 is a schematic diagram of a system 3200 comprising a generator 3202 in communication with a digital hub 3204, which then displays screen data and alert data 3220 on a local interface 3206 such as a laparoscopic screen 3216. The generator 3202 comprises a controller 3208 and a screen 3210. The controller 3208 of the generator 3202 transmits data 3218 to a controller 3212 of the digital hub 3204. The digital hub 3204 also comprises a screen 3214. The controller 3212 of the digital hub 3204 transmits screen data and alert data 3220 to the laparoscopic screen 3216 of the local interface 3206.

FIG. 170 is an augmented image 3230 of a live feed of a surgical area as visualized through a laparoscopic camera during a minimally invasive surgical procedure displayed on an intraoperative data display 3232. The laparoscopic field of view of the surgical area shows an overlay panel 3234 depicting optimal device performance (ODP) guide images or other instructions for use (IFU)/informational sources. The augmented image 3230 shows an on-screen display overlay panel 3234 shows a surgical device 3250 comprising a grip housing 3244, trigger 3242, shaft 3238 and blade with tissue pad 3236. The shaft 3238 is rotated by a rotation nob 3248. The surgical device 3250 also includes an energy button 3240 and an energy button 3246 with advanced hemostasis.

The overlay panel 3234 displays an image of a surgical device 3250 and ODP guide images or other IFU/informational sources. The images may be presented to the surgeon with surgical device information. The images may be static or animated images. The images may provide general surgical device 3250 information (as shown), or context specific surgical device information. For example, the bailout door of a surgical device 3250 may include a sensor to detect removal. When the bailout door is removed, the on-screen display overlay panel 3234 shows an image which provides instructions on the proper usage of the bailout mechanism. By way of another example, the surgeon encounters an alert while using the ultrasonic energy mode related to a surgical device technique. The on-screen display overlay panel 3234 shows information specific to how to best use the surgical device 3250 to avoid that alert.

FIG. 171 is a display screen 3300 showing an intraoperative data display 3302 comprising a secondary bottom edge configurable panel 3312. The intraoperative data display 3302 includes a surgical field of view of a live surgical feed 3303 with customized laparoscopic overlay fields 3318, 3320, 3322 and a secondary bottom edge configurable panel 3312. The intraoperative data display 3302 displays a navigation button 3304 to return back to the home screen. The intraoperative data display 3302 also provides a selectable surgeon profile 3306. The surgeon profile preferences may be saved, recalled, or edited. The intraoperative data display 3302 also provides several connectivity status indicators 3308. Overlays associated with the intraoperative data display overlay fields 3318, 3320, 3322 may be toggled with a display overlay toggle button 3310.

The intraoperative data display 3302 also includes a secondary configurable panel that changes dynamically based on the selected customized laparoscopic overlay fields 3318, 3320, 3322 displayed in the surgical field of view of a live surgical feed 3303 area of the intraoperative data display 3302 when the display overlay toggle button 3310 is toggled in the ON position. In the example illustrated in FIG. 171, a bottom edge configurable panel 3312 is displayed by selecting the bottom edge selection field 3322 in the surgical field of view of the live surgical feed 3303 portion of the intraoperative data display 3302. Different portions of the display may be selected including, for example, a top left corner selection field 3318, a top center selection field 3320, and a bottom edge selection field 3322.

The bottom edge configurable panel 3312 includes a panel alignment bar 3314 to align the bottom edge configurable panel 3312 in the left, center, or right position, here shown in the left position. Help indicators 3316 provide contextual information to the associated toggle button 3324, 3326, 3328, 3330. The bottom edge selection field 3322 may be configured using the configurable panel alignment button 3314, which shifts the bottom edge alignment left, center, and right. In other aspects, the bottom edge selection field 3322 may be moved top and bottom, for example. In addition to the configurable panel alignment button 3314, the bottom edge configurable panel 3312 comprises a first toggle button 3324, which enables/disables the energy panel display for ultrasonic/RF energy tool devices, including alerts, here shown in the ON position. A second toggle button 3326 enables/disables display of alerts only for ultrasonic/RF energy tool devices, here shown in the OFF position. A third toggle button 3328 enables/disables display of surgical stapler tool devices, including alerts, here shown in the OFF position. A fourth toggle button 3330 enables/disables display alerts only for surgical stapler tool devices, here shown in the ON position.

FIG. 172 is an alternative bottom edge configurable panel 3400. The alternative bottom edge configurable panel 3400 is displayed by selecting the bottom edge selection field 3282 in the surgical field of view of a live surgical feed 3263 portion of the intraoperative data display 3262 in FIG. 171. The alternative bottom edge configurable panel 3400 may be configured for customization of energy status and alerts. In the illustrated example, the alternative bottom edge configurable panel 3400 is displayed by toggling the display on monitor toggle button 3402 in the ON position. A first toggle button 3404 enables/disables energy device panel status, here shown in the ON position. A second toggle button 3406 enables/disables energy device panel alerts, here shown in the OFF position. A third toggle button 3408 enables/disables surgical stapler device status, here shown in the OFF position. A fourth toggle button 3410 enables/disables surgical stapler alerts, here shown in the OFF position. The alternative bottom edge configurable panel 3400 includes a panel alignment bar 3412 to align the alternative bottom edge configurable panel 3400 in the left, center, or right position, here shown in the center position. FIGS. 173-175 described hereinbelow describe additional configurable panels displayed by selecting other selection fields in the surgical field of view of a live surgical feed portion of the intraoperative data display.

FIG. 173 is a display screen 3500 showing an intraoperative data display 3502 comprising a secondary top left corner configurable panel 3522. The intraoperative data display 3502 includes a surgical field of view of a live surgical feed 3503 with customized laparoscopic overlay fields 3318, 3320, 3322 and a secondary top left corner configurable panel 3522. The intraoperative data display 3502 includes a navigation button to return back to the home screen, a selectable surgeon profile, and connectivity status indicators as described in connection with FIG. 171. Overlays associated with the intraoperative data display overlay fields 3318, 3320, 3322 may be toggled with a display overlay toggle button 3310.

The intraoperative data display 3502 also includes a secondary configurable panel that changes dynamically based on the selected customized laparoscopic overlay fields 3318, 3320, 3322 displayed in the surgical field of view of a live surgical feed 3503 area of the intraoperative data display 3502 when the display overlay toggle button 3310 is toggled in the ON position. In the example illustrated in FIG. 173, a top left corner configurable panel 3522 is displayed by selecting the top left corner selection field 3318 in the surgical field of view of the live surgical feed 3503 portion of the intraoperative data display 3502.

Selecting the top left corner selection field 3318 dynamically changes the visual display. For example, selecting the top left corner selection field 3318, displays the case information overlay 3504, which, in this example, is the case information panel overlay screen 3102 shown in FIGS. 157 and 158. Various toggle buttons are shown alongside the right vertical portion of the secondary top left corner configurable panel 3522. As previously discussed, the display overlay toggle button 3310 enables/disables the display of the overlay screens such as the case information overlay 3504. A first toggle button 3506 enables/disables all case information from the case information overlay 3504, here shown in the ON position. A second toggle button 3508 enables/disables patient name information from the case information overlay 3504, here shown in the ON position. A third toggle button 3510 enables/disables surgeon name information from the case information overlay 3504, here shown in the ON position. A fourth toggle button 3512 enables/disables case date information from the case information overlay 3504, here shown in the ON position. A fifth toggle button 3514 enables/disables total time for the case information from the case information overlay 3504, here shown in the ON position. A sixth toggle button 3516 enables/disables case metrics, which may include total number of device activations, uses, or other device metrics, from the case information overlay 3504, here shown in the ON position.

FIG. 174 is a display screen 3600 showing an intraoperative data display 3602 comprising a secondary top center configurable panel 3622. The intraoperative data display 3602 includes a surgical field of view of a live surgical feed 3603 with customized laparoscopic overlay fields 3318, 3320, 3322 and a secondary top center configurable panel 3622. The intraoperative data display 3602 includes a navigation button to return back to the home screen, a selectable surgeon profile, and connectivity status indicators as described in connection with FIG. 171. Overlays associated with the intraoperative data display overlay fields 3318, 3320, 3322 may be toggled with a display overlay toggle button 3310.

The intraoperative data display 3602 also includes a secondary configurable panel that changes dynamically based on the selected customized laparoscopic overlay fields 3318, 3320, 3322 displayed in the surgical field of view of a live surgical feed 3603 area of the intraoperative data display 3602 when the display overlay toggle button 3310 is toggled in the ON position. In the example illustrated in FIG. 174, a top center configurable panel 3622 is displayed by selecting the top center selection field 3320 in the surgical field of view of the live surgical feed 3603 portion of the intraoperative data display 3602.

Selecting the top center selection field 3320 dynamically changes the visual display. For example, selecting the top center selection field 3320, displays the systems notifications panel overlay 3604, which, in this example, is the systems notifications panel overlay 3104 shown in FIG. 160. Various toggle buttons are shown alongside the right vertical portion of the secondary top center configurable panel 3622. As previously discussed, the display overlay toggle button 3310 enables/disables the display of the overlay screens such as the systems notifications panel overlay 3604. A first toggle button 3506 enables/disables all alerts for the systems notifications panel overlay 3604, here shown in the ON position. A second toggle button 3608 enables/disables informational alerts for the informational notification bar 3616 of the systems notifications panel overlay 3604, here shown in the ON position. A third toggle button 3610 enables/disables minor alerts for the minor error alert bar 3618 of the systems notifications panel overlay 3604, here shown in the ON position. A fourth toggle button 3612 enables/disables medium alerts for the medium error alert bar 3620 of the systems notifications panel overlay 3604, here shown in the ON position. A fifth toggle button 3614 enables/disables the major alerts for the major error alert bar 3622 of the systems notifications panel overlay 3604, here shown in the ON position. Dynamic shading of the toggle button, e.g., the fifth toggle button 3614 as shown, provides a visual cue based on the selection status.

FIG. 175 is display screen 3700 showing an intraoperative data display 3702 comprising a secondary side edge configurable panel 3722. The intraoperative data display 3702 includes a surgical field of view of a live surgical feed 3703 with customized laparoscopic overlay fields 3318, 3320, 3322, 3716 and a secondary side edge configurable panel 3722. The intraoperative data display 3702 includes a navigation button to return back to the home screen, a selectable surgeon profile, and connectivity status indicators as described in connection with FIG. 171. Overlays associated with the intraoperative data display overlay fields 3318, 3320, 3322, 3716 may be toggled with a display overlay toggle button 3310.

The intraoperative data display 3702 also includes a secondary configurable panel that changes dynamically based on the selected customized laparoscopic overlay fields 3318, 3320, 3322, 3716 displayed in the surgical field of view of a live surgical feed 3703 area of the intraoperative data display 3702 when the display overlay toggle button 3310 is toggled in the ON position. In the example illustrated in FIG. 175, a side edge configurable panel 3722 is displayed by selecting the side edge selection field 3716 in the surgical field of view of the live surgical feed 3703 portion of the intraoperative data display 3702.

Selecting the side edge selection field 3716 dynamically changes the visual display. For example, selecting the side edge selection field 3716, displays the visible patient panel overlay 3704, which, in this example, is the visible patient panel overlay 3124 shown in FIG. 162. Various toggle buttons are shown alongside the right vertical portion of the secondary side edge configurable panel 3722. As previously discussed, the display overlay toggle button 3310 enables/disables the display of the overlay screens such as the visible patient panel overlay 3704. A first toggle button 3706 enables/disables all alerts for the visible patient panel overlay 3704 information, here shown in the ON position. A second toggle button 3708 enables/disables gas information for the visible patient panel overlay 3704, here shown in the ON position. A third toggle button 3710 enables/disables visible patient information for the visible patient panel overlay 3704, here shown in the ON position. A fourth toggle button 3712 enables/disables information from another module (Module 3) for the visible patient panel overlay 3704, here shown in the ON position. A fifth toggle button 3714 enables/disables information from yet another module (Module 4) for the visible patient panel overlay 3704, shown in the ON position.

FIG. 176 is a series of image panels 3800 displaying device troubleshooting information. A first image panel 3802 displays instructions to test the instrument. In the illustrated example, the instruction to the instrument is "Activate instrument for 2 seconds to run test." A second image panel 3804 indicates that testing is in progress and a third image panels 3806 shows the testing status. A fourth image panel 3808 provides instructions for troubleshooting with static images, animations, GIFS, or videos. In the illustrated example, the image panel 3808 displays an animation to "Tighten Assembly." A fifth image panel 3810 indicates an action for the instrument under test and, in the illustrated example, informs to "Open jaws during test."

FIG. 177 is a series of image panels 3900 displaying articulating surgical stapler features. A first image panel 3902 indicates surgical stapler articulation angle of the surgical stapler device. The angle may be shown numerically or visually. Second and third image panels 3904, 3906 indicate articulation angle updates based on device status and also show articulation direction. In one aspect, each time the articulation button is pressed or articulation angle changes, an updated measurement is sent to the digital hub 3204 (FIG. 169)/3006 (FIG. 156). The digital hub 3204 (FIG. 169), 3006 (FIG. 156) then uses the updated measurement to update the reflected angle as shown on the image panels 3902, 3904, 3906.

A fourth image panel 3908 is a standardized countdown indicator that appears when the surgical stapler jaw is closed. The countdown dynamically changes based on time. The device may be fired any time during the countdown sequence. A fifth image panel 3910 indicates that the device is ready to fire. Sixth, seventh, and eight image panels 3912, 3914, 3916 indicate the knife position along the sled. The knife position is shown in gray over the an illustration of a cartridge 3918 and dynamically changes based on the device. An illustration of a cartridge 3918 may be generic or specific to the cartridge installed in the surgical stapler. The knife position/surgical stapler image panels 3912, 3914, 3916 may dynamically change based on the type and size of the surgical stapler wirelessly connected. A knife position algorithm executes after or as the firing trigger of the surgical stapler is depressed and as the surgical stapler begins firing, the knife and sled begin to travel down the length of the surgical stapler A ninth image panel 3920 indicates that the operation is complete.

Each of the supplemental features displayed by the corresponding image panels 3902-3920 of the connected device dynamically update based on the current status of the device.

FIG. 178 is an alert/warning/information image panel 3922 displaying that the articulation limit has been reached.

FIG. 179 is an alert/warning/information image panel 3924 displaying that the device is in lockout mode.

FIG. 180 is an alert/warning/information image panel 3926 displaying that the device cannot articulate when jaws are closed.

FIG. 181 is a device image panel 4000 showing articulating surgical stapler features. The device image panel 4000 includes a device panel name 4002, here shown as surgical stapler 3000, and a device panel supplemental feature 4004, here shown as the countdown indicator.

FIG. 182 is a stacked alert/warning/information image panel 4010 displayed in a stacked configuration with device alert displaying that the articulation limit has been reached. The stacked image panel 4010 includes a top image panel 4012 indicating that the articulation limit has been reached. The stacked image panel 4010 includes a bottom image panel 4014 that indicates the name and type of the device, articulation angle, and articulation direction.

FIG. 183 is a schematic diagram of a system 4020 comprising a surgical stapler in communication with a digital hub over Bluetooth to execute an algorithm for the countdown timer image panel 4000 shown in FIGS. 177 and 181. The surgical stapler 4022 is in communication with the digital hub 4024 over a wireless network, such as Bluetooth, for example. The surgical stapler a controller 4028 and the digital hub 4024 comprises a controller 4030. The surgical stapler controller 4028 transmits wireless data 4026 to the digital hub controller 4030. When the surgical stapler 4022 clamps and sends a clamp status message to the digital hub 4024, the digital hub 4024 uses the clamp status message as a start command to initiate a countdown timer. If an unclamp message is received, the timer restarts to 0 and stop incrementing. If the timer reaches a set time, the timer is stopped and a flag is set.

FIG. 184 is a series of device image panels/alerts 4030 displaying ultrasonic instrument features. The device image panels are expandable or collapsible depending upon the features that are enabled or disabled by the user and/or the features that are enabled or disabled by the device connected. By way of example, a first device image panel 4032 can be expanded into the second device image panel 4034, which displays a default thermal image panel 4036 and a high thermal image panel 4038. The high thermal image panel 4038 displays the status of the device temperature by direct means (temperature sensing) or indirectly via other methods (algorithm based on time or other means). With reference to the default thermal image panel 4036, the thermal algorithm may be based on device activation status and total time elapsed, as well as time elapsed since the last activation. In other implementations, the thermal algorithm may be based on device characteristics and/or status such as resonant frequency, inferred state of the device, or direct measurement. Thermal status is displayed only while the device is not currently activating. While the device is inactive, the display is grayed out. The thermal status is displayed at all times in the high thermal image panel 4038 and corresponds to the current state of the device. In the illustrated example, the device is an ultrasonic instrument.

A third device image panel 4040 changes color as the device is being used to illustrate the mode of device operation as shown by internal image panels 4042, 4044, 4046. A fourth device image panel 4048 displays instrument alerts and associated images and text for that alert as shown in the alert image panel 4050. The alert image panel 4050 may provide visual indicator for the alert. Alerts may be composed of only text, only images, or a combination of text and images.

FIG. 185 is a chart 4060 describing pairing a surgical stapler instrument. The surgical stapler pairing may be implemented as user selectable pairing, connect on powerup, connect on powerup with button press, or RFID token. For user selectable pairing, the user would start a pairing mode on the capital equipment via a touchscreen. The capital equipment would then attempt to identify all valid devices of that type within a region, and the user would simply select the devices that they would like to connect to. Broadcasting would continue even after time has elapsed. Connect on powerup pairing may enable Bluetooth radio on powerup, and may be turned off if it is not connected to the client within a predetermined time. The capital equipment constantly scans for new devices and connects to them. Connect on powerup with button press requires the Bluetooth radio to be enabled on powerup and if it is not connected to the client within a predetermined time, turn the radio off. The capital equipment has a pairing button that once pressed scans/connects to the device. In RFID token pairing, the user utilizes an RFID card, packaged with each device, as a method for scanning in the new device and pairing with the capital equipment.

FIG. 186 is an image of a screen 4070 displaying pairing devices information. The screen 4070 provides system wide ability to connect/disconnect a variety of wired and wireless devices/equipment.

FIG. 187 is an image of a wireless surgical device 4080 comprising a unique identifier for pairing wireless devices.

FIG. 188 is an image of a screen 3090 displaying a link to optimal device performance (ODP) guide images or other electronic instructions for use (e-IFU). The user manual 4092 may link to e-IFU or ODP.

With reference also to FIGS. 1-188, FIG. 189 is a diagram of an augmented reality method 5000 employing a surgical instrument 77 and an augmented reality display 89 for use during a surgical procedure, according to one aspect of this disclosure. The method 5000 may be employed in conjunction with any of the augmented displays shown in FIGS. 131-168, 170-182, 184-186, and 188 and may be implemented with any of the systems shown in FIGS. 1-10, 169, and 183. In one aspect, the method 500 provides overlay of operational aspects or functions of a surgical instrument 77 onto the surgical laparoscopic video stream. The overlay may be related to the operation of one of the surgical instruments 77 being actively visualized and the overlay combines aspects of the tissue/organ interaction with functional data received from the surgical instrument 77. In another aspect, the surgical instrument 77 may be grasper or clamp and the aspect of the tissue could be incomplete capture of the tissue along with the clamp status or magnitude of the clamp. In another aspect, the surgical instrument 77 may be a surgical stapler and the aspect of the tissue may be tissue capture location or tissue compression and the aspect of the surgical stapler may be clamping or firing sufficiency, or other parameters. In another aspect, the surgical instrument 77 may be an advanced energy device and the tissue parameter may be impedance, cautery status, bleeding magnitude and the function of the surgical instrument 77 could be energy level, timing, clamp pressure, among other parameters.

In one aspect, the method 5000 is directed to overlay of data according to surgical instrument 77 utilization. According to the method 5000, an imaging device 38 captures 5002 a real image of a surgical area during a surgical procedure. A processor 85 receives 5004 functional data from the surgical instrument 77, determines 5006 an overlay related to an operational aspect of the surgical instrument 77, and combines 5008 an aspect of tissue in the surgical area with the functional data received from the surgical instrument 77. The augmented reality display 89, or local display 67, presents 5010 the overlay of the operational aspect of the surgical instrument 77 onto the real image of the surgical area. The functional data for the surgical instrument 77 may be received from the surgical instrument 77 directly or a surgical hub coupled processor or server.

With reference also to FIGS. 1-188, FIG. 190 is a diagram of an augmented reality method 5100 employing a surgical instrument 77 and an augmented reality display 89 for use during a surgical procedure, according to one aspect of this disclosure. The method 5100 may be employed in conjunction with any of the augmented displays shown in FIGS. 131-168, 170-182, 184-186, and 188 and may be implemented with any of the systems shown in FIGS. 1-10, 169, and 183.

In one aspect, the method 5100 is directed to overlay of data according to surgical instrument 77 utilization. The processor 85 monitors 5102 the performance of the surgical instrument 77 during a surgical procedure. The processor 85 determines 5104 the usage of the surgical instrument 77. The augmented reality display 89 displays 5112 alerts relative to the surgical instrument 77 performance considerations. The processor 85 determines 5122 collateral events, displays 5132 a status overlay of the surgical instrument 77, and displays 5134 an indication of the surgical instruments 77 on the augmented reality display 89.

Once the processor 85 determines 5104 the usage of the surgical instrument 77, the processor 85 determines 5106 whether the tissue grasped in the jaws of the surgical instrument 77 is within a range of the jaws and determines 5108 whether the tissue is properly balanced within the jaws of the surgical instrument 77 and displays 5118 incompatible usage alerts according to the state of the usage of the surgical instrument 77. If the tissue is out of range, the processor 85 displays 5116 a tissue out of range alert on the augmented reality display 8. If the tissue is incorrectly balanced within the jaws of the surgical instrument 77, the processor 85 displays 5118 an incorrect balance alert on the augmented reality display 89. As part of determining 5104 the usage of the surgical instrument 77, the processor 85 determines if the tissue capture between the jaws of the surgical instrument 77 is complete and if not displays 5110 an alert of incomplete tissue capture.

According to the method 5000, the processor 85 determines 5122 collateral events such as tissue tension and foreign object detection. If the processor 85 determines 5124 that the tissue tension is too high, the augmented reality display 89 displays 5126 a tissue tension alert. If the processor 85 detects 5128 a foreign object in the jaws of the surgical instrument 77, the augmented reality display 89 displays 5130 a foreign object detected alert. In any case, the augmented reality display 89 displays 5132 the surgical instrument 77 status overlay according to the results of the above mentioned determinations of tissue tension and foreign object detection. Finally, the augmented reality display 89 displays 5134 the surgical instrument 77 indication.

In accordance with either the method 5000, 5100 shown in FIGS. 189-190, the processor configures the data overlay to be displayed by the augmented reality display 89 as shown in FIGS. 156-188 above. Also, the augmented reality display 89 displays the dynamic status of the surgical instrument 77 function as shown in FIGS. 156-188.

Adaptation and Adjustability or Overlaid Instrument Information for Surgical Systems With reference also to FIGS. 1-188, FIG. 191 is a diagram of an augmented reality method 5150 employing a surgical instrument 77 and an augmented reality display 89 for use during a surgical procedure, according to one aspect of this disclosure. The method 5100 may be employed in conjunction with any of the augmented displays shown in FIGS. 131-168, 170-182, 184-186, and 188 and may be implemented with any of the systems shown in FIGS. 1-10, 169, and 183.

In one aspect, the method 5150 is directed to a functional overlay of surgical instrument 77 critical operations or parameters to clearly represent the surgical instrument 77 (e.g., surgical the stapler, energy device) or any aspect of the interaction between the surgical stapler 77 and tissue in the surgical area. In on aspect, the overlaid data may be adjusted by an aspect detected by the surgical hub 6 to modify the overlay from the information merely detected by the source surgical instrument 77 to add context. In another aspect, the augmented displays may be further adjusted or modified by the user and as a result also result in modifications of the surgical instrument 77 being monitored during the surgical procedure.

In one aspect, the method 5150 is directed to overlay of data according to surgical instrument 77 functionality of critical operations or parameters. According to the method 5150, an imaging device 38 captures 5152 a real image of a surgical area during a surgical procedure. A processor 85 receives 5154 functional data from the surgical instrument 77, determines 5156 an overlay related to a functional aspect of the surgical instrument 77, and combines 5158 an aspect of tissue in the surgical area with the functional data received from the surgical instrument 77. The augmented reality display 89, or local display 67, presents 5160 the overlay of the functional aspect of the surgical instrument 77 or an aspect of the interaction of the surgical instruments 77 with the tissue onto the real image of the surgical area. The functional data for the surgical instrument 77 may be received from the surgical instrument 77 directly or a surgical hub coupled processor or server. In one aspect, the processor 85 may modify 5162 the overlaid data by an aspect detected by a surgical hub to provide context regarding the surgical procedure. In another aspect, the processor 85 may modify 5164 the function of the surgical instrument based on the user modification 5162.

In accordance with the methods 5000, 5100, 5150 shown in FIGS. 189-191, the processor configures the data overlay to be displayed by the augmented reality display 89 as shown in FIGS. 156-188 above. Also, the augmented reality display 89 displays the dynamic status of the surgical instrument 77 function as shown in FIGS. 156-188.

With reference to FIGS. 1-191 above, the disclosure now turns to a description of a visual overlay of data specific to conditions or instruments used that need data feed to the user for context. Adaptation and adjustability of overlaid instrument information includes functional overlay of instrument critical operations or parameters to clearly represent a surgical stapler, energy device, or aspects of its interaction. In one aspect, the overlaid data is adjusted by an aspect detected by the surgical hub to modify the overlay from the information merely detected by the source instrument to add context. In another aspect, the displays may be adjusted or modified by the user and as a result also result in modifications of the instrument being monitored operation. The visual overlay provides information associated with procedural step or plan interaction, calculated or processed feedback or forecasting, adjustments of the visual overlay based on detected parameters, control of the overlay of the data onto a surgical site visualization stream including options for controlling location, size, placement, and coupling to moving objects within the field of view, and an overview visual overlay of instruments within the filed of view of the overlying device (i.e., AR device, AR glasses, etc.).

In one aspect, the visual overlay includes a procedural step or plan interaction according to one aspect of this disclosure includes utilization of the visual overlay onto the AR device 66 such as AR glasses or other augmented screen or local display 67 to display next or missing elements for the next procedural step based on the system's situational awareness as described in FIG. 11 above. The visual overlay provides highlights for surgeons. The visual overlay also provides highlighting for OR nurses or other staff. Virtual instrument templates for OR set up and the use of AR devices 66 such as AR glasses with AR device cameras 79 for scanning and introduction and removal of product. The visual overlay also highlights product that is necessary for the next surgical step and the way an instrument was handed to a nurse for reloading. The AR device 66 looks at the status of the current procedure with the next logical cartridge for use based on the procedure and understanding of the situational awareness and identifies and highlights it within the field of vision of the user.

Additional aspects of procedural step or plan interactions are described in U.S. patent application Ser. No. 16/729,740, filed Dec. 30, 2019, titled Visualization System Quantitative Data Overlaid With Data From At Least One Instrument Function Of A Powered Instrument In Communication With The System, which is incorporated herein by reference in its entirety. In particular reference is made to FIGS. 24, 25A-B, 30, 32A-D, 34, 35, and 36A-C and associated description, for example. Additional examples may be found in U.S. Pat. No. 9,788,907B1, filed Apr. 24, 2017, titled Automated Provision Of Real-Time Custom Procedural Surgical Guidance; US20190279524A1, filed Mar. 6, 2019, titled Techniques For Virtualized Tool Interaction; U.S. Pat. No. 10,758,309B1, filed Jul. 15, 2019, titled Methods And Systems For Using Computer-Vision To Enhance Surgical Tool Control During Surgeries; U.S. Pat. No. 10,729,502B1, filed Feb. 21, 2019, titled Intraoperative Surgical Event Summary; each of which is herein incorporated by reference in its entirety.

The visual overlay includes a calculated, processed feedback, or forecasting technique according to one aspect of this disclosure. In one aspect, the visual overlay includes projecting the path of the surgical instrument 77. For example, endoscopic assisted overlay to laparoscopic view and overlay laparoscopic to endoscopic view. Another aspect includes projecting the position of a robotic arm.

In one aspect, the calculated, processed feedback, or forecasting technique provides a separate visual overlay to an assistant at bedside of the manual motion needed for assistance in a robotic case. This may include providing a separate visual overlay to assist liver retractor repositioning needs, micromanipulator portion of manual handles up down or left right, or stapler position of manual handles up down or left right.

In one aspect, the calculated, processed feedback, or forecasting technique provides a projected overlay of a surgical stapler. For example, the system may provide a projected cut line overlay, a firing delay countdown timer, force on the knife, or forecast the articulation angle. The projected cut line overlay may include path overlay, cut length overlay, or staple cartridge length.

In one aspect, the calculated, processed feedback, or forecasting technique provides a projected overlay of an energy device. The projected overlay of the energy device may include impedance calculations, straight jaw or curved jaw, or forecast articulation angle. Additional aspects, include providing an overlay of a surgical stapler countdown timer and impedance calculations.

Additional examples of calculated, processed feedback, or forecasting techniques may be found in US20200237452A1 filed Feb. 20, 2020, titled Timeline Overlay On Surgical Video; US20200268469A1 filed Feb. 27, 2020, titled Image-Based System For Estimating Surgical Contact Force; US20200268472A1 filed Feb. 27, 2020, titled Estimating A Source And Extent Of Fluid Leakage During Surgery; US20190201102A1 field Nov. 6, 2018, titled Hub Recommendations From Real Time Analysis Of Procedure Variables Against A Baseline Highlighting Differences From The Optimal Solution (in particular FIGS. 17-19 and associated description); and U.S. Pat. No. 10,878, 966B2 filed Aug. 13, 2018, titled System And Method For Analysis And Presentation Of Surgical Procedure Videos; each of which is herein incorporated by reference in its entirety.

In one aspect, the visual overlay provides a method for adjusting the visual overlay based on detected parameters. One method for adjusting the visual overlay based on detected parameters includes detecting an aspect of a procedure or instrument to trigger adaptations of the data overlaid. One aspect provides an algorithm for aligning the optical axis of the camera to the orientation of the instrument. The algorithm may include automating angle change based on surgical task.

Another method for adjusting the visual overlay based on detected parameters includes an algorithm for compensating the AR depth. In one aspect, the algorithm includes adjusting a superimposed image by monitoring the surgeon 73 focus to auto adjust the depth of the augmented information. The algorithm also may include adjusting the focus, depth, or zoom by adjusting the missing elements algorithmically. The algorithm also may include using a structured light surface 3D model to augment onto.

Another method for adjusting the visual overlay based on detected parameters includes displaying base information when a device is active or connected. For all devices, the display may include device name, device manufacturer, device status such as, for example, ready or faulted. For surgical stapler devices, the display may include cartridge installation status or cartridge firing status. For energy devices, the display my include energy settings such as power level settings, mode of operation such as advanced hemostasis, minimum power, maximum power, and current mode of operation being used.

Another method for adjusting the visual overlay based on detected parameters includes an algorithm for handling alerts that appear in portions of the display screen that are out of focus. In one aspect, the algorithm includes adjusting the focus or resolution of the portion of the display where the alert is occurring even if it is outside the direct in-situ portion. In the case of tissue tension issues that are detected during colon mobilization, for example, macro tissue tension is due to pulling on the colon causing the detected tension to occur away from the in-situ interaction visualization of the laparoscope. The tension indication may create an adjustment in the focus, clarity, or breadth of the view or it could indicate in which direction the event is occurring outside of the field currently being viewed.

Another method for adjusting the visual overlay based on detected parameters includes an algorithm for overlaying information that has not been adjusted or modified. The information may include device name and serial number. The overlaid information may be in the form of static or dynamic data.

Another method for adjusting the visual overlay based on detected parameters includes an algorithm to enhance instrument performance by requiring more focus in the short term to ensure a complete task. For example, while a surgical stapler is cutting through thick tissue. Cutting through thick tissue causes the surgical stapler to slow down. The system detects this slow down and adjusts the overlay to highlight the surgical stapler, specifically, the knife location and the knife speed. This highlighting is to pull the surgeon's focus to the surgical stapler. The surgeon may determine that with the current circumstances, a cutting pause is the best course of action.

Another method for adjusting the visual overlay based on detected parameters includes an algorithm to improve the view when smoke fills the peritoneal cavity making the view from the laparoscopic camera difficult to see. The algorithm may include overlaying an infrared view while smoke is clouding the image.

In one aspect, the visual overlay provides a method for controlling the visual overlay of data onto a surgical site visualization stream. The method includes options for controlling location, size, placement, and coupling to moving objects within the field of view. The visual display also provides adaptability of aspects of the overlaid data to enable customization of the overlay.

One method for controlling the visual overlay of data onto a surgical site visualization stream includes a Simultaneous Localization and Mapping (SLAM) technique. The SLAM technique provides a framework for building a map of unknown location and unknown environment and determining an actual position within the map. The SLAM technique localizes sensors with surroundings (sensor signal processing) and maps environment structure (pose-graph optimization). Sensors provide a digital map of unknown environment and optimize the digital map based on continuous input of data and optimization of data as the wearer moves around the space.

A visual SLAM acquires images from cameras/images sensors using sparse and dense methods. A sparse method matches feature points. A dense method controls the brightness of images.

A light detection and ranging (LiDAR) SLAM employs a laser/distance sensor and is more precise and faster than a visual SLAM but not as detailed. Matching point clouds provide an iterative closest point and normal distributions transform. For example, Google's driverless cars uses LIDAR to acquire information on its local surroundings and (coupled with Google map information) makes determinations on driving based on mapping of surroundings.

A fused method adds in other data sources such as inertial measurement unit (IMU), global positioning system (GPS), etc. In accordance with a fused method, additional known information and mapping can be overlaid with the created mapping to provide additional information to the wearer.

One method for controlling the visual overlay of data onto a surgical site visualization stream includes controlling an overlay through a dedicated device. A single function device may be configured to provide dedicated control of the overlay (and only the overlay). As shown in FIG. 36, a touchscreen interface may be employed to control features of the display.

One method for controlling the visual overlay of data onto a surgical site visualization stream includes controlling an overlay through a multifunction device. A multifunctional device may be configured to support multiple different applications or functions that, in addition, enable control of the display.

One method for controlling the visual overlay of data onto a surgical site visualization stream includes controlling specific features within an overlay. One example includes controlling overlay transparency. Another example includes controlling overlay size to enable the clinical user to change the size of the images or elements that may be overlaid onto the screen to accommodate user preferences. Another example includes controlling font size to enable the clinical user to change the size of any text that may be overlaid onto the display to accommodate user preferences. Another example includes contextual control features. This method includes employing a configurable panel that changes dynamically based on the selected area of a window on the display. Another example includes controlling alerts and warnings. This method employs buttons to select the alignment and location of where the alerts and warnings may be presented as shown in FIG. 50. Additional features include information and case metrics that may be controlled within the overlay.

One method for controlling the visual overlay of data onto a surgical site visualization stream includes controlling elements of an overlay to provide contextualized help. The overlay includes user selected buttons and automatic prompting based on user actions. This may be helpful when a user incorrectly attempts to select a feature.

One method for controlling the visual overlay of data onto a surgical site visualization stream includes controlling and interacting with the overlay from surgeon audio commands. The surgeon may call out the desired visual overlay to be overlaid onto the main display monitor. For example, the surgeon may call out a command such "patient vitals overlay," "surgical stapler overlay," or "ultrasonic overlay" to cause these overlays to be overlaid onto the main display. In one aspect, the system may employ personal tracking aspects to distinguish between the different users in the operating room.

In one aspect, the visual overlay provides a method for providing an overview visual overlay of instruments within the filed of the overlaying device such as the AR device 66, for example. The visual overlay may be configured to provide an overview status of the devices, main configurations or users, and identification of devices to the user. The visual overlay also may be configured to provide intractable controls of the overview data that enables interactive setup of the device or reconfiguration.

FIG. 192 is an image of a staff view screen 5600 displaying customized overlays information. The staff view screen 5600 displays primary surgical display 5602 that enables customization of surgical overlays and includes three main screen portions. A first screen portion 5604 displays a surgeon preset to enable entering surgeon presets or default settings that can be saved, changed, or deleted. The first screen portion 5604 also includes a section that enables display overlays to turned On or Off and an overlay size portion that enables the adjustment of the primary surgical display 5602 from smaller to larger in three settings of Small, Medium, and Large.

A second screen portion 5606 of the primary surgical display 5602 is display to the right of the first screen portion. The second screen portion 5606 displays case information and overall device use date and enables editing the display of the case information. A right chevron 5612 can be tapped to access more granular ability to turn on/off individual overlays. A virtual switch slider button 5612 is used to turn on/off a group of overlays.

A third screen portion 5608 of the primary surgical display 5602 is displayed below the second screen portion 5606. The third screen portion 5608 displays energy panels and device alerts, and enables editing the display of the device panels. Similar to the second screen portion 5606, the third screen portion 5608 includes a right chevron 5616 that can be tapped to access more granular ability to turn on/off individual overlays and a virtual switch slider button 5618 to turn on/off a group of overlays.

A fourth screen portion 5610 of the primary surgical display 5602 is displayed below the third screen portion 5608. The fourth screen portion 5610 displays all system notifications and enables editing of the system notifications. Similar to the second and third screen portions 5606, 5608, the fourth screen portion 5610 includes a right chevron 5620 that can be tapped to access more granular ability to turn on/off individual overlays and a virtual switch slider button 5622 to turn on/off a group of overlays.

Tappable icons are provide at the bottom of the primary surgical display 5602 to provide additional functionality. For example, one tappable icon 5624 enables navigation to staff view screens.

FIG. 193 is an image of a staff view screen 5700 displaying detailed customization pop-up information. The staff view screen 5700 displays an edit case overlay screen 5702 over the primary surgical display 5602 screen. The edit case information overlay screen 5702 allows the ability to turn on/off individual overlay components. The edit case information overlay screen 5702 includes a series of virtual switch slider buttons 5704 to enable editing the patient first and last name, the surgeon first and last name, the time and date of the case (e.g., surgical procedure), the case time, number of instrument activations, or staple firings, for example.

FIG. 194 is an image of a staff view screen 5800 displaying staff view troubleshooting pop-up information. The staff view screen 5800 displays a staff view troubleshooting pop-up screen 5802 to provide troubleshooting information about system devices and components. A tappable icon 5084 provides device connection status and indicates if the system is properly connected to other capital equipment or devices. The troubleshooting pop-up screen 5802 shows a check ultrasonic connection generator error screen with a static image 5806 of an ultrasonic generator 5808. Additional troubleshooting screens with static images, gifs or animations may be provided. Troubleshooting screens may have multiple steps or multiple screens that a user can advance (not illustrated).

FIG. 195 is an image of a primary surgical display interactions screen 5900 displaying primary surgical display interactions. The primary surgical display interactions screen 5900 shows an instruments panel behavior screen 5902 with an overlay screen 5904 comprising three sections. A first section of the overlay screen 5904 shows device activation information including an instrument activation default panel 5906 and an instrument minimum active panel 5908. Information includes panel background changes from dark to light in activated state and active mode shown in dark text and inactive mode shown in faded opacity, for example.

A second section of the overlay screen 5904 shows instrument disable activation information including an instrument disable activation panel 5910, an alarm status panel 5912, and a disabled instrument panel 5914. When certain alarms are triggered, the instrument panel is grayed out to indicate that activation is disabled. This may apply only when the user is locked out of the device due to alarm status.

A third section of the overlay screen 5904 shows minimize information including a generic instrument default panel 5916 and a minimized panel 5918. The panels are minimized to a predetermined size after a predetermined period. The instrument type remains on the panel and the panel returns to default view when activation or notification occurs.

Situational awareness is the ability of some aspects of a surgical system to determine or infer information related to a surgical procedure from data received from databases and/or instruments. The information can include the type of procedure being undertaken, the type of tissue being operated on, or the body cavity that is the subject of the procedure. With the contextual information related to the surgical procedure, the surgical system can, for example, improve the manner in which it controls the modular devices (e.g., a robotic arm and/or robotic surgical tool) that are connected to it and provide contextualized information or suggestions to the surgeon during the course of the surgical procedure.

Mixed Reality Feedback Systems that Cooperate to Increase Efficient Perception of Complex Data Feeds One aspect of the following disclosure describes various overlays of surgical instrument operational aspects or functions onto a live video stream of a surgical area as visualized through a laparoscopic camera surgical field of view during a minimally invasive surgical procedure. The overlay is related to the operation of one of the surgical instruments or devices being actively visualized. The overlays combine aspects of tissue/organ interaction with functional data received from surgical instruments used in the surgical procedure. Surgical instruments may include graspers, clamps, staplers, ultrasonic, RF, or combination of each of these instruments. In regard to graspers and clamps, aspects of tissue parameters may include incomplete capture of the tissue along with the status of the clamp or magnitude of the clamp. In regard to a surgical stapler, aspects of tissue parameters may include tissue capture location, tissue compression, clamping, or firing sufficiency of a surgical stapler. In regard to advanced energy devices, such ultrasonic or RF devices, aspects of tissue parameters may include impedance, cautery status, bleeding magnitude, and aspects of instrument function may include energy level, timing, clamp pressure, among others, for examples. The augmented images shown in FIGS. 196-198 hereinbelow may be viewed on a local display, a remote display, and/or an AR device as described hereinabove in connection with FIGS. 1-10. Although the augmented images are described as being visualized through a laparoscopic camera during a minimally invasive surgical procedure, the images may be captured during non-invasive and invasive (e.g., open) surgical procedures without limiting the scope of this disclosure in this context. These aspects are described hereinbelow.

FIGS. 196-198 describe various augmented images visualized through a laparoscopic camera during a minimally invasive surgical procedure. An augmented reality display system is used during a surgical procedure. The augmented reality display system comprises an imaging device to capture a real image of a surgical area during the surgical procedure, an augmented reality display to present an overlay of an operational aspect of a surgical instrument onto the real image of the surgical area, and a processor. The overlay is related to the operational aspect of the surgical instrument being actively visualized. The overlay combines aspects of tissue interaction in the surgical area with functional data from the surgical instrument. The processor is configured to receive the functional data for the surgical instrument, determine the overlay related to the operation of the surgical instrument, and combine the aspect of the tissue in the surgical area with the functional data from the surgical instrument. The augmented images indicate alerts relative to device performance considerations, alerts of incompatible usage, alerts on incomplete capture. Incompatible usage includes tissue out range conditions and tissue incorrectly balanced within the jaws of the end effector. Additional augmented images provide an indication of collateral events including indication of tissue tension and indication of foreign object detection. Other augmented images indicate device status overlays and instrument indication.

FIGS. 196-198 also describe functional overlays of instrument critical operations or parameters to clearly represent the surgical stapler, energy device, or aspects of its interaction. In one aspect, the overlaid data is adjusted by an aspect detected by the surgical hub to modify the overlay from the information merely detected by the source instrument to add context. In another aspect, the displays may be adjusted or modified by the user and as a result also result in modifications of the surgical instrument being monitored operation.

FIGS. 196-198 describe an intraoperative display system for use during a surgical procedure. The system comprises a surgical monitor with an intraoperative data display of a surgical area. An advanced energy generator is coupled to an advanced energy surgical instrument. The advanced energy surgical instrument employs radio frequency (RF) energy and ultrasonic energy during a surgical procedure on a patient. A surgical hub is coupled to the advanced energy generator and to the surgical monitor. The surgical hub provides a live feed of the surgical area to the surgical monitor to display the live feed of the surgical area by the intraoperative data display. The intraoperative data display displays a view of the surgical area including the advanced energy surgical instrument grasping tissue and a panel overlay that displays information specific to the advanced energy surgical instrument.

One aspect, the intraoperative data display shows an end effector of the surgical instrument grasping tissue and a panel overlay displaying case information, systems notifications, or device panels, or any combination thereof, overlaid over the live surgical feed. A location, opacity, size and placement of the panel overlay is customized. The panel overlay is configured to be turned on or off individually or turned on/off as a group. The panel overlay is further configured to change dynamically to show state changes such as device activation or power level adjustment. The panel overlay depicts optimal device performance (ODP) guide images or other instructions for use (IFU)/informational sources.

In various aspects the panel overlay comprises at least one of data input information from capital equipment, generators, insufflator, smoke evacuator, electronic health record, laparoscope, computer, surgical devices, wired and wirelessly connected devices, surgeon profile preferences that may be saved, recalled or edited, or any combination thereof. The panel overlay may include case information including at least one of Patient Name, Surgeon Name, Case Time, or Instrument Activations, or combinations thereof. The panel overlay may include system notifications including at least one of connect instrument status, minor error alert, medium error alert, or major error alert, or any combination thereof. The panel overlay may include information associated with the surgical instrument connected to the system to provide advanced hemostasis. The panel overlay may include a visible patient panel overlay. The panel overlay may include a device panel overlay comprising at least one of device name, device settings, or device supplemental features, or any combination thereof. The panel overlay may include a plurality of panel overlays in a stacked configuration. The panel overlay may include a plurality of panel overlays in an expanded configuration. The panel overlay may display device troubleshooting information. The panel overlay may display at least one of alerts, warnings, device information, or device features, or any combination thereof.

In another aspect, the intraoperative data display comprises a secondary configurable panel. The secondary configurable panel changes dynamically based on the selected customized laparoscopic overlay fields displayed in the surgical field of view of a live surgical feed area of the intraoperative data display. The customized laparoscopic overlay fields comprise at least one of a bottom edge panel, a top left corner panel, a top center panel, or a side edge panel, or any combination thereof.

FIG. 196 is a system diagram 3000 of a surgical suite comprising a surgical monitor with intraoperative data display 3002 of a surgical area. An advanced energy generator 3004 is coupled to a surgical hub 3006 and to an advanced energy surgical instrument 3008. The advanced energy surgical instrument 3008 employs RF energy and ultrasonic energy during a surgical procedure on a patient 3010. The surgical hub 3006 provides a live feed 3014 of the surgical area, which is displayed by the intraoperative data display 3002. The intraoperative data display 3002 displays a view of the surgical area including the advanced energy surgical instrument 3008 grasping tissue and a panel overlay 3012 that displays information specific to the advanced energy surgical instrument 3008.

FIG. 197 is an augmented image 300 of a live feed of a surgical area 324 as visualized through a laparoscopic camera during a minimally invasive surgical procedure indicating tissue 322 insufficiently captured between the jaws 318 of a surgical instrument end effector 320 as a tissue aspect. The laparoscopic field of view 302 of the surgical area 324 shows a surgical instrument end effector 320 grasping tissue 322 with the jaws 318 of the end effector 320. The augmented image 300 shows a graphical alert overlay 304 superimposed on the image of the surgical area 324 to indicate insufficiently captured tissue 322 relative to the end of cut in the jaws 318 of the end effector 320.

The augmented image 300 also comprises a first sub image 308 showing a graphic image 306 of the general anatomy superimposed on or adjacent to the surgical field of view 302 and a reference frame 310 of the actual anatomy superimposed on or adjacent to the surgical field of view 302. The augmented image 300 also comprises a second sub image 312 showing the type of surgical instrument in use, the energy level if applicable, and the current surgical procedure. The second sub image 312 may be superimposed on or located adjacent to the surgical field of view 302. The augmented image 300 shows an ultrasonic surgical instrument being used in a surgical procedure at an energy level set to 5 Max to achieve advanced hemostasis. A graphic image 316 of the surgical instrument is shown superimposed on a graphic image 314 of the incomplete tissue capture alert overlay 304. Accordingly, the augmented image 300 provides several virtual objects that inform the OR team of insufficiently captured tissue 322 relative to the end of cut. The superimposed incomplete tissue capture alert overlay 304 applies to energy based surgical instruments as well as surgical stapler instruments, and the like.

FIG. 198 is an augmented image 3120 of a live feed of a surgical area as visualized through a laparoscopic camera during a minimally invasive surgical procedure displayed on an intraoperative data display 3122. showing an end effector 3108 of a surgical instrument 3008 grasping tissue 3110 and a screen with a visible patient panel overlay 3124, according to one aspect of this disclosure. The visible patient panel overlay 3124 may require an additional application to display content. The intraoperative data display 3122 also displays the case information panel overlay 3102 and the device panels overlay 3106. In the illustrated example, the systems notifications panel overlay 3104 is hidden.

The following description provides an alternative or cooperative extended reality communication to provide intuitive or data dense feeds of information to the surgeon or other OR personnel. In one aspect, the present disclosure provides a mixed reality, extended reality, and/or augmented reality feedback system and method that cooperate to increase efficient perception of complex data feeds. In one aspect, a first and a second augmented data feed is provided where at least one of the first or second data feeds generate overlays that are not part of a visual display. In another aspect, the visual display portion of a data feed or overlay may involve multiple cooperative image display systems that work in series with each other or are independently located. In another aspect, the non-visual communication of data may be through alone or a combination of audible, somatosensory, tactile, chemical (including smell), or thermal perception by the user. The present disclosure now describes a cooperative extended reality, mixed reality, or AR communication that includes a cooperative combination of one or more than one audible overlays and/or somatosensory overlays in cooperation with one or more than one visual overlays. Each of these cooperative overlays is described hereinbelow.

FIG. 199 illustrates an augmented reality system 5400 comprising an intermediate signal combiner 64 positioned in the communication path between an imaging module 38 and a surgical hub display 67. The signal combiner 64 combines sensor and/or image data received from an imaging module 38 and/or an AR device 66. The surgical hub 56 receives the combined data from the combiner 64 and overlays the data provided to the display 67, where the overlaid data is displayed. The AR device 66 combines data feeds from an imaging device 68 and a sensor device 5402. The combined data feeds may be provided from the AR device 66 to the combiner 64 for further overlaying with data feeds from the imaging module 38. In one aspect, a visual portion of an augmented overlay comprises multiple cooperative image displays. In one aspect, the multiple cooperative image displays work in series with each other. In another aspect, the multiple cooperative image displays are independently located. In various aspects, the data feeds may be provided by the sensor 90, speaker 91, and haptic controller 92 portions of the AR device 66.

The imaging device 68 may be a digital video camera. The signal combiner 64 may comprise a wireless heads-up display adapter to couple to the AR device 66 placed into the communication path of the display 67 to a console allowing the surgical hub 56 to overlay data on the display 67. In various aspects, the AR device 66 may display combinations of images, audible sounds, and/or somatosensory signals from the imaging module 38, the imaging device 68, and/or the sensor device 5402 in the form of overlays as part of the view provided to the surgeon as discussed hereinbelow. In various aspects, the display 67 may display combinations of images, audible sounds, and/or somatosensory signals from the imaging module 38, the imaging device 68, and/or the sensor device 5402 in the form of overlays as part of the view provided to the OR in general as discussed hereinbelow. In one aspect, the sensor device 5402 may be coupled to the AR device 66 via a filter 5404. In other aspects, an amplifier 5406 may be placed between the filter 5404 and the AR device 66 to amplify signals from the sensor device 5402.

The sensor device 5402 may be an audio device, a somatosensory device and/or combinations thereof. Somatosensory devices include, without limitation, thermal, chemical, and mechanical devices as discussed hereinbelow. In one aspect, the sensor device 5402 may be configured to sense a variety of audible input signals such as voice 5408, bio-markers 5410, beat/cadence 5412, among others. The audible signals may be filtered by the filter 5404 and amplified by the amplifier 5406. In one aspect, the surgeon 73, or other OR personnel, may receive stimulus inputs from a variety of somatosensory stimuli such as thermal stimulus 5414, chemical stimulus 5416, mechanical stimulus 5418. The audible inputs may be overlaid with images received from the imaging device 68 and/the imaging module 38. Similarly, somatosensory stimulus inputs may be overlaid with images received from the imaging device 68 and/the imaging module 38. The audible and somatosensory overlays may be displayed in the AR device 66 and/or the display 67.

In one aspect, the present disclosure provides an audible overlay based on an audible signal generated by the sensor device 5402. The audible signal may be filtered by the filter 5404, excluding or amplifying certain OR audio over others, and amplified by the amplifier 5405, for example. Filtering may increase or decrease the attentiveness of an overlay to control the magnitude of the user's attention to it. In one aspect, the sensor device 5402 receives voice commands and converts the voice commands into electrical signals. In one aspect, the sensor device 5402 includes a speech-to-text converter. The filter 5404 may be configured to filter specific commands to an OR assistant such as to position manual handles up/down or left/right for assistance to the surgeon 73 at a robot console, for example. In another aspect, filtering or amplifying may be based off of key words the surgeon 73 may speak during the surgical procedure.

The audible overlay provides an alternative way to help verify where in the procedural plan the surgeon 73 is located. For example, if the augmented reality system 5400 knows that the next step in the surgical procedure will require a grasper to move an organ for access, when the surgeon speaks the word "grasper," the augmented reality system 5400 can verify that the surgeon 73 and the surgical procedure are tracking appropriately. This additional control may be required when the surgeon 73 deviates slightly from the initial surgical procedure. For example, as the surgeon 73 requests a surgical instrument, such as surgical stapler, the augmented reality system 5400 recognizes the word "surgical stapler" or simply "stapler" and adjusts the surgeon's 73 main screen 67, or AR device 66, with the specific combination of visual and audible overlay for the digitally connected surgical instrument placement and firing. The augmented reality system 5400 further performs a pre-use check of the surgical instrument and communications prior to the surgeon 73 firing the surgical instrument. The volume of the audible overly portion may be increased or decreased based on the severity of the situation. The augmented reality system 5400 may be configured to turn down the volume of all background noise (e.g., radio, phones, etc.) if the current surgical procedure situation is deemed critical or a high risk. Knowing that a particular user is hearing challenged, the augmented reality system 5400 could respond by increasing the volume or adjusting the pitch to help the surgeon 73 can hear clearly.

In another aspect, surgical procedure specific filtering may be employed to isolate the audio to a specific surgical procedure. This type of filtering may be decided based on a risk-benefit analysis and assessment of the historical risks of the specific surgical procedure. For example, if the specific surgical procedure is a cholecystectomy, the need for the surgeon 73 to be tuned into the patient's heart rate and blood pressure are relatively low. Given the short surgical procedure time in combination with low risk of intra-operative complications, the augmented reality system 5400 could conclude, after a risk assessment calculation, that there is no reason that the surgeon 73 would need an audible overlay. The surgeon 73, however, can override the augmented reality system 5400 to mandate the presence of the audible overlays and other cooperative overlays.

In another aspect, the audible overlay may include overlaying audibly correlated feedback to certain patient bio-marker 5410 data. The bio-marker 5410 data may be the patient's heartbeat and the corresponding audible overlay of the patient's heartbeat enables the surgeon 73 to listen to the patient's heart as if he/she was using a stethoscope. Overlaying a sensed nerve stimulation may be employed to determine proximity and overload of a nerve. This could be done by increasing or decreasing both the volume and frequency of the audible overlay to enable the surgeon 73 to correlate electrical instrument location with the critical nerve.

In yet another aspect, the audible overlay may include overlaying a pre-defined beat/cadence 5412 to enable the surgeon to align with physical reactions. The beat/cadence 5412 can be further aligned to a key cadence off the surgical procedure or patient. Audible indication of unwanted tissue contact from a robotic surgical device that is outside of the surgical field of view.

In one aspect, the present disclosure provides a somatosensory overlay based on an somatosensory one or more than one somatosensory signal detected either by the sensor device 5402 or the surgeon 73. In certain aspects, somatosensory signals may be received by the sensor device 5402, filtered by the filter 5404, and amplified by the amplifier 5406, for example. The somatosensory signal may be employed as a cooperative somatosensory overlay with any of the audible overlays and/or image overlays described herein.

In one aspect, the somatosensory signal may be a thermal signal received by the surgeon 73 directly to stimulate certain thermoreceptors, or other non-specialized sense receptor, or the receptive portion of a sensory neuron, that codes absolute and relative changes in temperature, primarily within the innocuous range. The change in temperature of a surgical instrument handle or a portion of the handle enables the surgical instrument handle to be used as a proxy for the temperature of a related component of that surgical instrument. For example, with reference also to FIG. 9, in certain motorized surgical staplers 77, the motor and gearbox are located within the handle of the surgical stapler 77. This is the same area the surgeon 73 uses to hold and actuate the surgical stapler 77. This area will increase in temperature as the surgical stapler 77 is used. The temperature will be directly related to the work the surgical stapler 77 is required to perform during the surgical procedure. The surgeon 73 can feel this temperature increase during the surgical procedure. The surgeon 73 can use this physical temperature data input as a proxy to how the surgical instrument 77 is operating and will continue to operate. The handle becoming too hot to grasp is a clear indication that the surgical instrument 77 is working above its normal use. Motor heating will degrade the optimal performance of the system and this degradation may directly impact the outcome of a surgical procedural. For example, the surgical stapler may by be unable to cut/staple tissue within the clamped jaws, thus complicating the surgical procedure.

In another aspect, the somatosensory signal may stimulate certain chemoreceptors that respond primarily to chemical stimuli in the OR environment. These may be sensed by surgeon's 73 senses of taste and smell, for example, the surgeon 73 may smell burning electronics and as a result indicate turning off the surgical instrument as needed. In certain aspects, the somatosensory signal may be detected by the sensor device 5402 and as a result may be used to generate a somatosensory overlay in cooperation with any one of the audible overlays and/or image overlays.

In another aspect, a somatosensory signal may stimulate certain mechanoreceptors that respond primarily to touch, haptic, or vibratory stimuli, among others. In one aspect, a mechanical vibration of oscillation of a surgical instrument may be detected either by the surgeon 73 or the sensor device 5402. The sensed mechanical vibration of oscillation is employed by the augmented reality system 5400 to indicate that the present motion or direction of the surgical instrument 77 has a non-optimum outcome related to it and thus would require correction. The augmented reality system 5400 may be configured to indicate, at the end of the current drive/cut stroke, that the drive was "out of the ordinary." This may be an indication that the clamping force of the jaws of the surgical stapler 77 was out of range or the force to fire was higher than expected. These conditions may be indicated by a series of haptic buzzes to differentiate different indications. In one example, vibration at the end of a stroke of a surgical stapler 77 may indicate that the surgical stapler 77 cannot move any further in the indicated direction. In another example, vibration of the handle may indicate that a "hot blade" of an energy based surgical instrument is about to touch collateral tissue and thus avoid critical structures. A certain type of vibration may indicate that a robotic arm is at maximum extension. The augmented reality system 5400 may be configured to provide a haptic pulse sequence to alert the surgeon 73 that a maximum value has been reached.

In another aspect, the mechanoreceptors may respond to variations of the actuation force threshold of a surgical stapler. The variation in actuation force provide feedback to the user that it is lees desirable to actuate the surgical stapler 77 at this particular time. For example, during an initial clamping of the jaws on tissue with a surgical stapler 77, the surgeon 73 is physically able to feel how hard it is to clamp down on the tissue within the jaws. This direct physical input along with a sensor reading displaying a "measured" value would give two different inputs to this value.

In another aspect, the mechanoreceptors may respond to extendable stimulate elements to indicate the undesirability of using that control. The extendable portions could be extendible patterns that provide a differing "feel" rather than merely a column or cleat. For example, the knife of a surgical stapler 77 is partially extended and the surgeon 73 tries to release the closure system and the extendable elements activate on the release button indicating that it cannot be actuated at this time or in this sequence. The extendable portions could be extendible patterns that provide a differing "feel" rather than merely a column or cleat.

In another aspect, the mechanoreceptors may respond to force feedback to disable or disallow an action from being performed. For example, as a surgeon 73 attempts to fire a surgical stapler 77, the surgical hub detects a foreign object currently located within the jaws. Then, as the surgeon 73 attempts to pull the fire trigger, the device pushes back on the trigger, disallowing the surgeon to depress it.

In another aspect, a combination of multiple somatosensory outputs may be employed simultaneously to communicate interrelated data feeds. One skilled in the art would appreciate that the need to differentiate between two separate indications that both have the same standard feedback mode. In one aspect, one system feedback may indicate that it cannot be used based on the state of another system. In another aspect, backlit LEDs may be located within the control to indicate lack of function. The LEDs should be configured to clearly indicate two separate failures or states. Furthermore, the LED system is configured to resolve conflict between the multiple similar indicators activated simultaneously. Force sensing may be provided to OR assistant when inserting a circular stapler or rectal sizer.

In another aspect, the displays 67 within the OR may be employed to indicate between failure or indication. The overlay is displayed without interfering with the key displayed information. In one aspect, the overlay information is displayed around the border of the perimeter of the primary display 67 to reduce interference, and can change color with identification of tissue.

In another aspect, the somatosensory overlay may include an alternative feedback for device interactions based on the AR device 66 haptic feedback such as, for example, instrument collision, notification of imminent inadvertent tissue contact, elevated temperature instrument contact with adjacent tissue, heated glove combined with vibration to ensure the output is clearly conveyed, and/or advanced energy device completion of cycle. Yu et al. (Nature 575, 473-479; 2019), which is herein incorporated by reference, describes wearable skin-integrated technology that adheres to skin and can vibrate. These devices include 1.4 g, 12 (Nature 575, 473-479; 2019), which is herein incorporated by reference, describes wearable skin-integrated technology that adheres to skin and can vibrate. These devices include 1.4 g, 12-18 mm sized actuators that are wirelessly powered and controlled.

In another aspect, the somatosensory overlay may include visual feedback. The visual feedback somatosensory overlay may be used to indicate completion of cycle of an advanced energy device, incompatible assembly of systems, and unusable device in current configuration. Additional overlays include audible feedback through speakers. Safe overlays may be provided for handheld surgical instruments and robotic surgical instruments.

FIG. 200 illustrates a method 5500 of presenting an augmented overlay during a surgical procedure. With reference also to FIGS. 10 and 199, according to the method 5500, an imaging device 68 captures 5502 a real image of a surgical area during the surgical procedure. A first data feed is generated 5504 based on the captured real image. The first data feed is provided to the AR device 66. A sensor device 5402 generates 5506 a second data feed. The second data feed is also provided to the AR device 66. The AR device 66 comprising an augmented reality display 89, presents 5508 an augmented overlay based on the first and second data feeds. The augmented overlay comprises a visual portion and a non-visual visual portion.

In one aspect, according to the method 5500, the sensor device 5402 may receive a tactile signal, an audible signal, a chemical signal, or a thermal signal from one or more than one source such as voice 5408, bio-marker 5410, beat/cadence 5412, thermal stimulus 5414, chemical stimulus 5416, or mechanical stimulus 5418 sources. The tactile, audible, chemical, or thermal signals, or any combination thereof, are combined into the non-visual portion of the augmented overlay.

In one aspect, according to the method 5500, a filter 5404 may by filter signals received by the sensor device 5402. An amplifier 5406 amplifies the filtered signal.

In one aspect, according to the method 5500, a display 67 coupled to the AR device 66 displays the augmented overlay. The imaging module 38 generates a third data feed, which is combined with the augmented overlay and the combined augmented overlay is displayed on the display 67. The combiner 64 combines the third data feed with the augmented overlay. A surgical hub 56 communicates the augmented overlay to the display 67.

Various additional aspects of the subject matter described herein are set out in the following numbered examples:

Example 1: A method for presenting surgical data onto a livestream of a surgical field on a display during a surgical procedure, the method comprising detecting, by a control module, based on the display priority values, and presenting onto the livestream visual representations of the surgical data in accordance with the display arrangement.

Example 2: The method of Example 1, wherein presenting onto the livestream comprises overlaying the visual representations onto the livestream.

Example 3: The method of Examples 1 or 2, wherein the surgical data comprises first surgical data and second surgical data different than the first surgical data, wherein the first surgical data competes for presentation on the display with the second surgical data.

Example 4: The method of Example 3, wherein the display arrangement comprises an overlay arrangement of the first surgical data and the second surgical data onto the livestream based on the display priority values.

Example 5: The method of Example 3, wherein the display priority values comprise a first display priority value assigned to the first surgical data and a second display priority value less than the first display priority value assigned to the second surgical data, and wherein the display arrangement comprises overlaying the first surgical data onto the livestream but not the second surgical data.

Example 6: The method of Examples 3 or 4, wherein the display priority values comprise a first display priority value assigned to the first surgical data and a second display priority value less than the first display priority value assigned to the second surgical data, and wherein the display arrangement comprises overlaying the first surgical data onto the livestream before the second surgical data.

Example 7: The method of any one of Examples 1-6, wherein the display arrangement comprises generating different visual representations of the surgical data based the display priority values.

Example 8: The method of any one of Examples 1-7, wherein the display arrangement comprises selecting, for one or more display elements of visual representations of the surgical data, a color, a size, a shape, a display time, a display location, a display frequency, a highlighting, or a combination thereof based on the display priority values.

Example 9: The method of any one of Examples 1-8, wherein at least one of the display priority values is based on a failure to receive a parameter associated with a setting of a surgical instrument utilized in the surgical procedure.

Example 10: The method of any one of Examples 1-9, wherein at least one of the display priority values is based on a detection of an assembly of components of a surgical instrument utilized in the surgical procedure.

Example 11: The method of any one of Examples 1-10, wherein at least one of the display priority values is based on a distance in the surgical field between a critical surgical structure and a surgical instrument.

Example 12: A method for presenting surgical data onto a livestream of a surgical field on a display during a surgical procedure, the method comprising detecting, by a control module, first surgical data, generating, by a control module, a first visual representation of the first surgical data for presenting the first surgical data on the display, detecting, by a control module, second surgical data, generating, by a control module, a second visual representation of the second surgical data for presenting the second surgical data on the display, detecting, by a control module, a display conflict between the first surgical data and the second surgical data, determining, by a control module, a resolution of the display conflict in favor of one of one of the first visual representation and the second visual representation based on at least one of the first surgical data and the second surgical data, and determining, by a control module, a display arrangement of the first visual representation and the second visual representation in accordance with the resolution.

Example 13: The method of Example 12, wherein the display arrangement comprises selecting, for one or more display elements of the first and second visual representations, a color, a size, a shape, a display time, a display location, a display frequency, a highlighting, or a combination thereof.

Example 14: The method of Examples 12 or 13, wherein generating the first visual representation comprises retrieving, by a processor, a template from a memory, and populating the template with at least one value based on the first surgical data.

Example 15: A method for presenting surgical data onto a livestream of a surgical field on a display during a surgical procedure, the method comprising detecting a failure of a system resource to meet competing needs of different components of a computer-implemented interactive surgical system, in response to detecting the failure, displaying resource-allocation controls of the system resource on the livestream, displaying recommended adjustments to the resource-allocation controls, and adjusting power consumption of one or more of the different components based on user input through the resource-allocation controls.

Example 16: The method of Example 15, further comprising returning to a default resource allocation when the failure is no longer detected.

Example 17: The method of Examples 15 or 16, further comprising displaying visual content representative of the effects of the adjustments to the resource allocations.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of this disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, logic diagrams, and/or examples. Insofar as such block diagrams, logic diagrams, and/or examples contain one or more functions and/or operations, it will be understood by those within the art that each function and/or operation within such block diagrams, logic diagrams, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a control circuit, computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A method for presenting surgical data onto a livestream of a surgical field on a display during a surgical procedure, the method comprising:
- detecting, by a control module, surgical data that comprises first surgical data and second surgical data different than the first surgical data, wherein the first surgical data competes for presentation on the display with the second surgical data;
- assigning, by the control module, a first display priority value to the first surgical data and a second display priority value to the second surgical data, wherein at least one of the first and second display priority values is based on a failure to receive a parameter associated with a setting of a surgical instrument utilized in the surgical procedure;
- determining, by the control module, a display arrangement of the surgical data on the display based on the first display priority value assigned to the first surgical data and the second display priority value assigned to the second surgical data; and
- presenting, onto the livestream of the surgical field, visual representations of the surgical data in accordance with the display arrangement.

2. The method of claim 1, wherein presenting onto the livestream comprises overlaying the visual representations onto the livestream.

3. The method of claim 1, wherein the display arrangement comprises an overlay arrangement of at least one of the first surgical data or the second surgical data onto the livestream.

4. The method of claim 1, wherein the second display priority value assigned to the second surgical data is less than the first display priority value assigned to the first surgical data, and wherein the display arrangement comprises overlaying the first surgical data onto the livestream but not the second surgical data.

5. The method of claim 1, wherein the second display priority value assigned to the second surgical data is less than the first display priority value assigned to the first surgical data, and wherein the display arrangement comprises overlaying the first surgical data onto the livestream before the second surgical data.

6. The method of claim 1, further comprising:
- generating a first visual representation of the first surgical data and a second visual representation of the second surgical data based on the first and second display priority values.

7. The method of claim 1, wherein determining the display arrangement comprises selecting, for one or more display elements of visual representations of the surgical data, a color, a size, a shape, a display time, a display location, a display frequency, a highlighting, or a combination thereof based on the first and second display priority values.

8. The method of claim 1, wherein at least one of the first and second display priority values is further based on a detection of an assembly of components of a surgical instrument utilized in the surgical procedure.

9. The method of claim 1, wherein at least one of the first and second display priority values is further based on a distance in the surgical field between a critical surgical structure and a surgical instrument.

10. A surgical system comprising:

a processor configured to:
- detect surgical data that comprises first surgical data and second surgical data different than the first surgical data, wherein the first surgical data competes with the second surgical data for presentation onto a livestream of a surgical field;
- assign a first display priority value to the first surgical data and a second display priority value to the second surgical data, wherein at least one of the first and second display priority values is based on a failure to receive a parameter associated with a setting of a surgical instrument utilized in a surgical procedure;
- determine a display arrangement of the surgical data based on the first display priority value assigned to the first surgical data and the second display priority value assigned to the second surgical data; and
- present, onto the livestream of the surgical field, visual representations of the surgical data in accordance with the display arrangement.

11. The surgical system of claim 10, wherein presenting onto the livestream comprises overlaying the visual representations onto the livestream.

12. The surgical system of claim 10, wherein the display arrangement comprises an overlay arrangement of at least one of the first surgical data or the second surgical data onto the livestream.

13. The surgical system of claim 10, wherein the processor is further configured to:
- based on the second display priority value assigned to the second surgical data being less than the first display priority value assigned to the first surgical data, overlay the first surgical data onto the livestream and exclude the second surgical data from overlaying onto the livestream.

14. The surgical system of claim 10, wherein the processor is further configured to:
- based on the second display priority value assigned to the second surgical data being less than the first display priority value assigned to the first surgical data, overlay the first surgical data onto the livestream before the second surgical data.

15. The surgical system of claim 10, wherein the processor is further configured to:
- generate a first visual representation of the first surgical data based on the first display priority value assigned to the first surgical data; and
- generate a second visual representation of the second surgical data based on the second display priority value assigned to the second surgical data, wherein the visual representations of the surgical data comprise the first visual representation and the second visual representation.

16. The surgical system of claim 10, wherein the display arrangement comprises selecting, for one or more display elements of visual representations of the surgical data, a color, a size, a shape, a display time, a display location, a display frequency, a highlighting, or a combination thereof based on the first and second display priority values.

17. The surgical system of claim 10, wherein at least one of the first and second display priority values is based on a detection of an assembly of components of the surgical instrument utilized in the surgical procedure.

18. The surgical system of claim 10, wherein at least one of the first and second display priority values is based on a distance in the surgical field between a critical surgical structure and the surgical instrument.

19. A method for presenting surgical data onto a livestream of a surgical field on a display during a surgical procedure, the method comprising:

detecting, by a control module, surgical data that comprises first surgical data and second surgical data different than the first surgical data, wherein the first surgical data competes for presentation on the display with the second surgical data;

assigning, by the control module, a first display priority value to the first surgical data and a second display priority value to the second surgical data, wherein at least one of the first and second display priority values is based on a detection of an assembly of components of a surgical instrument utilized in the surgical procedure;

determining, by the control module, a display arrangement of the surgical data on the display based on the first display priority value assigned to the first surgical data and the second display priority value assigned to the second surgical data; and presenting, onto the livestream, visual representations of the surgical data in accordance with the display arrangement.

20. A surgical system comprising:

a processor configured to:

detect surgical data that comprises first surgical data and second surgical data different than the first surgical data, wherein the first surgical data competes with the second surgical data for presentation onto a livestream of a surgical field;

assign a first display priority value to the first surgical data and a second display priority value to the second surgical data, wherein at least one of the first and second display priority values is based on a detection of an assembly of components of a surgical instrument utilized in a surgical procedure;

determine a display arrangement of the surgical data based on the first display priority value assigned to the first surgical data and the second display priority value assigned to the second surgical data; and present, onto the livestream, visual representations of the surgical data in accordance with the display arrangement.

21. A method for presenting surgical data onto a livestream of a surgical field on a display during a surgical procedure, the method comprising:

detecting, by a control module, surgical data that comprises first surgical data and second surgical data different than the first surgical data, wherein the first surgical data competes for presentation on the display with the second surgical data;

assigning, by the control module, a first display priority value to the first surgical data and a second display priority value to the second surgical data, wherein at least one of the first and second display priority values is based on a distance in the surgical field between a critical surgical structure and a surgical instrument;

determining, by the control module, a display arrangement of the surgical data on the display based on the first display priority value assigned to the first surgical data and the second display priority value assigned to the second surgical data; and presenting, onto the livestream, visual representations of the surgical data in accordance with the display arrangement.

22. A surgical system comprising:

a processor configured to:

detect surgical data that comprises first surgical data and second surgical data different than the first surgical data, wherein the first surgical data competes with the second surgical data for presentation onto a livestream of a surgical field;

assign a first display priority value to the first surgical data and a second display priority value to the second surgical data, wherein at least one of the first and second display priority values is based on a distance in the surgical field between a critical surgical structure and a surgical instrument;

determine a display arrangement of the surgical data based on the first display priority value assigned to the first surgical data and the second display priority value assigned to the second surgical data; and present, onto the livestream, visual representations of the surgical data in accordance with the display arrangement.

* * * * *